US010919937B2

(12) United States Patent
Beswick et al.

(10) Patent No.: US 10,919,937 B2
(45) Date of Patent: Feb. 16, 2021

(54) BICYCLIC PEPTIDE LIGANDS AND USES THEREOF

(71) Applicant: BicycleTx Limited, Cambridge (GB)

(72) Inventors: Paul Beswick, Cambridge (GB); Gemma Elizabeth Mudd, Cambridge (GB); Kevin McDonnell, Lexington, MA (US); Gabriela Ivanova-Berndt, Cambridge (GB); Katerine Van Rietschoten, Cambridge (GB); David Witty, Cambridge (GB); Michael Skynner, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

(21) Appl. No.: 16/660,854

(22) Filed: Oct. 23, 2019

(65) Prior Publication Data

US 2020/0131228 A1  Apr. 30, 2020

Related U.S. Application Data

(60) Provisional application No. 62/749,241, filed on Oct. 23, 2018.

(51) Int. Cl.
*A61K 38/00* (2006.01)
*C07K 7/08* (2006.01)
*C07K 14/00* (2006.01)

(52) U.S. Cl.
CPC .............. *C07K 7/08* (2013.01); *C07K 14/001* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 6,552,065 B2 | 4/2003 | Remiszewski et al. | |
| 8,138,347 B2 | 3/2012 | Knight et al. | |
| 10,441,663 B2 | 10/2019 | Bennett et al. | |
| 10,532,106 B2 | 1/2020 | Teufel et al. | |
| 2014/0256596 A1* | 9/2014 | Tite | C07K 1/1075 506/18 |
| 2018/0311300 A1 | 11/2018 | Beswick et al. | |
| 2019/0134213 A1 | 5/2019 | Teufel et al. | |
| 2019/0389907 A1 | 12/2019 | Teufel et al. | |
| 2020/0129630 A1 | 4/2020 | Koehler et al. | |

FOREIGN PATENT DOCUMENTS

| | | | |
|---|---|---|---|
| WO | 2001042246 A2 | 6/2001 | |
| WO | 2002088112 A1 | 11/2002 | |
| WO | 2003063794 A2 | 8/2003 | |
| WO | 2004005348 A1 | 1/2004 | |
| WO | 2004019973 A1 | 3/2004 | |
| WO | 2004077062 A2 | 9/2004 | |
| WO | Z004089925 A1 | 10/2004 | |
| WO | 2005007623 A2 | 1/2005 | |
| WO | 2005113554 A2 | 12/2005 | |
| WO | 2006078161 A1 | 7/2006 | |
| WO | 2006078846 A1 | 7/2006 | |
| WO | 2006122806 A2 | 11/2006 | |
| WO | 2007016176 A2 | 2/2007 | |
| WO | 2007044729 A2 | 4/2007 | |
| WO | 2007053452 A1 | 5/2007 | |
| WO | 2007070514 A1 | 6/2007 | |
| WO | 2007084786 A1 | 7/2007 | |
| WO | 2007129161 A2 | 11/2007 | |
| WO | 2008039218 A2 | 4/2008 | |
| WO | 2008109943 A1 | 9/2008 | |
| WO | 2009098450 A2 | 8/2009 | |
| WO | 2009114512 A1 | 9/2009 | |
| WO | WO-11018227 A2 | 2/2011 | |
| WO | 2011090760 A1 | 7/2011 | |
| WO | 2016067035 A1 | 5/2016 | |
| WO | WO-2017191460 A1 | 11/2017 | |
| WO | WO-2018096365 A1 | 5/2018 | |
| WO | WO-18115203 A1 | 6/2018 | |
| WO | WO-18127699 A1 | 7/2018 | |
| WO | WO-2018197893 A1 | 11/2018 | |
| WO | WO-19002842 A1 | 1/2019 | |
| WO | WO-19034866 A1 | 2/2019 | |
| WO | WO-19034868 A1 | 2/2019 | |
| WO | WO-20084305 A1 | 4/2020 | |
| WO | WO-2020089627 A1 | 5/2020 | |

OTHER PUBLICATIONS

Chen et al., "Peptide Ligands Stabilized by Small Molecules," Angew. Chem. Int. Ed., vol. 53, 2014 (pp. 1602-1606).

Gokel et al., "Crown Ethers: Sensors for Ions and Molecular Scaffolds for Materials and Biological Models," Chem. Rev., vol. 104, 2004 (pp. 2723-2750).

Loktev et al., "Multicyclic Peptides as Scaffolds for the Development of Tumor Targeting Agents," Current Medicinal Chemistry, vol. 24, 2017 (pp. 2141-2155).

PCT International Search Report and Written Opinion for PCT/GB2019/053020, dated Jun. 23, 2020 by ISA/EP.

U.S. Appl. No. 16/838,367, filed Apr. 2, 2020.
U.S. Appl. No. 16/871,305, filed May 11, 2020.

(Continued)

*Primary Examiner* — Jeanette M Lieb

(74) *Attorney, Agent, or Firm* — Andrea L. C. Reid; Paul R. Fleming; Dechert LLP

(57) ABSTRACT

The present invention provides compounds, compositions thereof, and methods of using the same.

25 Claims, No Drawings

Specification includes a Sequence Listing.

(56) References Cited

OTHER PUBLICATIONS

PCT Application No. PCT/GB2020/051140, Filed May 11, 2020.
PCT Application No. PCT/GB2020/050505, Filed Mar. 3, 2020.
Bech et al., "Chemical Strategies for Half-Life Extension of Biopharmaceuticals: Lipidation and Its Alternatives," ACS Medicinal Chemistry Letters, vol. 9, No. 7, Jun. 2018 (pp. 577-580).
Berge et al., "Pharmaceutical Salts," Journal of Pharmaceutical Sciences, vol. 66, No. 1, Jan. 1977 (pp. 1-19).
Borrelli et al., "Cell Penetrating Peptides as Molecular Carriers for Anti-Cancer Agents," Molecules, vol. 23, No. 2, Feb. 2018 (28 pages).
Cherney et al., "Macrocyclic Amino Carboxylates as Selective MMP-8 Inhibitors," Journal of Medicinal Chemistry, vol. 11, No. 11, May 1998 (pp. 1749-1751).
Chiche et al., "Hypoxia-inducible carbonic anhydrase IX and XII promote tumor cell growth by counteracting acidosis through the regulation of the intracellular pH," Cancer Research, vol. 69, No. 1, Jan. 2009 (pp. 358-368).
Diaz-Perlas et al., "Branched BBB-shuttle peptides: chemoselective modification of proteins to enhance blood-brain barrier transport," Chemical Science, vol. 9, No. 44, Sep. 2018 (pp. 8409-8415).
Driggers et al., "The exploration of macrocydes for drug discovery—an underexploited structural class," Nature Review Drug Discovery, vol. 7, No. 7, Jul. 2008 (pp. 608-624).
Gandhi et al., "MP69-11 Carbonic Anhydrase IX Assay: A Paradigm Shift in Diagnosis of Malignant Cystic Renal Lesions," Journal of Urology, vol. 193, No. 4S, Apr. 2015 (Supplement pp. e870-e871).
Heinis et al., "Phage-encoded combinatorial chemical libraries based on bicyclic peptides," Nature Chemical Biology, vol. 5, No. 7, Jul. 2009 (pp. 502-507).
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," Journal of Organic Chemistry, vol. 50, No. 26, Dec. 1985 (pp. 5834-5838).
Lea and Simeonov, "Fluorescence polarization assays in small molecule screening," Expert Opinion in Drug Discovery, vol. 6, No. 1, Jan. 2011 (pp. 17-32).
Lovering et al., "Escape from flatland: increasing saturation as an approach to improving clinical success," Journal of Medicinal Chemistry, vol. 52, No. 21, Nov. 2009 (pp. 6752-6756).
Lovering, "Escape from Flatland 2: complexity and promiscuity ," Meducinal Chemistry Communication, vol. 4, No. 3, Dec. 2012 (pp. 515-519).
Neri and Supuran, "Interfering with pH regulation in tumours as a therapeutic strategy," Nature Review Drug Discovery, vol. 10, No. 10, Sep. 2011 (pp. 767-777).
Pietraszek et al., "Lumican: A new inhibitor of matrix metalloproteinase-14 activity," FEBS Letters, vol. 588, No. 23, Nov. 2014 (pp. 4319-4324).
Ramirez et al., "Defining Causative Factors Contributing in the Activation of Hedgehog Signaling in Diffuse Large B-Cell Lymphoma," Leukemia Research, vol. 36, No. 10, Oct. 2012 (pp. 1267-1273).
Remacle et al., "Novel MT1-MMP small-molecule inhibitors based on insights into hemopexin domain function in tumor growth," Cancer Research, vol. 72, No. 9, May 2012 (pp. 2339-2349).
Rostovtsev et al., "A Stepwise Huisgen Cycloaddition Process: Copper(I)-Catalyzed Regioselective "Ligation" of Azides and Terminal Alkynes," Angew. Chem. Int. Ed, vol. 41, Jul. 2002 (pp. 2596-2599).
Sounni et al., "MT1-MMP expression promotes tumor growth and angiogenesis through an up-regulation of vascular endothelial growth factor expression," FASEB Journal, vol. 16, No. 6, Apr. 2002 (pp. 555-564).
Sun et al., "Carbohydrate and Protein Immobilization onto Solid Surfaces by Sequential Diels-Alder and Azide-Alkyne Cycloadditions," Bioconjugate Chemistry, vol. 17, No. 1, Jan.-Feb. 2006 (pp. 52-57).
Supuran, "Carbonic anhydrases: novel therapeutic applications for inhibitors and activators," Nature Reviews Drug Discovery, vol. 7, No. 2, Feb. 2008 (pp. 168-181).
Timmerman et al., "Rapid and quantitative cyclization of multiple peptide loops onto synthetic scaffolds for structural mimicry of protein surfaces." ChemBioChem, vol. 6, No. 5, May 2005 (pp. 821-824).
Wang, "An exact mathematical expression for describing competitive binding of two different ligands to a protein molecule," FEBS Letters, vol. 360, No. 2, Feb. 1995 (pp. 111-114).
Wind et al., "Measuring carbonic anhydrase IX as a hypoxia biomarker: differences in concentrations in serum and Plasma using a commercial enzyme-linked immunosorbent assay due to influences of metal ions," Annals of Clinical Biochemistry, vol. 48, No. 2, Mar. 2011 (pp. 112-120).
Wu et al., "Structures of the CXCR4 chemokine GPCR with small-molecule and cyclic peptide antagonists," Science, vol. 330, No. 6007, Nov. 2010 (pp. 1066-1071).
Xiong et al., "Crystal Structure of the Extracellular Segment of Integrin αVβ3 in Complex with an Arg-Gly-Asp Ligand," Science, vol. 296, No. 5565, Apr. 2002 (pp. 151-155).
Zhao et al., "Structural basis of specificity of a peptidyl urokinase inhibitor, upain-1," Journal of Structural Biology, vol. 160, No. 1, Oct. 2007 (pp. 1-10).

\* cited by examiner

BICYCLIC PEPTIDE LIGANDS AND USES THEREOF

CROSS-REFERENCE TO RELATED APPLICATIONS

The present application claims priority to U.S. provisional application Ser. No. 62/749,241, filed Oct. 23, 2018, the entirety of which is hereby incorporated by reference.

TECHNICAL FIELD OF THE INVENTION

The present invention relates to polypeptides which are covalently bound to molecular scaffolds such that two or more peptide loops are subtended between attachment points to the scaffold. In particular, the invention describes scaffolds that are useful for the organization and presentation of the subtended peptide loops. The invention also describes peptides which are high affinity binders of carbonic anhydrase IX (CAIX) or membrane type 1 metalloprotease (MT1-MMP). The invention also includes pharmaceutical compositions comprising said peptide ligands and to the use of said peptide ligands in preventing, suppressing or treating a disease or disorder mediated by CAIX or MT1-MMP. The invention also describes peptides which are high affinity binders of CD38 (cluster of differentiation 38), also known as cyclic ADP ribose hydrolase is a glycoprotein found on the surface of many immune cells (white blood cells), including $CD4^+$, $CD8^+$, B lymphocytes and natural killer cells. CD38 also functions in cell adhesion, signal transduction and calcium signaling. The invention also describes peptides which are high affinity binders of EphA2 (ephrin type-A receptor 2) and PBP1A (penicillin-binding protein 1A). The invention also includes pharmaceutical compositions comprising said peptide ligands and to the use of said peptide ligands in preventing, suppressing or treating a disease or disorder mediated by CD38, EphA2, or PBP1A.

BACKGROUND OF THE INVENTION

Cyclic peptides are able to bind with high affinity and target specificity to protein targets and hence are an attractive molecule class for the development of therapeutics. In fact, several cyclic peptides are already successfully used in the clinic, as for example the antibacterial peptide vancomycin, the immunosuppressant drug cyclosporine or the anti-cancer drug octreotide (Driggers et al. (2008), Nat Rev Drug Discov 7 (7), 608-24). Good binding properties result from a relatively large interaction surface formed between the peptide and the target as well as the reduced conformational flexibility of the cyclic structures. Typically, macrocycles bind to surfaces of several hundred square angstrom, as for example the cyclic peptide CXCR4 antagonist CVX15 (400 Å2; Wu et al. (2007), Science 330, 1066-71), a cyclic peptide with the Arg-Gly-Asp motif binding to integrin αVb3 (355 Å2) (Xiong et al. (2002), Science 296 (5565), 151-5) or the cyclic peptide inhibitor upain-1 binding to urokinase-type plasminogen activator (603 Å2; Zhao et al. (2007), J Struct Biol 160 (1), 1-10).

Due to their cyclic configuration, peptide macrocycles are less flexible than linear peptides, leading to a smaller loss of entropy upon binding to targets and resulting in a higher binding affinity. The reduced flexibility also leads to locking target-specific conformations, increasing binding specificity compared to linear peptides. This effect has been exemplified by a potent and selective inhibitor of matrix metalloproteinase 8, MMP-8) which lost its selectivity over other MMPs when its ring was opened (Cherney et al. (1998), J Med Chem 41 (11), 1749-51). The favorable binding properties achieved through macrocyclization are even more pronounced in multicyclic peptides having more than one peptide ring as for example in vancomycin, nisin and actinomycin.

Different research teams have previously tethered polypeptides with cysteine residues to a synthetic molecular structure (Kemp and McNamara (1985), J. Org. Chem; Timmerman et al. (2005), ChemBioChem). Meloen and co-workers had used tris(bromomethyl)benzene and related molecules for rapid and quantitative cyclization of multiple peptide loops onto synthetic scaffolds for structural mimicry of protein surfaces (Timmerman et al. (2005), ChemBioChem). Methods for the generation of candidate drug compounds wherein said compounds are generated by linking cysteine containing polypeptides to a molecular scaffold as for example tris(bromomethyl)benzene are disclosed in WO 2004/077062 and WO 2006/078161.

Phage display-based combinatorial approaches have been developed to generate and screen large libraries of bicyclic peptides to targets of interest (Heinis et al. (2009), Nat Chem Biol 5 (7), 502-7 and WO2009/098450). Briefly, combinatorial libraries of linear peptides containing three cysteine residues and two regions of six random amino acids (Cys-(Xaa)6-Cys-(Xaa)6-Cys) were displayed on phage and cyclised by covalently linking the cysteine side chains to a small molecule (tris-(bromomethyl)benzene).

Such bicyclic constrained peptide binders (Bicycles) have proven to be especially effective binders for a variety of biological targets. As a result, there is a need to expand the scope of molecular scaffolds from the relatively planar tris-(bromomethyl)benzene to molecular scaffolds that possess a higher $sp^3$ content. The addition of $sp^3$ content which is defined as $Fsp^3$, where $Fsp^3=(sp^3$ hybridized carbons/total carbon count), in small molecules has been associated with higher success rates in clinical development due to improved physicochemical properties such as solubility (Lovering et al. (2009), J. Med. Chem. 52(21), 6752-6756; Lovering (2013), Med. Chem. Commun., 4, 515-519). Without being bound by any particular theory, it is believed that access to a larger variety of molecular scaffolds could potentially provide differential displays of the same amino acid sequence that may prove beneficial in increasing selectivity in addition to improving physicochemical properties. Therefore, there exists a need to develop a greater variety of molecular scaffolds for the preparation of bicyclic constrained peptide binders.

SUMMARY OF THE INVENTION

It has now been found that compounds of this invention, and pharmaceutically acceptable compositions thereof, are effective as inhibitors of CAIX, MT1-MMP, CD38, EphA2, or PBP1A. In certain embodiments, a compound of the invention is of formula I:

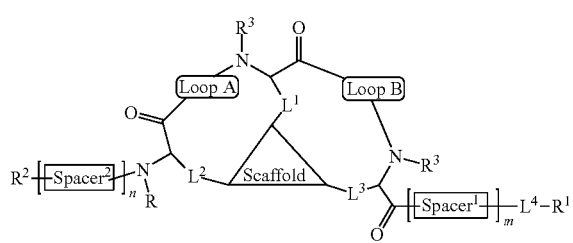

or a pharmaceutically acceptable salt thereof, wherein each variable is as defined and described herein. In certain embodiments, a compound of the invention is of formula II:

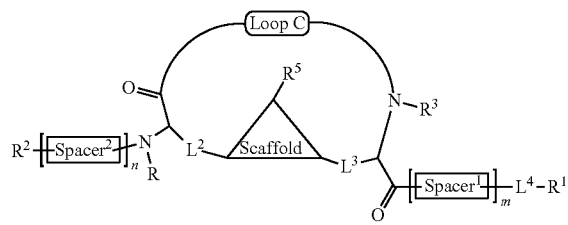

II or a pharmaceutically acceptable salt thereof, wherein each variable is as defined and described herein.

Compounds of the present invention, and pharmaceutically acceptable compositions thereof, are useful for treating a variety of diseases, disorders or conditions, associated with CAIX, MT1-MMP, CD38, EphA2, or PBP1A. Such diseases, disorders, or conditions include those described herein.

Compounds provided by this invention are also useful for the study of CAIX, MT1-MMP, CD38, EphA2, or PBP1A enzymes in biological and pathological phenomena; the study of these enzymes occurring in bodily tissues; and the comparative evaluation of new CAIX, MT1-MMP, CD38, EphA2, or PBP1A inhibitors in vitro or in vivo.

DETAILED DESCRIPTION OF CERTAIN EMBODIMENTS

1. General Description of Certain Embodiments of the Invention

In some embodiments, peptide sequences are treated with molecular scaffold reagents to form compounds of the present invention.

Compounds of the present invention, and compositions thereof, are useful as inhibitors of CAIX, MT1-MMP, CD38, EphA2, or PBP1A. In some embodiments, a provided compound inhibits CAIX. In some embodiments, a provided compound inhibits MT1-MMP. In some embodiments, a provided compound inhibits CD38. In some embodiments, a provided compound inhibits EphA2. In some embodiments, a provided compound inhibits PBP1A.

In certain embodiments, the present invention provides a compound of formula I:

I

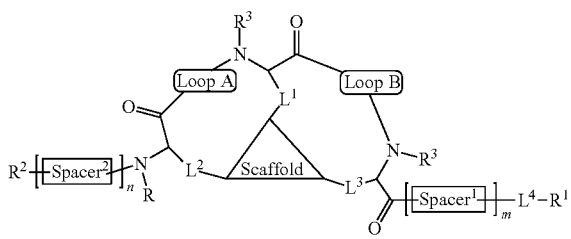

or a pharmaceutically acceptable salt thereof, wherein:
each of $L^1$, $L^2$, and $L^3$ is independently a covalent bond or a $C_{1-8}$ bivalent hydrocarbon chain wherein one, two or three methylene units of the chain are optionally and independently replaced by $-Cy^1-$, $-S-$, $-N(R)-$, $-O-$, $-C(O)-$, $-OC(O)-$, $-C(O)O-$, $-C(O)N(R)-$, $-N(R)C(O)-$, $-OC(O)N(R)-$, $-N(R)C(O)O-$, $-S(O)-$, $-S(O)_2-$, $-C(CH_3)=N-N(R)-$, $-N(R)N=C(CH_3)-$, $-N(R)CH_2C(O)-$, $-(CH_2CH_2O)_{1-10}-$,

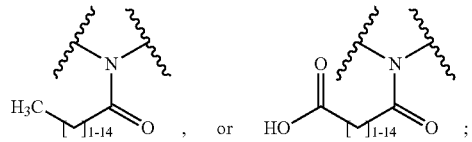

$L^4$ is a covalent bond, $-O-$, $-N(R)-$, or $-N(R)CH_2CH_2N(R)-$;

each R is independently hydrogen or $C_{1-4}$ aliphatic;

each $-Cy^1-$ is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur;

Scaffold is a trivalent group that connects and orients a cyclic peptide;

Loop A is a bivalent natural or unnatural amino acid residue or peptide attached to the amino acid residue linked to $L^1$ and the amino acid residue linked to $L^2$;

Loop B is a bivalent natural or unnatural amino acid residue or peptide attached to the amino acid residue linked to $L^1$ and the amino acid residue linked to $L^3$;

Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond;

Spacer$^2$ is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond;
each of $R^1$ and $R^2$ is independently R,

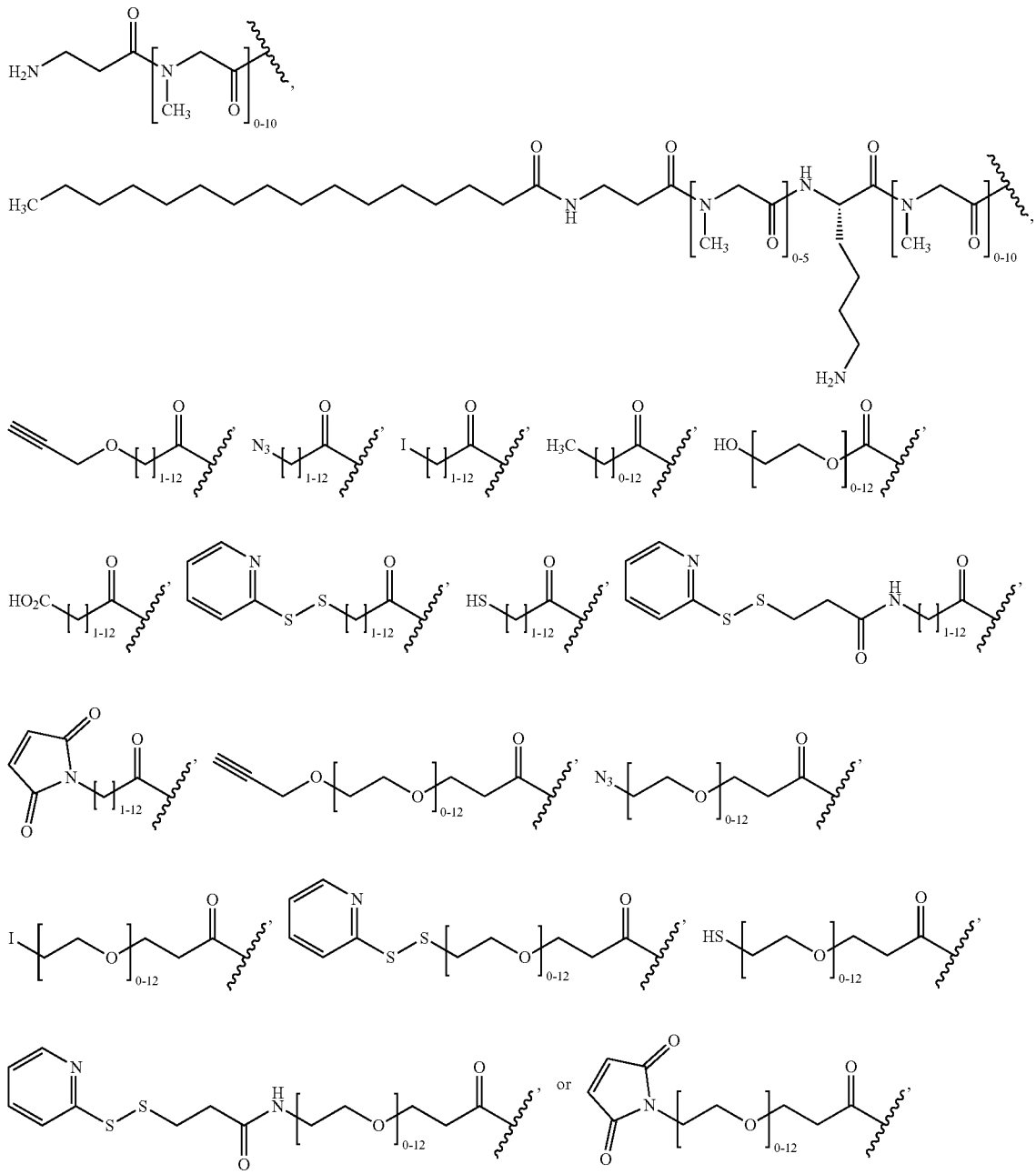

or -Linker-Conjugate;

each Linker is independently a covalent bond, or a $C_{1-8}$ bivalent hydrocarbon chain wherein one, two or three methylene units of the chain are optionally and independently replaced by -$Cy^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,

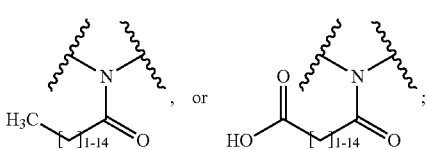

each Conjugate is independently a half life extension motif, a solubilizing group, a transporter recognition motif, a cell penetrant motif, a drug payload, or a detectable moiety;

each of $R^3$ is independently hydrogen or $C_{1-4}$ aliphatic;

m is 0 or 1; and n is 0 or 1.

In certain embodiments, the present invention provides a compound of formula II:

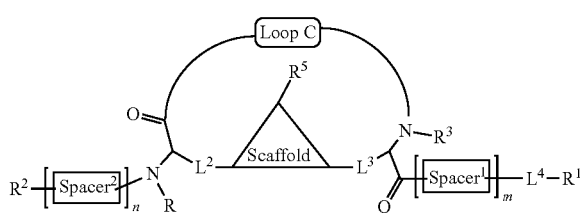

II or a pharmaceutically acceptable salt thereof, wherein:

each of $L^2$ and $L^3$ is independently a covalent bond or a $C_{1-8}$ bivalent hydrocarbon chain wherein one, two or three methylene units of the chain are optionally and independently replaced by -$Cy^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,

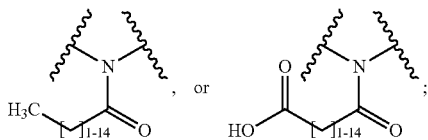

$L^4$ is a covalent bond, —O—, —N(R)—, or —N(R)CH$_2$CH$_2$N(R)—;

each R is independently hydrogen or $C_{1-4}$ aliphatic;

each -$Cy^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur;

Scaffold is a trivalent group that connects and orients a cyclic peptide;

Loop C is a peptide attached to the amino acid residue linked to $L^2$ and the amino acid residue linked to $L^3$;

Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond;

Spacer$^2$ is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond;

each of $R^1$ and $R^2$ is independently R,

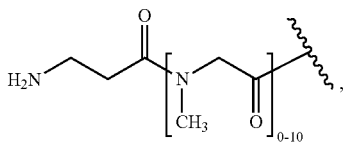

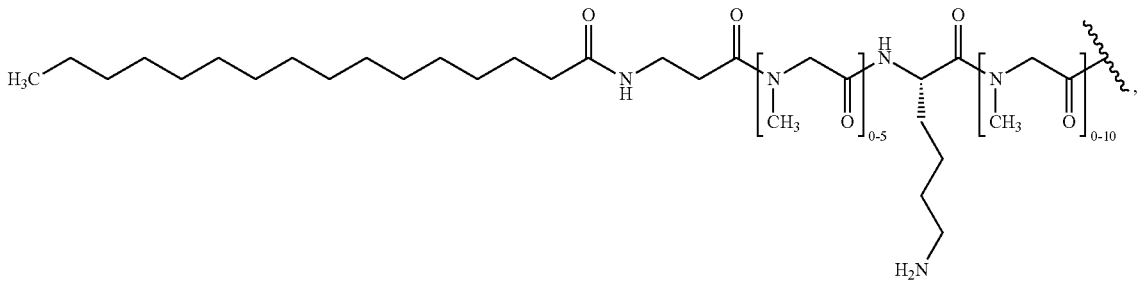

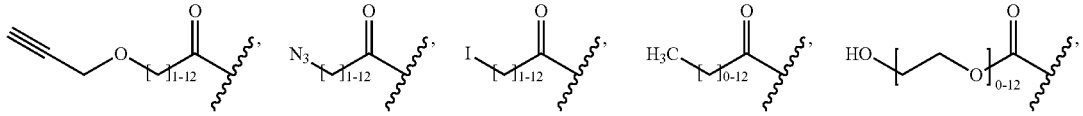

-continued

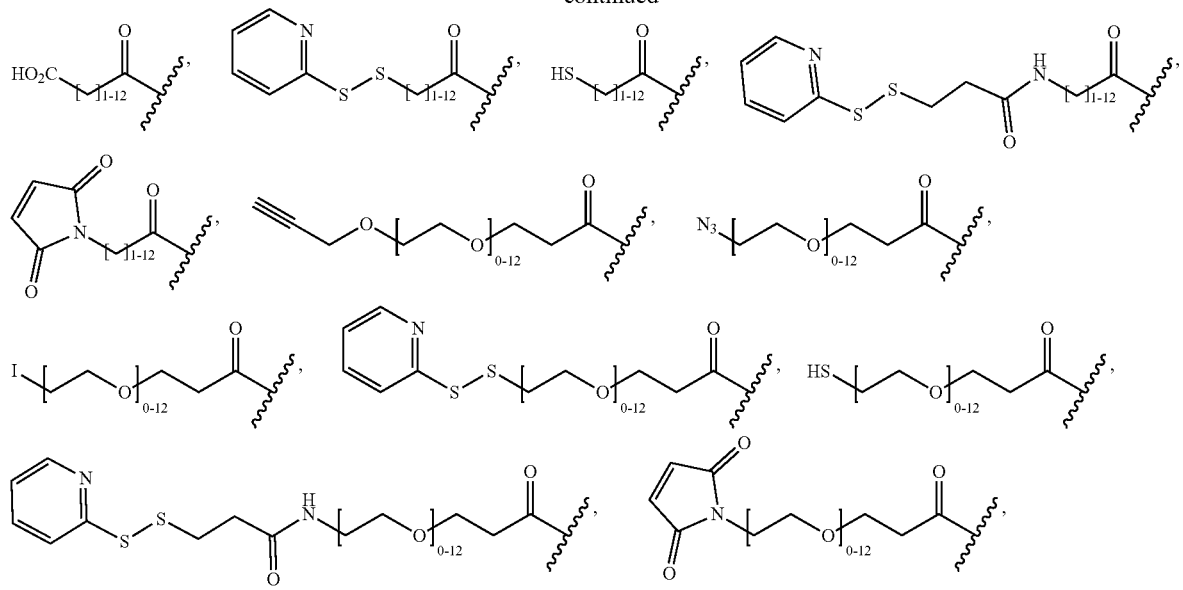

or -Linker-Conjugate;

each Linker is independently a covalent bond, or a $C_{1-8}$ bivalent hydrocarbon chain wherein one, two or three methylene units of the chain are optionally and independently replaced by -$Cy^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R) N=C(CH$_3$)—, —N(R)CH$_2$C(O)—, —(CH$_2$CH$_2$O)$_{1-10}$—,

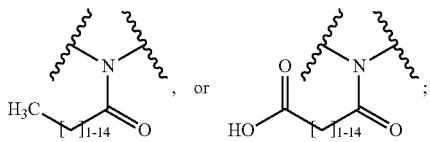

each Conjugate is independently a half life extension motif, a solubilizing group, a transporter recognition motif, a cell penetrant motif, a drug payload, or a detectable moiety;
each of $R^3$ is independently hydrogen or $C_{1-4}$ aliphatic;
$R^5$, together with the atom to which $R^5$ attaches to, form a moiety comprising a hydrogen bond acceptor (HBA) and/or a hydrogen bond donor (HBD), which forms a hydrogen bond with an amino acid residue of the peptide between $L^2$ and $L^3$;
m is 0 or 1; and
n is 0 or 1

2. Compounds and Definitions

Peptide Ligands

A peptide ligand, as referred to herein, refers to a peptide covalently bound to a molecular scaffold. In some embodiments, a peptide comprises two or more reactive groups (e.g. cysteine and tyrosine residues) which are capable of forming covalent bonds to the scaffold, and a sequence subtended between said reactive groups which is referred to as the loop sequence, since it forms a loop when the peptide is bound to the scaffold. In some embodiments, a peptide ligand forms one or more loop via one or more hydrogen bond to the scaffold. In some embodiments, a peptide comprises two cysteine residues and forms one or more hydrogen bond to a scaffold, and thus forms at least two loops on the scaffold. In some embodiments, a peptide comprises at least three cysteine residues and forms at least two loops on the scaffold.

Advantages of the Peptide Ligands

Certain bicyclic peptides of the present invention have a number of advantageous properties which enable them to be considered as suitable drug-like molecules for injection, inhalation, nasal, ocular, oral or topical administration. Without being bound by any particular theory, such advantageous properties may include:

Species cross-reactivity. This is a typical requirement for preclinical pharmacodynamics and pharmacokinetic evaluation;

Protease stability. Bicyclic peptide ligands should ideally demonstrate stability to plasma proteases, epithelial ("membrane-anchored") proteases, gastric and intestinal proteases, lung surface proteases, intracellular proteases and the like. Protease stability should be maintained between different species such that a bicycle lead candidate can be developed in animal models as well as administered with confidence to humans;

Desirable solubility profile. This is a function of the proportion of charged and hydrophilic versus hydrophobic residues and intra/inter-molecular H-bonding, which is important for formulation and absorption purposes;

An optimal plasma half-life in the circulation. Depending upon the clinical indication and treatment regimen, it may be required to develop a bicyclic peptide for short exposure in an acute illness management setting, or develop a bicyclic peptide with enhanced retention in the circulation, and is therefore optimal for the management of more chronic disease states. Other factors driving the desirable plasma half-life are requirements of sustained exposure for maximal therapeutic efficiency versus the accompanying toxicology due to sustained exposure of the agent; and Selectivity. Certain peptide ligands of the invention demonstrate good selectivity over other carbonic anhydrases and metalloproteases.

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

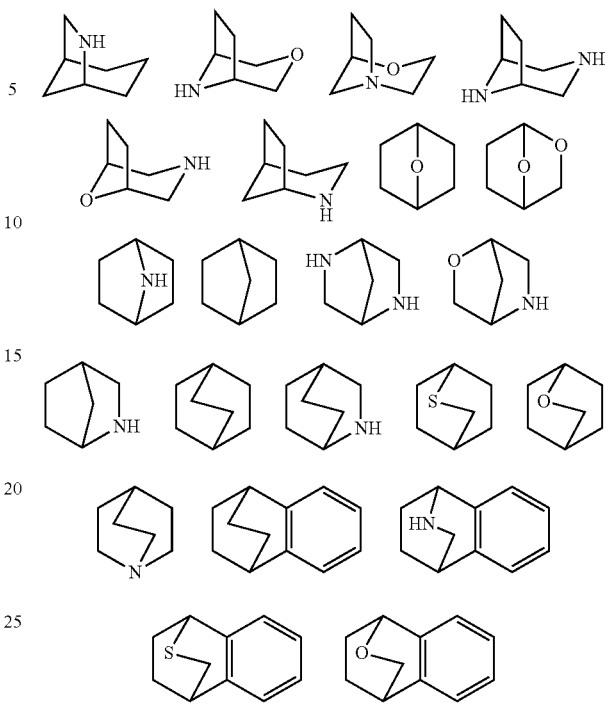

-continued

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_1$-6) hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

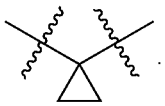 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —N(R°)C(NR°)N(R°)$_2$; —(CH$_2$)$_{0-4}$N(R°)C(O)NR°$_2$; —N(R°)C(S)NR°$_2$; —(CH$_2$)$_{0-4}$N(R)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$OC(O)NR°$_2$; —C(O)N(OR°)

R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\bullet$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, Rx, of a provided compound comprises one or more deuterium atoms.

As used herein, the term "inhibitor" is defined as a compound that binds to and/or inhibits CAIX, MT1-MMP, CD38, EphA2, or PBP1A with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P, $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in CAIX, MT1-MMP, CD38, EphA2, or PBP1A activity between a sample comprising a compound of the present invention, or composition thereof, and CAIX, MT1-MMP, CD38, EphA2, or PBP1A, and an equivalent sample comprising CAIX, MT1-MMP, CD38, EphA2, or PBP1A, in the absence of said compound, or composition thereof.

The term "hydrogen bond," as used herein, means a weak type of force that forms a special type of dipole-dipole attraction which occurs when a hydrogen atom bonded to a strongly electronegative atom exists in the vicinity of another electronegative atom with a lone pair of electrons. In order for a hydrogen bond to occur there must be both a hydrogen donor and an acceptor present. The donor in a hydrogen bond is the atom to which the hydrogen atom participating in the hydrogen bond is covalently bonded, and is usually a strongly electronegative atom such as N, O, or F. The hydrogen acceptor is the neighboring electronegative ion or molecule, and must posses a lone electron pair in order to form a hydrogen bond.

3. Description of Exemplary Embodiments

In certain embodiments, the present invention provides a compound of formula I:

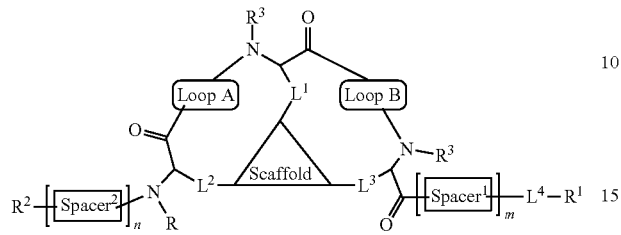

I or a pharmaceutically acceptable salt thereof, wherein:

each of $L^1$, $L^2$, and $L^3$ is independently a covalent bond or a $C_{1-8}$ bivalent hydrocarbon chain wherein one, two or three methylene units of the chain are optionally and independently replaced by -$Cy^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,

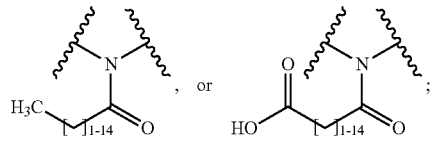

$L^4$ is a covalent bond, —O—, —N(R)—, or —N(R)CH$_2$CH$_2$N(R)—;

each R is independently hydrogen or $C_{1-4}$ aliphatic;

each -$Cy^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur;

Scaffold is a trivalent group that connects and orients a cyclic peptide;

Loop A is a bivalent natural or unnatural amino acid residue or peptide attached to the amino acid residue linked to $L^1$ and the amino acid residue linked to $L^2$;

Loop B is a bivalent natural or unnatural amino acid residue or peptide attached to the amino acid residue linked to $L^1$ and the amino acid residue linked to $L^3$;

Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond;

Spacer$^2$ is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond;

each of $R^1$ and $R^2$ is independently R,

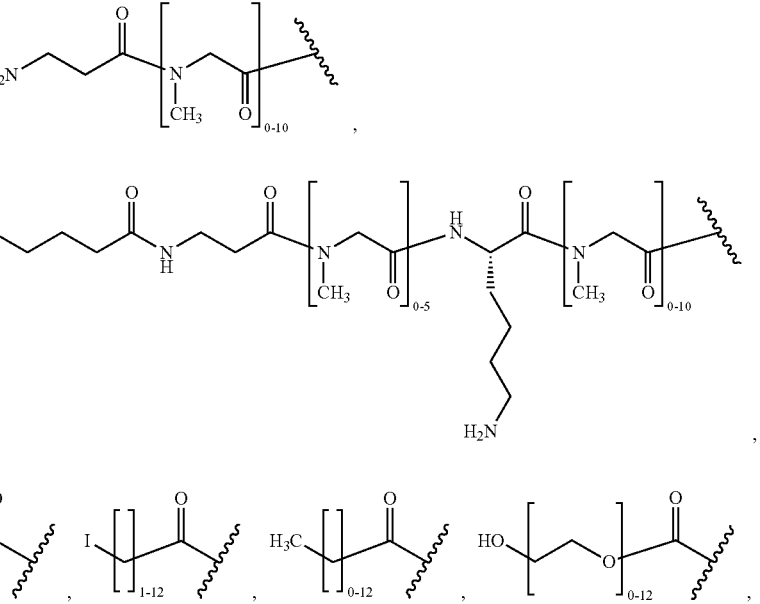

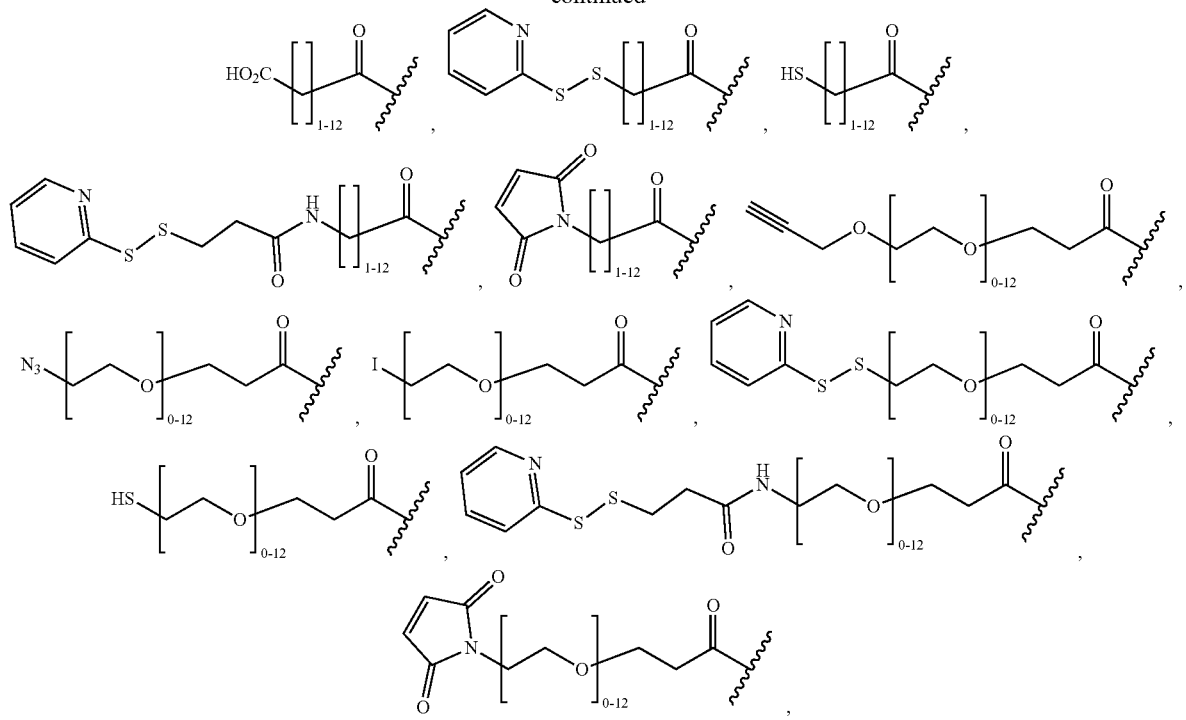

or -Linker-Conjugate;

each Linker is independently a covalent bond, or a $C_{1-8}$ bivalent hydrocarbon chain wherein one, two or three methylene units of the chain are optionally and independently replaced by -Cy$^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R) N=C(CH$_3$)—, —N(R)CH$_2$C(O)—, —(CH$_2$CH$_2$O)$_{1-10}$—,

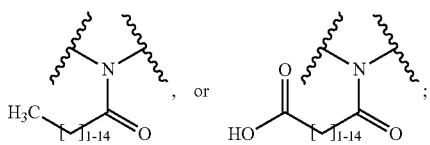

each Conjugate is independently a half life extension motif, a solubilizing group, a transporter recognition motif, a cell penetrant motif, a drug payload, or a detectable moiety;

each of $R^3$ is independently hydrogen or $C_{1-4}$ aliphatic;

m is 0 or 1; and n is 0 or 1

As defined above and described herein, each of $L^1$, $L^2$, and $L^3$ is independently a covalent bond or a $C_{1-8}$ bivalent hydrocarbon chain wherein one, two or three methylene units of the chain are optionally and independently replaced by -Cy$^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R) CH$_2$C(O)—, —(CH$_2$CH$_2$O)$_{1-10}$—,

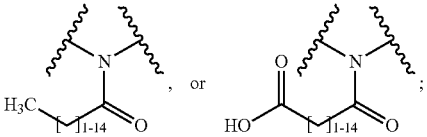

In some embodiments, each of $L^1$, $L^2$, and $L^3$ is a covalent bond. In some embodiments, each of $L^1$, $L^2$, and $L^3$ is —CH$_2$S—. In some embodiments, each of $L^1$, $L^2$, and $L^3$ is —CH$_2$NH—. In some embodiments, each of $L^1$, $L^2$, and $L^3$ is —CH$_2$O—. In some embodiments, each of $L^1$, $L^2$, and $L^3$ is —CH$_2$CH$_2$O—. In some embodiments, each of $L^1$, $L^2$, and $L^3$ is —CH$_2$CH$_2$CH$_2$CH$_2$NH—. In some embodiments, each of $L^1$, $L^2$, and $L^3$ is —CH$_2$N(CH$_3$)—. In some embodiments, each of $L^1$, $L^2$, and $L^3$ is —CH$_2$CH$_2$CH$_2$CH$_2$N(CH$_3$)—. In some embodiments, each of $L^1$, $L^2$, and $L^3$ is

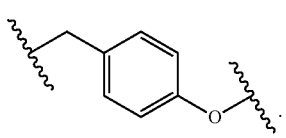

In some embodiments, $L^1$ is a covalent bond. In some embodiments, $L^1$ is —CH$_2$S—. In some embodiments, $L^1$ is —CH$_2$O—. In some embodiments, $L^1$ is —CH$_2$CH$_2$O—. In some embodiments, $L^1$ is —CH$_2$NH—. In some embodiments, $L^1$ is —CH$_2$CH$_2$CH$_2$CH$_2$NH—. In some embodiments, $L^1$ is —CH$_2$N(CH$_3$)—. In some embodiments, $L^1$ is —CH$_2$CH$_2$CH$_2$CH$_2$N(CH$_3$)—. In some embodiments, $L^1$ is —CH$_2$SCH$_2$—. In some embodiments, $L^1$ is —CH$_2$OCH$_2$—. In some embodiments, $L^1$ is —CH$_2$CH$_2$OCH$_2$—. In some embodiments, $L^1$ is —CH$_2$NHCH$_2$—. In some embodiments, L$^1$ is —CH$_2$N(CH$_3$)CH$_2$—. In some embodiments, L$^1$ is —CH$_2$CH$_2$CH$_2$CH$_2$NHCH$_2$—. In some embodiments, L$^1$ is —CH$_2$CH$_2$CH$_2$CH$_2$N(CH$_3$)CH$_2$—. In some embodiments, L$^1$ is —CH$_2$SCH$_2$C(O)NH—. In some embodiments, L$^1$ is —CH$_2$OCH$_2$C(O)NH—. In some embodiments, L$^1$ is —CH$_2$CH$_2$OCH$_2$C(O)NH—. In some embodiments, L$^1$ is —CH$_2$NHCH$_2$C(O)NH—. In some embodiments, L$^1$ is —CH$_2$N(CH$_3$)CH$_2$C(O)NH—. In some embodiments, L$^1$ is —CH$_2$CH$_2$CH$_2$CH$_2$NHCH$_2$C(O)NH—. In some embodiments, L$^1$ is —CH$_2$CH$_2$CH$_2$CH$_2$N(CH$_3$)CH$_2$C(O)NH—. In some embodiments, L$^1$ is —CH$_2$SCH$_2$C(O)—. In some embodiments, L$^1$ is —CH$_2$OCH$_2$C(O)—. In some embodiments, L$^1$ is —CH$_2$CH$_2$OCH$_2$C(O)—. In some embodiments, L$^1$ is —CH$_2$NHCH$_2$C(O)—. In some embodiments, L$^1$ is —CH$_2$N(CH$_3$)CH$_2$C(O)—. In some embodiments, L$^1$ is —CH$_2$CH$_2$CH$_2$CH$_2$NHCH$_2$C(O)—. In some embodiments, L$^1$ is —CH$_2$CH$_2$CH$_2$CH$_2$N(CH$_3$)CH$_2$C(O)—. In some embodiments, L$^1$ is —CH$_2$SCH$_2$CH$_2$C(O)NH—. In some embodiments, L$^1$ is —CH$_2$OCH$_2$CH$_2$C(O)NH—. In some embodiments, L$^1$ is —CH$_2$CH$_2$OCH$_2$CH$_2$C(O)NH—. In some embodiments, L$^1$ is —CH$_2$NHCH$_2$CH$_2$C(O)NH—. In some embodiments, L$^1$ is —CH$_2$N(CH$_3$)CH$_2$CH$_2$C(O)NH—. In some embodiments, L$^1$ is —CH$_2$CH$_2$CH$_2$CH$_2$NHCH$_2$C(O)NH—. In some embodiments, L$^1$ is —CH$_2$CH$_2$CH$_2$CH$_2$N(CH$_3$)CH$_2$CH$_2$C(O)NH—. In some embodiments, L$^1$ is —CH$_2$SCH$_2$CH$_2$C(O)—. In some embodiments, L$^1$ is —CH$_2$OCH$_2$CH$_2$C(O)—. In some embodiments, L$^1$ is —CH$_2$CH$_2$OCH$_2$CH$_2$C(O)—. In some embodiments, L$^1$ is —CH$_2$NHCH$_2$CH$_2$C(O)—. In some embodiments, L$^1$ is —CH$_2$N(CH$_3$)CH$_2$CH$_2$C(O)—. In some embodiments, L$^1$ is —CH$_2$CH$_2$CH$_2$CH$_2$NHCH$_2$CH$_2$C(O)—. In some embodiments, L$^1$ is —CH$_2$CH$_2$CH$_2$CH$_2$N(CH$_3$)CH$_2$CH$_2$C(O)—. In some embodiments, L$^1$ is

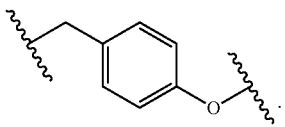 [SMILES: *Cc1ccc(O*)cc1]

In some embodiments, L$^1$ is selected from those depicted in Table 1, below.

In some embodiments, L$^2$ is a covalent bond. In some embodiments, L$^2$ is —CH$_2$S—. In some embodiments, L$^2$ is —CH$_2$O—. In some embodiments, L$^2$ is —CH$_2$CH$_2$O—. In some embodiments, L$^2$ is —CH$_2$NH—. In some embodiments, L$^2$ is —CH$_2$CH$_2$CH$_2$CH$_2$NH—. In some embodiments, L$^2$ is —CH$_2$N(CH$_3$)—. In some embodiments, L$^2$ is —CH$_2$CH$_2$CH$_2$CH$_2$N(CH$_3$)—. In some embodiments, L$^2$ is —CH$_2$SCH$_2$—. In some embodiments, L$^2$ is —CH$_2$OCH$_2$—. In some embodiments, L$^2$ is —CH$_2$CH$_2$OCH$_2$—. In some embodiments, L$^2$ is —CH$_2$NHCH$_2$—. In some embodiments, L$^2$ is —CH$_2$N(CH$_3$)CH$_2$—. In some embodiments, L$^2$ is —CH$_2$CH$_2$CH$_2$CH$_2$NHCH$_2$—. In some embodiments, L$^2$ is —CH$_2$CH$_2$CH$_2$CH$_2$N(CH$_3$)CH$_2$—. In some embodiments, L$^2$ is —CH$_2$SCH$_2$C(O)NH—. In some embodiments, L$^2$ is —CH$_2$OCH$_2$C(O)NH—. In some embodiments, L$^2$ is —CH$_2$CH$_2$OCH$_2$C(O)NH—. In some embodiments, L$^2$ is —CH$_2$NHCH$_2$C(O)NH—. In some embodiments, L$^2$ is —CH$_2$N(CH$_3$)CH$_2$C(O)NH—. In some embodiments, L$^2$ is —CH$_2$CH$_2$CH$_2$CH$_2$NHCH$_2$C(O)NH—. In some embodiments, L$^2$ is —CH$_2$CH$_2$CH$_2$CH$_2$N(CH$_3$)CH$_2$C(O)NH—. In some embodiments, L$^2$ is —CH$_2$SCH$_2$C(O)—. In some embodiments, L$^2$ is —CH$_2$OCH$_2$C(O)—. In some embodiments, L$^2$ is —CH$_2$CH$_2$OCH$_2$C(O)—. In some embodiments, L$^2$ is —CH$_2$NHCH$_2$C(O)—. In some embodiments, L$^2$ is —CH$_2$N(CH$_3$)CH$_2$C(O)—. In some embodiments, L$^2$ is —CH$_2$CH$_2$CH$_2$CH$_2$NHCH$_2$C(O)—. In some embodiments, L$^2$ is —CH$_2$CH$_2$CH$_2$CH$_2$N(CH$_3$)CH$_2$C(O)—. In some embodiments, L$^2$ is —CH$_2$SCH$_2$CH$_2$C(O)NH—. In some embodiments, L$^2$ is —CH$_2$OCH$_2$CH$_2$C(O)NH—. In some embodiments, L$^2$ is —CH$_2$CH$_2$OCH$_2$CH$_2$C(O)NH—. In some embodiments, L$^2$ is —CH$_2$NHCH$_2$CH$_2$C(O)NH—. In some embodiments, L$^2$ is —CH$_2$N(CH$_3$)CH$_2$CH$_2$C(O)NH—. In some embodiments, L$^2$ is —CH$_2$CH$_2$CH$_2$CH$_2$NHCH$_2$CH$_2$C(O)NH—. In some embodiments, L$^2$ is —CH$_2$CH$_2$CH$_2$CH$_2$N(CH$_3$)CH$_2$CH$_2$C(O)NH—. In some embodiments, L$^2$ is —CH$_2$SCH$_2$CH$_2$C(O)—. In some embodiments, L$^2$ is —CH$_2$OCH$_2$CH$_2$C(O)—. In some embodiments, L$^2$ is —CH$_2$CH$_2$OCH$_2$CH$_2$C(O)—. In some embodiments, L$^2$ is —CH$_2$NHCH$_2$CH$_2$C(O)—. In some embodiments, L$^2$ is —CH$_2$N(CH$_3$)CH$_2$CH$_2$C(O)—. In some embodiments, L$^2$ is —CH$_2$CH$_2$CH$_2$CH$_2$NHCH$_2$CH$_2$C(O)—. In some embodiments, L$^2$ is —CH$_2$CH$_2$CH$_2$CH$_2$N(CH$_3$)CH$_2$CH$_2$C(O)—. In some embodiments, L$^2$ is

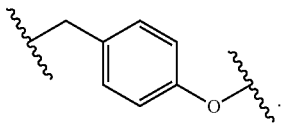 [SMILES: *Cc1ccc(O*)cc1]

In some embodiments, L$^2$ is selected from those depicted in Table 1, below.

In some embodiments, L$^3$ is a covalent bond. In some embodiments, L$^3$ is —CH$_2$S—. In some embodiments, L$^3$ is —CH$_2$O—. In some embodiments, L$^3$ is —CH$_2$CH$_2$O—. In some embodiments, L$^3$ is —CH$_2$NH—. In some embodiments, L$^3$ is —CH$_2$CH$_2$CH$_2$CH$_2$NH—. In some embodiments, L$^3$ is —CH$_2$N(CH$_3$)—. In some embodiments, L$^3$ is —CH$_2$CH$_2$CH$_2$CH$_2$N(CH$_3$)—. In some embodiments, L$^3$ is —CH$_2$SCH$_2$—. In some embodiments, L$^3$ is —CH$_2$OCH$_2$—. In some embodiments, L$^3$ is —CH$_2$CH$_2$OCH$_2$—. In some embodiments, L$^3$ is —CH$_2$NHCH$_2$—. In some embodiments, L$^3$ is —CH$_2$N(CH$_3$)CH$_2$—. In some embodiments, L$^3$ is —CH$_2$CH$_2$CH$_2$CH$_2$NHCH$_2$—. In some embodiments, L$^3$ is —CH$_2$CH$_2$CH$_2$CH$_2$N(CH$_3$)CH$_2$—. In some embodiments, L$^3$ is —CH$_2$SCH$_2$C(O)NH—. In some embodiments, L$^3$ is —CH$_2$OCH$_2$C(O)NH—. In some embodiments, L$^3$ is —CH$_2$CH$_2$OCH$_2$C(O)NH—. In some embodiments, L$^3$ is —CH$_2$NHCH$_2$C(O)NH—. In some embodiments, L$^3$ is —CH$_2$N(CH$_3$)CH$_2$C(O)NH—. In some embodiments, L$^3$ is —CH$_2$CH$_2$CH$_2$CH$_2$NHCH$_2$C(O)NH—. In some embodiments, L$^3$ is —CH$_2$CH$_2$CH$_2$CH$_2$N(CH$_3$)CH$_2$C(O)NH—. In some embodiments, L$^3$ is —CH$_2$SCH$_2$C(O)—. In some embodiments, L$^3$ is —CH$_2$OCH$_2$C(O)—. In some embodiments, L$^3$ is —CH$_2$CH$_2$OCH$_2$C(O)—. In some embodiments, L$^3$ is —CH$_2$NHCH$_2$C(O)—. In some embodiments, L$^3$ is —CH$_2$N(CH$_3$)CH$_2$C(O)—. In some embodiments, L$^3$ is —CH$_2$CH$_2$CH$_2$CH$_2$NHCH$_2$C(O)—. In some embodiments, L$^3$ is —CH$_2$CH$_2$CH$_2$CH$_2$N(CH$_3$)CH$_2$C(O)—. In some embodiments, L$^3$ is —CH$_2$SCH$_2$CH$_2$C(O)NH—. In some embodiments, L$^3$ is —CH$_2$OCH$_2$CH$_2$C(O)NH—. In some embodiments, L$^3$ is —CH$_2$CH$_2$OCH$_2$CH$_2$C(O)NH—. In some embodiments, L$^3$ is —CH$_2$NHCH$_2$CH$_2$C(O)NH—.

In some embodiments, L³ is —CH₂N(CH₃)CH₂CH₂C(O)NH—. In some embodiments, L³ is —CH₂CH₂CH₂CH₂NHCH₂CH₂C(O)NH—. In some embodiments, L³ is —CH₂CH₂CH₂CH₂N(CH₃)CH₂CH₂C(O)NH—. In some embodiments, L³ is —CH₂SCH₂CH₂C(O)—. In some embodiments, L³ is —CH₂OCH₂CH₂C(O)—. In some embodiments, L³ is —CH₂CH₂OCH₂CH₂C(O)—. In some embodiments, L³ is —CH₂NHCH₂CH₂C(O)—. In some embodiments, L³ is —CH₂N(CH₃)CH₂CH₂C(O)—. In some embodiments, L³ is —CH₂CH₂CH₂CH₂NHCH₂CH₂C(O)—. In some embodiments, L³ is —CH₂CH₂CH₂CH₂N(CH₃)CH₂CH₂C(O)—. In some embodiments, L³ is

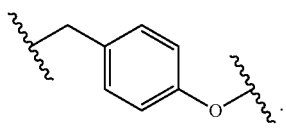 [SMILES: *Cc1ccc(O*)cc1]

In some embodiments, L³ is selected from those depicted in Table 1, below.

As defined above and described herein, L⁴ is a covalent bond, —O—, —N(R)—, or —N(R)CH₂CH₂N(R)—.

In some embodiments, L⁴ is a covalent bond. In some embodiments, L⁴ is —O—. In some embodiments, L⁴ is —N(R)—, wherein R is as described herein. In some embodiments, L⁴ is —N(R)CH₂CH₂N(R)—, wherein R is as described herein.

In some embodiments, L⁴ is —NH—. In some embodiments, L⁴ is —NHCH₂CH₂NH—.

In some embodiments, L⁴ is selected from those depicted in Table 1, below.

As defined above and described herein, each R is independently hydrogen or C₁₋₄ aliphatic.

In some embodiments, R is H. In some embodiments, R is C₁₋₄ aliphatic.

In some embodiments, R is C₁₋₄ alkyl. In some embodiments, R is methyl. In some embodiments, R is ethyl. In some embodiments, R is isopropyl. In some embodiments, R is propyl. In some embodiments, R is butyl. In some embodiments, R is isobutyl. In some embodiments, R is t-butyl.

In some embodiments, R is selected from those depicted in Table 1, below.

As defined above and described herein, each -Cy¹- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur.

In some embodiments, -Cy¹- is an optionally substituted phenylene. In some embodiments, -Cy¹- is an optionally substituted 3-7 membered saturated or partially unsaturated carbocyclylene. In some embodiments, -Cy¹- is an optionally substituted 4-7 membered saturated or partially unsaturated heterocyclylene having 1-2 heteroatoms independently selected from nitrogen, oxygen, or sulfur. In some embodiments, -Cy¹- is an optionally substituted 10-12 membered saturated or partially unsaturated bicyclic heterocyclylene having 1-4 heteroatoms independently selected from nitrogen, oxygen, or sulfur. In some embodiments, -Cy¹- is an optionally substituted 10-12 membered saturated or partially unsaturated tricyclic heterocyclylene having 1-4 heteroatoms independently selected from nitrogen, oxygen, or sulfur. In some embodiments, -Cy¹- is an optionally substituted 10-12 membered partially saturated bicyclic heteroarylene having 1-4 heteroatoms independently selected from nitrogen, oxygen, or sulfur. In some embodiments, -Cy¹- is an optionally substituted 10-12 membered partially saturated tricyclic heteroarylene having 1-4 heteroatoms independently selected from nitrogen, oxygen, or sulfur. In some embodiments, -Cy¹- is an optionally substituted 9-12 membered bicyclic heteroarylene having 1-4 heteroatoms independently selected from nitrogen, oxygen, or sulfur. In some embodiments, -Cy¹- is an optionally substituted 19-20 membered partially unsaturated tetracyclic heteroarylene having 1-4 heteroatoms independently selected from nitrogen, oxygen, or sulfur. In some embodiments, -Cy¹- is an optionally substituted 5-6 membered heteroarylene having 1-4 heteroatoms independently selected from nitrogen, oxygen, or sulfur.

In some embodiments, -Cy¹- is selected from those depicted in Table 1, below.

As defined above and described herein, Scaffold is a trivalent group that connects and orients a cyclic peptide.

In some embodiments, Scaffold is

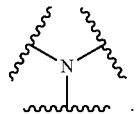 [SMILES: *N(*)*]

In some embodiments, Scaffold is

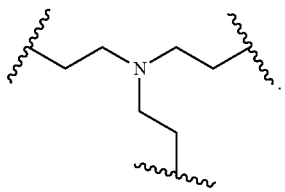 [SMILES: *CCN(CC*)CC*]

In some embodiments, Scaffold is

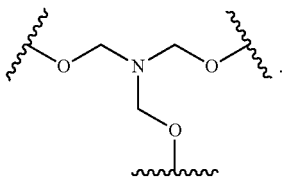 [SMILES: *OCN(CO*)CO*]

In some embodiments, Scaffold is
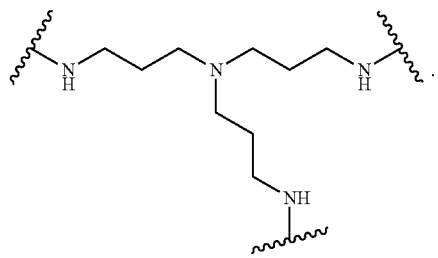 [SMILES: *NCCCN(CCCN*)CCCN*]
In some embodiments, Scaffold is
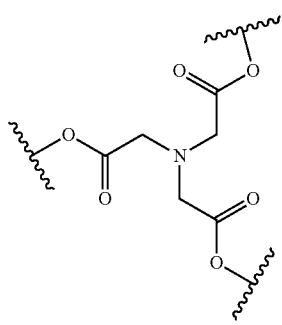
In some embodiments, Scaffold is
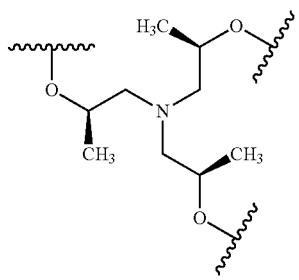
In some embodiments, Scaffold is
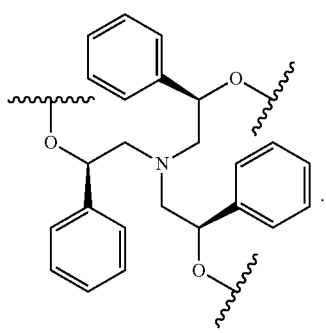 [SMILES: *O[C@@H](CN(C[C@H](O*)c1ccccc1)C[C@H](O*)c1ccccc1)c1ccccc1]
In some embodiments, Scaffold is
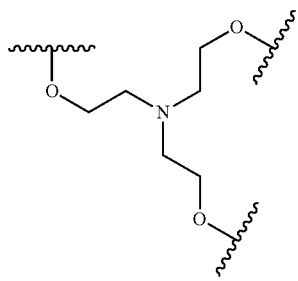
In some embodiments, Scaffold is
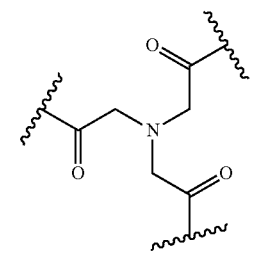
In some embodiments, Scaffold is
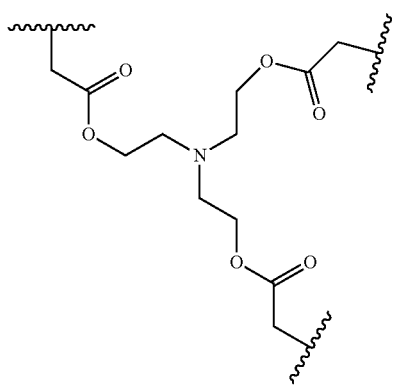
In some embodiments, Scaffold is
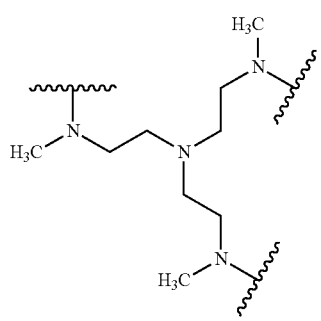

In some embodiments, Scaffold is
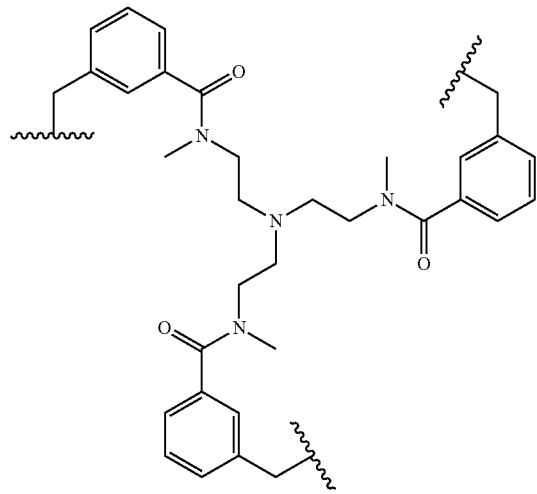
In some embodiments, Scaffold is
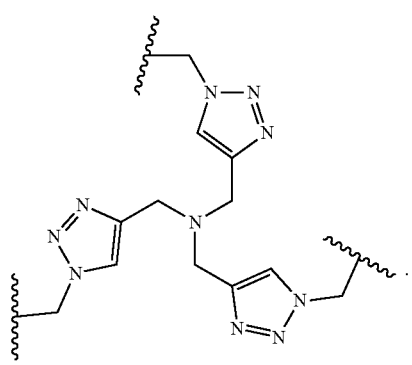 [SMILES: *Cn1cc(CN(Cc2cn(C*)nn2)Cc2cn(C*)nn2)nn1]
In some embodiments, Scaffold is
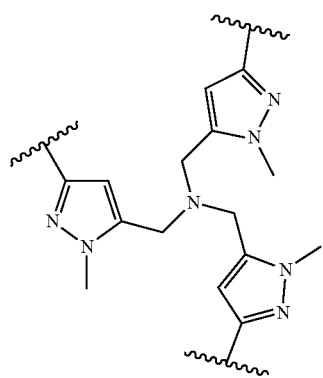
In some embodiments, Scaffold is
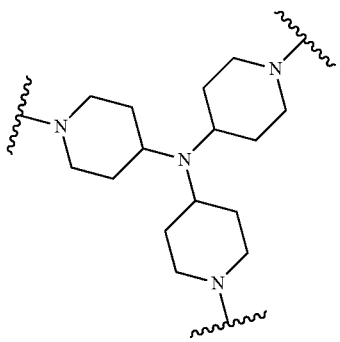
In some embodiments, Scaffold is
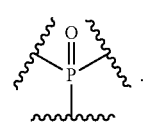
In some embodiments, Scaffold is
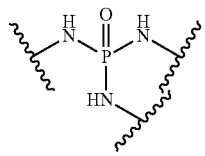
In some embodiments, Scaffold is
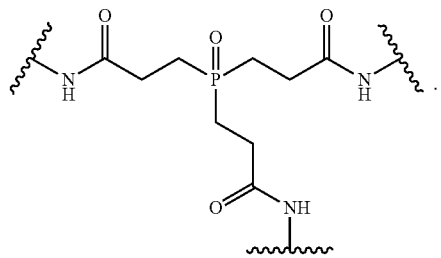 [SMILES: *NC(=O)CCP(=O)(CCC(=O)N*)CCC(=O)N*]
In some embodiments, Scaffold is
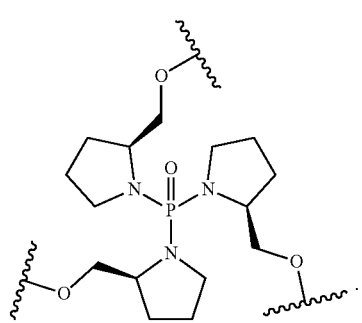 [SMILES: *OC[C@@H]1CCCN1P(=O)(N1CCC[C@H]1CO*)N1CCC[C@H]1CO*]

In some embodiments, Scaffold is

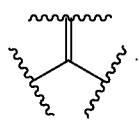 [SMILES: *C(*)=*]

In some embodiments, Scaffold is

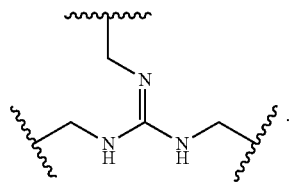 [SMILES: *CN=C(NC*)NC*]

In some embodiments, Scaffold is

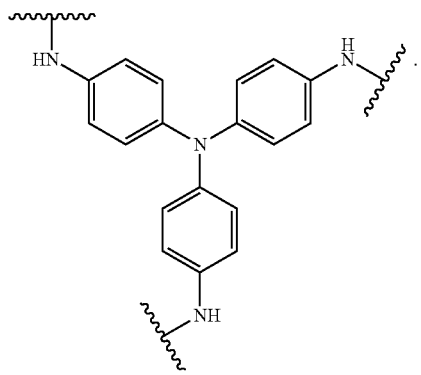 [SMILES: *Nc1ccc(N(c2ccc(N*)cc2)c2ccc(N*)cc2)cc1]

In some embodiments, Scaffold is

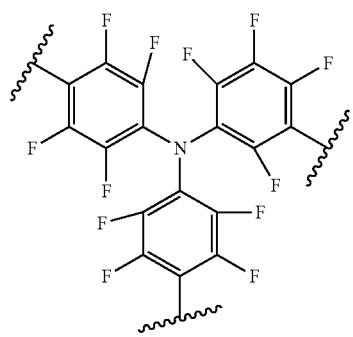

In some embodiments, Scaffold is Ring A, which is selected from the group consisting of 18-crown-6, 1,7,13-triaza-18-crown-6, and a 3-12-membered optionally substituted, saturated, partially unsaturated, bridged bicyclic, bridged tricyclic, propellane, or aromatic ring having 0-6 heteroatoms independently selected from nitrogen, oxygen, or sulfur.

In some embodiments, Scaffold is Ring B, which is an optionally substituted 6-18 membered cyclophane having 0-9 heteroatoms independently selected from nitrogen, oxygen, or sulfur.

In some embodiments, Scaffold is Ring B, which is an optionally substituted cyclophane having 1-5 aromatic or heteroaromatic ring units and aliphatic chains bridging two ring units, wherein one, two or three methylene units of each aliphatic chain are optionally and independently replaced by —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, or —S(O)$_2$—.

In some embodiments, Scaffold is

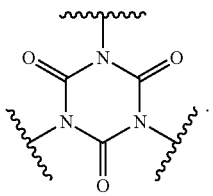 [SMILES: *n1c(=O)n(*)c(=O)n(*)c1=O]

In some embodiments, Scaffold is

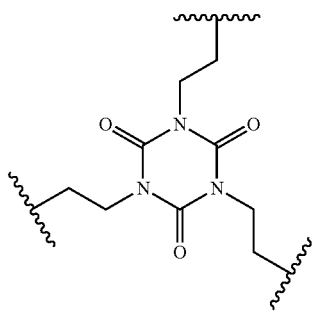

In some embodiments, Scaffold is

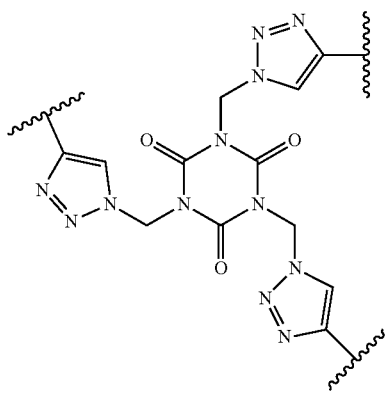

In some embodiments, Scaffold is
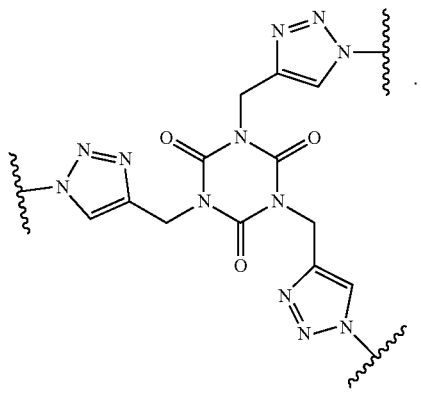 [SMILES: *n1cc(Cn2c(=O)n(Cc3cn(*)nn3)c(=O)n(Cc3cn(*)nn3)c2=O)nn1]
In some embodiments, Scaffold is
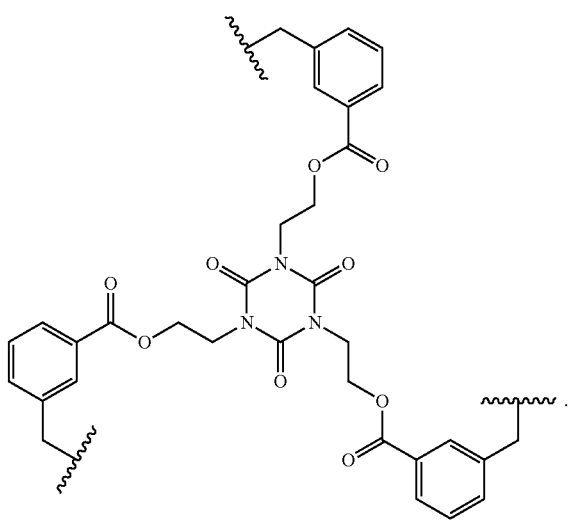 [SMILES: *Cc1cccc(C(=O)OCCn2c(=O)n(CCOC(=O)c3cccc(C*)c3)c(=O)n(CCOC(=O)c3cccc(C*)c3)c2=O)c1]
In some embodiments, Scaffold is
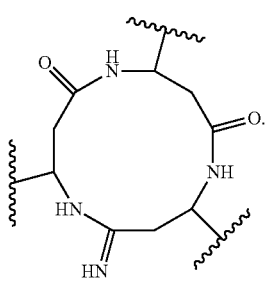 [SMILES: *C1CC(=O)NC(*)CC(=O)NC(*)CC(=N)N1]
In some embodiments, Scaffold is
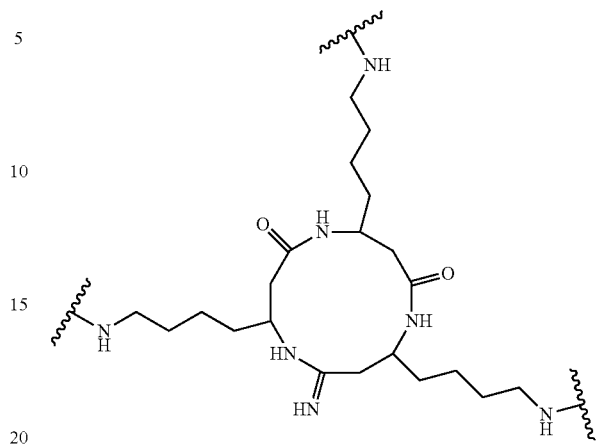
In some embodiments, Scaffold is
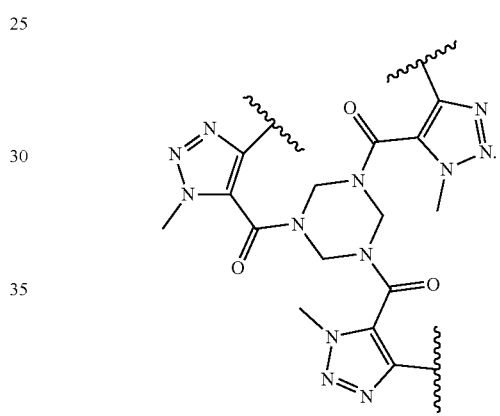
In some embodiments, Scaffold is
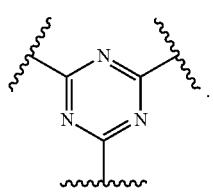 [SMILES: *c1nc(*)nc(*)n1]
In some embodiments, Scaffold is
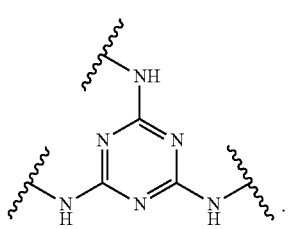 [SMILES: *Nc1nc(N*)nc(N*)n1]

In some embodiments, Scaffold is
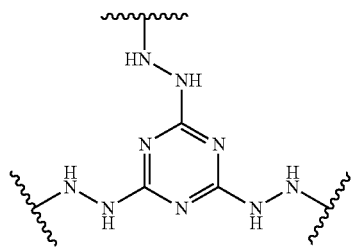
In some embodiments, Scaffold is
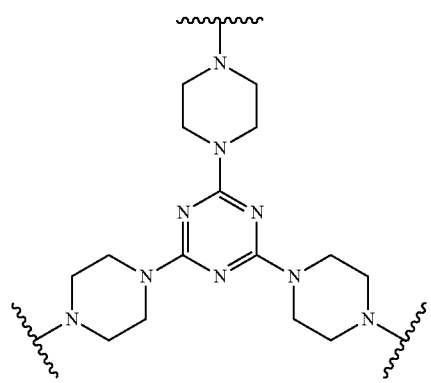
In some embodiments, Scaffold is
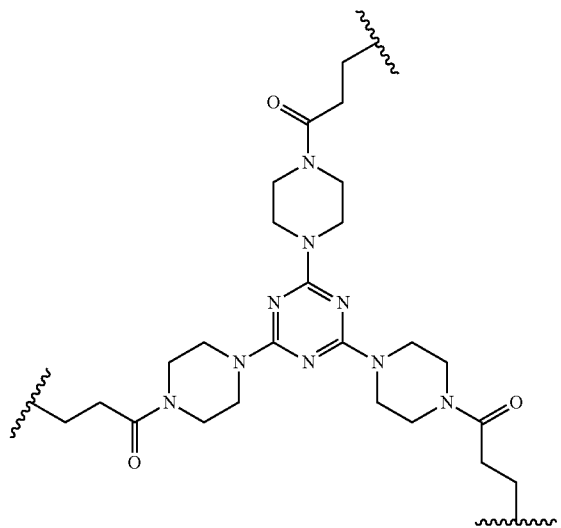
In some embodiments, Scaffold is
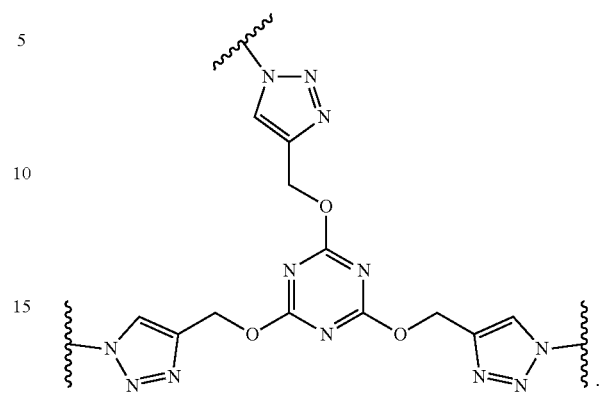
In some embodiments, Scaffold is
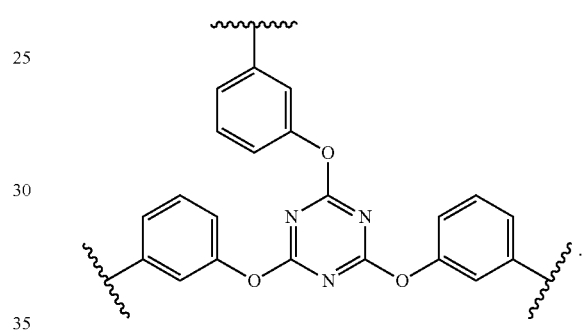
In some embodiments, Scaffold is
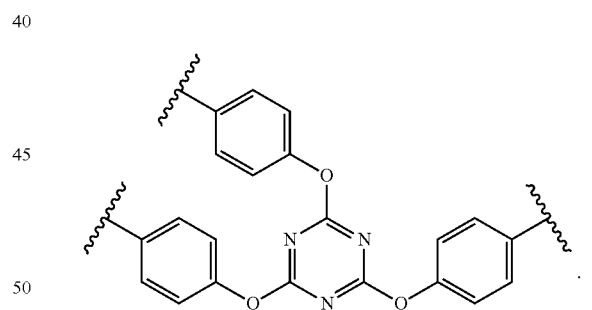
In some embodiments, Scaffold is
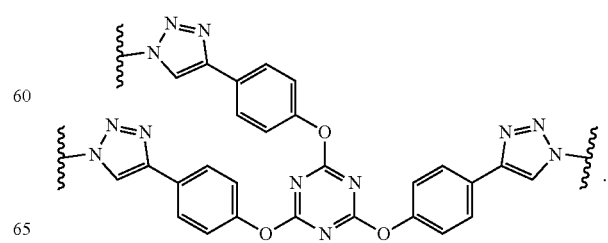

| 37 | 38 |
In some embodiments, Scaffold is
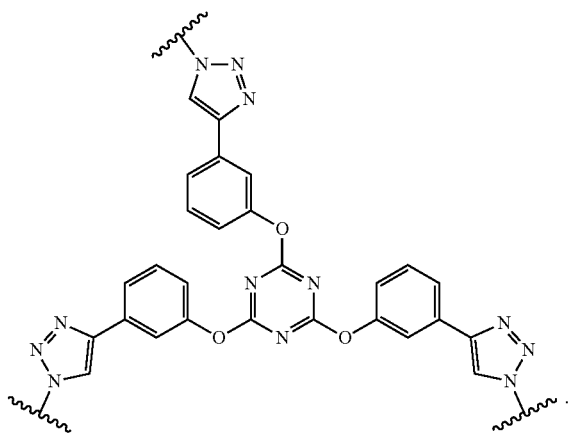 [SMILES: *n1cc(-c2cccc(Oc3nc(Oc4cccc(-c5cn(*)nn5)c4)nc(Oc4cccc(-c5cn(*)nn5)c4)n3)c2)nn1]
In some embodiments, Scaffold is
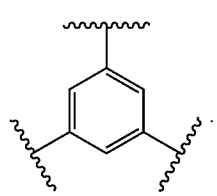 [SMILES: *c1cc(*)cc(*)c1]
In some embodiments, Scaffold is
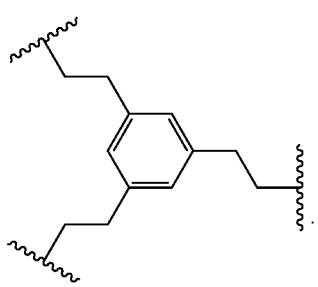 [SMILES: *CCc1cc(CC*)cc(CC*)c1]
In some embodiments, Scaffold is
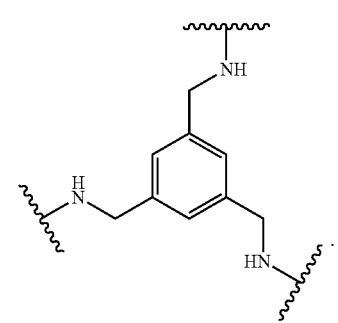 [SMILES: *NCc1cc(CN*)cc(CN*)c1]
In some embodiments, Scaffold is
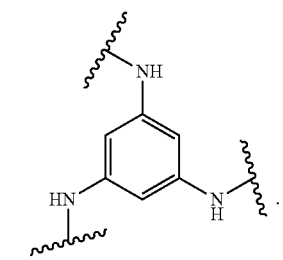 [SMILES: *Nc1cc(N*)cc(N*)c1]
In some embodiments, Scaffold is
In some embodiments, Scaffold is
In some embodiments, Scaffold is
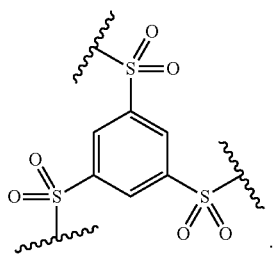 [SMILES: *S(=O)(=O)c1cc(S(*)(=O)=O)cc(S(*)(=O)=O)c1]

39
In some embodiments, Scaffold is
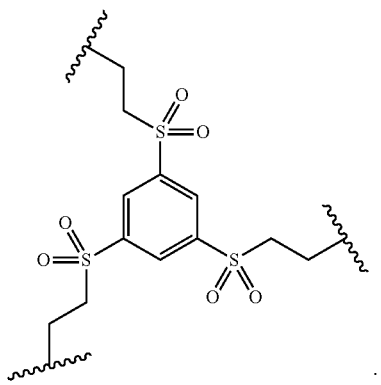 [SMILES: *CCS(=O)(=O)c1cc(S(=O)(=O)CC*)cc(S(=O)(=O)CC*)c1]
In some embodiments, Scaffold is
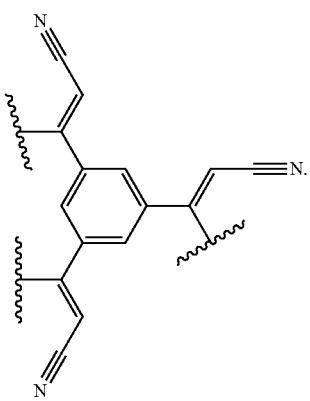 [SMILES: */C(=C\C#N)c1cc(/C(*)=C/C#N)cc(/C(*)=C/C#N)c1]
In some embodiments, Scaffold is
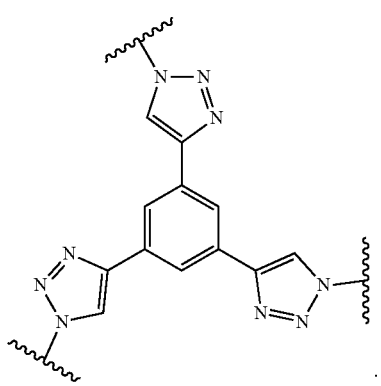 [SMILES: *n1cc(-c2cc(-c3cn(*)nn3)cc(-c3cn(*)nn3)c2)nn1]
40
In some embodiments, Scaffold is
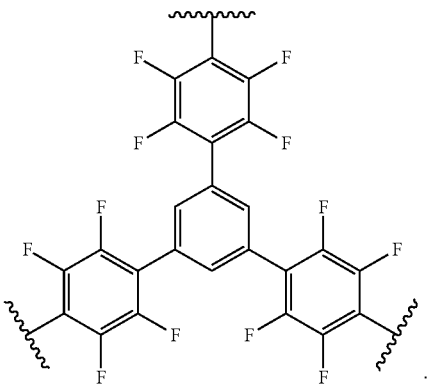 [SMILES: *c1c(F)c(F)c(-c2cc(-c3c(F)c(F)c(*)c(F)c3F)cc(-c3c(F)c(F)c(*)c(F)c3F)c2)c(F)c1F]
In some embodiments, Scaffold is
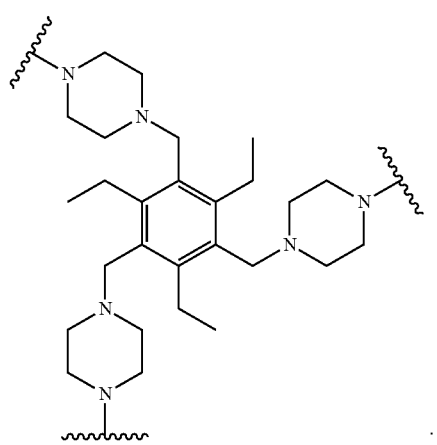 [SMILES: *N1CCN(Cc2c(CC)c(CN3CCN(*)CC3)c(CC)c(CN3CCN(*)CC3)c2CC)CC1]
In some embodiments, Scaffold is
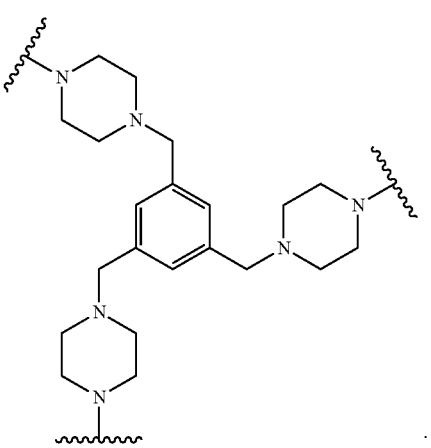 [SMILES: *N1CCN(Cc2cc(CN3CCN(*)CC3)cc(CN3CCN(*)CC3)c2)CC1]

In some embodiments, Scaffold is
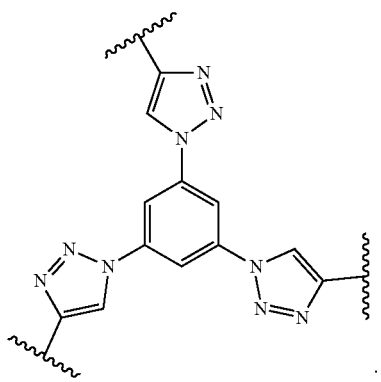 [SMILES: *c1cn(-c2cc(-n3cc(*)nn3)cc(-n3cc(*)nn3)c2)nn1]
In some embodiments, Scaffold is
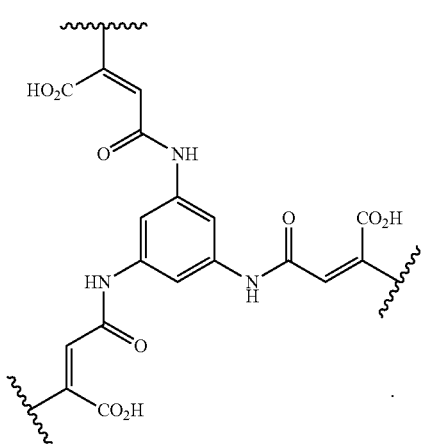 [SMILES: */C(=C/C(=O)Nc1cc(NC(=O)/C=C(/*)C(=O)O)cc(NC(=O)/C=C(/*)C(=O)O)c1)C(=O)O]
In some embodiments, Scaffold is
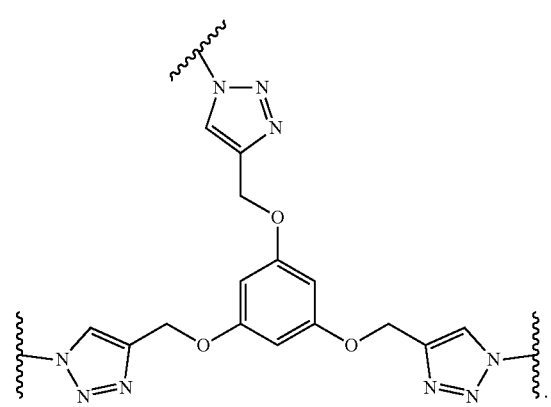 [SMILES: *n1cc(COc2cc(OCc3cn(*)nn3)cc(OCc3cn(*)nn3)c2)nn1]
In some embodiments, Scaffold is
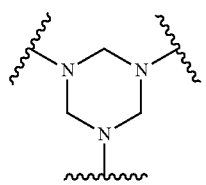
In some embodiments, Scaffold is
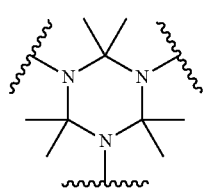
In some embodiments, Scaffold is
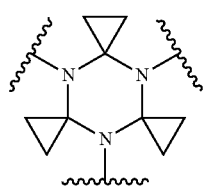
In some embodiments, Scaffold is
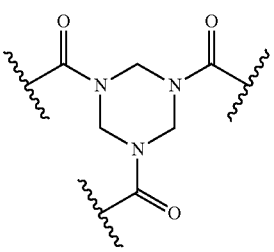
In some embodiments, Scaffold is
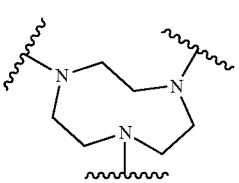

In some embodiments, Scaffold is
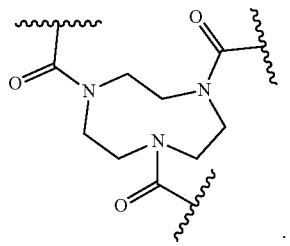 [SMILES: *C(=O)N1CCN(C(*)=O)CCN(C(*)=O)CC1]
In some embodiments, Scaffold is
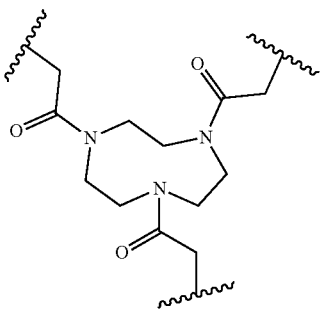
In some embodiments, Scaffold is
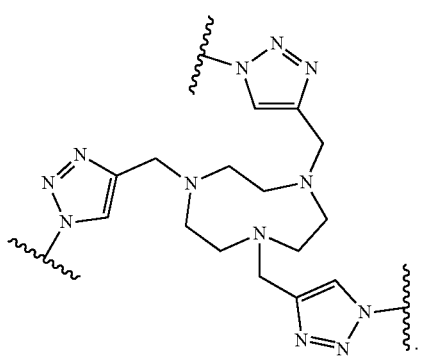 [SMILES: *n1cc(CN2CCN(Cc3cn(*)nn3)CCN(Cc3cn(*)nn3)CC2)nn1]
In some embodiments, Scaffold is
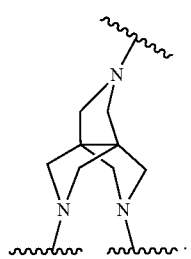 [SMILES: *N1CC23CN(*)CC2(C1)CN(*)C3]
In some embodiments, Scaffold is
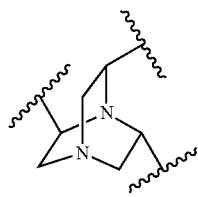
In some embodiments, Scaffold is
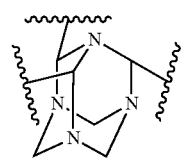
In some embodiments, Scaffold is
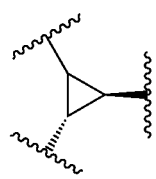
In some embodiments, Scaffold is
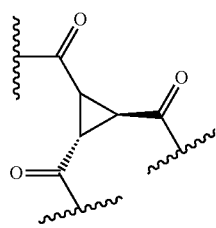
In some embodiments, Scaffold is
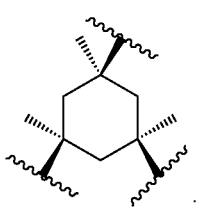

In some embodiments, Scaffold is
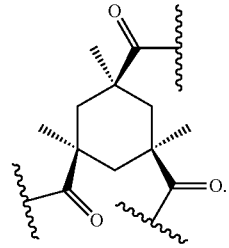 [SMILES: *C(=O)[C@]1(C)C[C@](C)(C(*)=O)C[C@](C)(C(*)=O)C1]
In some embodiments, Scaffold is
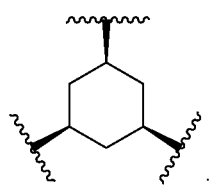 [SMILES: *[C@H]1C[C@@H](*)C[C@@H](*)C1]
In some embodiments, Scaffold is
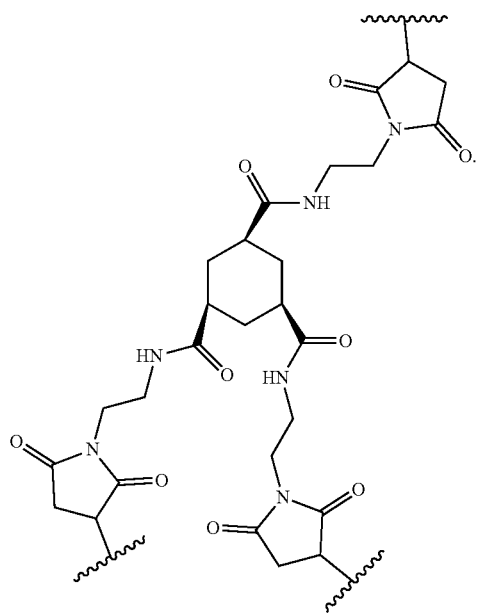 [SMILES: *C1CC(=O)N(CCNC(=O)[C@H]2C[C@@H](C(=O)NCCN3C(=O)CC(*)C3=O)C[C@@H](C(=O)NCCN3C(=O)CC(*)C3=O)C2)C1=O]
In some embodiments, Scaffold is
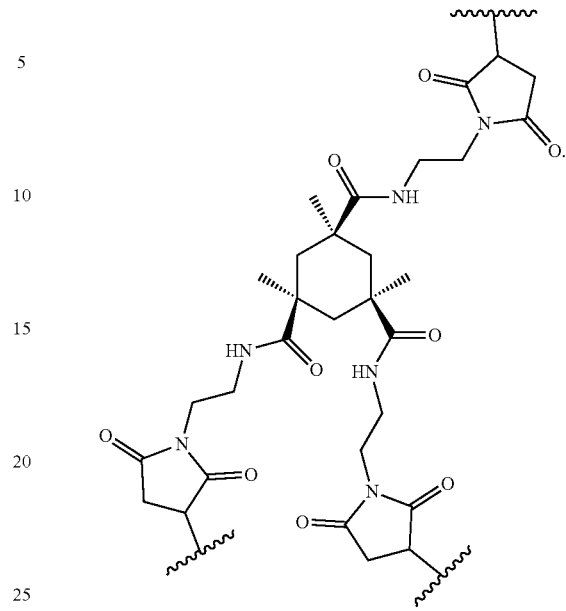
In some embodiments, Scaffold is
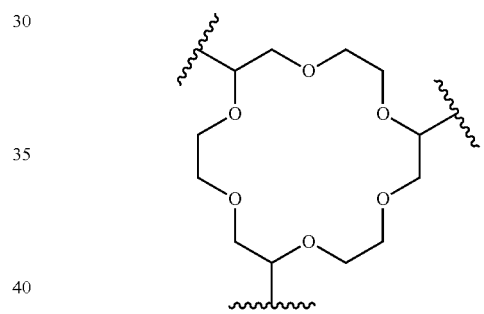
In some embodiments, Scaffold is
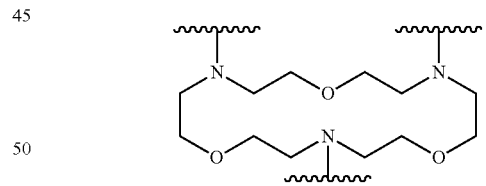
In some embodiments, Scaffold is
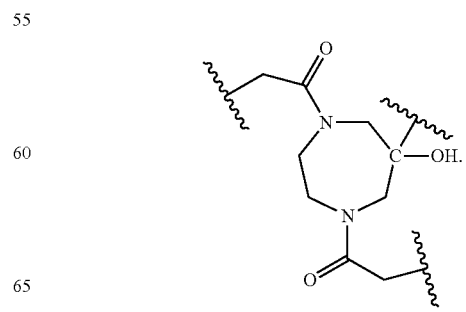

In some embodiments, Scaffold is
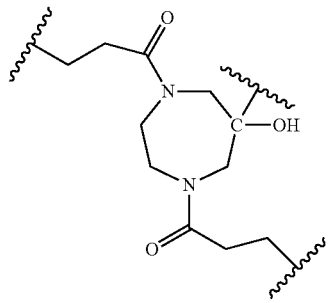
In some embodiments, Scaffold is
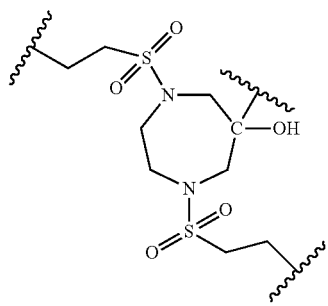
In some embodiments, Scaffold is
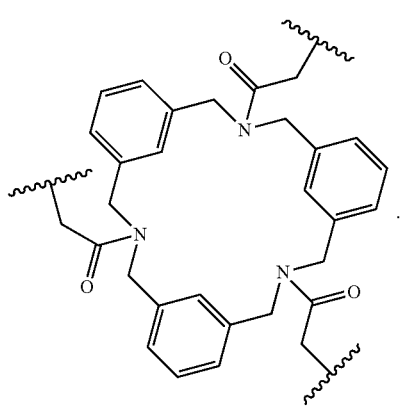 [SMILES: *CC(=O)N1Cc2cccc(c2)CN(C(=O)C*)Cc2cccc(c2)CN(C(=O)C*)Cc2cccc(c2)C1]
In some embodiments, Scaffold is
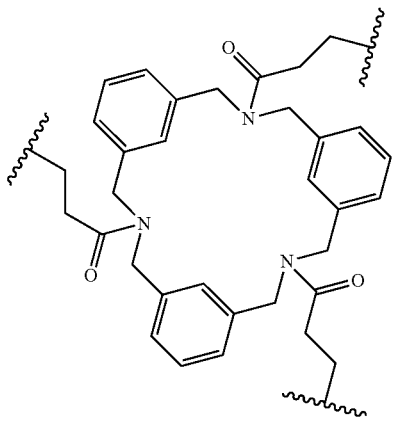
In some embodiments, Scaffold is
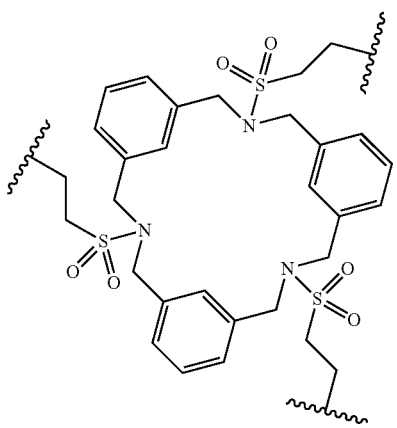
In some embodiments, Scaffold is
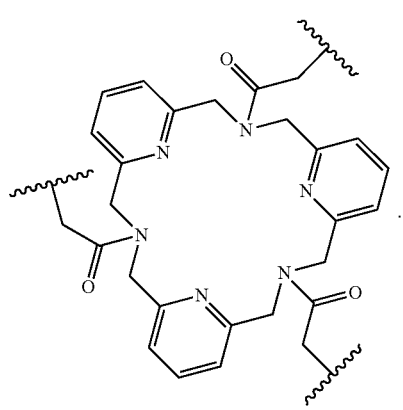 [SMILES: *CC(=O)N1Cc2cccc(n2)CN(C(=O)C*)Cc2cccc(n2)CN(C(=O)C*)Cc2cccc(n2)C1]

In some embodiments, Scaffold is
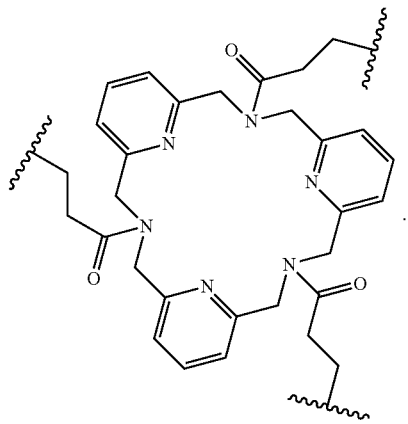 [SMILES: *CCC(=O)N1Cc2cccc(n2)CN(C(=O)CC*)Cc2cccc(n2)CN(C(=O)CC*)Cc2cccc(n2)C1]
In some embodiments, Scaffold is
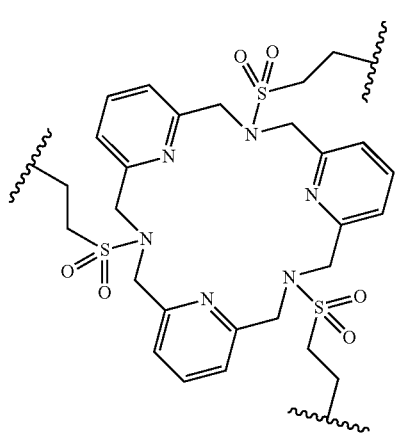
In some embodiments, Scaffold is
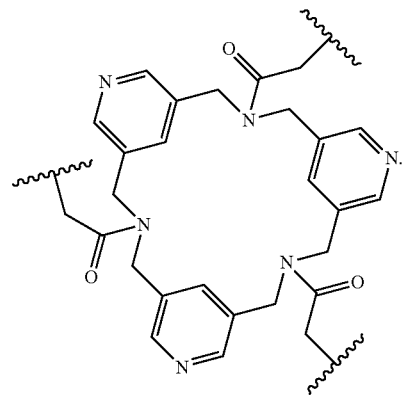 [SMILES: *CC(=O)N1Cc2cncc(c2)CN(C(=O)C*)Cc2cncc(c2)CN(C(=O)C*)Cc2cncc(c2)C1]
In some embodiments, Scaffold is
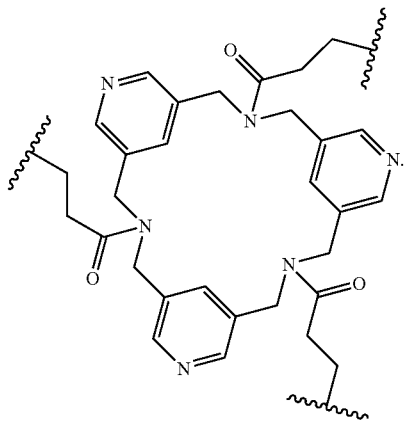 [SMILES: *CCC(=O)N1Cc2cncc(c2)CN(C(=O)CC*)Cc2cncc(c2)CN(C(=O)CC*)Cc2cncc(c2)C1]
In some embodiments, Scaffold is
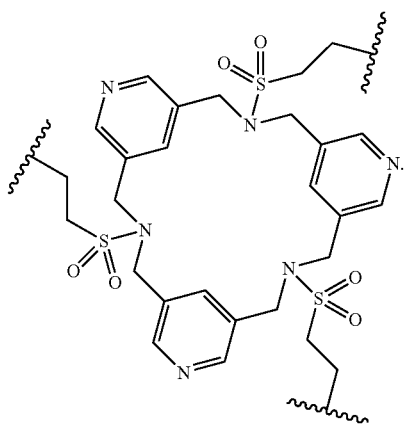 [SMILES: *CCS(=O)(=O)N1Cc2cncc(c2)CN(S(=O)(=O)CC*)Cc2cncc(c2)CN(S(=O)(=O)CC*)Cc2cncc(c2)C1]
In some embodiments, Scaffold is
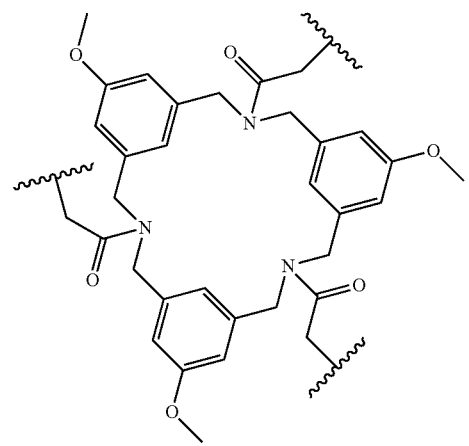

51
In some embodiments, Scaffold is
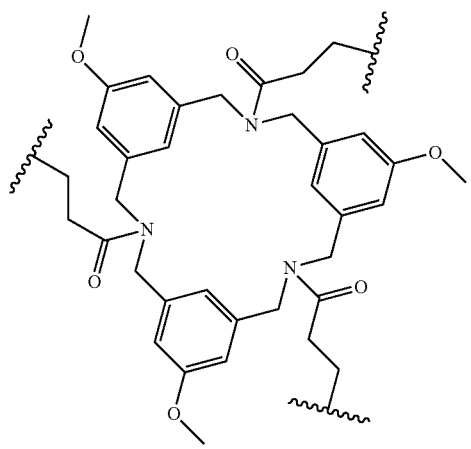
In some embodiments, Scaffold is
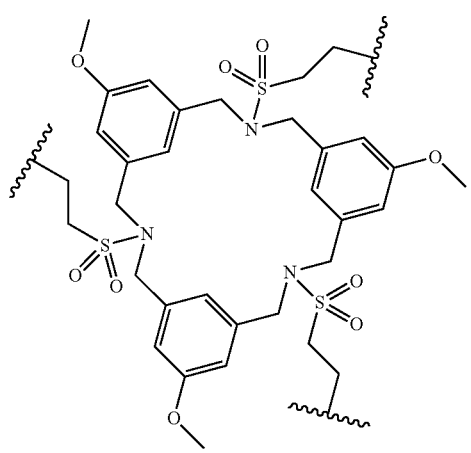
In some embodiments, Scaffold is
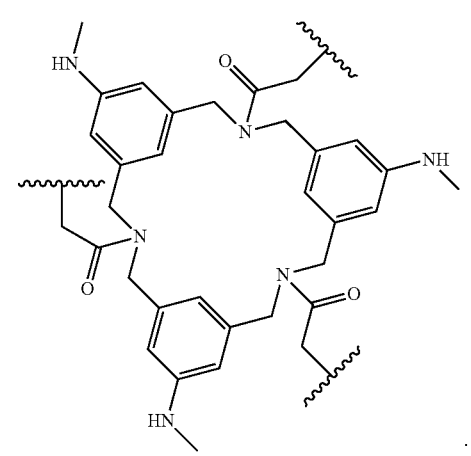 [SMILES: *CC(=O)N1Cc2cc(cc(NC)c2)CN(C(=O)C*)Cc2cc(cc(NC)c2)CN(C(=O)C*)Cc2cc(cc(NC)c2)C1]
52
In some embodiments, Scaffold is
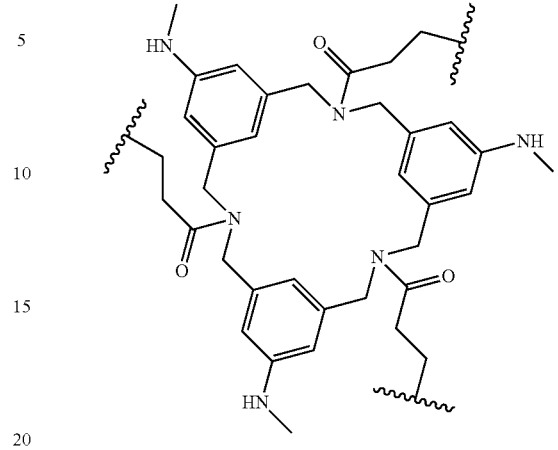
In some embodiments, Scaffold is
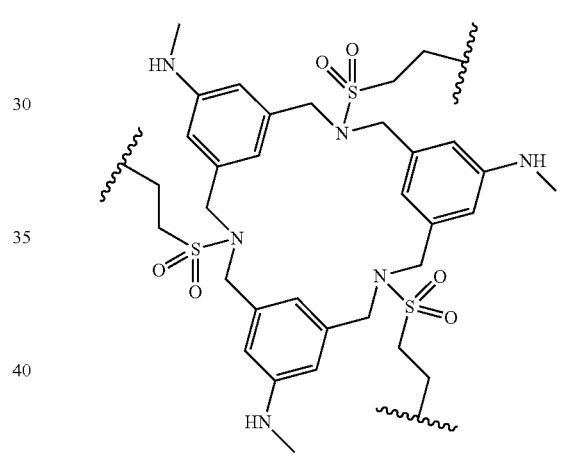
In some embodiments, Scaffold is
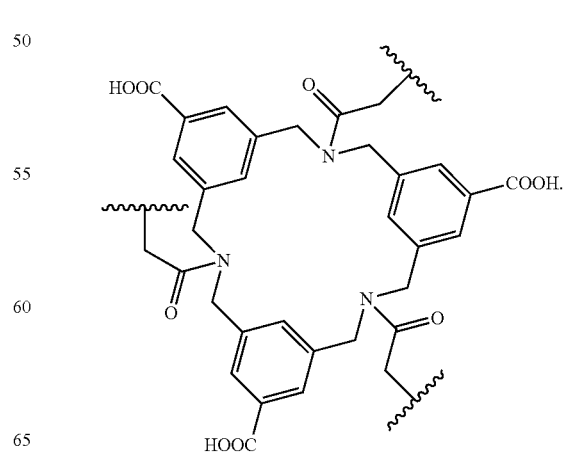

53
In some embodiments, Scaffold is
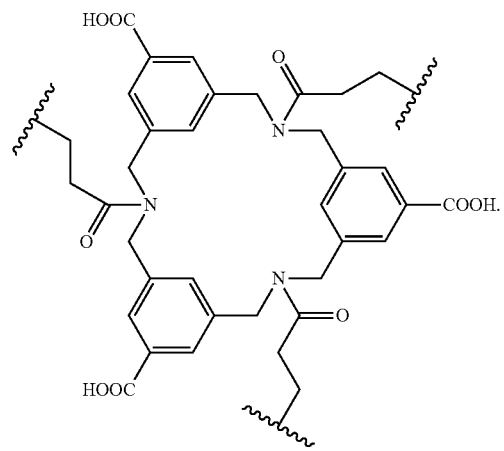 [SMILES: *CCC(=O)N1Cc2cc(cc(C(=O)O)c2)CN(C(=O)CC*)Cc2cc(cc(C(=O)O)c2)CN(C(=O)CC*)Cc2cc(cc(C(=O)O)c2)C1]
In some embodiments, Scaffold is
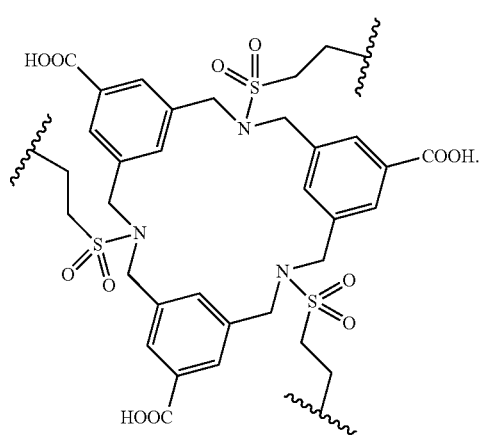 [SMILES: *CCS(=O)(=O)N1Cc2cc(cc(C(=O)O)c2)CN(S(=O)(=O)CC*)Cc2cc(cc(C(=O)O)c2)CN(S(=O)(=O)CC*)Cc2cc(cc(C(=O)O)c2)C1]
In some embodiments, Scaffold is
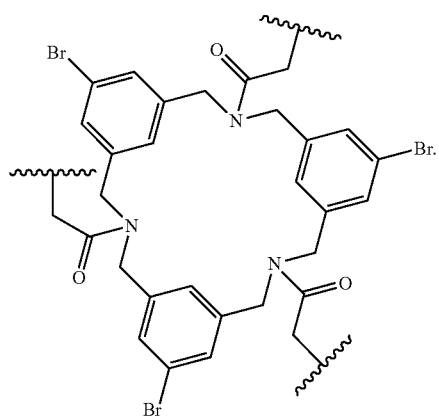 [SMILES: *CC(=O)N1Cc2cc(Br)cc(c2)CN(C(=O)C*)Cc2cc(Br)cc(c2)CN(C(=O)C*)Cc2cc(Br)cc(c2)C1]
54
In some embodiments, Scaffold is
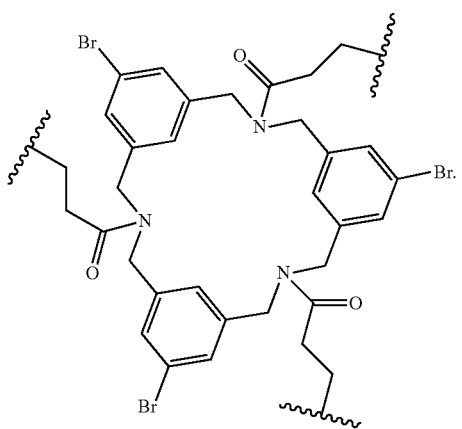 [SMILES: *CCC(=O)N1Cc2cc(Br)cc(c2)CN(C(=O)CC*)Cc2cc(Br)cc(c2)CN(C(=O)CC*)Cc2cc(Br)cc(c2)C1]
In some embodiments, Scaffold is
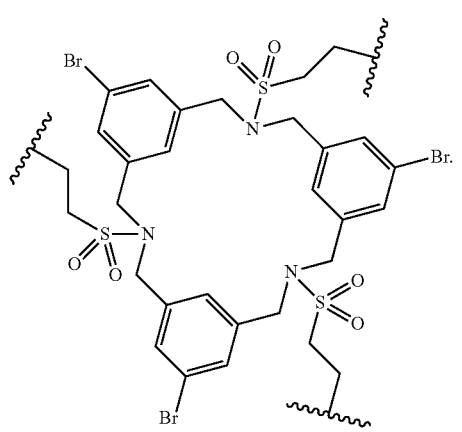 [SMILES: *CCS(=O)(=O)N1Cc2cc(Br)cc(c2)CN(S(=O)(=O)CC*)Cc2cc(Br)cc(c2)CN(S(=O)(=O)CC*)Cc2cc(Br)cc(c2)C1]
In some embodiments, Scaffold is
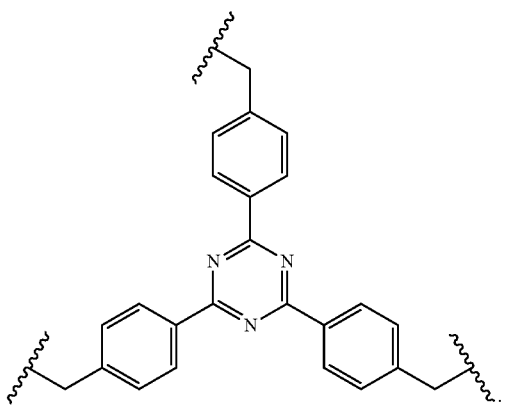 [SMILES: *Cc1ccc(-c2nc(-c3ccc(C*)cc3)nc(-c3ccc(C*)cc3)n2)cc1]

In some embodiments, Scaffold is

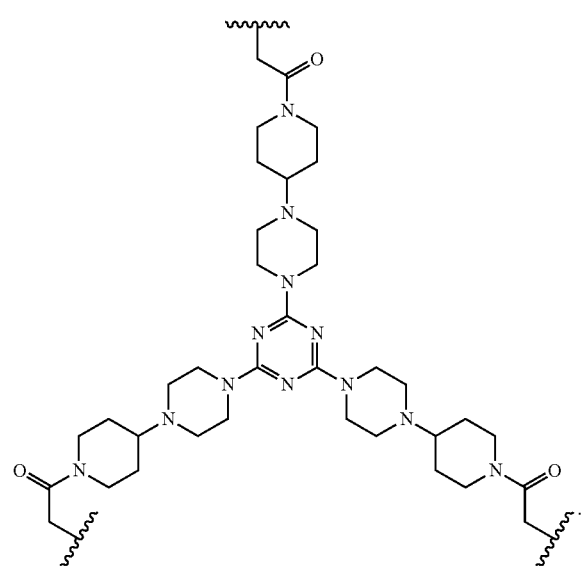 [SMILES: *CC(=O)N1CCC(N2CCN(c3nc(N4CCN(C5CCN(C(=O)C*)CC5)CC4)nc(N4CCN(C5CCN(C(=O)C*)CC5)CC4)n3)CC2)CC1]

In some embodiments, Scaffold is

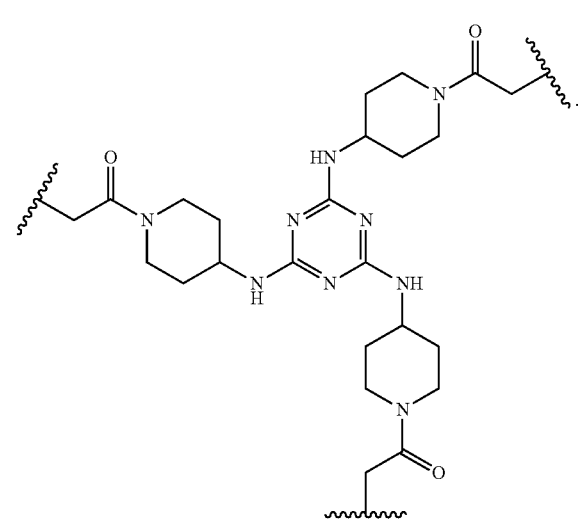 [SMILES: *CC(=O)N1CCC(Nc2nc(NC3CCN(C(=O)C*)CC3)nc(NC3CCN(C(=O)C*)CC3)n2)CC1]

In some embodiments, Scaffold is

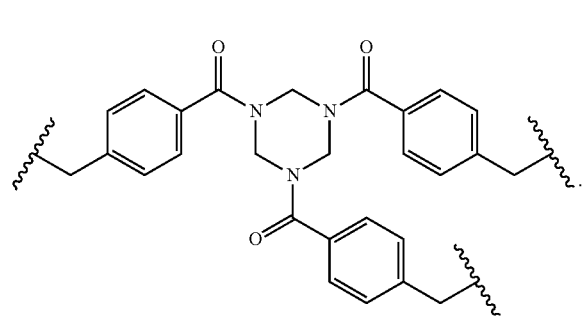 [SMILES: *Cc1ccc(C(=O)N2CN(C(=O)c3ccc(C*)cc3)CN(C(=O)c3ccc(C*)cc3)C2)cc1]

In some embodiments, Scaffold is

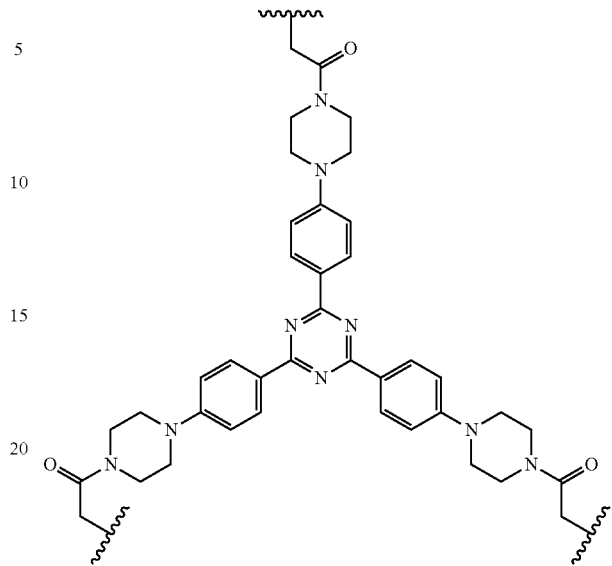

In some embodiments, Scaffold is

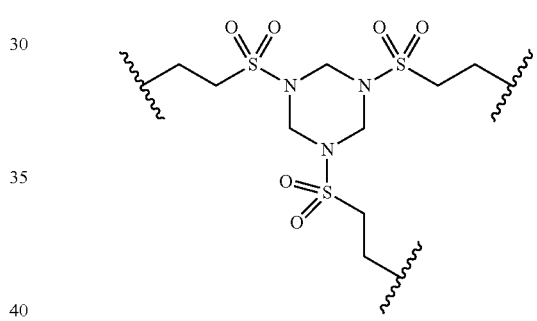

In some embodiments, Scaffold is

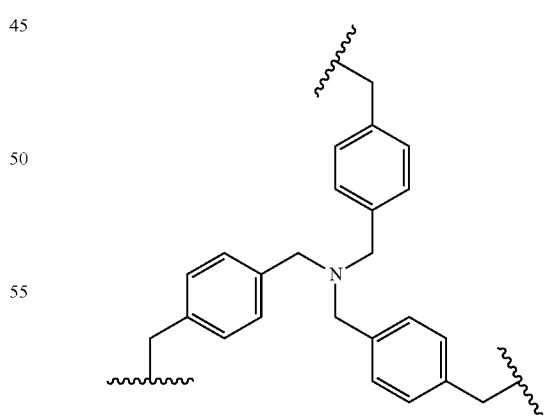

In some embodiments, Scaffold is selected from those depicted in Table 1, below.

As defined above and described herein, Loop A is a bivalent natural or unnatural amino acid residue or peptide attached to the amino acid residue linked to $L^1$ and the amino acid residue linked to $L^2$. In some embodiments, Loop A is a bivalent natural amino acid residue attached to the amino acid residue linked to $L^1$ and the amino acid residue linked to $L^2$. In some embodiments, Loop A is a bivalent unnatural amino acid residue attached to the amino acid residue linked to $L^1$ and the amino acid residue linked to $L^2$. In some embodiments, Loop A is a bivalent peptide attached to the amino acid residue linked to $L^1$ and the amino acid residue linked to $L^2$.

In some embodiments, Loop A is

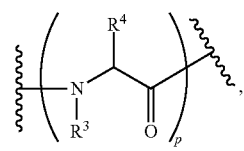

wherein:
- each of $R^3$ is independently hydrogen or $C_{1-4}$ aliphatic, as described herein;
- each of $R^4$ is independently hydrogen, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or
- an $R^4$ group and its adjacent $R^3$ group are optionally taken together with their intervening atoms to form a 4-8 membered saturated or partially unsaturated monocyclic heterocyclic ring having 1-2 heteroatoms independently selected from nitrogen, oxygen, or sulfur; and
- p is 1-15.

In some embodiments, Loop A is

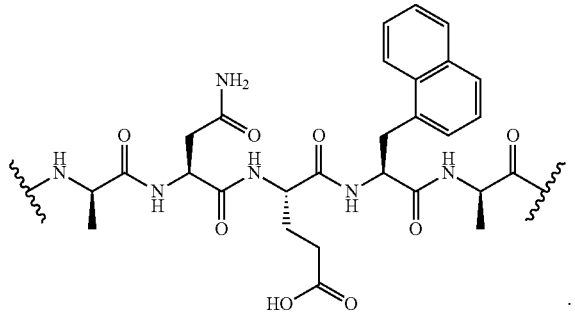 [SMILES: *N[C@H](C)C(=O)N[C@@H](CC(N)=O)C(=O)N[C@@H](CCC(=O)O)C(=O)N[C@@H](Cc1cccc2ccccc12)C(=O)N[C@H](C)C(*)=O]

In some embodiments, Loop A is

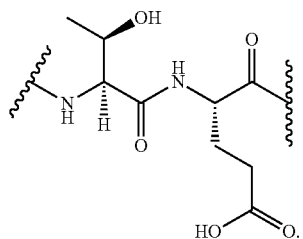 [SMILES: *N[C@H](C(=O)N[C@@H](CCC(=O)O)C(*)=O)[C@@H](C)O]

In some embodiments, Loop A is

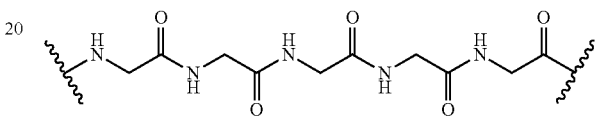

In some embodiments, Loop A is

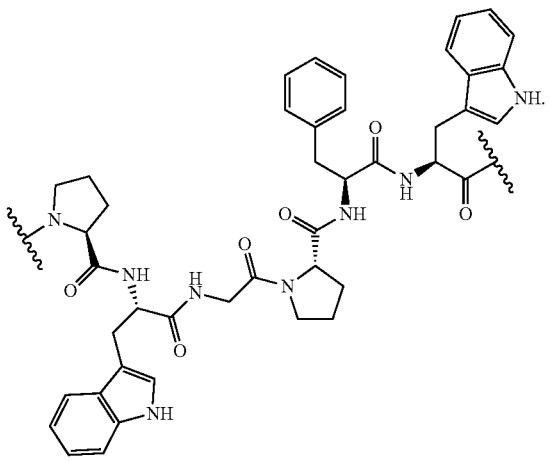 [SMILES: *C(=O)[C@H](Cc1c[nH]c2ccccc12)NC(=O)[C@H](Cc1ccccc1)NC(=O)[C@@H]1CCCN1C(=O)CNC(=O)[C@H](Cc1c[nH]c2ccccc12)NC(=O)[C@@H]1CCCN1*]

In some embodiments, Loop A is

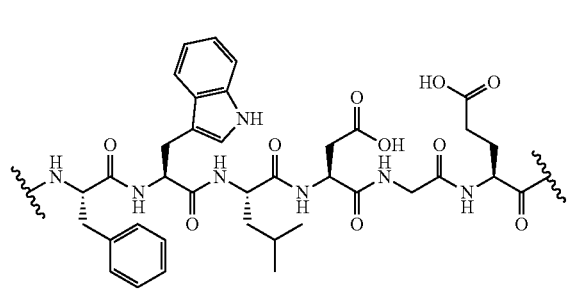

In some embodiments, Loop A is

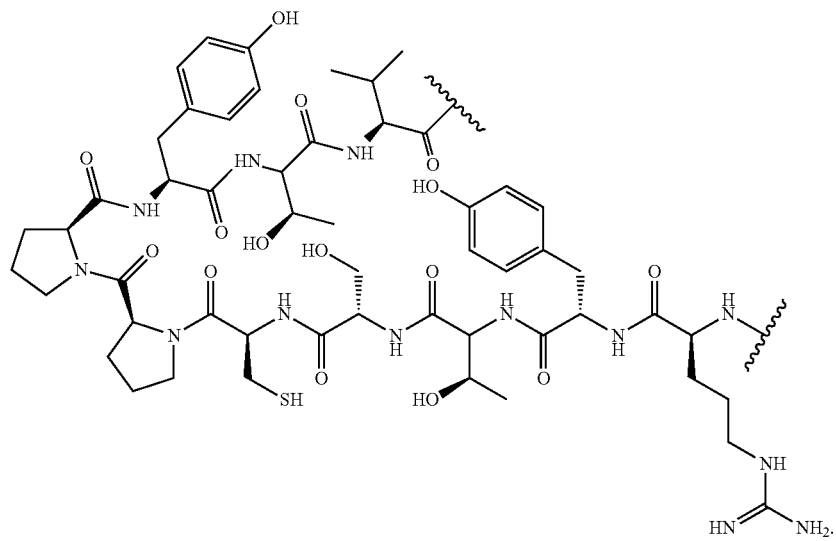 [SMILES: *N[C@@H](CCCNC(=N)N)C(=O)N[C@@H](Cc1ccc(O)cc1)C(=O)NC(C(=O)N[C@@H](CO)C(=O)N[C@@H](CS)C(=O)N1CCC[C@H]1C(=O)N1CCC[C@H]1C(=O)N[C@@H](Cc1ccc(O)cc1)C(=O)NC(C(=O)N[C@H](C(*)=O)C(C)C)[C@@H](C)O)[C@@H](C)O]

As defined above and described herein, Loop B is a bivalent natural or unnatural amino acid residue or peptide attached to the amino acid residue linked to $L^1$ and the amino acid residue linked to $L^3$. In some embodiments, Loop B is a bivalent natural amino acid residue attached to the amino acid residue linked to $L^1$ and the amino acid residue linked to $L^3$. In some embodiments, Loop B is a bivalent unnatural amino acid residue attached to the amino acid residue linked to $L^1$ and the amino acid residue linked to $L^3$. In some embodiments, Loop B is a bivalent peptide attached to the amino acid residue linked to $L^1$ and the amino acid residue linked to $L^3$.

In some embodiments, Loop B is

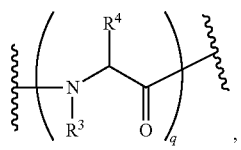

wherein:
each of $R^3$ is independently hydrogen or $C_{1-4}$ aliphatic, as described herein;
each of $R^4$ is independently hydrogen, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or
an $R^4$ group and its adjacent $R^3$ group are optionally taken together with their intervening atoms to form a 4-8 membered saturated or partially unsaturated monocyclic heterocyclic ring having 1-2 heteroatoms independently selected from nitrogen, oxygen, or sulfur; and
q is 1-15.

In some embodiments, Loop B is

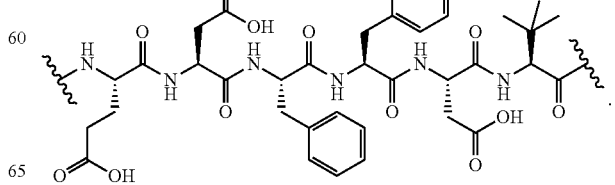

In some embodiments, Loop B is
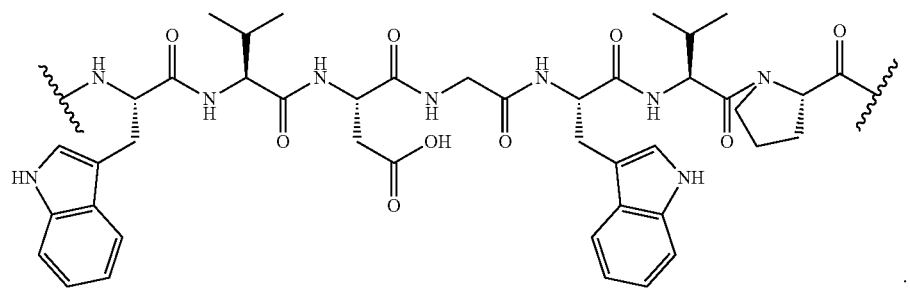 [SMILES: *N[C@@H](Cc1c[nH]c2ccccc12)C(=O)N[C@H](C(=O)N[C@@H](CC(=O)O)C(=O)NCC(=O)N[C@@H](Cc1c[nH]c2ccccc12)C(=O)N[C@H](C(=O)N1CCC[C@H]1C(*)=O)C(C)C)C(C)C]
In some embodiments, Loop B is
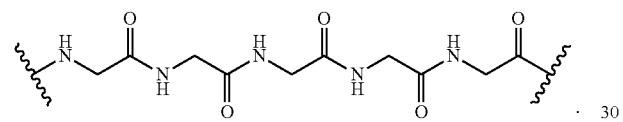
In some embodiments, Loop B is
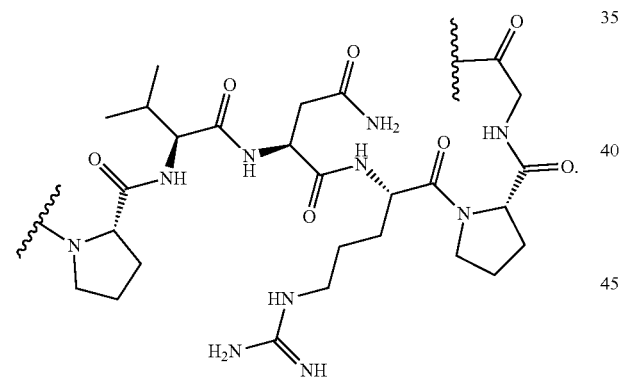
In some embodiments, Loop B is
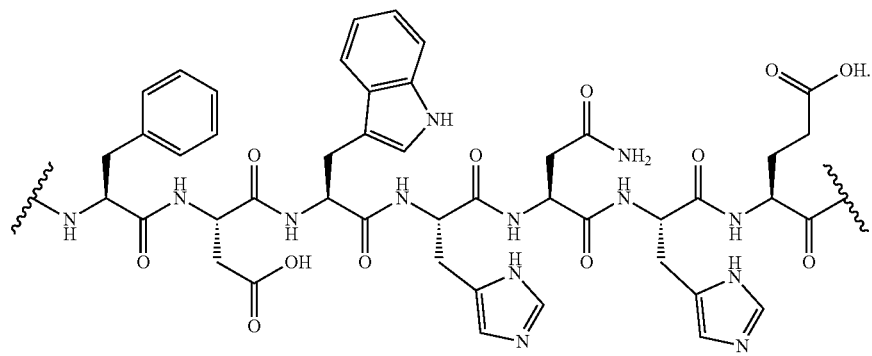 [SMILES: *N[C@@H](Cc1ccccc1)C(=O)N[C@@H](CC(=O)O)C(=O)N[C@@H](Cc1c[nH]c2ccccc12)C(=O)N[C@@H](Cc1cnc[nH]1)C(=O)N[C@@H](CC(N)=O)C(=O)N[C@@H](Cc1cnc[nH]1)C(=O)N[C@@H](CCC(=O)O)C(*)=O]

In some embodiments, Loop B is

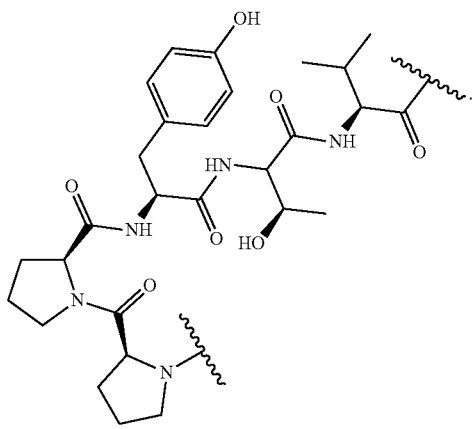 [SMILES: *C(=O)[C@@H](NC(=O)C(NC(=O)[C@H](Cc1ccc(O)cc1)NC(=O)[C@@H]1CCCN1C(=O)[C@@H]1CCCN1*)[C@@H](C)O)C(C)C]

In some embodiments, Loop A comprises 1-15 amino acid residues and Loop B comprises 1-15 amino acid residues.

In some embodiments, Loop A comprises 5 amino acid residues and Loop B comprises 5 amino acid residues. In some embodiments, Loop A comprises 6 amino acid residues and Loop B comprises 5 amino acid residues. In some embodiments, Loop A comprises 2 amino acid residues and Loop B comprises 7 amino acid residues. In some embodiments, Loop A comprises 3 amino acid residues and Loop B comprises 7 amino acid residues. In some embodiments, Loop A comprises 3 amino acid residues and Loop B comprises 9 amino acid residues. In some embodiments, Loop A comprises 3 amino acid residues and Loop B comprises 6 amino acid residues. In some embodiments, Loop A comprises 2 amino acid residues and Loop B comprises 6 amino acid residues. In some embodiments, Loop A comprises 6 amino acid residues and Loop B comprises 5 amino acid residues.

In some embodiments, Loop A is

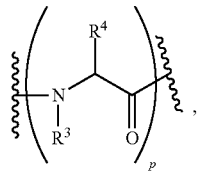

and Loop B is

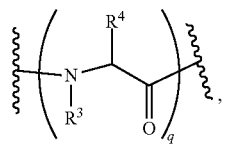

wherein each of $R^3$, $R^4$, p, and q is independently as described herein. In some embodiments, p is 5, and q is 5. In some embodiments, p is 6, and q is 5. In some embodiments, p is 2, and q is 7. In some embodiments, p is 3, and q is 7. In some embodiments, p is 3, and q is 9. In some embodiments, p is 3, and q is 6. In some embodiments, p is 2, and q is 6. In some embodiments, p is 6, and q is 5.

In some embodiments, Loop A is selected from those depicted in Table 1, below. In some embodiments, Loop B is selected from those depicted in Table 1, below.

As defined above and described herein, Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond.

In some embodiments, Spacer$^1$ is a covalent bond. In some embodiments, Spacer$^1$ is a natural amino acid wherein the amino group is connected to the C-terminus of the Bicycle via an amide bond. In some embodiments, Spacer$^1$ is a unnatural amino acid wherein the amino group is connected to the C-terminus of the Bicycle via an amide bond. In some embodiments, Spacer$^1$ is a peptide wherein the N-terminal amino group of the peptide is connected to the C-terminus of the Bicycle via an amide bond.

In some embodiments, Spacer$^1$ is L-Alanine. In some embodiments, Spacer$^1$ is D-Alanine.

In some embodiments, Spacer$^1$ is

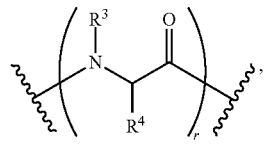

wherein:
each of $R^3$ is independently hydrogen or $C_{1-4}$ aliphatic, as described herein;
each of $R^4$ is independently hydrogen, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or
an $R^4$ group and its adjacent $R^3$ group are optionally taken together with their intervening atoms to form a 4-8 membered saturated or partially unsaturated monocyclic heterocyclic ring having 1-2 heteroatoms independently selected from nitrogen, oxygen, or sulfur; and
r is 0-4.

In some embodiments, Spacer$^1$ is selected from those depicted in Table 1, below.

As defined above and described herein, Spacer$^2$ is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond.

In some embodiments, Spacer$^2$ is a covalent bond. In some embodiments, Spacer$^2$ is a natural amino acid wherein the acid is connected to the N-terminus of the Bicycle via an amide bond. In some embodiments, Spacer$^2$ is a unnatural amino acid wherein the acid is connected to the N-terminus of the Bicycle via an amide bond. In some embodiments, Spacer² is a peptide wherein the C-terminal acid of the peptide is connected to the N-terminus of the Bicycle via an amide bond.

In some embodiments, Spacer² is L-Alanine. In some embodiments, Spacer² is D-Alanine.

In some embodiments, Spacer² is

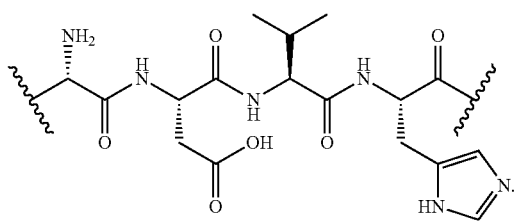 [SMILES: *C(=O)[C@H](Cc1cnc[nH]1)NC(=O)[C@@H](NC(=O)[C@H](CC(=O)O)NC(=O)[C@H](*)N)C(C)C]

In some embodiments, Spacer² is

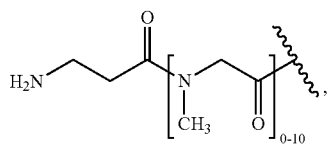

wherein:

each of $R^3$ is independently hydrogen or $C_{1-4}$ aliphatic, as described herein;

each of $R^4$ is independently hydrogen, or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur; or an $R^4$ group and its adjacent $R^3$ group are optionally taken together with their intervening atoms to form a 4-8 membered saturated or partially unsaturated monocyclic heterocyclic ring having 1-2 heteroatoms independently selected from nitrogen, oxygen, or sulfur; and s is 0-4.

In some embodiments, Spacer² is selected from those depicted in Table 1, below.

As defined above and described herein, each of $R^1$ and $R^2$ is independently R,

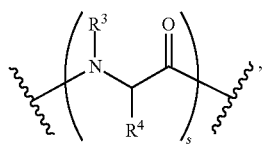

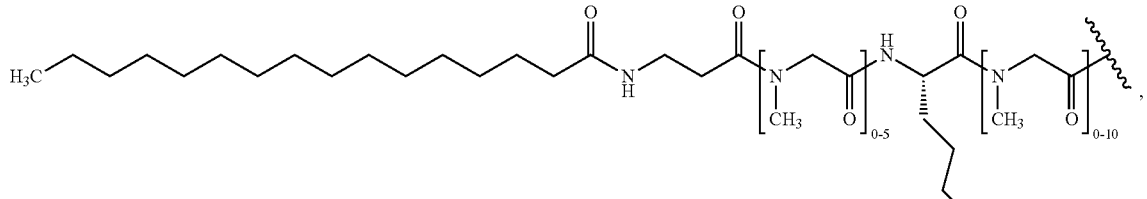

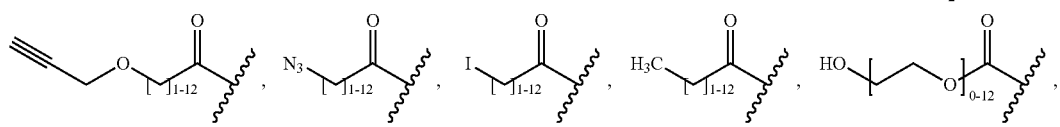

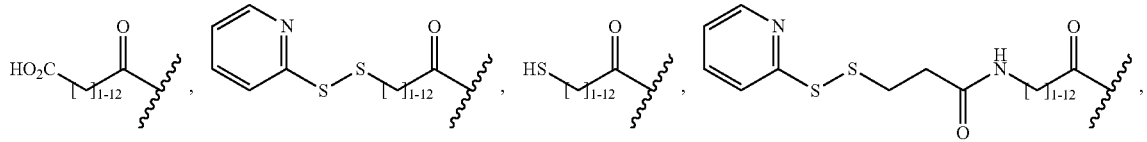

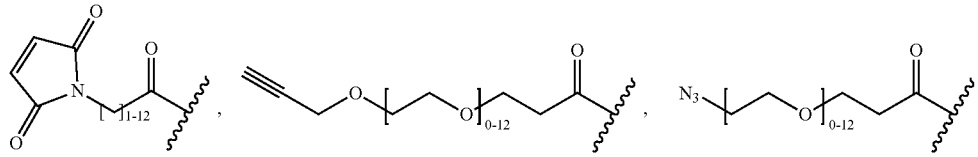

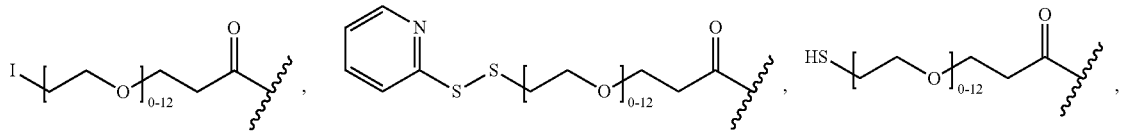

-continued
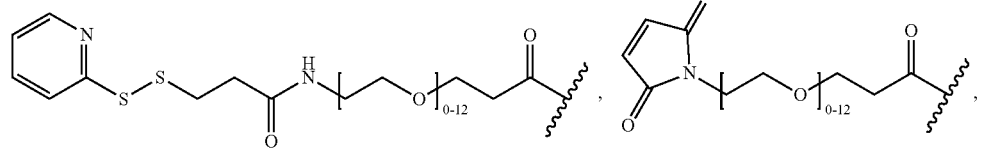
or -Linker-Conjugate.
In some embodiments, R¹ is R. In some embodiments, R¹ is
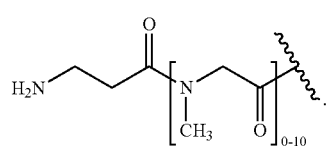
In some embodiments, R¹ is
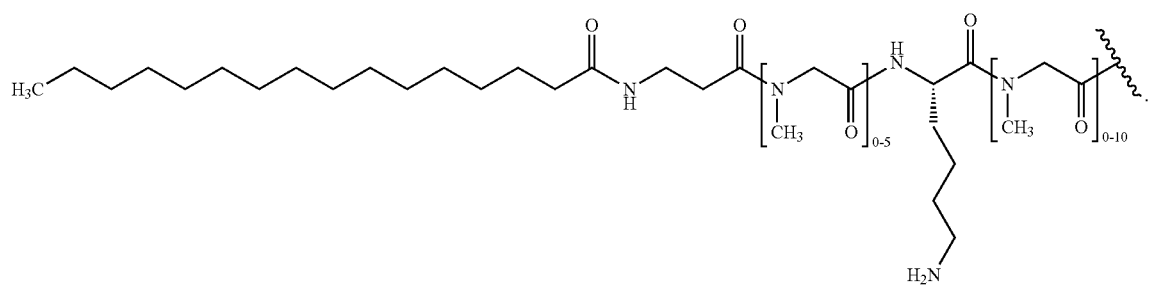
In some embodiments, R¹ is
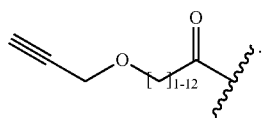
In some embodiments, R¹ is
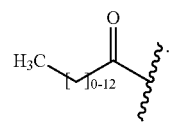
In some embodiments, R¹ is
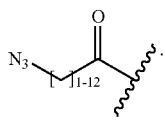
In some embodiments, R¹ is
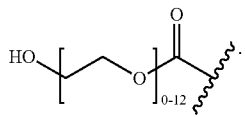
In some embodiments, R¹ is
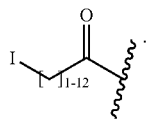
In some embodiments, R¹ is
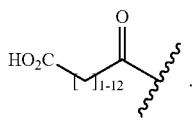

In some embodiments, R¹ is

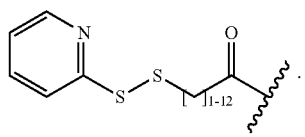

In some embodiments, R¹ is

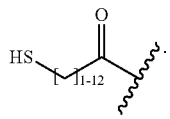

In some embodiments, R¹ is

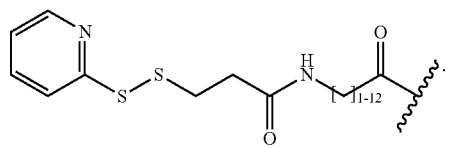

In some embodiments, R¹ is

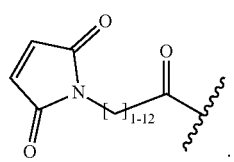

In some embodiments, R¹ is

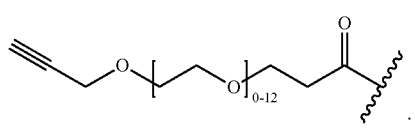

In some embodiments, R¹ is

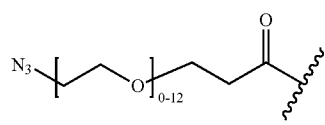

In some embodiments, R¹ is

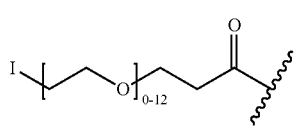

In some embodiments, R¹ is

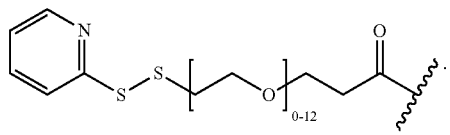

In some embodiments, R¹ is

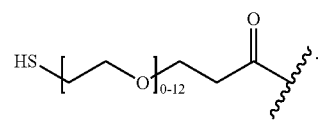

In some embodiments, R¹ is

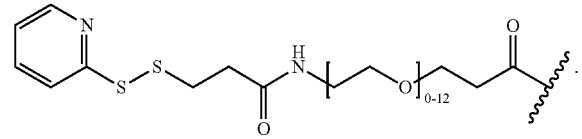

In some embodiments, R¹ is

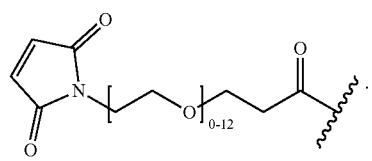

In some embodiments, R¹ is -Linker-Conjugate, wherein each of Linker and Conjugate is independently as described herein.

In some embodiments, R¹ is

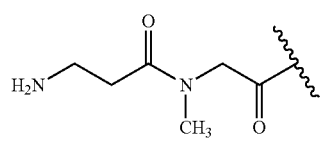

In some embodiments, R¹ is

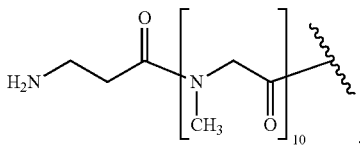

In some embodiments, R¹ is selected from those depicted in Table 1, below.

In some embodiments, $R^2$ is R. In some embodiments, $R^2$ is
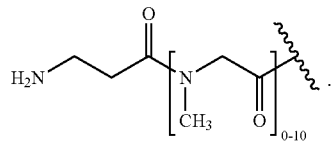
In some embodiments, $R^2$ is
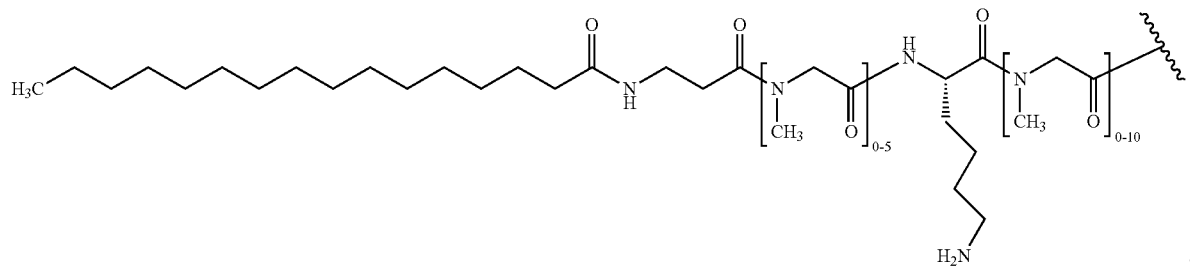
In some embodiments, $R^2$ is
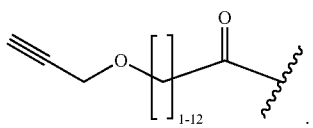
In some embodiments, $R^2$ is
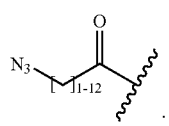
In some embodiments, $R^2$ is
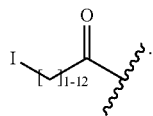
In some embodiments, $R^2$ is
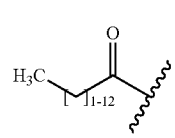
In some embodiments, $R^2$ is
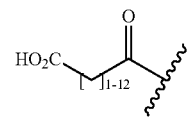
In some embodiments, $R^2$ is
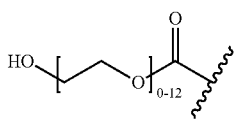
In some embodiments, $R^2$ is
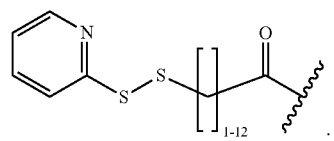
In some embodiments, $R^2$ is
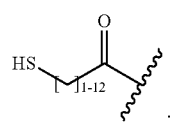
In some embodiments, $R^2$ is
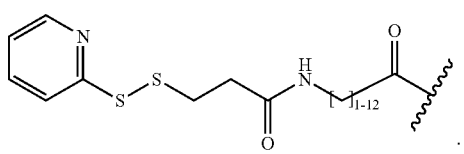

In some embodiments, R² is

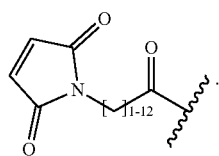

In some embodiments, R² is

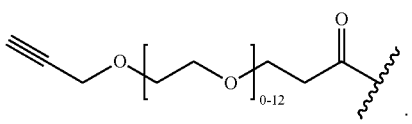

In some embodiments, R² is

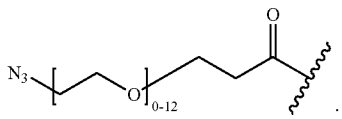

In some embodiments, R² is

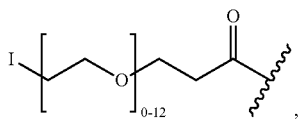

In some embodiments, R² is

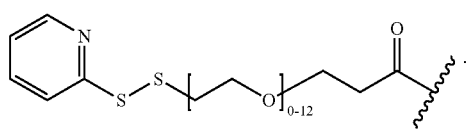

In some embodiments, R² is

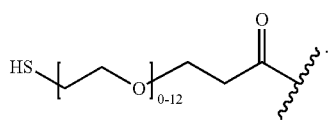

In some embodiments, R² is

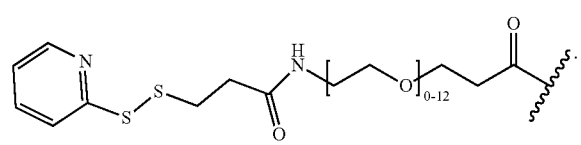

In some embodiments, R² is

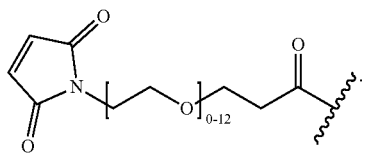

In some embodiments, R² is -Linker-Conjugate, wherein each of Linker and Conjugate is independently as described herein.

In some embodiments, R² is

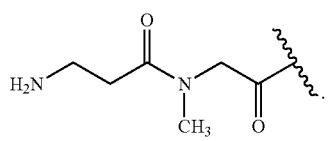 [SMILES: *C(=O)CN(C)C(=O)CCN]

In some embodiments, R² is

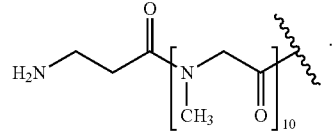

In some embodiments, R² is

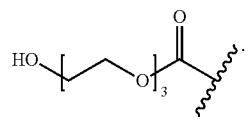

In some embodiments, R² is

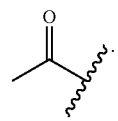

In some embodiments, R² is selected from those depicted in Table 1, below.

As defined above and described herein, each Linker is independently a covalent bond, or a $C_{1-8}$ bivalent hydrocarbon chain wherein one, two or three methylene units of the chain are optionally and independently replaced by -Cy¹-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)₂—, —C(CH₃)=N—N(R)—, —N(R)N=C(CH₃)—, —N(R)CH₂C(O)—, —(CH₂CH₂O)₁₋₁₀—,

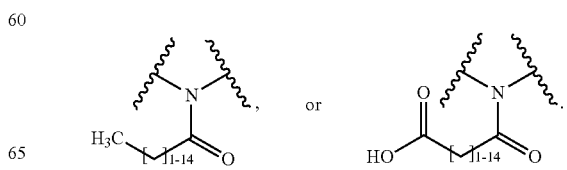

In some embodiments, Linker is a covalent bond. In some embodiments, Linker is a $C_{1-8}$ bivalent hydrocarbon chain wherein one, two or three methylene units of the chain are optionally and independently replaced by $-Cy^1-$, $-S-$, $-N(R)-$, $-O-$, $-C(O)-$, $-OC(O)-$, $-C(O)O-$, $-C(O)N(R)-$, $-N(R)C(O)-$, $-OC(O)N(R)-$, $-N(R)C(O)O-$, $-S(O)-$, $-S(O)_2-$, $-C(CH_3)=N-N(R)-$, $-N(R)N=C(CH_3)-$, $-N(R)CH_2C(O)-$, $-(CH_2CH_2O)_{1-10}-$,

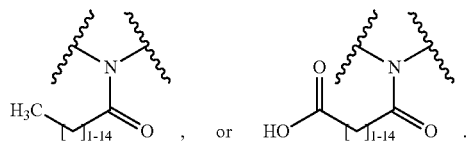

In some embodiments, Linker is a $C_{1-8}$ bivalent hydrocarbon chain wherein one, two or three methylene units of the chain are optionally and independently replaced by $-Cy^1-$. In some embodiments, Linker is a $C_{1-8}$ bivalent hydrocarbon chain wherein one, two or three methylene units of the chain are optionally and independently replaced by $-S-$. In some embodiments, Linker is a $C_{1-8}$ bivalent hydrocarbon chain wherein one, two or three methylene units of the chain are optionally and independently replaced by $-N(R)-$. In some embodiments, Linker is a $C_{1-8}$ bivalent hydrocarbon chain wherein one, two or three methylene units of the chain are optionally and independently replaced by $-O-$. In some embodiments, Linker is a $C_{1-8}$ bivalent hydrocarbon chain wherein one, two or three methylene units of the chain are optionally and independently replaced by $-C(O)-$. In some embodiments, Linker is a $C_{1-8}$ bivalent hydrocarbon chain wherein one, two or three methylene units of the chain are optionally and independently replaced by $-OC(O)-$. In some embodiments, Linker is a $C_{1-8}$ bivalent hydrocarbon chain wherein one, two or three methylene units of the chain are optionally and independently replaced by $-C(O)O-$. In some embodiments, Linker is a $C_{1-8}$ bivalent hydrocarbon chain wherein one, two or three methylene units of the chain are optionally and independently replaced by $-C(O)N(R)-$. In some embodiments, Linker is a $C_{1-8}$ bivalent hydrocarbon chain wherein one, two or three methylene units of the chain are optionally and independently replaced by $-N(R)C(O)-$. In some embodiments, Linker is a $C_{1-8}$ bivalent hydrocarbon chain wherein one, two or three methylene units of the chain are optionally and independently replaced by $-OC(O)N(R)-$. In some embodiments, Linker is a $C_{1-8}$ bivalent hydrocarbon chain wherein one, two or three methylene units of the chain are optionally and independently replaced by $-N(R)C(O)O-$. In some embodiments, Linker is a $C_{1-8}$ bivalent hydrocarbon chain wherein one, two or three methylene units of the chain are optionally and independently replaced by $-S(O)-$. In some embodiments, Linker is a $C_{1-8}$ bivalent hydrocarbon chain wherein one, two or three methylene units of the chain are optionally and independently replaced by $-S(O)_2-$. In some embodiments, Linker is a $C_1$-8 bivalent hydrocarbon chain wherein one, two or three methylene units of the chain are optionally and independently replaced by $-C(CH_3)=N-N(R)-$. In some embodiments, Linker is a $C_{1-8}$ bivalent hydrocarbon chain wherein one, two or three methylene units of the chain are optionally and independently replaced by $-N(R)N=C(CH_3)-$. In some embodiments, Linker is a $C_{1-8}$ bivalent hydrocarbon chain wherein one, two or three methylene units of the chain are optionally and independently replaced by $-N(R)CH_2C(O)-$. In some embodiments, Linker is a $C_{1-8}$ bivalent hydrocarbon chain wherein one, two or three methylene units of the chain are optionally and independently replaced by $-(CH_2CH_2O)_{1-10}-$. In some embodiments, Linker is a $C_{1-8}$ bivalent hydrocarbon chain wherein one, two or three methylene units of the chain are optionally and independently replaced by

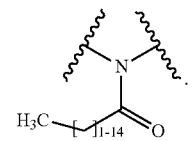

In some embodiments, Linker is a $C_{1-8}$ bivalent hydrocarbon chain wherein one, two or three methylene units of the chain are optionally and independently replaced by

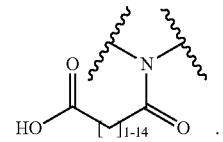

In some embodiments, Linker is selected from those depicted in Table 1, below.

As defined above and described herein, each Conjugate is independently a half life extension motif, a solubilizing group, a transporter recognition motif, a cell penetrant motif, a drug payload, or a detectable moiety.

In some embodiments, Conjugate is a half life extension motif. In some embodiments, a half life extension motif comprises, or is, a lipid. In some embodiments, a half life extension motif comprises, or is, a fatty acid. In some embodiments, a fatty acid is a dietary fatty acid, for example, myristic acid or palmitic acid. In some embodiments, a lipid is selected from:

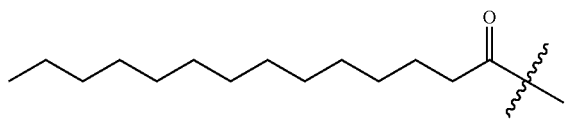

Insulin detemir

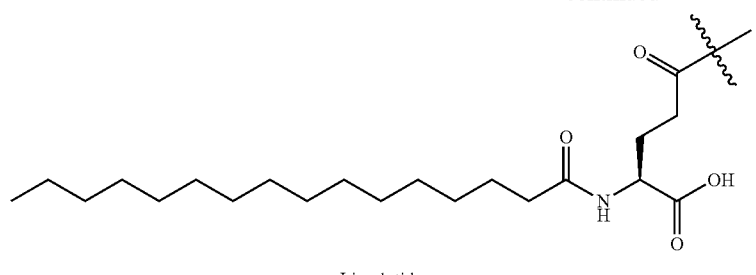
Liraglutide
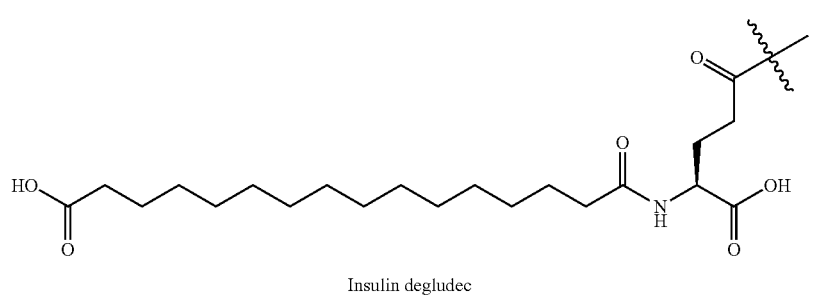
Insulin degludec
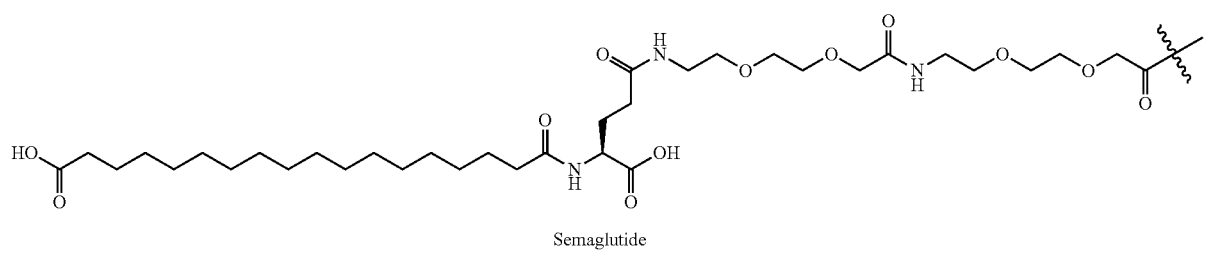
Semaglutide
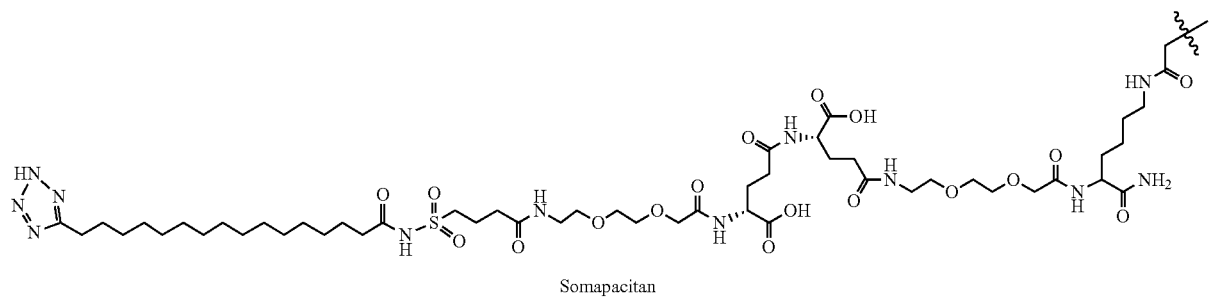
Somapacitan
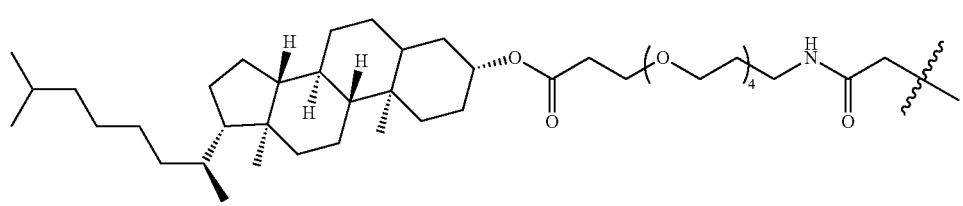
Cholesterol-like half-life extenders -continued

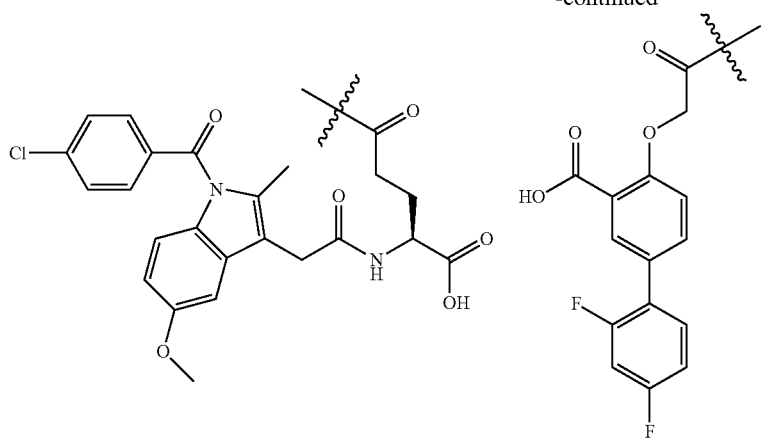

Mono-valent small-molecule albumin binders

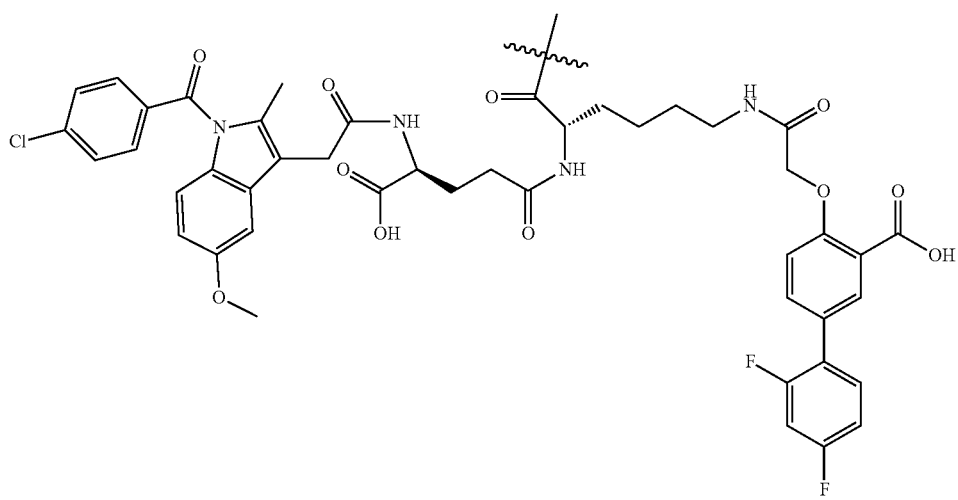

Di-valent small-molecule albumin binders

In some embodiments, a half life extension motif is selected from those described in Bech et al, *ACS Med. Chem. Lett.* 2018, 9, 577-580, the content of which is incorporated herein by reference in its entirety.

In some embodiments, Conjugate is a solubilizing group. In some embodiments, a solubilizing group is a polar chain. In some embodiments, a polar chain is a poly sarcosine. In some embodiments, a polar chain is a polyethylene glycol (PEG). In some embodiments, a solubilizing group comprises an ionised group, including but not limited to: carboxylic acid, sulphonic acid, amine, or quaternary ammonium group such as guanidine.

In some embodiments, Conjugate is a transporter recognition motif. In some embodiments, a transporter recognition motif is selected from those described in Diaz-Perlas et al., *Chem. Sci.,* 2018, (DOI: 10.1039/C8SC02415D), the content of which is incorporated herein by reference in its entirety.

In some embodiments, a transporter recognition motif is a blood-brain barrier (BBB) shuttle peptide. In some embodiments, a BBB shuttle peptide is selected from:

| | |
|---|---|
| THRre_1f | pwvpswmpprhtKGK(CF)G |
| THRre_2f | (pwvpswmpprht)$_2$KKGK(CF)G |
| THRre_1m | pwvpswmpprhtKGK(Mal)G |
| THRre_2m | (pwvpswmpprht)$_2$KKGK(Mal)G |
| THRre_1c | pwvpswmpprhtkkc |
| THRre_2c | (pwvpswmpprht-O$_2$Oc)$_2$kkkc. |

In some embodiments, Conjugate is a cell penetrant motif. In some embodiments, a cell penetrant motif is a cell penetrating peptide. In some embodiments, a cell penetrant motif is TAT (sequence: GRKKRRQRRRPPQC). In some embodiments, a cell penetrant motif is a cell penetrating peptide selected from those described in Borrelli et al., *Molecules* 2018, 23, 295, the content of which is incorporated herein by reference in its entirety.

In some embodiments, Conjugate is a drug payload. In some embodiments, a drug payload is a Toxin. As used herein, a Toxin refers to a chemotherapeutic agent. In some embodiments, a Toxin is connected at any available position. In some embodiments, a Toxin is connected at any available —OH, —C(O)OH, —SH, —NH$_2$, or —NHCH$_3$.

In some embodiments, a Toxin is monomethyl auristatin E (MMAE):

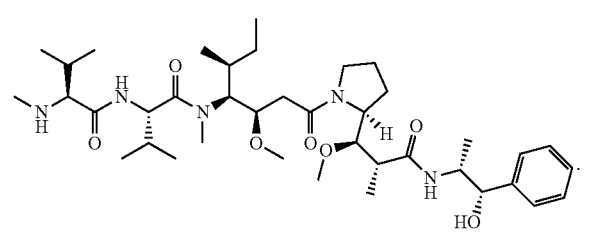 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

In some embodiments, a Toxin is monomethyl auristatin F (MMAF):

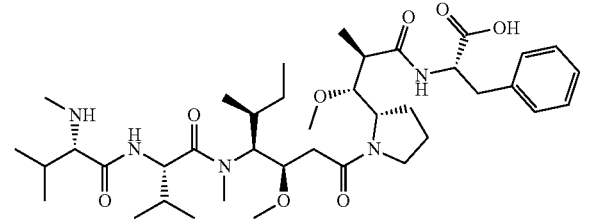 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

In some embodiments, a Toxin is DM1:

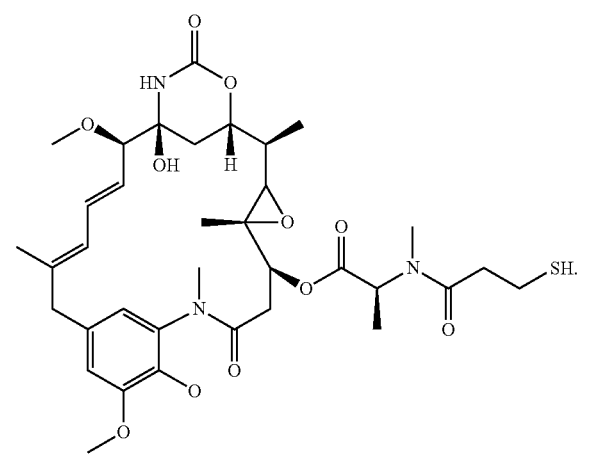 [SMILES: COc1cc2cc(c1O)N(C)C(=O)C[C@H](OC(=O)[C@H](C)N(C)C(=O)CCS)[C@@]1(C)OC1[C@H](C)[C@@H]1C[C@@](O)(NC(=O)O1)[C@H](OC)/C=C/C=C(\C)C2]

In some embodiments, a Toxin is DM4:

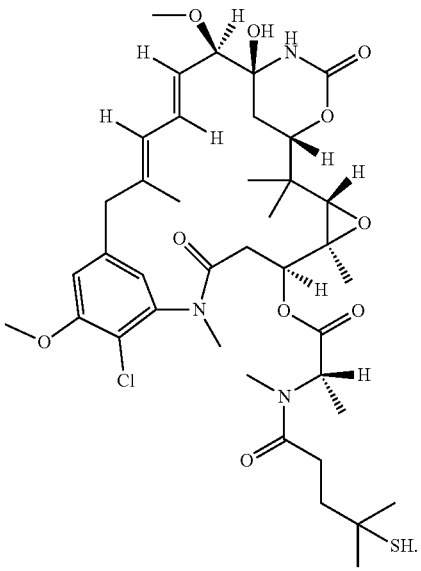 [SMILES: COc1cc2cc(c1Cl)N(C)C(=O)C[C@H](OC(=O)[C@H](C)N(C)C(=O)CCC(C)(C)S)[C@]1(C)O[C@H]1C(C)(C)[C@@H]1C[C@@](O)(NC(=O)O1)[C@H](OC)/C=C/C=C(\C)C2]

In some embodiments, a Toxin is SN38:

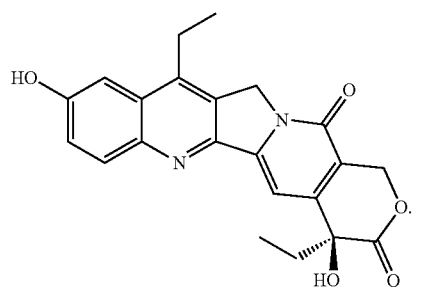 [SMILES: CCc1c2c(nc3ccc(O)cc13)-c1cc3c(c(=O)n1C2)COC(=O)[C@]3(O)CC]

In some embodiments, a Toxin is doxorubicin:

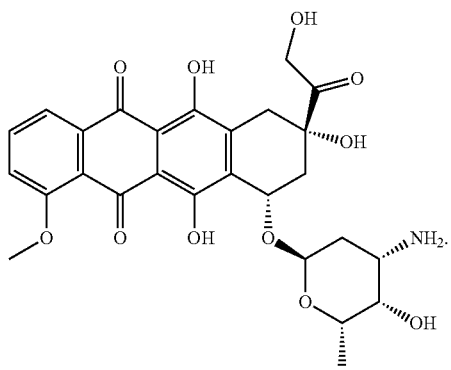 [SMILES: COc1cccc2c1C(=O)c1c(O)c3c(c(O)c1C2=O)C[C@@](O)(C(=O)CO)C[C@@H]3O[C@H]1C[C@H](N)[C@H](O)[C@H](C)O1]

In some embodiments, a Toxin is a duocarmycin analog:

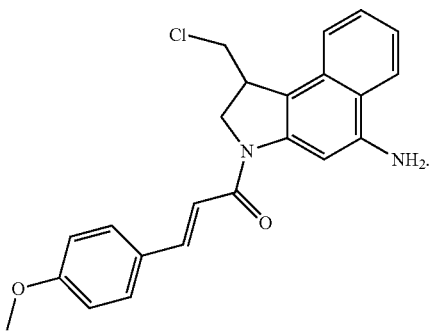 [SMILES: COc1ccc(/C=C/C(=O)N2CC(CCl)c3c2cc(N)c2ccccc32)cc1]

In some embodiments, Conjugate is a detectable moiety. In some embodiments, a detectable moiety is any moiety capable of being detected.

One of ordinary skill in the art will appreciate that a variety of detectable moieties are amenable to achieve the imaging effects of the present invention.

As used herein, "M" is a metal.

In some embodiments, a detectable moiety is connected at any available position. In some embodiments, a detectable moiety is connected at any available —OH, —C(O)OH, —SH, —NH$_2$, or —NHCH$_3$.

In some embodiments, a detectable moiety is 1,4,7,10-tetraazacyclododecane-1,4,7,10-tetraacetic acid (also known as DOTA, DotA, or tetraxetan):

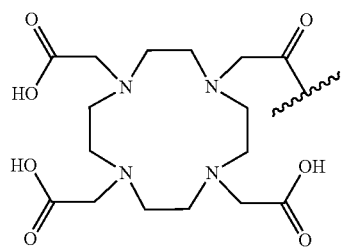

In some embodiments, a detectable moiety is Bn-DOTA:

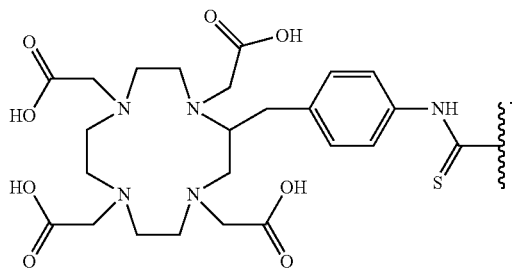 [SMILES: *C(=S)Nc1ccc(CC2CN(CC(=O)O)CCN(CC(=O)O)CCN(CC(=O)O)CCN2CC(=O)O)cc1]

In some embodiments, a detectable moiety is Bn-oxo-DOTA:

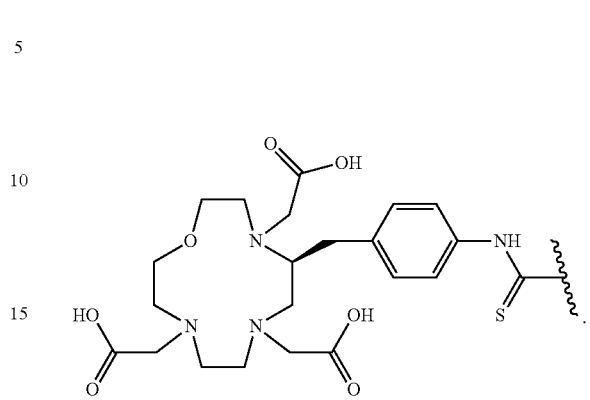

In some embodiments, a detectable moiety is Bn-PCTA:

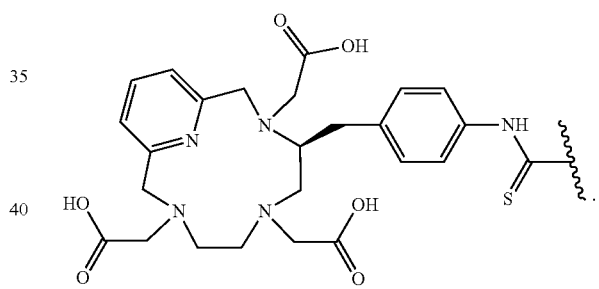

In some embodiments, a detectable moiety is TETA:

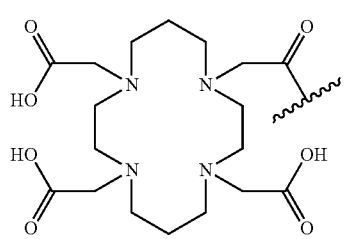

In some embodiments, a detectable moiety is Bn-NOTA:
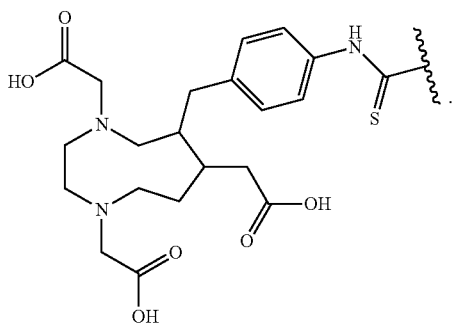 [SMILES: *C(=S)Nc1ccc(CC2CN(CC(=O)O)CCN(CC(=O)O)CCC2CC(=O)O)cc1]
In some embodiments, a detectable moiety is Bn-DTPA:
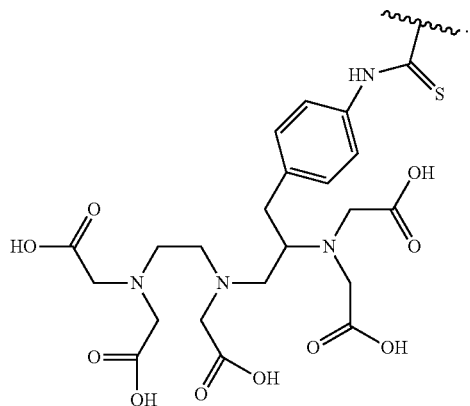
In some embodiments, a detectable moiety is CHX-A"-DTPA:
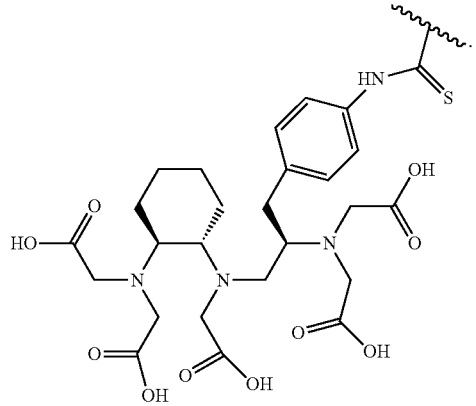 [SMILES: *C(=S)Nc1ccc(C[C@H](CN(CC(=O)O)[C@H]2CCCC[C@@H]2N(CC(=O)O)CC(=O)O)N(CC(=O)O)CC(=O)O)cc1]
In some embodiments, a detectable moiety is 2B3M-DTPA:
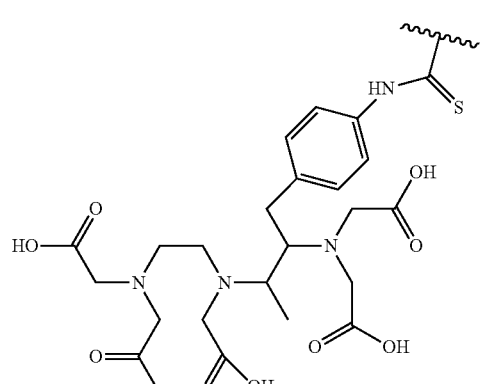
In some embodiments, a detectable moiety is a desferrioxamine (DFO):
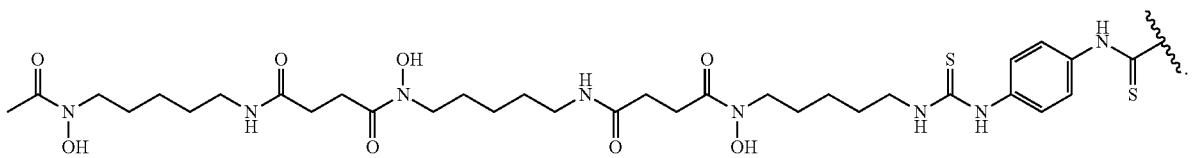 [SMILES: *C(=S)Nc1ccc(NC(=S)NCCCCCN(O)C(=O)CCC(=O)NCCCCCN(O)C(=O)CCC(=O)NCCCCCN(O)C(C)=O)cc1]

In some embodiments, a detectable moiety is a heptamethine dye:

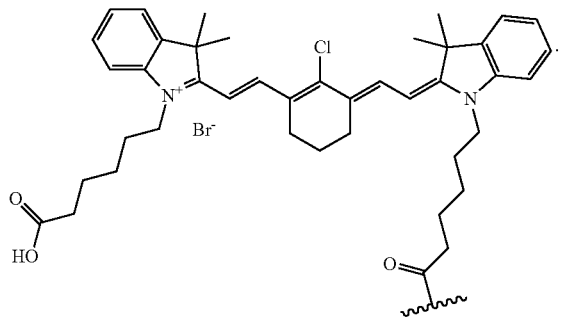 [SMILES: *C(=O)CCCCCN1/C(=C/C=C2\CCCC(/C=C/C3=[N+](CCCCCC(=O)O)c4ccccc4C3(C)C)=C2Cl)C(C)(C)c2ccccc21 ; [Br-]]

In some embodiments, a detectable moiety is a Bn-DOTA complex with a metal:

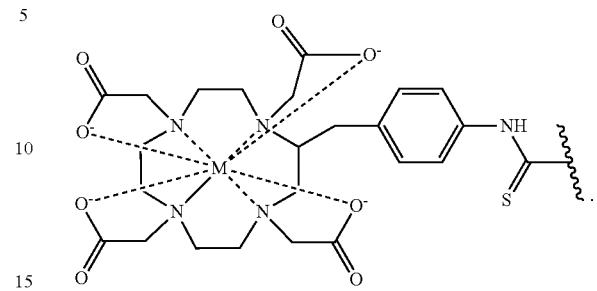

In some embodiments, a detectable moiety is Fluorescein:

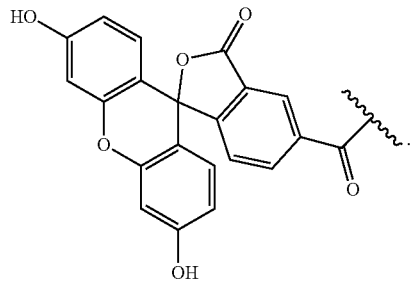 [SMILES: *C(=O)c1ccc2c(c1)C(=O)OC21c2ccc(O)cc2Oc2cc(O)ccc21]

In some embodiments, a detectable moiety is a Bn-oxo-DOTA complex with a metal

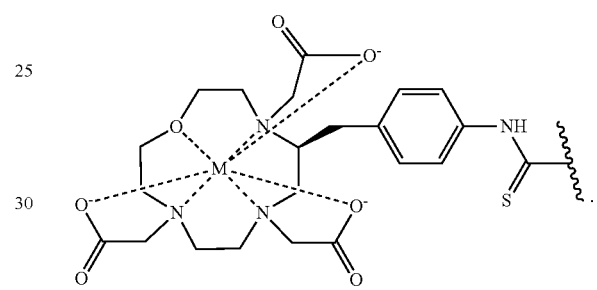

In some embodiments, a detectable moiety is Alexafluor488:

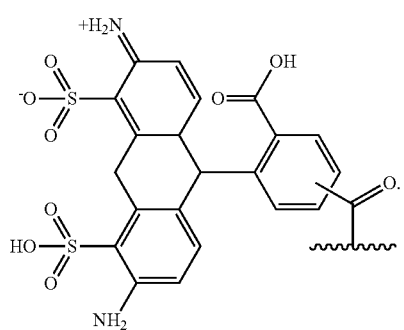

In some embodiments, a detectable moiety is a Bn-PCTA complex with a metal:

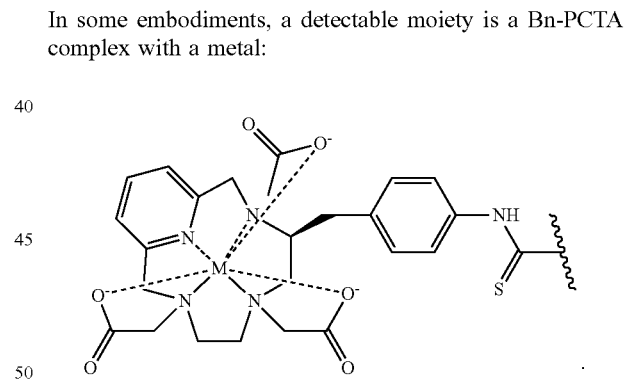

In some embodiments, a detectable moiety is a DOTA complex with a metal:

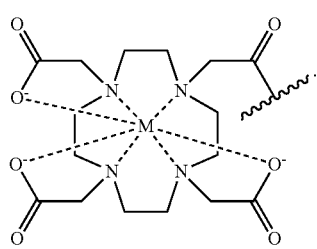

In some embodiments, a detectable moiety is a TETA complex with a metal:

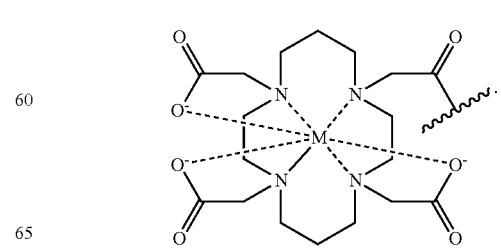

In some embodiments, a detectable moiety is a Bn-NOTA complex with a metal:

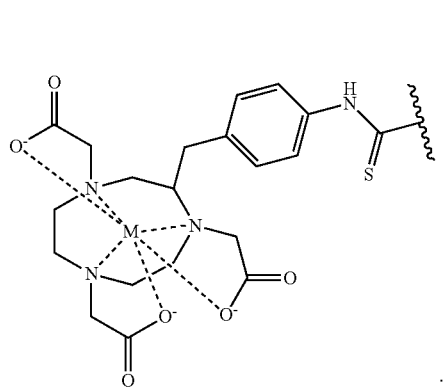

In some embodiments, a detectable moiety is a Bn-DTPA complex with a metal:

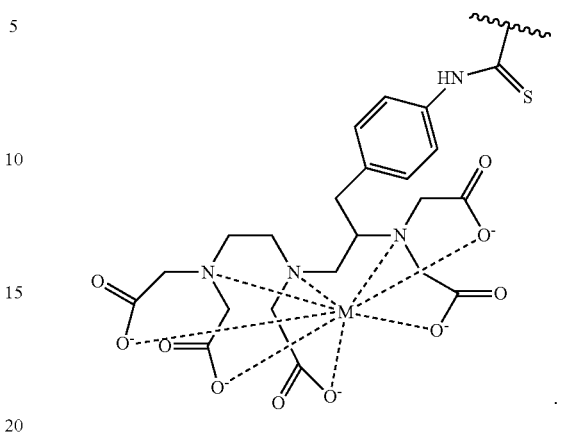

In some embodiments, a detectable moiety is a CHX-A"-DTPA complex with a metal:

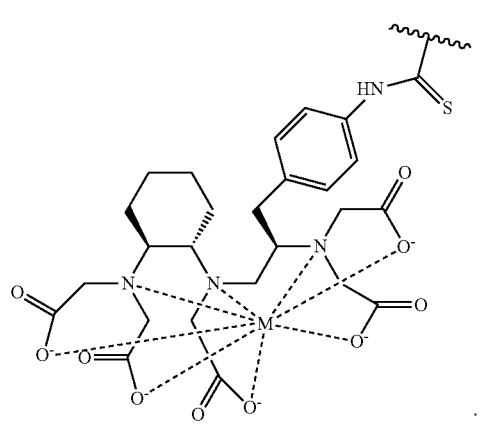

In some embodiments, a detectable moiety is a 2B3M-DTPA complex with a metal:

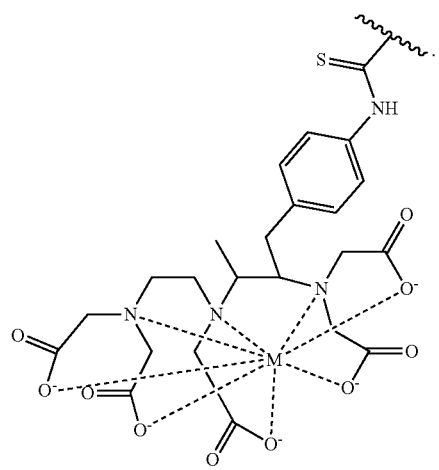

In some embodiments, a detectable moiety is a desferrioxamine (DFO) complex with a metal:

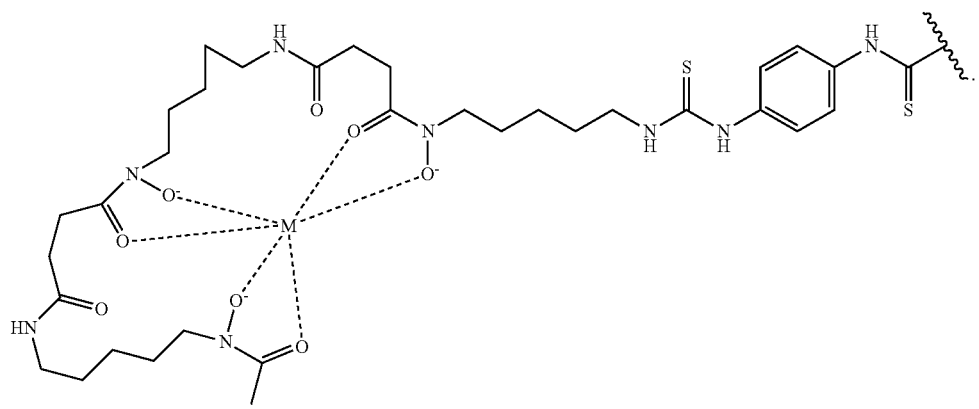

In some embodiments, a detectable moiety forms a complex with a metal.

In some embodiments, a detectable moiety is a scorpionate. In some embodiments, a detectable moiety is

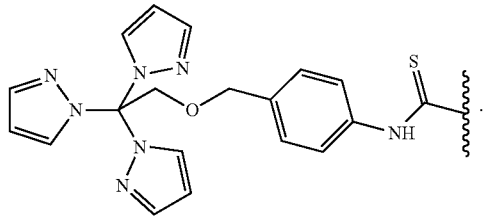 [SMILES: *C(=S)Nc1ccc(COCC(n2cccn2)(n2cccn2)n2cccn2)cc1 ; "."]

In some embodiments, a detectable moiety is a nanomaterial. In some embodiments, a detectable moiety is a quantum dot.

In some embodiments, Conjugate is selected from those depicted in Table 1, below.

As defined above and described herein, Ring A is selected from the group consisting of 18-crown-6, 1,7,13-triaza-18-crown-6, and a 3-12-membered optionally substituted, saturated, partially unsaturated, bridged bicyclic, bridged tricyclic, propellane, or aromatic ring having 0-6 heteroatoms independently selected from nitrogen, oxygen, or sulfur.

In some embodiments, Ring A is 18-crown-6. In some embodiments, Ring A is 1,7,13-triaza-18-crown-6. In some embodiments, Ring A is a 3-12-membered optionally substituted, saturated, partially unsaturated, bridged bicyclic, bridged tricyclic, propellane, or aromatic ring having 0-6 heteroatoms independently selected from nitrogen, oxygen, or sulfur.

In some embodiments, Ring A is a 7-membered optionally substituted, saturated, partially unsaturated, bridged bicyclic, bridged tricyclic, propellane, or aromatic ring having 0-6 heteroatoms independently selected from nitrogen, oxygen, or sulfur. In some embodiments, Ring A is a 7-membered optionally substituted, saturated ring having 0-3 heteroatoms independently selected from nitrogen, oxygen, or sulfur. In some embodiments, Ring A is a 7-membered optionally substituted, saturated, ring having 1-3 heteroatoms independently selected from nitrogen or oxygen.

In some embodiments, Ring A is optionally substituted with 0-3 oxo, methyl, ethyl or spiroethylene groups. In some embodiments, Ring A is optionally substituted with 0-3 —OR, —N(R)$_2$, or —COOR, wherein R is as described herein. In some embodiments, Ring A is optionally substituted with 0-3 —OH, —OCH$_3$, —NHCH$_3$, or —COOH.

In some embodiments, Ring A is

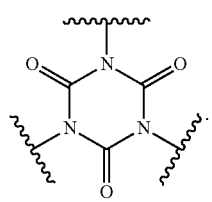 [SMILES: *n1c(=O)n(*)c(=O)n(*)c1=O]

In some embodiments, Ring A is

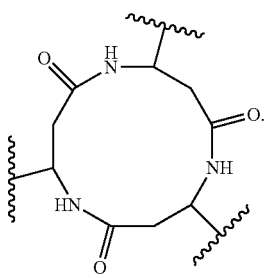 [SMILES: *C1CC(=O)NC(*)CC(=O)NC(*)CC(=O)N1]

In some embodiments, Ring A is

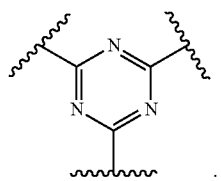 [SMILES: *c1nc(*)nc(*)n1]

In some embodiments, Ring A is

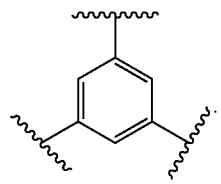 [SMILES: *c1cc(*)cc(*)c1]

In some embodiments, Ring A is

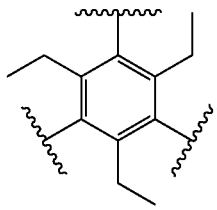

In some embodiments, Ring A is

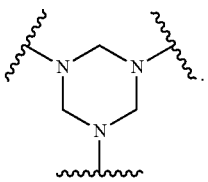 [SMILES: *N1CN(*)CN(*)C1]

In some embodiments, Ring A is
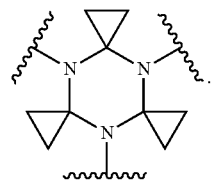 [SMILES: *N1C2(CC2)N(*)C2(CC2)N(*)C12CC2]
In some embodiments, Ring A is
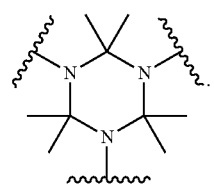
In some embodiments, Ring A is
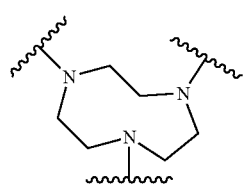
In some embodiments, Ring A is
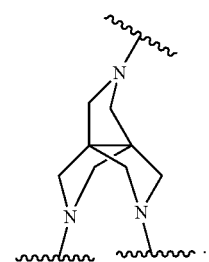 [SMILES: *N1CC23CN(*)CC2(C1)CN(*)C3]
In some embodiments, Ring A is
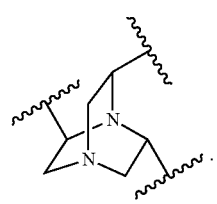 [SMILES: *C1CN2CC(*)N1C(*)C2]
In some embodiments, Ring A is
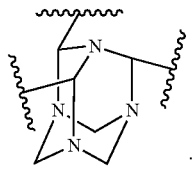 [SMILES: *C1N2CN3CN(C2)C(*)N1C3*]
In some embodiments, Ring A is
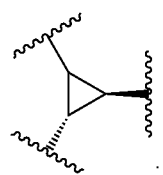
In some embodiments, Ring A is
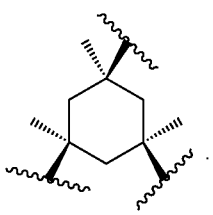
In some embodiments, Ring A is
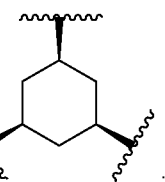
In some embodiments, Ring A is
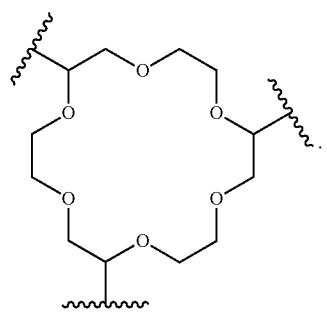 [SMILES: *C1COCCOC(*)COCCOC(*)COCCO1]

In some embodiments, Ring A is

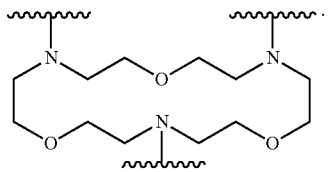 [SMILES: *N1CCOCCN(*)CCOCCN(*)CCOCC1]

In some embodiments, Ring A is

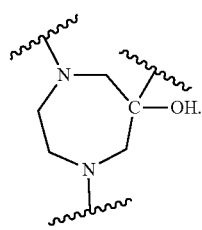 [SMILES: *N1CCN(*)CC(*)(O)C1]

In some embodiments, Ring A is selected from those depicted in Table 1, below.

As defined above and described herein, in some embodiments, Ring B is an optionally substituted 6-18 membered cyclophane having 0-9 heteroatoms independently selected from nitrogen, oxygen, or sulfur.

In some embodiments, Ring B is a 6-18 membered cyclophane having 0-9 heteroatoms independently selected from nitrogen, oxygen, or sulfur, optionally substituted with 0-6 —OR, —N(R)$_2$, or —COOR, wherein R is as described herein. In some embodiments, Ring B is optionally substituted with 0-3 —OR, —N(R)$_2$, or —COOR, wherein R is as described herein. In some embodiments, Ring B is optionally substituted with 0-3 —OCH$_3$, —NHCH$_3$, or —COOH.

As defined above and described herein, in some embodiments, Ring B is an optionally substituted cyclophane having 1-5 aromatic or heteroaromatic ring units and aliphatic chains bridging two ring units, wherein one, two or three methylene units of each aliphatic chain are optionally and independently replaced by —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, or —S(O)$_2$—.

In some embodiments, Ring B is an optionally substituted cyclophane having 2, 3, or 4 aromatic or heteroaromatic ring units. In some embodiments, Ring B is an optionally substituted cyclophane having 3 aromatic or heteroaromatic ring units. In some embodiments, an aromatic or heteroaromatic ring unit of a cyclophane is independently a 5- or 6-membered ring. In some embodiments, an aromatic or heteroaromatic ring unit of a cyclophane is a phenyl ring. In some embodiments, an aromatic or heteroaromatic ring unit of a cyclophane is a pyridine ring. In some embodiments, one, two or three methylene units of an aliphatic chain of a cyclophane are optionally and independently replaced by —N(R)—, —O—, or —C(O)—. In some embodiments, one, two or three methylene units of an aliphatic chain of a cyclophane are optionally and independently replaced by —N(R)—.

In some embodiments, Ring B is

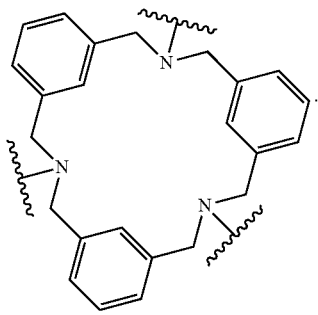 [SMILES: *N1Cc2cccc(c2)CN(*)Cc2cccc(c2)CN(*)Cc2cccc(c2)C1]

In some embodiments, Ring B is

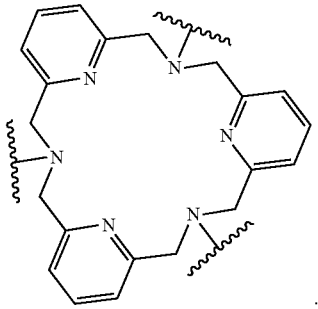 [SMILES: *N1Cc2cccc(n2)CN(*)Cc2cccc(n2)CN(*)Cc2cccc(n2)C1]

In some embodiments, Ring B is

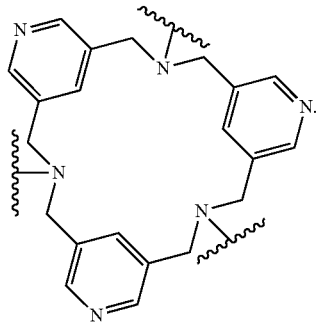 [SMILES: *N1Cc2cncc(c2)CN(*)Cc2cncc(c2)CN(*)Cc2cncc(c2)C1]

In some embodiments, Ring B is

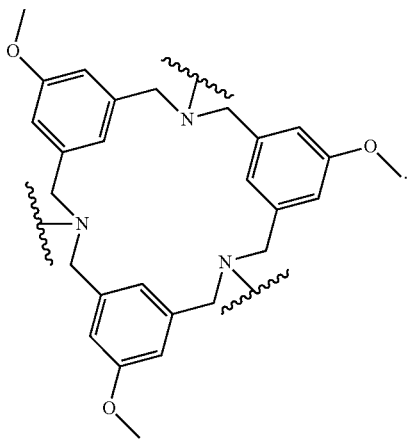 [SMILES: *N1Cc2cc(cc(OC)c2)CN(*)Cc2cc(cc(OC)c2)CN(*)Cc2cc(cc(OC)c2)C1]

In some embodiments, Ring B is

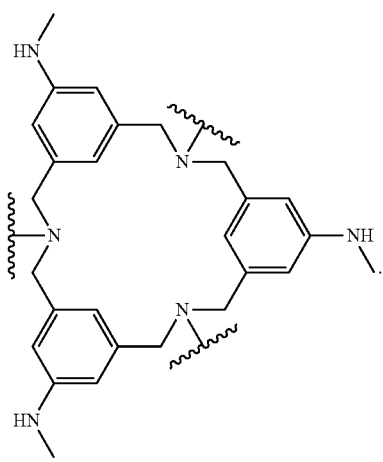 [SMILES: *N1Cc2cc(cc(NC)c2)CN(*)Cc2cc(cc(NC)c2)CN(*)Cc2cc(cc(NC)c2)C1]

In some embodiments, Ring B is

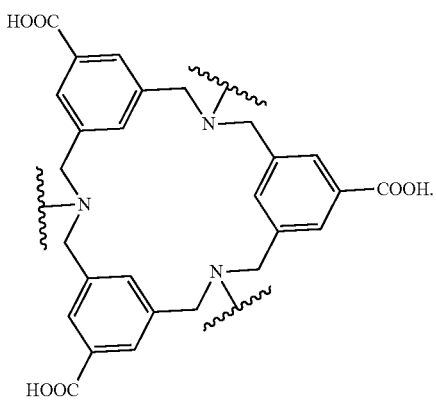 [SMILES: *N1Cc2cc(cc(C(=O)O)c2)CN(*)Cc2cc(cc(C(=O)O)c2)CN(*)Cc2cc(cc(C(=O)O)c2)C1]

In some embodiments, Ring B is selected from those depicted in Table 1, below.

As defined above and described herein, in some embodiments, each $R^4$ is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, $R^4$ is hydrogen. In some embodiments, $R^4$ is an optionally substituted $C_{1-6}$ aliphatic. In some embodiments, $R^4$ is an optionally substituted 3-8 membered saturated or partially unsaturated monocyclic carbocyclic ring. In some embodiments, $R^4$ is an optionally substituted phenyl. In some embodiments, $R^4$ is an optionally substituted 8-10 membered bicyclic aromatic carbocyclic ring. In some embodiments, $R^4$ is an optionally substituted 4-8 membered saturated or partially unsaturated monocyclic heterocyclic ring having 1-2 heteroatoms independently selected from nitrogen, oxygen, or sulfur. In some embodiments, $R^4$ is an optionally substituted 5-6 membered monocyclic heteroaromatic ring having 1-4 heteroatoms independently selected from nitrogen, oxygen, or sulfur. In some embodiments, $R^4$ is an optionally substituted 8-10 membered bicyclic heteroaromatic ring having 1-5 heteroatoms independently selected from nitrogen, oxygen, or sulfur.

In some embodiments, $R^4$ is methyl. In some embodiments, $R^4$ is

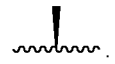

In some embodiments, $R^4$ is

In some embodiments, $R^4$ is

In some embodiments, $R^4$ is

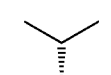

In some embodiments, $R^4$ is

In some embodiments, $R^4$ is

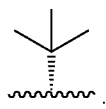

In some embodiments, $R^4$ is

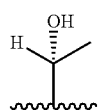

wherein the site of attachment has (S) stereochemistry. In some embodiments, $R^4$ is

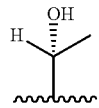

wherein the site of attachment has (R) stereochemistry.

In some embodiments, $R^4$ is

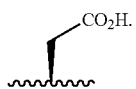

In some embodiments, $R^4$ is

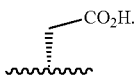

In some embodiments, $R^4$ is

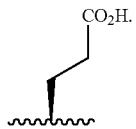

In some embodiments, $R^4$ is

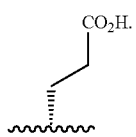

In some embodiments, $R^4$ is

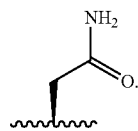

In some embodiments, $R^4$ is

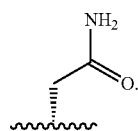

In some embodiments, $R^4$ is

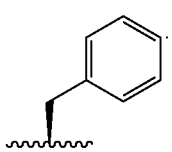

In some embodiments, $R^4$ is

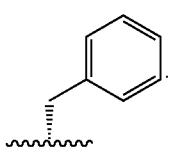

In some embodiments, $R^4$ is

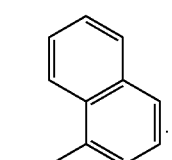

In some embodiments, $R^4$ is

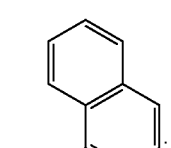
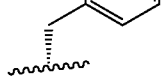

In some embodiments, R⁴ is
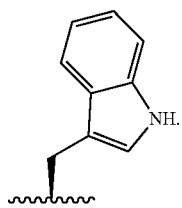
In some embodiments, R⁴ is
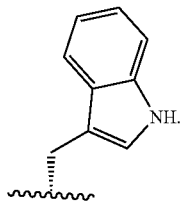
In some embodiments, R⁴ is
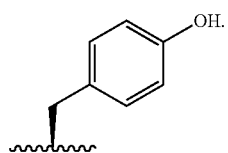
In some embodiments, R⁴ is
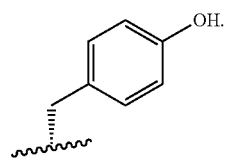
In some embodiments, R⁴ is
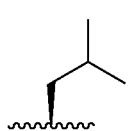
In some embodiments, R⁴ is
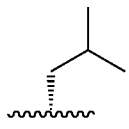
In some embodiments, R⁴ is
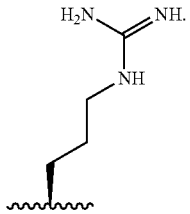
In some embodiments, R⁴ is
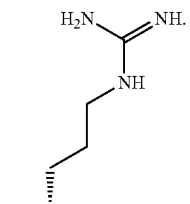
In some embodiments, R⁴ is
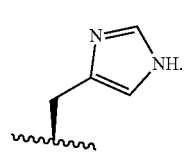
In some embodiments, R⁴ is
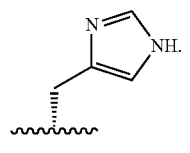
In some embodiments, R⁴ is
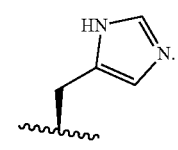
In some embodiments, R⁴ is
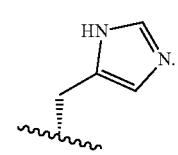

In some embodiments, R⁴ is

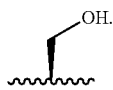

In some embodiments, R⁴ is

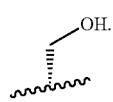

In some embodiments, R⁴ is selected from those depicted in Table 1, below.

As defined above and described herein, in some embodiments, each R³ is independently hydrogen or $C_{1-4}$ aliphatic.

In some embodiments, R³ is hydrogen. In some embodiments, R³ is $C_{1-4}$ aliphatic. In some embodiments, R³ is $C_{1-4}$ alkyl. In some embodiments, R³ is methyl. In some embodiments, R³ is ethyl. In some embodiments, R³ is propyl. In some embodiments, R³ is isopropyl. In some embodiments, R³ is butyl. In some embodiments, R³ is isobutyl. In some embodiments, R³ is t-butyl. In some embodiments, R³ is selected from those depicted in Table 1, below.

As defined above and described herein, in some embodiments, an R³ group and its adjacent R⁴ group are optionally taken together with their intervening atoms to form a 4-8 membered saturated or partially unsaturated monocyclic heterocyclic ring having 1-2 heteroatoms independently selected from nitrogen, oxygen, or sulfur.

In some embodiments, an R³ group and its adjacent R⁴ group are taken together with their intervening atoms to form

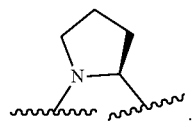 [SMILES: *[C@@H]1CCCN1*]

In some embodiments, an R³ group and its adjacent R⁴ group are taken together with their intervening atoms to form

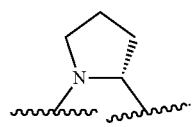 [SMILES: *[C@H]1CCCN1*]

In some embodiments, an R³ group and its adjacent R⁴ group are taken together with their intervening atoms to form a group selected from those depicted in Table 1, below.

As defined above and described herein, m is 0 or 1.
In some embodiments, m is 0. In some embodiments, m is 1.
In some embodiments, m is selected from those depicted in Table 1, below.
As defined above and described herein, n is 0 or 1.
In some embodiments, n is 0. In some embodiments, n is 1.
In some embodiments, n is selected from those depicted in Table 1, below.

In certain embodiments, the present invention provides a compound of formula I-a, wherein Scaffold is Ring A, thereby forming a compound of formula I-a:

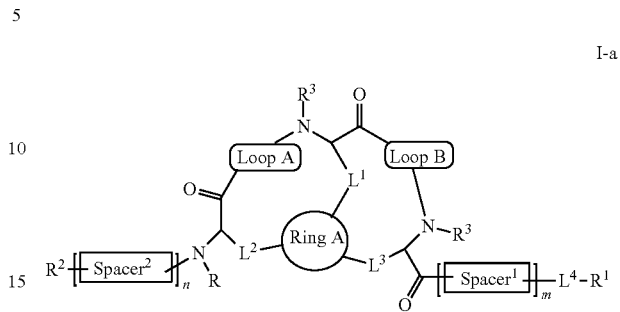

I-a or a pharmaceutically acceptable salt thereof, wherein each of Loop A, Loop B, Ring A, L¹, L², L³, L⁴, Spacer¹, Spacer², R, R¹, R², R³, R⁴, m, n, r, and s is as defined above and described in embodiments herein, both singly and in combination.

In certain embodiments, the present invention provides a compound of formula I-b, wherein Scaffold is Ring B, thereby forming a compound of formula I-b:

I-b or a pharmaceutically acceptable salt thereof, wherein each of Loop A, Loop B, Ring B, L¹, L², L³, L⁴, Spacer¹, Spacer², R, R¹, R², R³, m, and n is as defined above and described in embodiments herein, both singly and in combination.

In certain embodiments, the present invention provides a compound of formula I-c, wherein Loop A is Loop B is Space¹ is
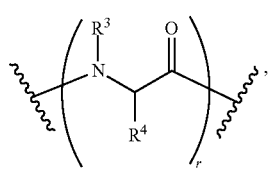
and Peptide² is
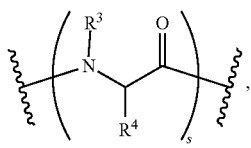
thereby forming a compound of formula I-c:
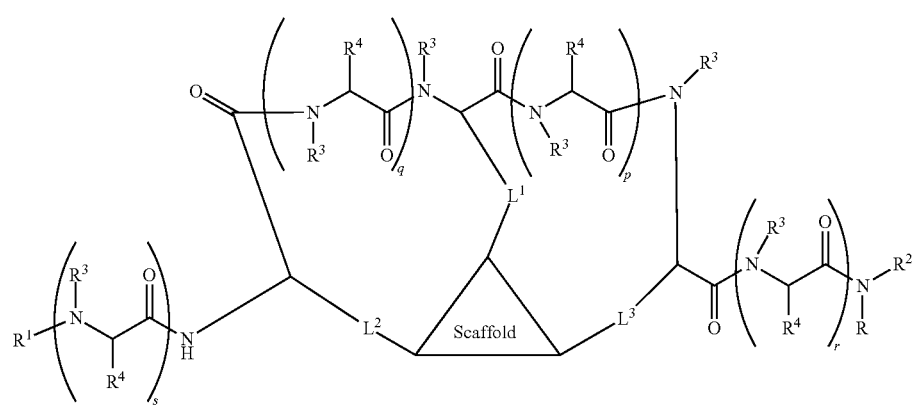
I-c
or a pharmaceutically acceptable salt thereof, wherein each of Scaffold, $L^1$, $L^2$, $L^3$, R, $R^1$, $R^2$, $R^3$, $R^4$, p, q, r, and s is as defined above and described in embodiments herein, both singly and in combination.
In certain embodiments, a compound of the invention is a compound of formula I-d:
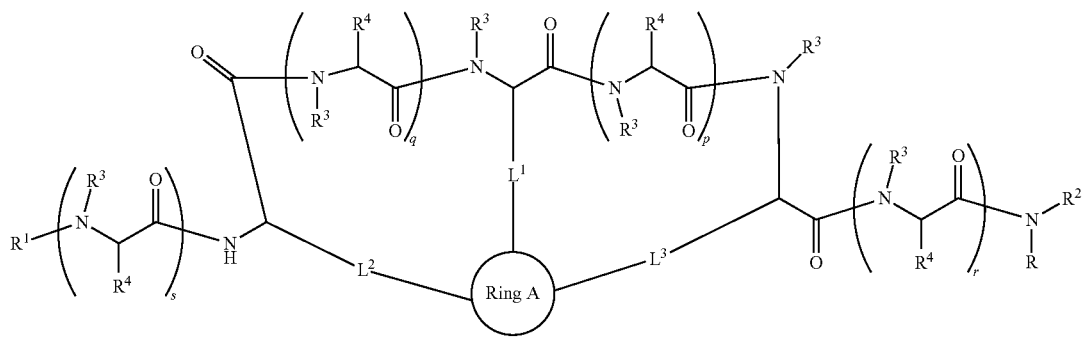
I-d or a pharmaceutically acceptable salt thereof, wherein each of Ring A, $L^1$, $L^2$, $L^3$, R, $R^1$, $R^2$, $R^3$, $R^4$, p, q, r, and s is as defined above and described in embodiments herein, both singly and in combination.

In certain embodiments, a compound of the invention is a compound of formula I-e:

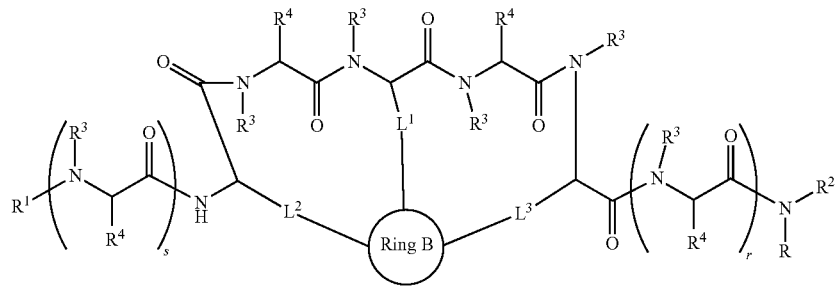

I-e or a pharmaceutically acceptable salt thereof, wherein each of Ring B, $L^1$, $L^2$, $L^3$, R, $R^1$, $R^2$, $R^3$, $R^4$, p, q, r, and s is as defined above and described in embodiments herein, both singly and in combination.

In certain embodiments, the present invention provides a compound of formula II:

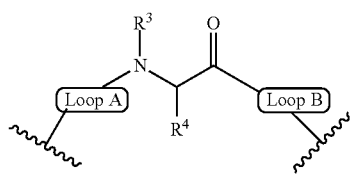

II or a pharmaceutically acceptable salt thereof, wherein:
each of Scaffold, $L^2$, $L^3$, $L^4$, Spacer$^1$, Spacer$^2$, R, $R^1$, $R^2$, $R^3$, m, and n is as defined above and described in embodiments herein, both singly and in combination;
Loop C is a bivalent natural or unnatural peptide attached to the amino acid residue linked to $L^2$ and the amino acid residue linked to $L^3$;
$R^5$, together with the atom to which $R^5$ attaches to, form a moiety comprising a hydrogen bond acceptor (HBA) and/or a hydrogen bond donor (HBD), which forms a hydrogen bond with an amino acid residue of the peptide between $L^2$ and $L^3$.

As defined above and described herein, Loop C is a bivalent natural or unnatural peptide attached to the amino acid residue linked to $L^2$ and the amino acid residue linked to $L^3$.

In some embodiments, Loop C is

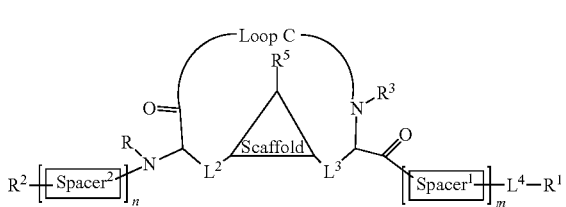

wherein each of Loop A, Loop B, $R^3$, and $R^4$ is as defined above and described in embodiments herein, both singly and in combination.

In some embodiments, Loop C is

In some embodiments, Loop C is

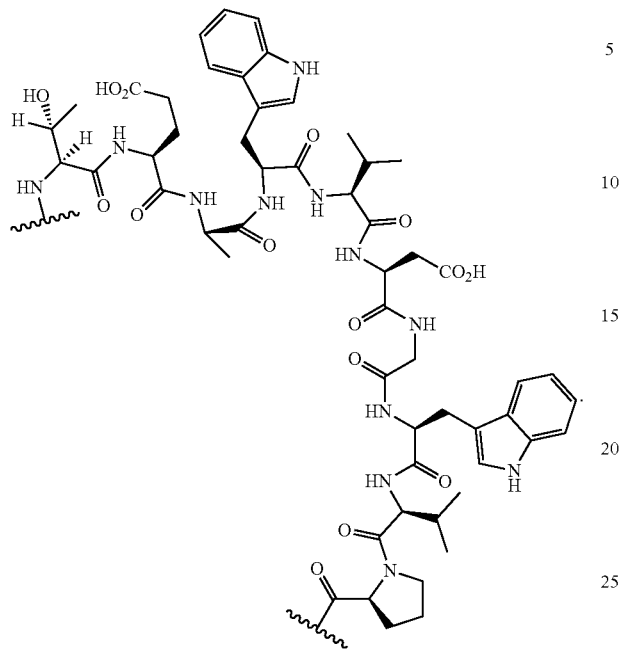

In some embodiments, Loop C is selected from those depicted in Table 2, below.

As defined above and described herein, $R^5$, together with the atom to which $R^5$ attaches to, form a moiety comprising a hydrogen bond acceptor (HBA) and/or a hydrogen bond donor (HBD), which forms a hydrogen bond with an amino acid residue of the peptide between $L^2$ and $L^3$.

In some embodiments, $R^5$ is hydrogen, which forms a hydrogen bond with an amino acid residue of Loop C.

In some embodiments, $R^5$ is hydrogen, wherein the atom to which $R^5$ attaches to forms a hydrogen bond with an amino acid residue of Loop C.

In some embodiments, $R^5$ comprises a hydrogen bond acceptor (HBA), which forms a hydrogen bond with an amino acid residue of Loop C.

In some embodiments, $R^5$ comprises a hydrogen bond donor (HBD), which forms a hydrogen bond with an amino acid residue of Loop C.

In some embodiments, $R^5$, together with the atom to which $R^5$ attaches to, form a —C(O)— group, wherein the O forms a hydrogen bond with an amino acid residue of Loop C.

In some embodiments, $R^5$, together with the atom to which $R^5$ attaches to, form a —NH— group, wherein the N or H forms a hydrogen bond with an amino acid residue of Loop C.

In some embodiments, $R^5$ comprises, or is, a —OH group, wherein the H forms a hydrogen bond with an amino acid residue of Loop C, and wherein R is as defined above and described in embodiments herein.

In some embodiments, $R^5$ comprises, or is, a —N(R)H group, wherein the H forms a hydrogen bond with an amino acid residue of Loop C, and wherein R is as defined above and described in embodiments herein.

In some embodiments, $R^5$ comprises a —C(O)— group, wherein the O forms a hydrogen bond with an amino acid residue of Loop C.

In some embodiments, $R^5$ is selected from those depicted in Table 2, below.

In some embodiments,

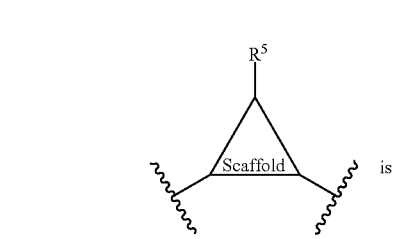 is

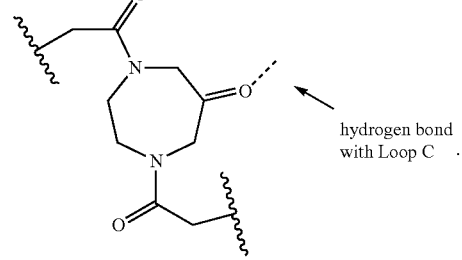

In some embodiments, is

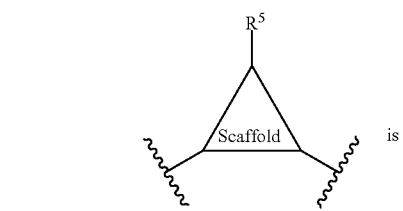

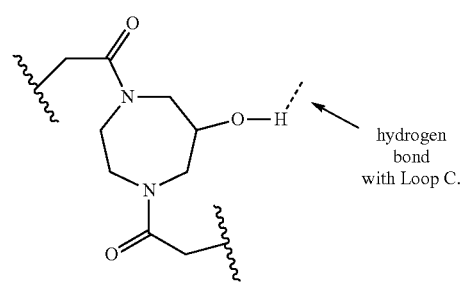

In some embodiments

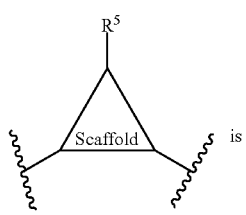 is

-continued

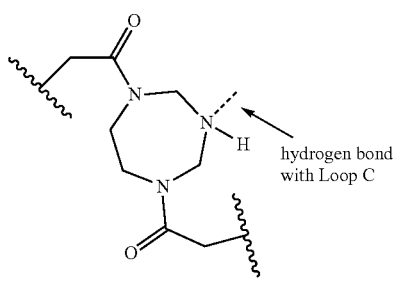

In some embodiments,

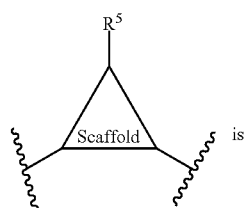 is

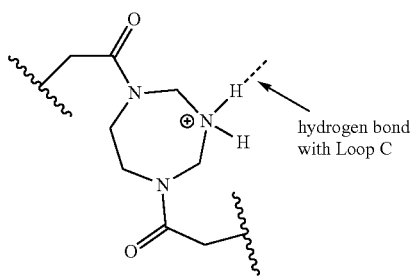

In some embodiments, is

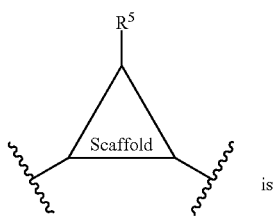 is

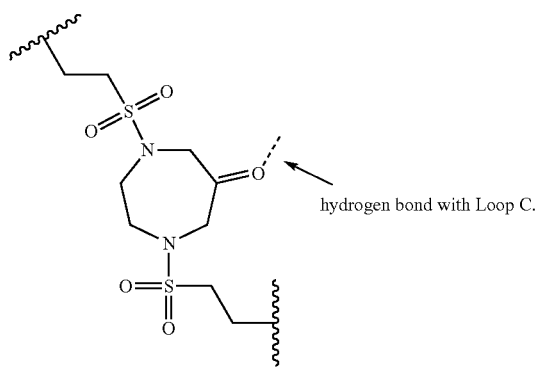

In some embodiments, the present invention provides a compound of formula II-a:

II-a

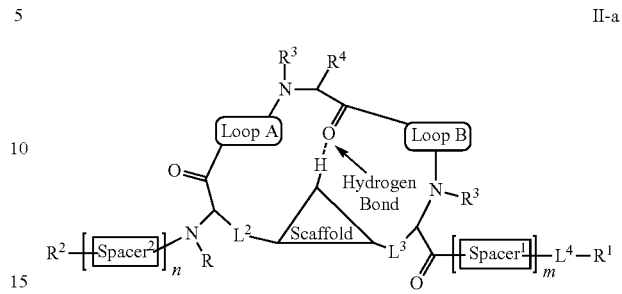

or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination.

In some embodiments, the present invention provides a compound of formula II-b:

II-b

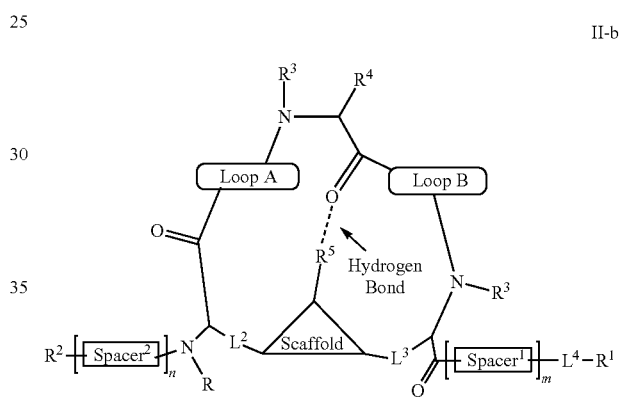

or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, $R^5$, m, and n is as defined above and described in embodiments herein, both singly and in combination, and wherein $R^5$ comprises a hydrogen bond donor (HBD), as defined above and described in embodiments herein.

In some embodiments, the present invention provides a compound of formula II-c:

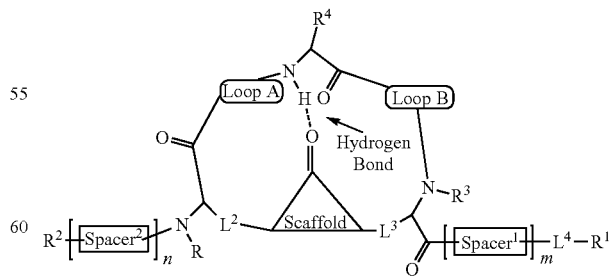

or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination.

In some embodiments, the present invention provides a compound of formula II-d:

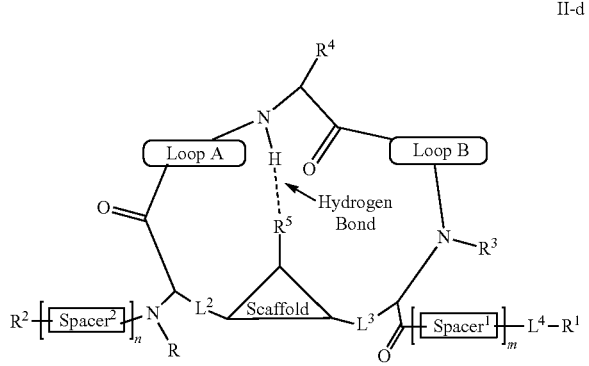

II-d or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, $R^5$, m, and n is as defined above and described in embodiments herein, both singly and in combination, and wherein $R^5$ comprises a hydrogen bond acceptor (HBA), as defined above and described in embodiments herein.

In some embodiments, the present invention provides a compound of formula II-e:

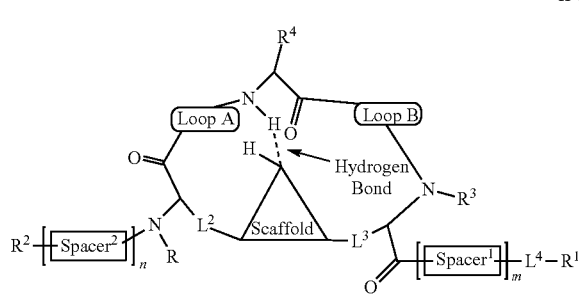

II-e or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination, and the atom to which $R^5$ (which is H in formula II-e) attaches to forms a hydrogen bond with an amino acid residue as shown in formula II-e.

In some embodiments, the present invention provides a compound of formula II-f:

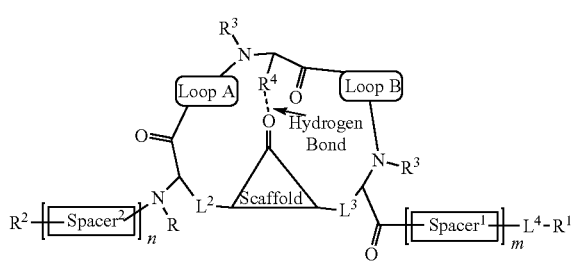

II-f or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination, and one or more $R^4$ independently comprises a hydrogen bond donor (HBD), as defined above and described in embodiments herein.

In some embodiments, the present invention provides a compound of formula II-g:

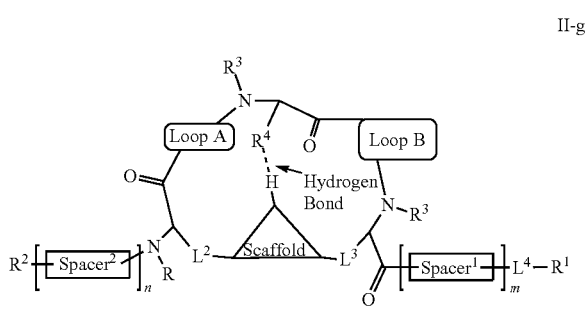

II-g or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination, and one or more $R^4$ independently comprises a hydrogen bond acceptor (HBA), as defined above and described in embodiments herein.

In some embodiments, the present invention provides a compound of formula II-h:

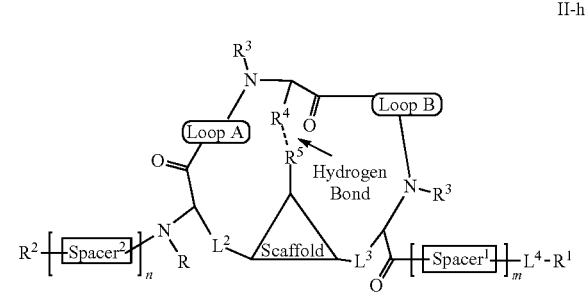

II-h or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, $R^5$, m, and n is as defined above and described in embodiments herein, both singly and in combination, and wherein a $R^4$ comprises a hydrogen bond acceptor (HBA) or a hydrogen bond donor (HBD), and forms a hydrogen bond with $R^5$.

In some embodiments, the present invention provides a compound of formula II-i:

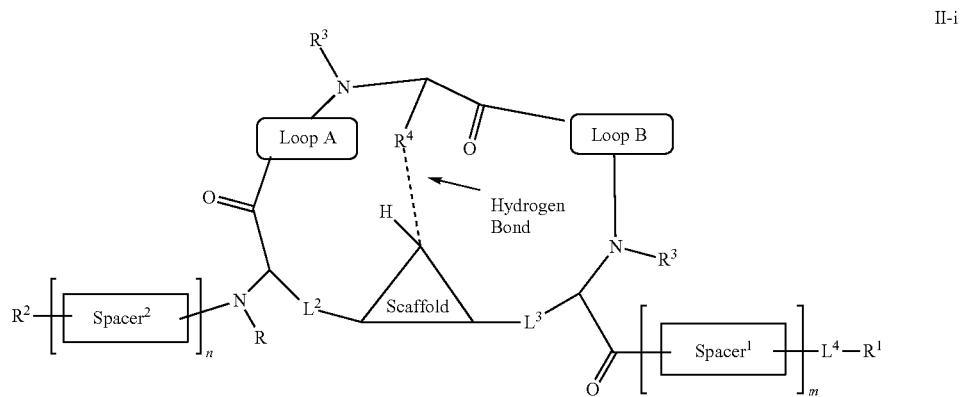

or a pharmaceutically acceptable salt thereof, wherein each of Scaffold, Loop A, Loop B, $L^2$, $L^3$, $L^4$, Spacer$^1$, Spacer$^2$, R, $R^1$, $R^2$, $R^3$, $R^4$, m, and n is as defined above and described in embodiments herein, both singly and in combination, and wherein a $R^4$ comprises a hydrogen bond donor (HBD), and forms a hydrogen bond with the atom to which $R^5$ (which is H in formula II-i) attaches.

Exemplary compounds of the invention are set forth in Table 1 and Table 2, below.

TABLE 1

Exemplary compounds

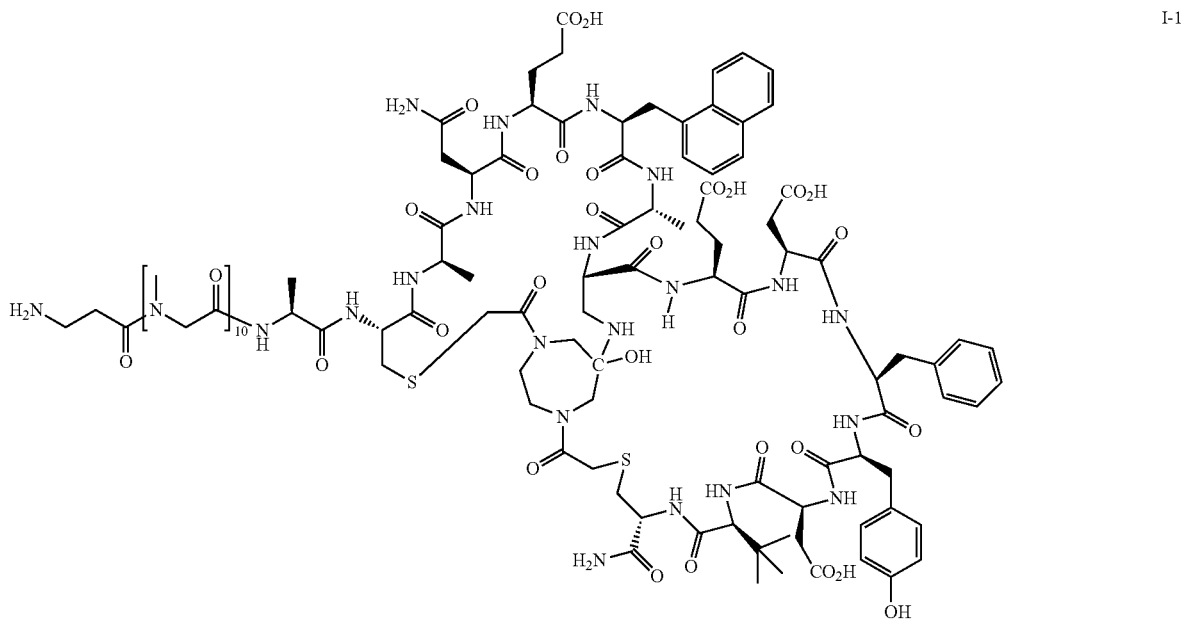

I-1

TABLE 1-continued
Exemplary compounds
I-2
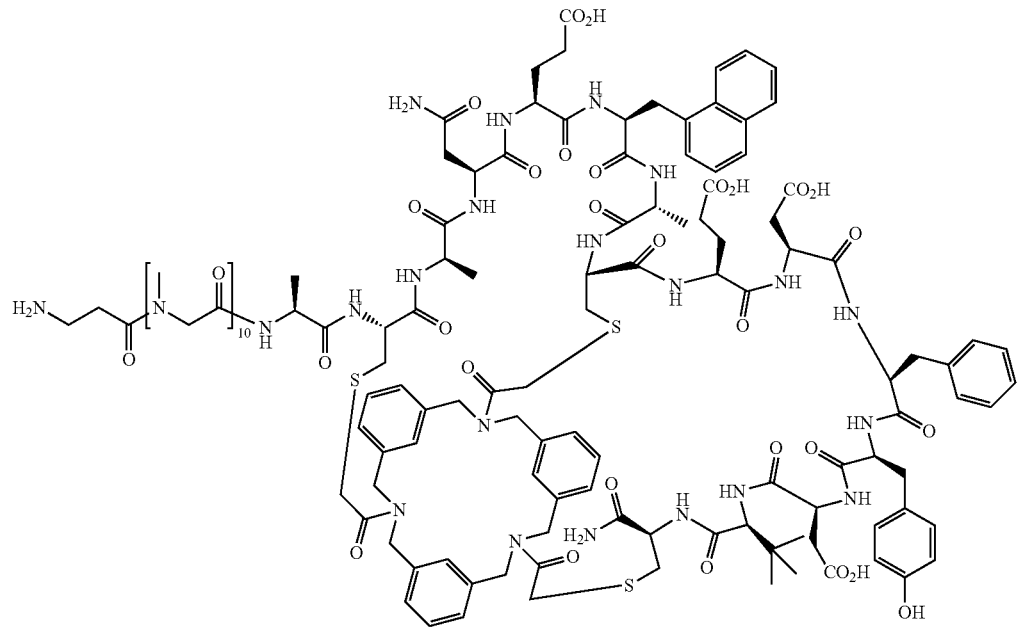
I-3
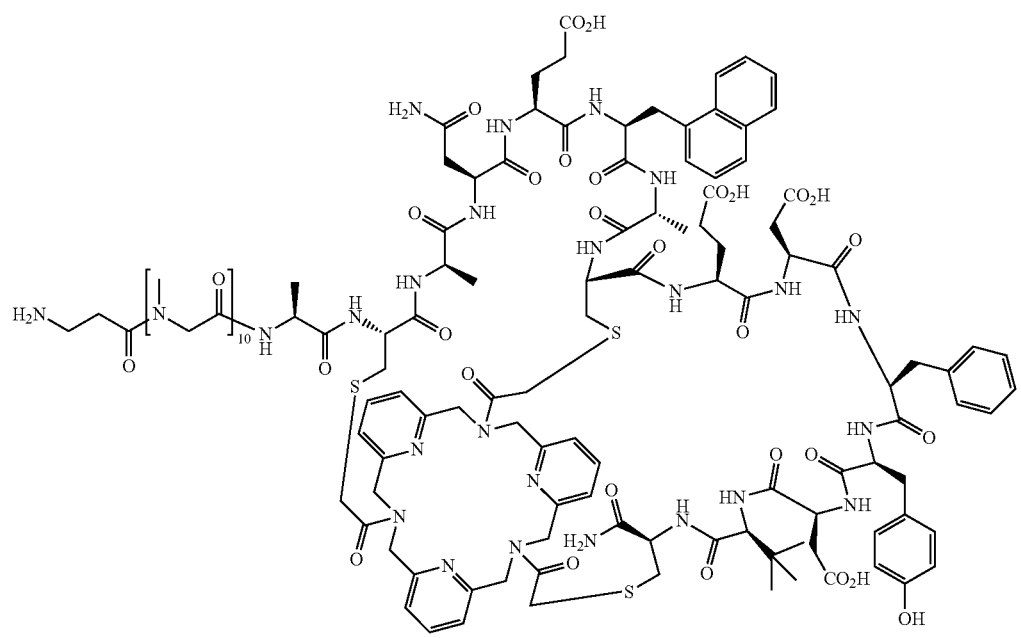

TABLE 1-continued
Exemplary compounds
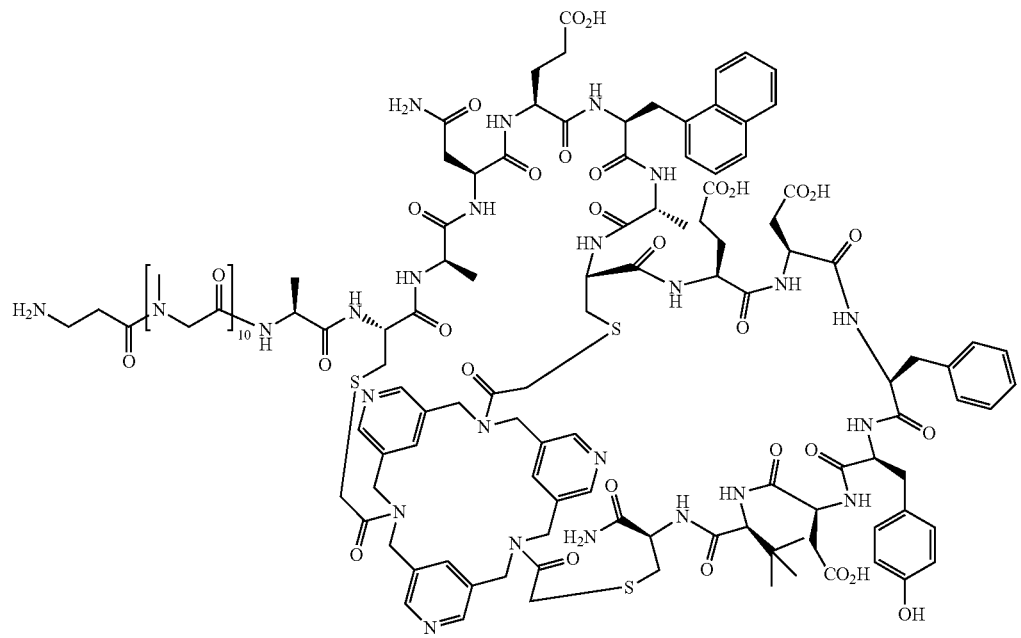
I-4
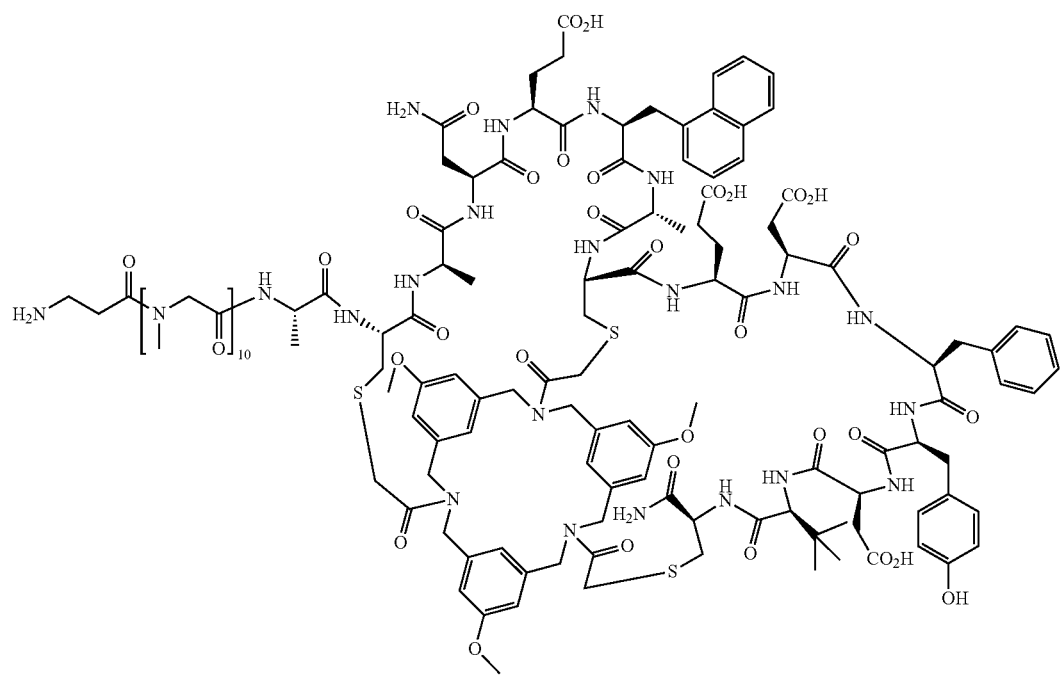
I-5

TABLE 1-continued
Exemplary compounds
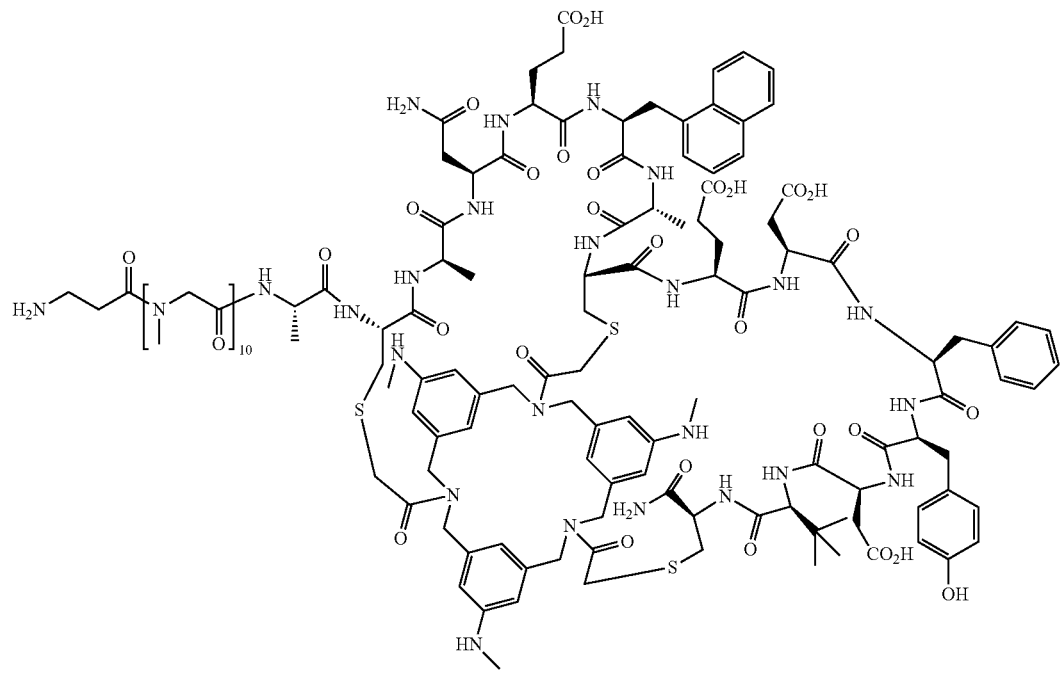
I-6
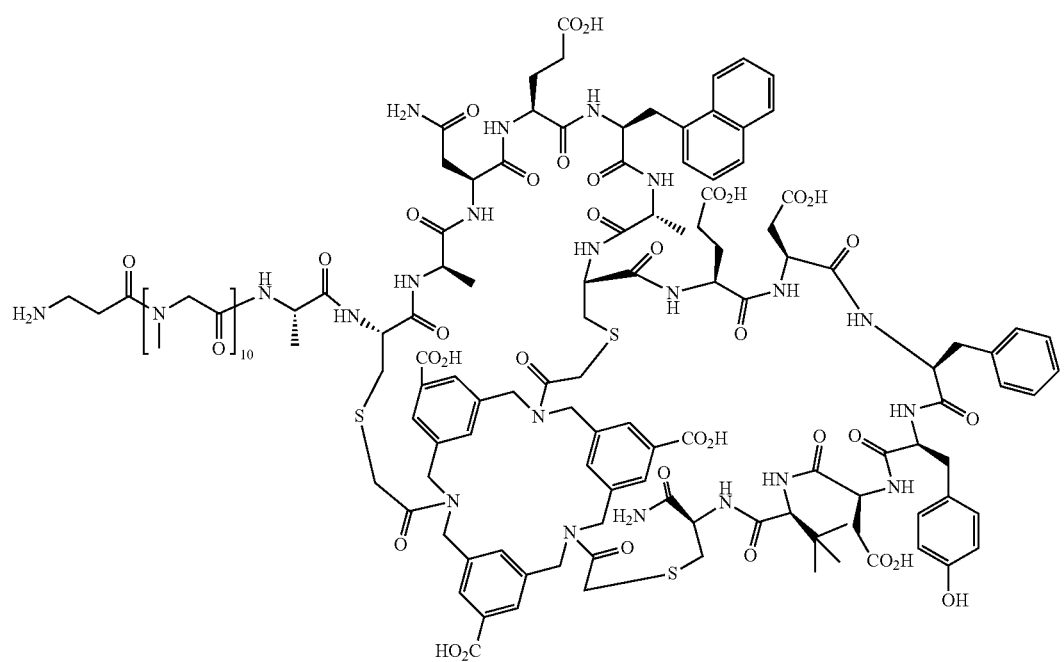
I-7

TABLE 1-continued
Exemplary compounds
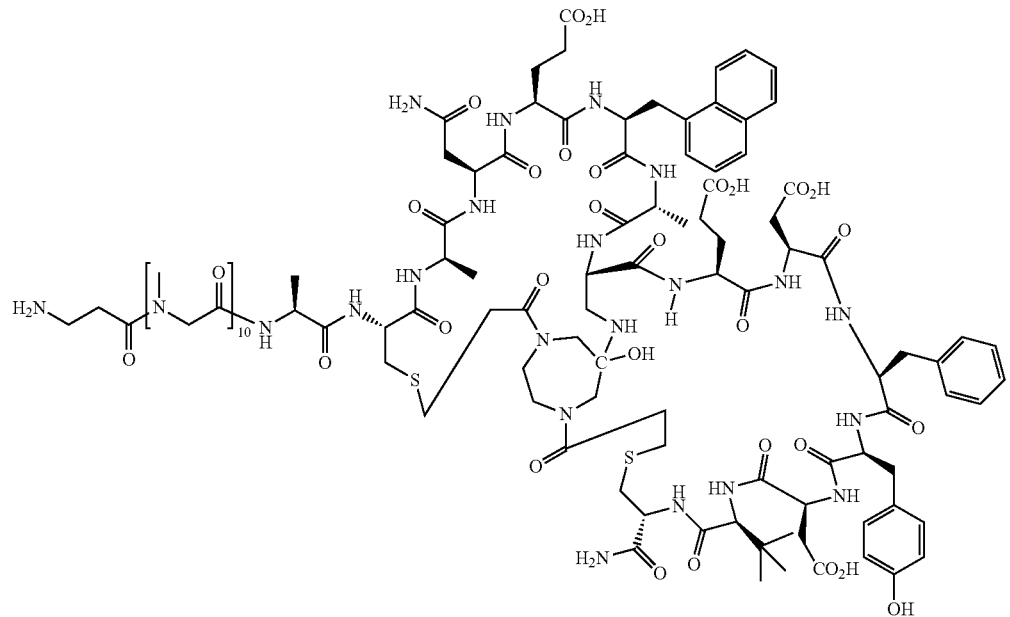
I-8
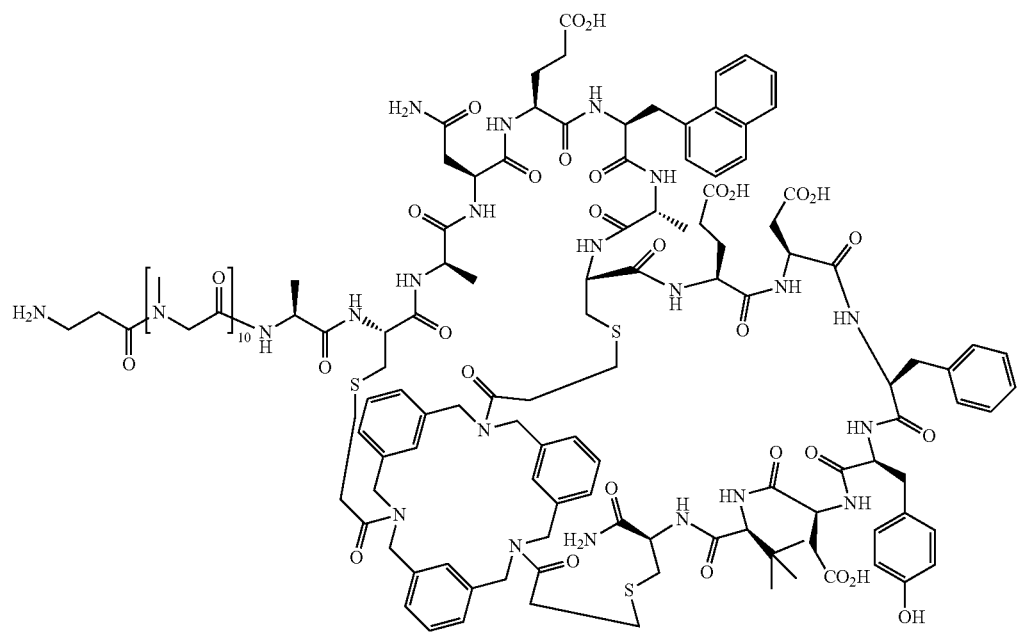
I-9

TABLE 1-continued
Exemplary compounds
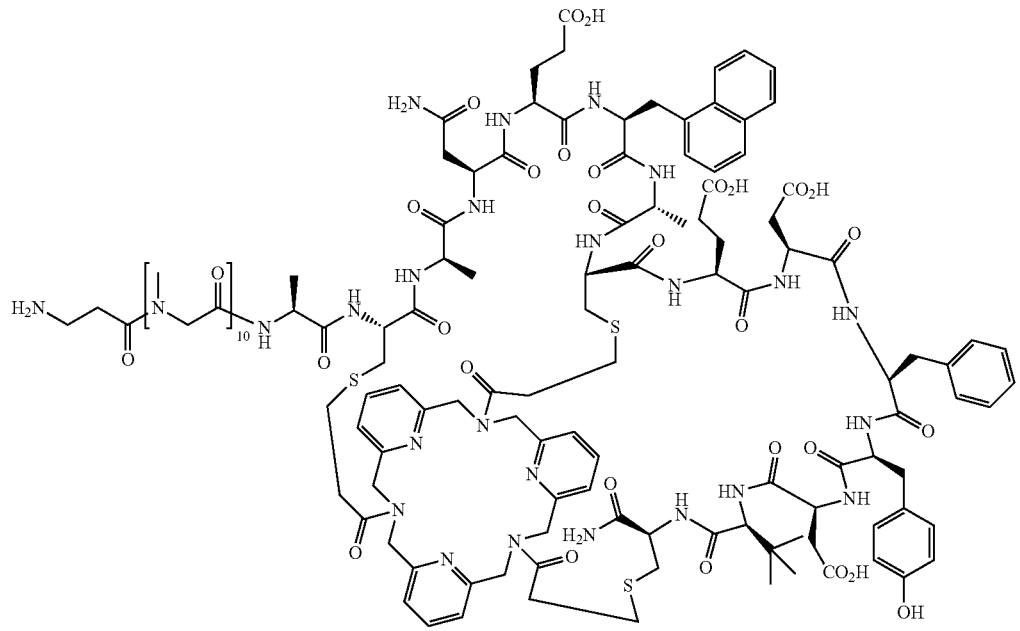
I-10
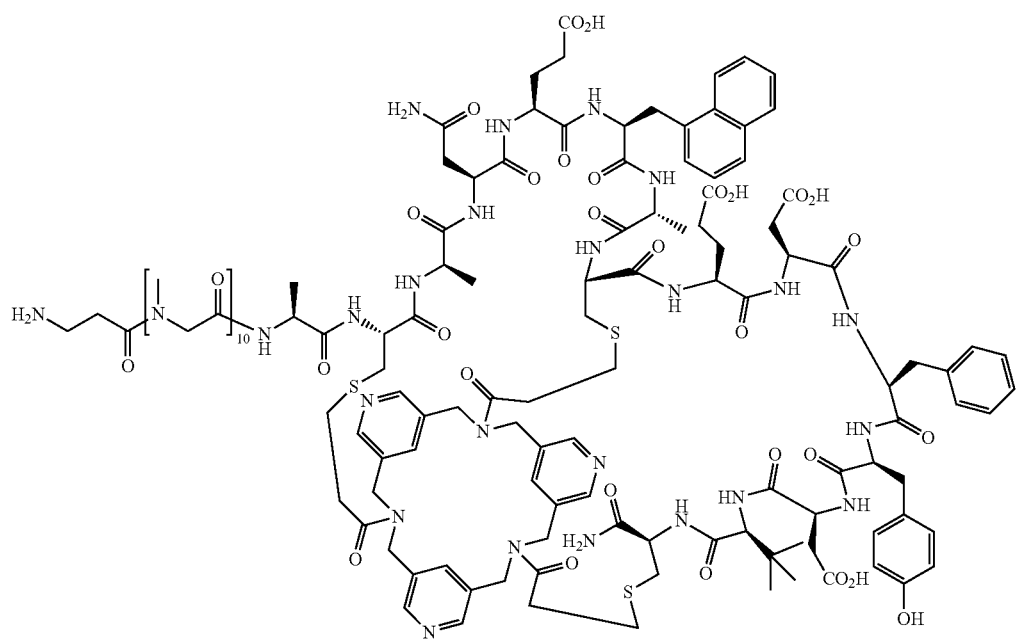
I-11

TABLE 1-continued
Exemplary compounds
I-12
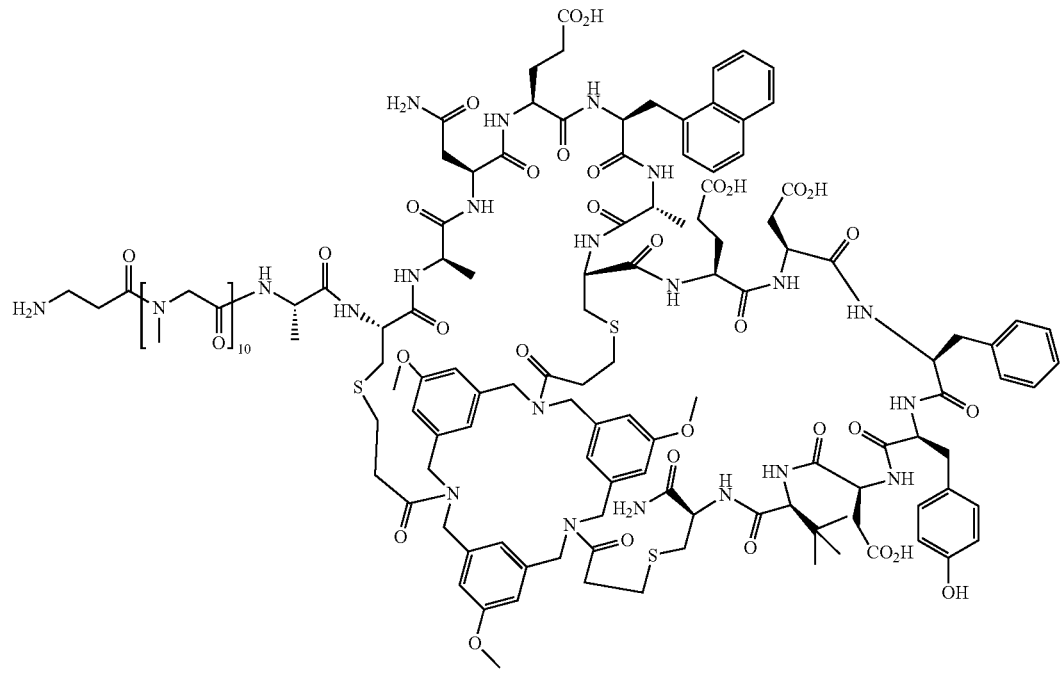
I-13
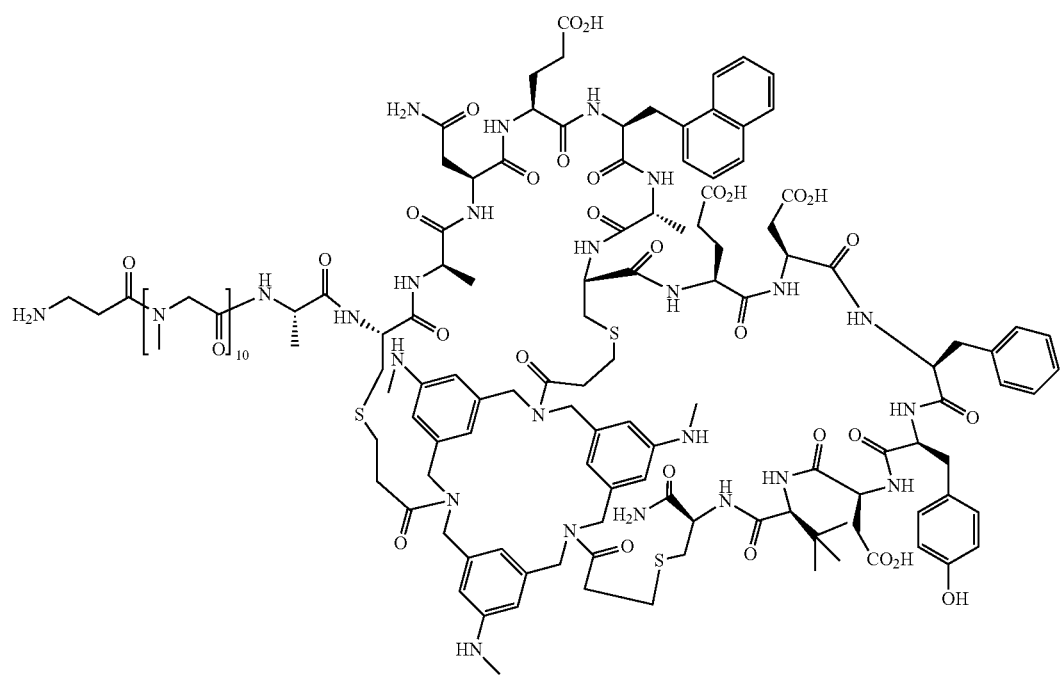

TABLE 1-continued
Exemplary compounds
I-14
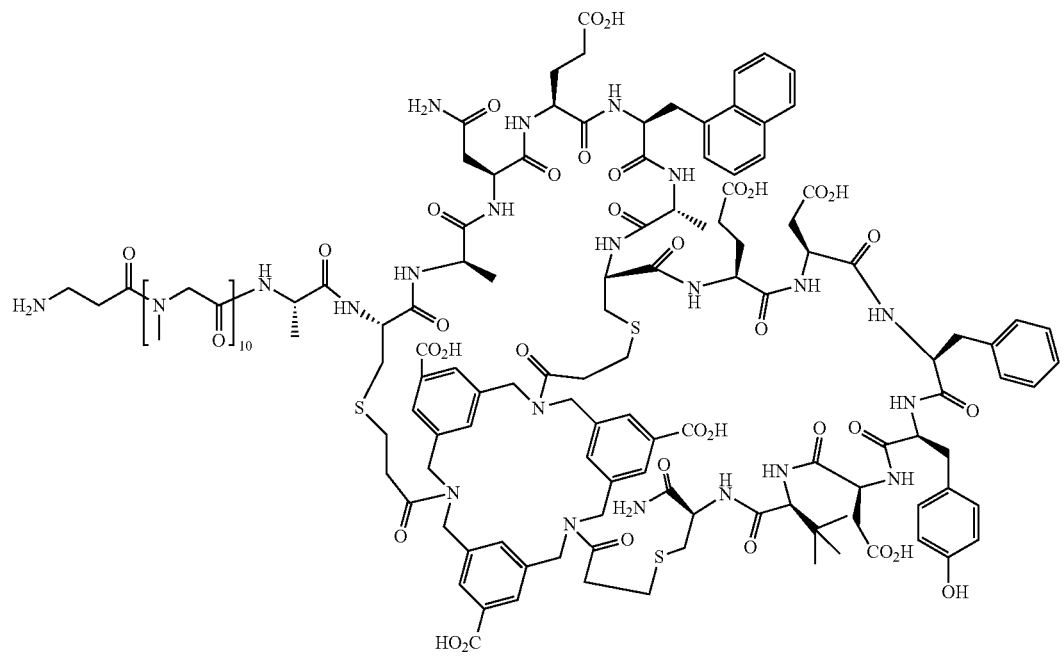
I-15
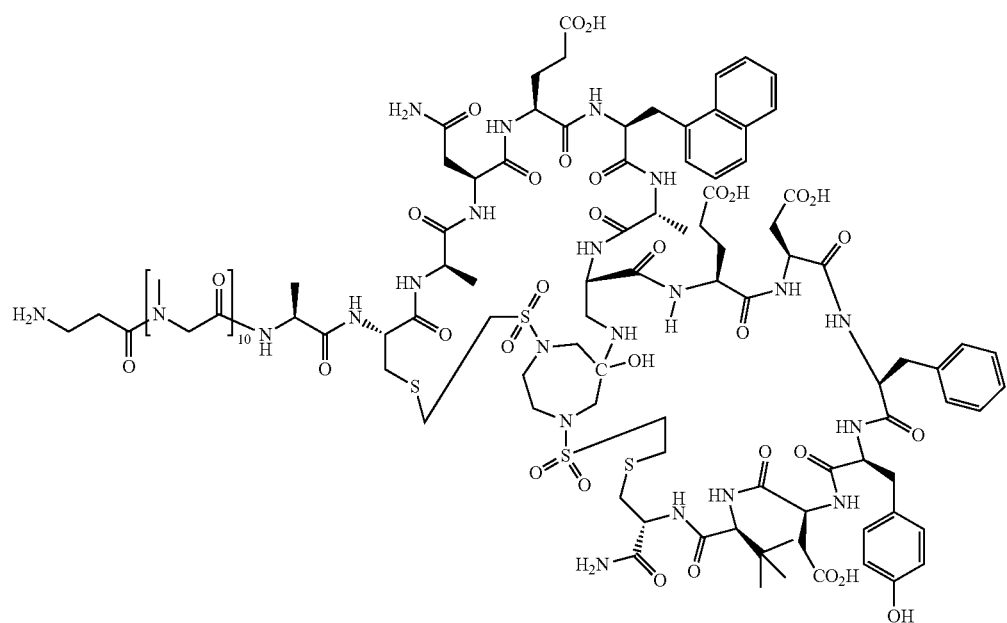

TABLE 1-continued
Exemplary compounds
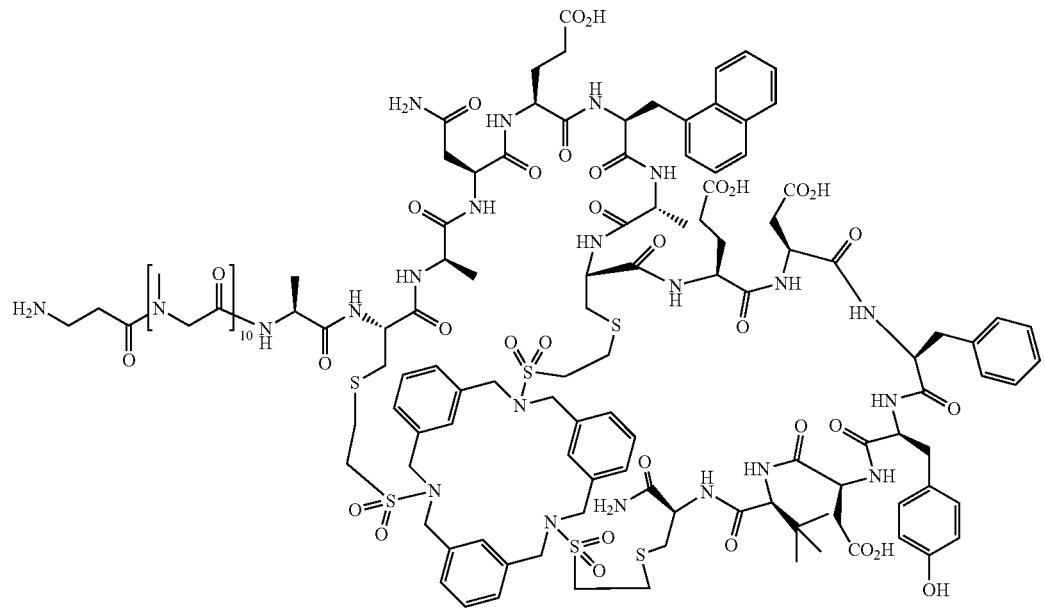
I-16
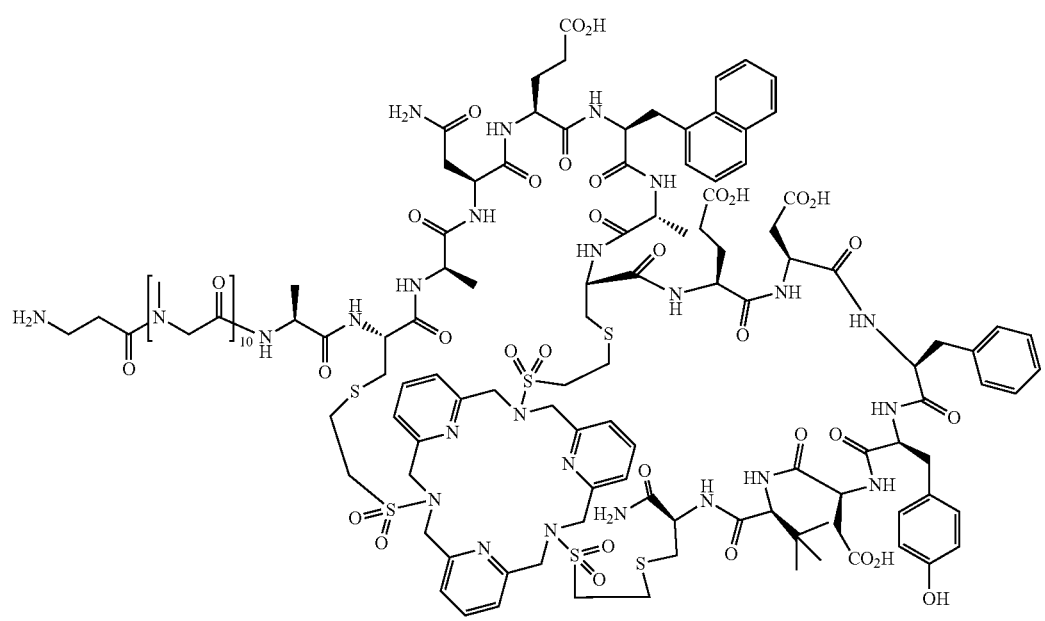
I-17

TABLE 1-continued
Exemplary compounds
I-18
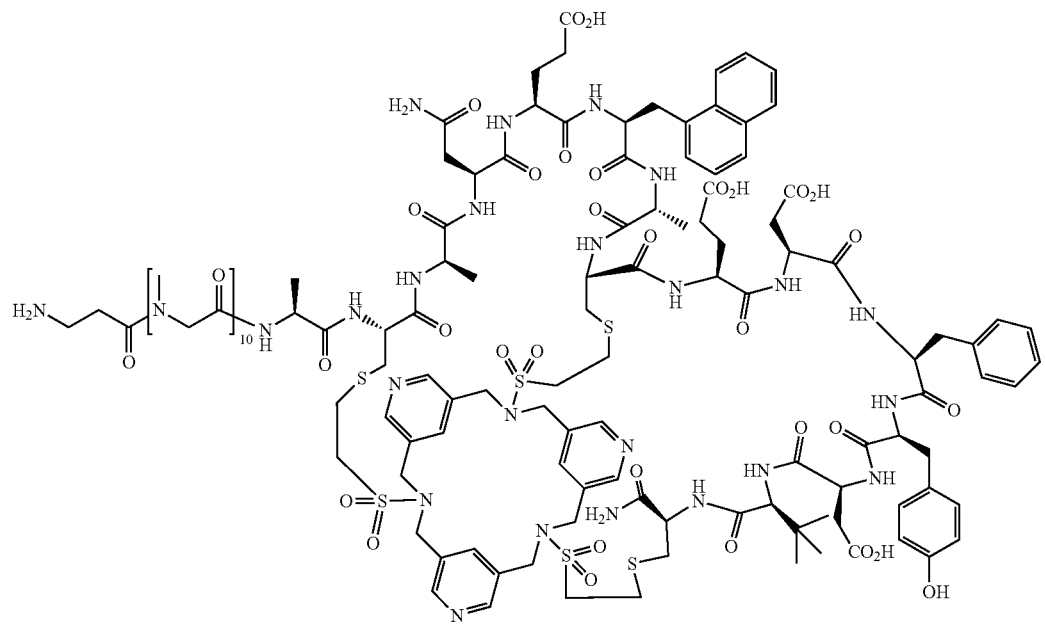
I-19
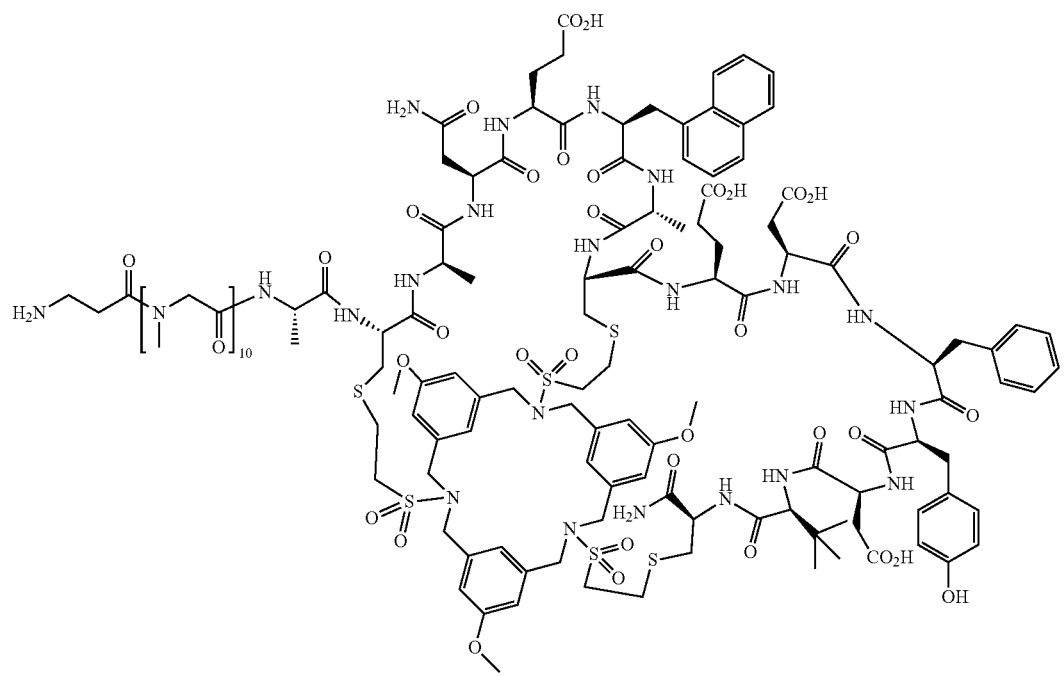

TABLE 1-continued
Exemplary compounds
I-20
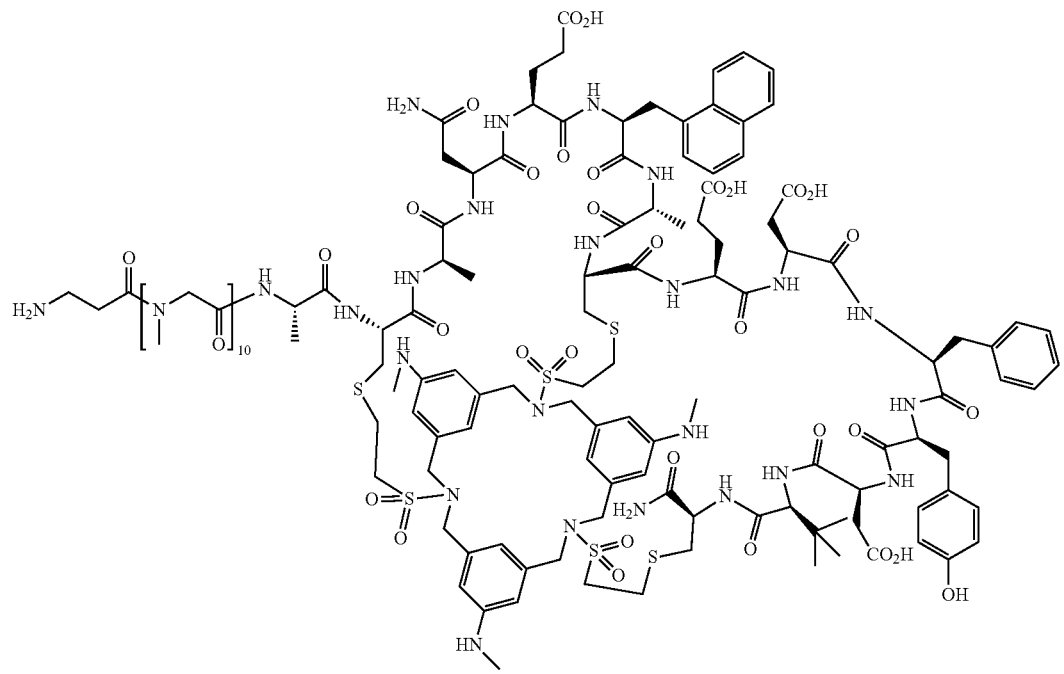
I-21
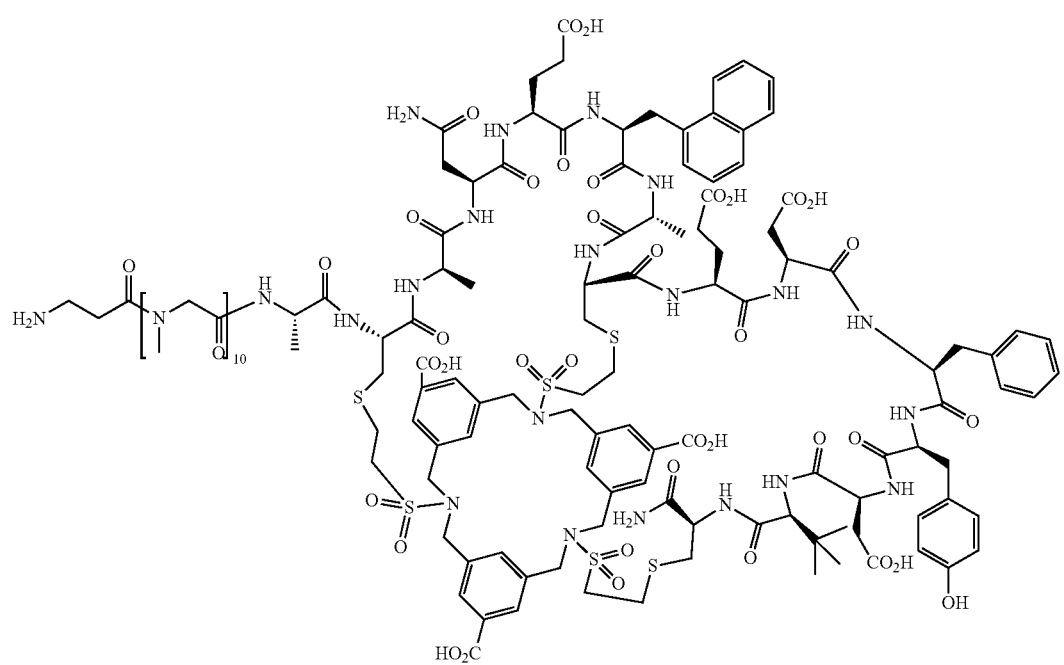

TABLE 1-continued
Exemplary compounds
I-22
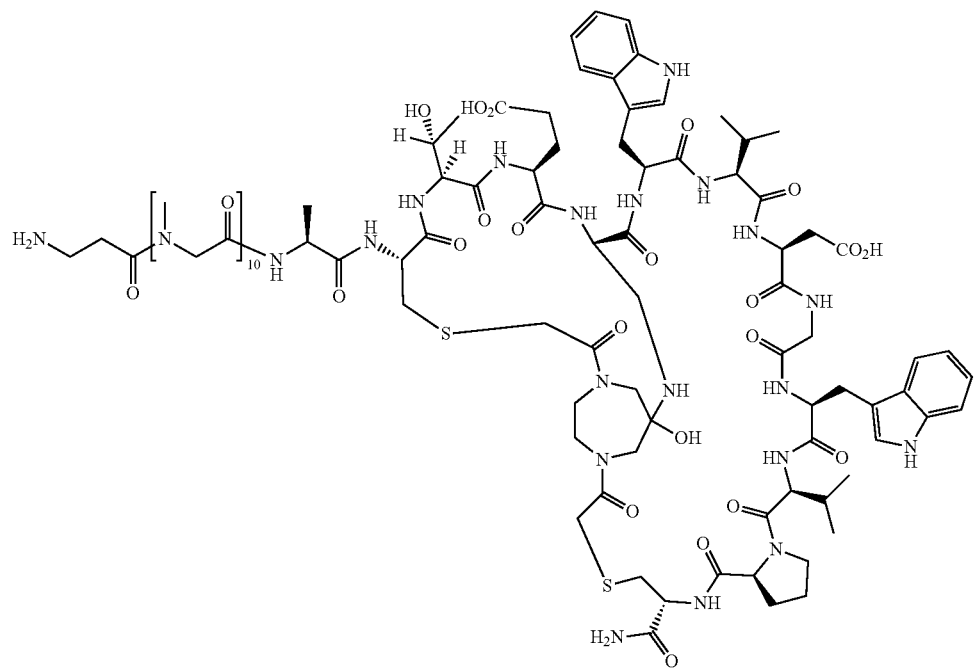
I-23
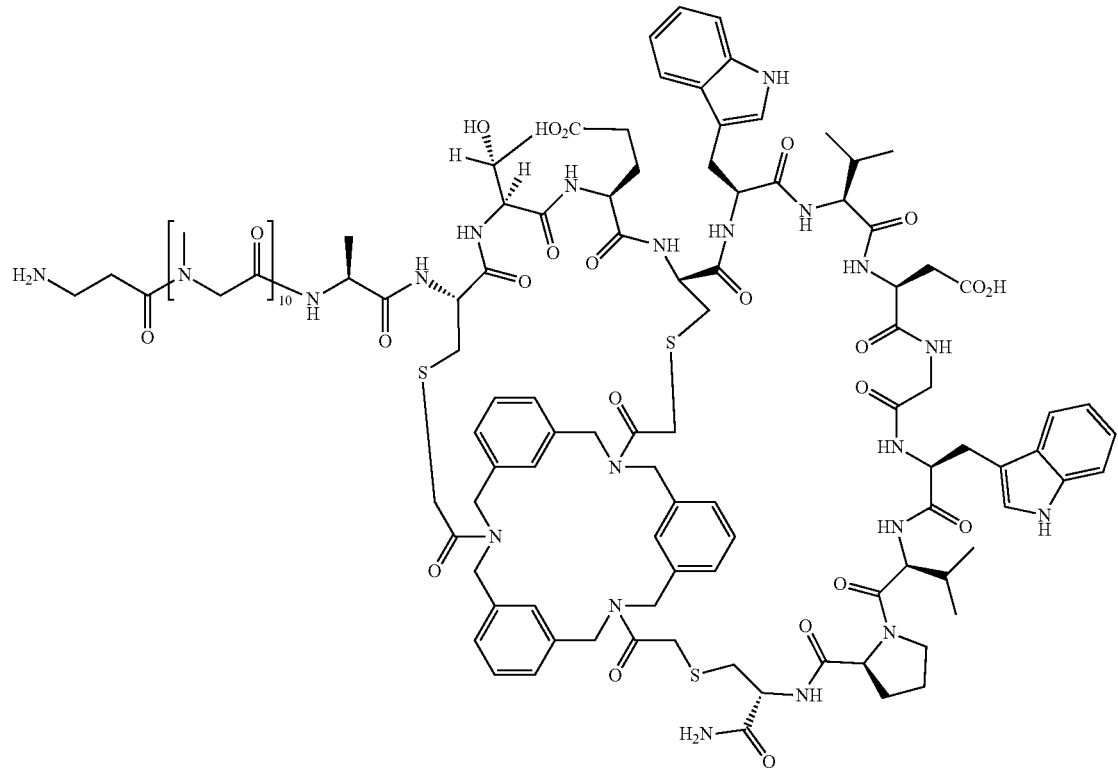

TABLE 1-continued
Exemplary compounds
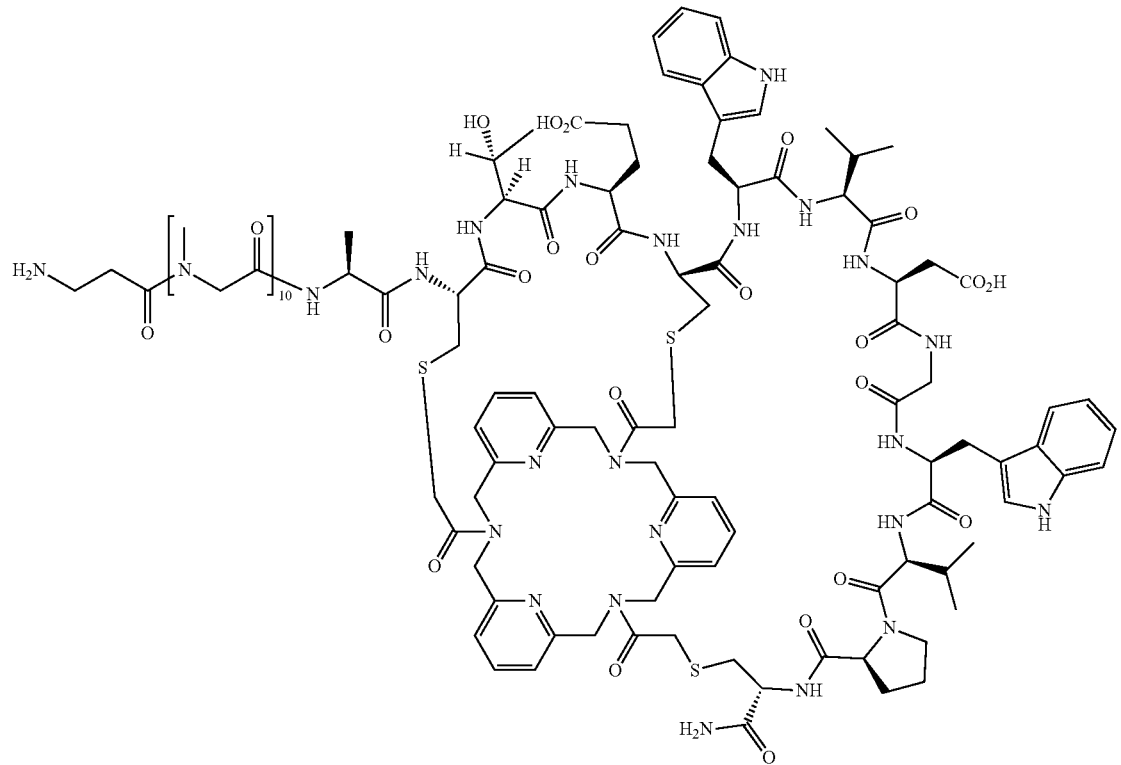
I-24
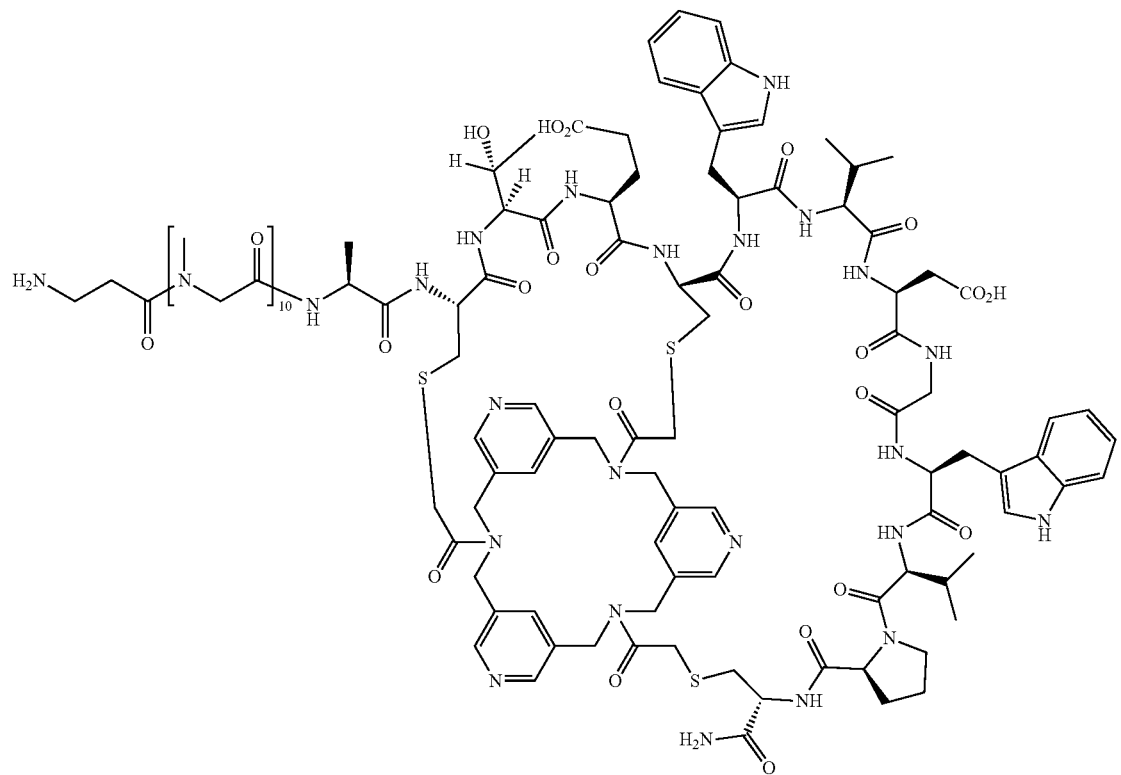
I-25

TABLE 1-continued
Exemplary compounds
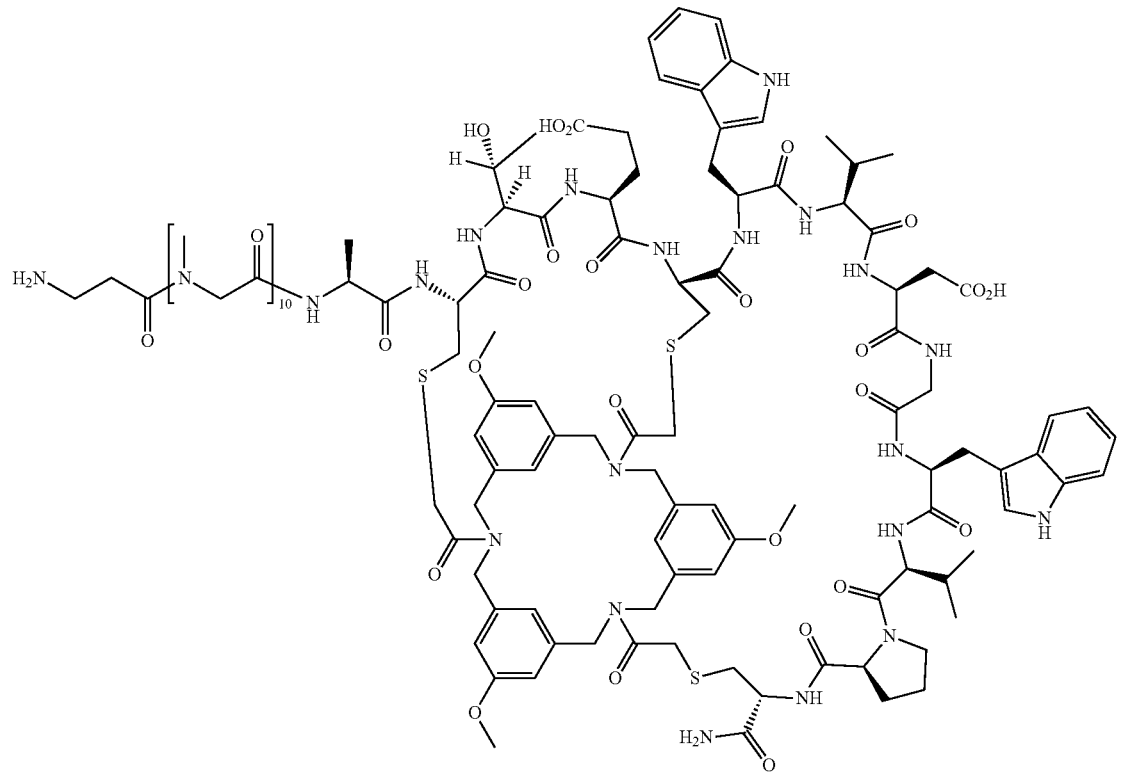
I-26
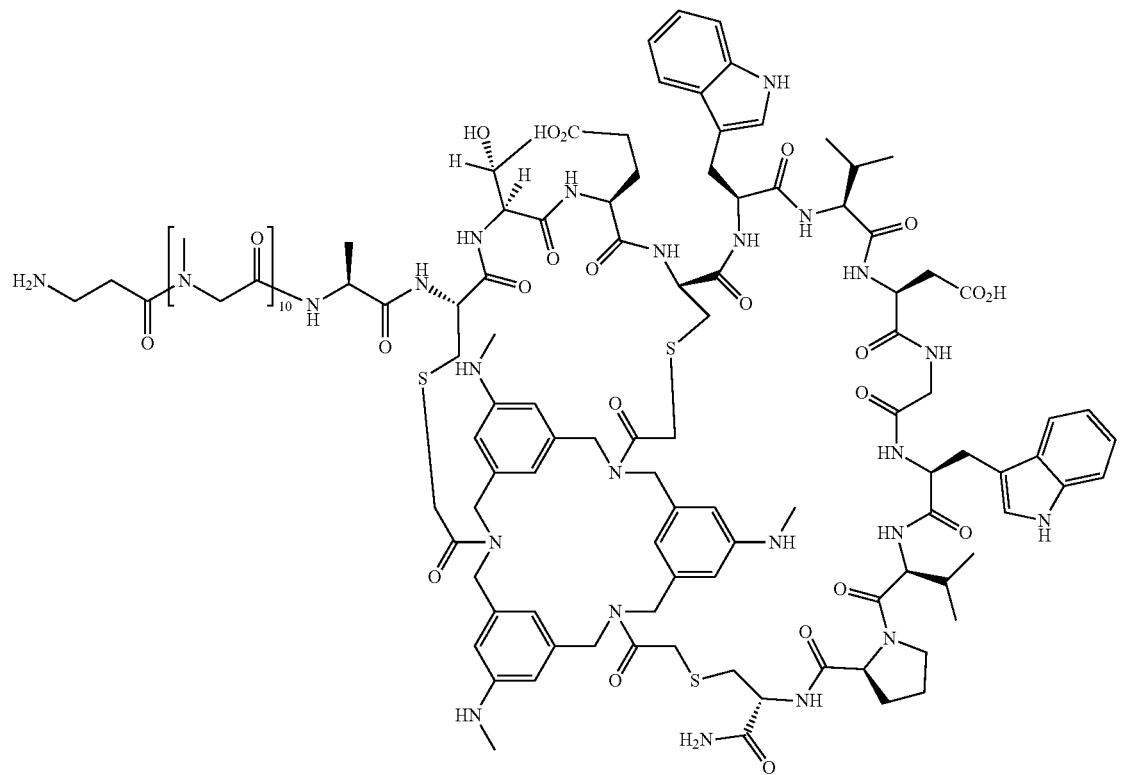
I-27

TABLE 1-continued
Exemplary compounds
I-28
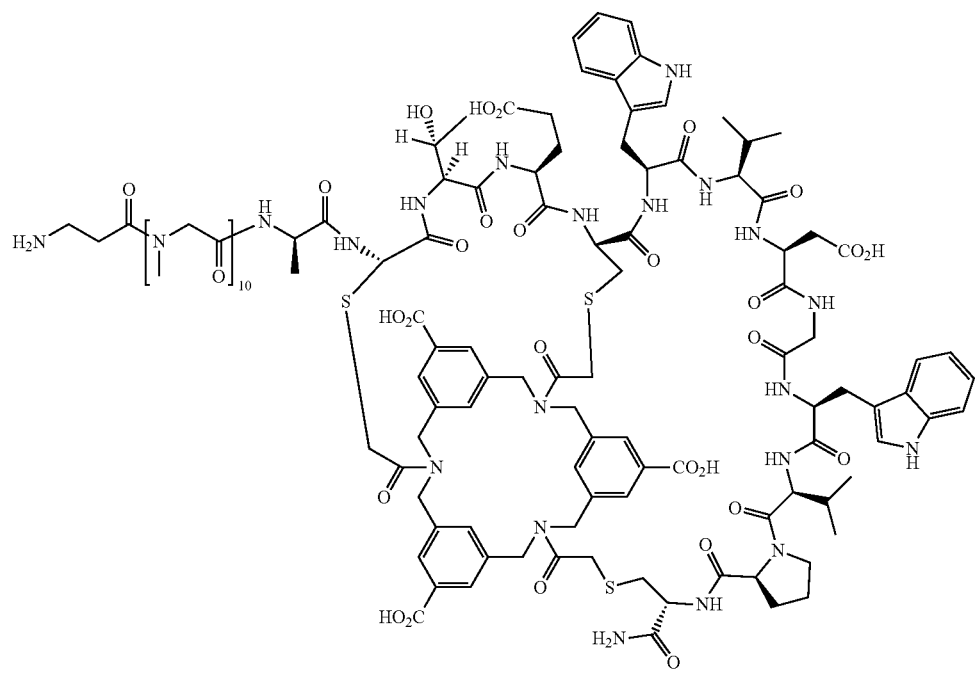
I-29
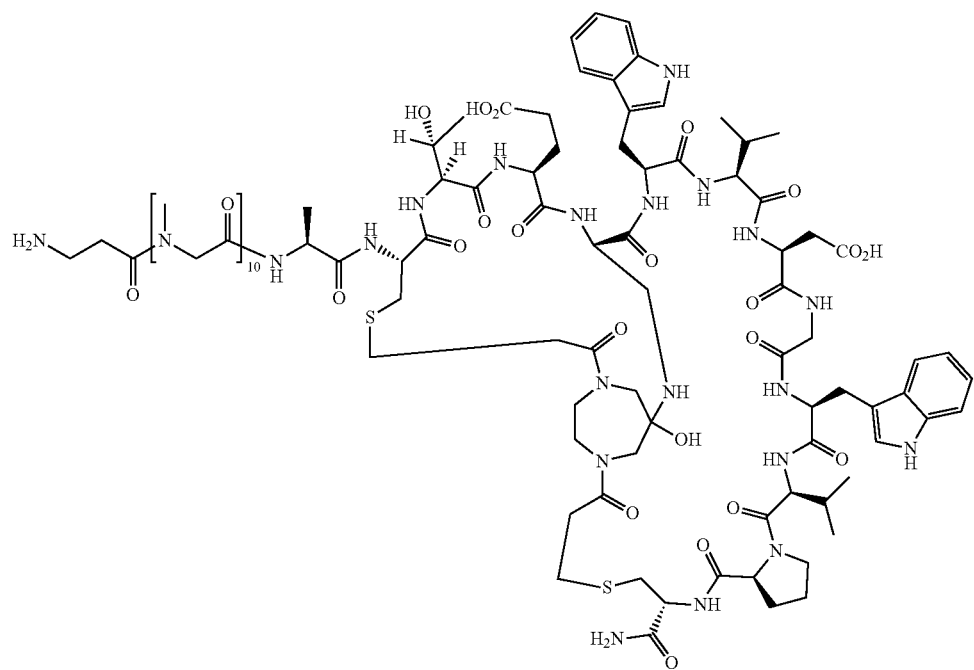

TABLE 1-continued
Exemplary compounds
I-30
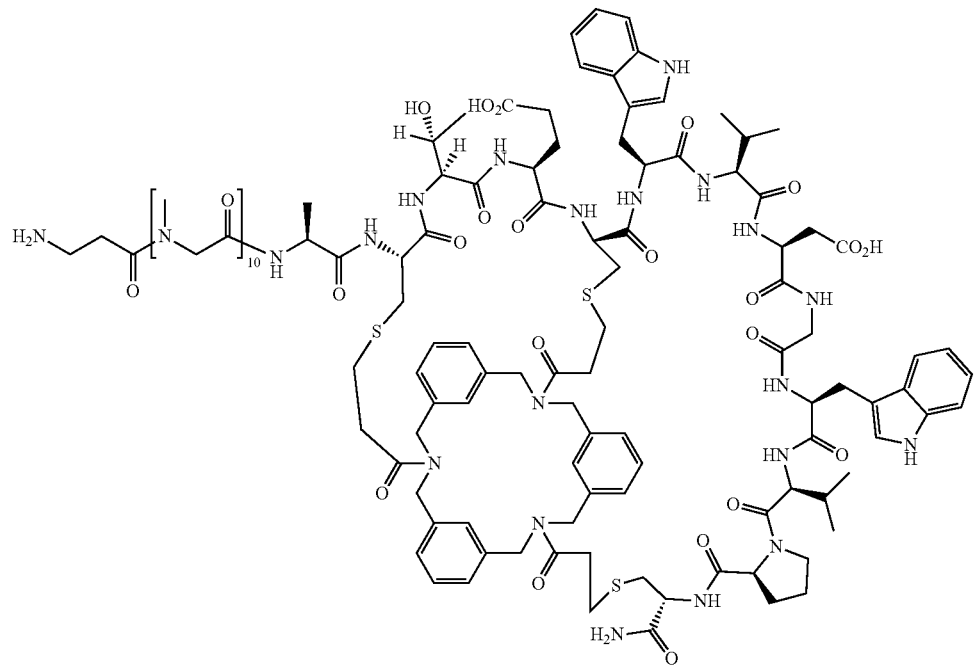
I-31
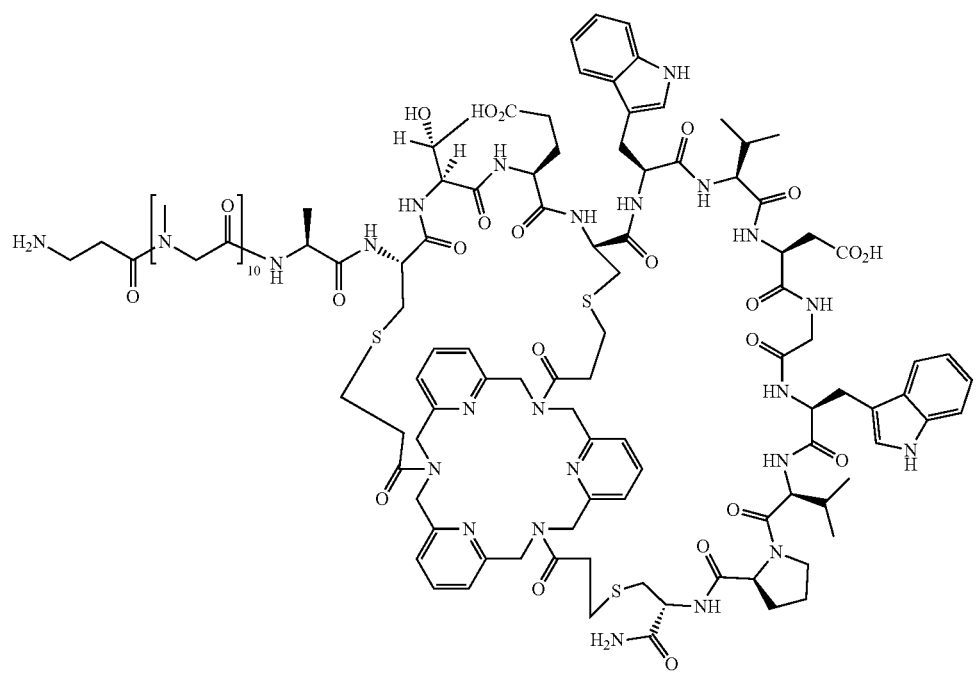

TABLE 1-continued
Exemplary compounds
I-32
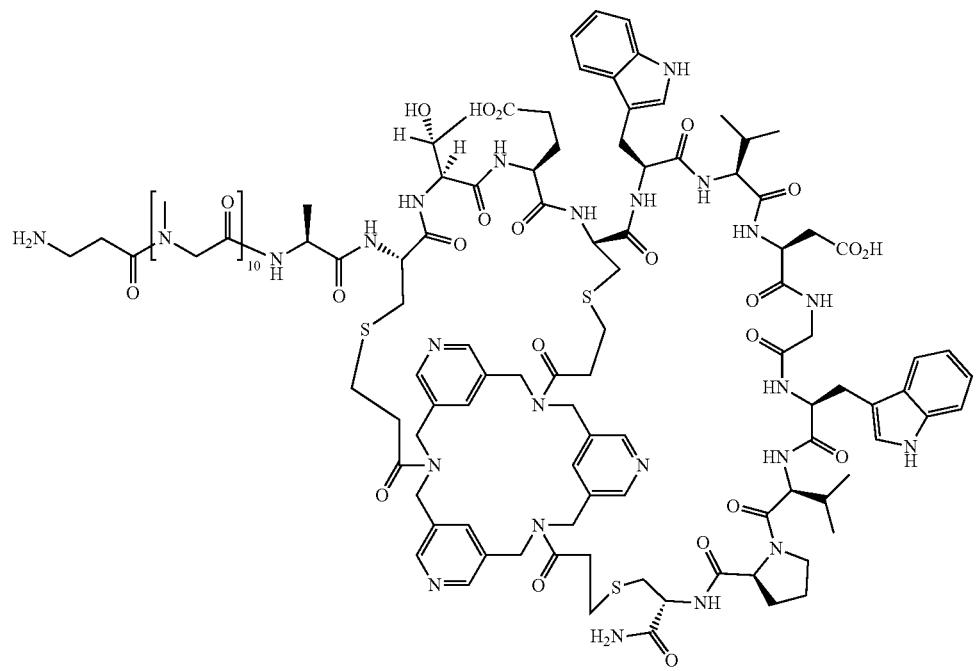
I-33
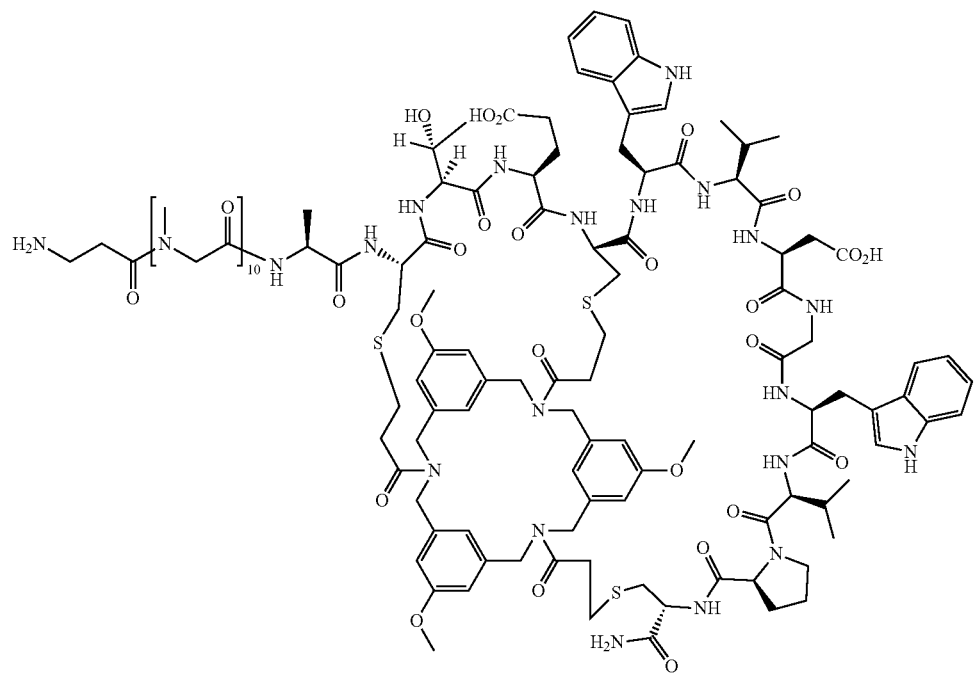

TABLE 1-continued
Exemplary compounds
I-34
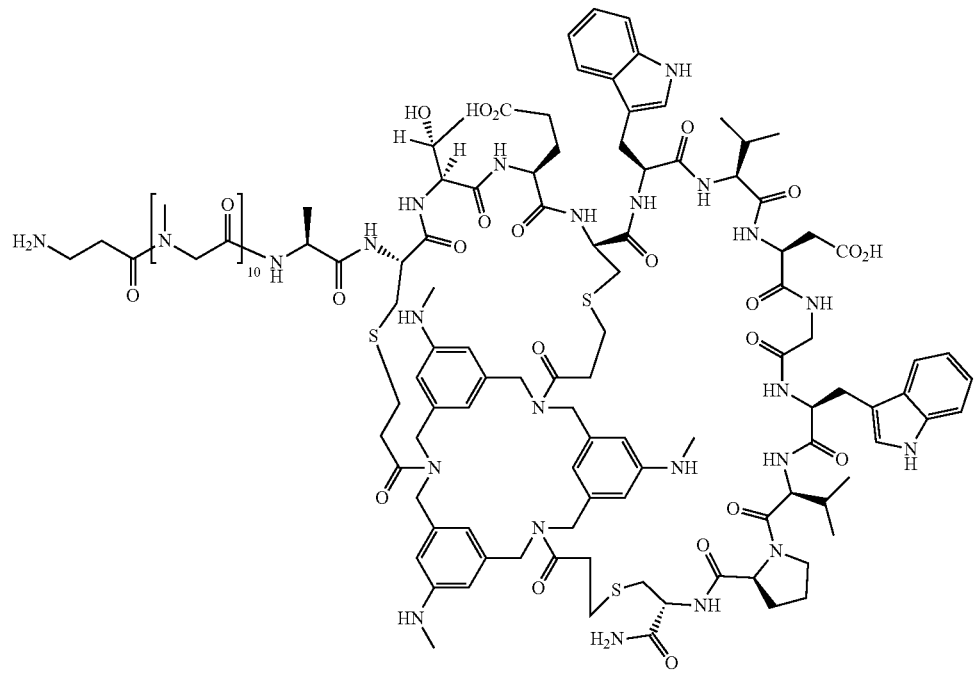
I-35
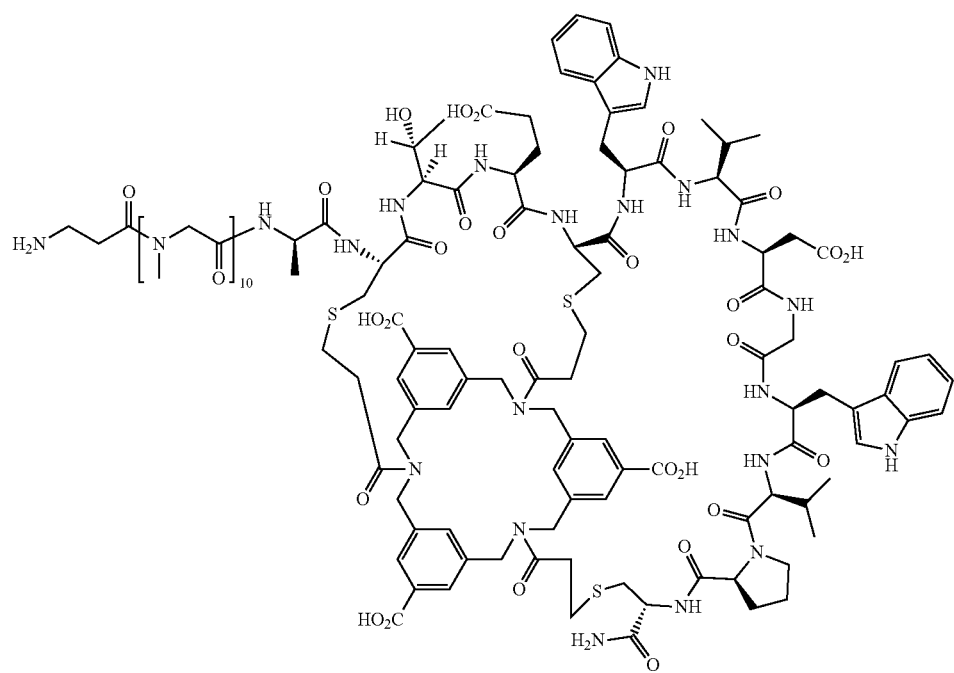

TABLE 1-continued
Exemplary compounds
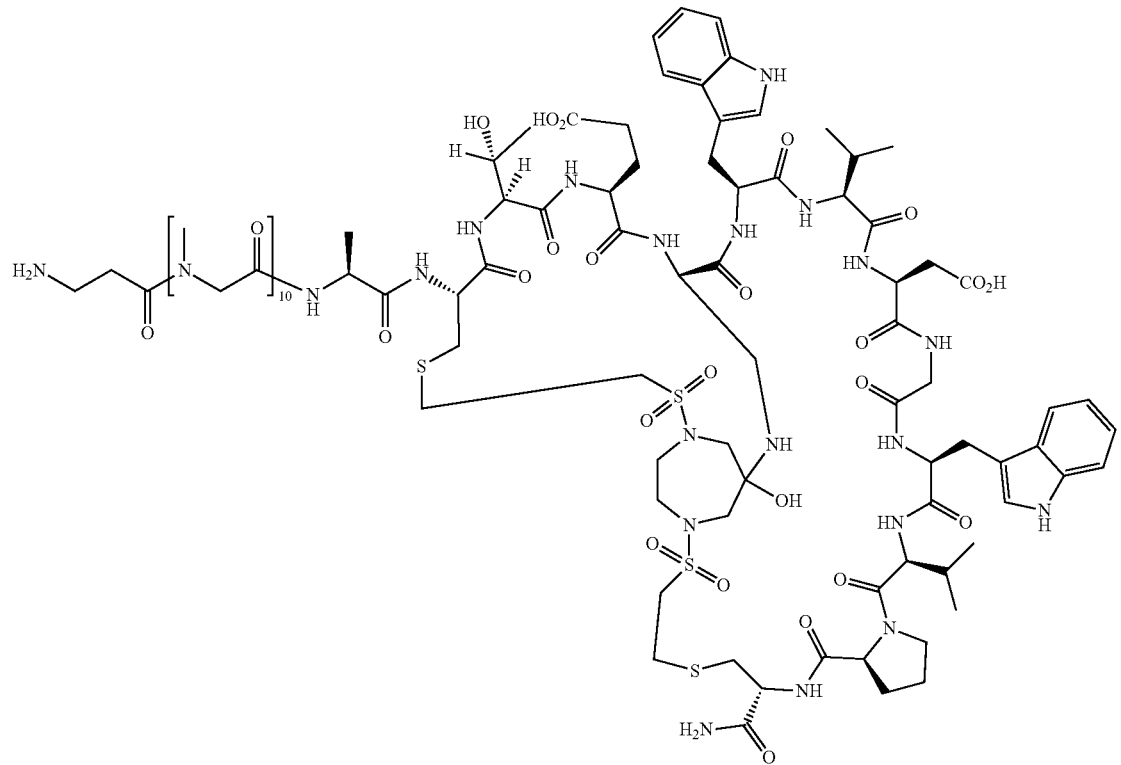
I-36
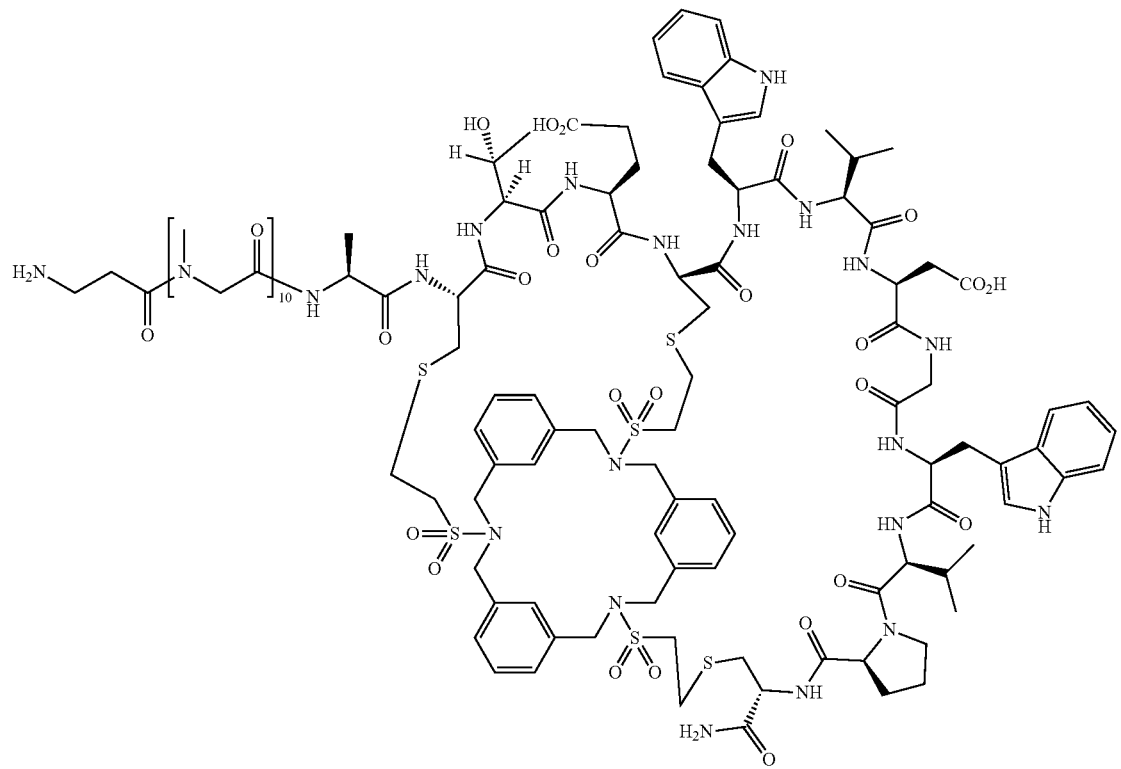
I-37

TABLE 1-continued
Exemplary compounds
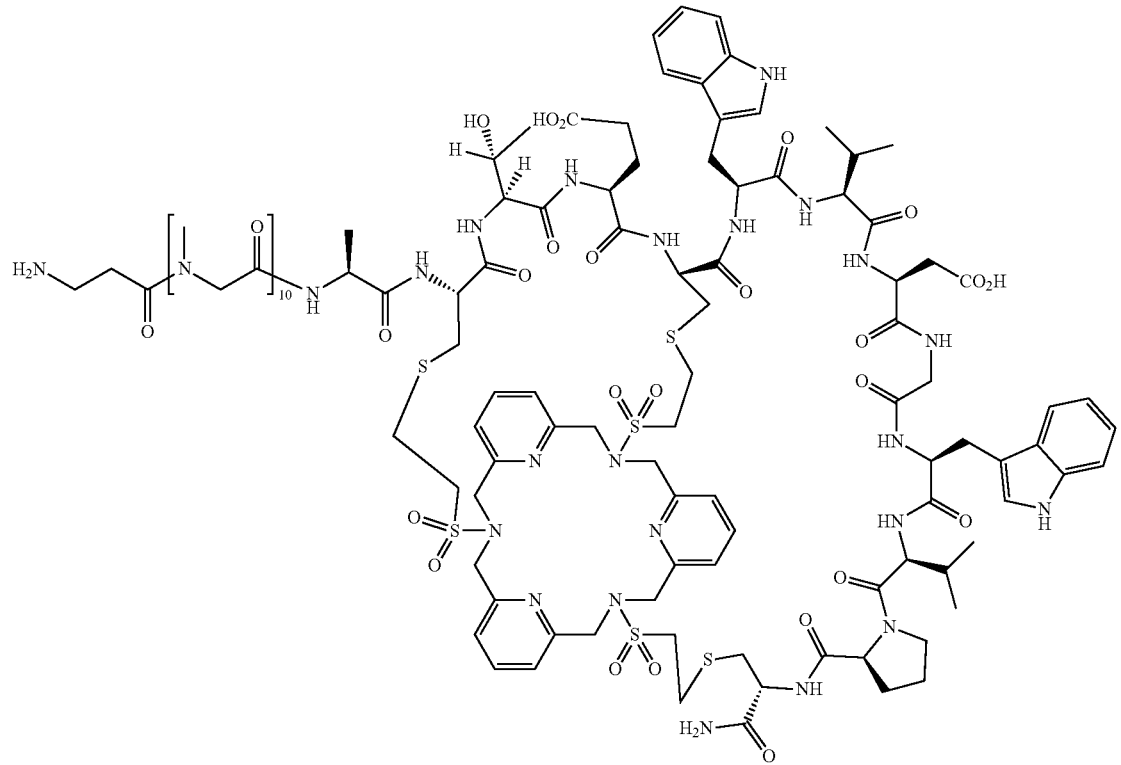
I-38
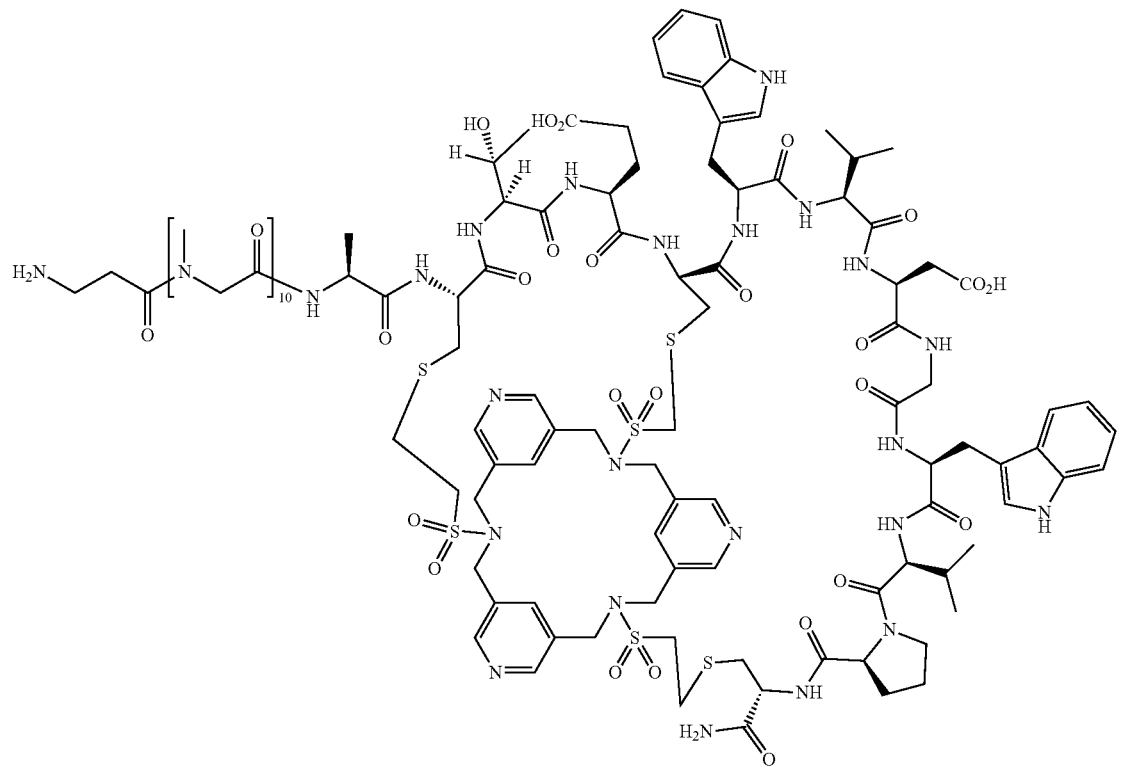
I-39

TABLE 1-continued
Exemplary compounds
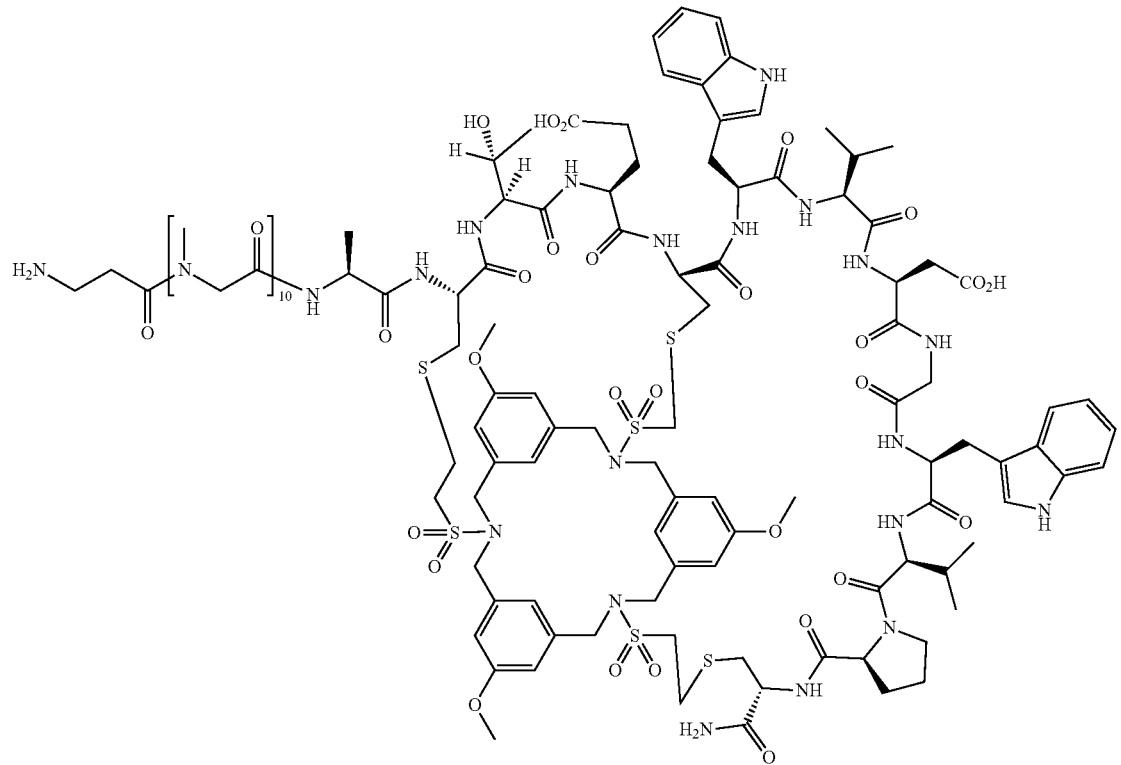
I-40
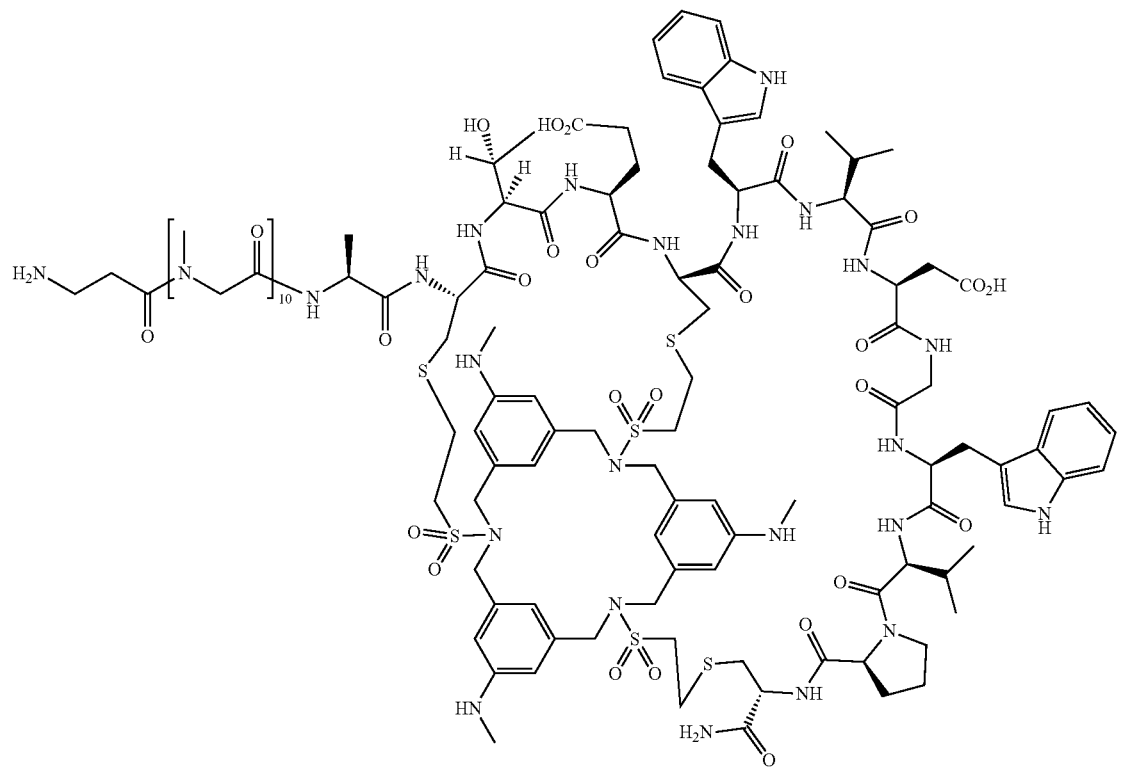
I-41

TABLE 1-continued
Exemplary compounds
I-42
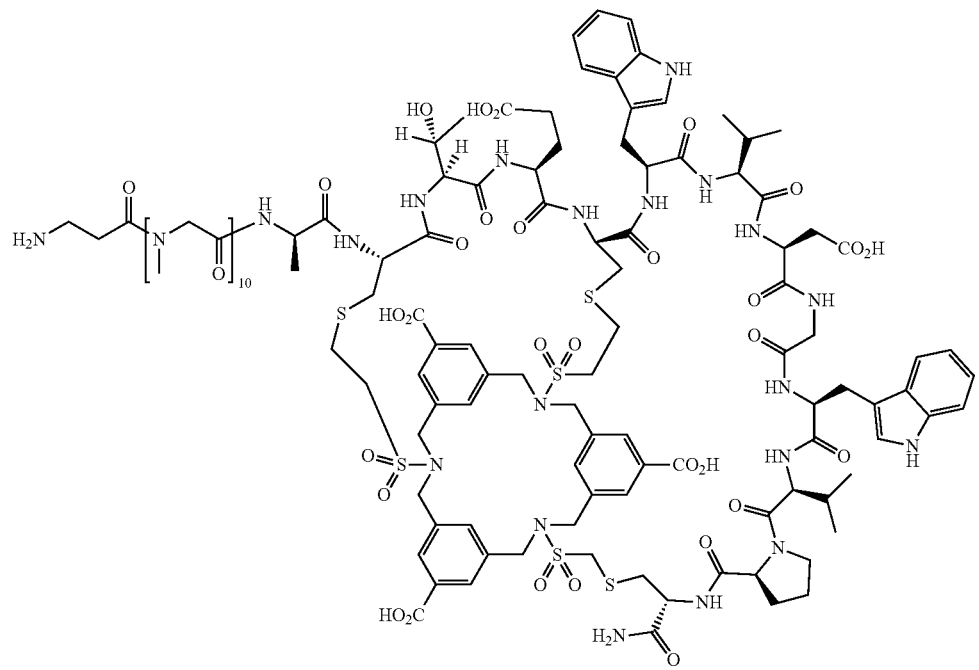
I-43
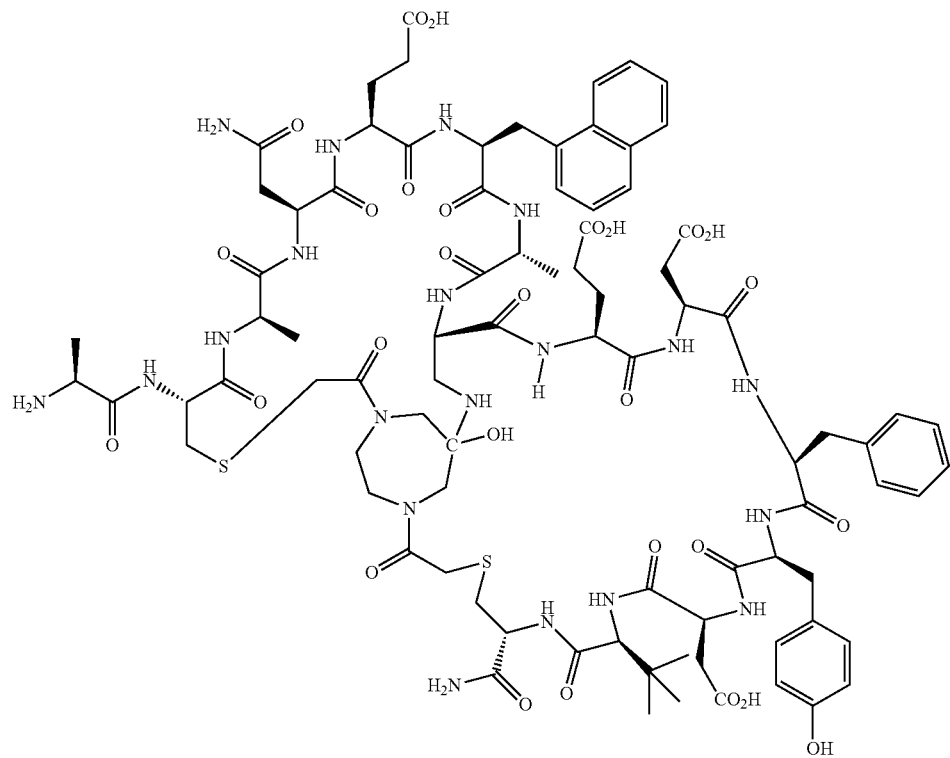 [SMILES: C[C@H](N)C(=O)N[C@H]1CSCC(=O)N2CCN3CC(O)(C2)NC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCC3=O]

TABLE 1-continued
Exemplary compounds
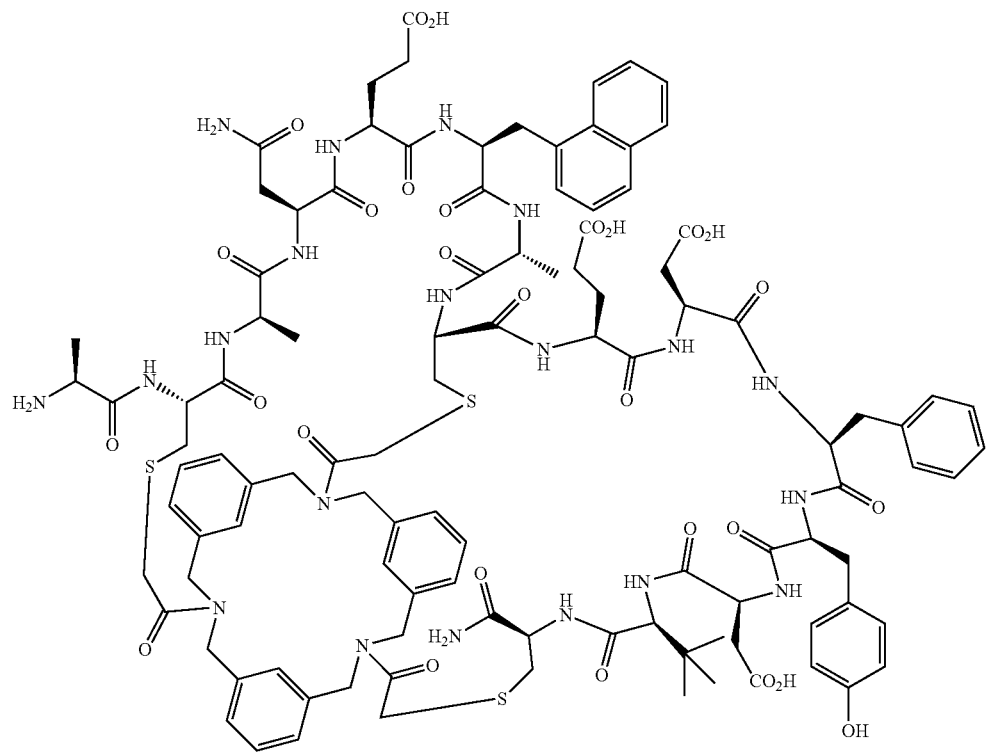 [SMILES: C[C@H](N)C(=O)N[C@H]1CSCC(=O)N2Cc3cccc(c3)CN3Cc4cccc(c4)CN(Cc4cccc(c4)C2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCC3=O]
I-44
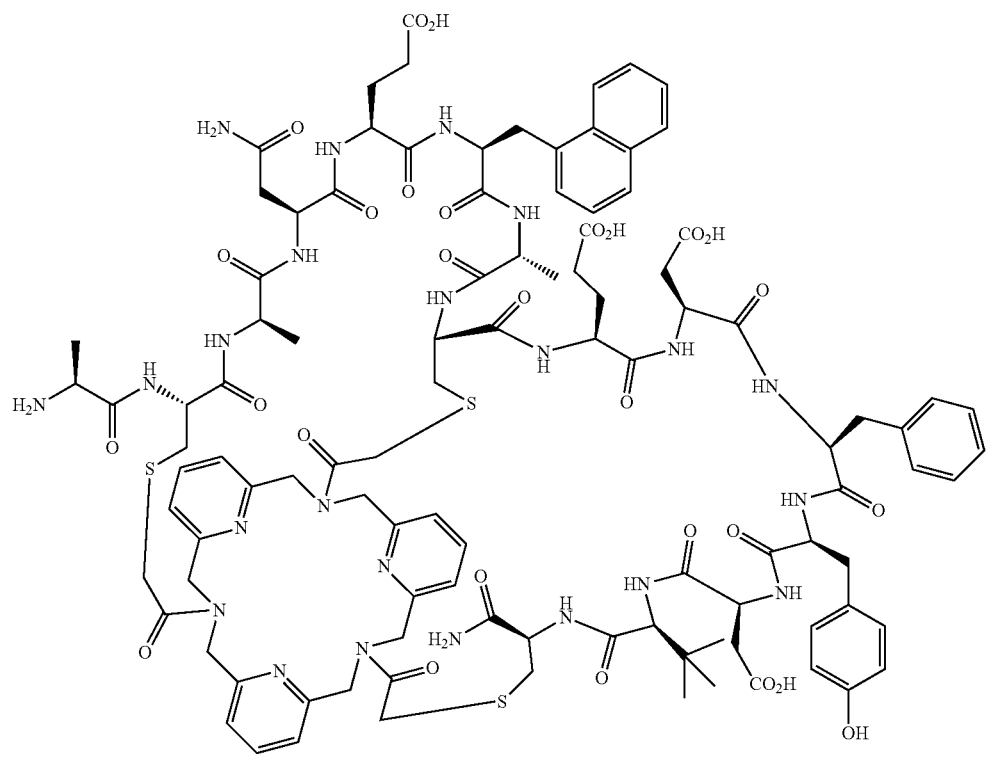 [SMILES: C[C@H](N)C(=O)N[C@H]1CSCC(=O)N2Cc3cccc(n3)CN3Cc4cccc(n4)CN(Cc4cccc(n4)C2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCC3=O]
I-45

TABLE 1-continued
Exemplary compounds
I-46
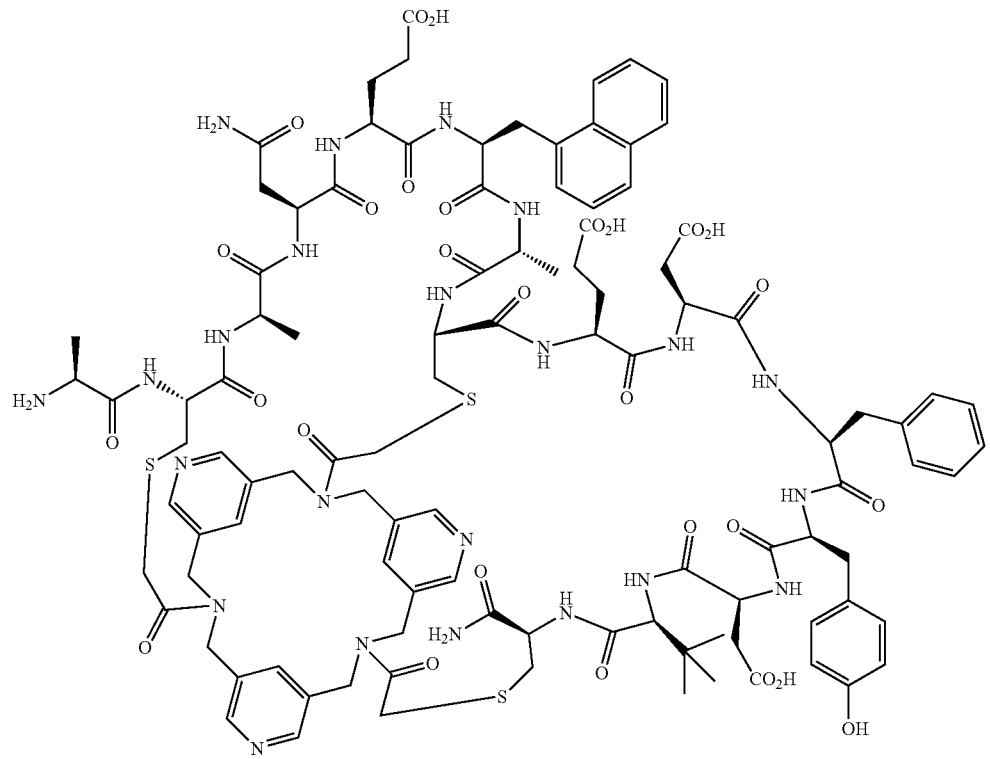 [SMILES: C[C@H](N)C(=O)N[C@H]1CSCC(=O)N2Cc3cncc(c3)CN3Cc4cncc(c4)CN(Cc4cncc(c4)C2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCC3=O]
I-47
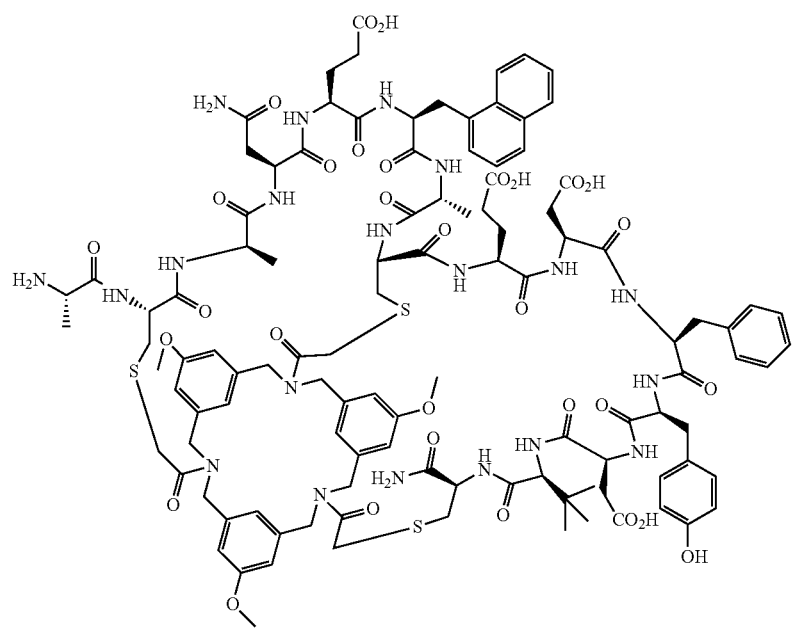 [SMILES: COc1cc2cc(c1)CN1Cc3cc(cc(OC)c3)CN3Cc4cc(cc(OC)c4)CN(C2)C(=O)CSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCC3=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCC1=O]

TABLE 1-continued
Exemplary compounds
I-48
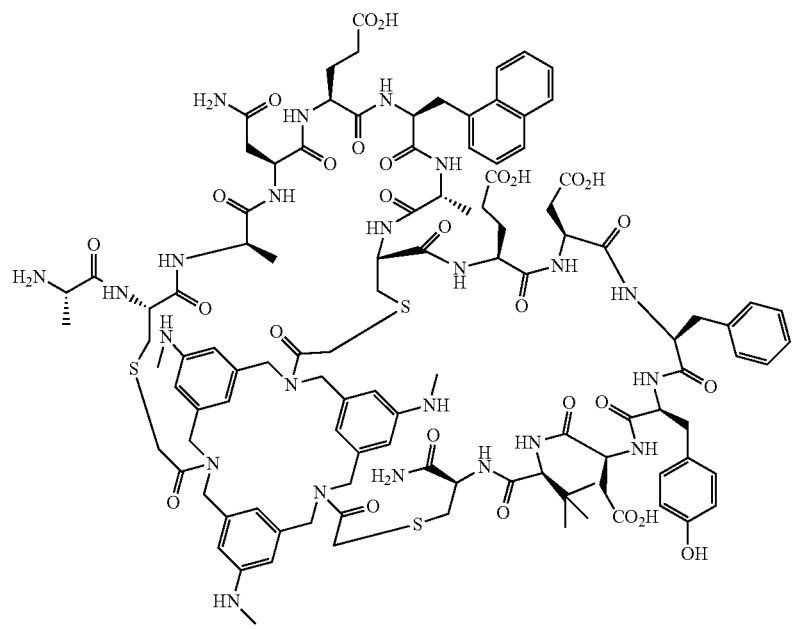 [SMILES: CNc1cc2cc(c1)CN1Cc3cc(cc(NC)c3)CN3Cc4cc(cc(NC)c4)CN(C2)C(=O)CSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCC3=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCC1=O]
I-49
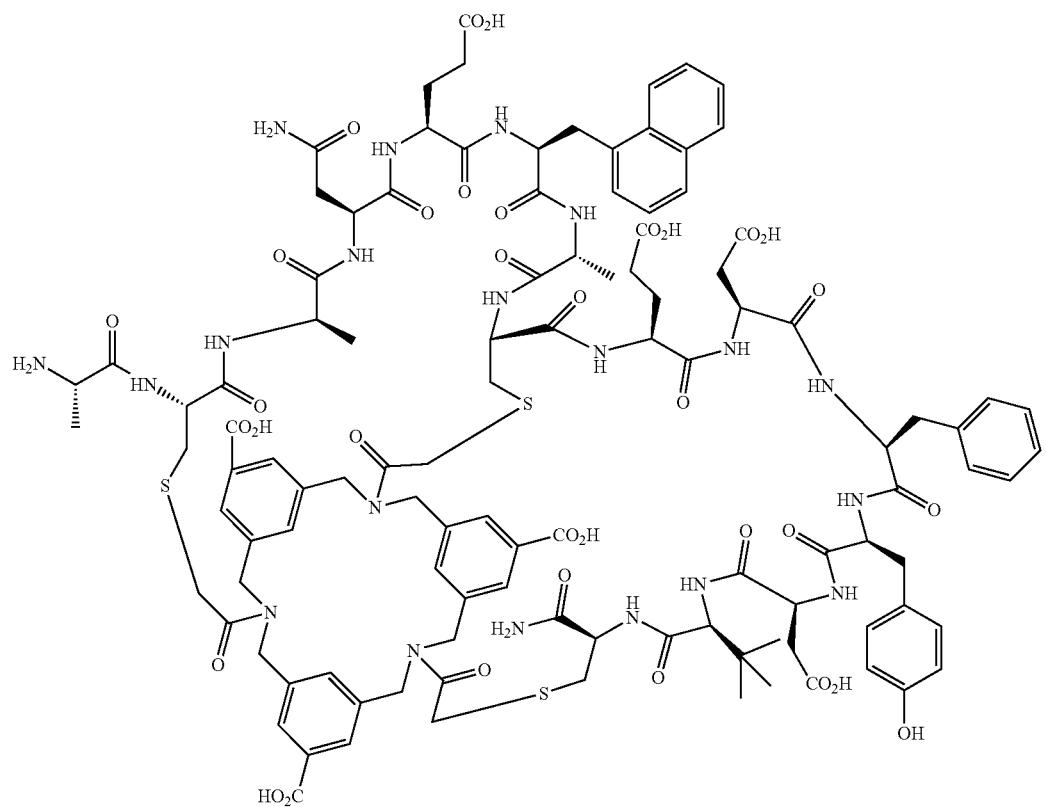 [SMILES: C[C@H](N)C(=O)N[C@H]1CSCC(=O)N2Cc3cc(cc(C(=O)O)c3)CN3Cc4cc(cc(C(=O)O)c4)CN(Cc4cc(cc(C(=O)O)c4)C2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCC3=O]

TABLE 1-continued
Exemplary compounds
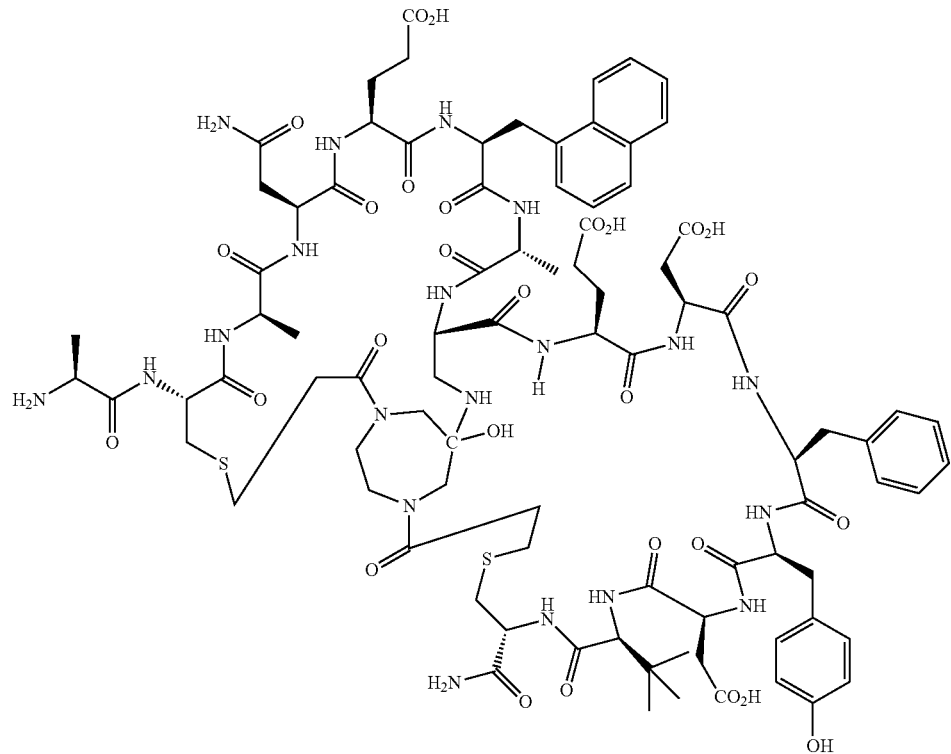 [SMILES: C[C@H](N)C(=O)N[C@H]1CSCCC(=O)N2CCN3CC(O)(C2)NC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCC3=O]
I-50
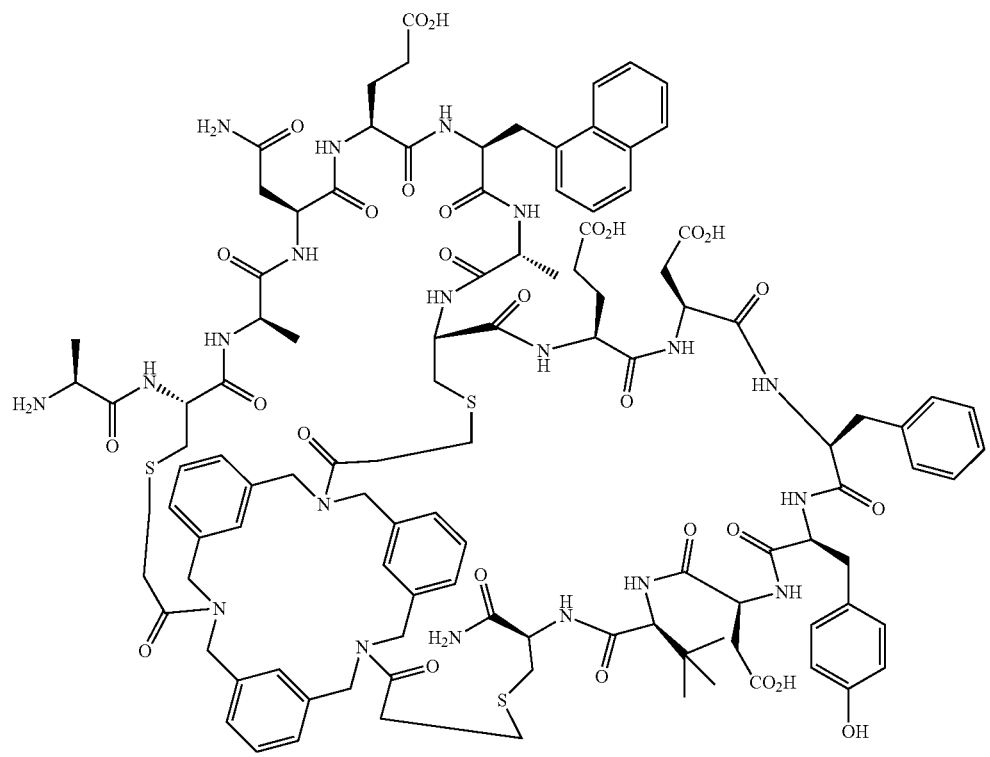 [SMILES: C[C@H](N)C(=O)N[C@H]1CSCCC(=O)N2Cc3cccc(c3)CN3Cc4cccc(c4)CN(Cc4cccc(c4)C2)C(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCC3=O]
I-51

TABLE 1-continued
Exemplary compounds
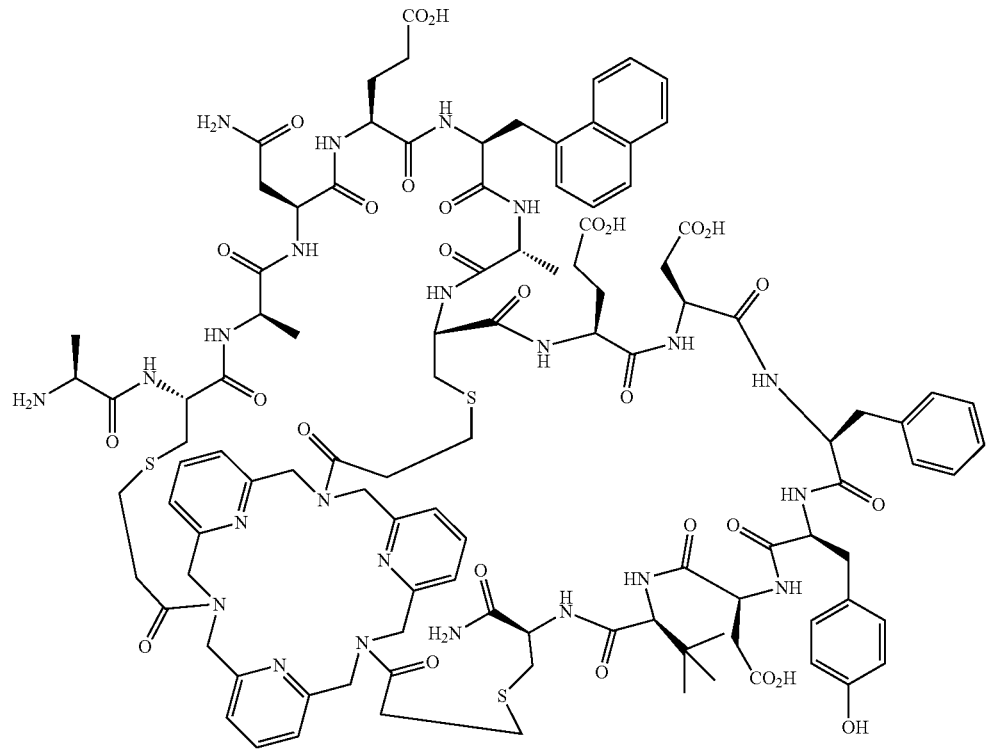 [SMILES: C[C@H](N)C(=O)N[C@H]1CSCCC(=O)N2Cc3cccc(n3)CN3Cc4cccc(n4)CN(Cc4cccc(n4)C2)C(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCC3=O]
I-52
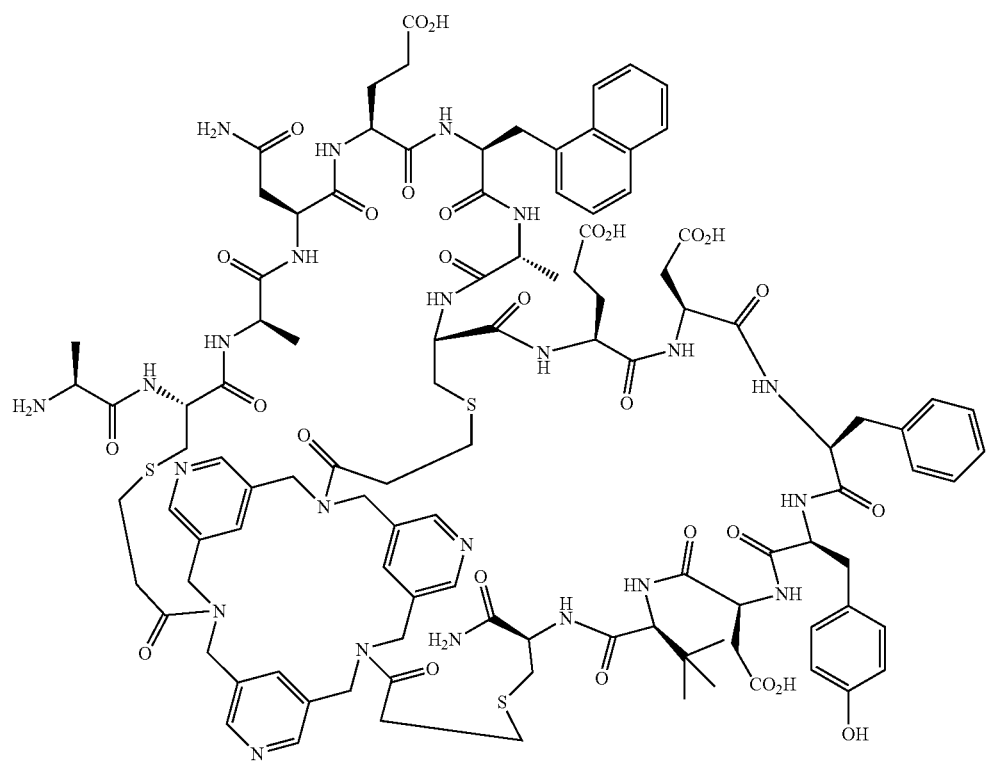 [SMILES: C[C@H](N)C(=O)N[C@H]1CSCCC(=O)N2Cc3cncc(c3)CN3Cc4cncc(c4)CN(Cc4cncc(c4)C2)C(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCC3=O]
I-53

TABLE 1-continued
Exemplary compounds
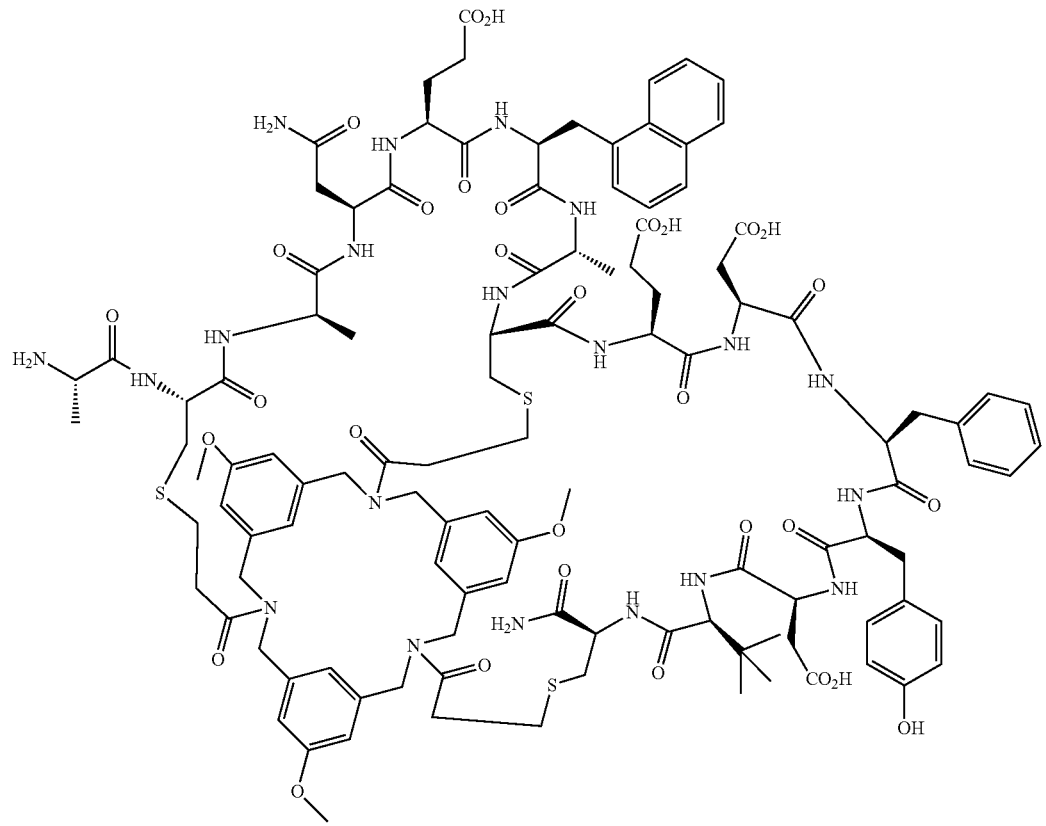 [SMILES: COc1cc2cc(c1)CN1Cc3cc(cc(OC)c3)CN3Cc4cc(cc(OC)c4)CN(C2)C(=O)CCSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCCC3=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCCC1=O]
I-54
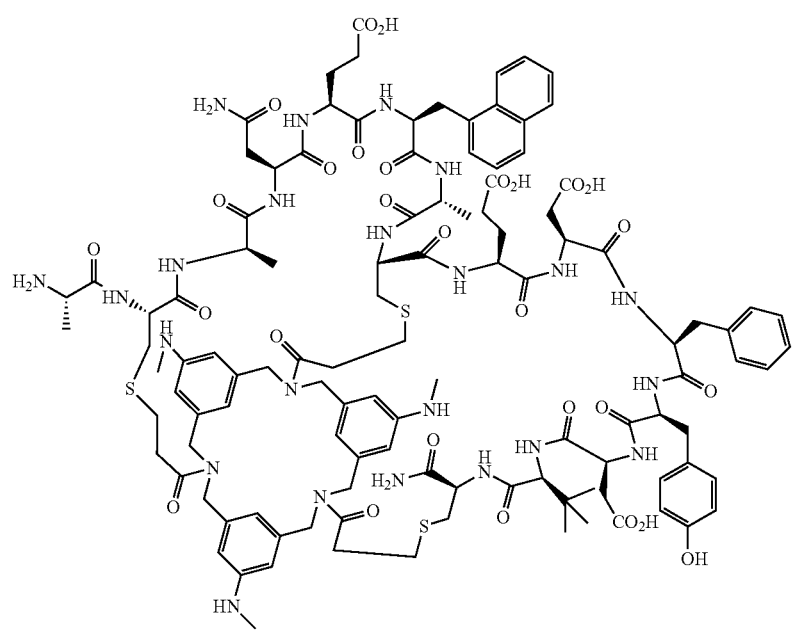 [SMILES: CNc1cc2cc(c1)CN1Cc3cc(cc(NC)c3)CN3Cc4cc(cc(NC)c4)CN(C2)C(=O)CCSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCCC3=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCCC1=O]
I-55

TABLE 1-continued
Exemplary compounds
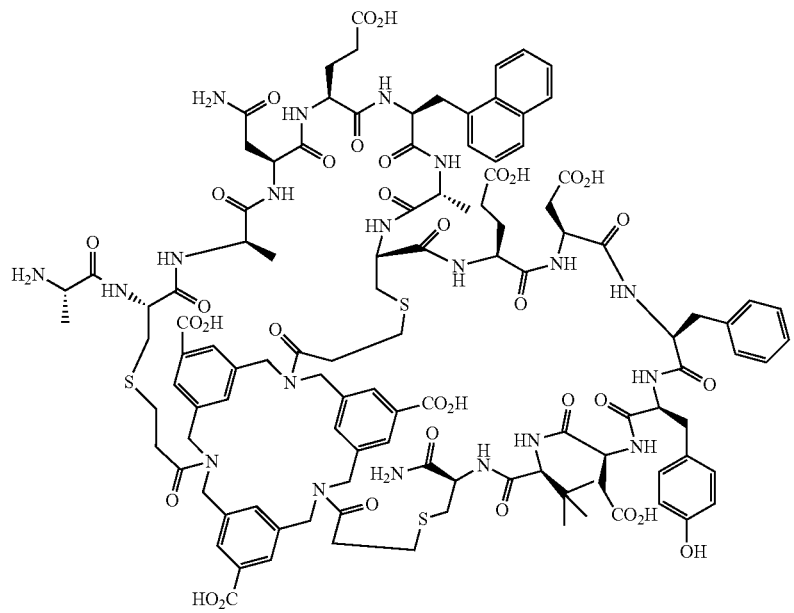 [SMILES: C[C@H](N)C(=O)N[C@H]1CSCCC(=O)N2Cc3cc(cc(C(=O)O)c3)CN3Cc4cc(cc(C(=O)O)c4)CN(Cc4cc(cc(C(=O)O)c4)C2)C(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCC3=O]
I-56
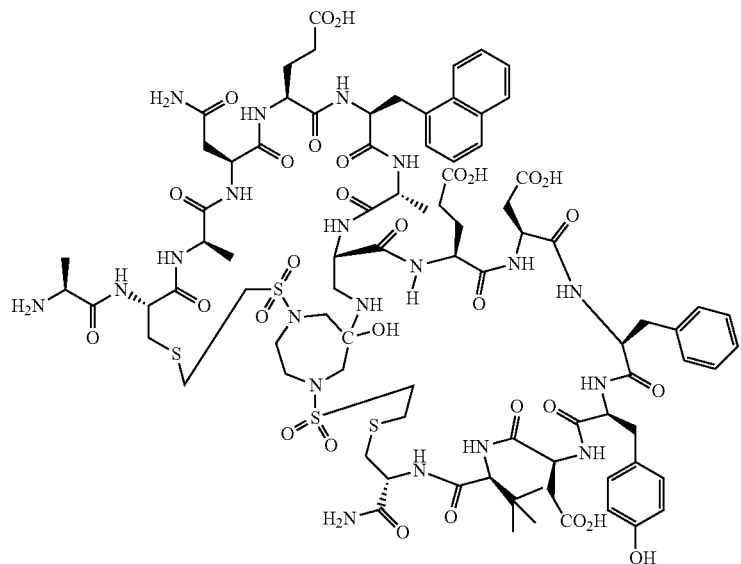 [SMILES: C[C@H](N)C(=O)N[C@H]1CSCCS(=O)(=O)N2CCN3CC(O)(C2)NC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCS3(=O)=O]
I-57

TABLE 1-continued
Exemplary compounds
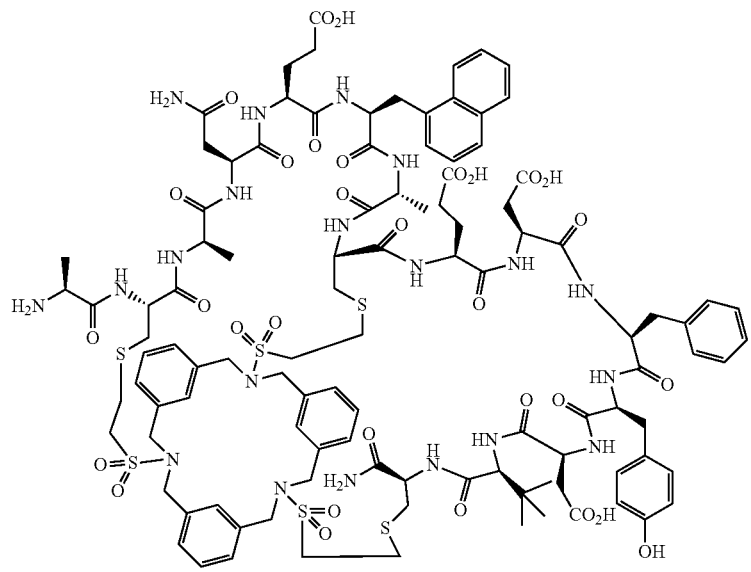 [SMILES: C[C@H](N)C(=O)N[C@H]1CSCCS(=O)(=O)N2Cc3cccc(c3)CN3Cc4cccc(c4)CN(Cc4cccc(c4)C2)S(=O)(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCS3(=O)=O]
I-58
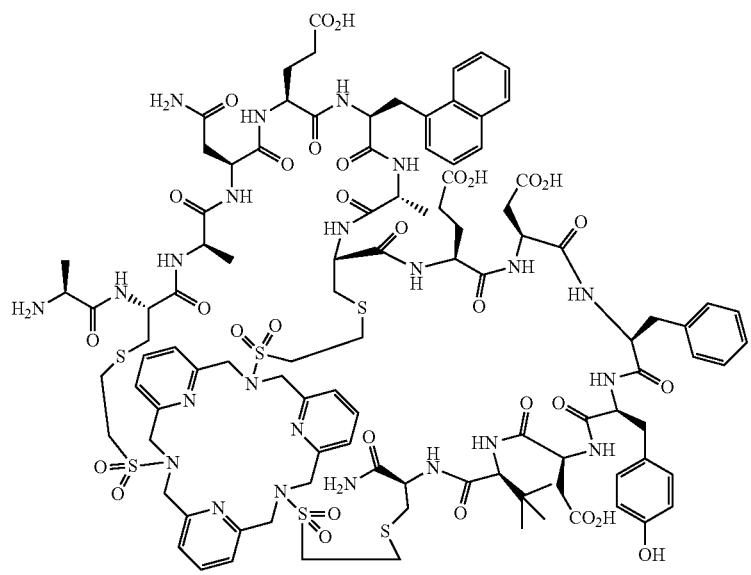 [SMILES: C[C@H](N)C(=O)N[C@H]1CSCCS(=O)(=O)N2Cc3cccc(n3)CN3Cc4cccc(n4)CN(Cc4cccc(n4)C2)S(=O)(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCS3(=O)=O]
I-59

TABLE 1-continued
Exemplary compounds
I-60
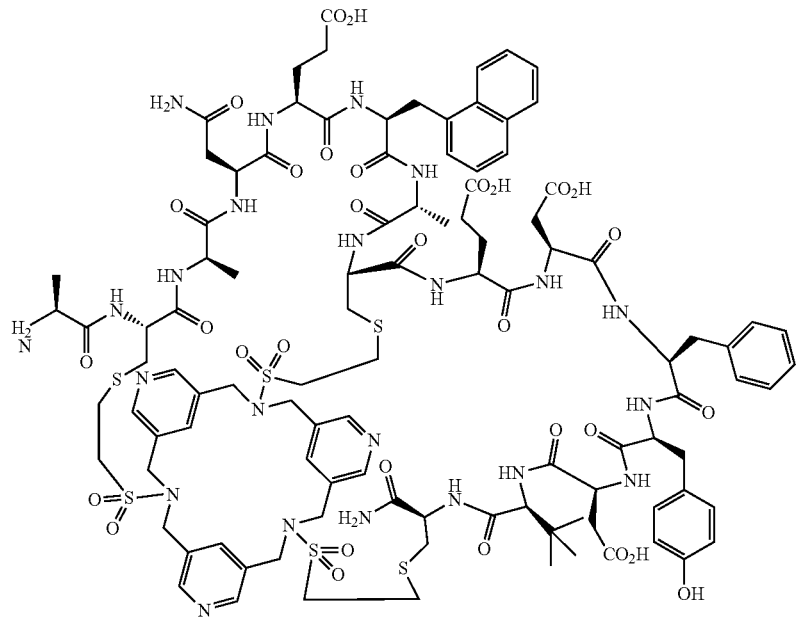 [SMILES: C[C@H](N)C(=O)N[C@H]1CSCCS(=O)(=O)N2Cc3cncc(c3)CN3Cc4cncc(c4)CN(Cc4cncc(c4)C2)S(=O)(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCS3(=O)=O]
I-61
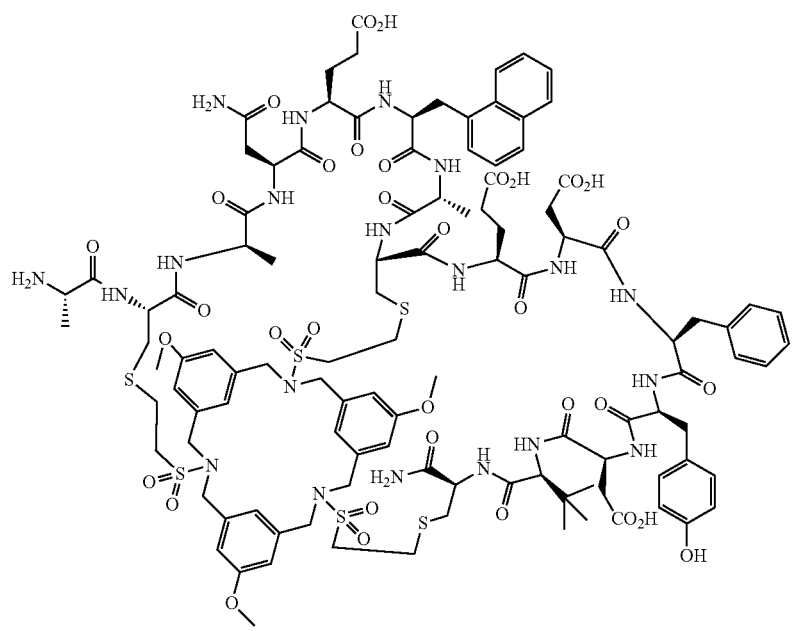 [SMILES: COc1cc2cc(c1)CN1Cc3cc(cc(OC)c3)CN3Cc4cc(cc(OC)c4)CN(C2)S(=O)(=O)CCSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCCS3(=O)=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCCS1(=O)=O]

TABLE 1-continued
Exemplary compounds
I-62
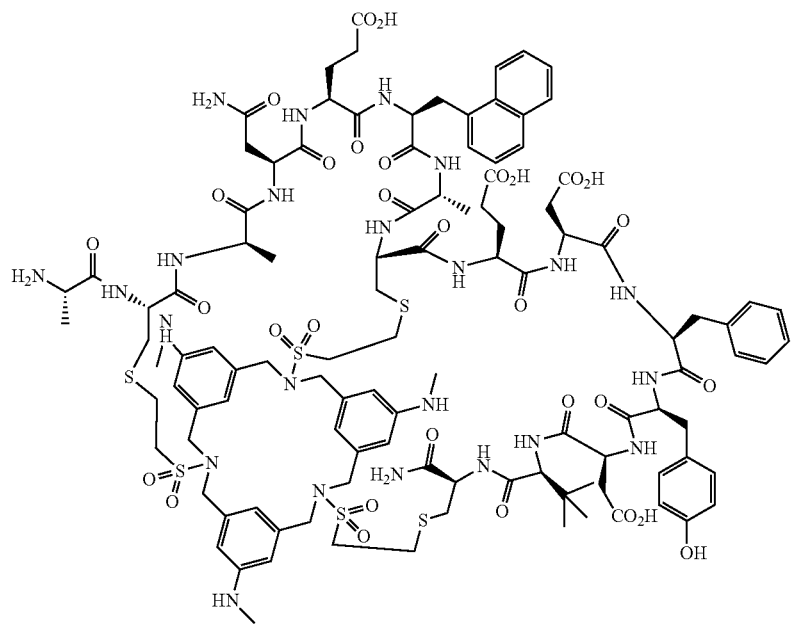 [SMILES: CNc1cc2cc(c1)CN1Cc3cc(cc(NC)c3)CN3Cc4cc(cc(NC)c4)CN(C2)S(=O)(=O)CCSC[C@@H](C(N)=O)NC(=O)[C@H](C(C)(C)C)NC(=O)[C@H](CC(=O)O)NC(=O)[C@H](Cc2ccc(O)cc2)NC(=O)[C@H](Cc2ccccc2)NC(=O)[C@H](CC(=O)O)NC(=O)[C@H](CCC(=O)O)NC(=O)[C@H](CSCCS3(=O)=O)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC(=O)[C@@H](NC(=O)[C@H](C)N)CSCCS1(=O)=O]
I-63
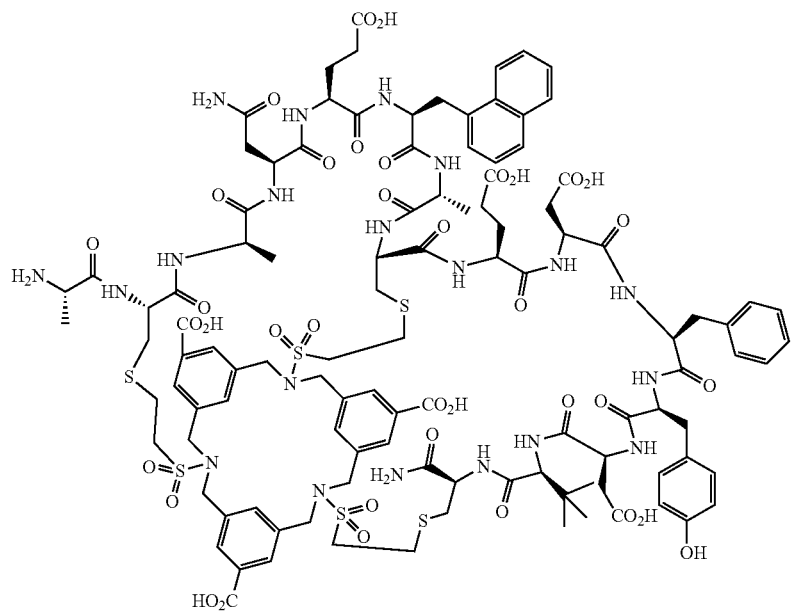 [SMILES: C[C@H](N)C(=O)N[C@H]1CSCCS(=O)(=O)N2Cc3cc(cc(C(=O)O)c3)CN3Cc4cc(cc(C(=O)O)c4)CN(Cc4cc(cc(C(=O)O)c4)C2)S(=O)(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)N[C@H](C(N)=O)CSCCS3(=O)=O]

TABLE 1-continued
Exemplary compounds
I-64
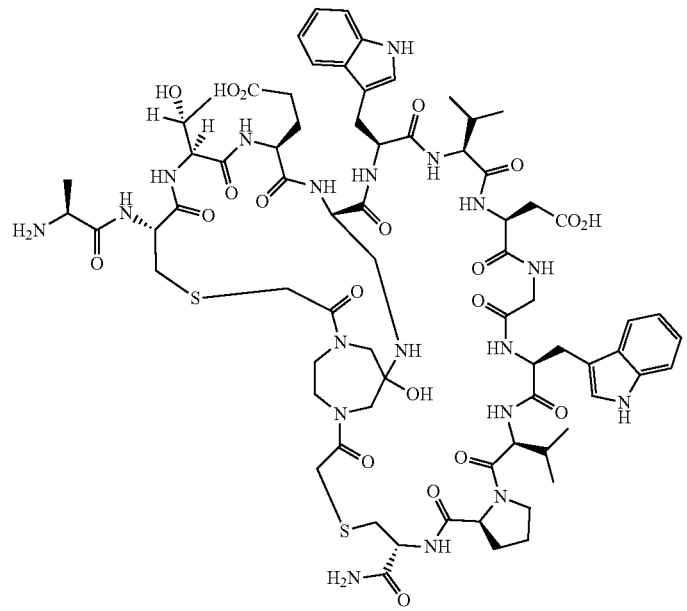
I-65
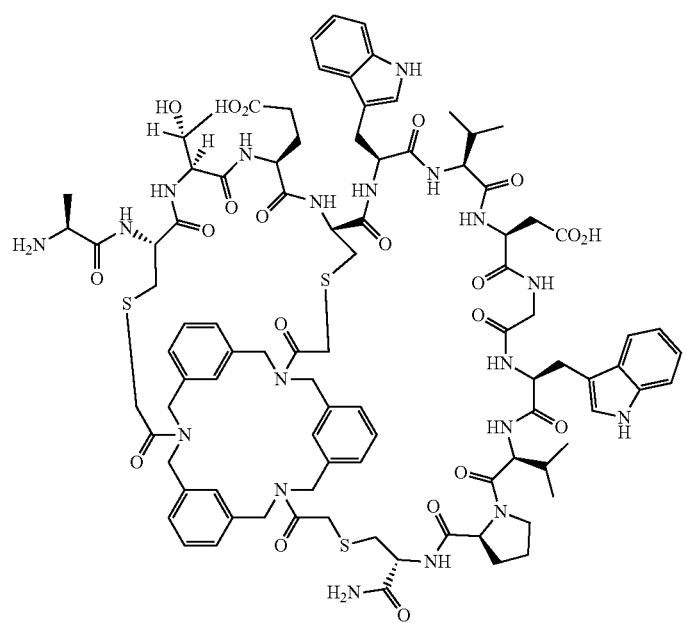

TABLE 1-continued
Exemplary compounds
I-66
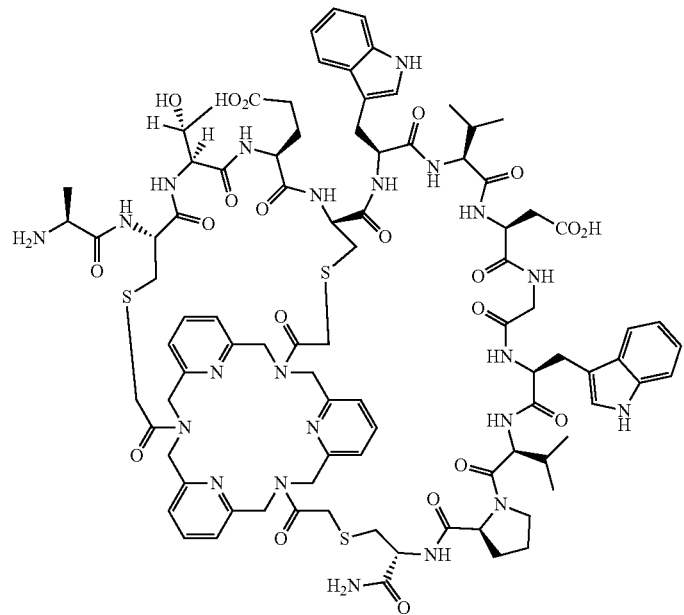
I-67
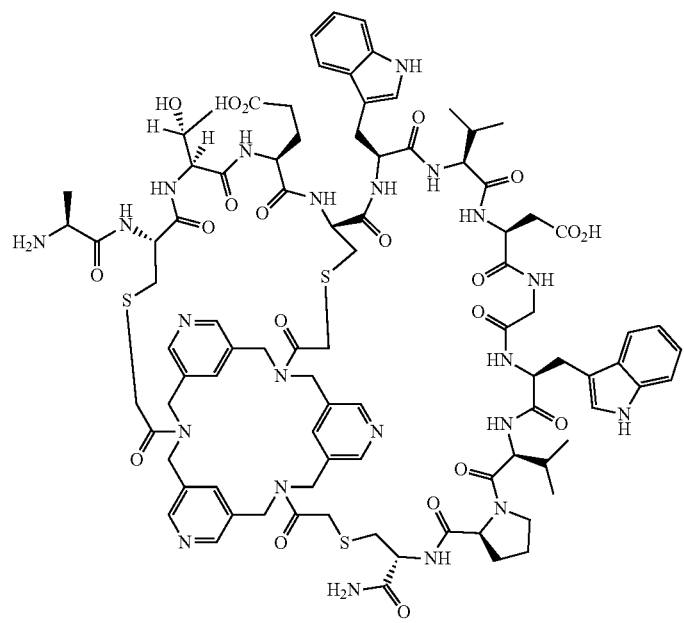

TABLE 1-continued
Exemplary compounds
I-68
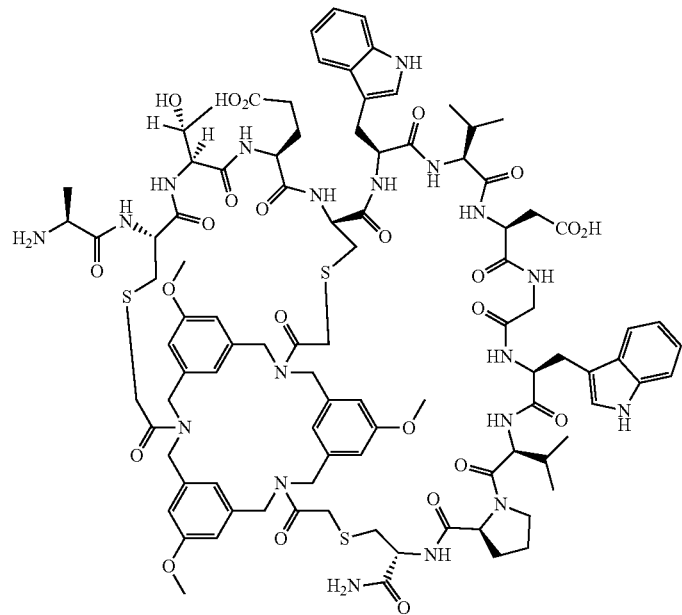
I-69
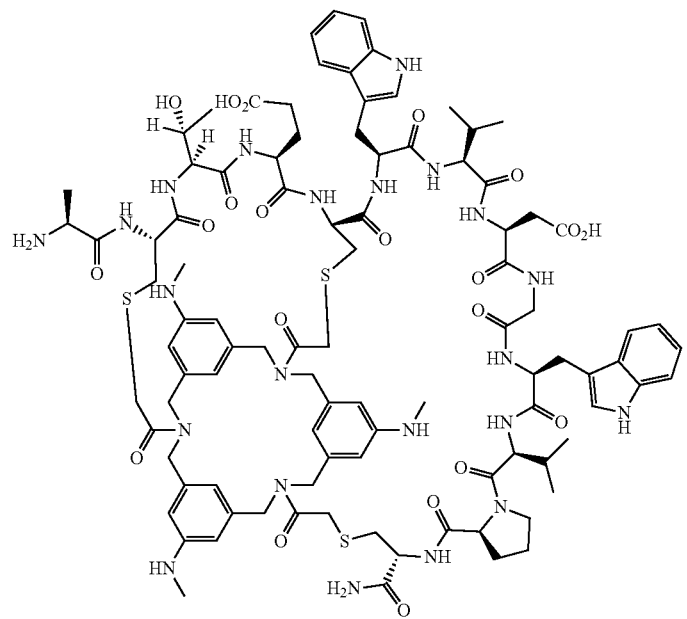

TABLE 1-continued
Exemplary compounds
I-70
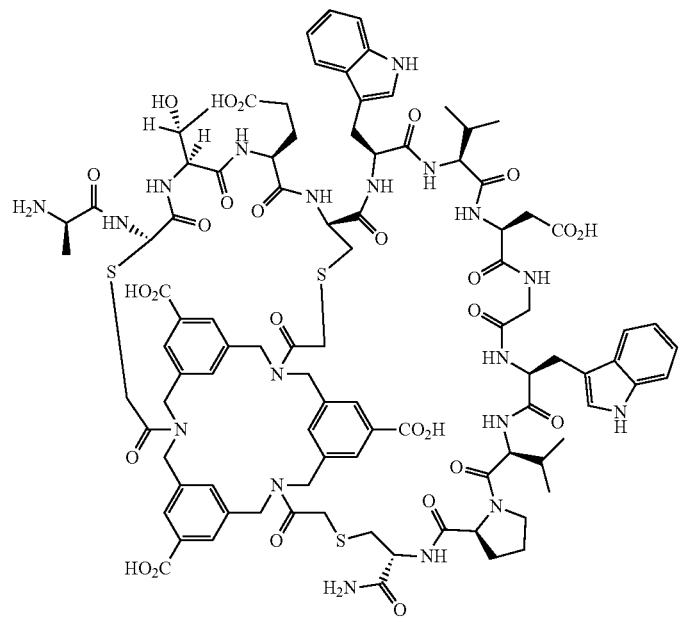
I-71
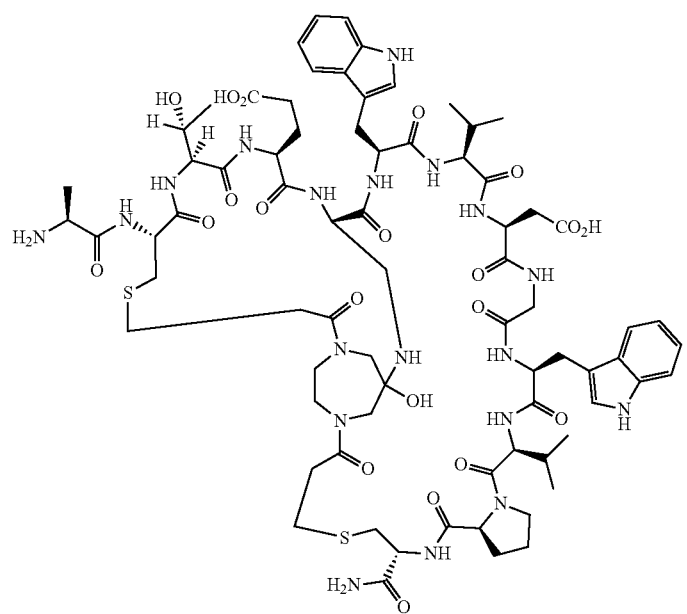

TABLE 1-continued
Exemplary compounds
I-72
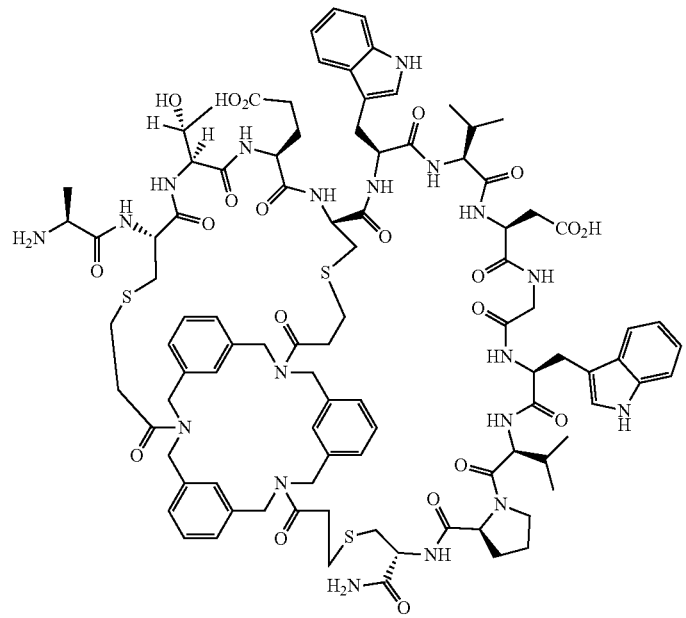
I-73
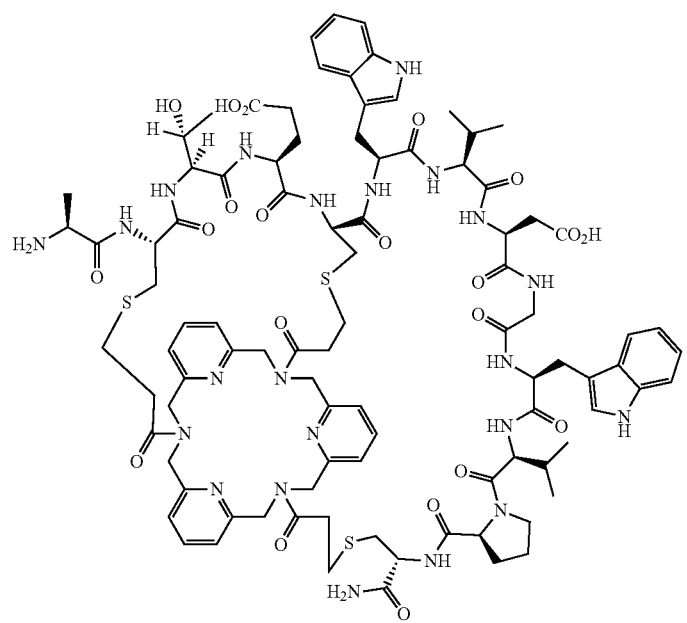

TABLE 1-continued
Exemplary compounds
I-74
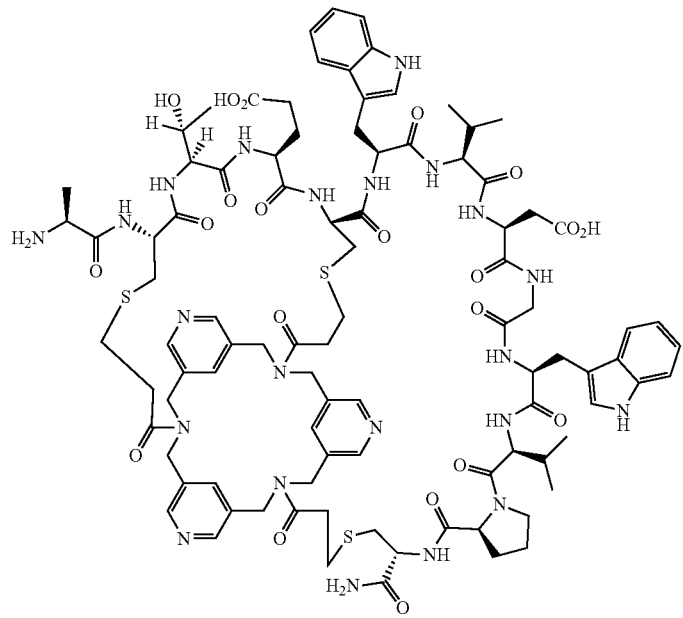
I-75
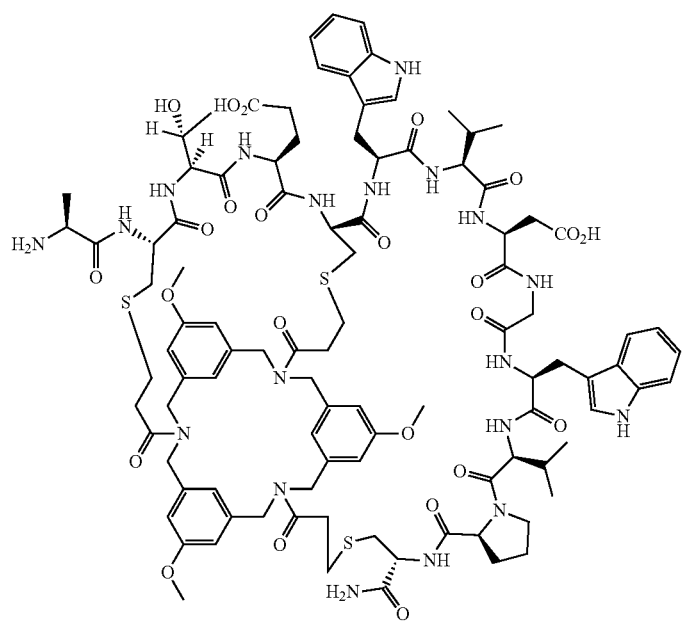

TABLE 1-continued
Exemplary compounds
I-76
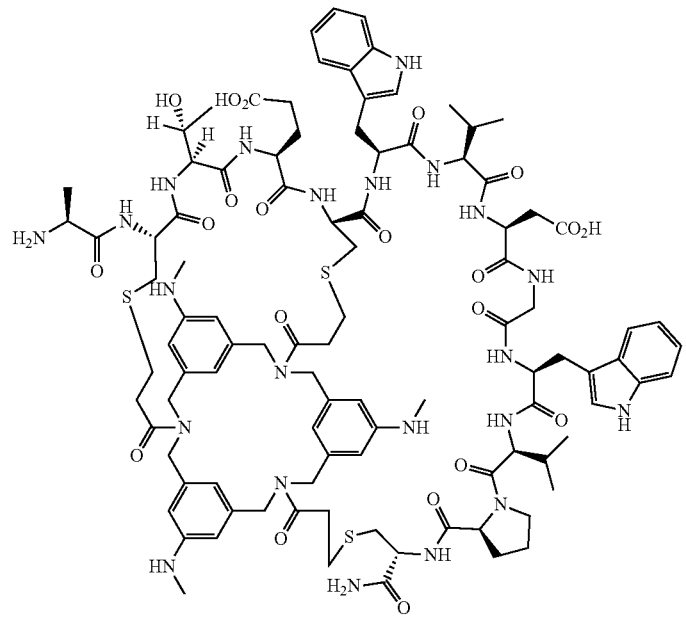
I-77
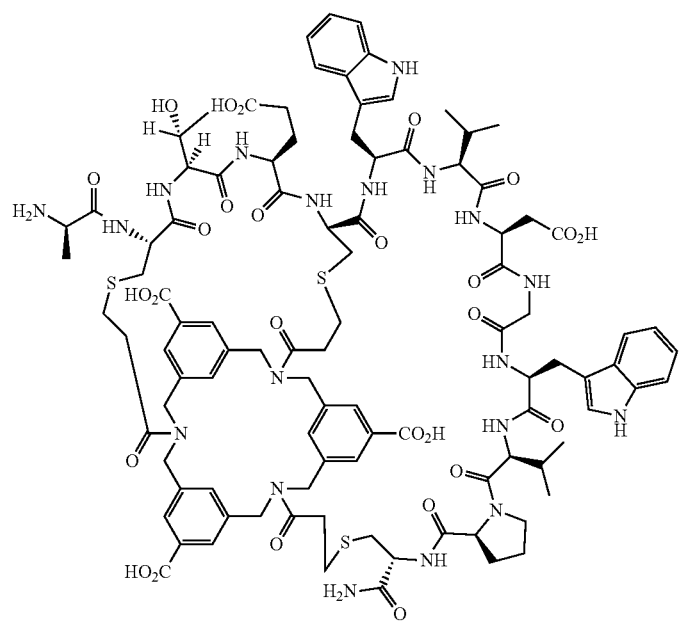

TABLE 1-continued
Exemplary compounds
I-78
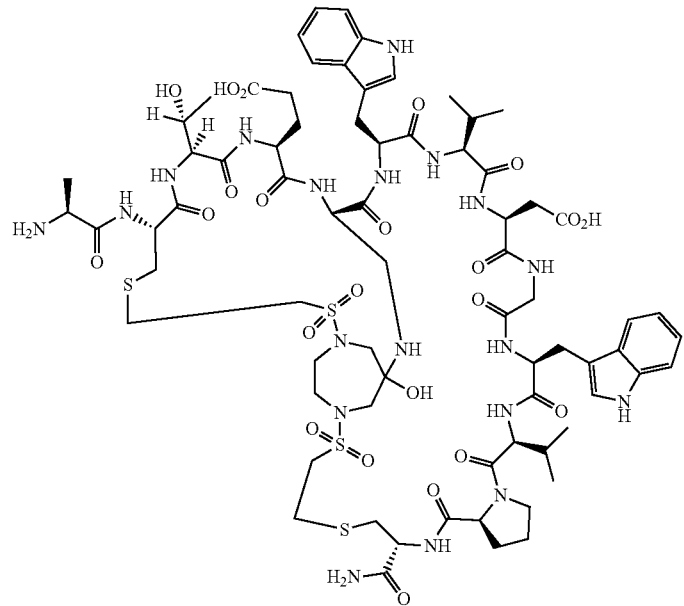
I-79
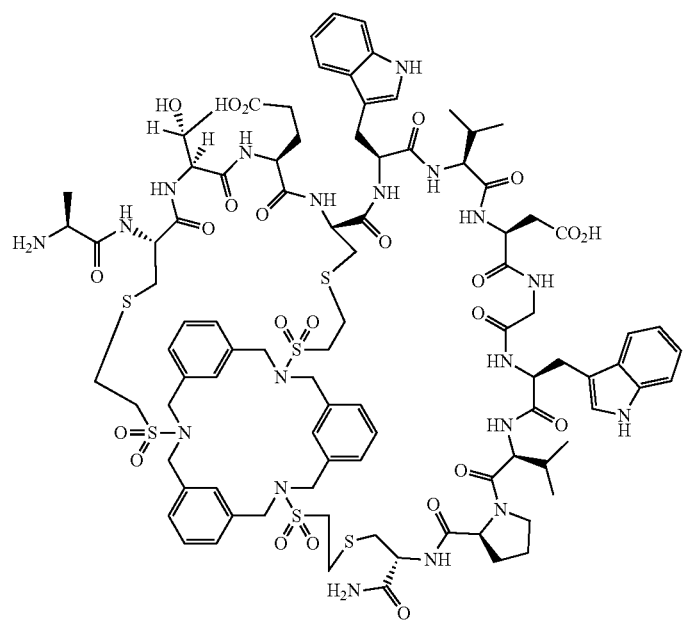

TABLE 1-continued
Exemplary compounds
I-80
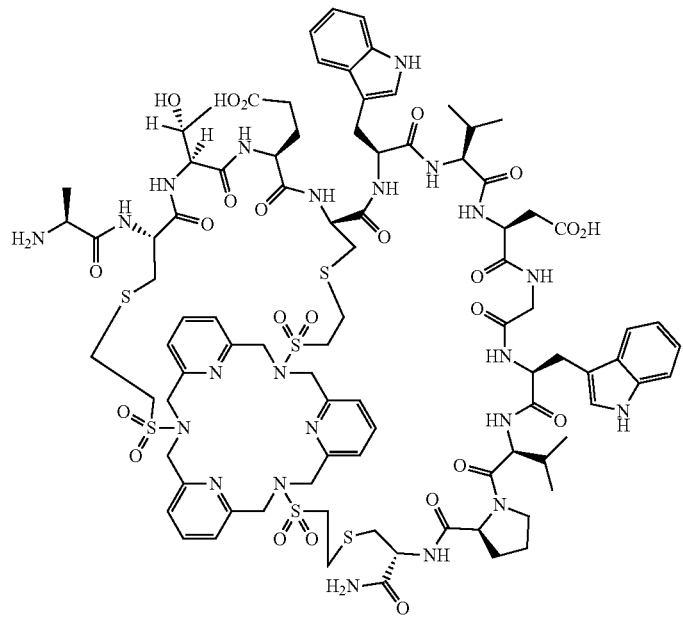
I-81
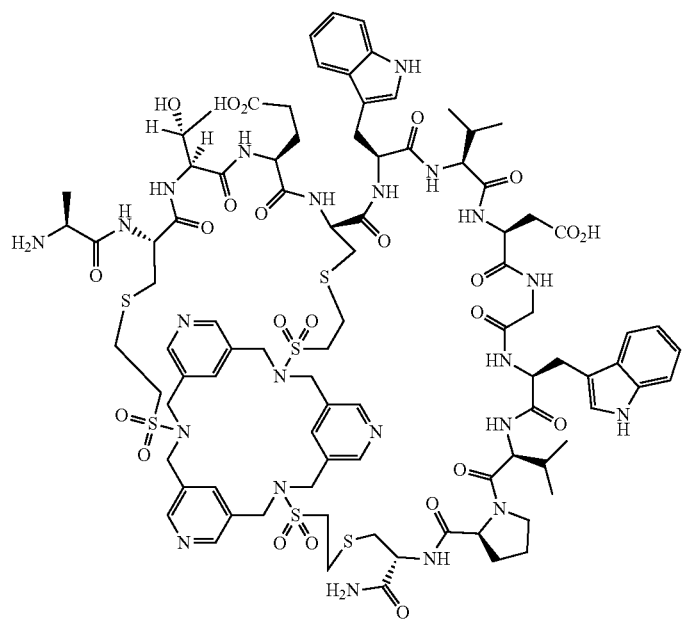

TABLE 1-continued
Exemplary compounds
I-82
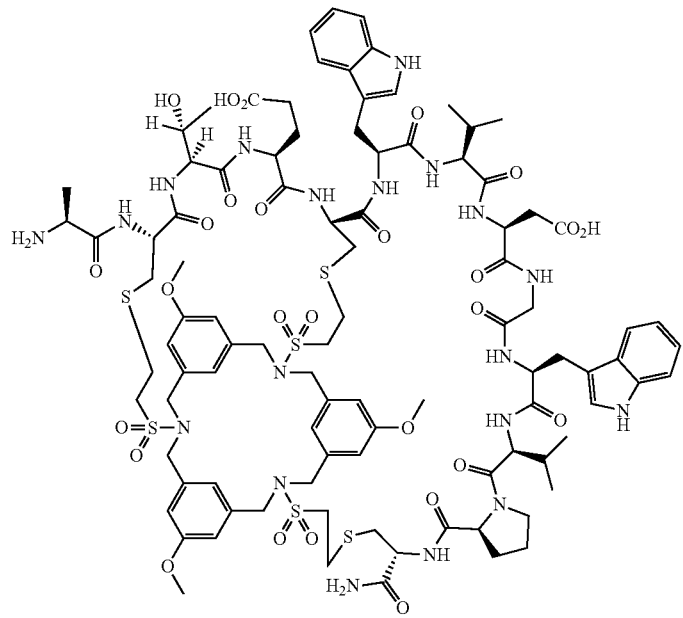
I-83
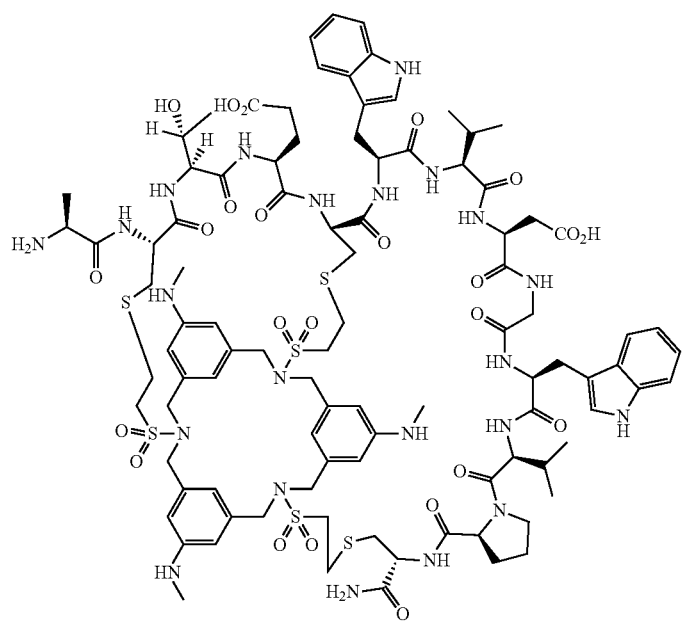

| Exemplary compounds |
|---|
| 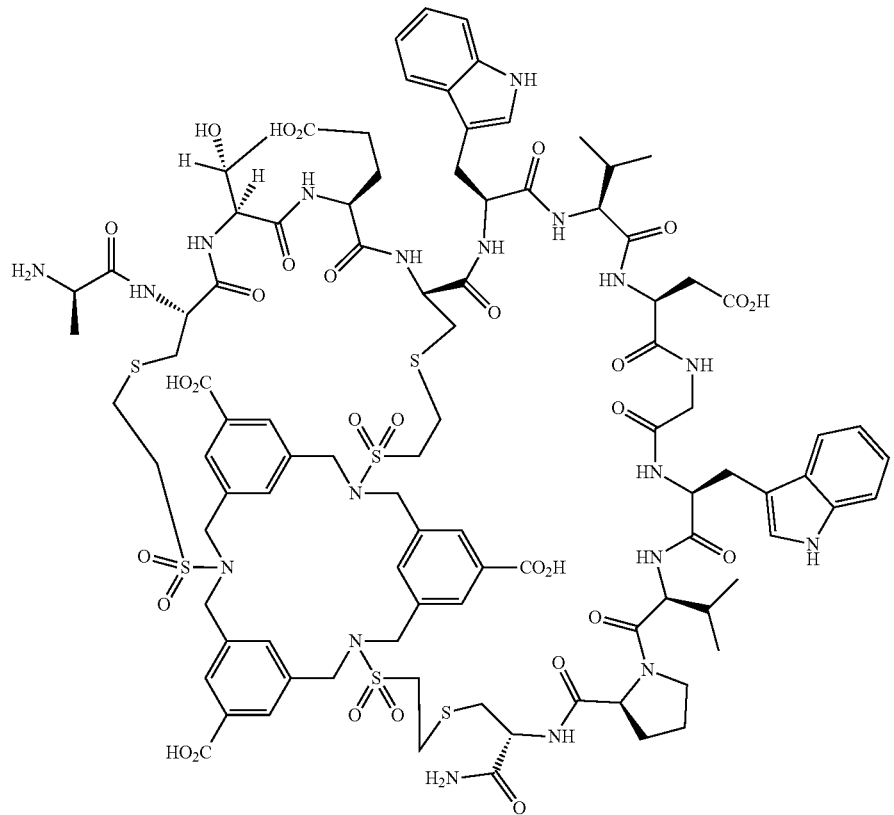 I-84 |
| 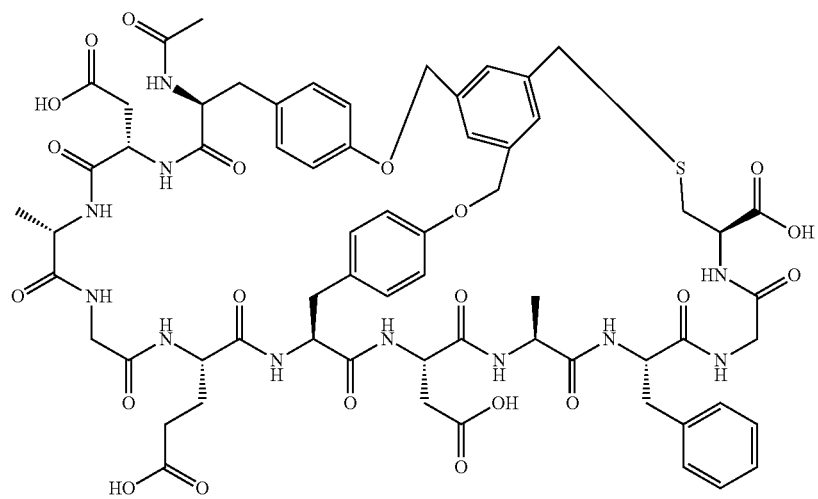 [SMILES: CC(=O)N[C@H]1Cc2ccc(cc2)OCc2cc3cc(c2)CSC[C@@H](C(=O)O)NC(=O)CNC(=O)[C@H](Cc2ccccc2)NC(=O)[C@H](C)NC(=O)[C@H](CC(=O)O)NC(=O)[C@H](Cc2ccc(cc2)OC3)NC(=O)[C@H](CCC(=O)O)NC(=O)CNC(=O)[C@H](C)NC(=O)[C@H](CC(=O)O)NC1=O] I-85 |

TABLE 1-continued
Exemplary compounds
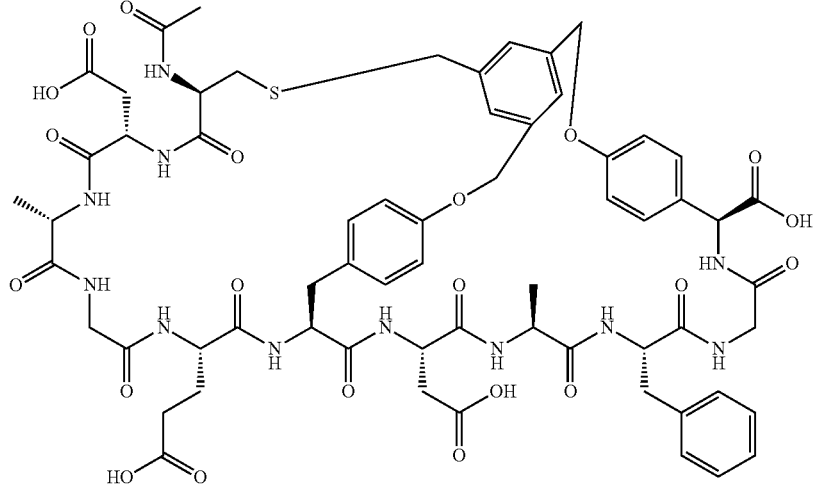 [SMILES: CC(=O)N[C@H]1CSCc2cc3cc(c2)COc2ccc(cc2)[C@@H](C(=O)O)NC(=O)CNC(=O)[C@H](Cc2ccccc2)NC(=O)[C@H](C)NC(=O)[C@H](CC(=O)O)NC(=O)[C@H](Cc2ccc(cc2)OC3)NC(=O)[C@H](CCC(=O)O)NC(=O)CNC(=O)[C@H](C)NC(=O)[C@H](CC(=O)O)NC1=O]
I-86
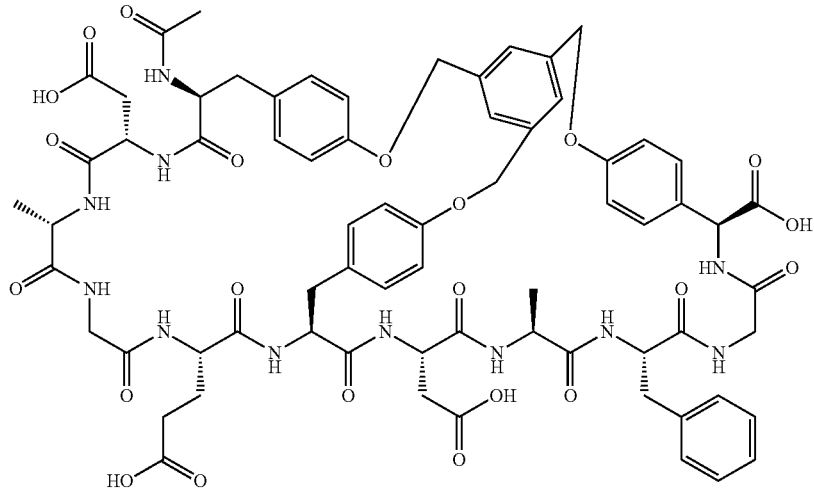 [SMILES: CC(=O)N[C@H]1Cc2ccc(cc2)OCc2cc3cc(c2)COc2ccc(cc2)[C@@H](C(=O)O)NC(=O)CNC(=O)[C@H](Cc2ccccc2)NC(=O)[C@H](C)NC(=O)[C@H](CC(=O)O)NC(=O)[C@H](Cc2ccc(cc2)OC3)NC(=O)[C@H](CCC(=O)O)NC(=O)CNC(=O)[C@H](C)NC(=O)[C@H](CC(=O)O)NC1=O]
I-87
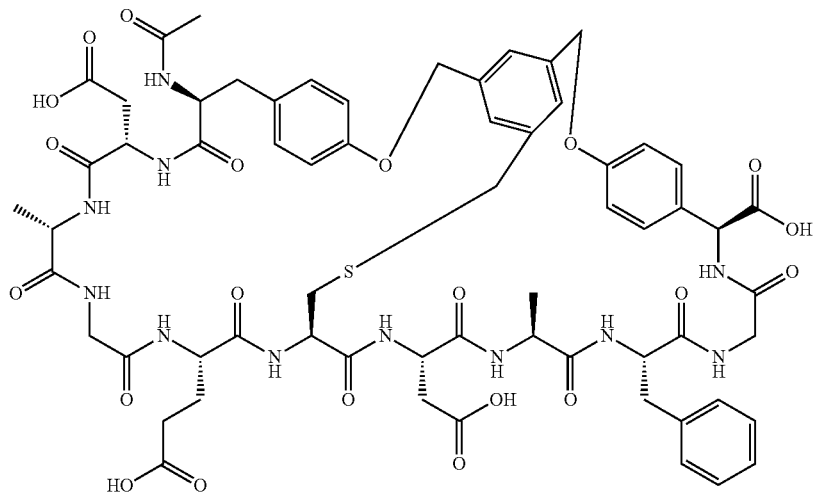 [SMILES: CC(=O)N[C@H]1Cc2ccc(cc2)OCc2cc3cc(c2)CSC[C@H](NC(=O)[C@H](CCC(=O)O)NC(=O)CNC(=O)[C@H](C)NC(=O)[C@H](CC(=O)O)NC1=O)C(=O)N[C@@H](CC(=O)O)C(=O)N[C@@H](C)C(=O)N[C@@H](Cc1ccccc1)C(=O)NCC(=O)N[C@H](C(=O)O)c1ccc(cc1)OC3]
I-88

TABLE 1-continued
Exemplary compounds
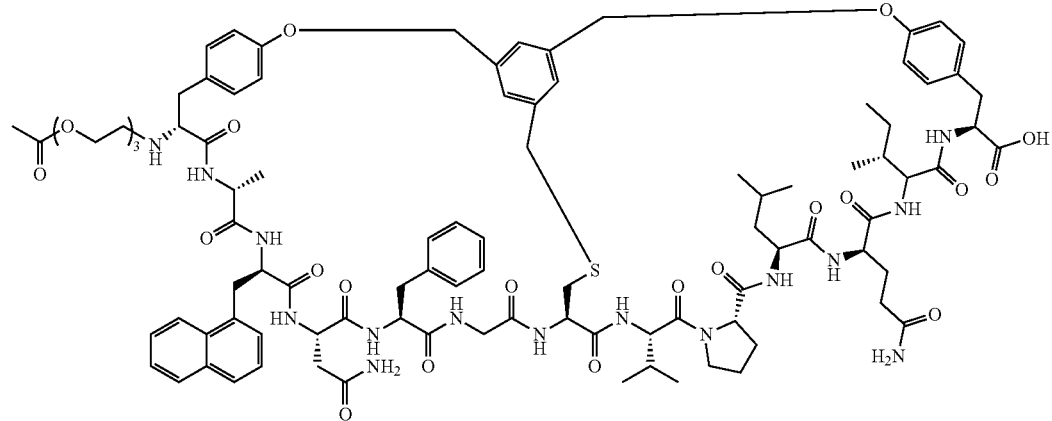
I-89
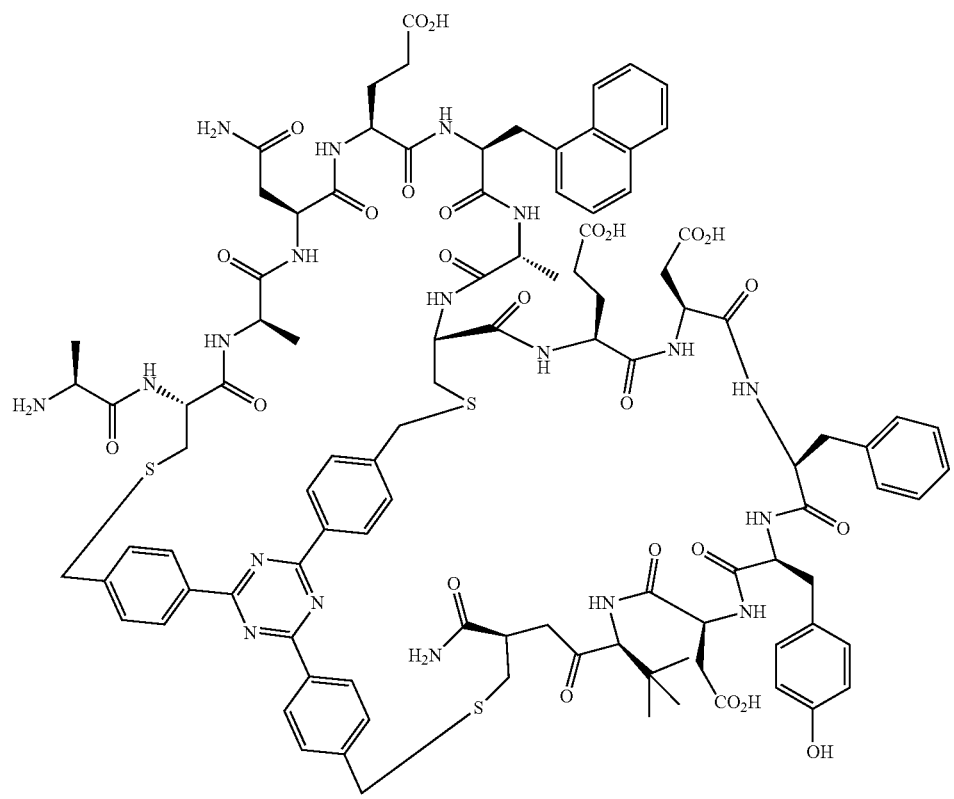 [SMILES: C[C@H](N)C(=O)N[C@H]1CSCc2ccc(cc2)-c2nc3nc(n2)-c2ccc(cc2)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCc1ccc-3cc1]
I-90

TABLE 1-continued
Exemplary compounds
I-91
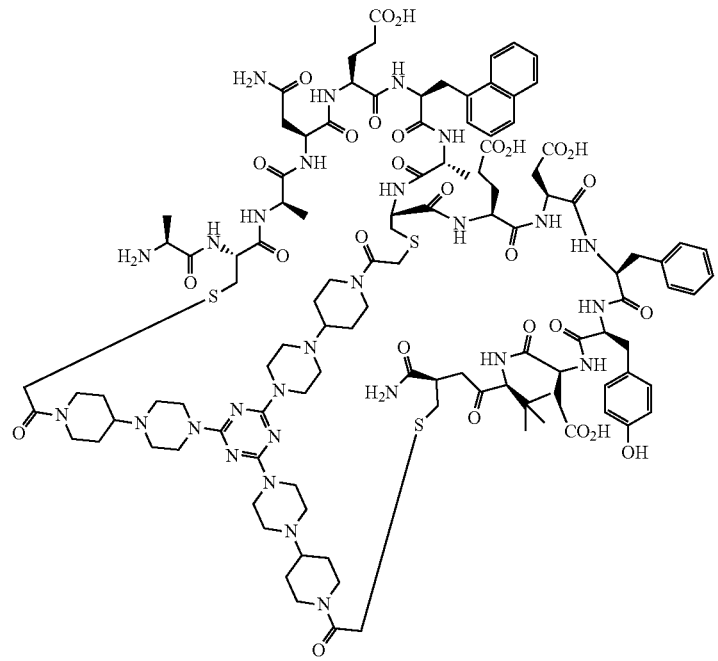 [SMILES: C[C@H](N)C(=O)N[C@H]1CSCC(=O)N2CCC(CC2)N2CCN(CC2)c2nc3nc(n2)N2CCN(CC2)C2CCN(CC2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCC(=O)N1CCC(CC1)N1CCN3CC1]
I-92
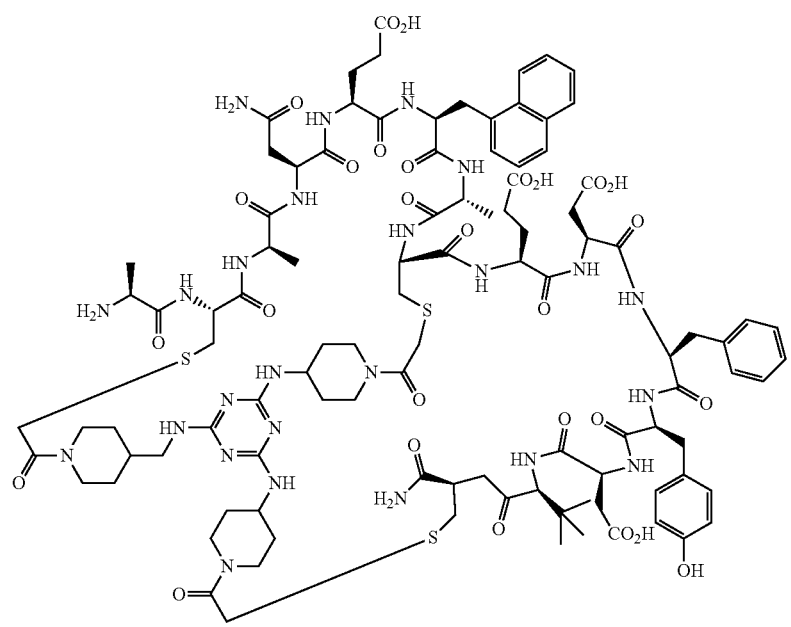 [SMILES: C[C@H](N)C(=O)N[C@H]1CSCC(=O)N2CCC(CC2)CNc2nc3nc(n2)NC2CCN(CC2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCC(=O)N1CCC(CC1)N3]

TABLE 1-continued
Exemplary compounds
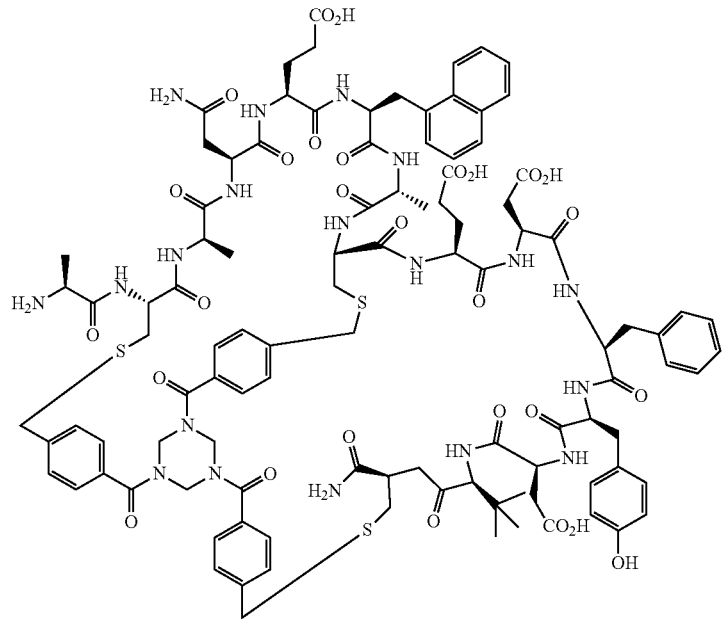 [SMILES: C[C@H](N)C(=O)N[C@H]1CSCc2ccc(cc2)C(=O)N2CN3CN(C2)C(=O)c2ccc(cc2)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCc1ccc(cc1)C3=O]
I-93
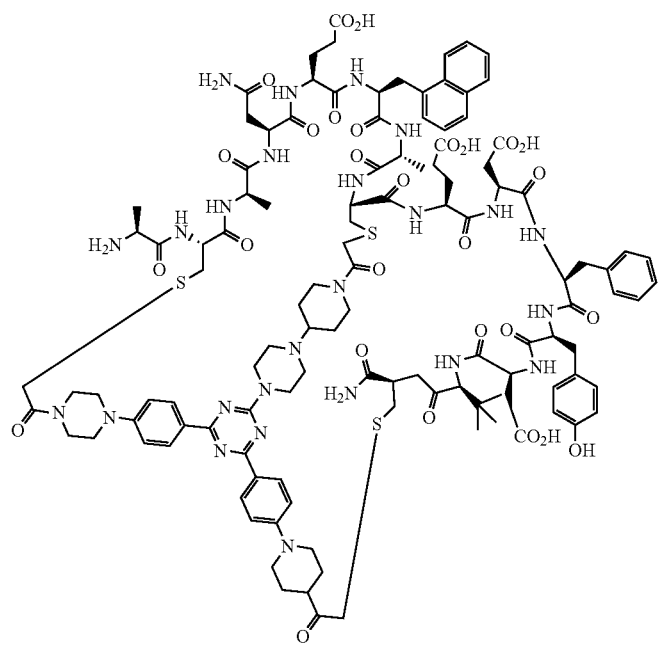 [SMILES: C[C@H](N)C(=O)N[C@H]1CSCC(=O)N2CCN(CC2)c2ccc(cc2)-c2nc3nc(n2)N2CCN(CC2)C2CCN(CC2)C(=O)CSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCC(=O)C1CCN(CC1)c1ccc-3cc1]
I-94

TABLE 1-continued
Exemplary compounds
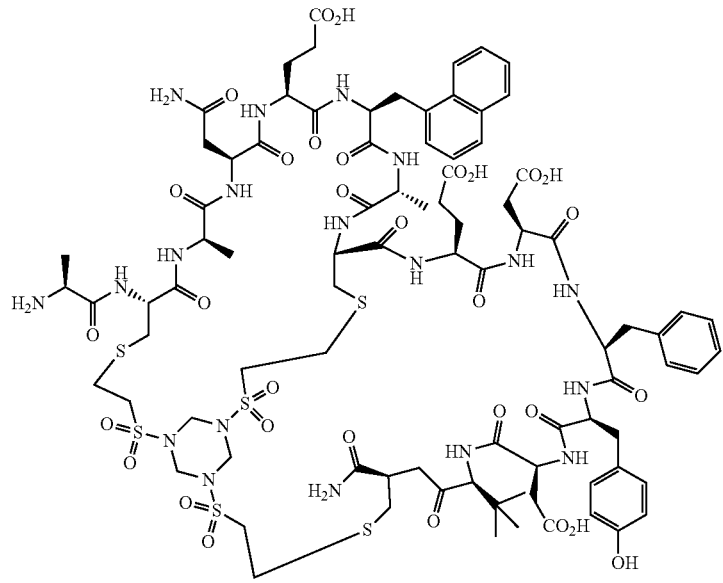 [SMILES: C[C@H](N)C(=O)N[C@H]1CSCCS(=O)(=O)N2CN3CN(C2)S(=O)(=O)CCSC[C@H](NC(=O)[C@@H](C)NC(=O)[C@H](Cc2cccc4ccccc24)NC(=O)[C@H](CCC(=O)O)NC(=O)[C@H](CC(N)=O)NC(=O)[C@@H](C)NC1=O)C(=O)N[C@@H](CCC(=O)O)C(=O)N[C@@H](CC(=O)O)C(=O)N[C@@H](Cc1ccccc1)C(=O)N[C@@H](Cc1ccc(O)cc1)C(=O)N[C@@H](CC(=O)O)C(=O)N[C@@H](C(C)(C)C)C(=O)C[C@H](C(N)=O)CSCCS3(=O)=O]
I-95
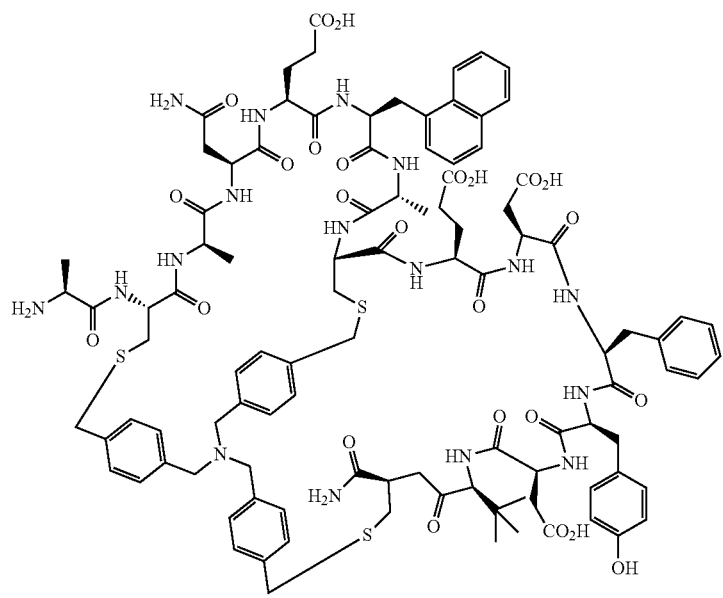 [SMILES: C[C@H](N)C(=O)N[C@H]1CSCc2ccc(cc2)CN2Cc3ccc(cc3)CSC[C@@H](C(N)=O)CC(=O)[C@H](C(C)(C)C)NC(=O)[C@H](CC(=O)O)NC(=O)[C@H](Cc3ccc(O)cc3)NC(=O)[C@H](Cc3ccccc3)NC(=O)[C@H](CC(=O)O)NC(=O)[C@H](CCC(=O)O)NC(=O)[C@H](CSCc3ccc(cc3)C2)NC(=O)[C@@H](C)NC(=O)[C@H](Cc2cccc3ccccc23)NC(=O)[C@H](CCC(=O)O)NC(=O)[C@H](CC(N)=O)NC(=O)[C@@H](C)NC1=O]
I-96

TABLE 1-continued
Exemplary compounds
I-97
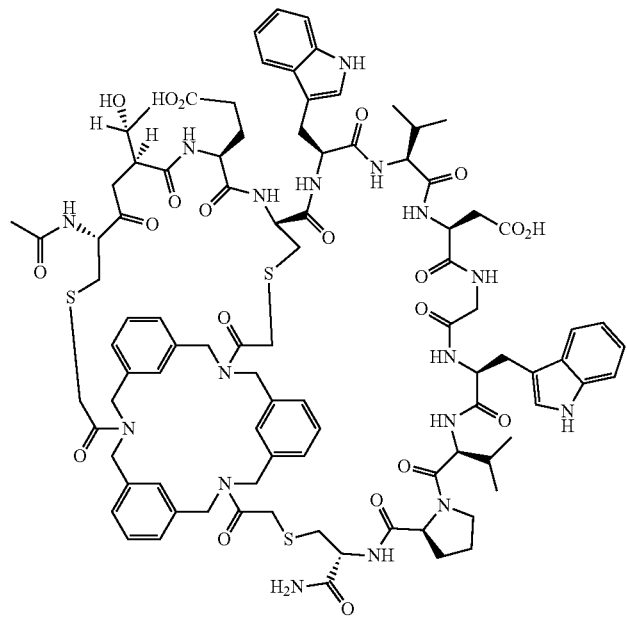
I-98
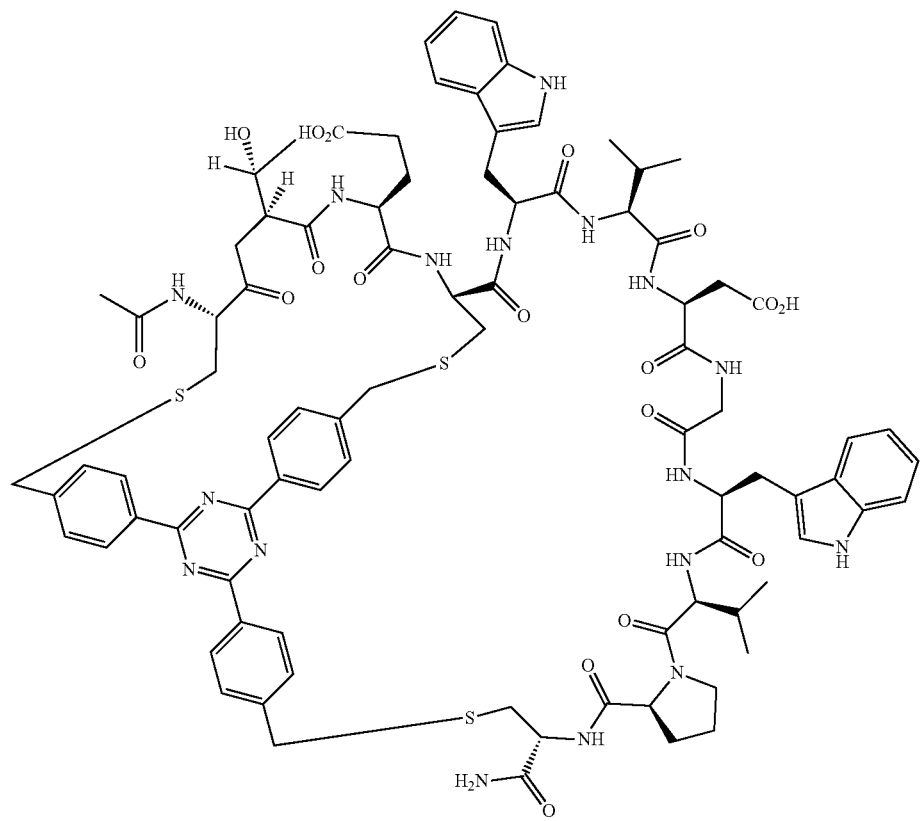

TABLE 1-continued
Exemplary compounds
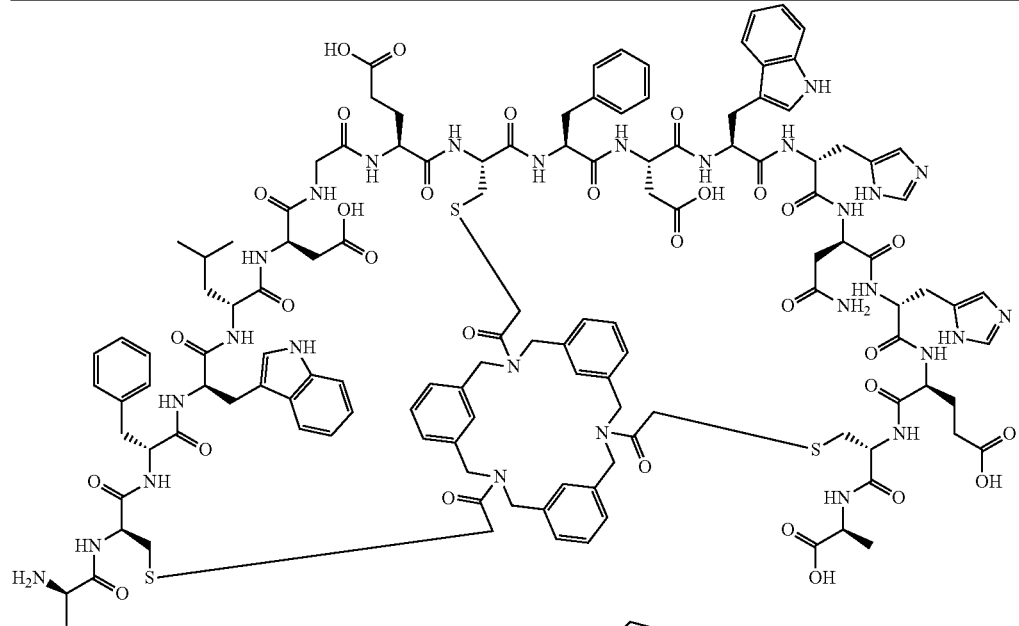 [SMILES: CC(C)C[C@H]1NC(=O)[C@@H](Cc2c[nH]c3ccccc23)NC(=O)[C@@H](Cc2ccccc2)NC(=O)[C@H](NC(=O)[C@@H](C)N)CSCC(=O)N2Cc3cccc(c3)CN3Cc4cccc(c4)CN(Cc4cccc(c4)C2)C(=O)CSC[C@H](NC(=O)[C@H](CCC(=O)O)NC(=O)CNC(=O)[C@@H](CC(=O)O)NC1=O)C(=O)N[C@@H](Cc1ccccc1)C(=O)N[C@@H](CC(=O)O)C(=O)N[C@@H](Cc1c[nH]c2ccccc12)C(=O)N[C@H](Cc1cnc[nH]1)C(=O)N[C@H](CC(N)=O)C(=O)N[C@H](Cc1cnc[nH]1)C(=O)N[C@@H](CCC(=O)O)C(=O)N[C@H](C(=O)N[C@@H](C)C(=O)O)CSCC3=O]
I-99
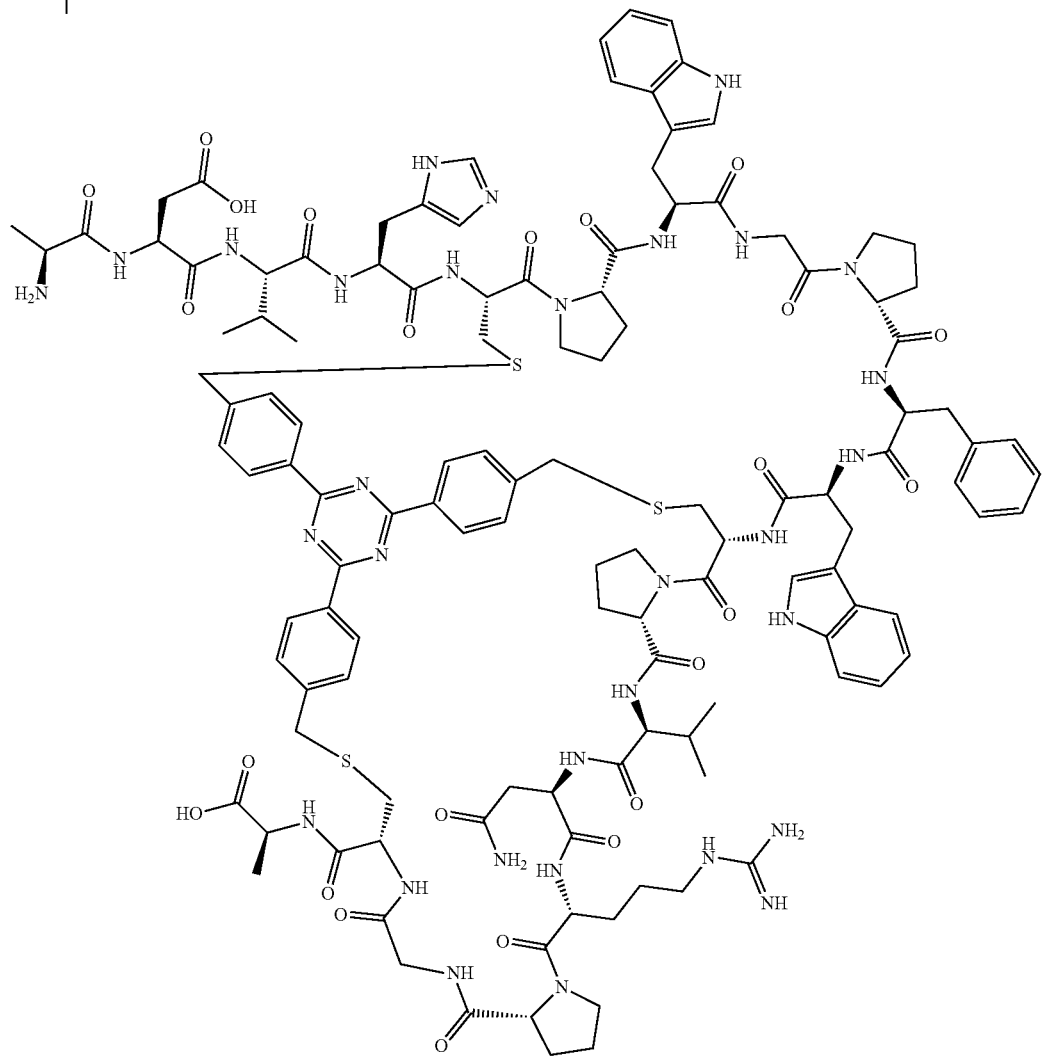 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCc2ccc(cc2)-c2nc3nc(n2)-c2ccc(cc2)CSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCc1ccc-3cc1]
I-100

TABLE 1-continued
Exemplary compounds
I-101
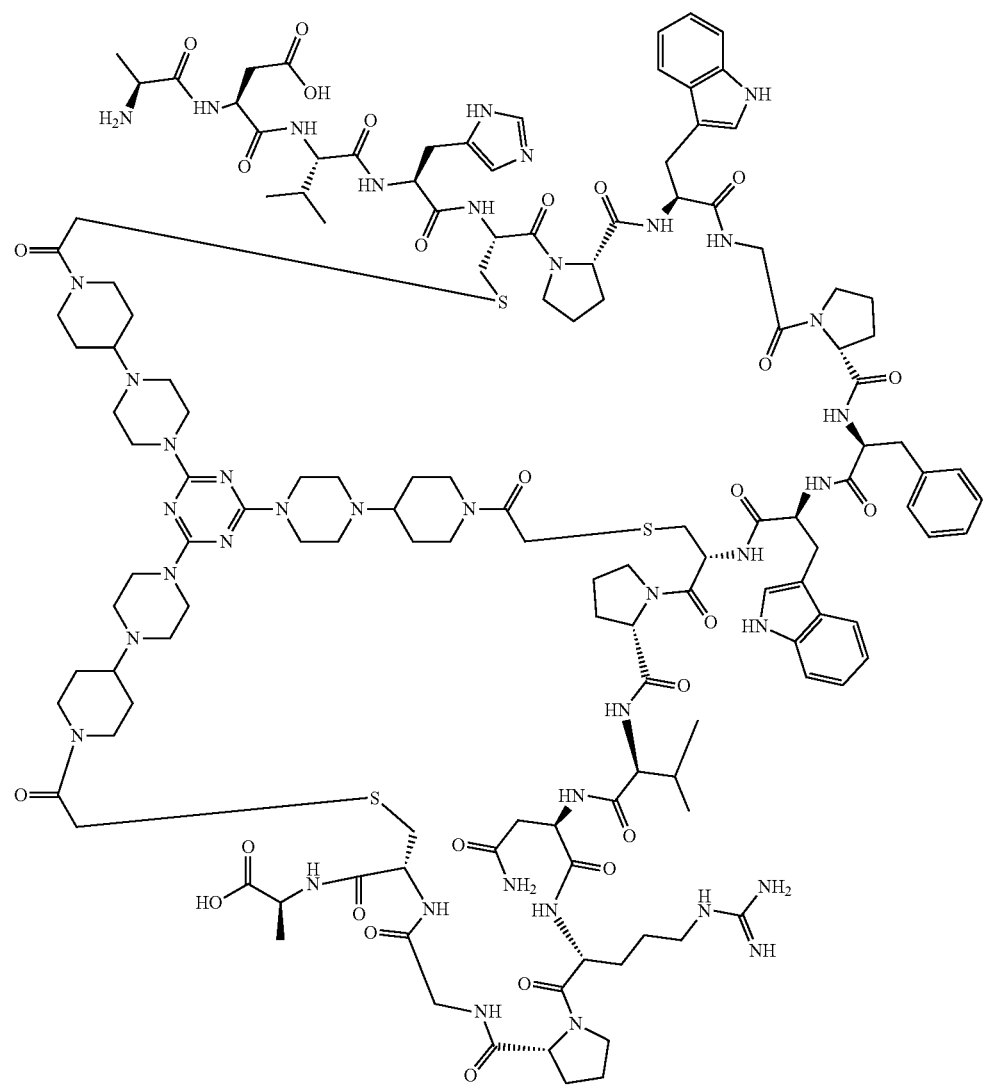 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCC(=O)N2CCC(CC2)N2CCN(CC2)c2nc3nc(n2)N2CCN(CC2)C2CCN(CC2)C(=O)CSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCC(=O)N1CCC(CC1)N1CCN3CC1]

TABLE 1-continued
Exemplary compounds
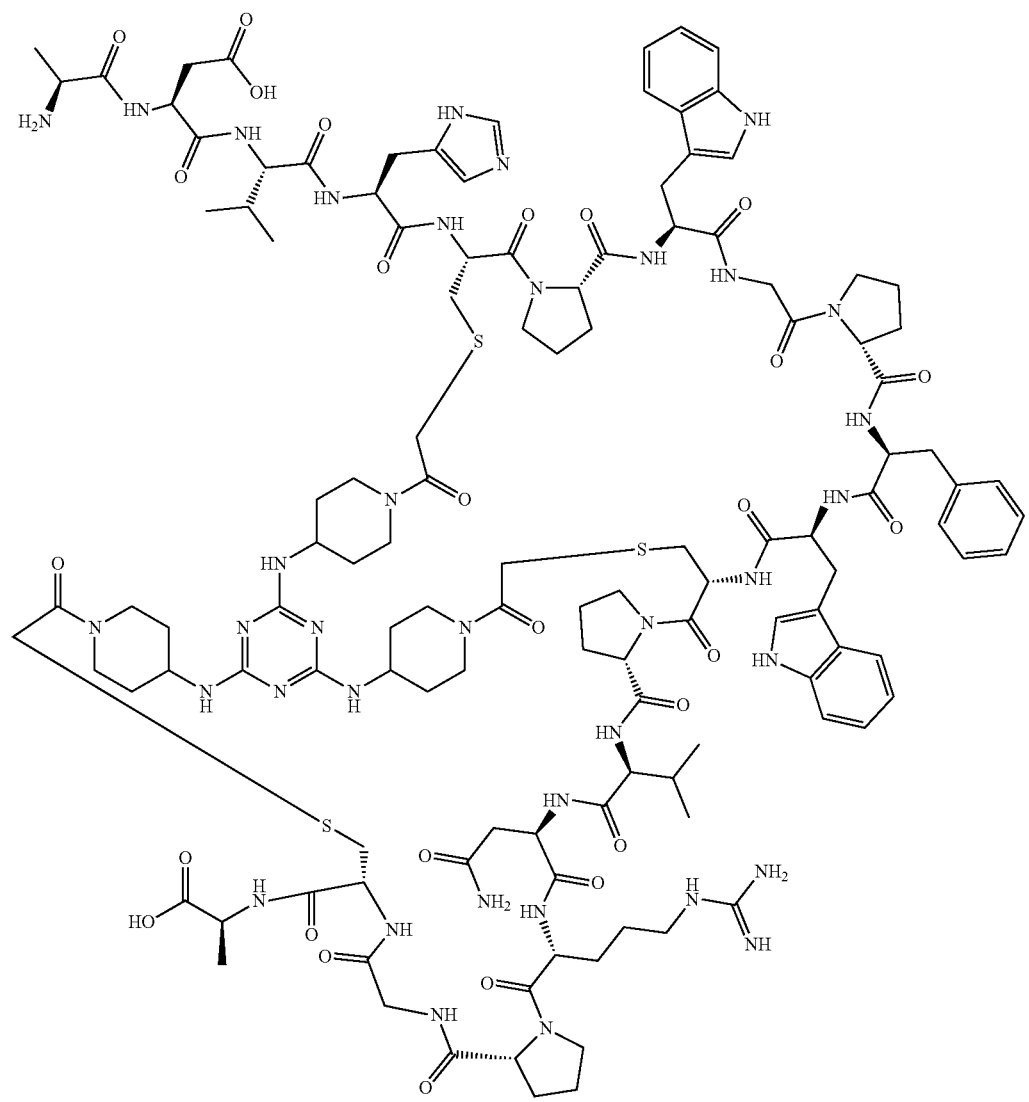 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCC(=O)N2CCC(CC2)Nc2nc3nc(n2)NC2CCN(CC2)C(=O)CSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCC(=O)N1CCC(CC1)N3]
I-102

TABLE 1-continued
Exemplary compounds
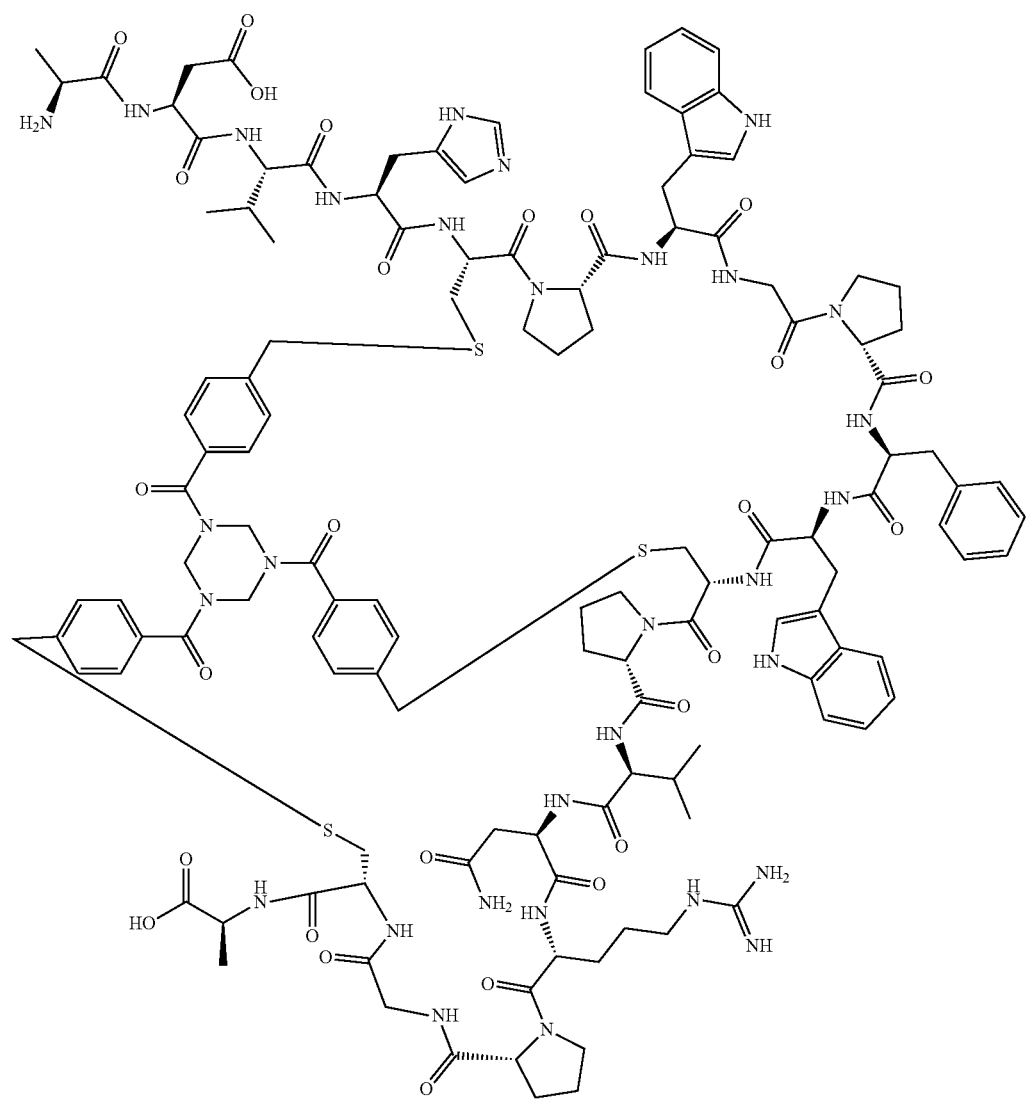 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCc2ccc(cc2)C(=O)N2CN3CN(C2)C(=O)c2ccc(cc2)CSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCc1ccc(cc1)C3=O]
I-103

TABLE 1-continued
Exemplary compounds
I-104
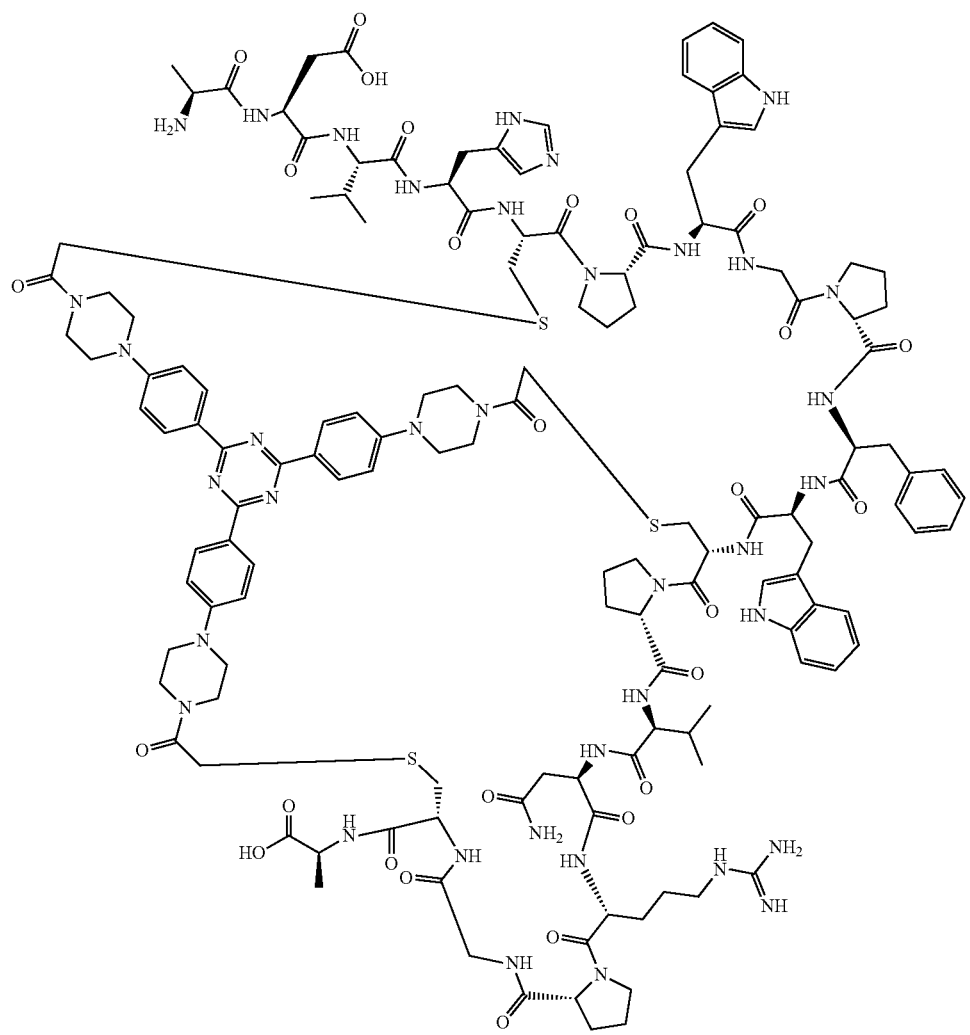 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCC(=O)N2CCN(CC2)c2ccc(cc2)-c2nc3nc(n2)-c2ccc(cc2)N2CCN(CC2)C(=O)CSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCC(=O)N1CCN(CC1)c1ccc-3cc1]

TABLE 1-continued
Exemplary compounds
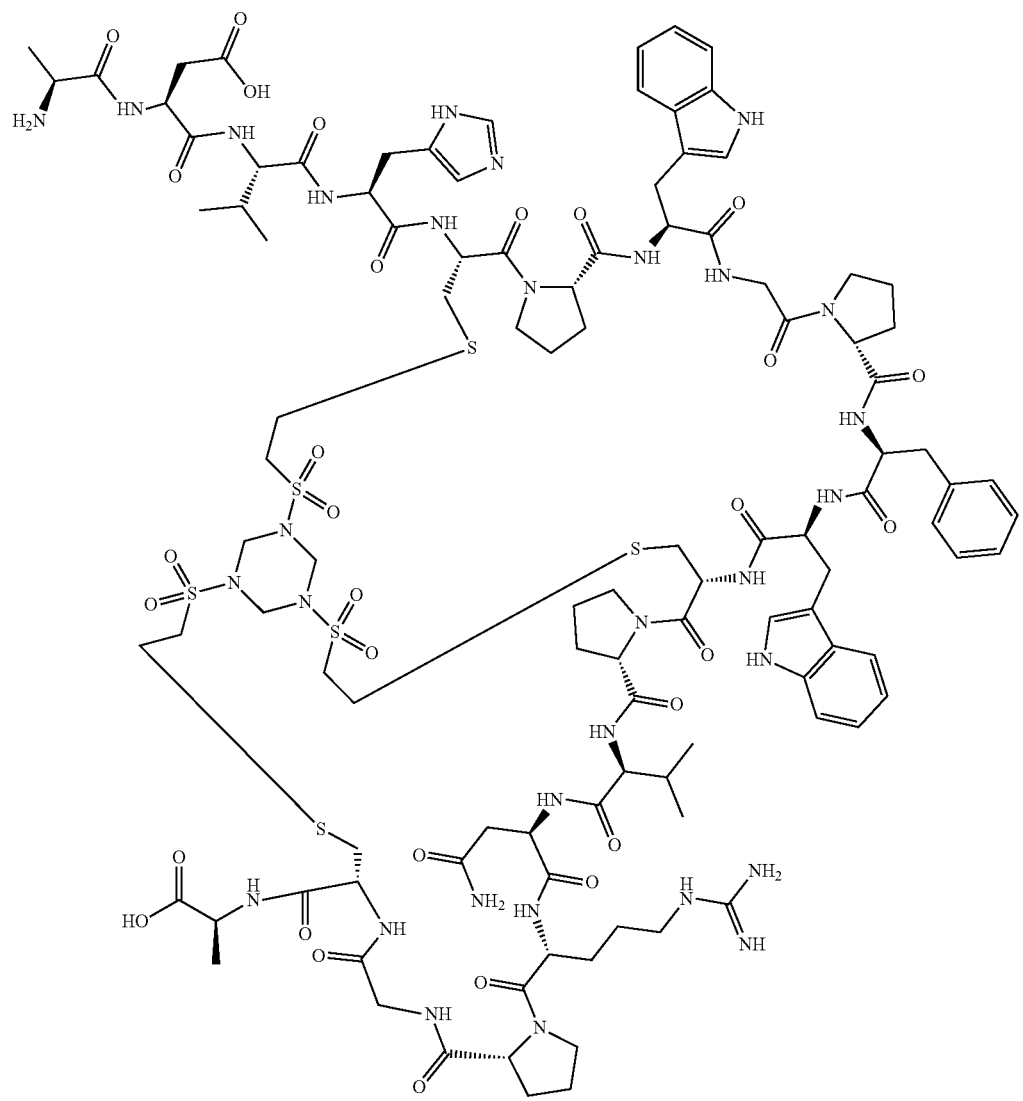 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCCS(=O)(=O)N2CN3CN(C2)S(=O)(=O)CCSC[C@H](NC(=O)[C@H](Cc2c[nH]c4ccccc24)NC(=O)[C@H](Cc2ccccc2)NC(=O)[C@H]2CCCN2C(=O)CNC(=O)[C@H](Cc2c[nH]c4ccccc24)NC(=O)[C@@H]2CCCN2C1=O)C(=O)N1CCC[C@H]1C(=O)N[C@@H](C(C)C)C(=O)N[C@H](CC(N)=O)C(=O)N[C@H](CCCNC(=N)N)C(=O)N1CCC[C@@H]1C(=O)NCC(=O)N[C@H](C(=O)N[C@@H](C)C(=O)O)CSCCS3(=O)=O]
I-105

TABLE 1-continued
Exemplary compounds
I-106
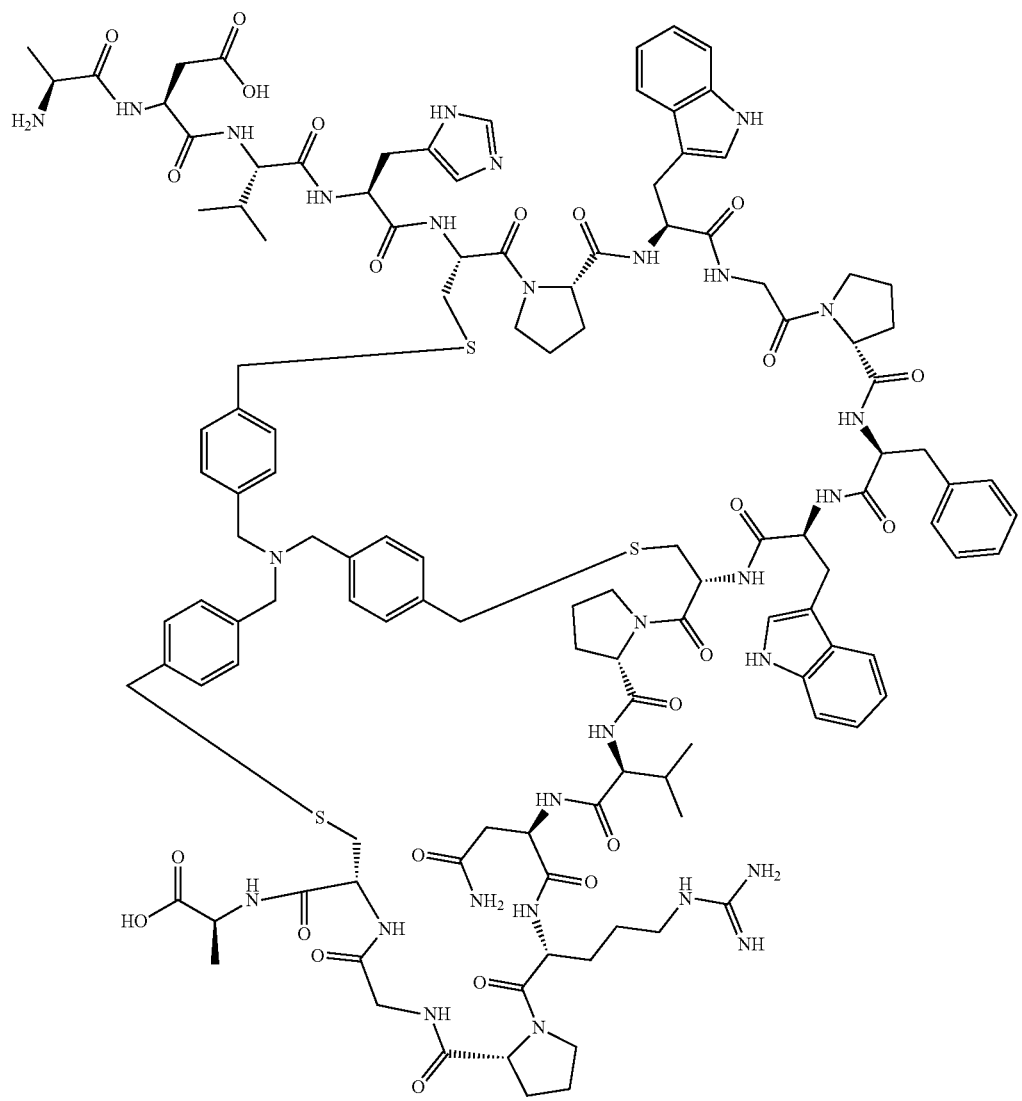 [SMILES: CC(C)[C@H](NC(=O)[C@H](CC(=O)O)NC(=O)[C@H](C)N)C(=O)N[C@@H](Cc1cnc[nH]1)C(=O)N[C@H]1CSCc2ccc(cc2)CN2Cc3ccc(cc3)CSC[C@@H](C(=O)N[C@@H](C)C(=O)O)NC(=O)CNC(=O)[C@H]3CCCN3C(=O)[C@@H](CCCNC(=N)N)NC(=O)[C@@H](CC(N)=O)NC(=O)[C@H](C(C)C)NC(=O)[C@@H]3CCCN3C(=O)[C@H](CSCc3ccc(cc3)C2)NC(=O)[C@H](Cc2c[nH]c3ccccc23)NC(=O)[C@H](Cc2ccccc2)NC(=O)[C@H]2CCCN2C(=O)CNC(=O)[C@H](Cc2c[nH]c3ccccc23)NC(=O)[C@@H]2CCCN2C1=O]

TABLE 1-continued
Exemplary compounds
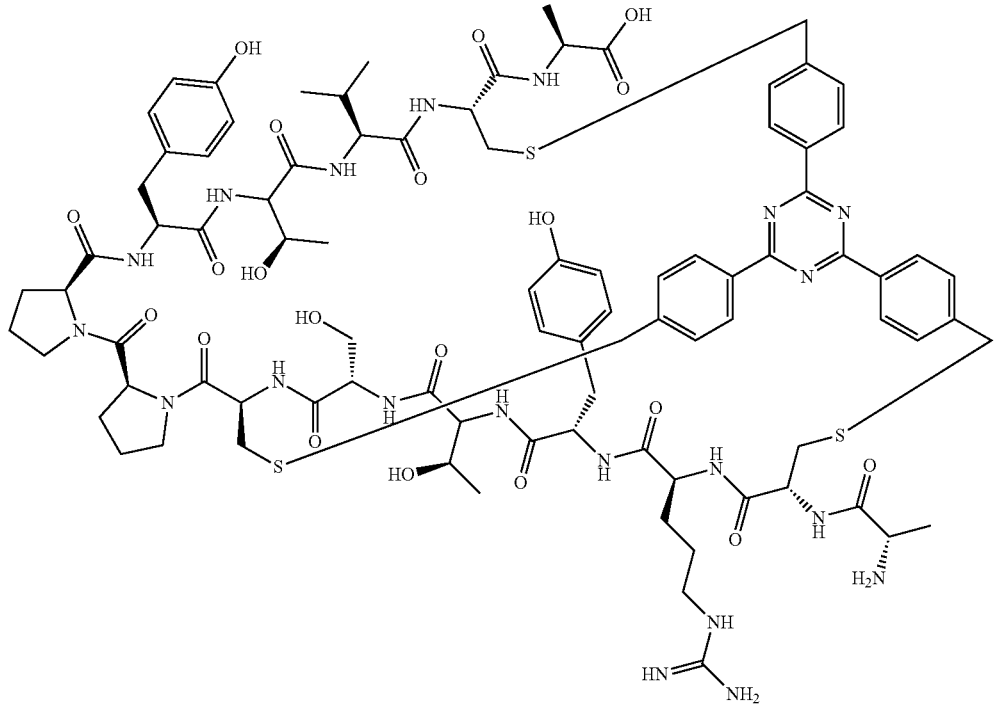 [SMILES: CC(C)[C@@H]1NC(=O)C([C@@H](C)O)NC(=O)[C@H](Cc2ccc(O)cc2)NC(=O)[C@@H]2CCCN2C(=O)[C@@H]2CCCN2C(=O)[C@@H]2CSCc3ccc(cc3)-c3nc(nc(n3)-c3ccc(cc3)CSC[C@@H](C(=O)N[C@@H](C)C(=O)O)NC1=O)-c1ccc(cc1)CSC[C@H](NC(=O)[C@H](C)N)C(=O)N[C@@H](CCCNC(=N)N)C(=O)N[C@@H](Cc1ccc(O)cc1)C(=O)NC([C@@H](C)O)C(=O)N[C@@H](CO)C(=O)N2]
I-107
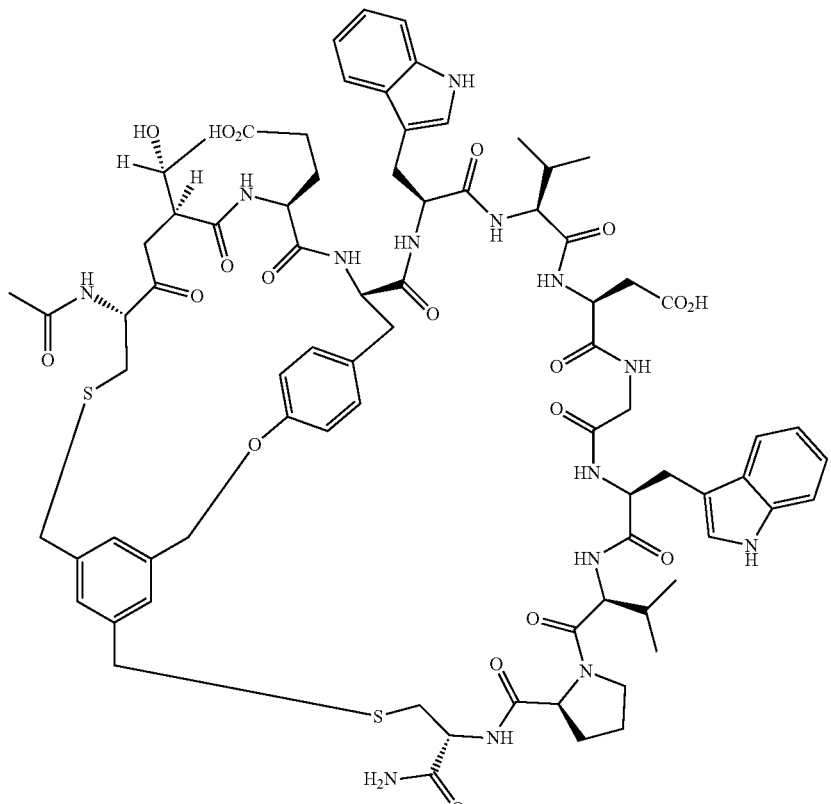
I-108

TABLE 1-continued
Exemplary compounds
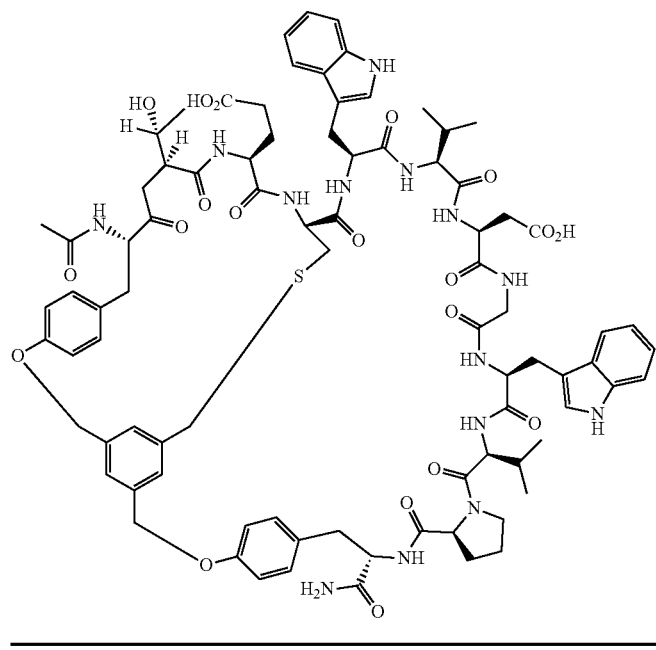
I-109
In some embodiments, the present invention provides a compound set forth in Table 2, or a pharmaceutically acceptable salt thereof.
TABLE 2
Exemplary compounds
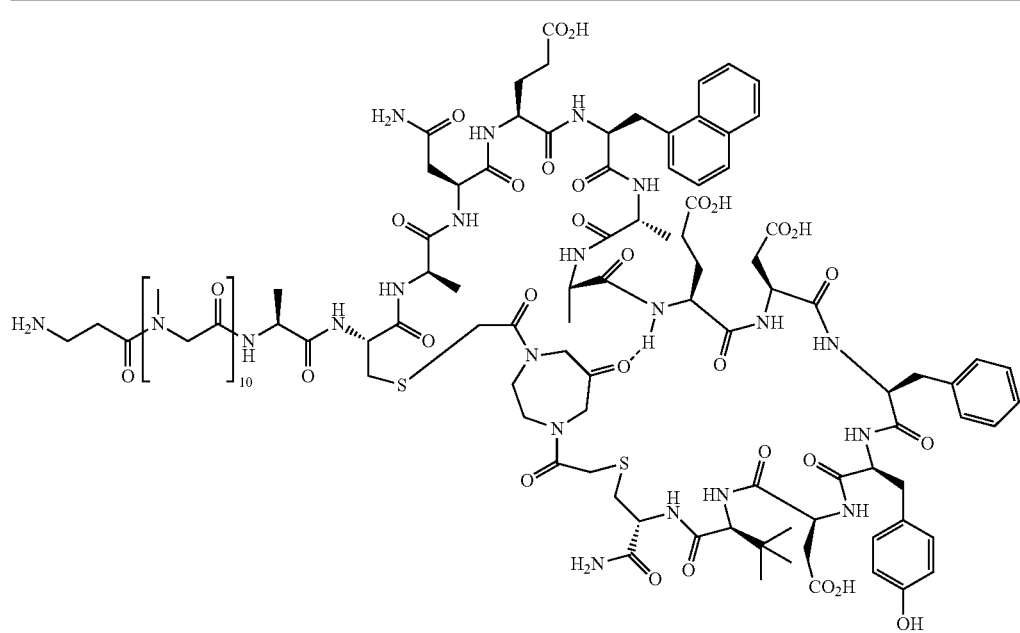
II-1

TABLE 2-continued
Exemplary compounds
II-2
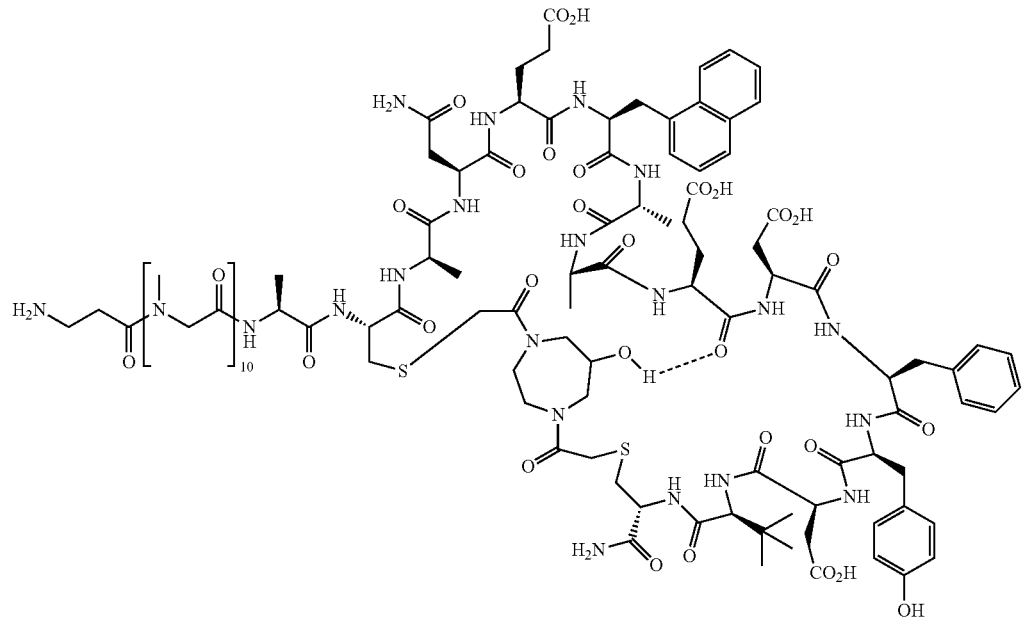
II-3

TABLE 2-continued
Exemplary compounds
II-4
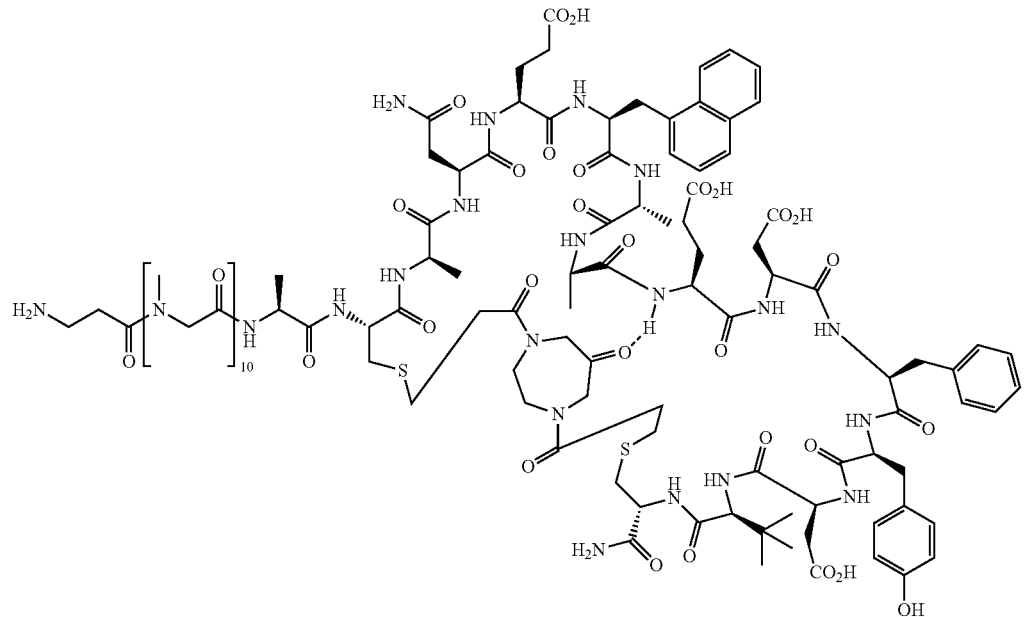
II-5
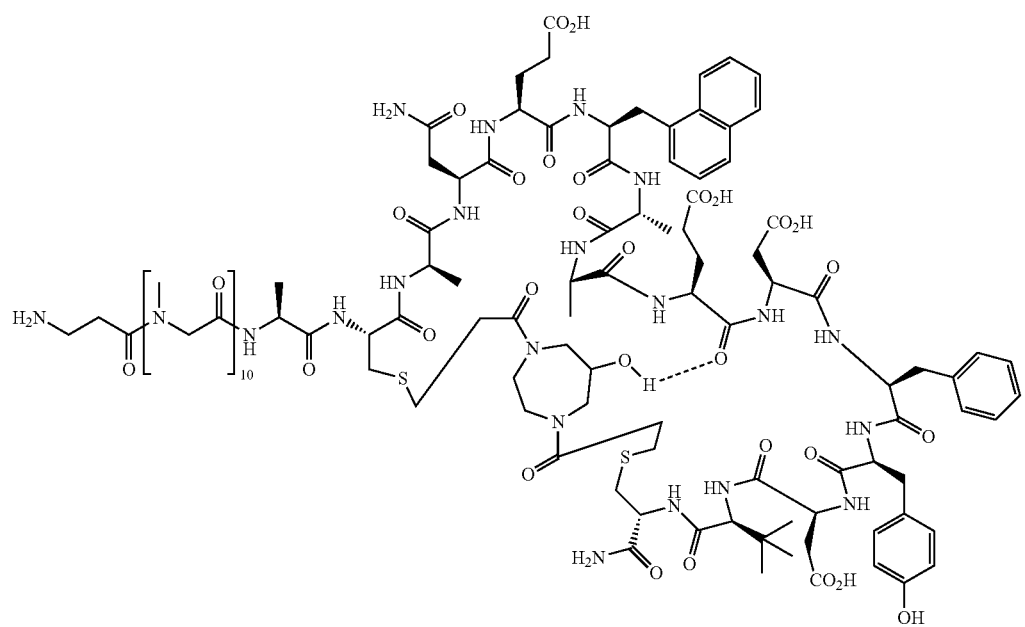

TABLE 2-continued
Exemplary compounds
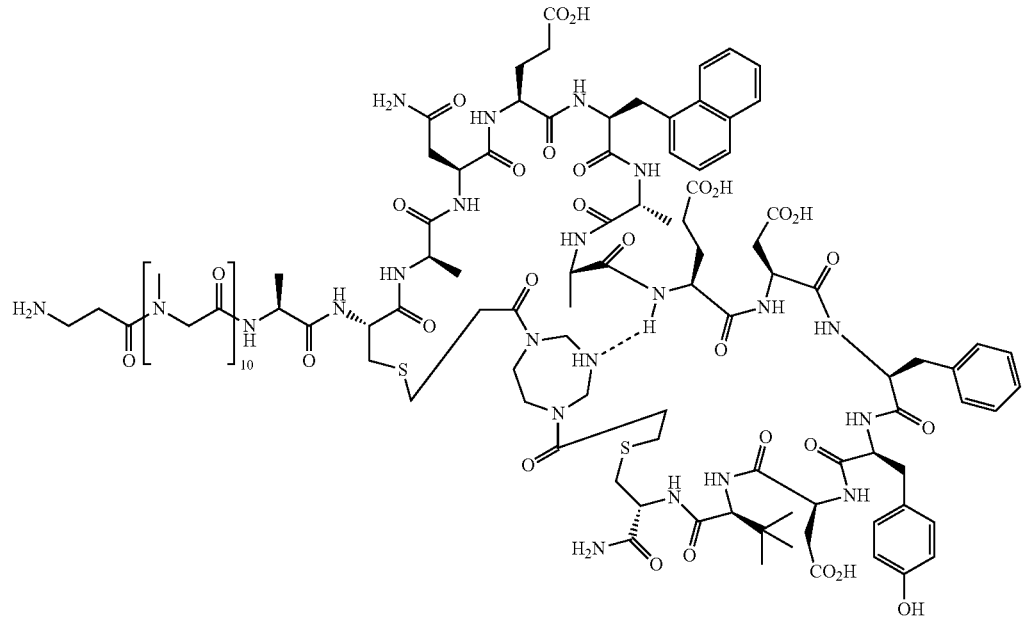
II-6
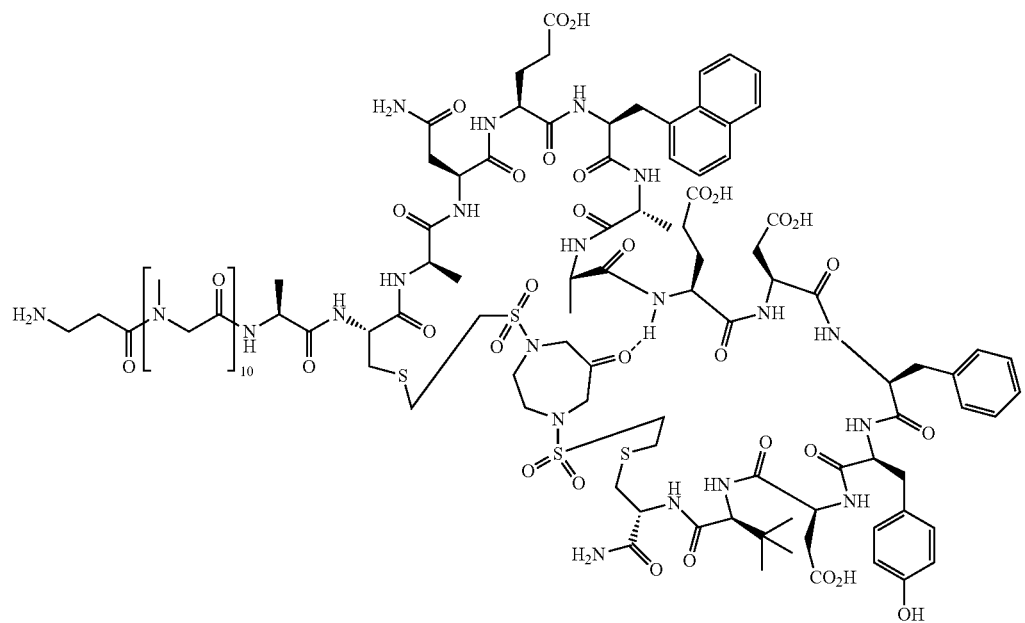
II-7

TABLE 2-continued
Exemplary compounds
II-8
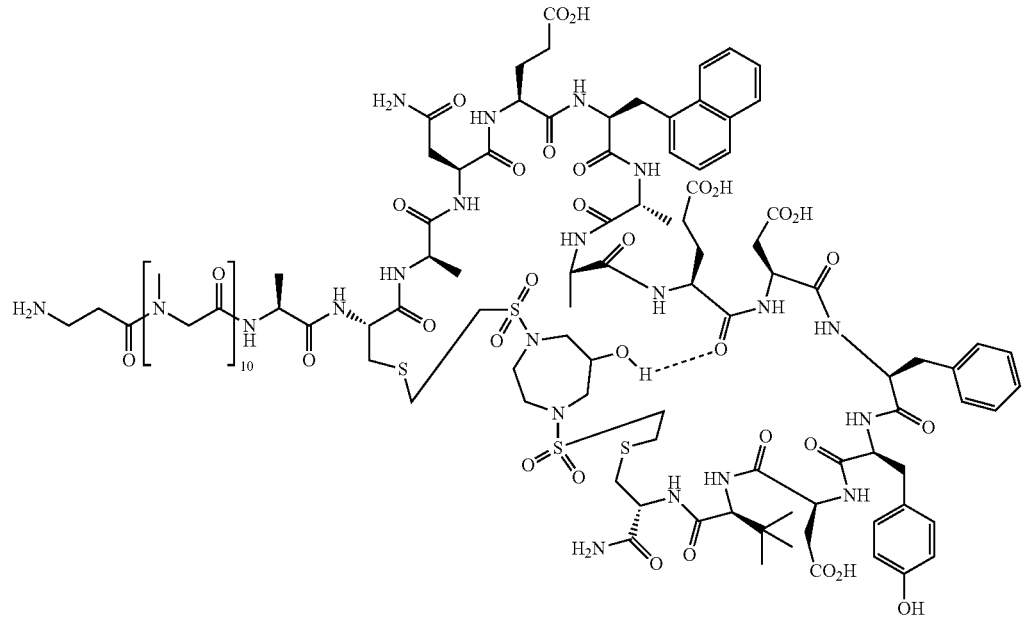
II-9
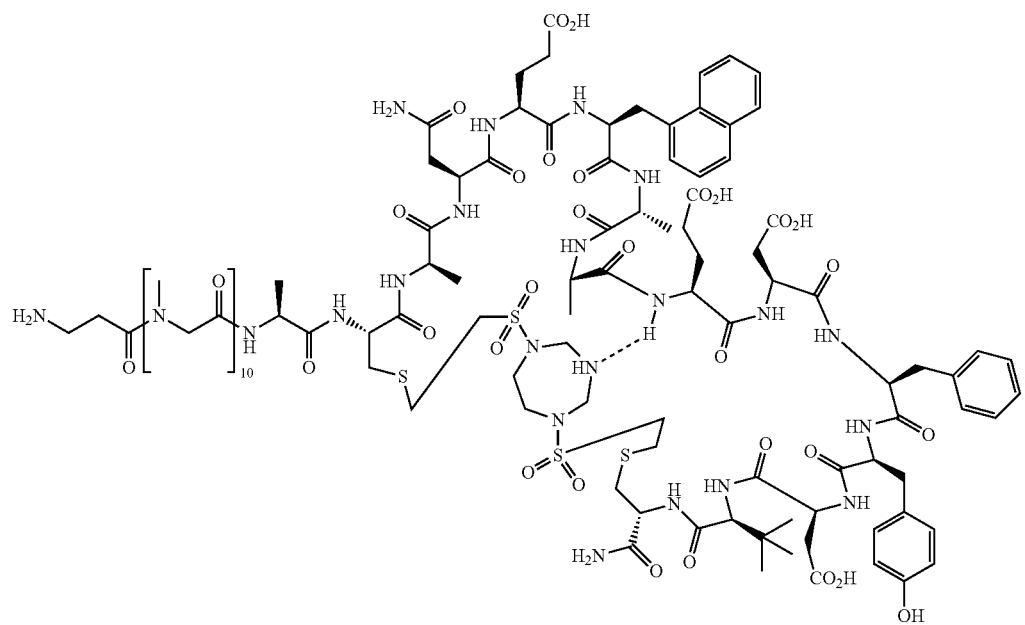

TABLE 2-continued
Exemplary compounds
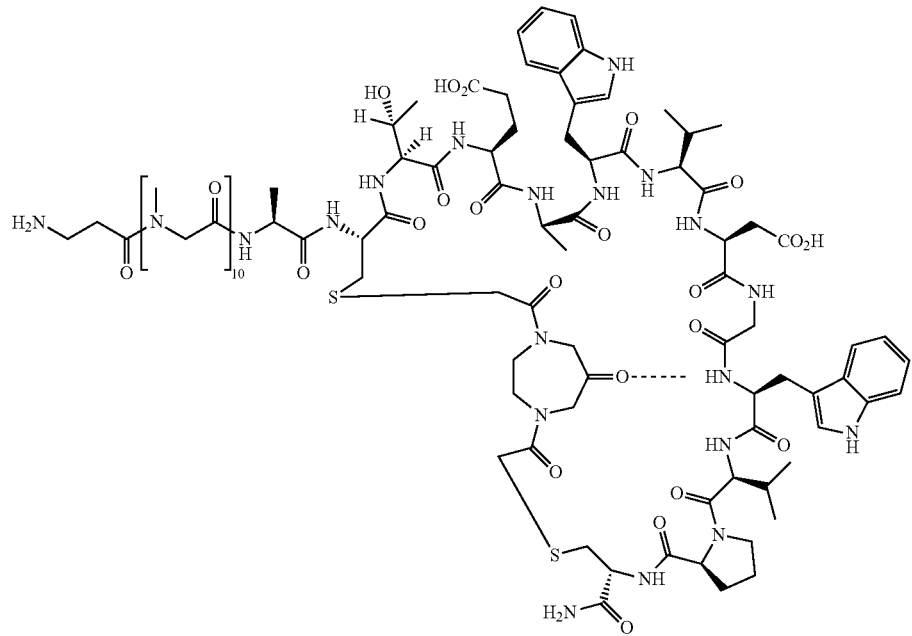
II-10
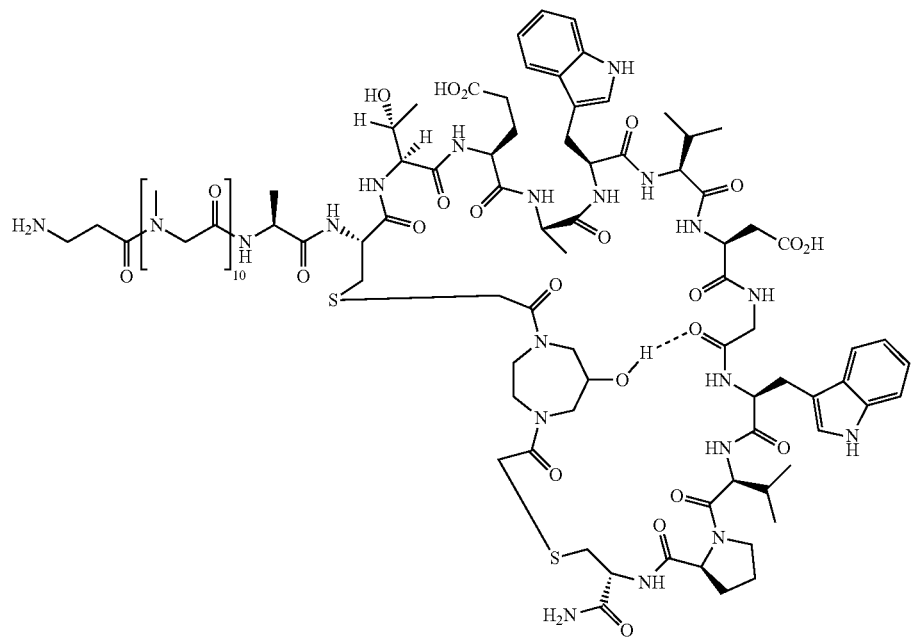
II-11

TABLE 2-continued
Exemplary compounds
II-12
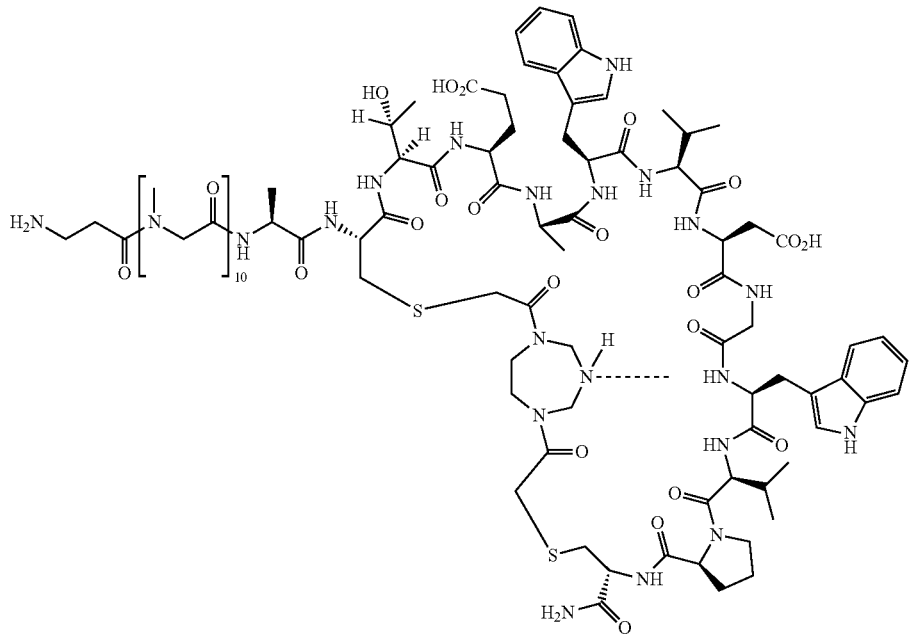
II-13
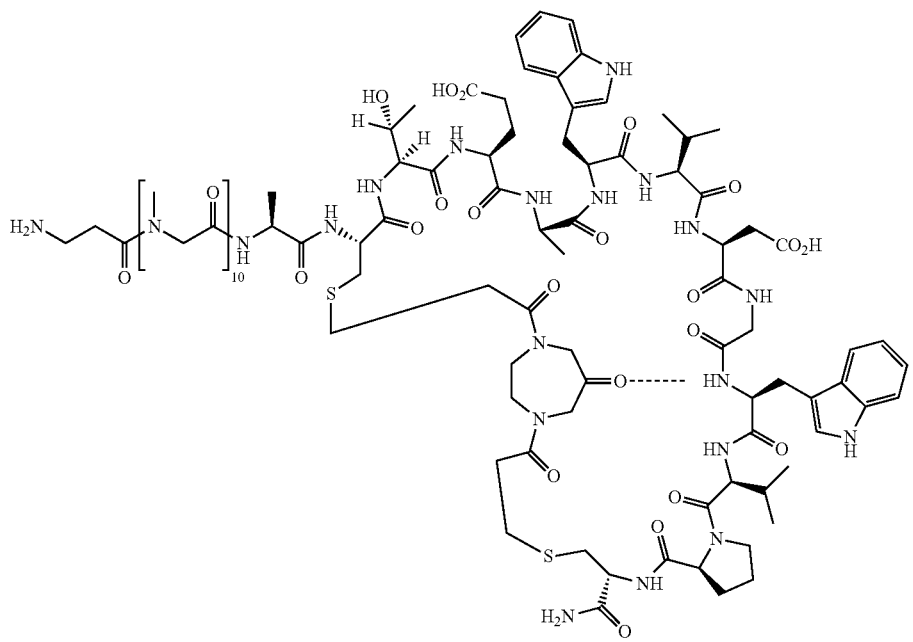

TABLE 2-continued
Exemplary compounds
II-14
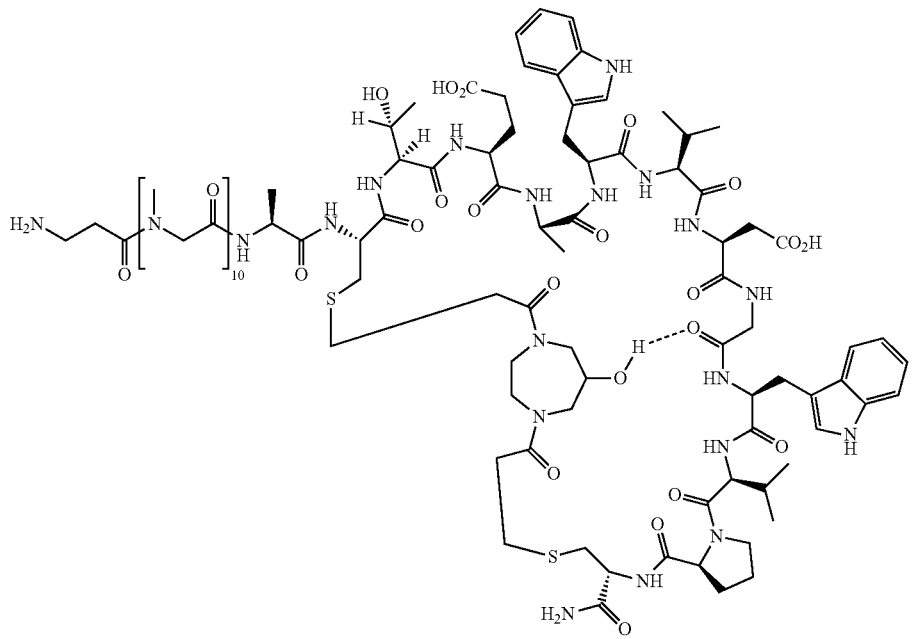
II-15
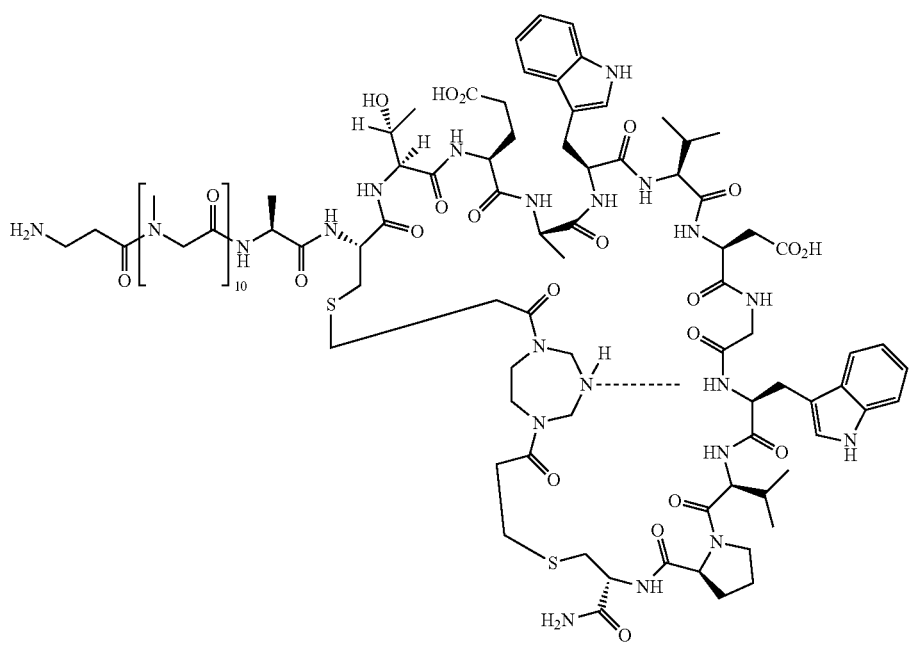

TABLE 2-continued
Exemplary compounds
II-16
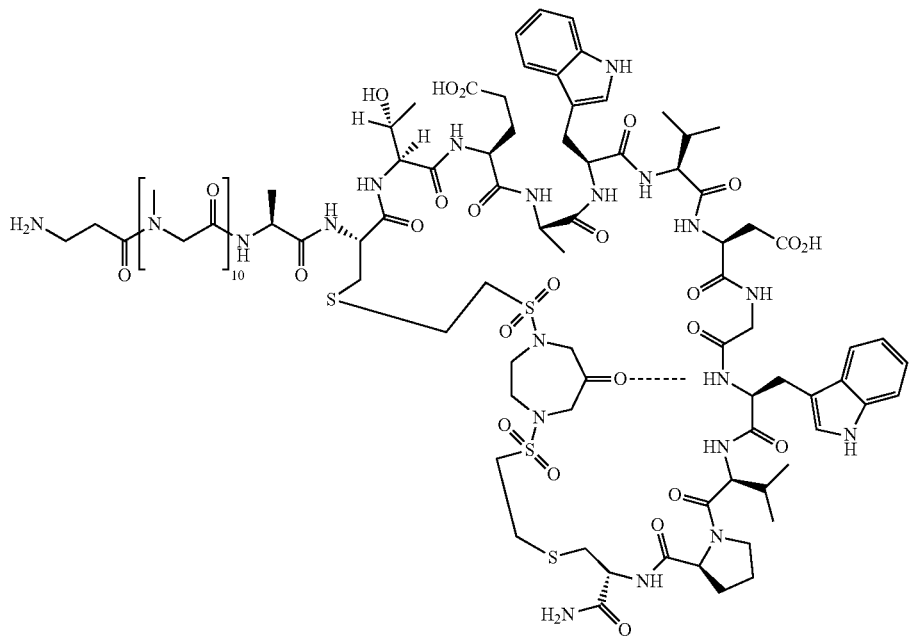
II-17
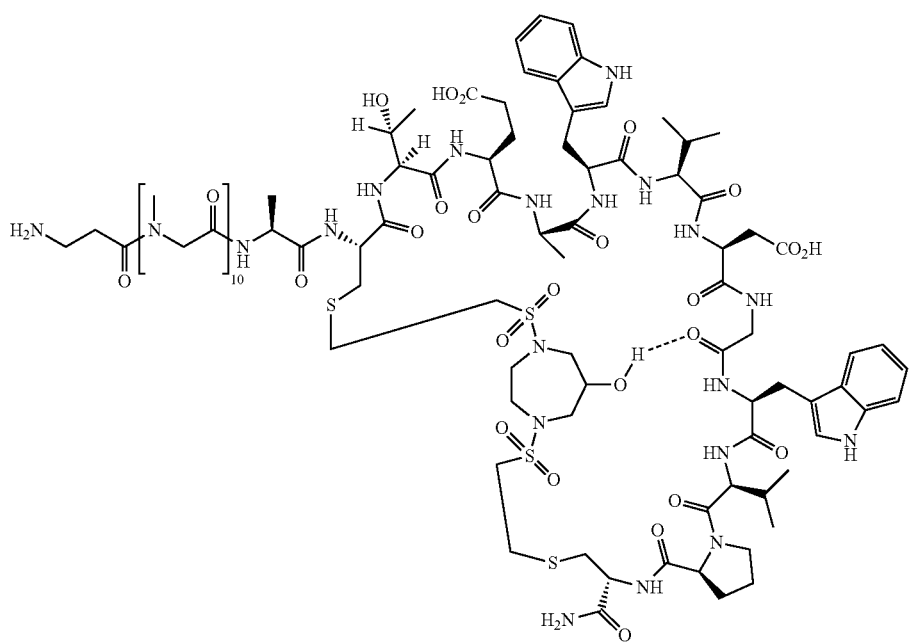

TABLE 2-continued
Exemplary compounds
II-18
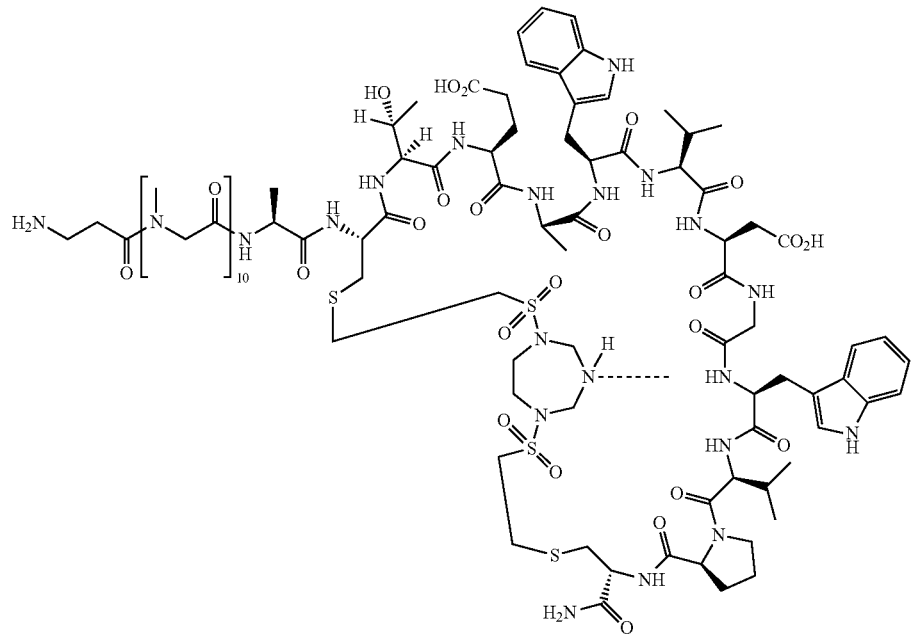
II-19
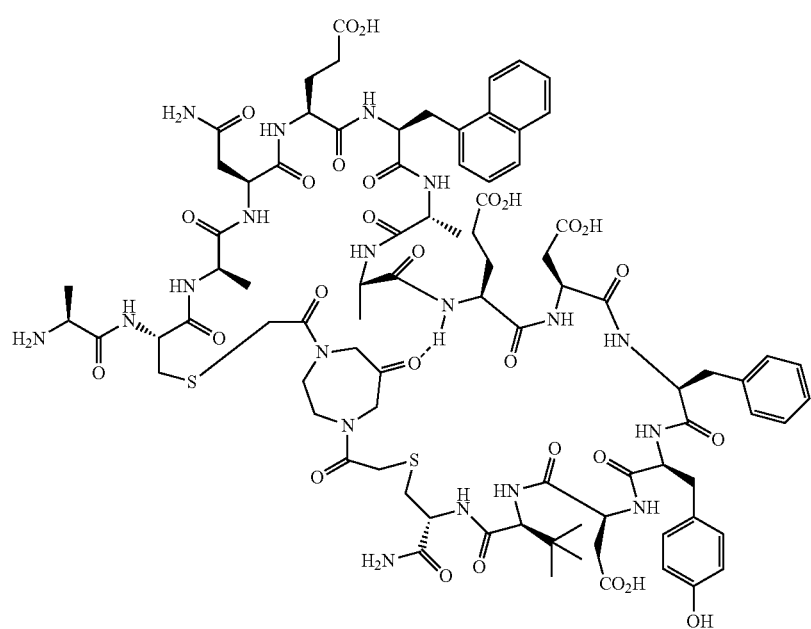

TABLE 2-continued
Exemplary compounds
II-20
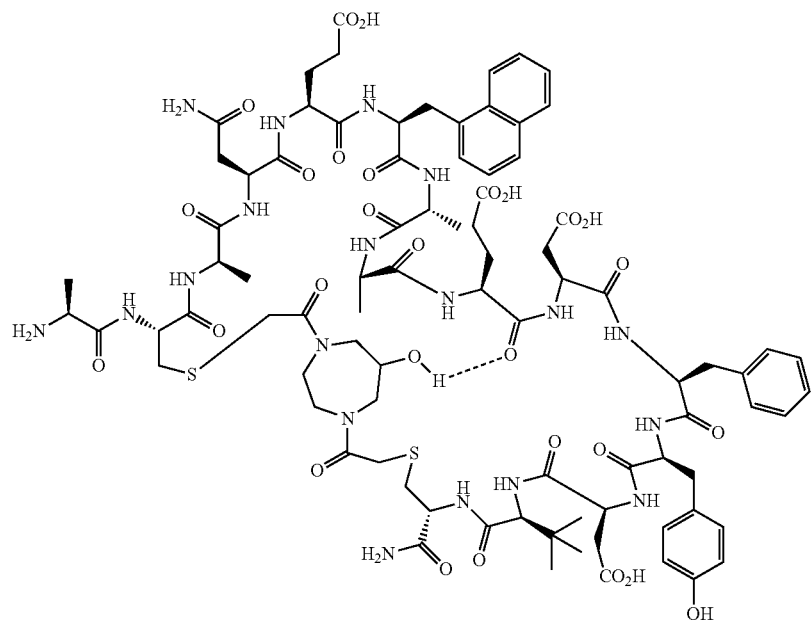
II-21
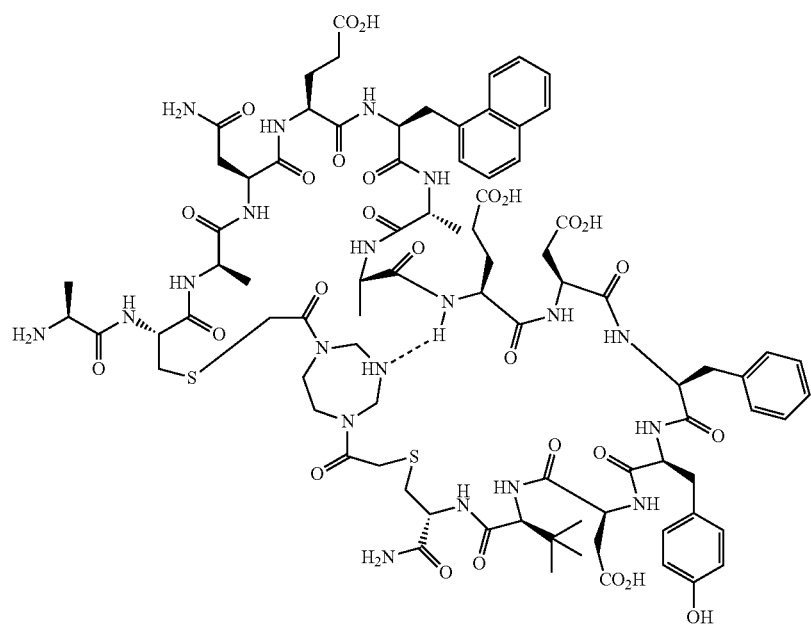

TABLE 2-continued
Exemplary compounds
II-22
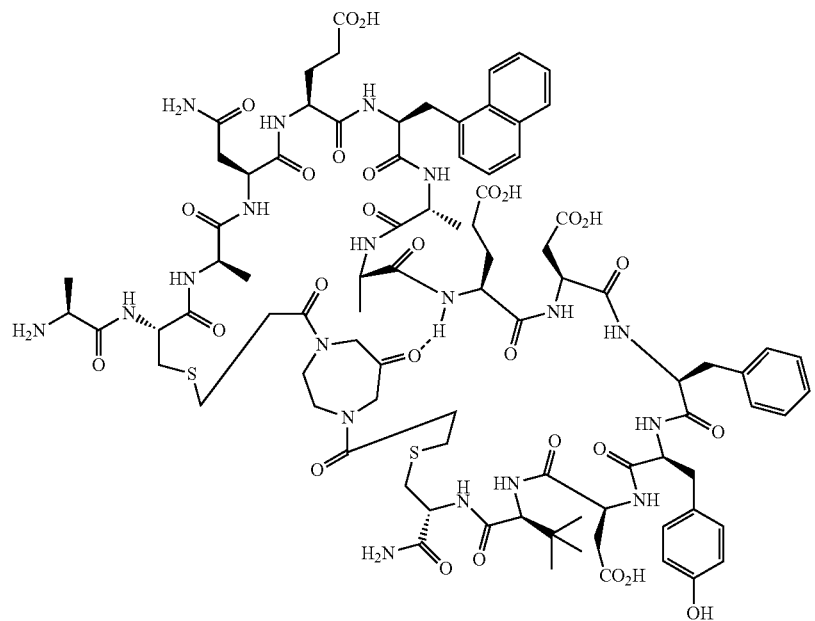
II-23
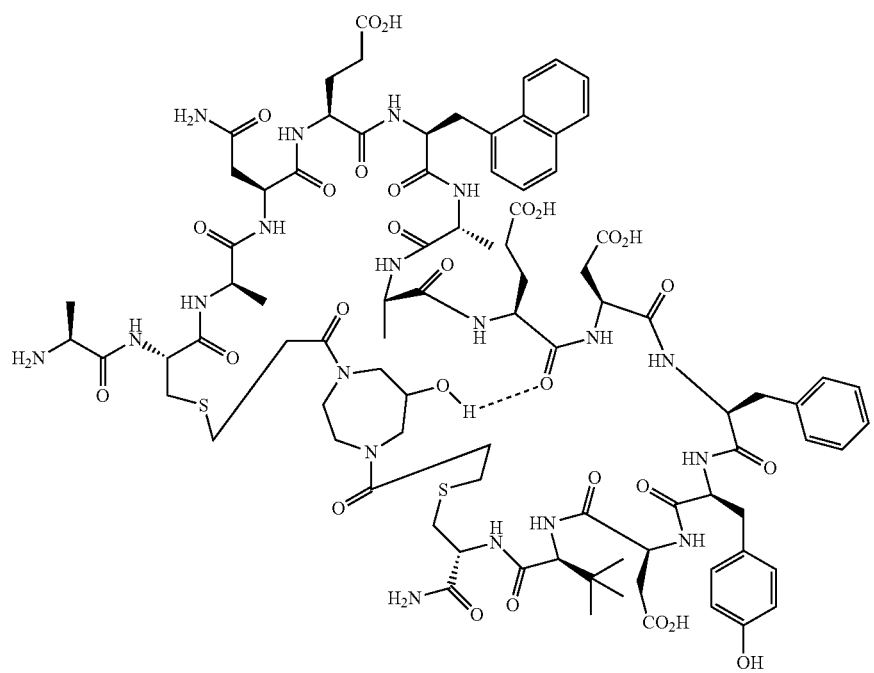

TABLE 2-continued
Exemplary compounds
II-24
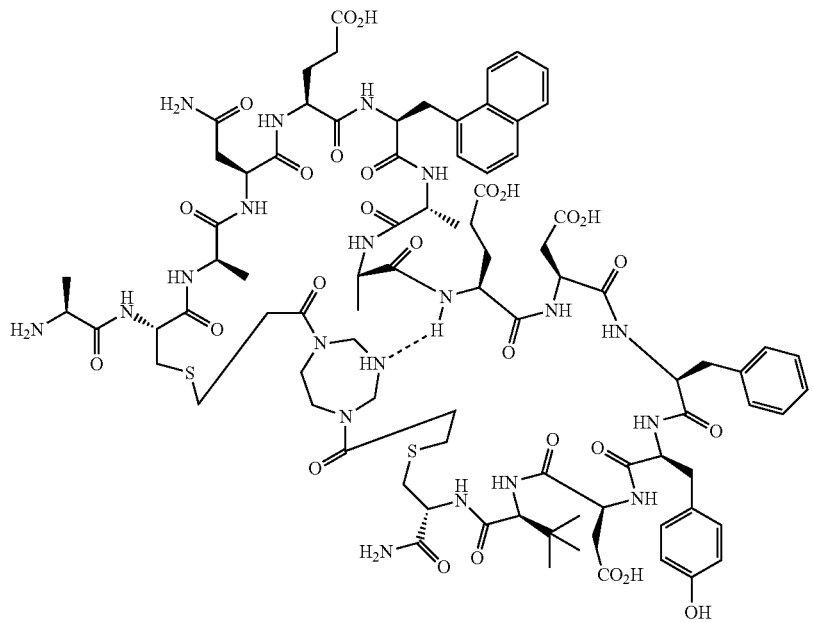
II-25
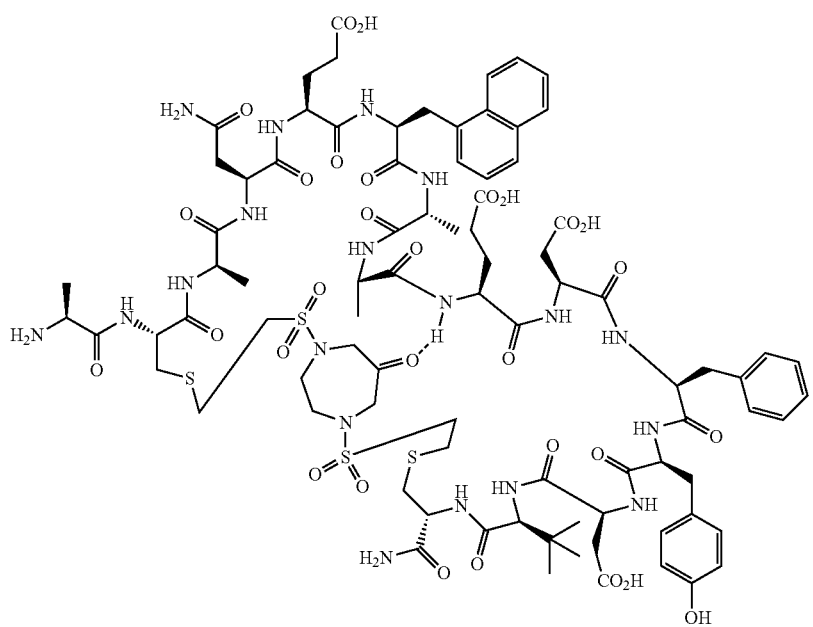

TABLE 2-continued
Exemplary compounds
II-26
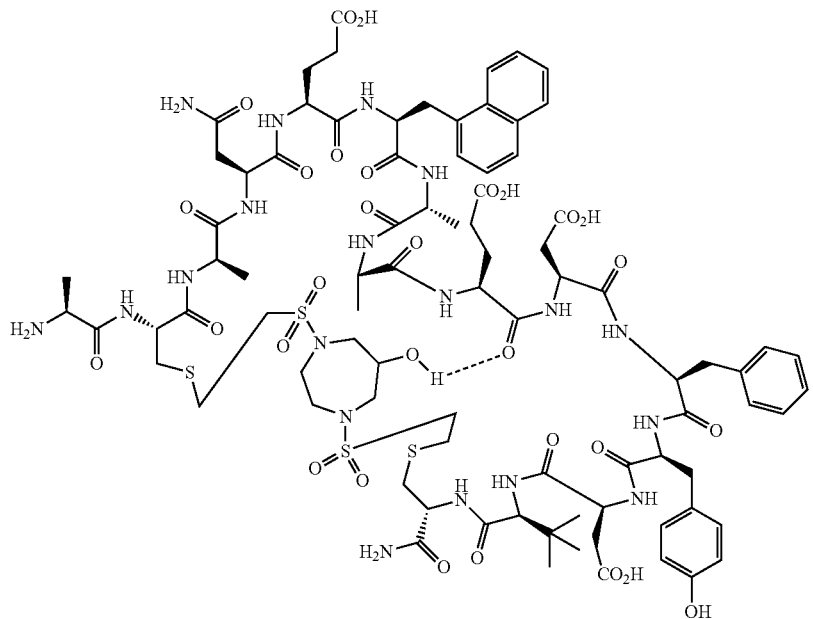
II-27
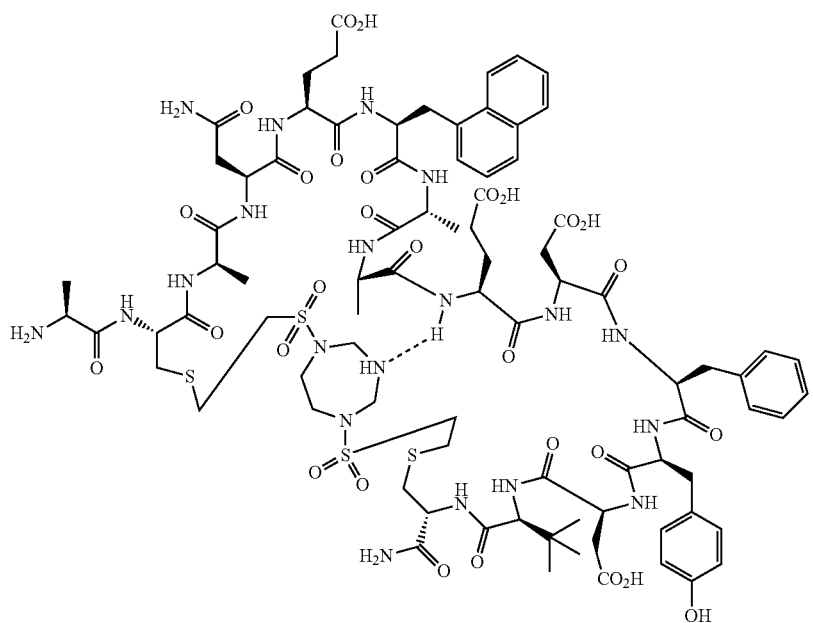

TABLE 2-continued
Exemplary compounds
II-28
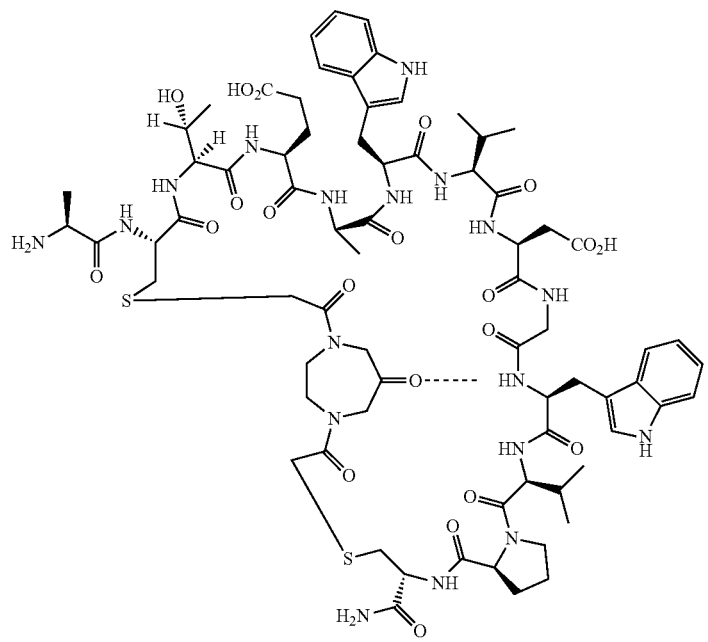
II-29
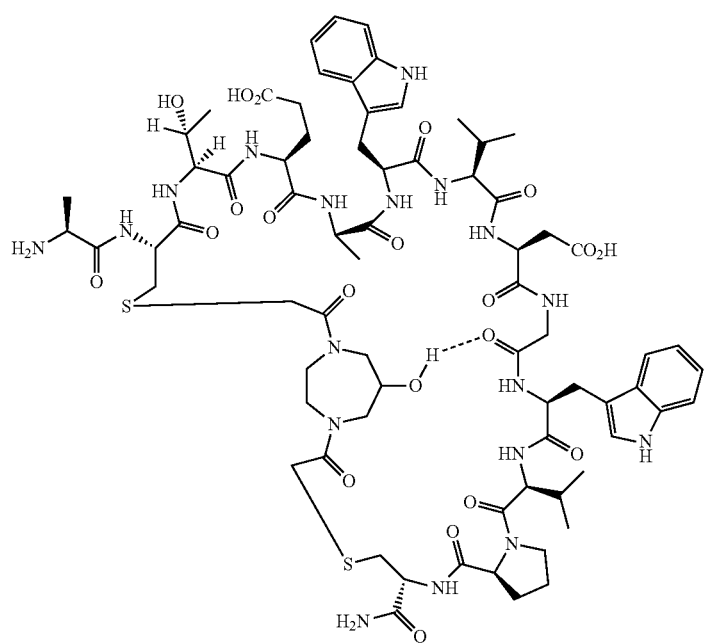

TABLE 2-continued
Exemplary compounds
II-30
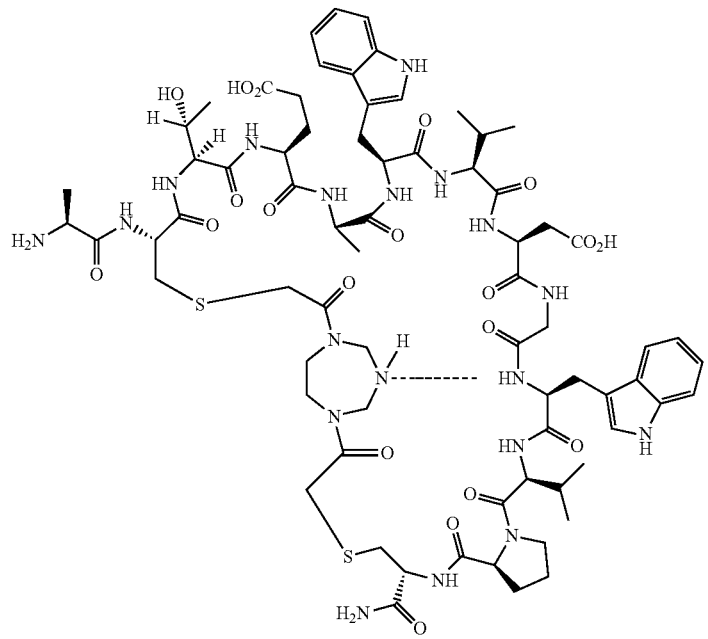
II-31
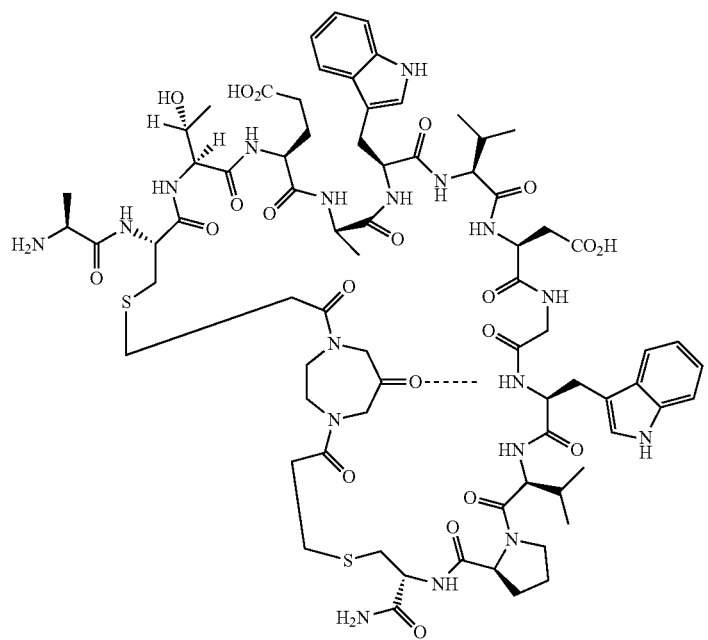

TABLE 2-continued
Exemplary compounds
II-32
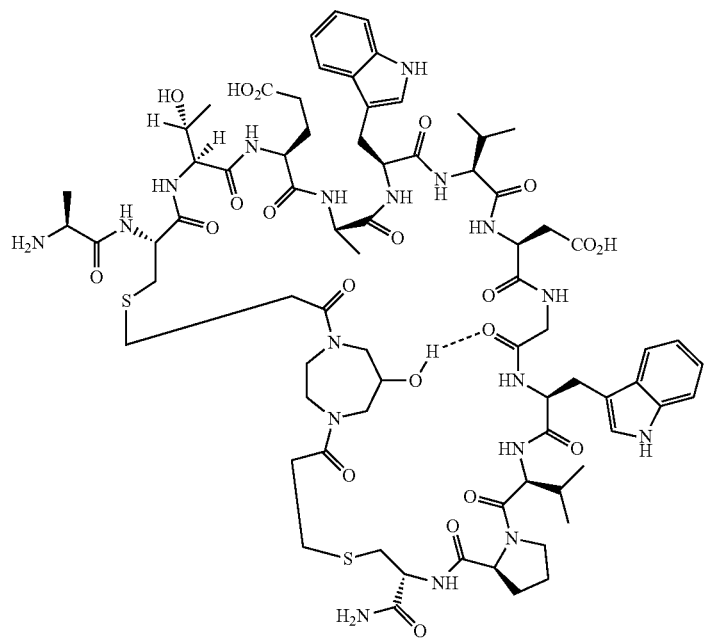
II-33
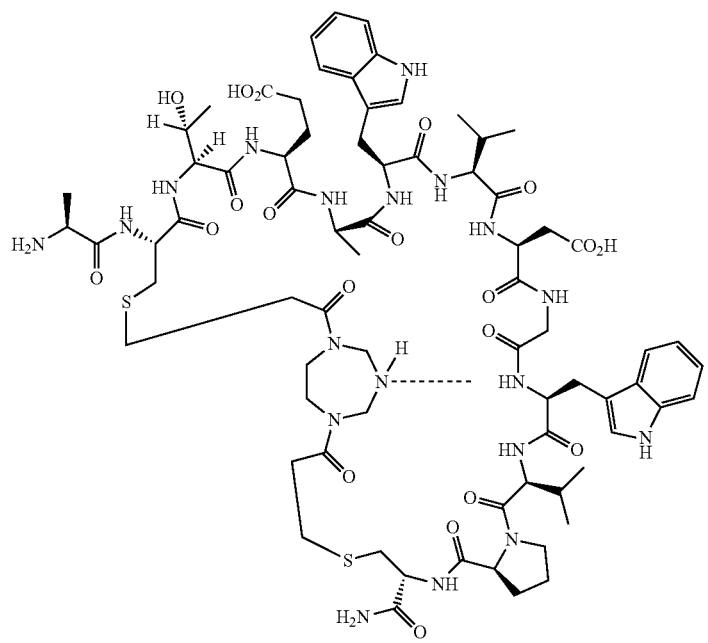

TABLE 2-continued
Exemplary compounds
II-34
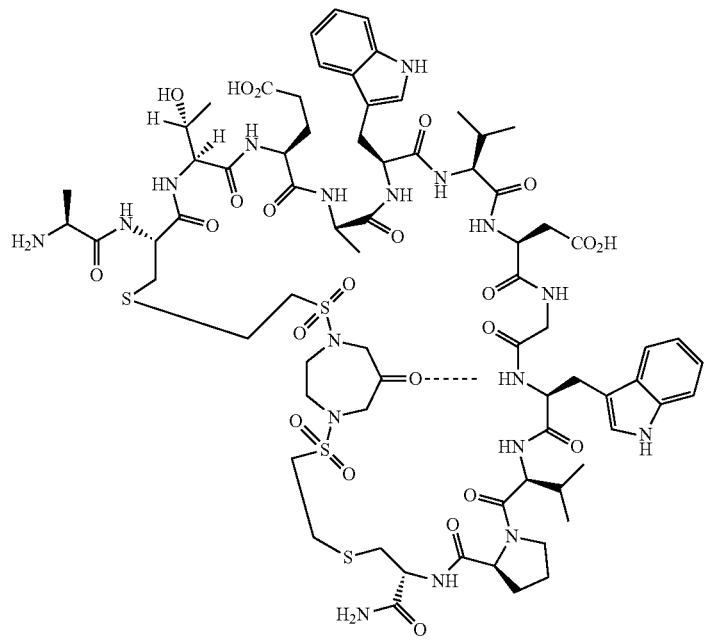
II-35
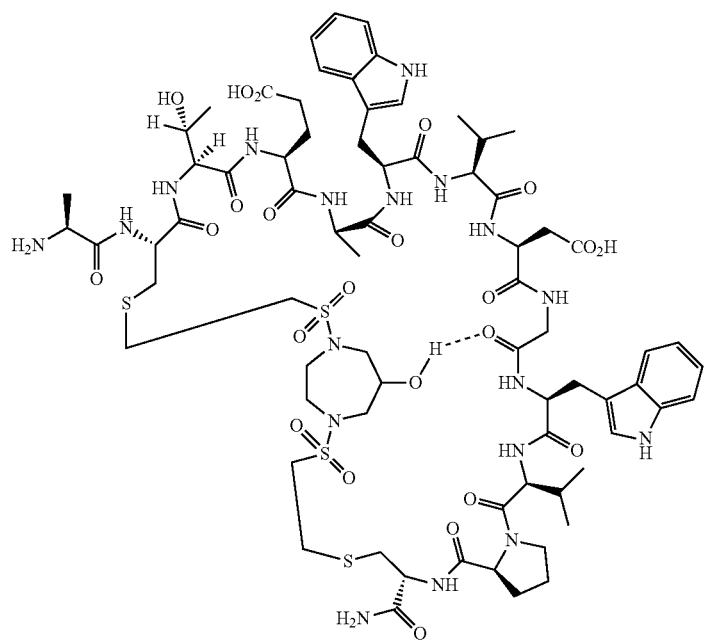

TABLE 2-continued

Exemplary compounds

II-36

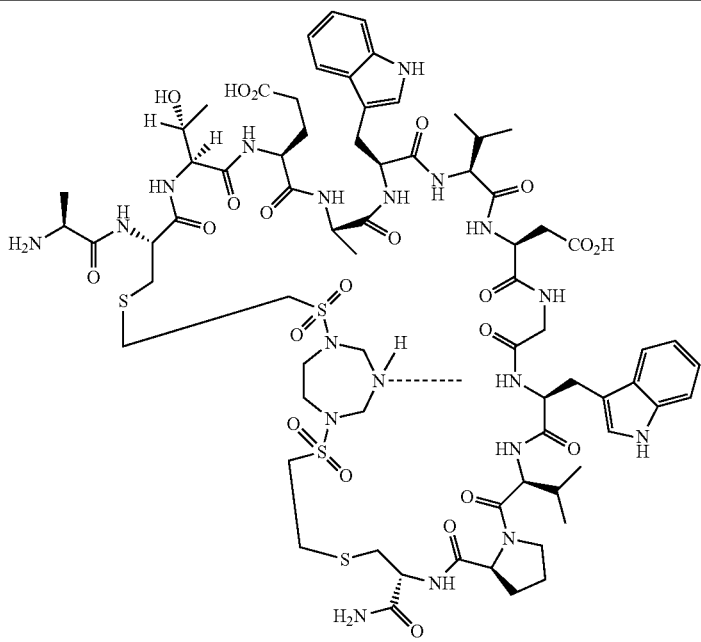

4. General Methods of Providing the Present Compounds

The compounds of this invention may be prepared or isolated in general by synthetic and/or semi-synthetic methods known to those skilled in the art for analogous compounds and by methods described in detail in the Examples, herein.

The compounds of this invention may be prepared by treating a peptide with a molecular scaffold reagent. The molecular scaffold reagent comprises the Scaffold and reactive functionality such as leaving groups ("LG") or Michael acceptors ("MA"), that allow the peptide to form covalent bonds with the molecular scaffold via displacement of the leaving group or addition to the Michael acceptor group followed by subsequent protonation of the addition complex.

The exemplary compounds of Table 1 and Table 2 are formed by treating peptides with various molecular scaffold reagents.

One such peptide is peptide 1 (17-69-07-N241), which has the following amino acid sequence:

(SEQ ID NO: 1)
βAla-Sar10-A-C(D-Ala)NE(1Nal)(D-Ala)CEDFYD (tBuGLy)C

The bicyclic peptide formed by treating 17-69-07-N241 with the molecular scaffold reagent 1,3,5-tris(bromomethyl) benzene ("TBMB") as described in WO 2016/067035 affords an MT1-MMP binder with a $K_d$ of 1.2 nM.

Another such peptide is peptide 2, which has the following amino acid sequence:

(SEQ ID NO: 2)
βAla-Sar10-A-CTECWVDGWVPC.

The bicyclic peptide formed by treating 2 with the molecular scaffold reagent 1,3,5-tris(bromomethyl)benzene ("TBMB") as described in the UK provisional application P2120 affords a CAIX binder with a $K_d$ of 10 nM.

One such peptide is peptide 3, which has the following amino acid sequence:

(SEQ ID NO: 3)
A-C(D-Ala)NE(1Nal)(D-Ala)CEDFYD(tBuGLy)C

In the Schemes below, where a particular Michael acceptor ("MA"), leaving group ("LG"), or transformation condition is depicted, one of ordinary skill in the art will appreciate that other Michael acceptors, leaving groups, and transformation conditions are also suitable and are contemplated. Such acceptors, groups and transformations are described in detail in March's *Advanced Organic Chemistry: Reactions, Mechanisms, and Structure*, M. B. Smith and J. March, $5^{th}$ Edition, John Wiley & Sons, 2001, *Comprehensive Organic Transformations*, R. C. Larock, $2^{nd}$ Edition, John Wiley & Sons, 1999, and *Protecting Groups in Organic Synthesis*, T. W. Greene and P. G. M. Wuts, $3^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

In certain embodiments, the present invention provides a method for preparing a compound of formula I according to the steps depicted in Scheme I set forth below:

Scheme I

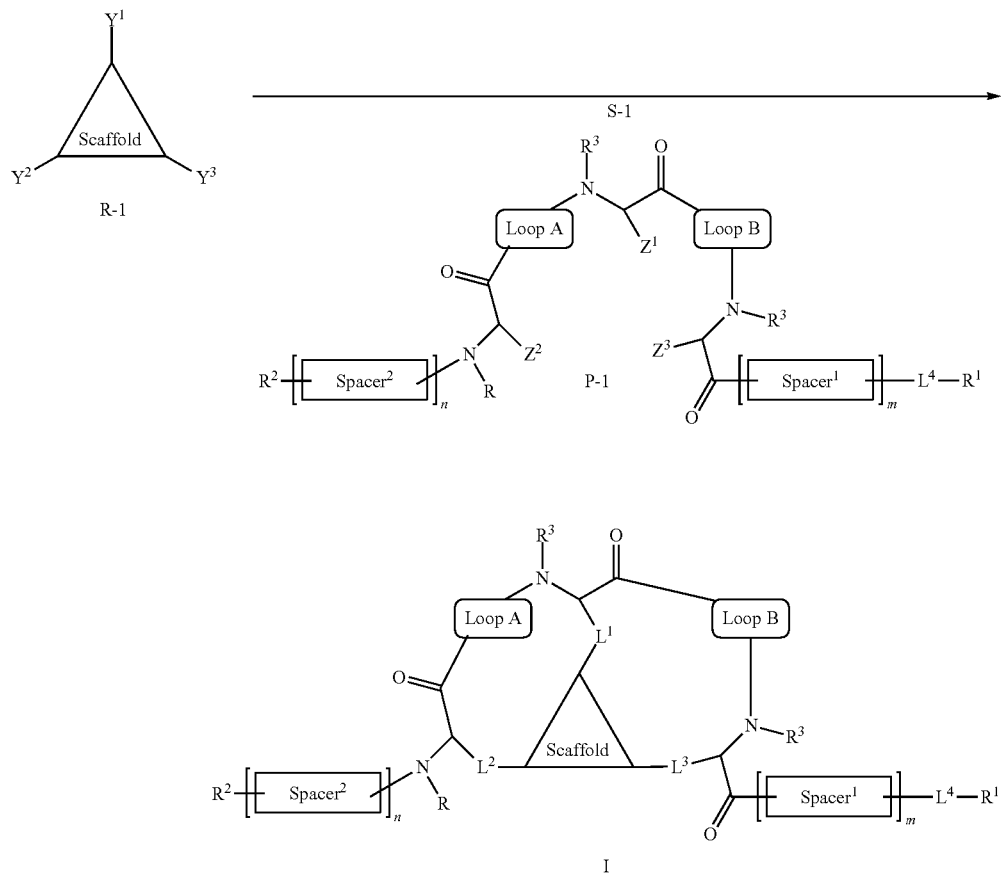

In Scheme I above, each of $L^1$, $L^2$, $L^3$, $L^4$, Scaffold, Loop A, Loop B, R, Spacer$^1$, Spacer$^2$, $R^1$, $R^2$, $R^3$, m, and n is as defined above and below and in classes and subclasses as described herein; $Y^1$ and $Z^1$ form $L^1$; $Y^2$ and $Z^2$ form $L^2$; and $Y^3$ and $Z^3$ form $L^3$.

In certain embodiments, the present invention provides a method for preparing a compound of formula II according to the steps depicted in Scheme II set forth below:

Scheme II

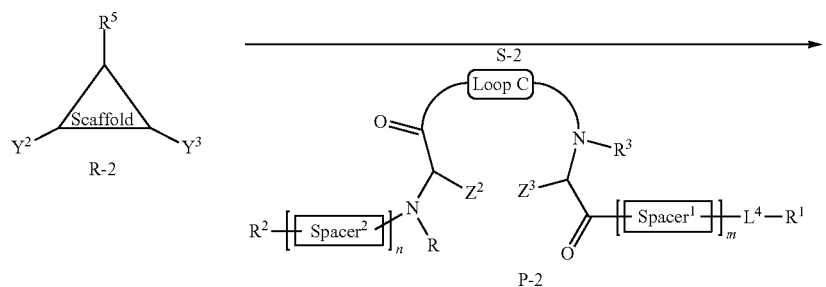

-continued

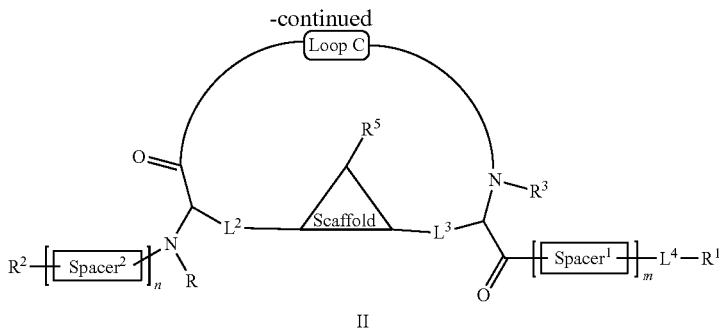

II

In Scheme II above, each of $L^2$, $L^3$, $L^4$, Scaffold, Loop C, R, Spacer[1], Spacer[2], $R^1$, $R^2$, $R^3$, $R^5$, m, and n is as defined above and below and in classes and subclasses as described herein; $Y^2$ and $Z^2$ form $L^2$; and $Y^3$ and $Z^3$ form $L^3$.

The formation of $L^1$ (reaction between $Y^1$ and $Z^1$), $L^2$ (reaction between $Y^2$ and $Z^2$), and $L^3$ (reaction between $Y^3$ and $Z^3$) can be achieved by a number of synthesis methods known to one skilled in the art.

For example, in some embodiments, one or more of $L^1$, $L^2$, and $L^3$ are formed by a leaving group (LG) displacement reaction. In some embodiments, each of $Y^1$, $Y^2$, and $Y^3$ is a LG. In some embodiments, a LG is a halogen. In some embodiments, a LG is chlorine. In some embodiments, a LG is a sulfonate. In some embodiments, a base is added to promote the displacement. In some embodiments, the base is ammonium carbonate. In some embodiments, the base is an amine. In some embodiments the reaction further comprises a solvent. In some embodiments the solvent is acetonitrile. In some embodiments the solvent is a mixture of water and acetonitrile. In some embodiments, a catalyst is added to promote the displacement. In some embodiments, the catalyst is generated from $3^{rd}$ Generation XPhos precatalyst. In some embodiments, the solvent is tert-butanol. In some embodiments, the solvent is a mixture of water and tert-butanol.

In some embodiments, one or more of $L^1$, $L^2$, and $L^3$ are formed by a Michael Addition reaction. In some embodiments, each of $Y^1$, $Y^2$, and $Y^3$ is a Michael Acceptor (MA). In some embodiments, a MA is an α,β-unsaturated amide. In some embodiments, a MA is an α,β-unsaturated ketone. In some embodiments, a MA is an α,β-unsaturated ester. In some embodiments, a MA is an α,β-unsaturated sulfone. In some embodiments, a MA is an α,β-unsaturated nitrile. In some embodiments, a base is added to promote the Michael addition. In some embodiments, the base is ammonium carbonate. In some embodiments, the base is an amine. In some embodiments the reaction further comprises a solvent. In some embodiments the solvent is acetonitrile. In some embodiments the solvent is a mixture of water and acetonitrile.

In some embodiments, one or more of $L^1$, $L^2$, and $L^3$ are formed by a click reaction. In some embodiments, $Y^1$ comprises an alkyne group, and $Z^1$ comprises an azide group. In some embodiments, $Y^1$ comprises an azide group, and $Z^1$ comprises an alkyne group. In some embodiments, $Y^2$ comprises an alkyne group, and $Z^2$ comprises an azide group. In some embodiments, $Y^2$ comprises an azide group, and $Z^2$ comprises an alkyne group. In some embodiments, $Y^3$ comprises an alkyne group, and $Z^3$ comprises an azide group. In some embodiments, $Y^3$ comprises an azide group, and $Z^3$ comprises an alkyne group. In some embodiments, each of $Y^1$, $Y^2$, and $Y^3$ comprises an alkyne group, and each of $Z^1$, $Z^2$, and $Z^3$ comprises an azide group. In some embodiments, each of $Y^1$, $Y^2$, and $Y^3$ comprises an azide group, and each of $Z^1$, $Z^2$, and $Z^3$ comprises an alkyne group.

In some embodiments, one or more of $L^1$, $L^2$, and $L^3$ are formed by a reductive amination. In some embodiments, $Y^1$ comprises a carbonyl group, and $Z^1$ comprises a —$N(R)_2$ group. In some embodiments, $Y^2$ comprises a carbonyl group, and $Z^2$ comprises a —$N(R)_2$ group. In some embodiments, $Y^3$ comprises a carbonyl group, and $Z^3$ comprises a —$N(R)_2$ group. In some embodiments, each of $Y^1$, $Y^2$, and $Y^3$ comprises a carbonyl group, and each of $Z^1$, $Z^2$, and $Z^3$ comprises a —$N(R)_2$ group.

In some embodiments, one or more of $L^1$, $L^2$, and $L^3$ are formed by a hemi-acetal/ketal formation reaction. In some embodiments, $Y^1$ comprises a carbonyl group, and $Z^1$ comprises a —OH group. In some embodiments, $Y^2$ comprises a carbonyl group, and $Z^2$ comprises a —OH group. In some embodiments, $Y^3$ comprises a carbonyl group, and $Z^3$ comprises a —OH group. In some embodiments, each of $Y^1$, $Y^2$, and $Y^3$ comprises a carbonyl group, and each of $Z^1$, $Z^2$, and $Z^3$ comprises a —OH group.

In certain embodiments, R-1 is of formula

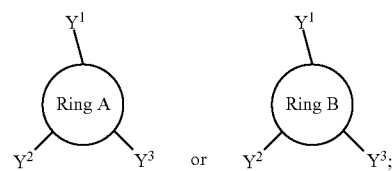

wherein each of $Y^1$, $Y^2$, $Y^3$, Ring A, and Ring B is defined above and below and in classes and subclasses as described herein.

In certain embodiments, R-2 is of formula

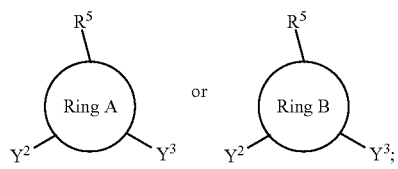

wherein each of $Y^2$, $Y^3$, $R^5$, Ring A, and Ring B is defined above and below and in classes and subclasses as described herein.

One of skill in the art will appreciate that compounds of the invention may contain one or more stereocenters, and may be present as an racemic or diastereomeric mixture.

One of skill in the art will also appreciate that there are many methods known in the art for the separation of isomers to obtain stereoenriched or stereopure isomers of those compounds, including but not limited to HPLC, chiral HPLC, fractional crystallization of diastereomeric salts, kinetic enzymatic resolution (e.g. by fungal-, bacterial-, or animal-derived lipases or esterases), and formation of covalent diastereomeric derivatives using an enantioenriched reagent.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. "March's Advanced Organic Chemistry", $5^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CAIX, MT1-MMP, CD38, EphA2, or PBP1A, or a mutant thereof, in a biological sample or in a patient. In certain embodiments, the amount of compound in compositions of this invention is such that is effective to measurably inhibit CAIX, MT1-MMP, CD38, EphA2, or PBP1A, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CAIX, MT1-MMP, CD38, EphA2, or PBP1A, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Certain bicyclic peptides of the invention have specific utility as CAIX binding agents.

Various forms of the enzyme carbonic anhydrase (CA) catalyze hydration of carbon dioxide to generate bicarbonate anion (HCO3−) and a proton. Substrates of the reaction which is catalyzed by CA regulate a number of physiological processes, including formation and transport of CO2, protons and bicarbonate anion, such as respiration, maintenance of pH levels, bone development and other processes. In the human organism, 12 catalytically active CA isoenzymes were identified which differ in their cellular localization and their expression in various tissues.

Clinical regulation of the activity of human carbonic anhydrase (hCA) by small molecular inhibitors proved to be reliable therapeutic method for a number of human diseases and already for several decades it remains a major component of therapy for high blood pressure, glaucoma, hyperthyrosis and hypoglycemia (Supuran (2008) Nat. Rev. Drug Discov. 7, 168). Classical inhibitors of carbonic anhydrases, binding into the active site of CA, are aromatic or heteroaromatic sulfonamides.

Human carbonic anhydrase IX (hCAIX) is an isoform bound to the outer cell membrane (its catalytic domain is located in the extracellular space). At physiological conditions, hCAIX is expressed only in specific tissues of gastrointestinal tract. Its overexpression was shown during hypoxia in cancer cells both in vitro and in vivo. Expression of hCAIX was detected in carcinomas of cervix, ovaries, kidneys, esophagus, lungs, breasts and brain. In tumors, hCAIX is a molecule crucial for the maintenance of intracellular pH on normal level and its expression provides the hypoxic tumor cells with an advantage in growth at acidic conditions (Chiche et al. (2009) Cancer Res 69, 358). hCAIX enzyme is thus a convenient target for development of specific inhibitors used as anti-cancer therapeutics with new mechanism of action (Neri and Supuran (2011) Nature Reviews 10, 767).

Polypeptide ligands selected according to the method of the present invention may be employed in in vivo therapeutic and prophylactic applications, in vitro and in vivo diagnostic applications, in vitro assay and reagent applications, and the like. Ligands having selected levels of specificity are useful in applications which involve testing in non-human animals, where cross-reactivity is desirable, or in diagnostic applications, where cross-reactivity with homologues or paralogues needs to be carefully controlled. In some applications, such as vaccine applications, the ability to elicit an immune response to predetermined ranges of antigens can be exploited to tailor a vaccine to specific diseases and pathogens.

Substantially pure peptide ligands of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

According to a further aspect of the invention, there is provided a peptide ligand or a drug conjugate as defined herein, for use in preventing, suppressing or treating a disease or disorder mediated by CAIX.

According to a further aspect of the invention, there is provided a method of preventing, suppressing or treating a disease or disorder mediated by CAIX, which comprises administering to a patient in need thereof an effector group and drug conjugate of the peptide ligand as defined herein.

In one embodiment, the CAIX is mammalian CAIX. In a further embodiment, the mammalian CAIX is human CAIX (hCAIX).

In one embodiment, the disease or disorder mediated by CAIX is selected from cancer.

In another aspect, certain bicyclic peptides of the invention have specific utility as high affinity binders of membrane type 1 metalloprotease (MT1-MMP, also known as MMP14). MT1-MMP is a transmembrane metalloprotease that plays a major role in the extracellular matrix remodeling, directly by degrading several of its components and indirectly by activating pro-MMP2. MT1-MMP is crucial for tumor angiogenesis (Sounni et al (2002) FASEB J. 16(6), 555-564) and is over-expressed on a variety of solid tumors, therefore the MT1-MMP-binding bicycle peptides of the present invention have particular utility in the targeted treatment of cancer, in particular solid tumors such as non-small cell lung carcinomas. In one embodiment, the bicyclic peptide of the invention is specific for human MT1-MMP. In a further embodiment, the bicyclic peptide of the invention is specific for mouse MT1-MMP. In a yet further embodiment, the bicyclic peptide of the invention is specific for human and mouse MT1-MMP. In a yet further embodiment, the bicyclic peptide of the invention is specific for human, mouse and dog MT1-MMP.

Compounds and compositions described herein are generally useful for the inhibition of carbonic anhydrase or metalloprotease activity of one or more enzymes.

The activity of a compound utilized in this invention as an inhibitor of CAIX, MT1-MMP, CD38, EphA2, or PBP1A, or a mutant thereof, may be assayed in vitro, in vivo or in a cell line. Alternative in vitro assays quantitate the ability of the inhibitor to bind to CAIX, MT1-MMP, CD38, EphA2, or PBP1A. Inhibitor binding may be measured by radiolabeling the inhibitor prior to binding, isolating the inhibitor/CAIX or inhibitor/MT1-MMP complex and determining the amount of radiolabel bound. Alternatively, inhibitor binding may be determined by running a competition experiment where new inhibitors are incubated with CAIX, MT1-MMP, CD38, EphA2, or PBP1A bound to known radioligands. Representative in vitro and in vivo assays useful in assaying an MT1-MMP inhibitor include those described and disclosed in: Pietraszek et al., (2014) FEBS Letters 588(23), 4319-4324; Cheltsov et al., (2012) Cancer Res. 72(9), 2339-49; and WO 2009/098450, each of which is herein incorporated by reference in its entirety. Representative in vitro and in vivo assays useful in assaying a CAIX inhibitor include those described and disclosed in: Wind et al., (2011) Ann Clin Biochem. 48(2), 112-120; Gandhi et al., (2015) J. Urology 193(4), e870-e871; and WO 2004/005348, each of which is herein incorporated by reference in its entirety. Detailed conditions for assaying a compound utilized in this invention as an inhibitor of CAIX, MT1-MMP, CD38, EphA2, or PBP1A, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of CAIX, MT1-MMP, CD38, EphA2, or PBP1A and are therefore useful for treating one or more disorders associated with activity of CAIX, MT1-MMP, CD38, EphA2, or PBP1A. Thus, in certain embodiments, the present invention provides a method for treating a CAIX-mediated, MT1-MMP-mediated, CD38-mediated, EphA2-mediated, or PBP1A-mediated disorder comprising the step of administering to a patient in need thereof a compound of the present invention, or pharmaceutically acceptable composition thereof.

As used herein, the terms "CAIX-mediated", "MT1-MMP-mediated", "CD38-mediated", EphA2-mediated", or "PBP1A-mediated" disorders, diseases, and/or conditions as used herein means any disease or other deleterious condition in which CAIX, MT1-MMP, CD38, EphA2, or PBP1A, or a mutant thereof, are known to play a role. Accordingly, another embodiment of the present invention relates to treating or lessening the severity of one or more diseases in which CAIX, MT1-MMP, CD38, EphA2, or PBP1A, or a mutant thereof, are known to play a role.

Examples of cancers (and their benign counterparts) which may be treated (or inhibited) include, but are not limited to tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); hematological malignancies (i.e. leukemias, lymphomas) and pre-malignant hematological disorders and disorders of borderline malignancy including hematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukemias, natural killer [NK] cell lymphomas, Hodgkin's lymphomas, hairy cell leukemia, monoclonal gammopathy of uncertain significance, plasmacytoma, multiple myeloma, and post-transplant lymphoproliferative disorders), and hematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and pediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

In a further embodiment, the cancer is selected from cancer of the cervix, ovary, kidney, esophagus, lung, breast and brain.

References herein to the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide ligands in protecting against or treating the disease are available. The use of animal model systems is facilitated by the present invention, which allows the development of polypeptide ligands which can cross react with human and animal targets, to allow the use of animal models.

Furthermore, the invention provides the use of a compound according to the definitions herein, or a pharmaceutically acceptable salt, or a hydrate or solvate thereof for the preparation of a medicament for the treatment of a proliferative disease.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of the invention and one or more additional therapeutic agents. The therapeutic agent may be administered together with a compound of the invention, or may be administered prior to or following administration of a compound of the invention. Suitable therapeutic agents are described in further detail below. In certain embodiments, a compound of the invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of the invention may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating a hematological malignancy comprising administering to a patient in need thereof a compound of the invention and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a compound of the invention and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a compound of the invention and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of the invention and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of the invention and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a compound of the invention and one or more additional therapeutic agents selected from chlorarnbucil (Leukeran®), cyclophosphamlide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a compound of the invention and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleroderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of the invention and a PI3K inhibitor, wherein the disease is selected from a cancer, a neurodegenerative disorder, an angiogenic disorder, a viral disease, an autoimmune disease, an inflammatory disorder, a hormrone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocyic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of the invention and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphigus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), buccally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting carbonic anhydrase activity in a biological sample comprising the step of contacting said biological sample with a compound of this invention, or a composition comprising said compound.

According to another embodiment, the invention relates to a method of inhibiting metalloprotease activity in a biological sample comprising the step of contacting said biological sample with a compound of this invention, or a composition comprising said compound.

According to another embodiment, the invention relates to a method of inhibiting CAIX, MT1-MMP, CD38, EphA2, or PBP1A, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of CAIX, MT1-MMP, CD38, EphA2, or PBP1A, or a mutant thereof, activity in a biological sample is useful for a variety of purposes that are known to one of skill in the art. Examples of such purposes include, but are not limited to, biological assays.

Another embodiment of the present invention relates to a method of inhibiting carbonic anhydrase or metalloprotease activity in a patient comprising the step of administering to said patient a compound of the present invention, or a composition comprising said compound.

According to another embodiment, the invention relates to a method of inhibiting CAIX, MT1-MMP, CD38, EphA2, or PBP1A, or a mutant thereof, activity in a patient comprising the step of administering to said patient a compound of the present invention, or a composition comprising said compound. In other embodiments, the present invention provides a method for treating a disorder mediated by CAIX, MT1-MMP, CD38, EphA2, or PBP1A, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethyl-amino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtubulin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides;

colchicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3K$\alpha$, PI3K$\gamma$, PI3K$\delta$, PI3K$\beta$, PI3K-C2$\alpha$, PI3K-C2$\beta$, PI3K-C2$\gamma$, Vps34, p110-$\alpha$, p110-$\beta$, p110-$\gamma$, p110-$\delta$, p85-$\alpha$, p85-$\beta$, p55-$\gamma$, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1: Synthesis of Scaffolds—Molecular Scaffold Reagents A and A' (MSR-A and MSR-A')

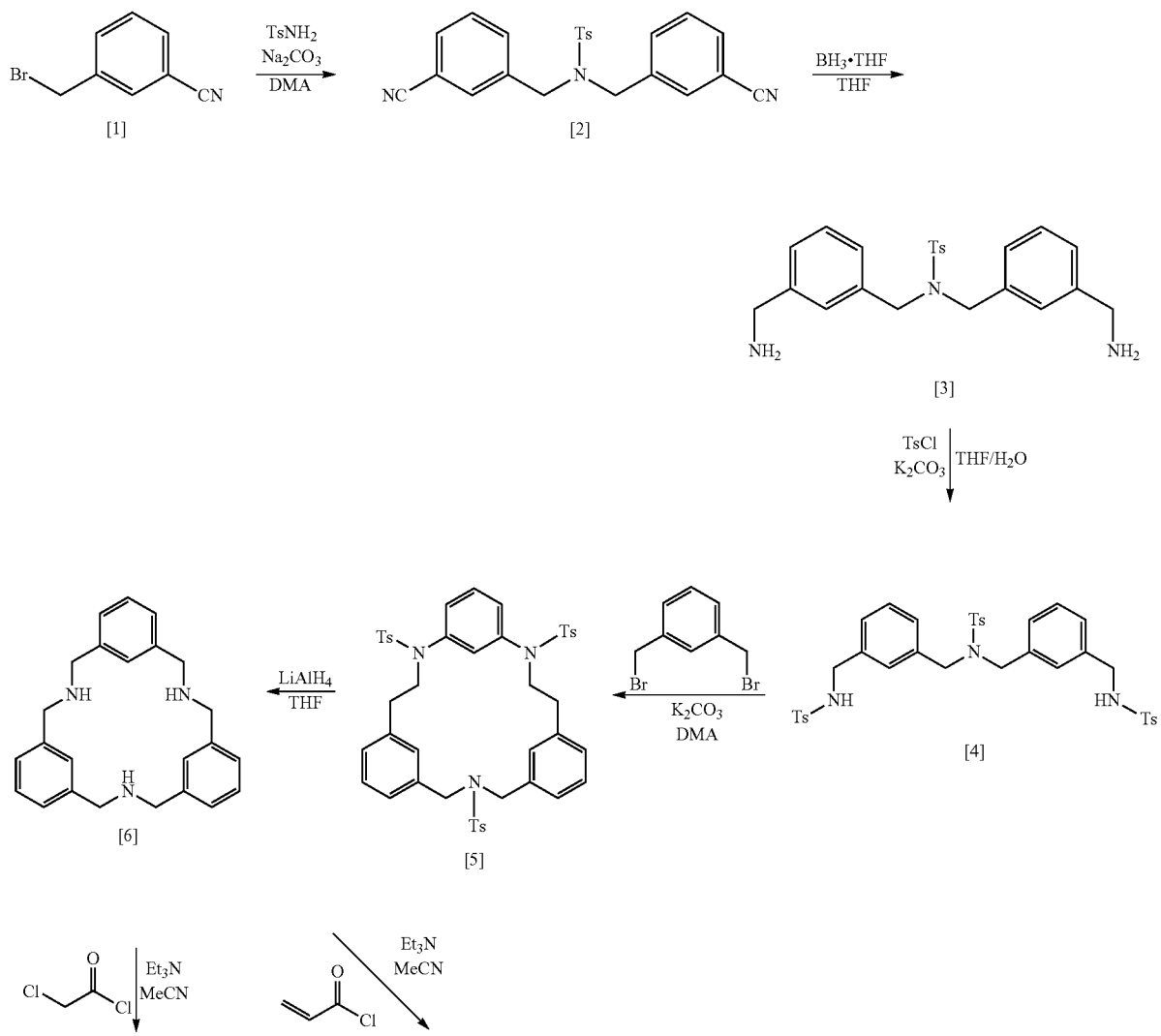

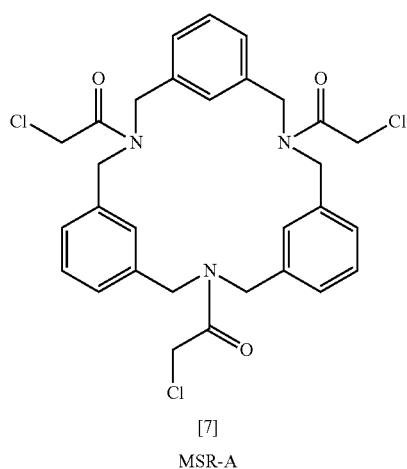
[7]
MSR-A

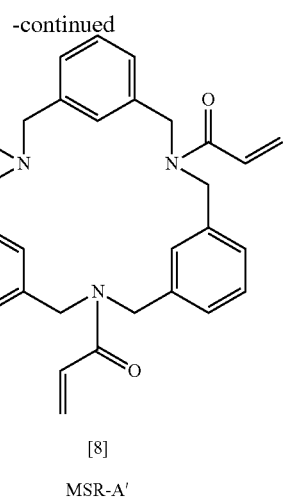
[8]
MSR-A'

1.1. Step 1

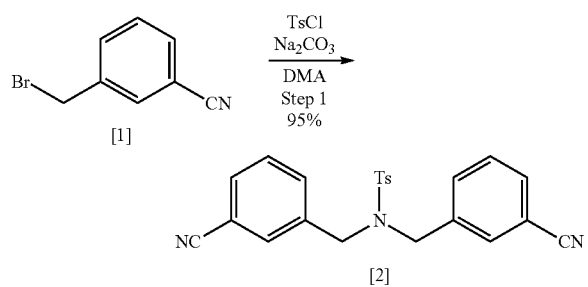

3-(Bromomethyl)benzonitrile (5 g, 24.2 mmol) was added to a suspension of 4-toluenesulphonamide (2.2 g, 12 mmol) and potassium carbonate (5.2 g, 37.7 mmol) in dimethylacetamide (30 ml) and the reaction was heated to 60° C. for 16 hours. After cooling the mixture was filtered and the mother liquors diluted with ethyl acetate and water. The phases were separated, the organic layer dried (MgSO$_4$) and the solvent evaporated to afford the desired product as a brown solid (5.06 g). $^1$H NMR (300 MHz, CDCl$_3$) 2.50 (3H, s), 4.30 (4H, s), 7.15 (2H, s), 7.35 (6H, m), 7.45 (2H, m), 7.75 (2H, d). LCMS M+H$^+$=402, C$_{23}$H$_{19}$N$_3$O$_2$S requires 401; RT=3.00 mins.

1.2. Step 2

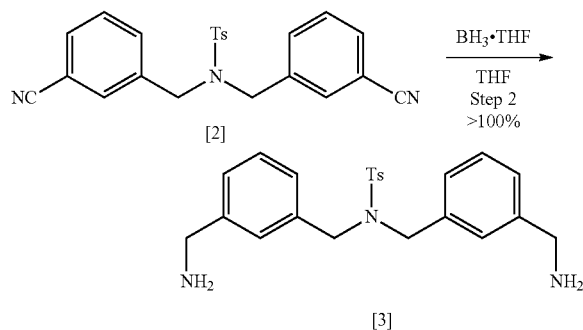

Borane tetrahydrofuran (48 ml, 48 mmol, 1.0 M in tetrahydrofuran) was added dropwise to a solution of [2] (4.8 g, 12 mmol) in tetrahydrofuran (50 ml) under N$_2$ and the reaction was stirred for 3 hours. The reaction was quenched by the addition of saturated aqueous ammonium chloride and stirred for 1 hour. The solvent was evaporated and dioxane (120 ml) was added. This was treated with 5M HCl (100 ml) and the mixture stirred for 20 hours. The solvent was evaporated and the mixture treated with dichloromethane to form a solid. The solvent was evaporated and the remaining aqueous layer separated by decantation. The solid was washed with diethyl ether and dried in vacuo to afford the desired product as a di.HCl salt (6.45 g). $^1$H NMR (300 MHz, DMSO) 2.45 (3H, s), 3.90 (4H, m), 4.30 (4H, s), 7.10 (2H, s), 7.15-7.45 (6H, m), 7.50 (2H, d), 7.25 (2H, d) 8.50 (6H, br s). LCMS M+H$^+$=410, C$_{23}$H$_{27}$N$_3$O$_2$S requires 409; RT=1.05 mins.

1.3. Step 3

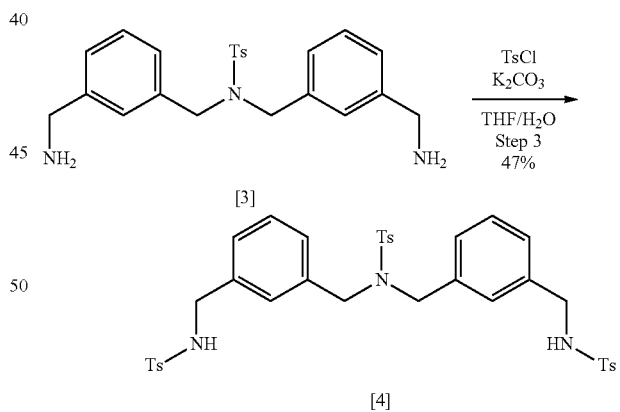

Potassium carbonate (2.9 g, 20.98 mmol) in water (20 ml) was added to a suspension of the [3] (2 g, 4.15 mmol) in tetrahydrofuran (60 ml) and the mixture was stirred for 2 minutes. p-Toluenesulphonyl chloride (1.58 g, 8.29 mmol) in tetrahydrofuran (20 ml) was added and the mixture was stirred for 30 minutes. The reaction was heated to 65° C. under N$_2$ for 16 hours. The reaction mixture was cooled to room temperature and the solvent evaporated to afford a crude oil. This was dissolved in ethyl acetate and water was added. The organic layer was collected and further washed with 2M HCl, saturated brine, dried (MgSO$_4$) and the solvent evaporated to afford a crude solid. This was purified by chromatography (200 g silica, 30 to 40% ethyl acetate/iso-hexane) to afford the desired product as a colourless solid (1.39 g). $^1$H NMR (300 MHz, CDCl$_3$) 2.45 (6H, s), 2.50 (3H, s), 3.95 (4H, d), 4.20 (4H, s), 5.15 (2H, t), 6.90 (2H, s), 7.00 (4H, m), 7.15 (2H, m), 7.30 (6H, m), 7.75 (6H, d). LCMS M+H$^+$=718, C$_{37}$H$_{39}$N$_3$O$_6$S$_3$ requires 717; RT=3.26 mins.

1.4. Step 4

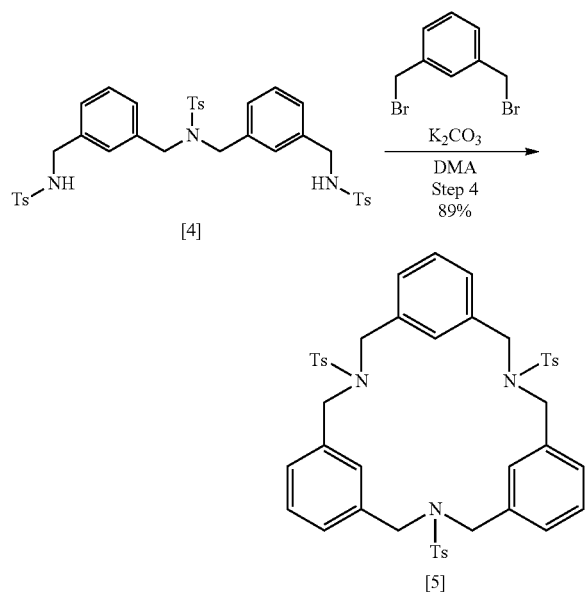

A solution of the α,α', dibromo-m-xylene (1.06 g, 4.01 mmol) in dimethylacetamide (40 ml) was added via syringe pump over 6 hours to a mixture of [4] (2.23 g, 3.11 mmol) and potassium carbonate (0.57 g, 4.13 mmol) in dimethylacetamide (310 ml) at 80° C. under nitrogen and the reaction was stirred for an additional 90 minutes and then room temperature for 18 hours. The solvent was evaporated and the crude purified by chromatography (100 g, silica, 30 to 50% ethyl acetate/iso-hexane) to afford the desired product as a white solid (2.28 g). $^1$H NMR (300 MHz, DMSO) 2.50 (9H, s), 4.05 (12H, s), 6.45 (3H, s), 6.95 (6H, d), 7.10 (3H, t), 7.45 (6H, d), 7.75 (6H, d). LCMS M+H$^+$=820, C$_{45}$H$_{45}$N$_3$O$_6$S$_3$ requires 819; RT=3.84 min 1.5. Step 5

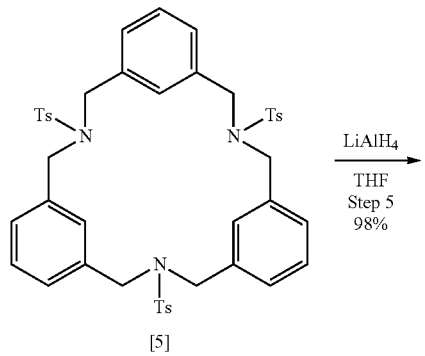

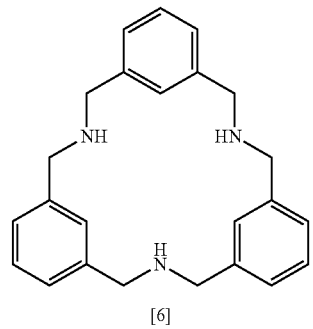

A solution of lithium aluminium hydride (12 ml, 12 mmol, 1.0M in tetrahydrofuran) was added to a solution of [5] (1 g, 1.2 mmol) in dry tetrahydrofuran (20 ml) at room temperature. The reaction was heated at reflux for 4 hours before cooling to room temperature. Diethyl ether (50 ml) was added followed by water (1 ml), sodium hydroxide (2M, 2 ml) and water (1 ml). The mixture was vigorously stirred for 1 hour. The resulting solid was filtered off and washed with tetrahydrofuran. The combined solvents were evaporated to afford a crude gum. This was purified by SCX (20 g cartridge) eluting with methanol followed by 1% ammonium hydroxide in methanol and the desired fractions collected and evaporated to afford the product as a waxy solid (0.426 g). $^1$H NMR (300 MHz, DMSO) 3.65 (12H, s), 7.20 (9H, m), 7.60 (3H, s). LCMS M+H$^+$=358, C$_{24}$H$_{27}$N$_3$ requires 357; RT=0.29 mins 1.6. Step 6

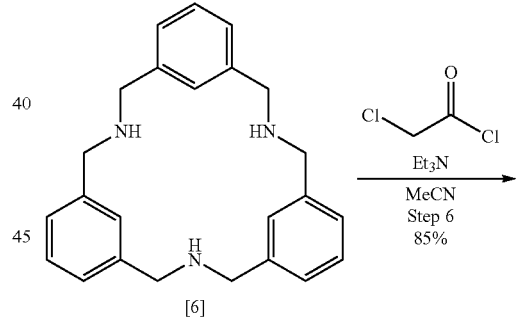

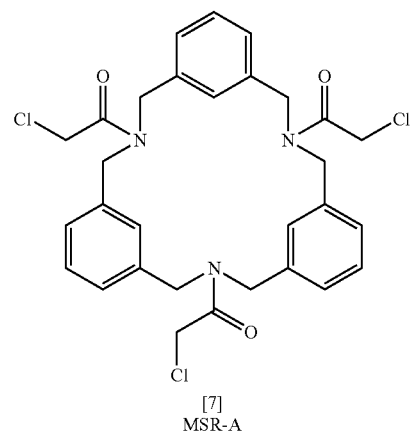

Chloroacetyl chloride (0.137 ml, 1.74 mmol) was added to a solution of [6] (0.2 g, 0.56 mmol) and triethylamine (0.312 ml, 2.24 mmol) in acetonitrile (10 ml) under $N_2$ and the reaction was stirred for 1 hour. The solvent was evaporated, the crude material suspended in ethyl acetate and washed with water. The organic layer was dried ($MgSO_4$) and the solvent evaporated. The product (MSR-A) was isolated by trituration from diethyl ether as a light brown solid (280 mg). $^1$H NMR (300 MHz, $CDCl_3$) 4.25 (6H, s), 4.50 (12H, br s), 6.75 (3H, br s), 7.30 (9H, br m). LCMS M+H$^+$=586, $C_{30}H_{30}^{35}Cl_3N_3O_3$ requires 585; RT=2.63 mins 1.7. Step 7

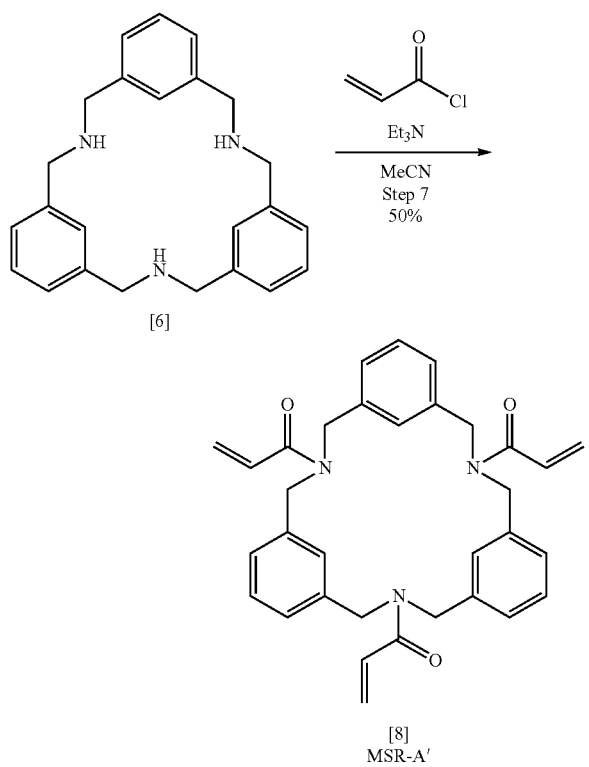

[6]

[8]
MSR-A'

Acryloyl chloride (0.178 ml, 2.2 mmol) was added to a solution of [6] (0.253 g, 0.71 mmol) and triethylamine (0.395 ml, 2.83 mmol) in acetonitrile (10 ml) under $N_2$ and the reaction was stirred for 1 hour. The solvent was evaporated, the crude material suspended in ethyl acetate and washed with water. The organic layer was dried ($MgSO_4$) and the solvent evaporated. The product (MSR-A') was isolated by trituration from diethyl ether as a light brown solid (182 mg). $^1$H NMR (300 MHz, $CDCl_3$) 4.40 (6H, br s), 4.50 (6H, br s), 5.75 (3H, d), 6.45 (3H, d), 6.70 (3H, dd), 6.75 (3H, br s), 7.10 (3H, br s), 7.30 (6H, br m). LCMS M+H$^+$=520, $C_{33}H_{33}N_3O_3$ requires 519; RT=2.28 mins.

Example 2: Peptide Synthesis

Molecular Scaffold Reagent with Leaving Groups

Peptide synthesis was based on Fmoc chemistry, using a Symphony peptide synthesizer manufactured by Peptide Instruments and a Syro II synthesizer by MultiSynTech. Standard Fmoc-amino acids were employed (Sigma, Merck), with appropriate side chain protecting groups: where applicable standard coupling conditions were used in each case, followed by deprotection using standard methodology. Peptides were purified using HPLC and following isolation they were modified with a molecular scaffold reagent with leaving groups. For this, linear peptide was diluted with $H_2O$ up to ~35 mL, ~500 μL of 100 mM molecular scaffold reagent in acetonitrile was added, and the reaction was initiated with 5 mL of 1 M $NH_4HCO_3$ in $H_2O$. The reaction was allowed to proceed for ~30-60 min at RT, and lyophilized once the reaction had completed (as judged by MALDI). Following lyophilization, the reaction mixture was loaded onto a Gemini C18 column (Phenomenex). Solvents ($H_2O$, acetonitrile) were acidified with 0.1% trifluoroacetic acid. The gradient ranged from 30-70% acetonitrile in 15 minutes, at a flowrate of 15-20 mL/min, using a Gilson preparative HPLC system. Pure fractions containing the desired product were pooled, lyophilized and kept at −20° C. for storage.

Molecular Scaffold Reagent containing Michael Acceptors

Alternatively, peptides were purified using HPLC and following isolation they were modified with a molecular scaffold reagent containing Michael acceptors. For this, linear peptide was diluted with 50:50 MeCN:$H_2O$ up to ~35 mL, ~500 μL of 100 mM molecular scaffold reagent containing Michael acceptors in acetonitrile was added, and the reaction was initiated with 5 mL of 1 M $NH_4HCO_3$ in $H_2O$. The reaction was allowed to proceed for ~30-60 min at RT, and lyophilized once the reaction had completed (as judged by MALDI). Once completed, 1 mL of 1M L-Cysteine hydrochloride monohydrate (Sigma) in $H_2O$ was added to the reaction for ~60 min at RT to quench any excess molecular scaffold reagent containing Michael acceptors.

Following lyophilization, the modified peptide was purified as above, while replacing the Luna C8 with a Gemini C18 column (Phenomenex), and changing the acid to 0.1% trifluoroacetic acid. Pure fractions containing the correct desired product were pooled, lyophilized and kept at −20° C. for storage.

All amino acids, unless noted otherwise, were used in the L-configurations.

The following linear peptides were prepared based on Fmoc chemistry, using a Symphony peptide synthesizer manufactured by Peptide Instruments and a Syro II synthesizer by Multi SynTech.

(SEQ ID NO: 1)

βAla-Sar 10-A-C(D-Ala)NE(1 Nal)(D-Ala)CEDFYD(tBuGLy)C

A-C(D-Ala)NE(1 Nal)(D-Ala)CEDFYD(tBuGLy)C (SEQ ID NO: 2)

βAla-Sar 10-A-CTECWVDGWVPC (SEQ ID NO: 3)

Peptide 4:
(SEQ ID NO: 4)
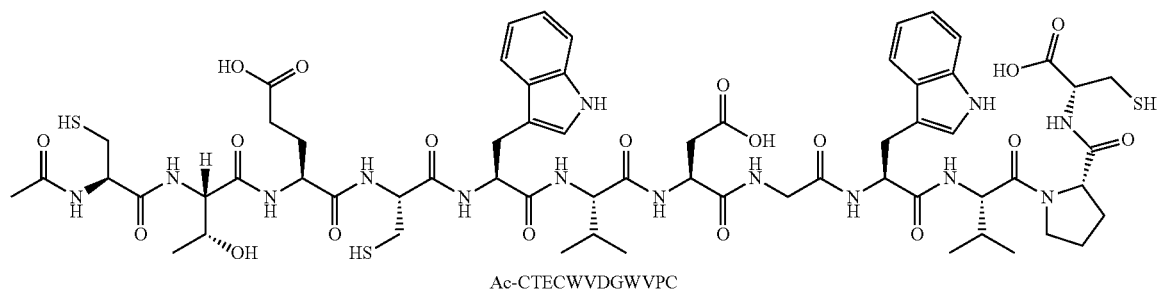
Ac-CTECWVDGWVPC
Peptide 5:
(SEQ ID NO: 5)
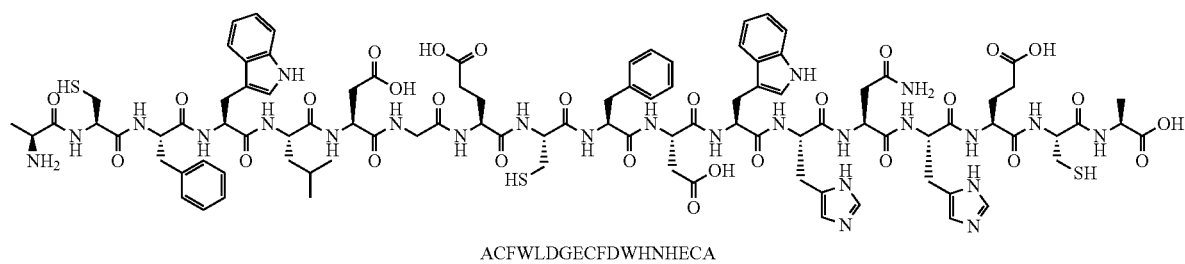
ACFWLDGECFDWHNHECA
Peptide 6:
(SEQ ID NO: 6)
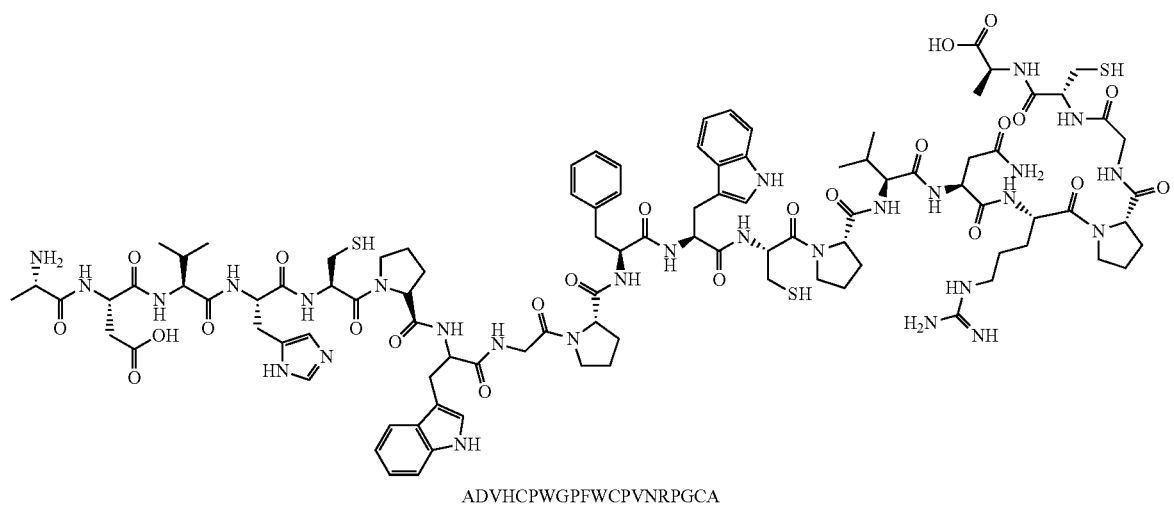
ADVHCPWGPFWCPVNRPGCA Peptide 7:
(SEQ ID NO: 7)
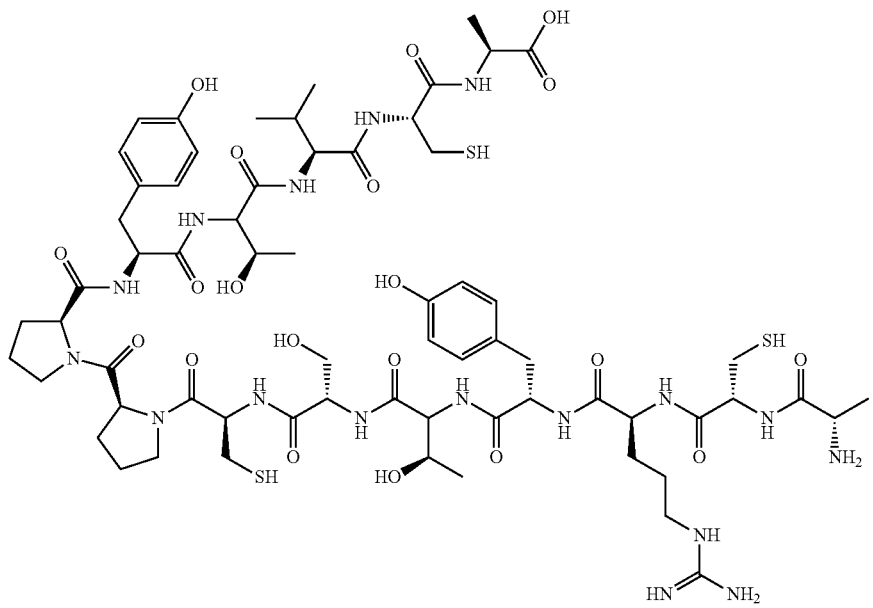
ACRYTSCPPYTVCA
Peptide 8:
(SEQ ID NO: 8)
A-C(D-Ala)NE(1 Nal)(D-Ala)AEDFYD(tBuGLy)C
Peptide 9:
(SEQ ID NO: 9)
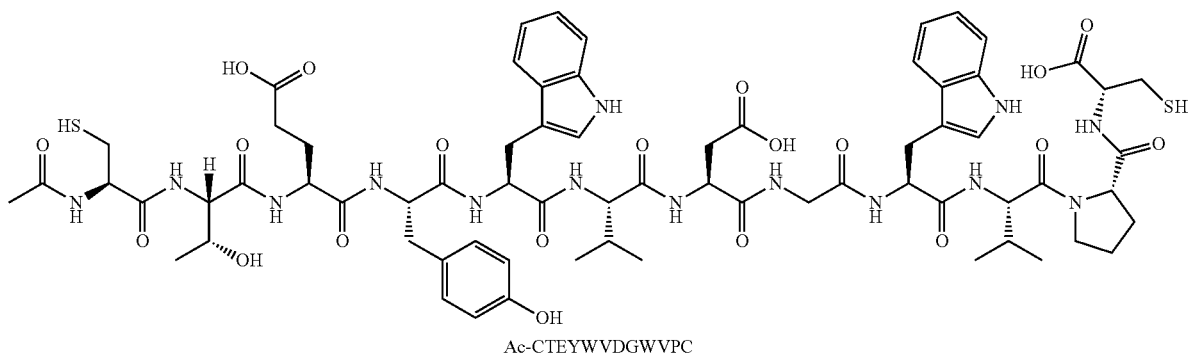
Ac-CTEYWVDGWVPC
Peptide 10:
(SEQ ID NO: 10)
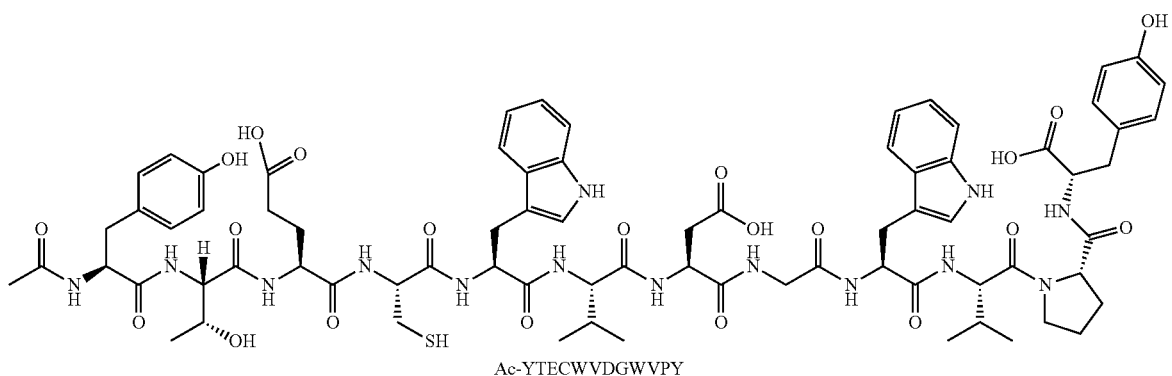
Ac-YTECWVDGWVPY

Example 3. Preparation of Cyclic Peptides

Cyclization Protocol

The linear peptides and all scaffolds were solved in acetonitrile/water 50/50 at 5 mM concentration. The peptide solutions were further diluted in 1M Ammonium bicarbonate (AMBIC) to final concentration 1 mM.

3 ml 1 mM linear peptide solution was mixed with 1 ml 5 mM scaffold solution (linear peptide/scaffold molar ratio 1/1.6). The reaction mixture was kept at room temperature overnight and the cyclization completion was confirmed by LC-MS (Acquity UPLC CSH C18 column, 1.7 μm, 2.1×30 mm; acetonitrile/water/HCOOH containing buffers and 15 to 600 acetonitrile gradient elution over 10 min). The cyclic peptide was purified using RP-HPLC (Gemini C18—semi prep column, 5 μm, 110 Å, 250×10 mm; acetonitrile/water/TFA containing buffers and 20 to 80% acetonitrile gradient elution over 20 min). Results of the cyclization protocol are provided in Table 3 below.

TABLE 3,

Cyclization Protocol Results.

| Compound | Linear Peptide | Molecular Scaffold Reagent | MW | m/z found |
|---|---|---|---|---|
| I-23 | SEQ ID NO: 2 | MSR-A ([7] in Example 1) | 2726 | m/z 1364 [M + 2H]$^{2+}$ |
| I-44 | SEQ ID NO: 3 | MSR-A ([7] in Example 1) | 2238 | m/z 1121 [M + 2H]$^{2+}$ |
| I-90 | SEQ ID NO: 3 | MSR-B | 2107 | m/z 1054 [M + 2H]$^{2+}$ |
| I-91 | SEQ ID NO: 3 | MSR-C | 2465 | m/z 1234 [M + 2H]$^{2+}$ |
| I-92 | SEQ ID NO: 3 | MSR-D | 2197 | m/z 1100 [M + 2H]$^{2+}$ |
| I-93 | SEQ ID NO: 3 | MSR-E | 2196 | m/z 2197 [M + H]$^{+}$ |
| I-94 | SEQ ID NO: 3 | MSR-F | 2445 | m/z 2446 [M + H]$^{+}$ |
| I-95 | SEQ ID NO: 3 | MSR-G | 2197 | m/z 2198 [M + H]$^{+}$ |
| I-96 | SEQ ID NO: 3 | MSR-H | 2085 | m/z 1044 [M + 2H]$^{2+}$ |
| I-98 | SEQ ID NO: 4 | MSR-B | 1784 | m/z 893 [M + 2H]$^{2+}$ |
| I-99 | SEQ ID NO: 5 | MSR-A | 2524 | m/z 1263 [M + 2H]$^{2+}$ |
| I-100 | SEQ ID NO: 6 | MSR-B | 2558 | m/z 1280 [M + 2H]$^{2+}$ |
| I-101 | SEQ ID N0: 6 | MSR-C | 2915.5 | m/z 1099 [M + 2H]$^{2+}$ |
| I-102 | SEQ ID NO: 6 | MSR-D | 2708 | m/z 1355 [M + 2H]$^{2+}$ |
| I-103 | SEQ ID NO: 6 | MSR-E | 2646 | m/z 2647 [M + H]$^{+}$ |
| I-104 | SEQ ID NO: 6 | MSR-F | 2894 | m/z 2895 [M + H]$^{+}$ |
| I-105 | SEQ ID NO: 6 | MSR-G | 2646 | m/z 2647 [M + H]$^{+}$ |
| I-106 | SEQ ID NO: 6 | MSR-H | 2536 | m/z 1269 [M + 2H]$^{2+}$ |
| I-107 | SEQ ID NO: 7 | MSR-B | 1880 | m/z 941 [M + 2H]$^{2+}$ |
| II-19 | SEQ ID NO: 8 | MSR-I | 1924 | m/z 963 [M + 2H]$^{2+}$ |
| II-25 | SEQ ID NO: 8 | MSR-J | 2024 | m/z 1013 [M + 2H]$^{2+}$ |

Example 4: CAIX Assay

CAIX Competition Binding Assay. Affinity of the peptides of the invention for human CAIX (Ki) is determined using a competition fluorescence polarization assay analogous to that described in Dubois et al. (2011) Radiotherapy and Oncology 99(3), 424-43 using A-(CAECWID-GWVPC)-A-Sar6-K(Fl), (SEQ ID NO: 11), as the fluorescent ligand.

Results of the CAIX Competition Binding Assay are reported in Table 4. Compounds described as "A" have a K$_i$ less than 0.5 μM. Compounds described as "B" have a K, equal to or greater than 0.5 μM and less than 1 μM. Compounds described as "C" have a K, equal to or greater than 1 μM and less than 10 μM. Compounds described as "D" have a K, equal to or greater than 10 μM.

TABLE 4

CAIX Competition Binding Assay Results n = 2).

| Compound | K$_i$(μM) |
|---|---|
| 1-23 | D |
| 1-98 | A |
| 1-108 | A |
| 1-109 | B |

Example 5: Dissociation Rate Constant Determination of Bicyclic Binders to MT1-MMP Direct Binding Fluorescence Polarization (Anisotropy) Assays Direct Binding Fluorescence Polarization or Anisotropy Assays are performed by titrating a constant concentration of fluorescent tracer (here, the fluoresceinated bicyclic peptide to be studied) with its binding partner (here, the MT1-MMP hemopexin domain). As the concentration of binding partner increases during the titration, the polarization signal changes in proportion to the fraction of bound and unbound material. This allows determination of dissociation rates (K$_d$) quantitatively. Assay data can be fit using standard ligand binding equations.

Typically, concentrations of the tracer are ideally well below the K$_d$ of the tracer:titrant pair, and concentrations chosen are usually at ~1 nM or less. The titrant (binding partner) concentration is varied from 0.1 nM up to typically 5 μM. The range is chosen such that the maximum change in fluorescent polarization can be observed. Buffers employed are phosphate buffered saline in the presence of 0.01% Tween. Experiments were run in black 384 well low-bind/low volume plates (Corning 3820), and the fluorescent polarization signal was measured using a BMG Pherastar FS plate reader. Fluorescent tracers referred to in the text are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar5). This can be done during Fmoc solid phase synthesis or post-synthetically (after cyclization with the molecular scaffold reagent and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6). Thus, N-terminal tracers can have a molecular format described as Fluo-Gly-Sar5-A(Bicycle-CoreSequence), and (BicycleCoreSequence)-A-Sar6-K (Fluo) for a C-terminally fluoresceinated construct.

Results of the MT1-MMP Direct Binding Fluorescence Polarization are reported in Table 5. Compounds described as "A" have a $K_i$ less than 0.5 µM. Compounds described as "B" have a $K_i$ equal to or greater than 0.5 µM and less than 1 µM. Compounds described as "C" have a $K_i$ equal to or greater than 1 µM and less than 10 µM. Compounds described as "D" have a $K_i$ equal to or greater than 10 µM.

TABLE 5

MT1-MMP Direct Binding Fluorescence Polarization Results (n=2).

| Compound | $K_i$ (µM) |
|---|---|
| 1-44 | D |
| 1-90 | A |
| 1-91 | A |
| 1-92 | B |
| 1-93 | A |
| 1-94 | A |
| 1-95 | B |
| 1-96 | A |

Example 6: Competition Assays Using Fluorescence Polarization (Anisotropy)

Due to their high affinities to the MT1-MMP Hemopexin domain (PEX), the fluoresceinated derivatives of certain MT1-MMP binding bicycle peptides can be used for competition experiments (using FP for detection). Here, a preformed complex of PEX with the fluorescent PEX-binding tracer is titrated with free, non-fluoresceinated bicyclic peptide. Since MT1-MMP binding bicycle peptides are expected to bind at the same site, the titrant will displace the fluorescent tracer from PEX. Dissociation of the complex can be measured quantitatively, and the $K_d$ of the competitor (titrant) to the target protein determined. The advantage of the competition method is that the affinities of non-fluoresceinated bicyclic peptides can be determined accurately and rapidly.

Concentrations of tracer are usually at the $K_d$ or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarization. The drop in fluorescence polarization is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting is performed using Sigmaplot 12.0 and uses an adapted version of the equation described by Zhi-Xin Wang (FEBS Letters 360 (1995) 111-114).

Example 7: Preparation of Molecular Scaffold Reagent B (MSR-B)

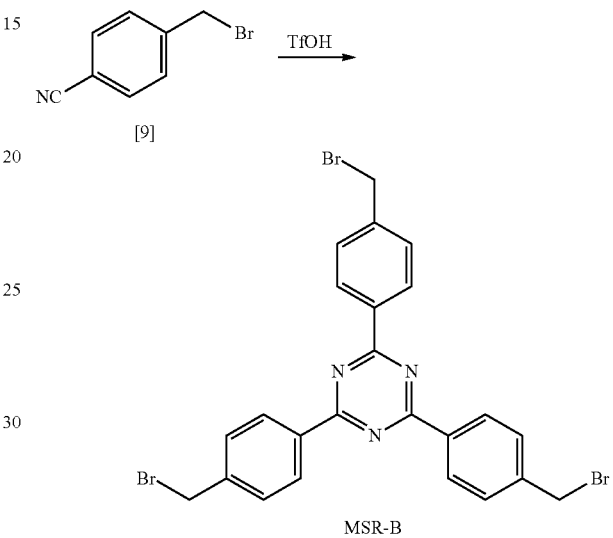

4-Cyanobenzyl bromide [9] (2.5 g, 12.8 mmol) was added portionwise to trifluoromethanesulphonic acid (3 ml, 33.9 mmol) at 0° C. under $N_2$ and the resultant mixture was stirred at room temperature for 18 h. This was poured onto stirred ice/water mixture and basified with saturated aqueous sodium bicarbonate. The resultant solid was collected by filtration, washed with water and dried under reduced pressure to afford the title compound (MSR-B) as a white solid (2.35 g, 94%). $^1$H NMR (300 MHz, CDCl$_3$) 4.60 (6H, s), 7.60 (6H, d), 8.75 (6H, d). $^{13}$C NMR (75 MHz, CDCl$_3$) 32.7, 129.3, 129.4, 136.1, 142.3, 171.1. LCMS M+H$^+$=589, $C_{24}H_{18}Br_3N_3$ requires 588; RT=4.21 mins.

Example 8: Preparation of Molecular Scaffold Reagent C (MSR-C)

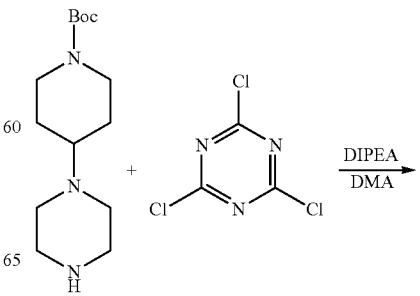

311
-continued

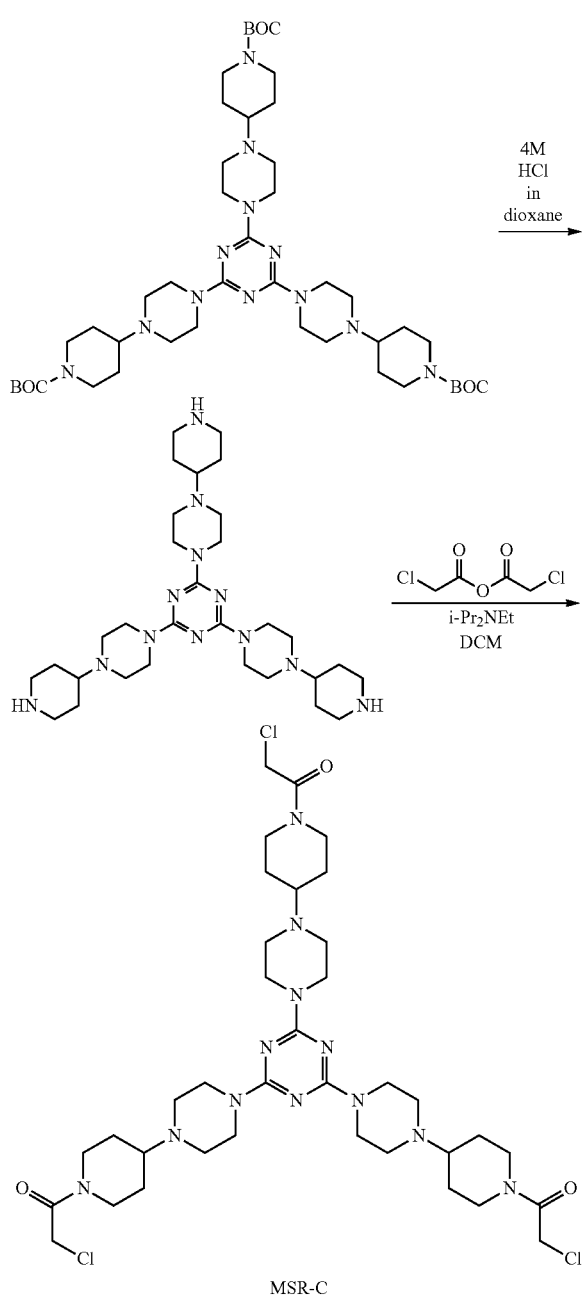

MSR-C

Step A: tert-butyl 4-[4-[4,6-bis[4-(1-tert-butoxycarbonyl-4-piperidyl)piperazin-1-yl]-1,3,5-triazin-2-yl]piperazin-1-yl]piperidine-1-carboxylate tert-butyl 4-piperazin-1-ylpiperidine-1-carboxylate (650 mg, 2.41 mmol), cyanuric chloride (144 mg, 0.78 mmol) and diisopropylethylamine (1.35 mL, 7.75 mmol) were dissolved in dimethylacetamide (12 mL) and the reaction was stirred at 80° C. for 3 days. The reaction was added dropwise into stirring water (200 mL) and the resulting solid was isolated by filtration and dried under vacuum at 50° C. overnight. This was purified by chromatography (80 g cartridge, 0 to 10% MeOH/DCM), the desired fractions collected and evaporated to afford the title compound as a tan solid (570 mg, 83%). $^1$H NMR (300 MHz, CDCl$_3$) 1.45 (33H, m), 1.81 (6H, d), 2.40 (3H, t), 2.54 (12H, s), 2.70 (6H, t), 3.76 (12H, s), 4.16 (6H, d). LCMS M+H$^+$=884, C$_{45}$H$_{78}$N$_{12}$O$_6$ requires 883; RT=2.29 mins.

Step B: 2,4,6-tris[4-(4-piperidyl)piperazin-1-yl]-1,3,5-triazine hydrochloride

4M HCl in dioxane (5 mL) was added to a solution of the tert-butyl 4-[4-[4,6-bis[4-(1-tert-butoxycarbonyl-4-piperidyl)piperazin-1-yl]-1,3,5-triazin-2-yl]piperazin-1-yl]piperidine-1-carboxylate (570 mg, 0.65 mmol) in dioxane (10 mL) and the reaction was stirred at room temperature for 18 h. The reaction mixture was evaporated to afford the title compound as a tan solid (440 mg, 98%). $^1$H NMR (300 MHz, DMSO) 1.99 (6H, m), 2.30 (6H, d), 2.95 (12H, m), 3.48 (21H, m), 4.69 (6H, d). LCMS M+H$^+$=583, C$_{30}$H$_{54}$N$_{12}$ requires 582; RT=0.19 mins.

Step C: 1-[4-[4-[4,6-bis[4-[1-(2-chloroacetyl)-4-piperidyl]piperazin-1-yl]-1,3,5-triazin-2-yl]piperazin-1-yl]-1-piperidyl]-2-chloro-ethanone A solution of chloroacetic anhydride (428 mg, 2.51 mmol) in dichloromethane (10 mL) was added dropwise to a suspension of the 2,4,6-tris[4-(4-piperidyl)piperazin-1-yl]-1,3,5-triazine hydrochloride (525 mg, 0.76 mmol) and diisopropylethylamine (812 µL, 4.55 mmol) in dichloromethane (30 mL) cooled to 0° C. and the reaction was stirred at 0° C. for 2 hrs. A repeat addition of diisopropylethylamine (812 µL, 4.55 mmol) and chloroacetic anhydride (428 mg, 2.51 mmol) in dichloromethane (10 mL) and the reaction stirred for a further 1 hr at 0° C. giving a complete solution. The reaction was diluted with sat. aq. Sodium bicarbonate and dichloromethane and the phases separated. The organic layer was dried (MgSO$_4$) and the solvent evaporated to afford a crude oil. This was triturated with diethyl ether then pentane to afford the title compound (MSR-C) as a tan solid (401 mg, 68%). NMR (300 MHz, CDCl$_3$) 1.52 (9H, m), 1.90 (6H, m), 2.55 (12H, m), 2.66 (3H, m), 3.12 (3H, m), 3.76 (12H, m), 3.92 (3H, d), 4.06 (6H, q), 4.59 (3H, d). LCMS M+H$^+$=811, C$_{36}$H$_{57}$Cl$_3$N$_{12}$O$_3$ requires 810; RT=0.33 mins.

Example 9: Preparation of Molecular Scaffold Reagent D (MSR-D)

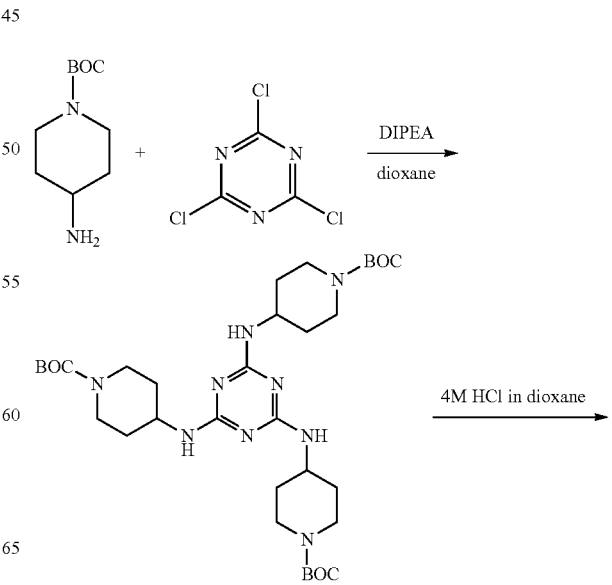

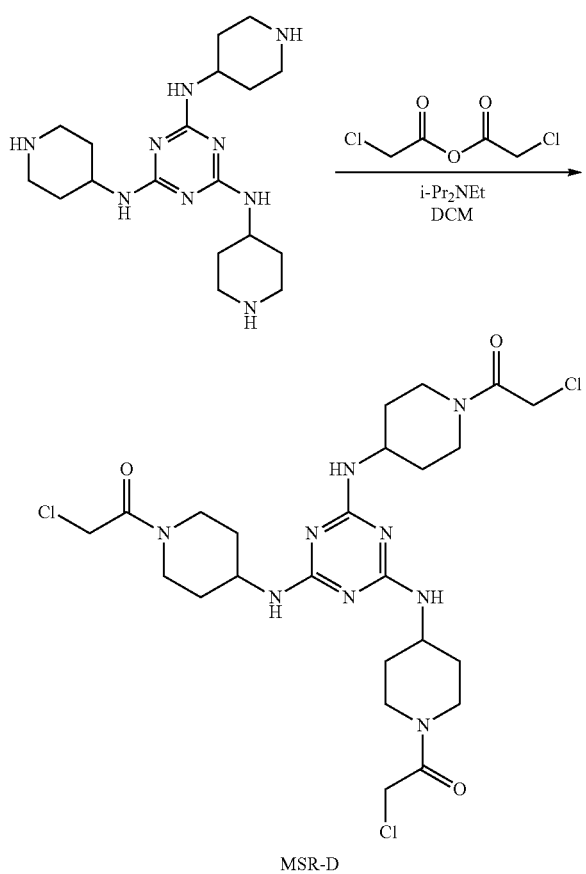

MSR-D

Step A: tert-butyl 4-[[4,6-bis[(1-tert-butoxycarbonyl-4-piperidyl)amino]-1,3,5-triazin-2-yl]amino]piperidine-1-carboxylate Tert-butyl 4-aminopiperidine-1-carboxylate (1.33 g, 6.70 mmol), cyanuric chloride (400 mg, 2.15 mmol) and diisopropylethylamine (3.76 mL, 21.58 mmol) were suspended in dioxane (30 mL) and the reaction was stirred at 80° C. overnight. A further portion of tert-butyl 4-aminopiperidine-1-carboxylate (1.33 g, 6.70 mmol) was added and the mixture stirred over 3 days. A further portion of tert-butyl 4-aminopiperidine-1-carboxylate (1.33 g, 6.70 mmol) was added and the mixture stirred over a further 2 days. The reaction was diluted with ethyl acetate and washed with sat. aq. sodium bicarbonate then brine. The organics were dried (MgSO4), filtered and the solvent evaporated to afford a crude oil. This was purified by chromatography (80 g cartridge, 5 to 100% EtOAc/iso-hexane), the desired fractions collected and evaporated to afford the title compound as a tan solid (1.202 g, 83%). $^1$H NMR (300 MHz, CDCl$_3$) 1.35 (6H, m), 1.45 (27H, s), 1.95 (6H, d), 2.89 (6H, t), 3.95 (6H, m), 4.66 (3H, bs). LCMS M+H$^+$=676, $C_{33}H_{57}N_9O_6$ requires 675; RT=2.29 mins.

Step B: N2,N4,N6-tris(4-piperidyl)-1,3,5-triazine-2,4,6-triamine hydrochloride

4M HCl in dioxane (10 mL) was added to a solution of the tert-butyl 4-[[4,6-bis[(1-tert-butoxycarbonyl-4-piperidyl)amino]-1,3,5-triazin-2-yl]amino]piperidine-1-carboxylate (695 mg, 1.03 mmol) in dioxane (10 mL) and the reaction was stirred at room temperature for 18 h. The reaction mixture was filtered and the filter cake washed with diethyl ether and pentane and dried under vacuum to afford the title compound as a tan solid (484 mg, 97%). $^1$H NMR (300 MHz, DMSO) 1.74 (6H, m), 1.99 (6H, m), 3.00 (6H, m), 3.28 (6H, m), 4.00 (3H, m). LCMS M+H$^+$=376, $C_{18}H_{33}N_9$ requires 375; RT=0.19 mins.

Step C: 2-chloro-1-[4-[[4-[[1-(2-chloroacetyl)-4-piperidyl]amino]-6-[[1-[1-(chloromethyl)vinyl]-4-piperidyl]amino]-1,3,5-triazin-2-yl]amino]-1-piperidyl]ethanone A solution of chloroacetic anhydride (620 mg, 3.63 mmol) in dichloromethane (10 mL) was added dropwise to a suspension of the N2,N4,N6-tris(4-piperidyl)-1,3,5-triazine-2,4,6-triamine hydrochloride (532 mg, 1.10 mmol) and diisopropylethylamine (1.15 mL, 6.60 mmol) in dichloromethane (30 mL) cooled to 0° C. and the reaction was stirred at 0° C. for 2 hrs. The reaction was diluted with sat. aq. Sodium bicarbonate and dichloromethane and the phases separated. The organic layer was dried (MgSO$_4$) and the solvent evaporated to afford a tan solid. This was triturated with diethyl ether then pentane to afford the title compound (MSR-D) as a tan solid (540 mg, 81%). NMR (300 MHz, CDCl$_3$) 1.45 (6H, m), 2.07 (6H, m), 2.91 (3H, t), 3.25 (3H, t), 3.85 (3H, d), 4.07 (9H, m), 4.42 (3H, d), 4.69 (3H, bs). LCMS M+H$^+$=604, $C_{24}H_{36}Cl_3N_9O_3$ requires 603; RT=1.25 mins.

Example 10: Preparation of Molecular Scaffold Reagent E (MSR-E)

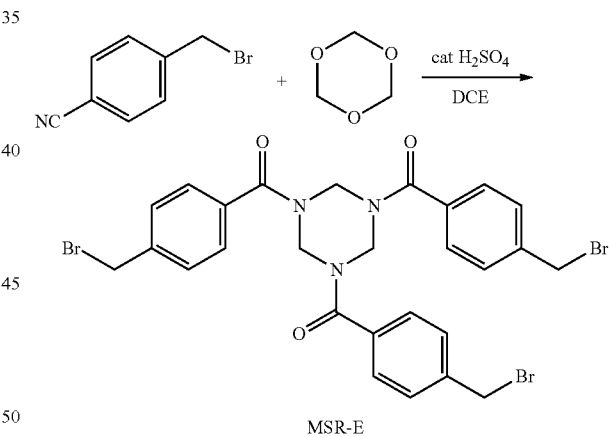

MSR-E

Sulphuric acid (2 drops) was added to a solution of the 4-cyanobenzyl bromide (1.64 g, 8.3 mmol) in dichloroethane (10 mL) and the reaction was heated to 90° C. To this was added a suspension of the paraformaldehyde (500 mg, 5.55 mmol) and 4-cyanobenzyl bromide (1.64 g, 8.3 mmol) in dichloroethane (10 mL) dropwise and the resultant mixture stirred at 90° C. for 5 h. The reaction was cooled and a solid filtered off and washed with methanol (3×). The combined organics were evaporated to afford a crude solid. The solid was washed with ethyl acetate (3×) to afford the title compound (MSR-E) as a white solid (963 mg, 26%). $^1$H NMR (300 MHz, CDCl$_3$) 4.65 (6H, br s), 5.35 (6H, br s), 7.40 (12H, br s). $^{13}$C NMR (75 MHz, CDCl$_3$) 33.9, 62.8, 126.5, 128.2, 129.7, 140.9, 169.2. LCMS M+H$^+$=679, $C_{27}H_{24}Br_3N_3O_3$ requires 678; RT=2.90 mins.

Example 11: Preparation of Molecular Scaffold Reagent F (MSR-F)

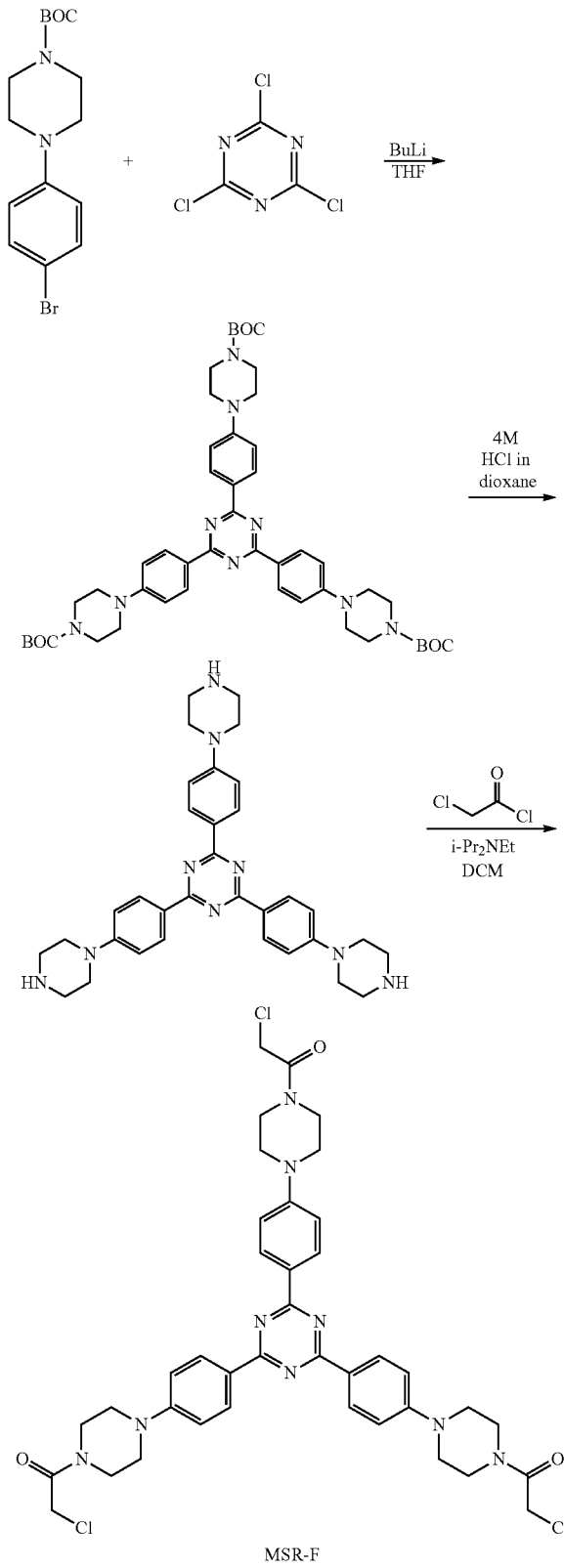

MSR-F

Step A: tert-butyl 4-[4-[4,6-bis[4-(4-tert-butoxycarbonylpiperazin-1-yl)phenyl]-1,3,5-triazin-2-yl]phenyl]piperazine-1-carboxylate n-Butyllithium (1.6M in THF, 2.58 mL, 6.46 mmol) was added dropwise to a solution of the tert-butyl 4-(4-bromophenyl)piperazine-1-carboxylate (2.02 g, 5.92 mmol) in THF (40 mL) at −78° C. under $N_2$ and the reaction was stirred for 90 minutes. Cyanuric chloride (331 mg, 1.79 mmol) in THF (8 mL) was added dropwise to the reaction mixture and stirring was continued at −78° C. for 3 h. The reaction was quenched by the addition of saturated aqueous sodium bicarbonate followed by warming to room temperature. Water and ethyl acetate were added followed by separation of the phases. The organic layer was dried ($MgSO_4$) and evaporated to afford a crude oil. This was purified by chromatography (80 g cartridge, 0 to 50% EtOAc/i-hexane), the desired fractions collected and evaporated, followed by trituation from $Et_2O$ to afford the title compound as a pale yellow solid (448 mg, 30%). $^1$H NMR (300 MHz, $CDCl_3$) 1.00 (27H, s), 3.35 (12H, m), 3.60 (12H, m), 7.00 (6H, d), 8.65 (6H, d). LCMS M+H$^+$=862, $C_{48}H_{63}N_9O_6$ requires 861; RT=4.81 mins.

Step B: 2,4,6-tris(4-piperazin-1-ylphenyl)-1,3,5-triazine trihydrochloride

4M HCl in dioxane (10 mL) was added to a suspension of the tert-butyl 4-[4-[4,6-bis[4-(4-tert-butoxycarbonylpiperazin-1-yl)phenyl]-1,3,5-triazin-2-yl]phenyl]piperazine-1-carboxylate (448 mg, 0.52 mmol) in dioxane (20 mL) and the reaction was stirred at room temperature for 18 h. The reaction mixture was evaporated to afford the title compound as an orange solid (332 mg, 96%). $^1$H NMR (300 MHz, DMSO) 3.35 (12H, br s), 3.60 (12H, br s), 7.15 (6H, d), 8.55 (6H, d), 9.25 (6H, br s). LCMS M+H$^+$=562, $C_{33}H_{39}N_9$ requires 561; RT=0.82 mins.

Step C: 1-[4-[4-[4,6-bis[4-[4-(2-chloroacetyl)piperazin-1-yl]phenyl]-1,3,5-triazin-2-yl]phenyl]piperazin-1-yl]-2-chloro-ethanone Chloroacetyl chloride (101 µL, 1.28 mmol) was added dropwise to a solution of the 2,4,6-tris(4-piperazin-1-ylphenyl)-1,3,5-triazine trihydrochloride (245 mg, 0.365 mmol) and diisopropylethylamine (635 µL, 3.65 mmol) in dichloromethane (15 mL) and the reaction was stirred at room temperature for 1 h. The reaction was diluted with water and dichloromethane and the phases separated. The organic layer was dried ($MgSO_4$) and the solvent evaporated to afford a crude oil. This was triturated with diethyl ether to afford the title compound (MSR-F) as a light brown solid (221 mg, 77%). NMR (300 MHz, $CDCl_3$) 3.40 (12H, m), 3.70 (6H, m), 3.80 (6H, m), 4.10 (6H, s), 7.00 (6H, d), 8.65 (6H, d). LCMS M+H$^+$=790, $C_{39}H_{42}Cl_3N_9O_3$ requires 789; RT=3.09 mins.

Example 12: Preparation of Molecular Scaffold Reagent G (MSR-G)

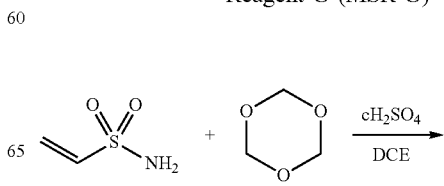

317

-continued

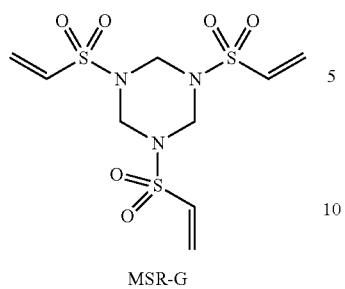

MSR-G

To a solution of the vinylsulphonamide (200 mg, 1.87 mmol) and paraformaldehyde (56 mg, 1.87 mmol) in dichloroethane (2 mL) was added conc. Sulphuric acid (1 drop) and the reaction sealed. This was heated to 90° C. for 5 h. After cooling the reaction mixture was diluted with dichloromethane and water. The phases were separated and the organic layer dried (MgSO$_4$). The solvent was evaporated to afford the title compound (MSR-G) as a waxy solid (200 mg, 89%). NMR (300 MHz, CDCl$_3$) 4.90 (6H, s), 6.05 (3H, d), 6.35 (3H, d), 6.60 (3H, m). LCMS M+H+=358, C$_9$H$_{15}$N$_3$O$_6$S$_3$ requires 357; RT=1.75 mins.

Example 13: Preparation of Molecular Scaffold Reagent H (MSR-H)

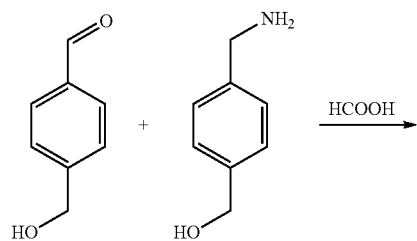

318

-continued

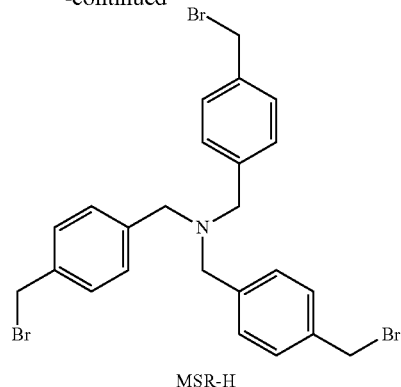

MSR-H

Step A: [4-[[bis[[4-(hydroxymethyl)phenyl]methyl]amino]methyl]phenyl]methanol

A mixture of 4-hydroxybenzaldehyde (509 mg, 3.74 mmol), 4-hydroxybenzylamine (256 mg, 1.87 mmol) and formic acid (71 μL, 1.87 mmol) was heated in a sealed tube at 70° C. for 18 h. After cooling the reaction was suspended in dichloromethane and the mixture stirred for 1 h. The solid was collected by filtration. This was purified by chromatography (40 g cartridge, 0 to 100% EtOAc/i-hexane) to afford the title compound as a colourless solid (94 mg, 15%). NMR (300 MHz, MeOD) 3.50 (6H, s), 4.05 (6H, s), 7.30 (6H, d), 7.35 (6H, d). LCMS M+H+=378, C$_{24}$H$_{27}$NO$_3$ requires 377; RT=0.78 mins.

Step B: 1-[4-(bromomethyl)phenyl]-N,N-bis[[4-(bromomethyl)phenyl]methyl]methanamine A mixture of the [4-[[bis[[4-(hydroxymethyl)phenyl]methyl]amino]methyl]phenyl]methanol (90 mg, 0.24 mmol) in 48% HBr (2 mL) was stirred at room temperature for 72 h. The mixture was diluted with dichloromethane and water and the phases separated. The organic layer was dried (MgSO$_4$) and the solvent evaporated to afford the title compound (MSR-H) as a light brown solid (106 mg, 79%). NMR (300 MHz, CDCl$_3$) 4.20 (6H, br s), 4.45 (6H, s), 7.50 (6H, m), 7.65 (6H, m). LCMS M+H+=567, C$_{24}$H$_{24}$Br$_3$N requires 566; RT=3.35 mins.

Example 14: Preparation of Molecular Scaffold Reagent I (MSR-I), 1,4-bis(2-bromoacetyl)-1,4-diazepan-6-one

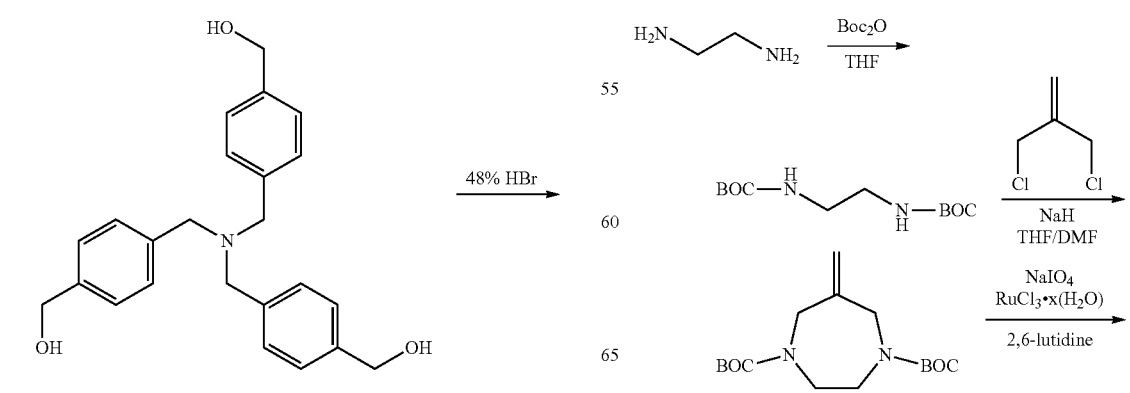

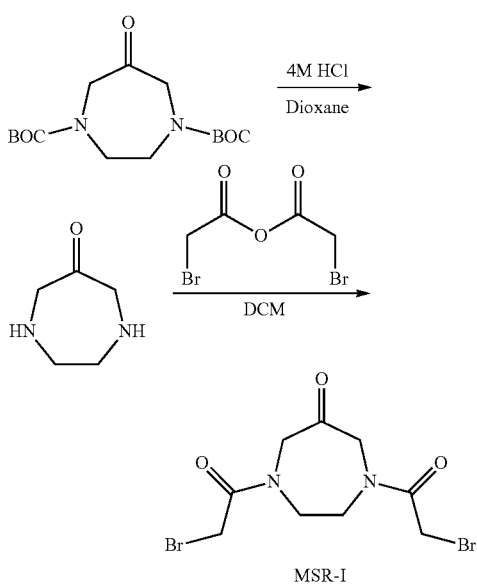

Step A: tert-butyl N-[2-(tert-butoxycarbonylamino) ethyl]carbamate

To a stirred solution of ethane-1,2-diamine (1.8 g, 30 mmol) in THF (30 mL) at 0° C. was added dropwise a solution of the Di-tert-butyl dicarbonate (14.4 g, 66 mmol) in THF (12 mL) and the reaction was stirred at room temperature for 18 h. The solvent was evaporated and the residue partitioned between water and DCM. The organic layer was collected, passed through a phase separator and the solvent evaporated. This was dissolved in DCM and then concentrated to approximately ½ volume and the title compound was collected by filtration as a white solid (4.1 g, 52%). $^1$H NMR (300 MHz, CDCl$_3$) 1.45 (18H, s), 3.25 (4H, s), 4.85 (2H, br s).

Step B: Di-tert-butyl 6-methylene-1,4-diazepane-1,4-dicarboxylate

To a stirred suspension of sodium hydride (60% suspension in oil) (1.74 g, 43.5 mmol) in N,N-dimethylformamide (36 mL) at 0° C. was added 2-chloro-2-(chloromethyl)prop-1-ene (1.54 mL, 14.5 mmol). To this was added tert-butyl N-[2-(tert-butoxycarbonylamino)ethyl]carbamate (3.78 g, 14.5 mmol) in THF (36 mL). After 15 minutes the ice-bath was removed and the reaction stirred at room temperature for 18 h. The reaction was quenched by the addition of saturated ammonium chloride (100 mL) and the mixture concentrated to remove the THF. The aqueous was extracted with EtOAc (3×) and the combined organics were dried (MgSO4) and the solvent evaporated to afford a crude solid. This was purified (silica, 0 to 20% EtOAc/i-hexane) to afford the title compound as a white solid (2.24 g, 49%). $^1$H NMR (300 MHz, CDCl$_3$) 1.45 (18H, s), 3.45 (4H, m), 3.90 (2H, m), 4.0 (2H, m), 4.95 (2H, m).

Step C: Di-tert-butyl 6-oxo-1,4-diazepane-1,4-dicarboxylate

To a stirred solution of di-tert-butyl 6-methylene-1,4-diazepane-1,4-dicarboxylate (2.24 g, 7.17 mmol) in DCM (43 mL) and MeCN (43 mL) was added 2,6-lutidine (1.66 mL, 14.3 mmol) and sodium periodate (6.13 g, 28.7 mmol) in water (64 mL). Finally ruthenium (III) chloride hydrate (52 mg, 0.25 mmol) in water 7.2 mL) was added drop wise and the reaction was stirred for 1 h. The reaction was diluted with water (200 mL) and extracted with DCM (3×). The combined organics were passed through a phase separator and the solvent evaporated. This was purified (silica 0 to 30% EtOAc/i-hexane) to afford the title compound as a white solid (1.94 g, 86%). $^1$H NMR (300 MHz, CDCl$_3$) 1.50 (18H, s), 3.60 (4H, br s), 3.90 (4H, m).

Step D: 1,4-diazepan-6-one

To a stirred suspension of di-tert-butyl 6-oxo-1,4-diazepane-1,4-dicarboxylate (0.97 g, 3.1 mmol) in DCM 15.5 mL) was added 4M HCl in dioxane (15.5 mL) and the reaction was stirred for 4 h. The solvent was evaporated and the residue passed through an SCX cartridge eluting with MeOH/water followed by 1M ammonia in MeOH to afford the title compound. This was used immediately in the next step.

Step E: 1,4-bis(2-bromoacetyl)-1,4-diazepan-6-one

Bromoacetic anhydride (1.77 g, 6.82 mmol) in DCM (11 mL) was added to a solution of 1,4-diazepan-6-one (~3.1 mmol) in DCM (20 mL) at 0° C. and the mixture was stirred for 30 minutes. A solid was filtered off and the solvent was evaporated. This was purified (silica 0 to 3% MeOH/EtOAc) to afford a yellow gum. This was triturated with diethyl ether to afford the title compound (MSR-I) as a light brown solid (529 mg, 48%). $^1$H NMR (300 MHz, CDCl$_3$) 3.85 (5.5H, m), 3.95 (2.7H, m), 4.15 (1.1H, m), 4.25 (2.7H, m) mixture of rotamers. LCMS M+H$^+$=355, C$_{12}$H$_{12}$Br$_2$N$_2$O$_3$ requires 354; RT=1.16 mins.

Using a similar procedure, MSR-J was prepared:

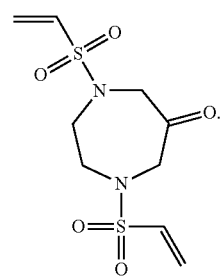 [SMILES: C=CS(=O)(=O)N1CCN(S(=O)(=O)C=C)CC(=O)C1]

Example 15. Preparation of Cyclic Peptides Comprising a Tyrosine Linkage

The linear peptides and all scaffolds were solved in acetonitrile/water 50/50 at 5 mM concentration. The peptide solutions were further diluted in 1M potassium carbonate to final concentration 1 mM.

3 ml 1 mM linear peptide solution was mixed with 1 ml 5 mM scaffold solution (linear peptide/scaffold molar ratio 1/1.6). The reaction mixture was kept at room temperature overnight and the cyclisation completion was confirmed by LC-MS (Acquity UPLC CSH C18 column, 1.7 µm, 2.1×30 mm; acetonitrile/water/HCOOH containing buffers and 15 to 60% acetonitrile gradient elution over 10 min). The cyclic peptide was purified using RP-HPLC (Gemini C18—semi prep column, 5 μm, 110 Å, 250×10 mm; acetonitrile/water/TFA containing buffers and 20 to 80% acetonitrile gradient elution over 20 min). Results of the cyclization protocol are provided in Table 6 below.

TABLE 6

Cyclization Protocol Results for Cyclic Peptides comprising a Tyrosine Linkage.

| Compound | Linear Peptide | MW | m/z found |
|---|---|---|---|
| I-108 | SEQ ID NO:9 | 1613 | m/z 1614 [M=H]$^+$ |
| I-109 | SEQ ID NO:10 | 1673 | m/z 1674 [M=H]$^+$ |

Example 16. EphA2 SPR Assay

SPR Measurements: Non-Fc fusion proteins were biotinylated with EZ-Link™ Sulfo-NHS-LC-Biotin for 1 hour in 4 mM sodium acetate, 100 mM NaCl, pH 5.4 with a 3× molar excess of biotin over protein. The degree of labelling was determined using a Fluorescence Biotin Quantification-Kit (Thermo) after dialysis of the reaction mixture into PBS. For analysis of peptide binding, a Biacore T200 10 instrument was used utilising a XanTec CMD500D chip. Streptavidin was immobilized on the chip using standard amine-coupling chemistry at 25° C. with HBS—N (10 mM HEPES, 0.15 M NaCl, pH 7.4) as the running buffer. Briefly, the carboxymethyl dextran surface was activated with a 7 min injection of a 1:1 ratio of 0.4 M 1-ethyl-3-(3-dimethylaminopropyl) carbodiimide hydrochloride (EDC)/0.1 M N-hydroxy succinimide (NHS) at a flow rate of 10 μl/min. For capture of streptavidin, the protein was diluted to 0.2 mg/ml in 10 mM sodium acetate (pH 4.5) and captured by injecting 120 μl onto the activated chip surface. Residual activated groups were blocked with a 7 min injection of 1 M ethanolamine (pH 8.5):HBS—N (1:1). Buffer was changed to PBS/0.05% Tween 20 and biotinylated EphA2 was captured to a level of 500-1500 RU using a dilution of protein to 0.2 μM in buffer. A dilution series of the peptides was prepared in this buffer with a final DMSO concentration of 0.5% with a top peptide concentration was 50 or 100 nM and 6 further 2-fold dilutions. The SPR analysis was run at 25° C. at a flow rate of 90 l/min with 60 seconds association and 900-1200 seconds dissociation. Data were corrected for DMSO excluded volume effects. All data were double-referenced for blank injections and reference surface using standard processing procedures and data processing and kinetic fitting were performed using Scrubber software, version 2.0c (BioLogic Software).

Data were fitted using simple 1:1 binding model allowing for mass transport effects where appropriate for binding of Bicycle Drug Conjugates, a Biacore 3000 instrument was used. For biotinylated proteins immobilisation levels were 1500 RU and the top concentration was 100 nM. Otherwise the method was the same as described above using either the CMD500D or a CM5 chip (GE Healthcare). For the Fc-tagged proteins, a CM5 chip was activated as described above and then goat anti-human IgG antibody (Thermo-Fisher H10500) was diluted to 20 μg/ml in 10 mM sodium acetate pH 5.0 and captured to approximately 3000 RU. The surface was then blocked as described above. Subsequent capture of the Fc-tagged proteins was carried out to obtain approximately 200-400 RU of the target protein. All proteins were reconstituted as per manufacturer's suggested buffers and concentrations and captured using 5-10 μg/ml protein in PBS/0.05% Tween 20

Results of the EphA2 SPR Assay are reported in Table 7. Compounds described as "A" have a $K_d$ less than 0.5 μM. Compounds described as "B" have a $K_d$ equal to or greater than 0.5 μM and less than 1 μM. Compounds described as "C" have a $K_d$ equal to or greater than 1 μM and less than 10 μM. Compounds described as "D" have a $K_d$ equal to or greater than 10 μM.

TABLE 7

EphA2 SPR Assay Results (n = 2).

| Compound | $K_d$(μM) |
|---|---|
| I-100 | A |
| I-101 | A |
| I-102 | D |
| I-103 | D |
| I-104 | A |
| I-105 | A |
| I-106 | A |

Example 17. PBP1A Fluorescence Polarization Competition Binding Assay

Fluorescence polarization competition was carried out using a BODIPY labelled Penicillin tracer and unlabelled peptides, for competition to an unmodified PBP protein. Polarization was measured using a PHERAstar FS by BMG Labtech fitted with a FP 485 520 520 optic module.

Fluorescent BODIPY labelled penicillin at 5 mM in DMSO were diluted to 6.25 nM in binding buffer (10 mM HEPES, pH8, 300 mM NaCl, 2% glycerol). Unmodified PBP were diluted to 2 μM in binding buffer. A two-fold dilution series of unmodified peptide was prepared across 12 wells in binding buffer, with the highest final well concentration being 60 μM, and the lowest concentration being 50 nM. 5 al of the unmodified peptide dilution series or Carbenicillin were added to 12 wells of a 384-Well NBS™ Low Volume Microplate (Fisher Scientific). 10 μl diluted fluorescent BODIPY labelled penicillin (6.25 nM) were then added to the 12 wells containing the unmodified peptide dilutions. 10 ul of unmodified PBP (2 μM) were then added to the 12 wells containing unmodified peptide and fluorescent BODIPY labelled penicillin to bring the total volume to 25 μl, and the final concentration of Fluorescent BODIPY labelled penicillin to 2.5 nM and unmodified PBP to 800 nM.

A control well lacking unmodified peptide was prepared with a final fluorescent BODIPY labelled penicillin concentration of 2.5 nM and a final concentration of unmodified PBP of 800 nM to a final volume of 25 µl in binding buffer. A second control well lacking unmodified peptide and unmodified PBP was prepared with a final fluorescent BODIPY labelled penicillin concentration of 2.5 nM to a final volume of 25 µl in binding buffer.

Fluorescence polarisation was measured every 5 minutes for a period of one hour at room temperature. The gain and focal height were optimised using the control well lacking unmodified peptide and unmodified PBP. Wells were excited at 485 nm, and emission detection was set at 520 nm.

Data were analysed in GraphPad software to derive values for the inhibition constant. Experiments were repeated at least three times.

Example 18. CD38 Competition Binding Assay

Affinity of the peptides of the invention for human CD38 (Ki) was determined using a fluorescence polarisation assay, using the method reported by Lea et al (Expert Opin Drug Discov. 2011 6(1): 17-3).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

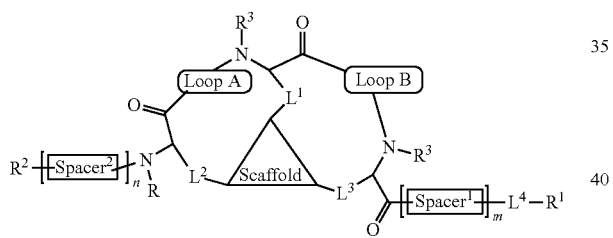

I or a pharmaceutically acceptable salt thereof, wherein:

each of $L^1$, $L^2$, and $L^3$ is independently a covalent bond or a $C_{1-8}$ bivalent hydrocarbon chain wherein one, two or three methylene units of the chain are optionally and independently replaced by -Cy$^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,

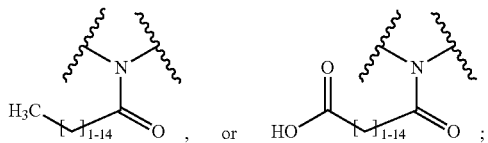

$L^4$ is a covalent bond, —O—, —N(R)—, or —N(R)CH$_2$CH$_2$N(R)—;

each R is independently hydrogen or $C_{1-4}$ aliphatic;

each -Cy$^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur;

Scaffold is a trivalent group that connects and orients a cyclic peptide selected from the group consisting of

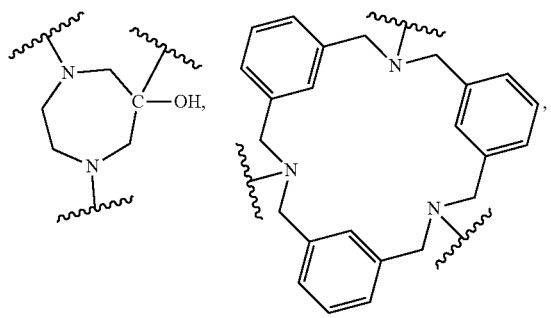

331
-continued
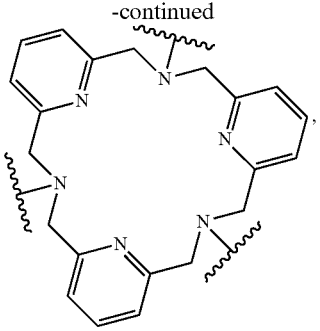
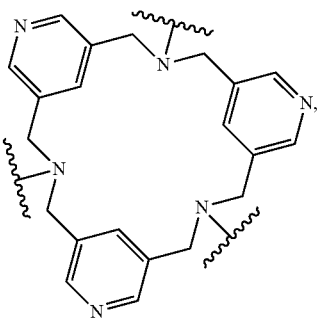
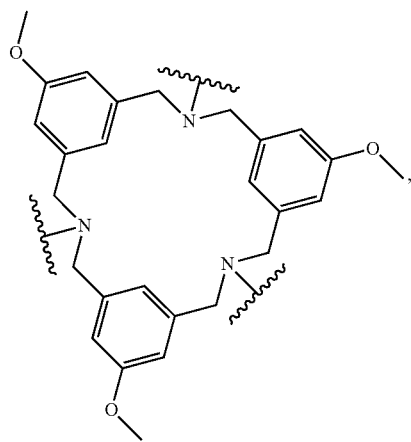
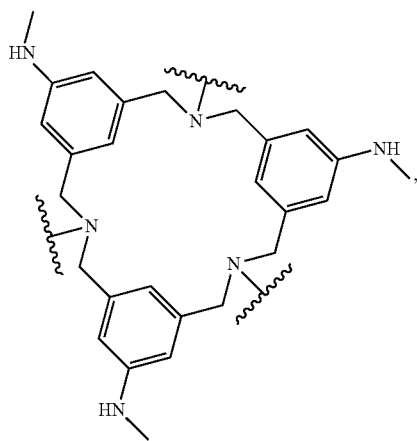
332
-continued
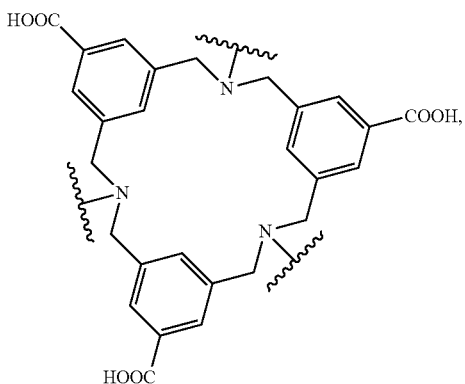
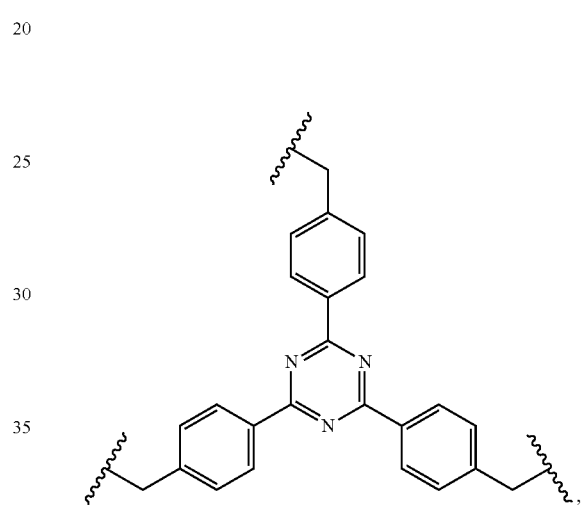
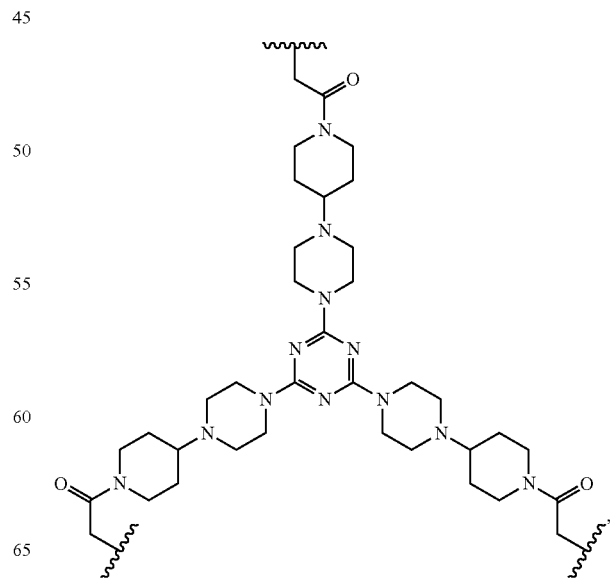

333
-continued

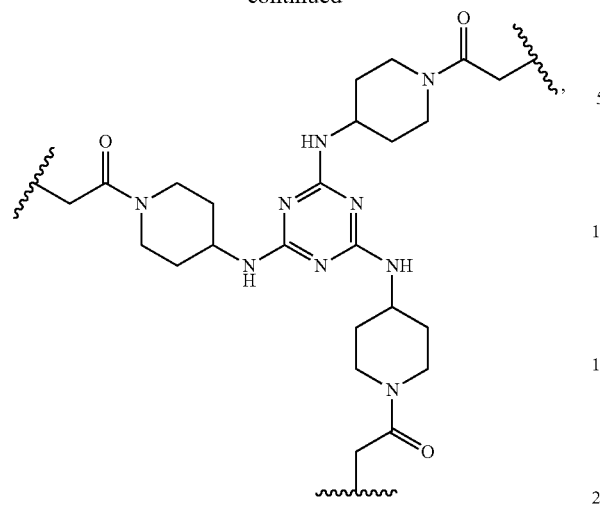

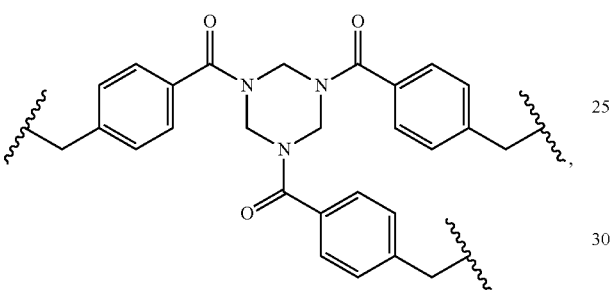

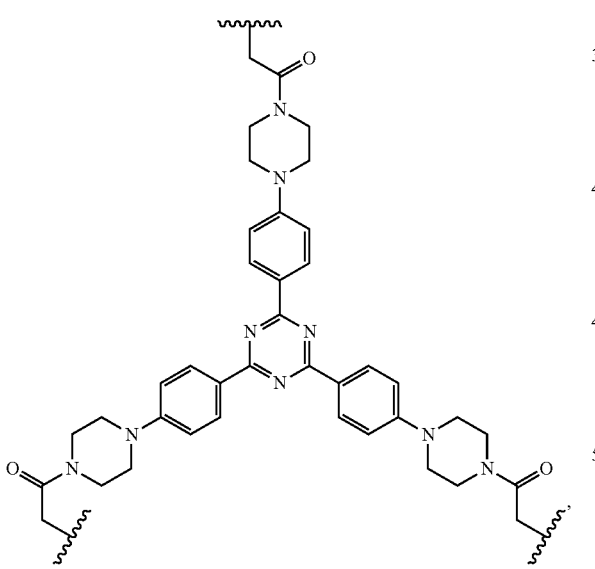

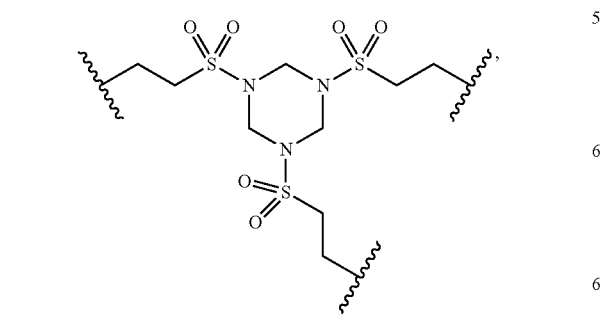

334
-continued

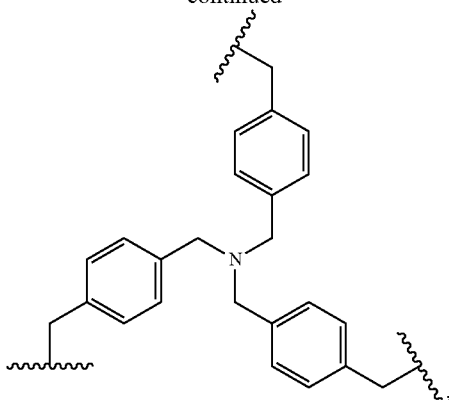

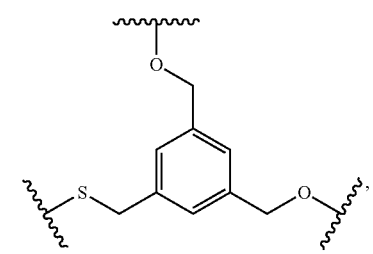 [SMILES: *OCc1cc(CS*)cc(CS*)c1]

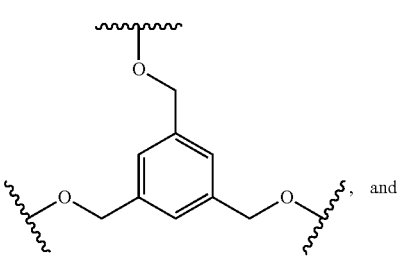

, and

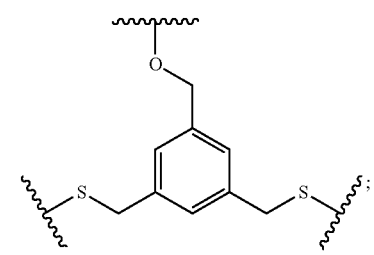

Loop A is a bivalent natural or unnatural amino acid residue or peptide attached to the amino acid residue linked to $L^1$ and the amino acid residue linked to $L^2$;

Loop B is a bivalent natural or unnatural amino acid residue or peptide attached to the amino acid residue linked to $L^1$ and the amino acid residue linked to $L^3$;

Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond;

Spacer² is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond;

each of R¹ and R² is independently R,

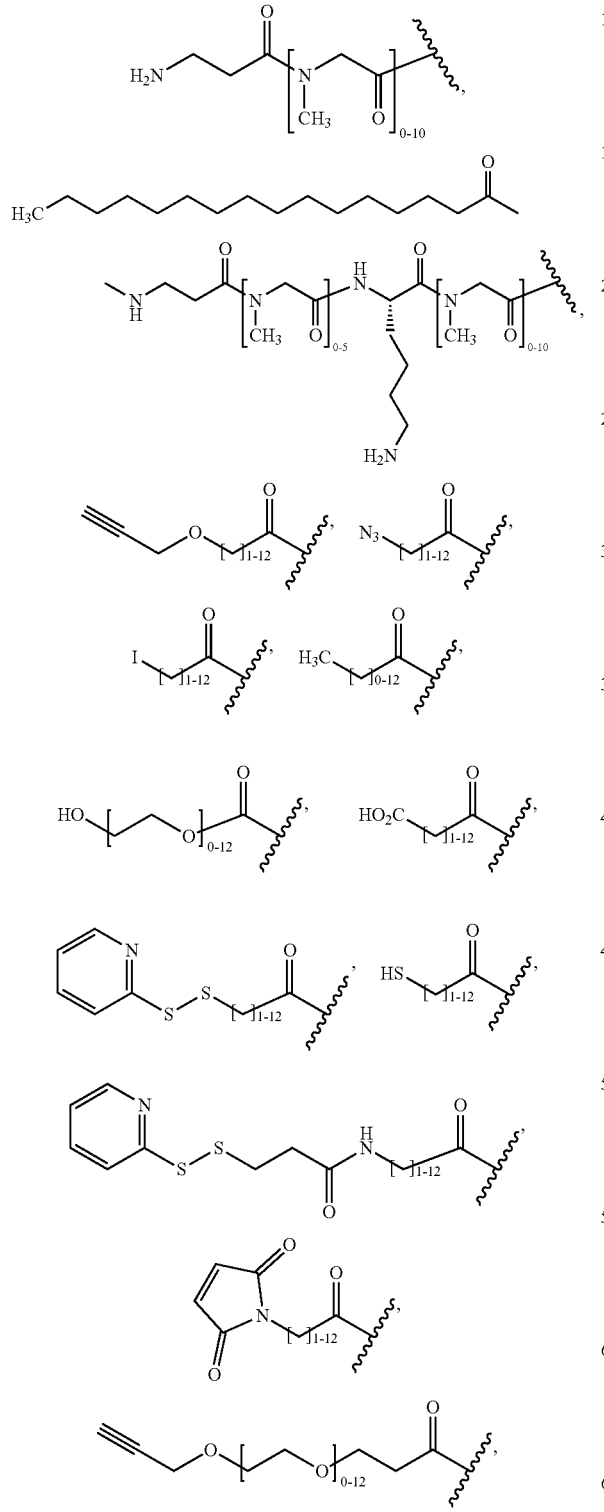

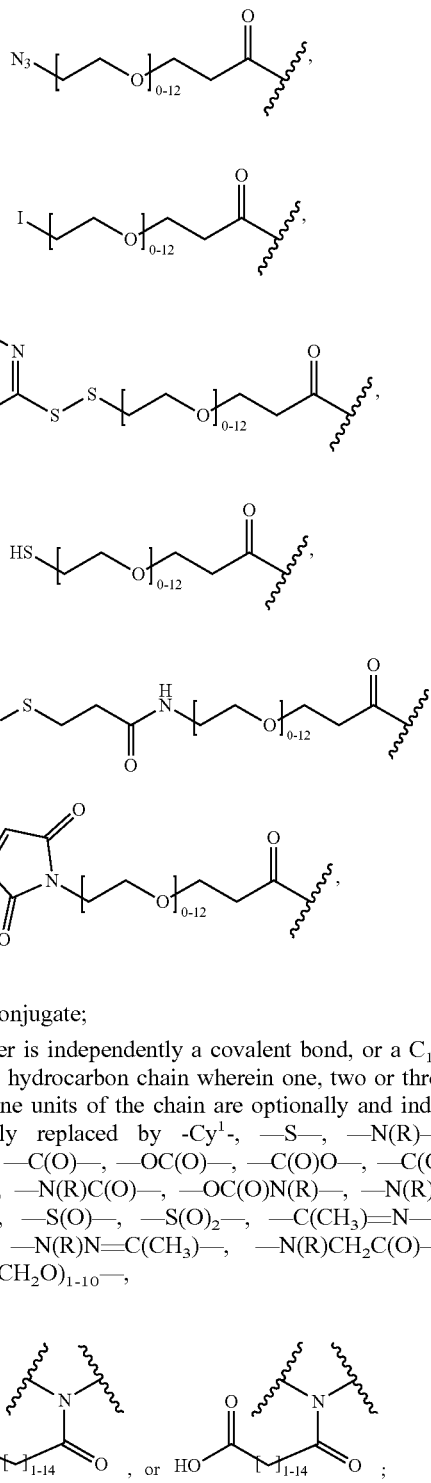

or -Linker-Conjugate;

each Linker is independently a covalent bond, or a $C_{1-8}$ bivalent hydrocarbon chain wherein one, two or three methylene units of the chain are optionally and independently replaced by -Cy¹-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)₂—, —C(CH₃)=N—N(R)—, —N(R)N=C(CH₃)—, —N(R)CH₂C(O)—, —(CH₂CH₂O)$_{1-10}$—,

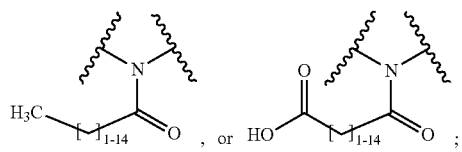

each Conjugate is independently a half life extension motif, a solubilizing group, a transporter recognition motif, a cell penetrant motif, a drug payload, or a detectable moiety;

each R³ is independently hydrogen or $C_{1-4}$ aliphatic;

m is 0 or 1; and n is 0 or 1.

2. The compound of claim 1, wherein the compound is selected from
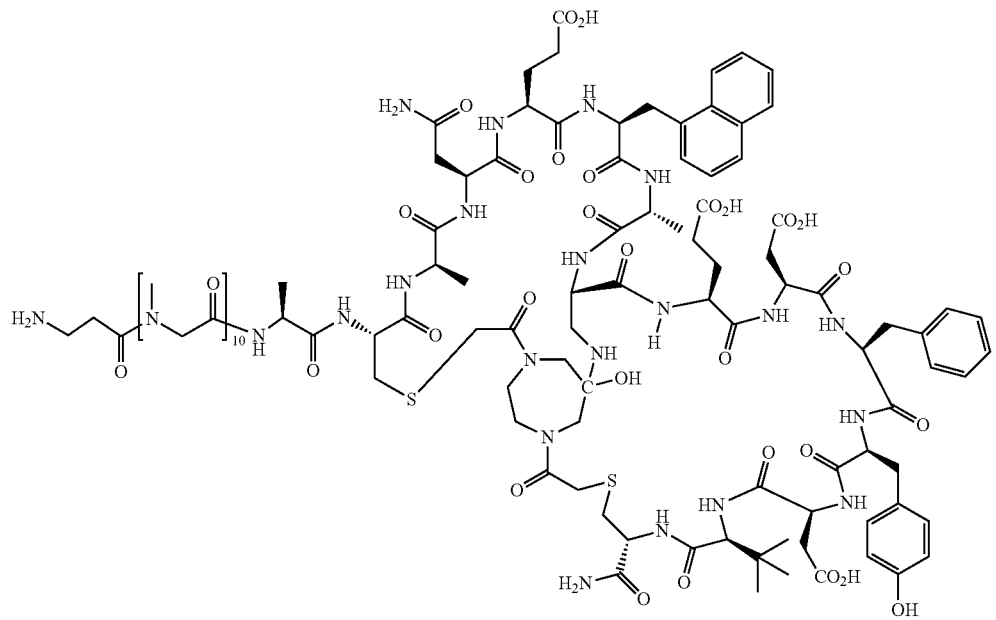
I-1
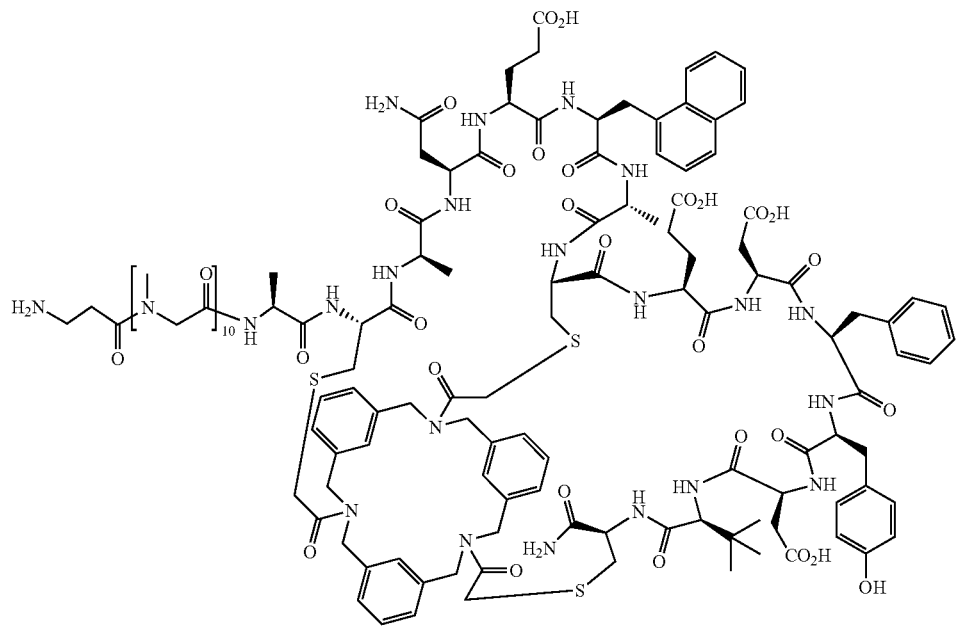
I-2

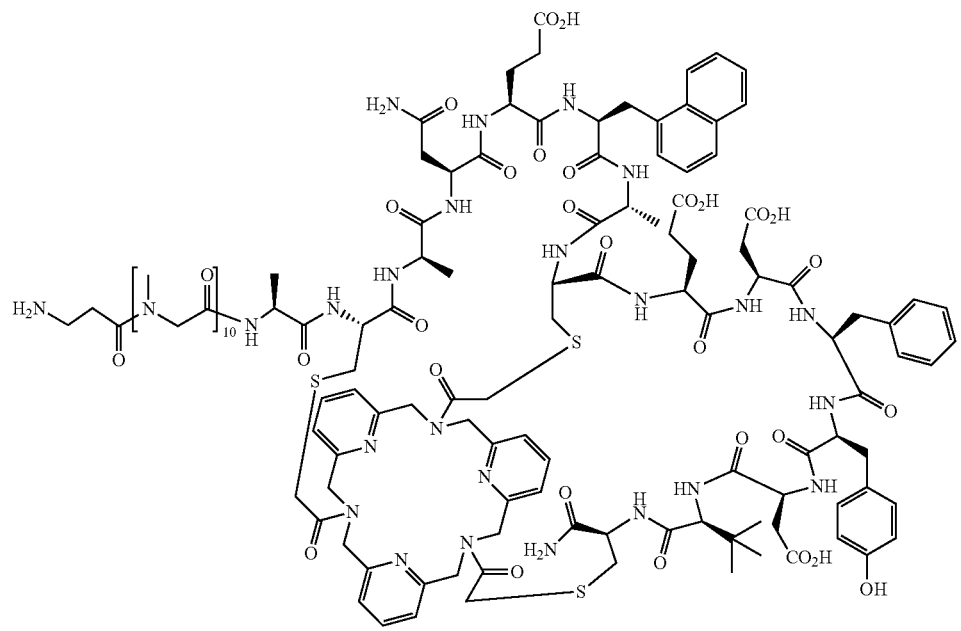
I-3
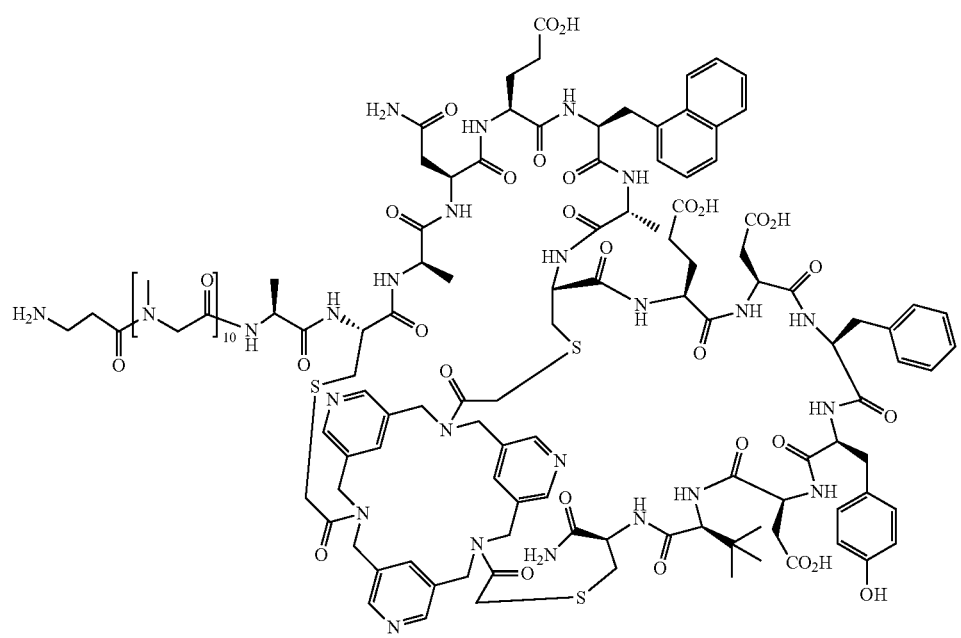
I-4

-continued
I-5
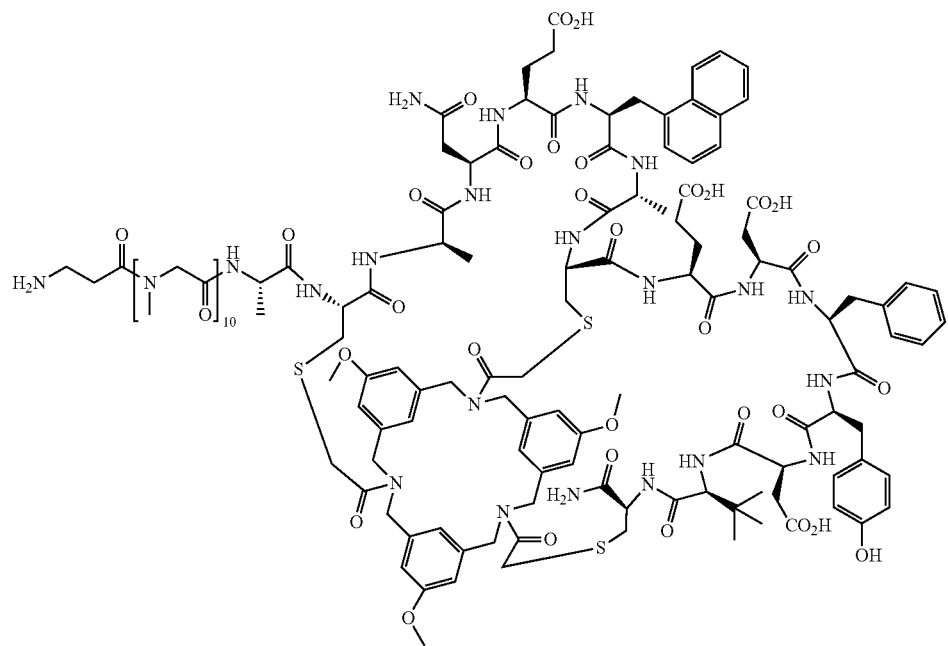
I-6
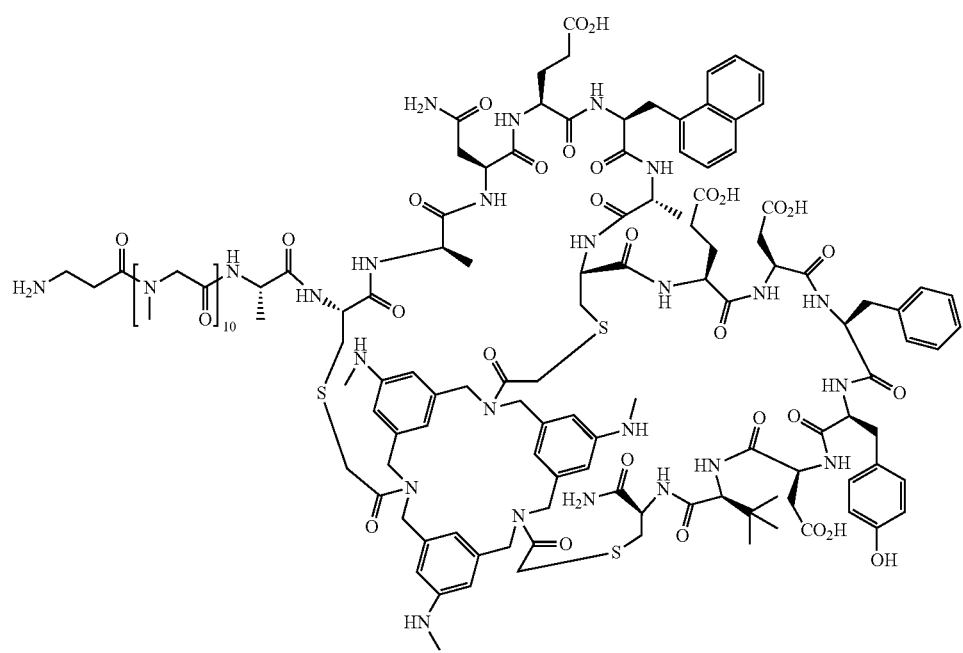

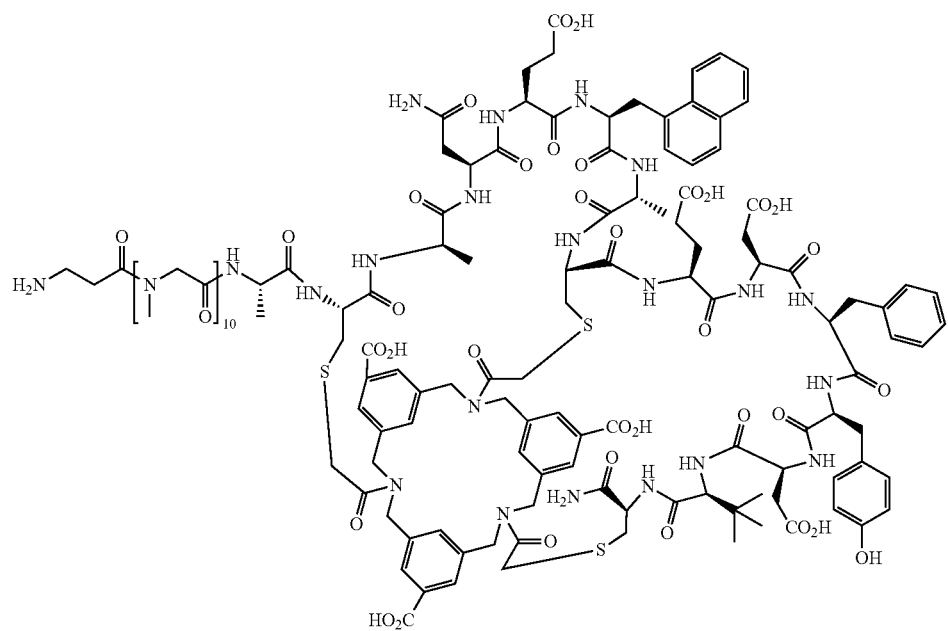
I-7
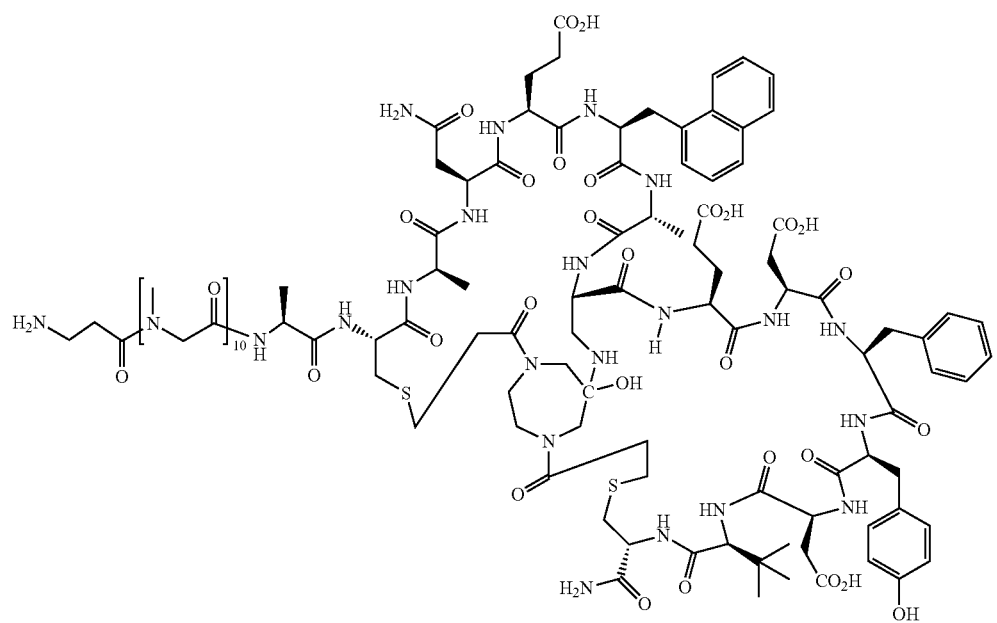
I-8

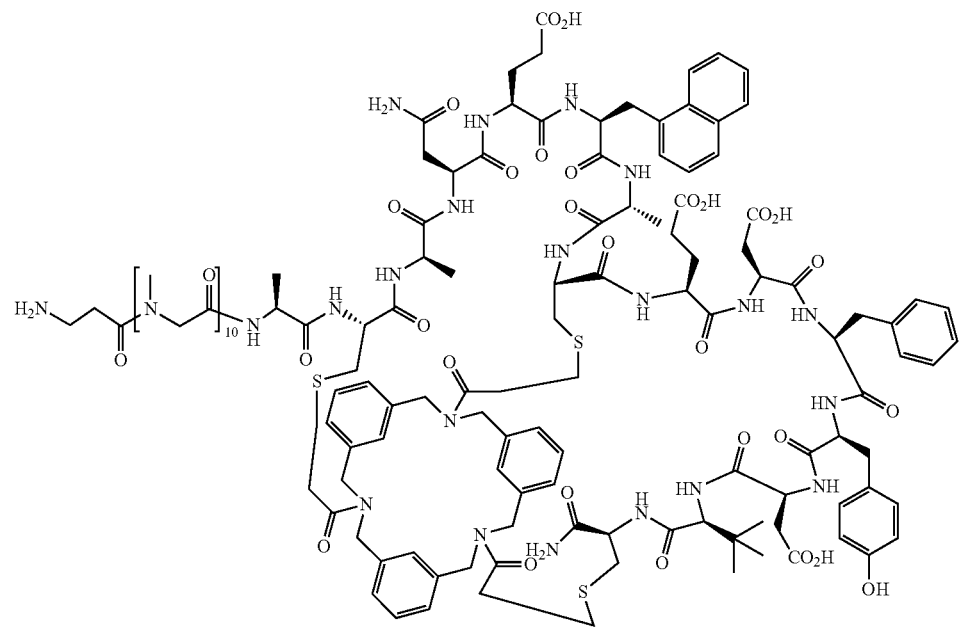
I-9
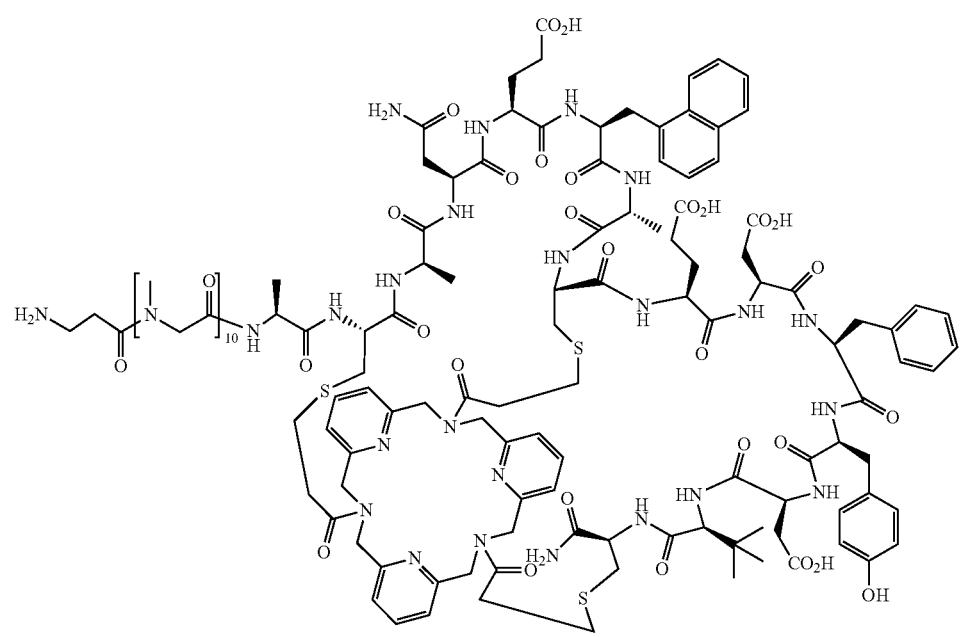
I-10

I-11
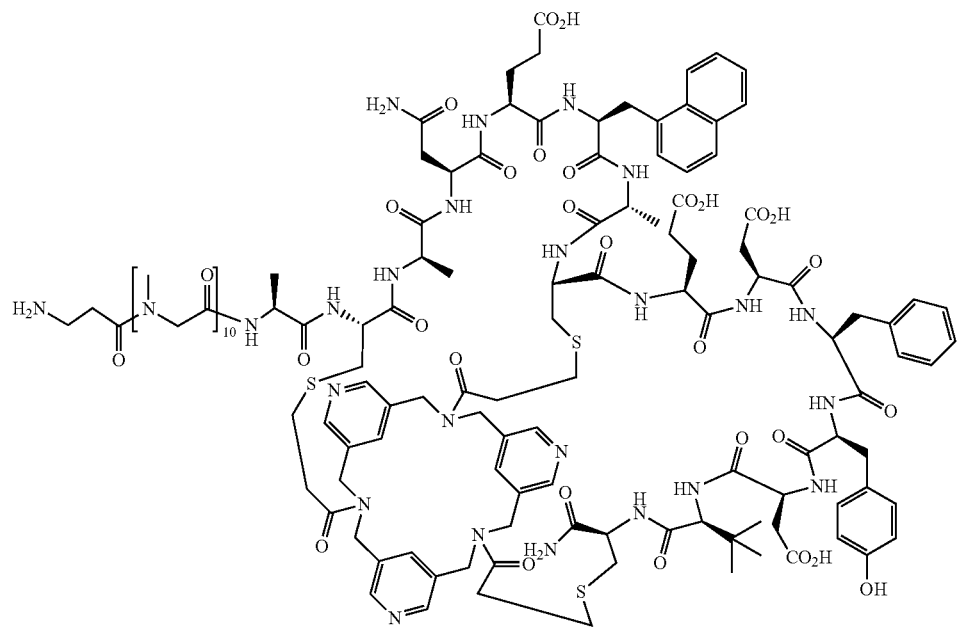
I-12
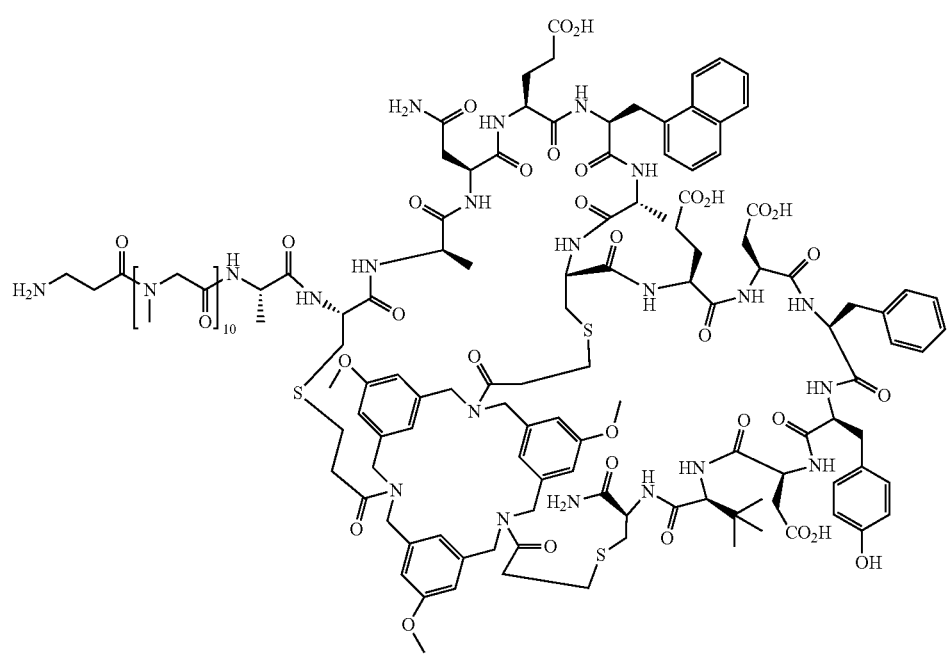

I-13
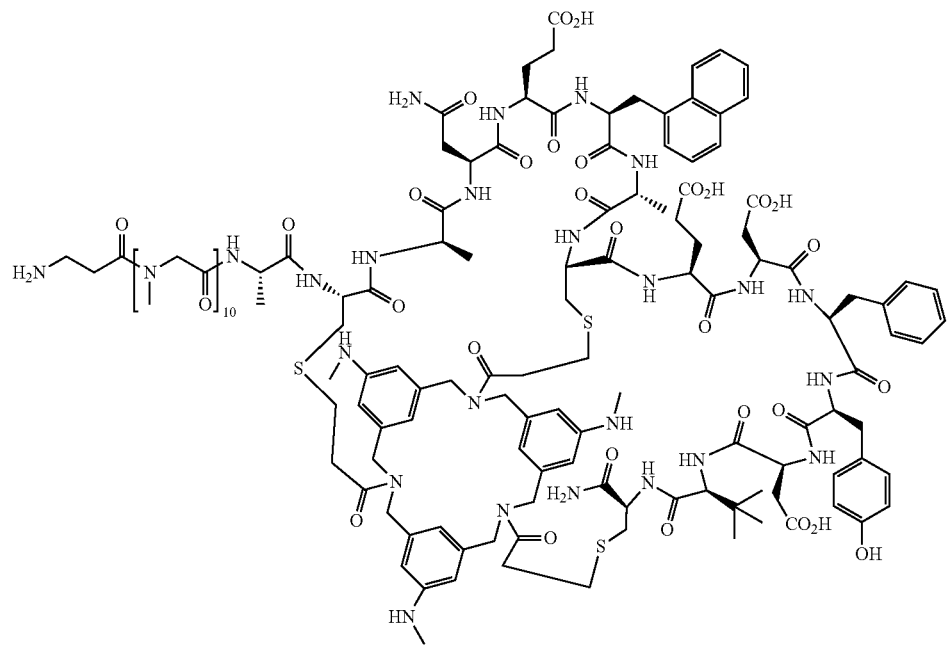
I-14
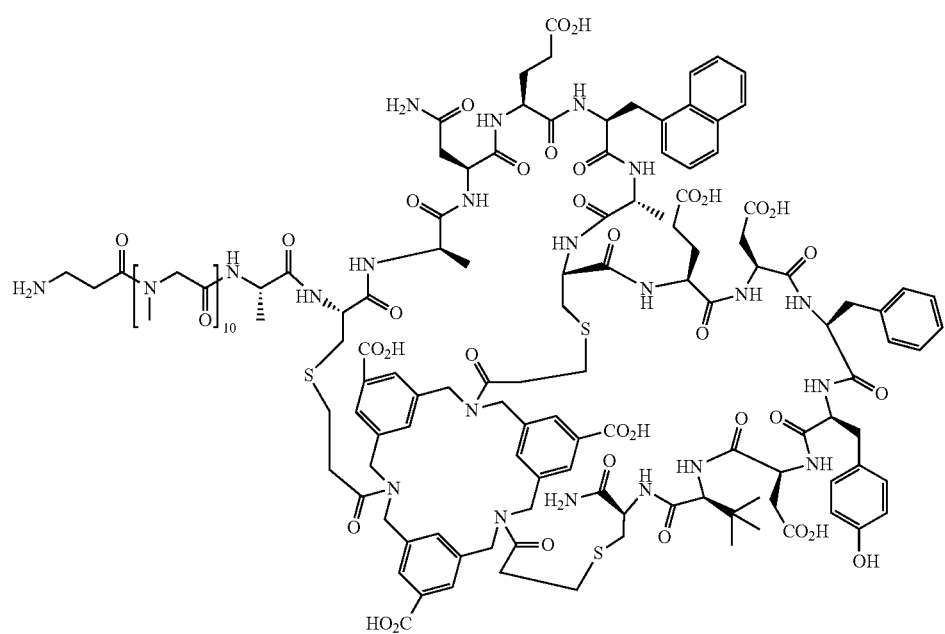

I-15
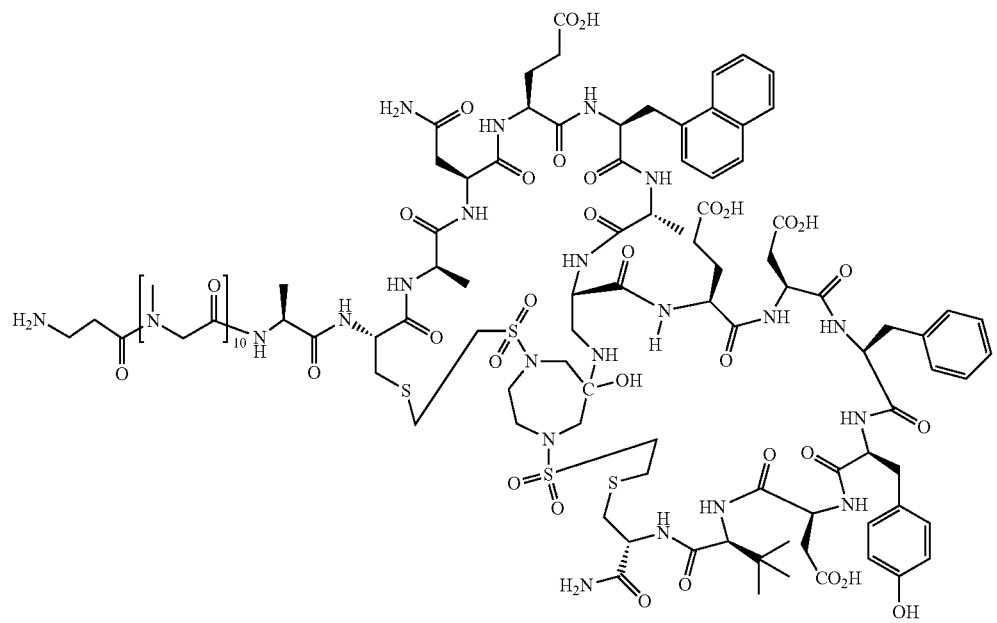
I-16
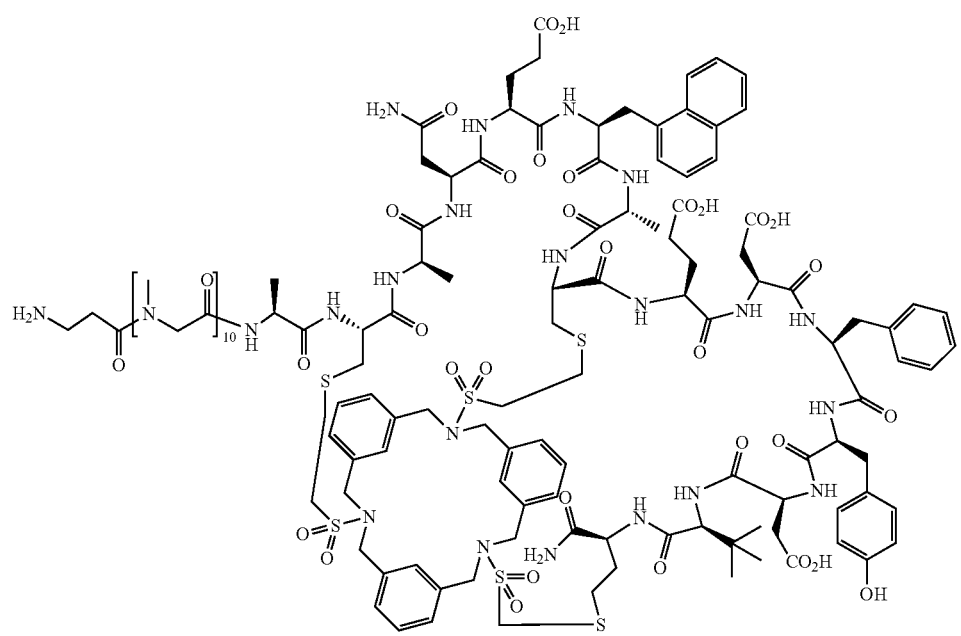

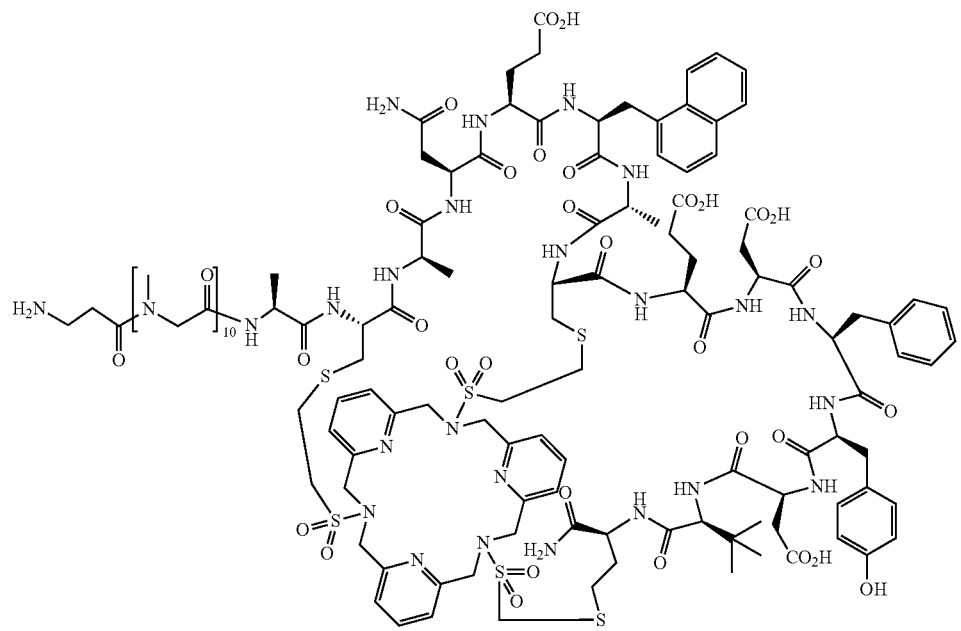
I-17
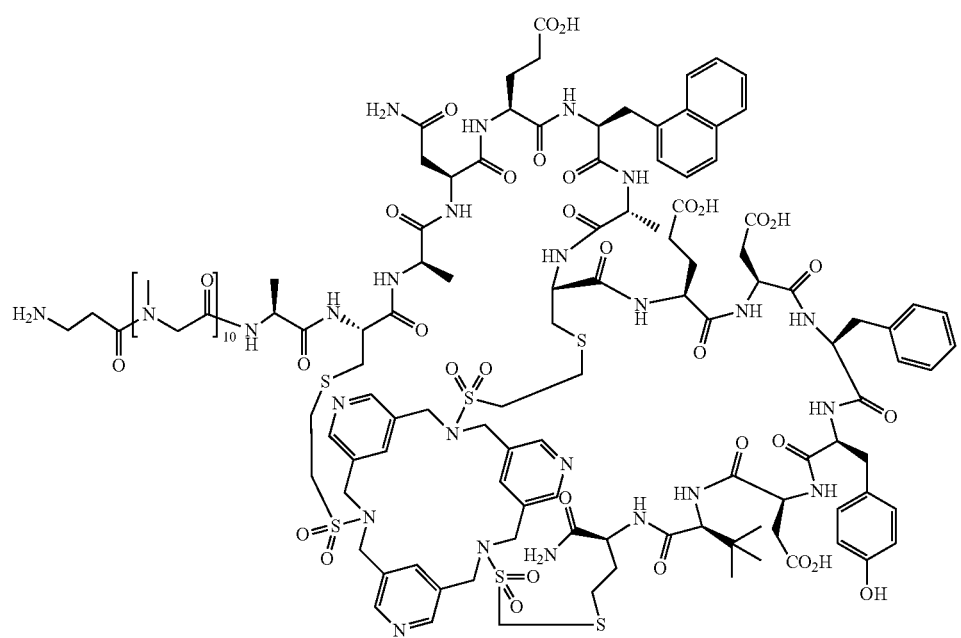
I-18

-continued
I-19
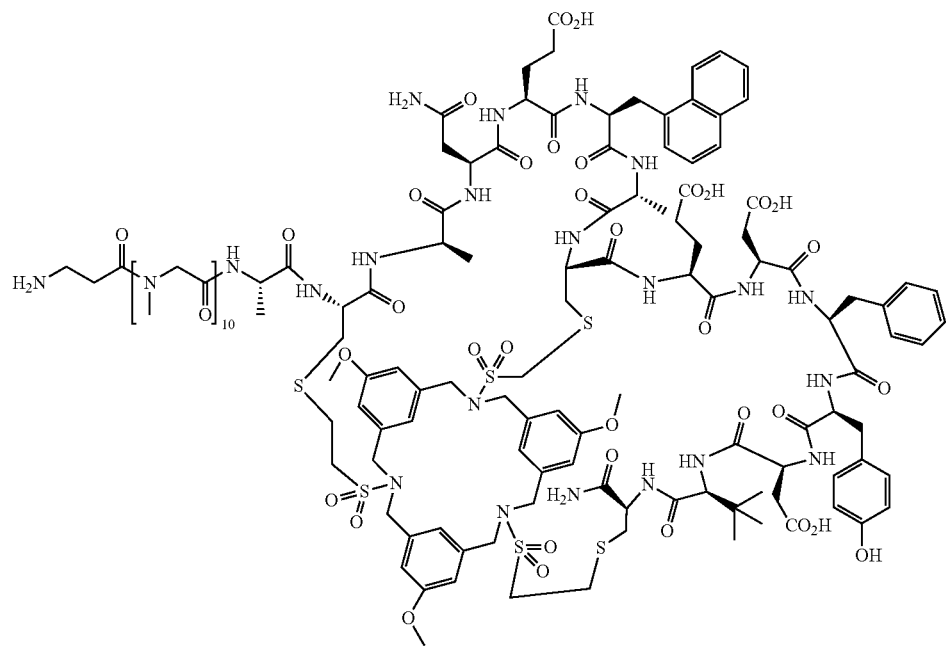
I-20
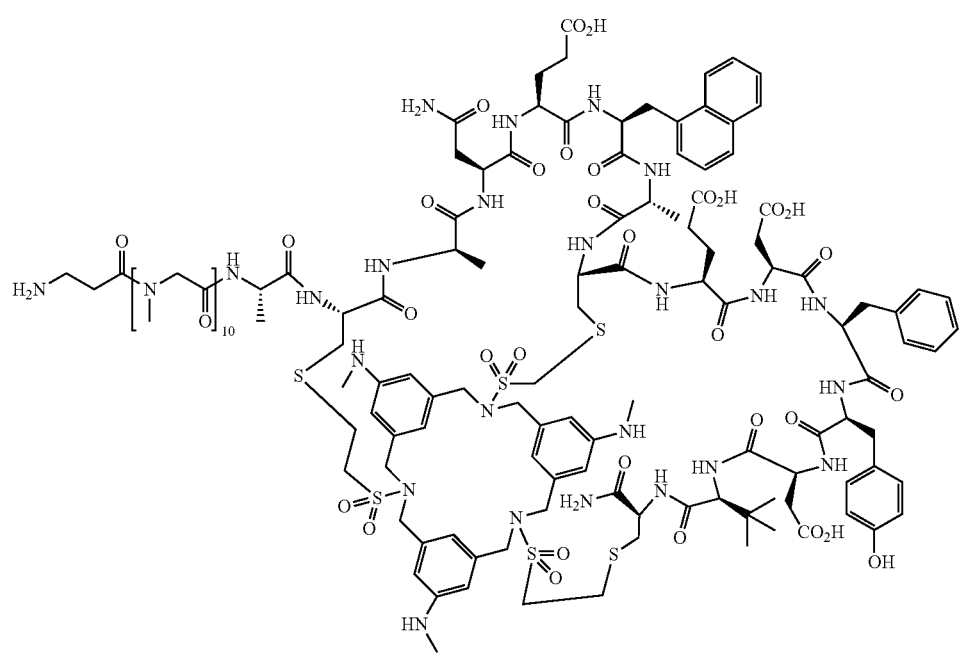

I-21
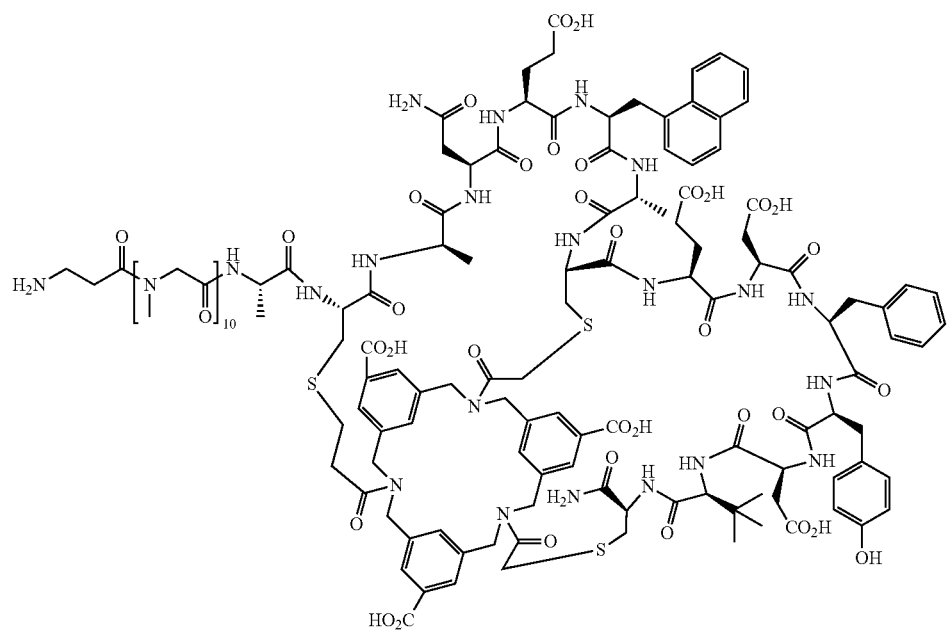
I-22
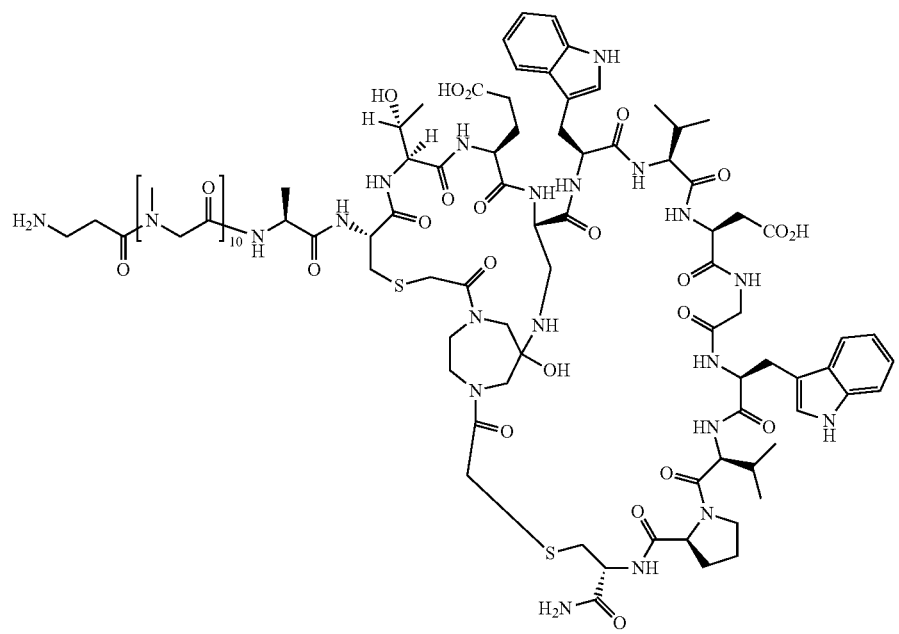

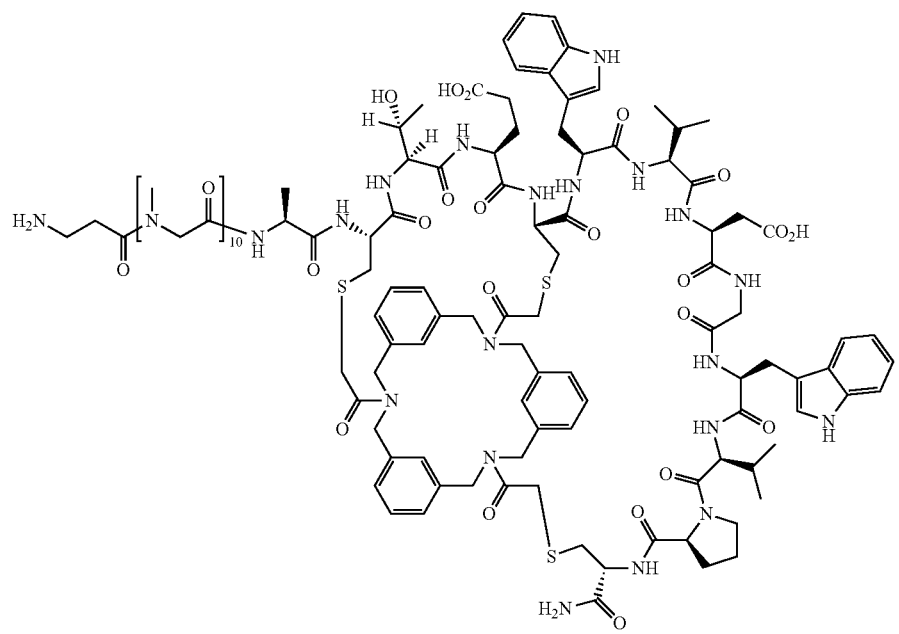
I-23
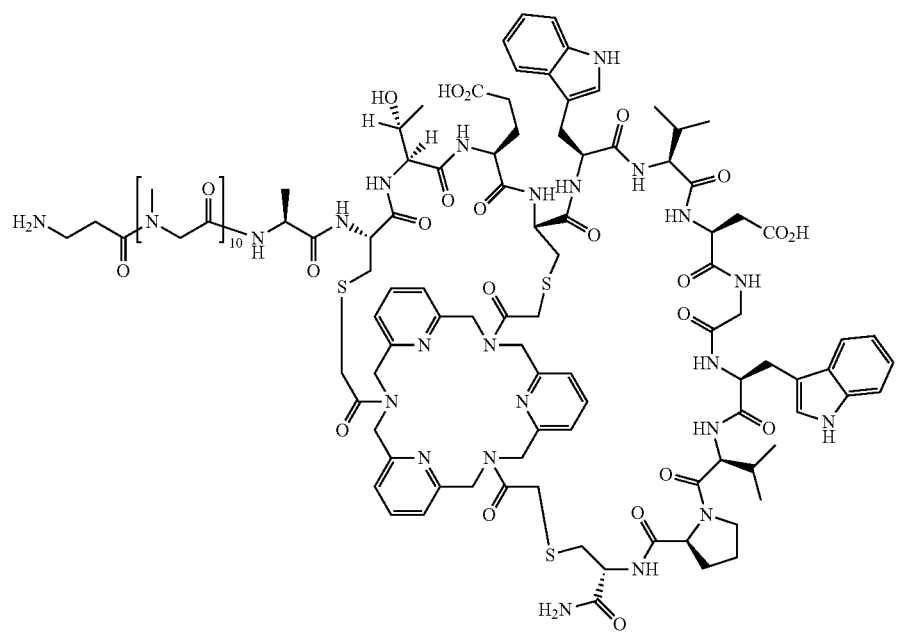
I-24

I-25
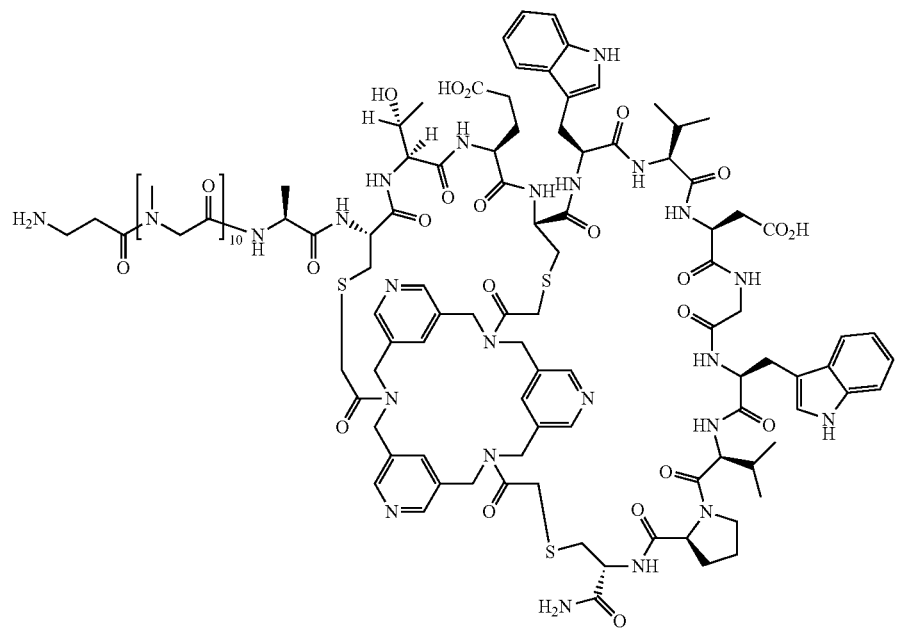
I-26
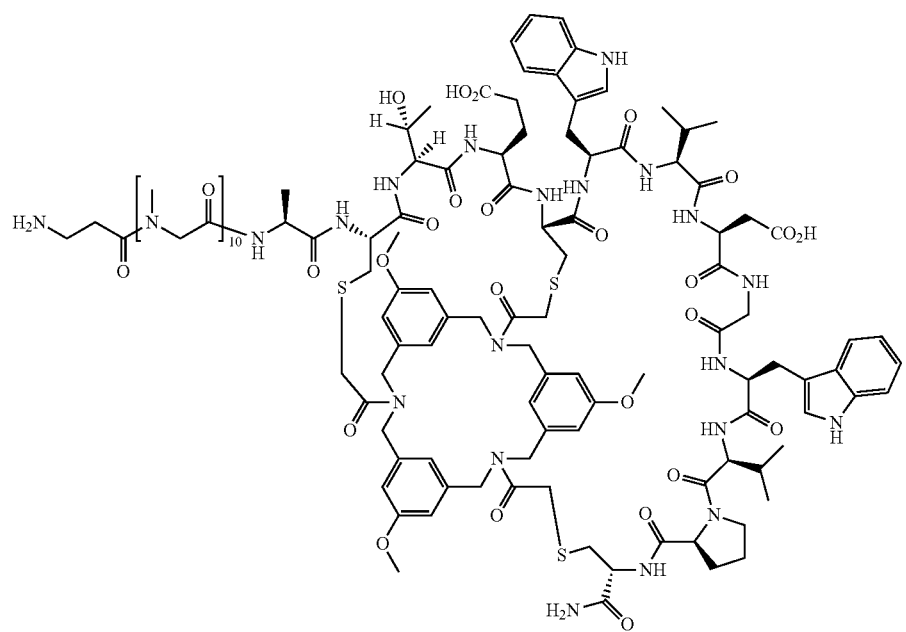

-continued
I-27
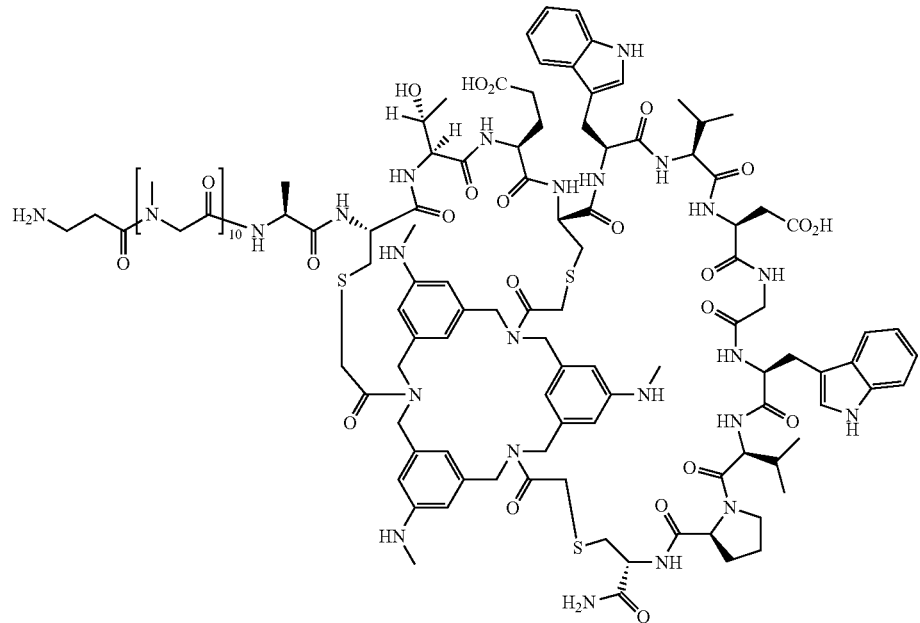
I-28
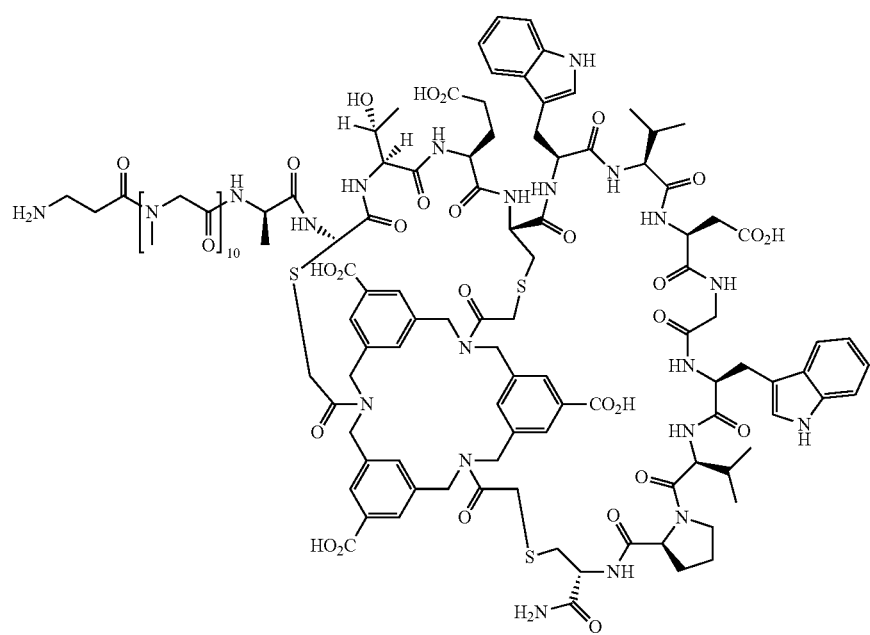

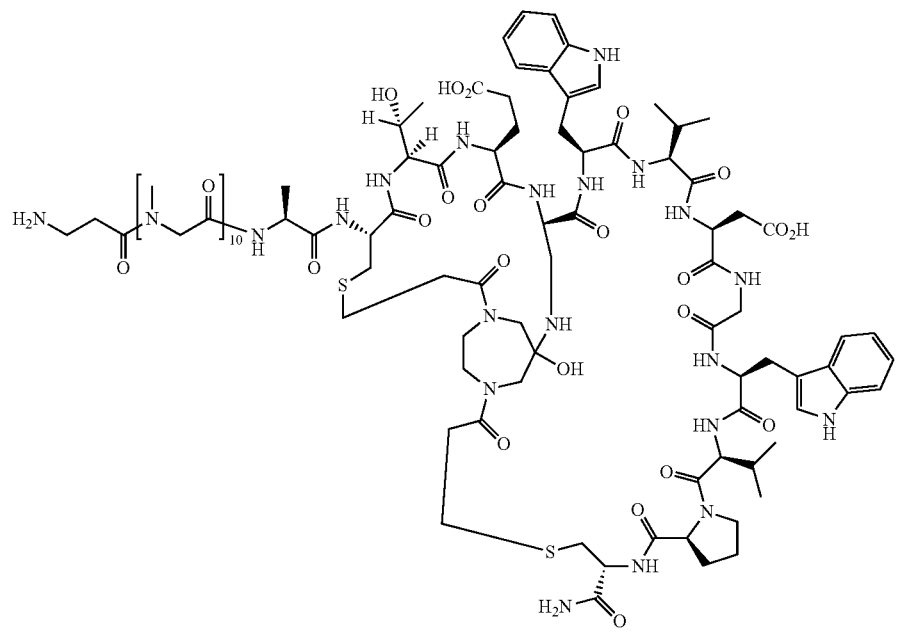
I-29
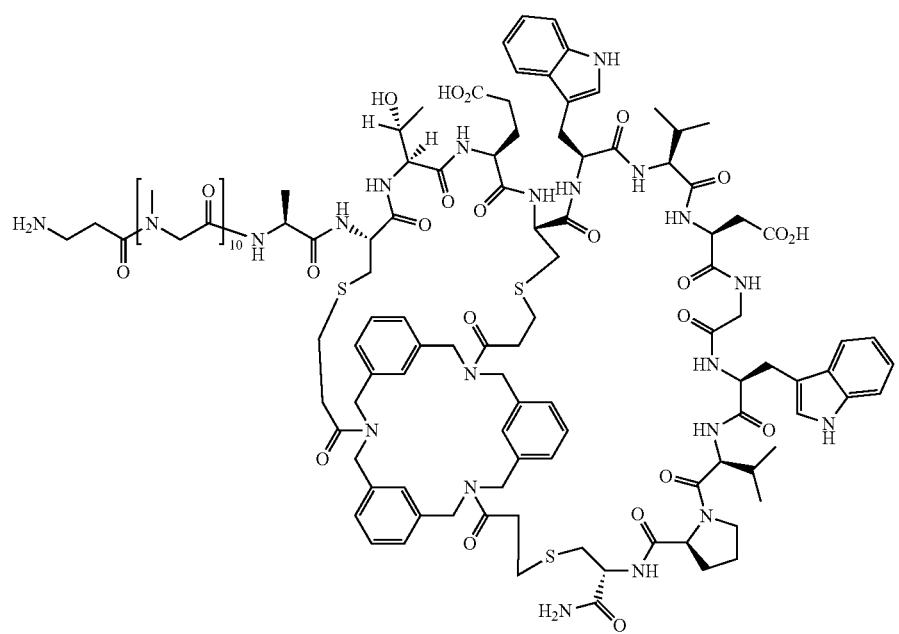
I-30

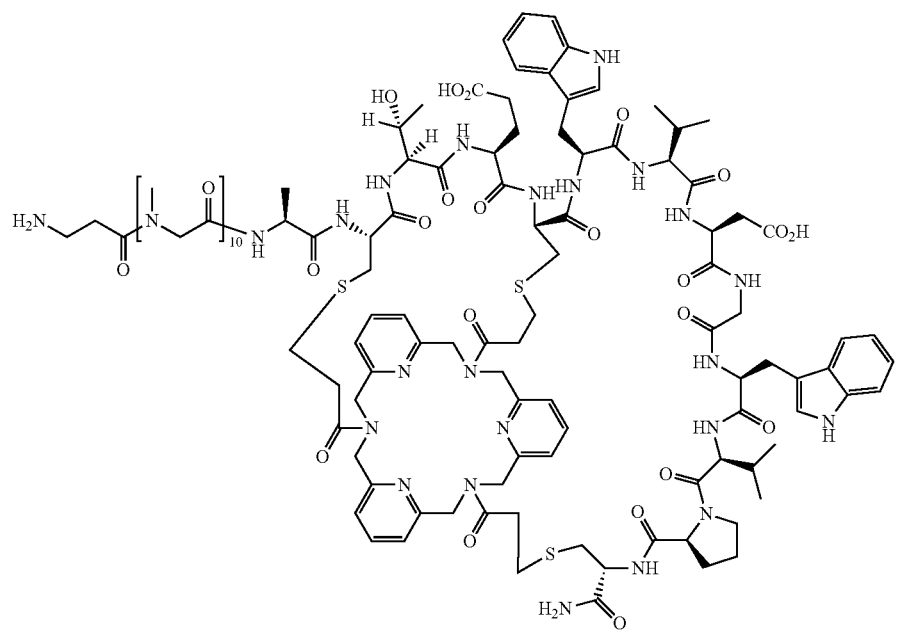
I-31
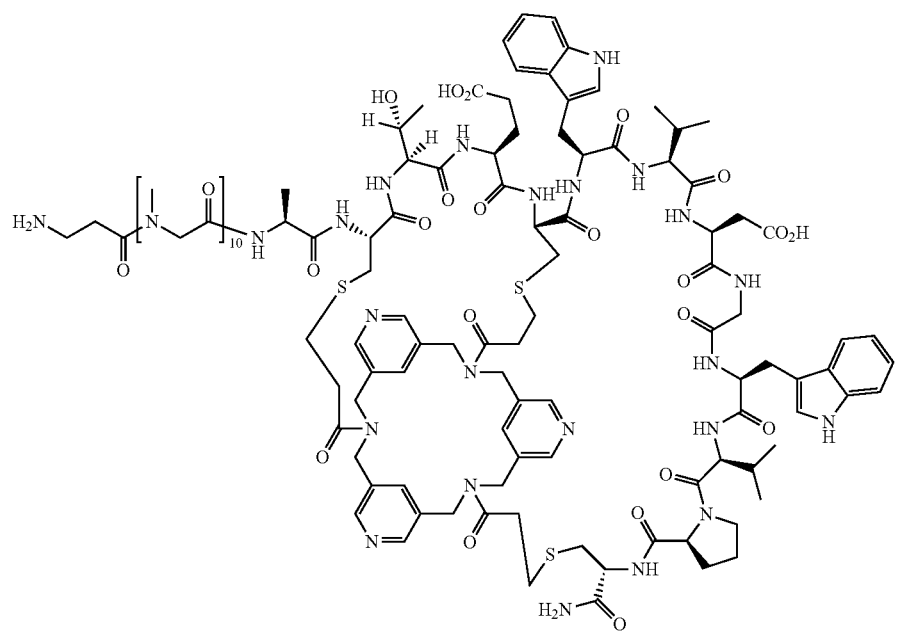
I-32

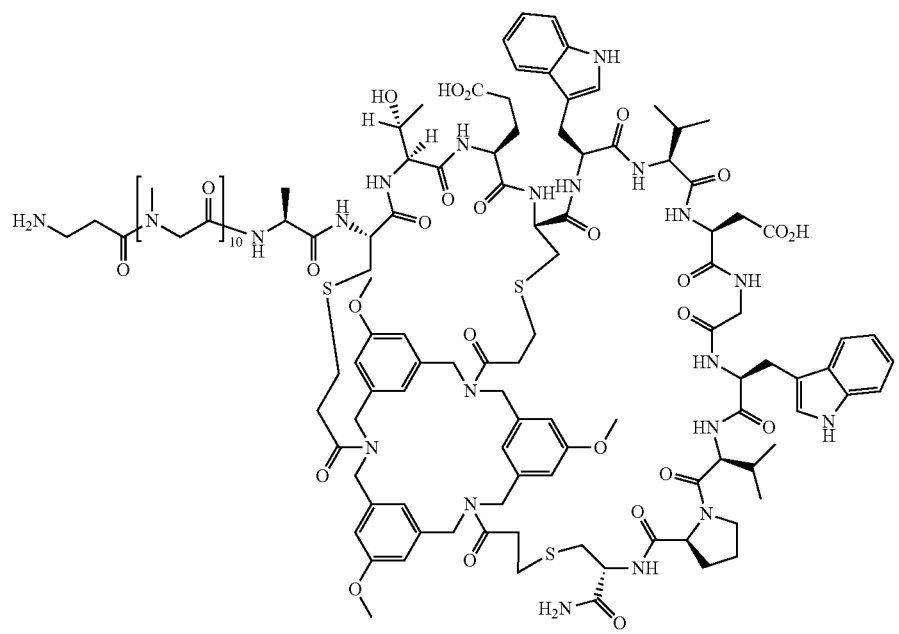
I-33
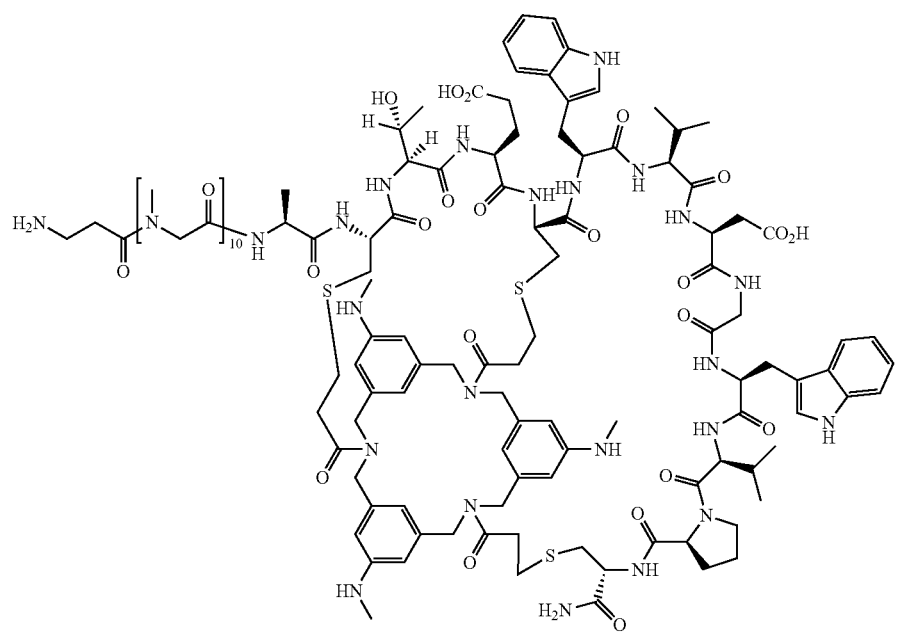
I-34

I-35
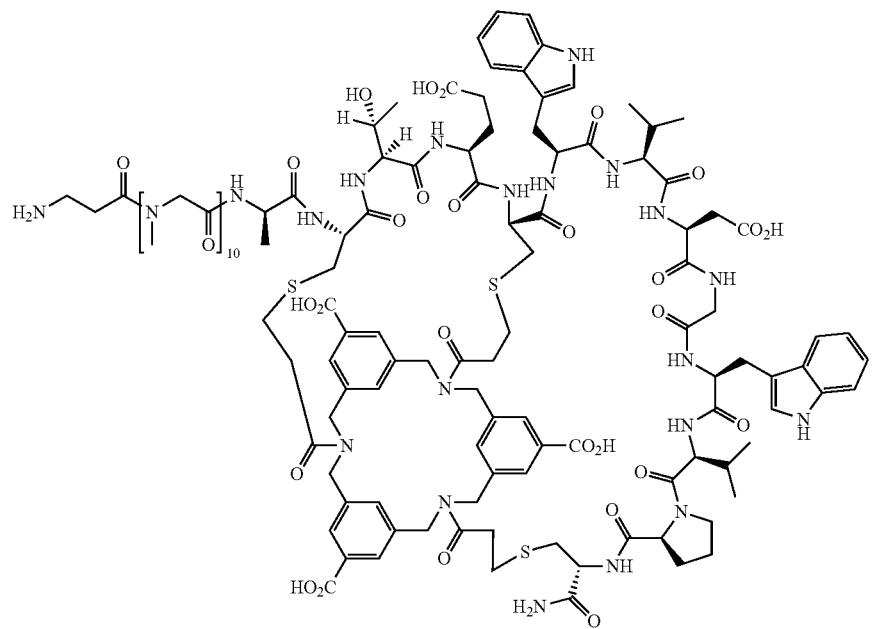
I-36
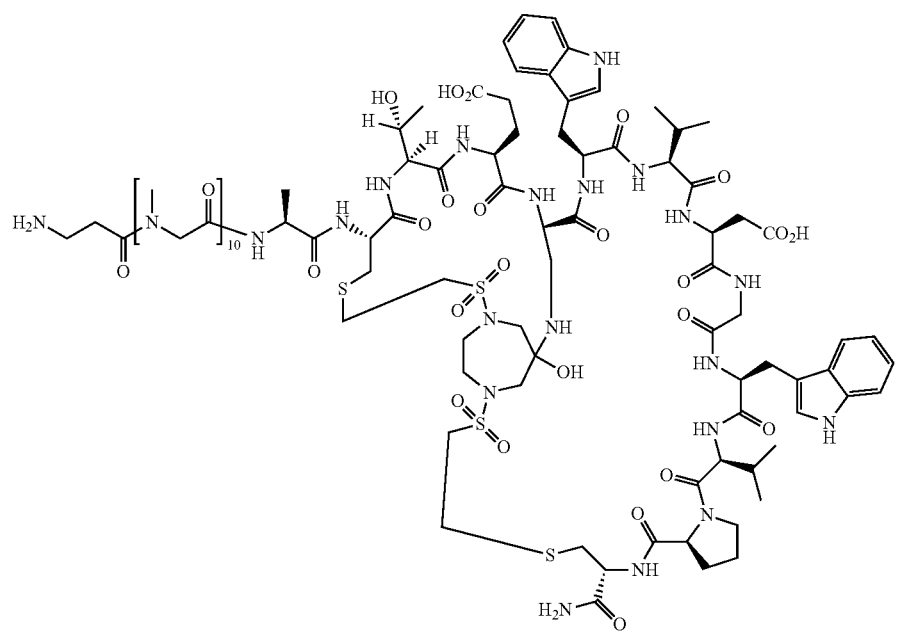

I-37
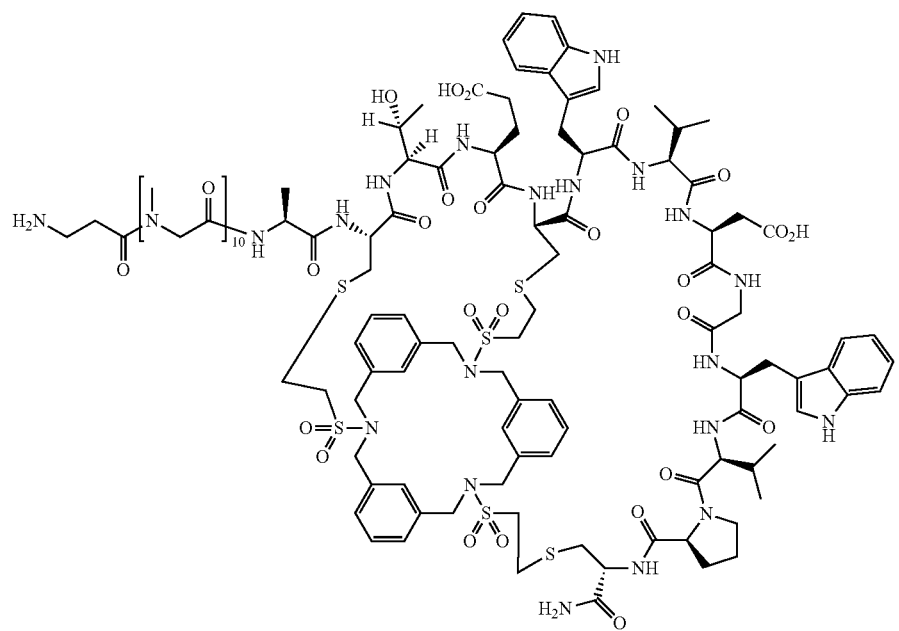
I-38
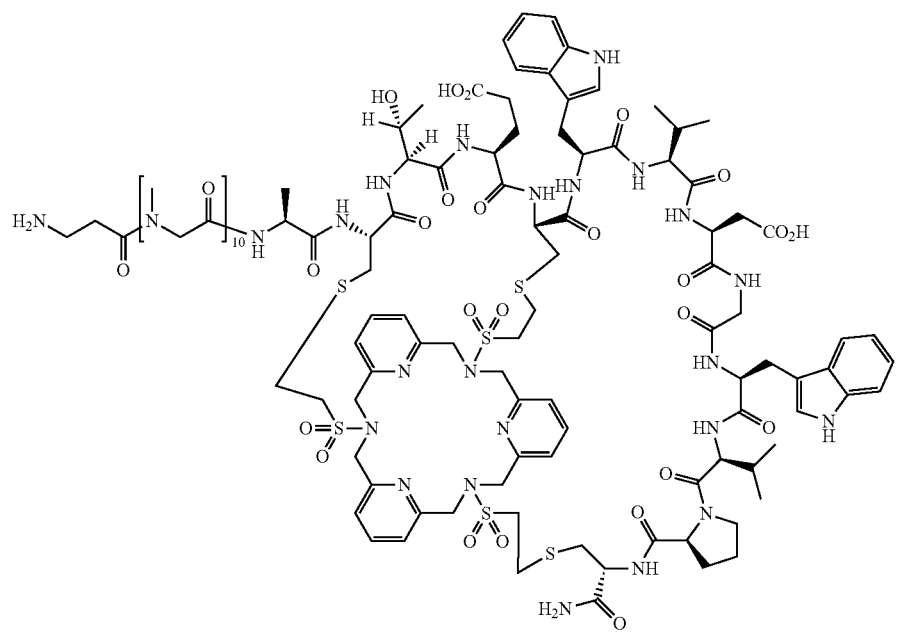

-continued
I-39
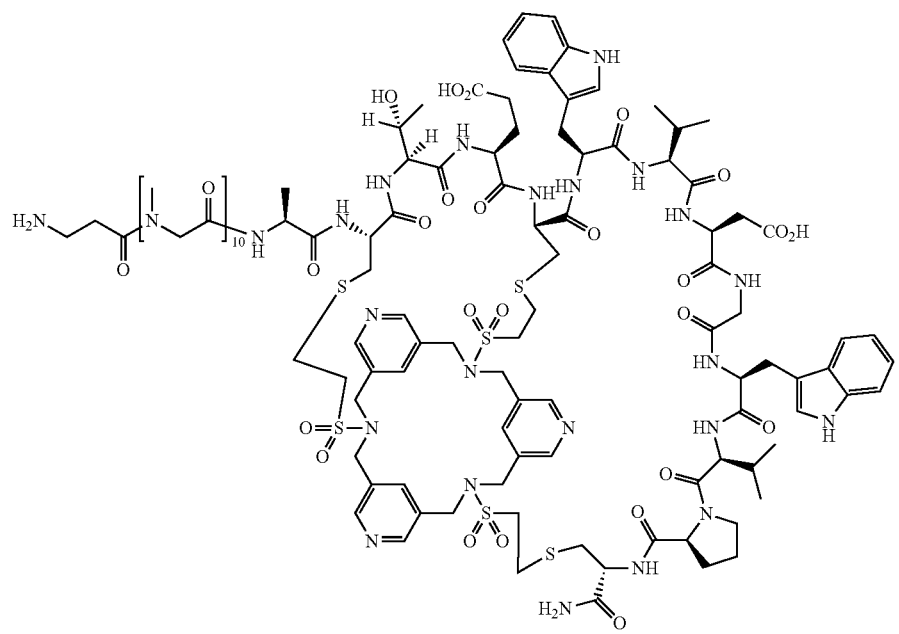
I-40
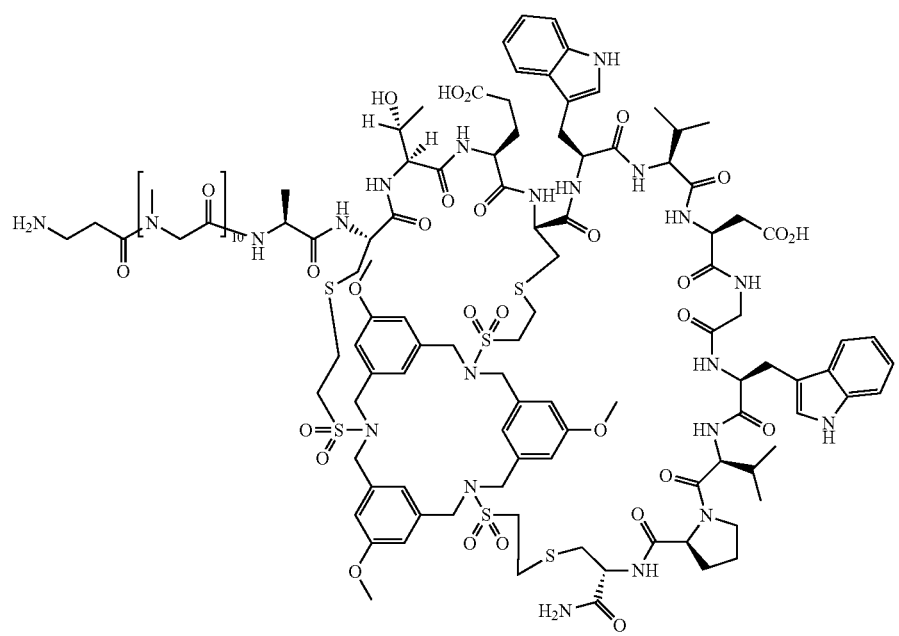

-continued
I-41
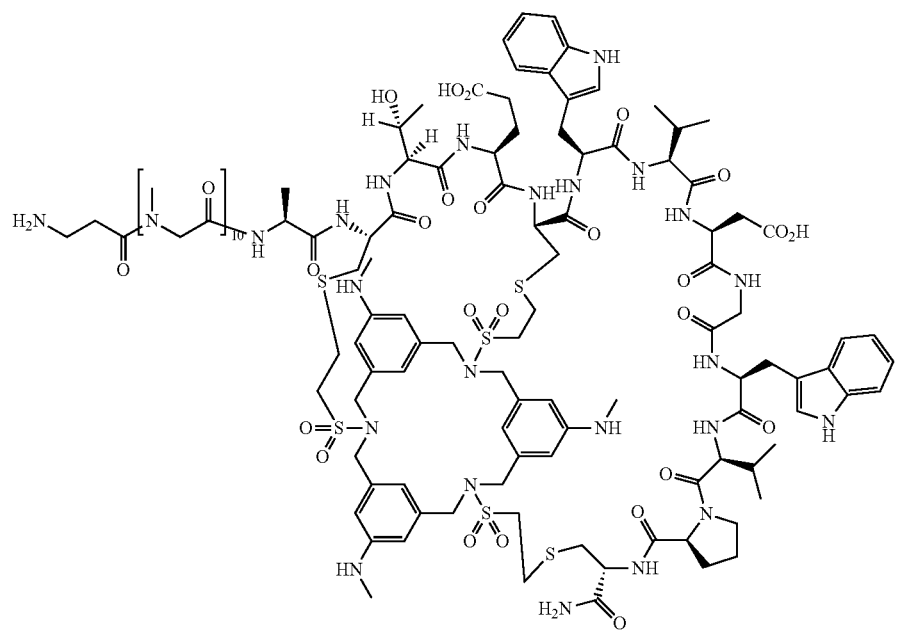
I-42
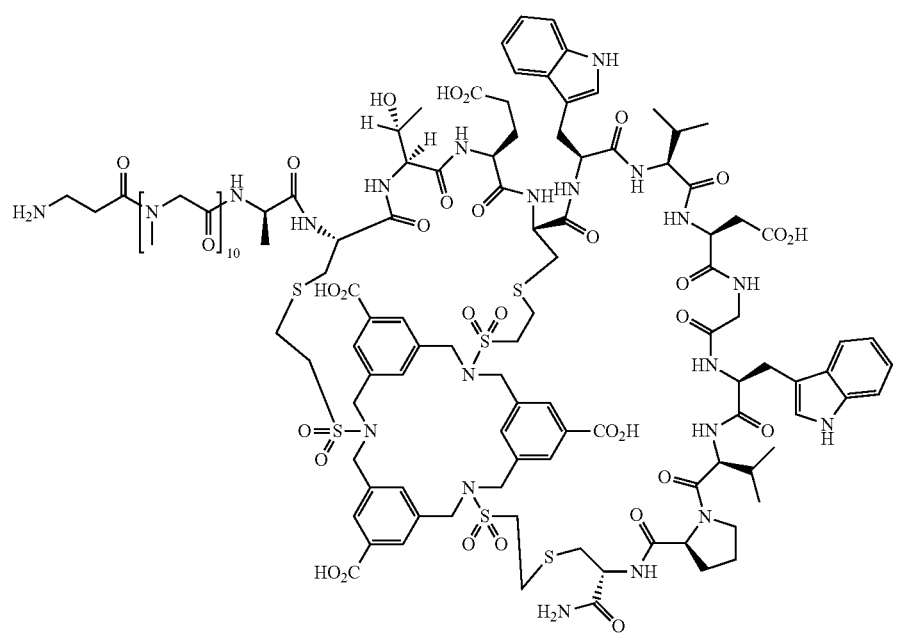

I-43
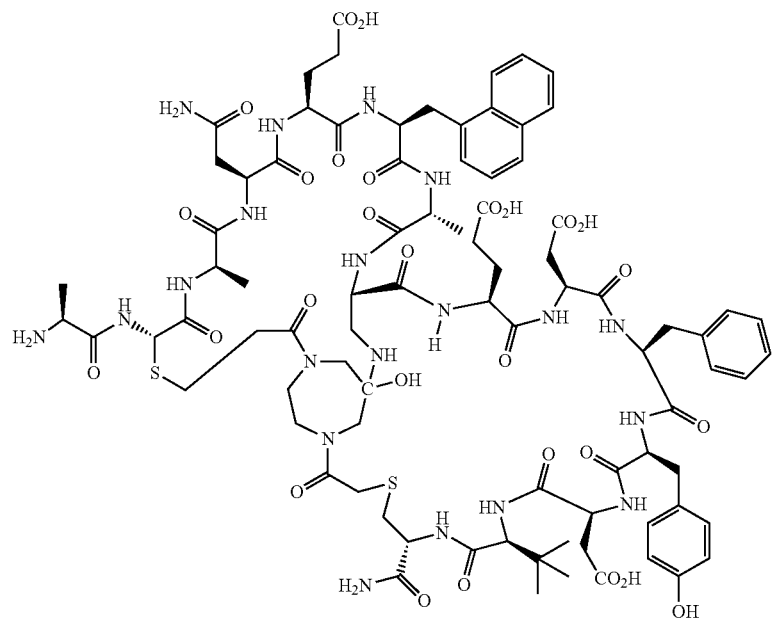
I-44
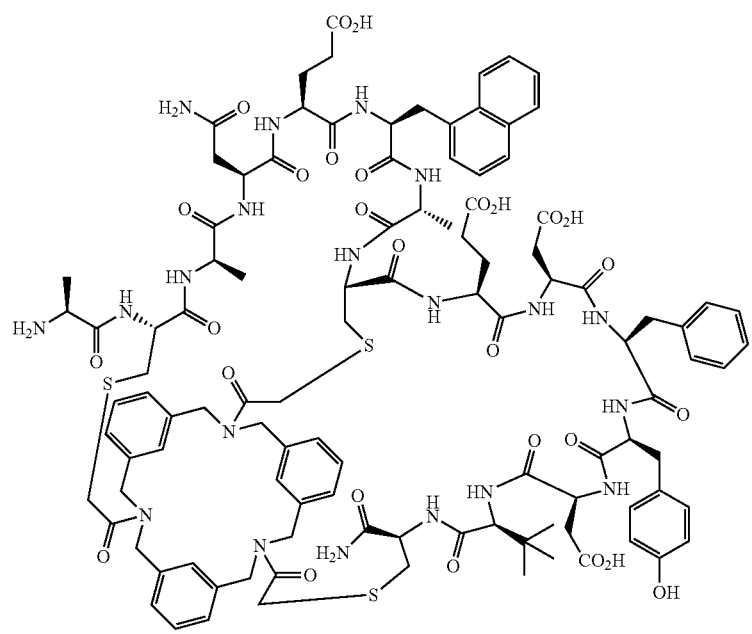

I-45
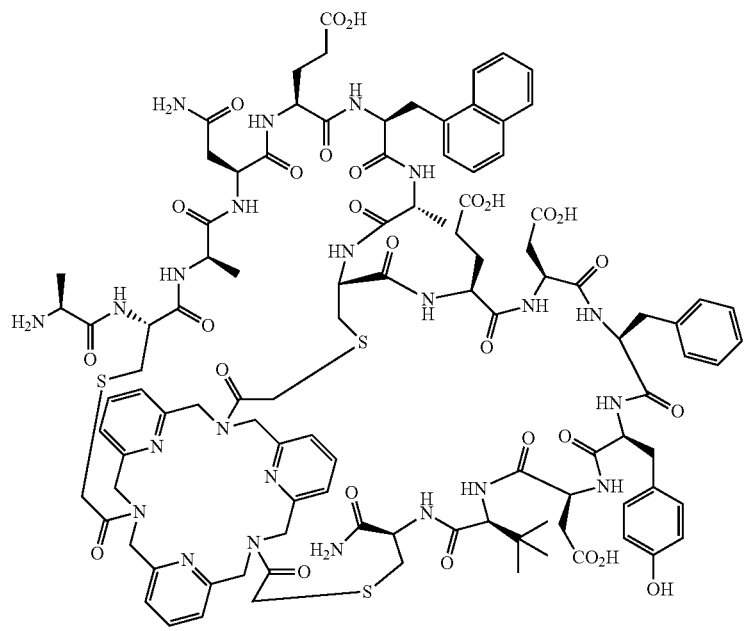
I-46
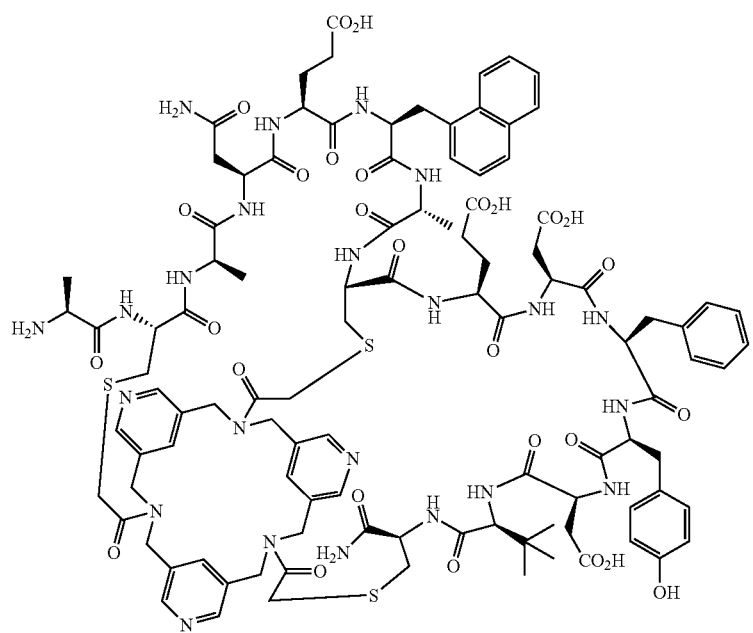

I-47
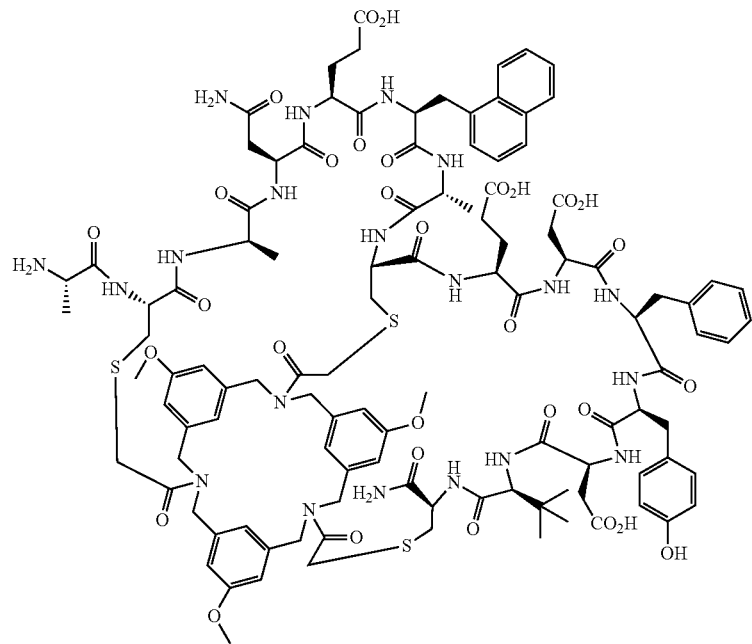
I-48
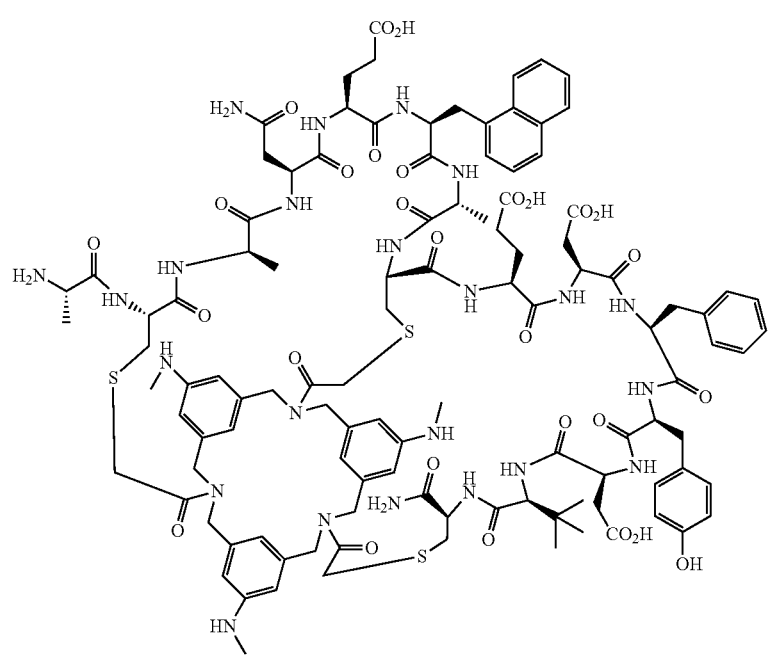

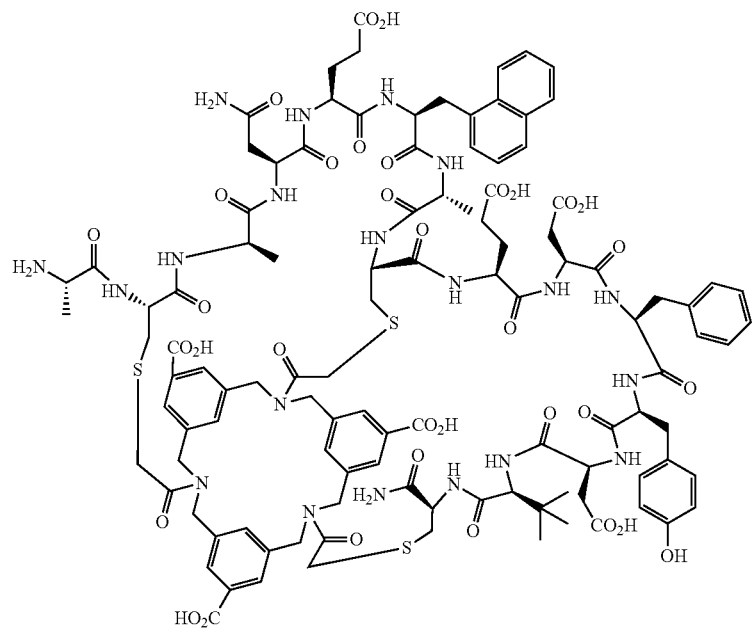
I-49
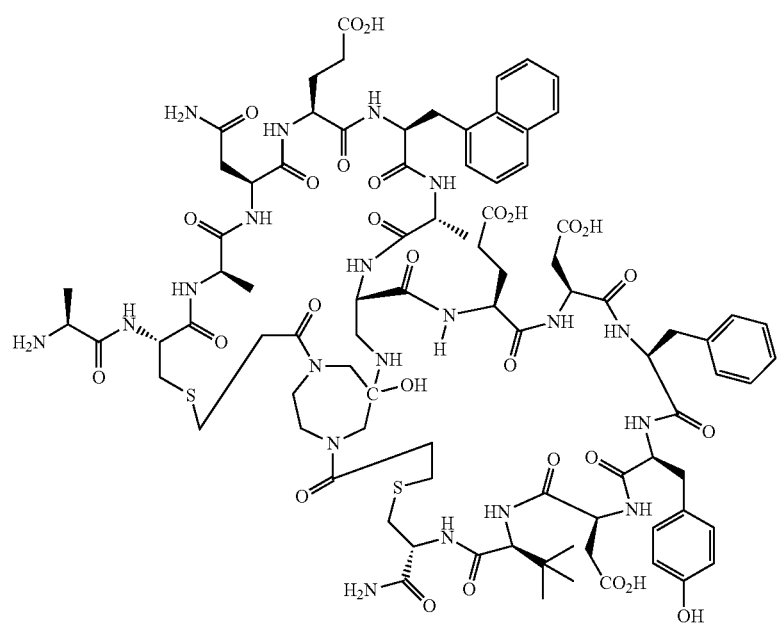
I-50

I-51
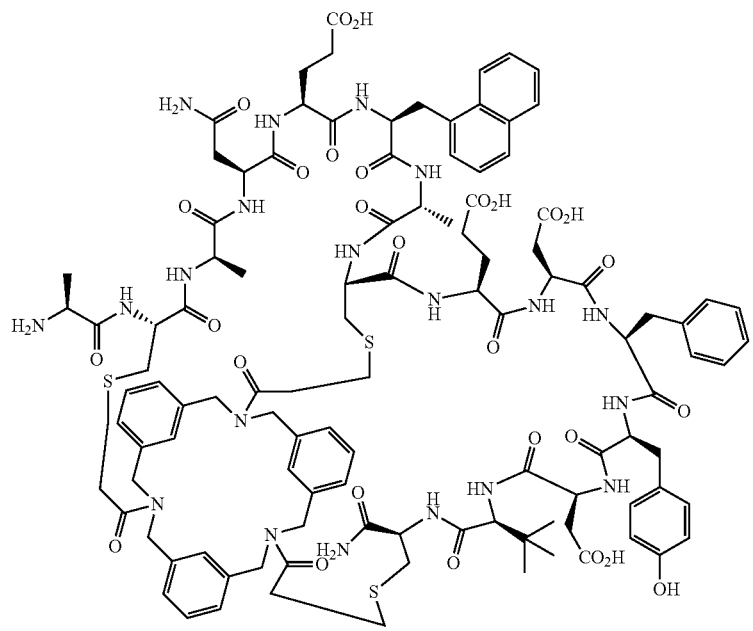
I-52
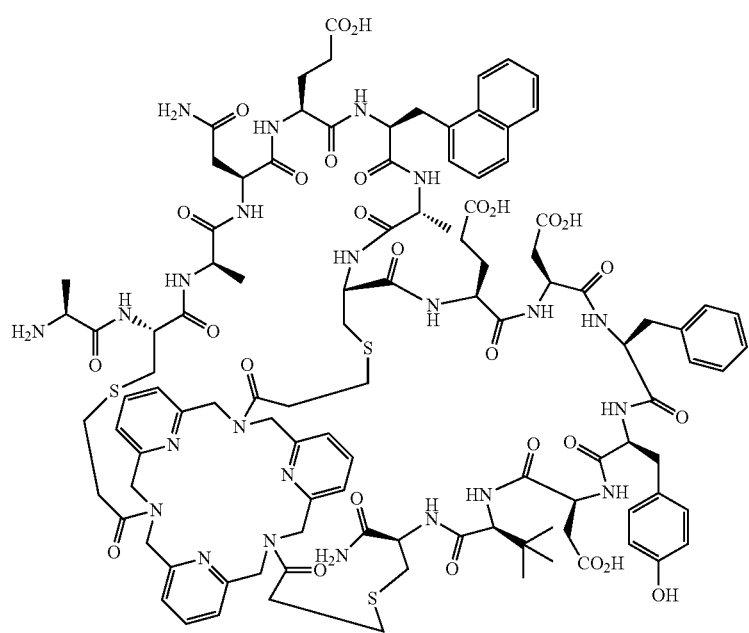

I-53
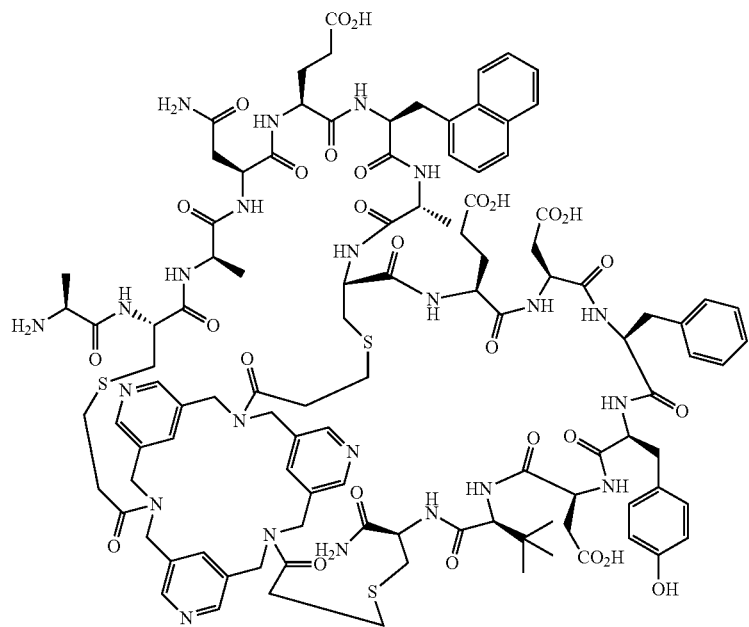
I-54
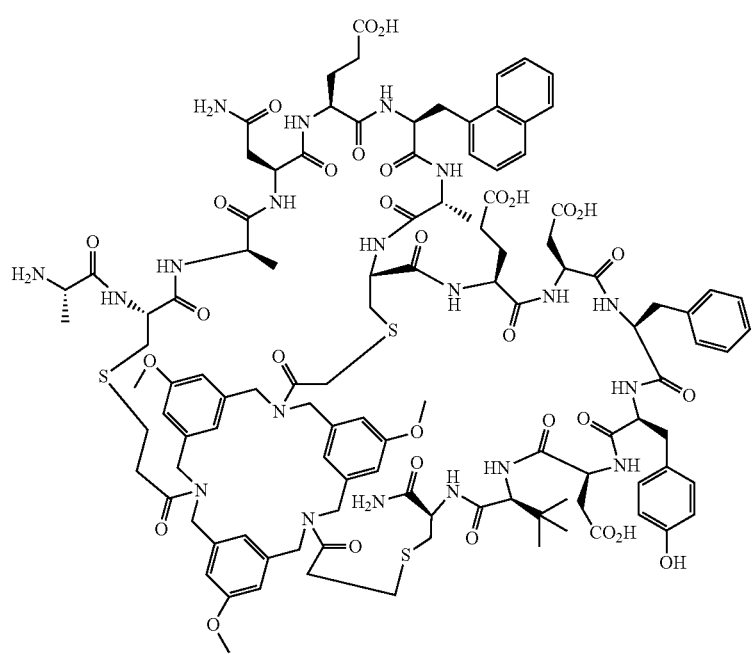

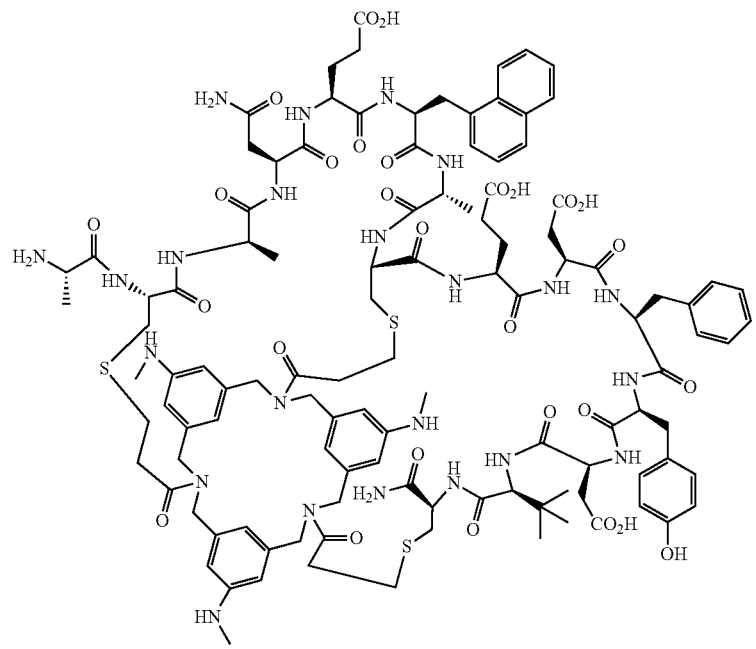
I-55
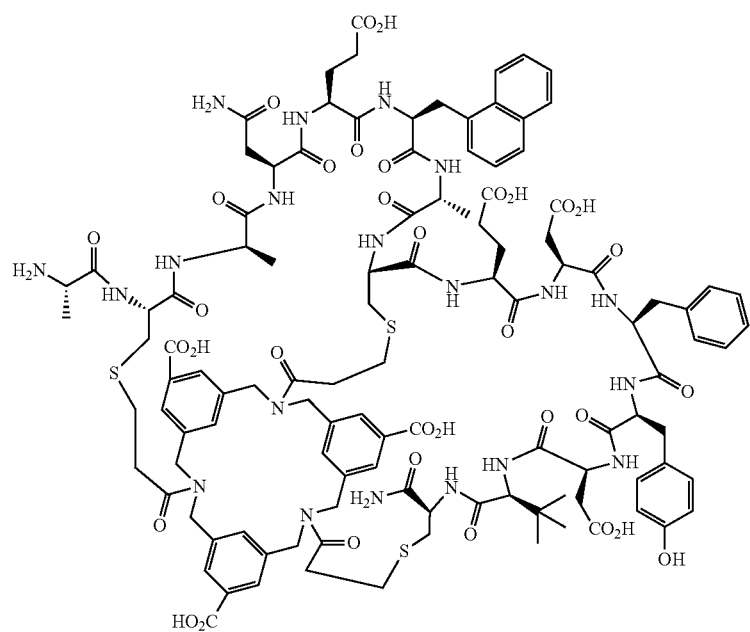
I-56

I-57
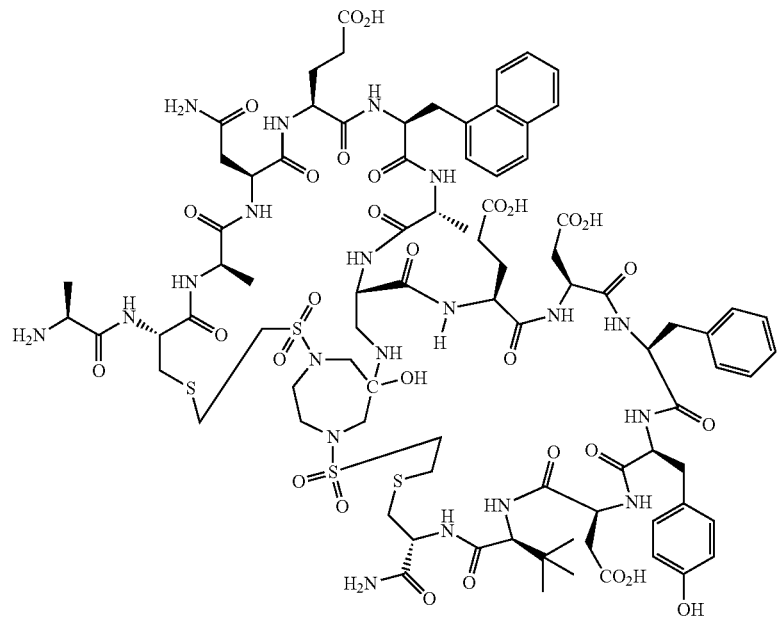
I-58
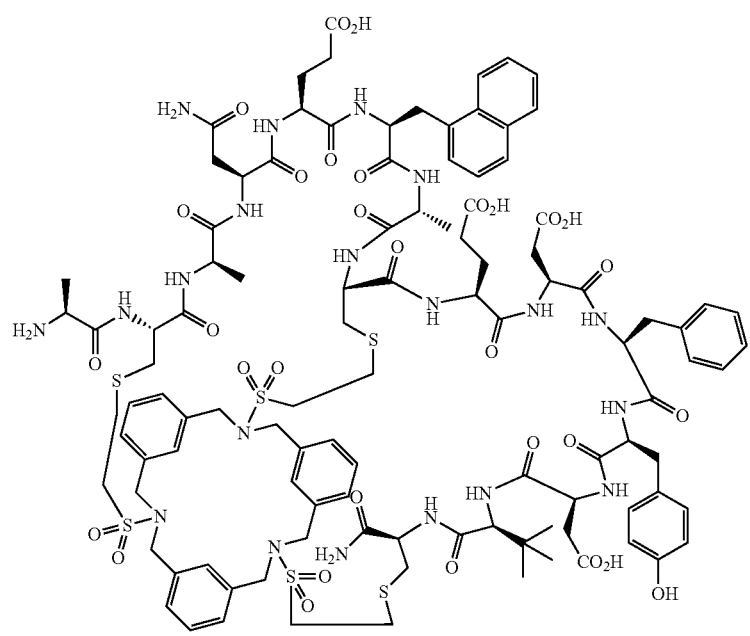

I-59
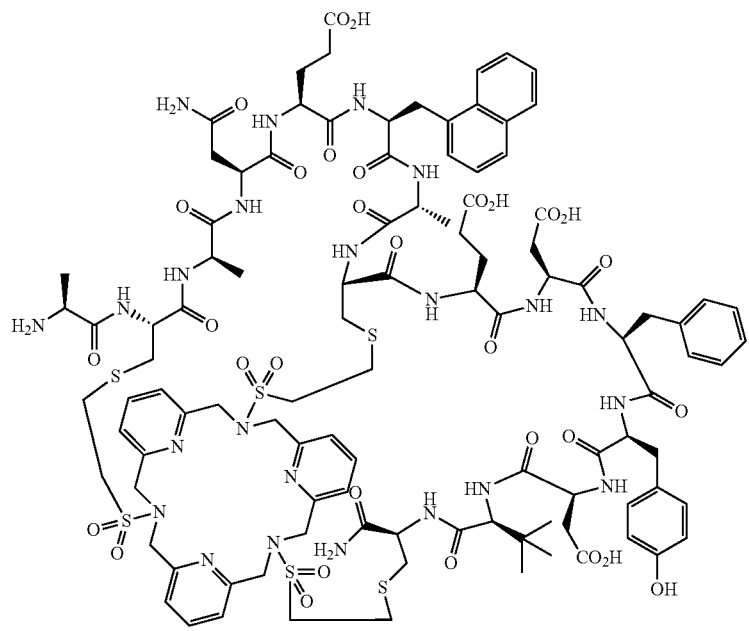
I-60
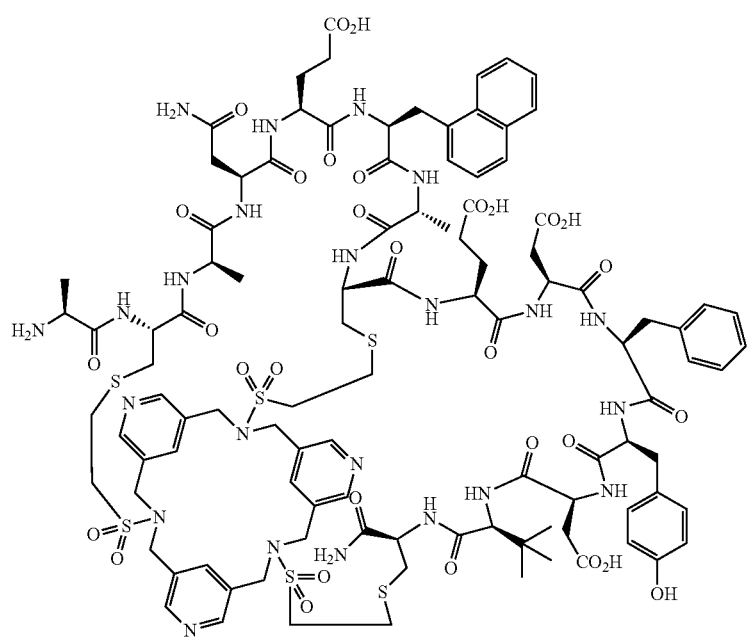

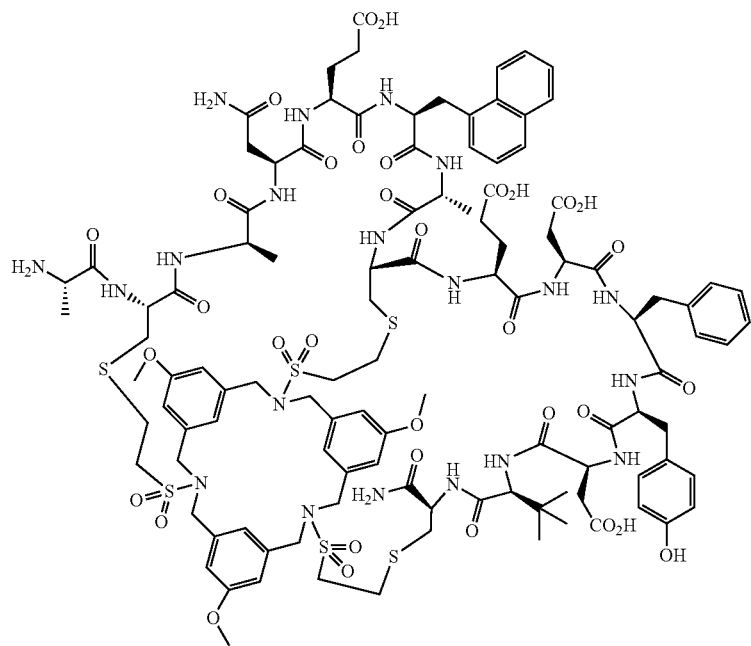
I-61
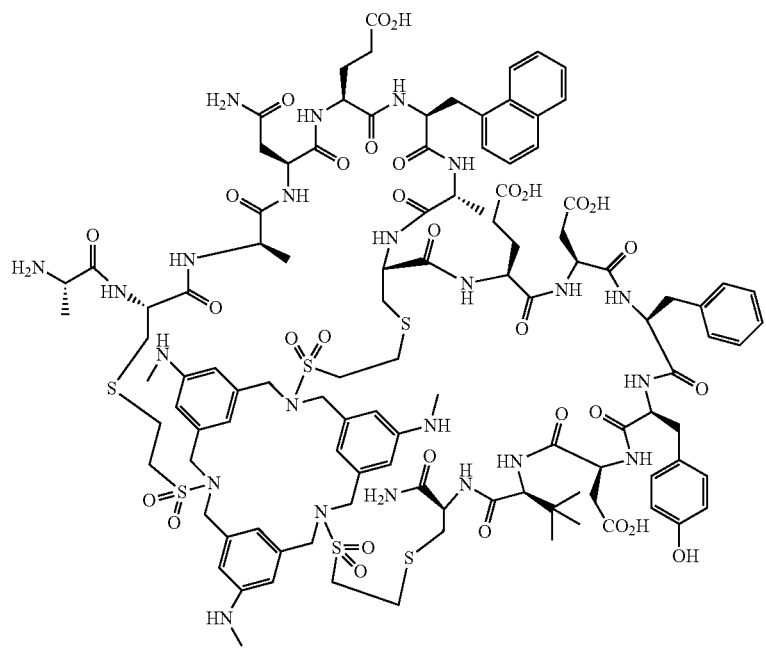
I-62

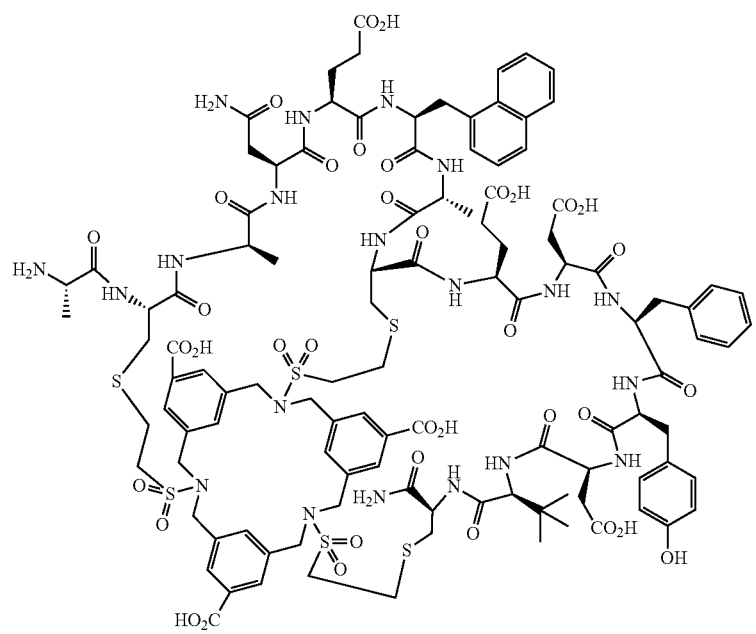
I-63
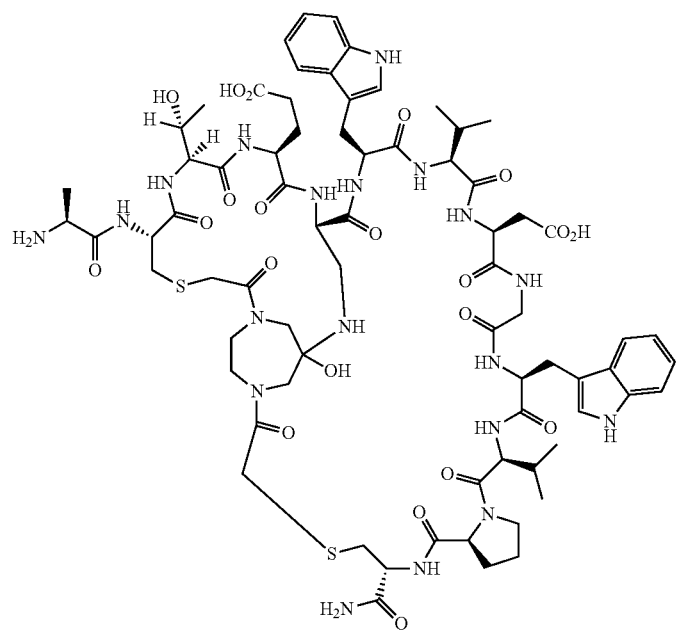
I-64

I-65
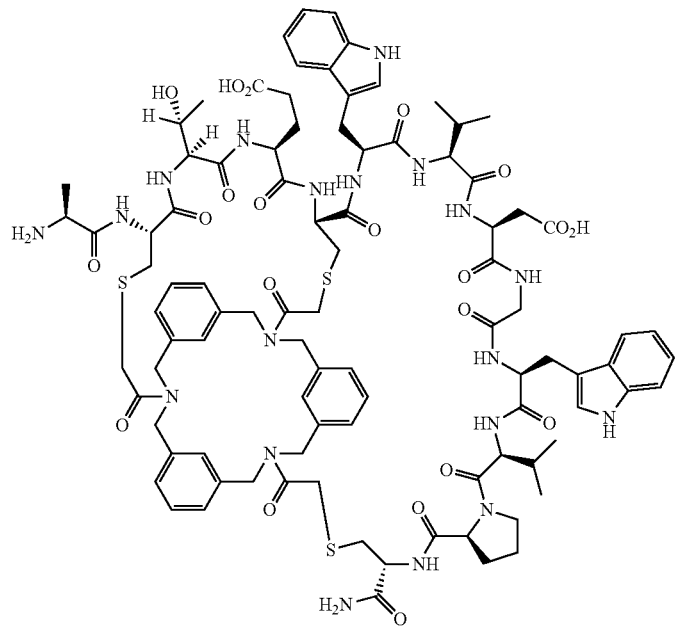
I-66
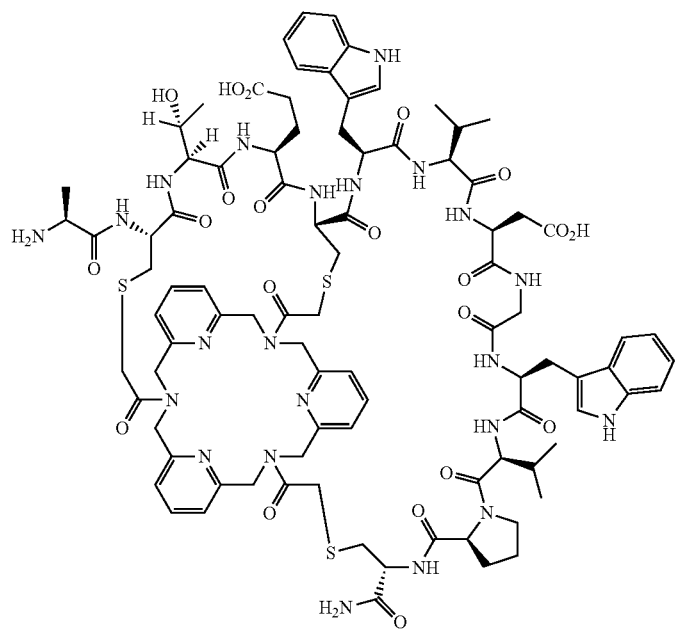

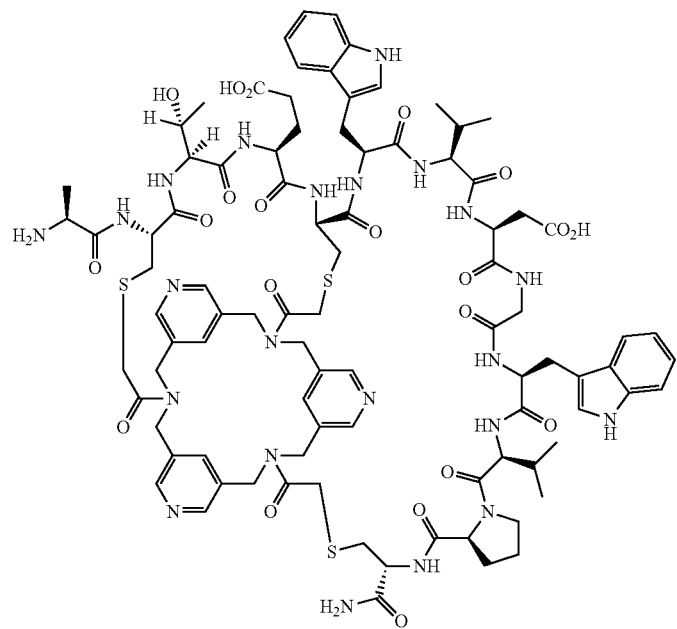
I-67
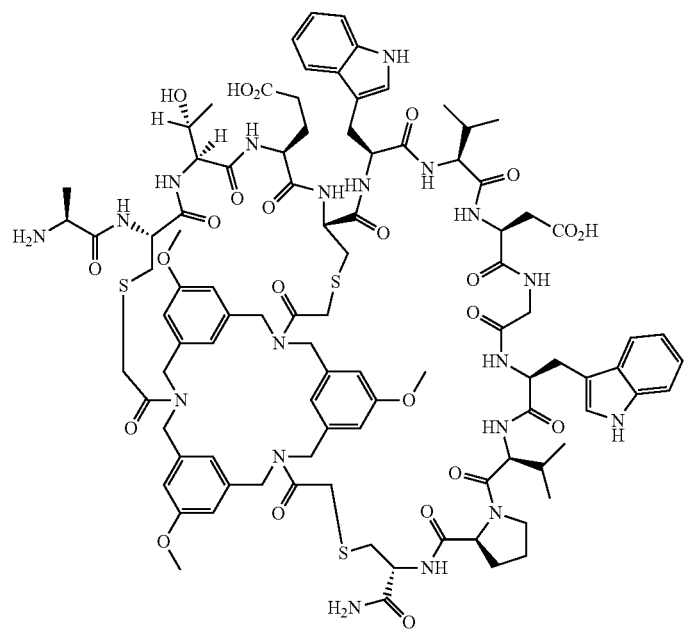
I-68

I-69
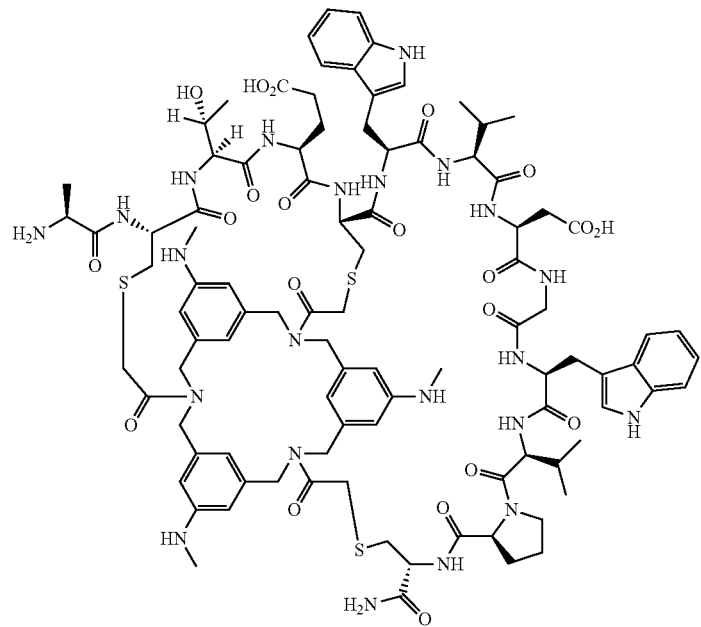
I-70
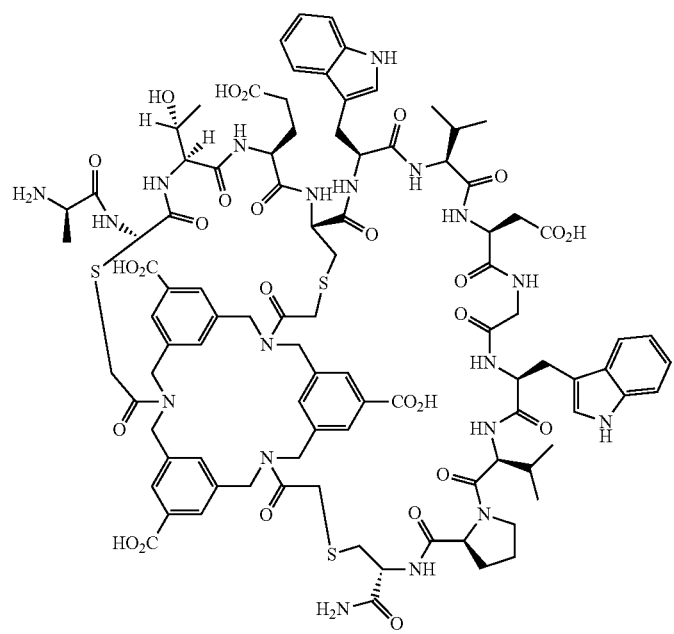

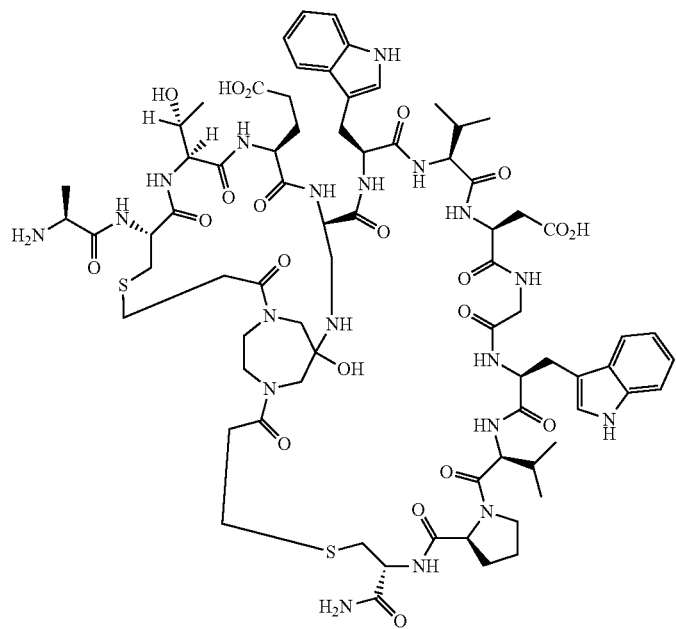
I-71
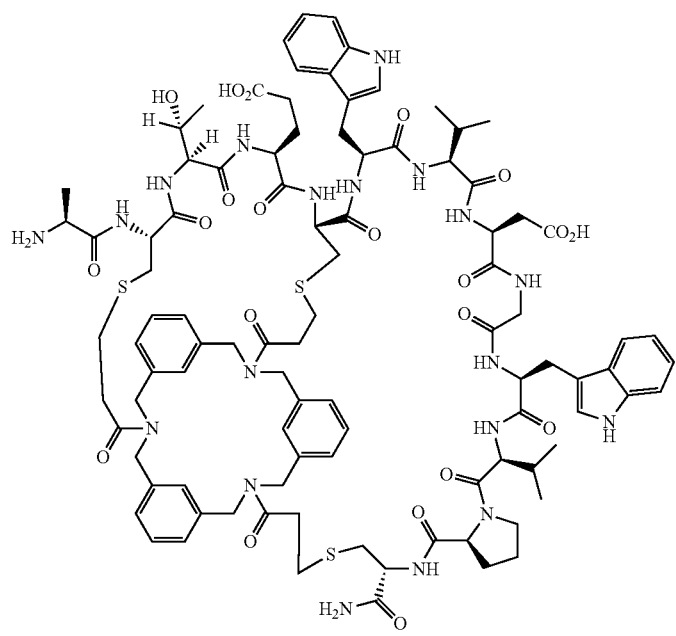
I-72

I-73
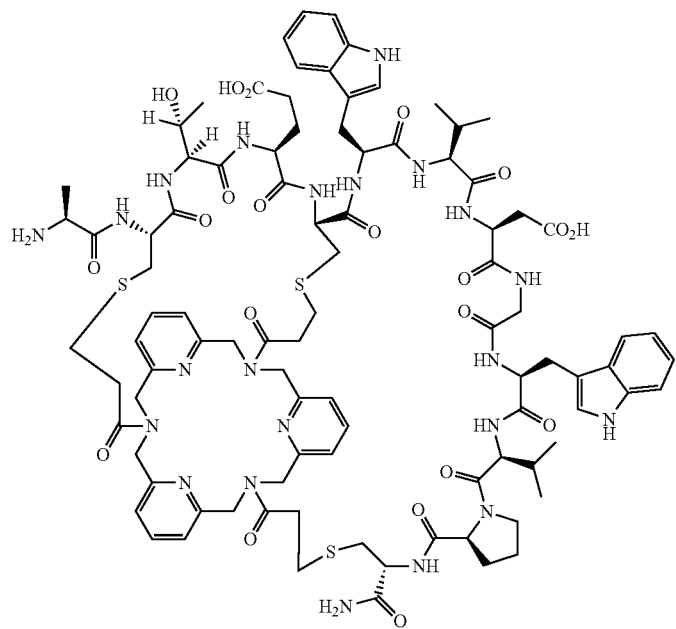
I-74
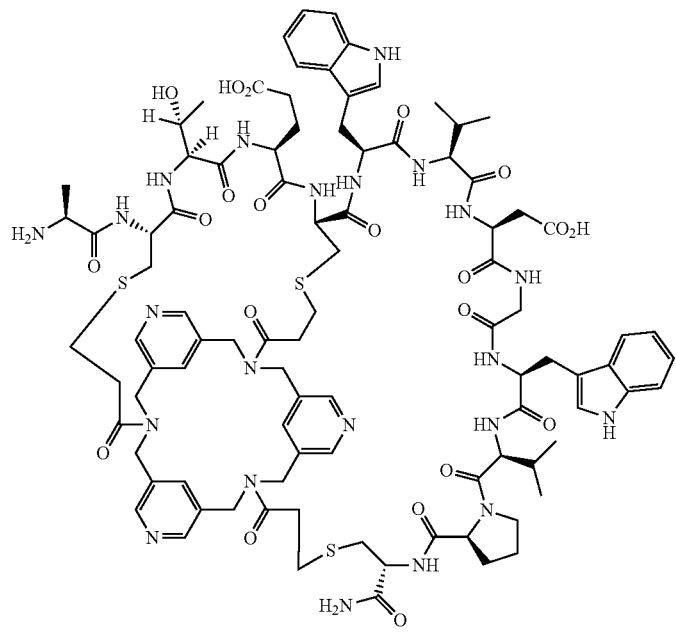

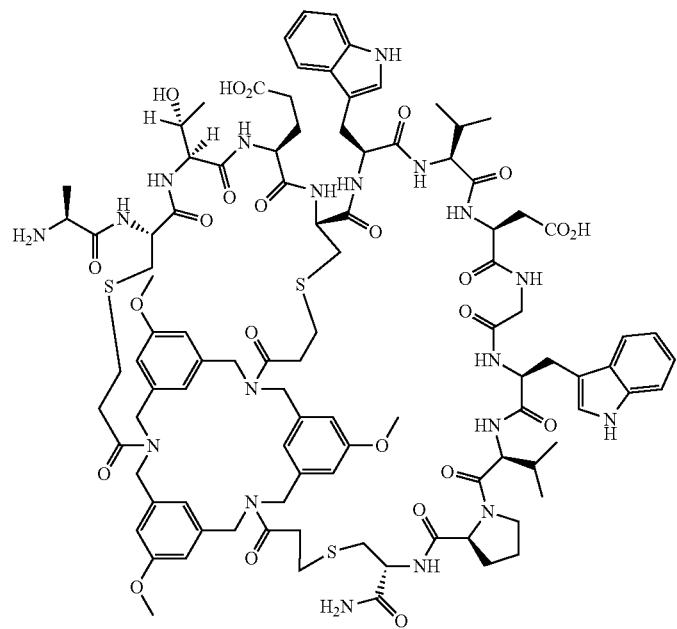
I-75
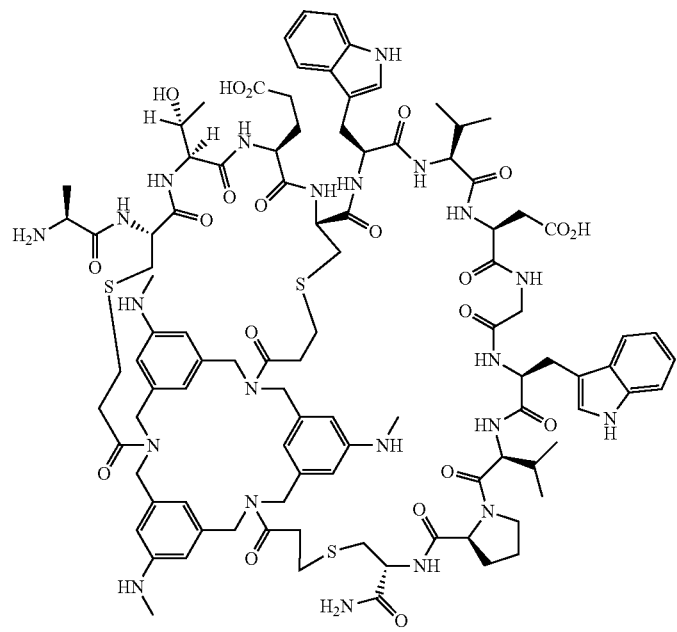
I-76

I-77
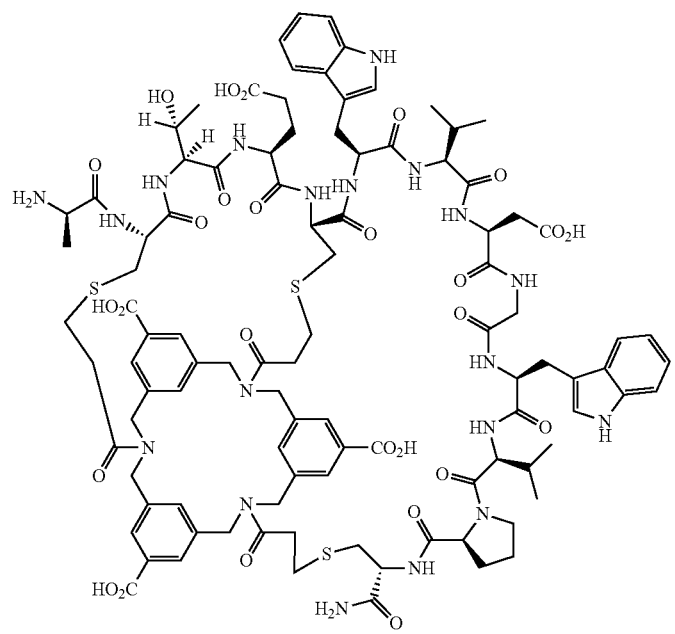
I-78
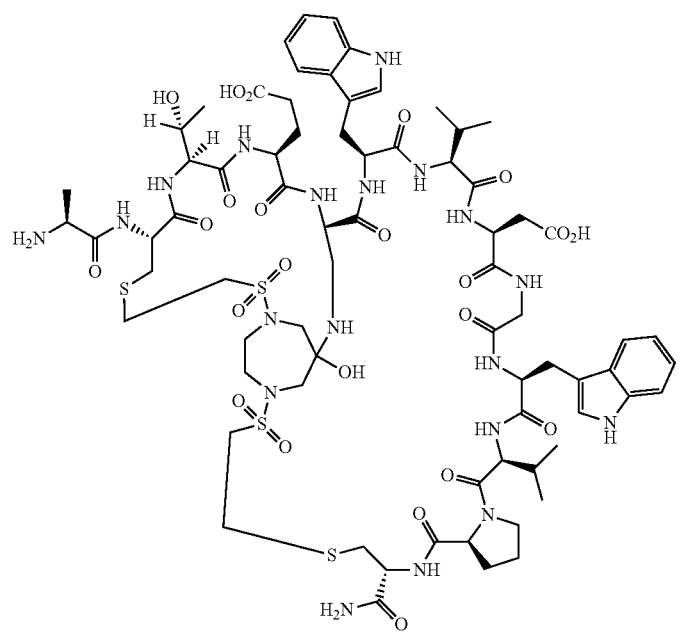

I-79
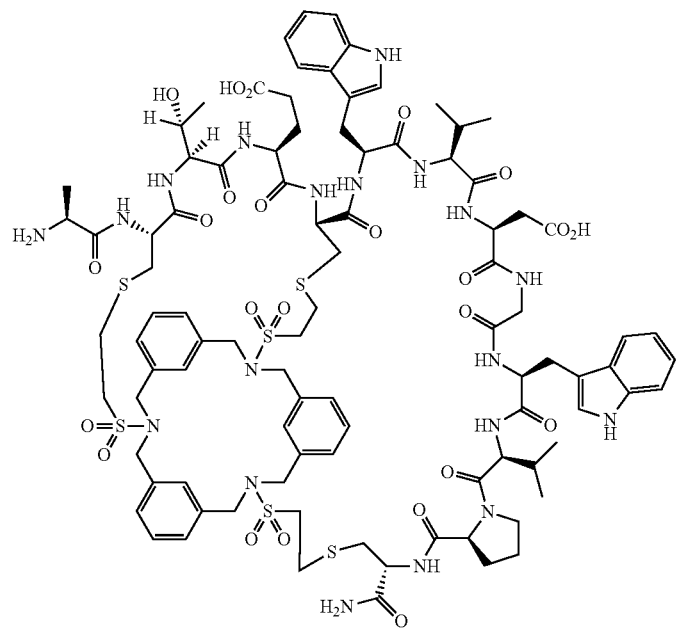
I-80
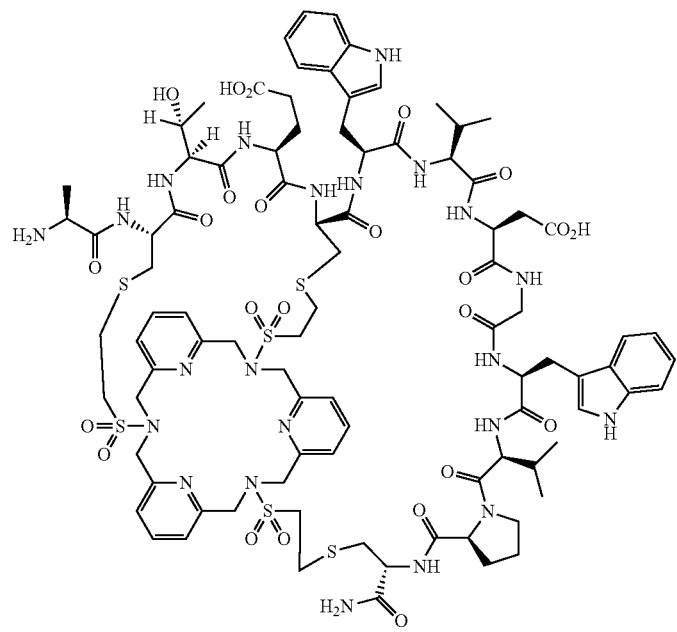

I-81
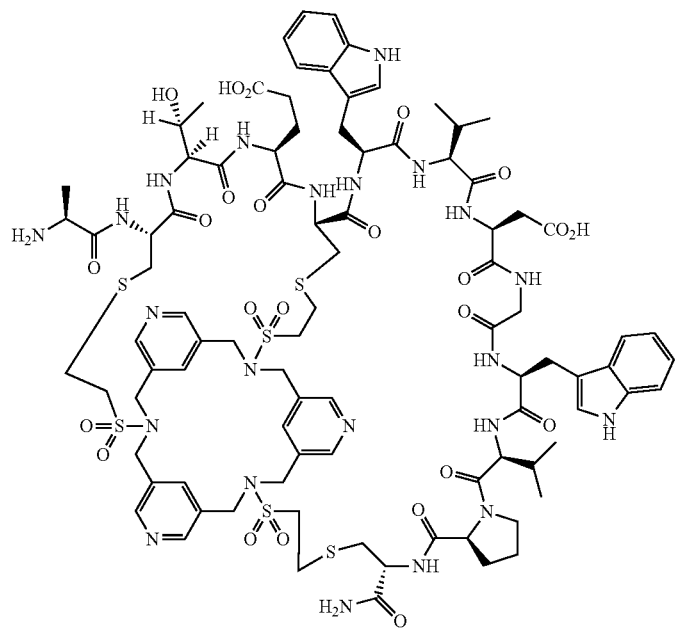
I-82
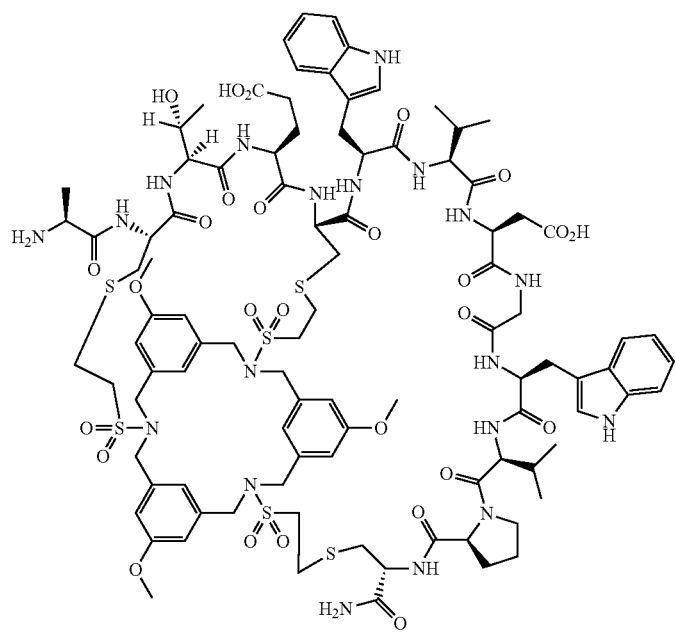

I-83
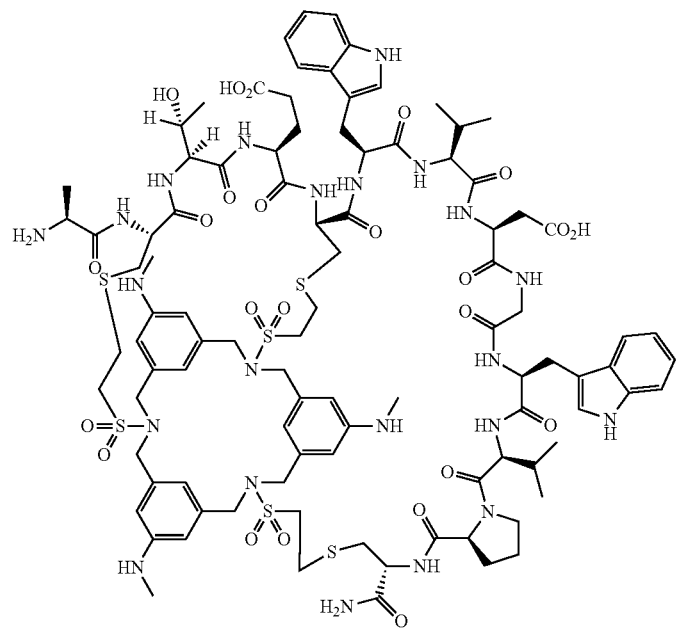
I-84
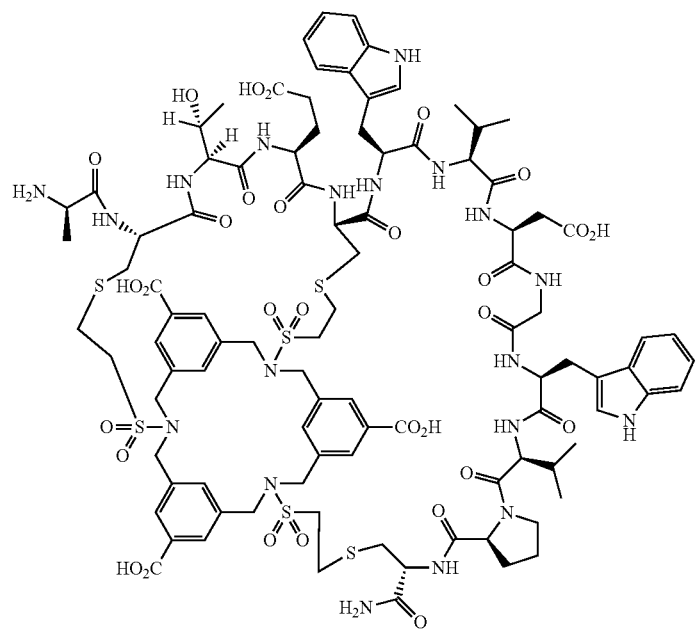

-continued
I-85
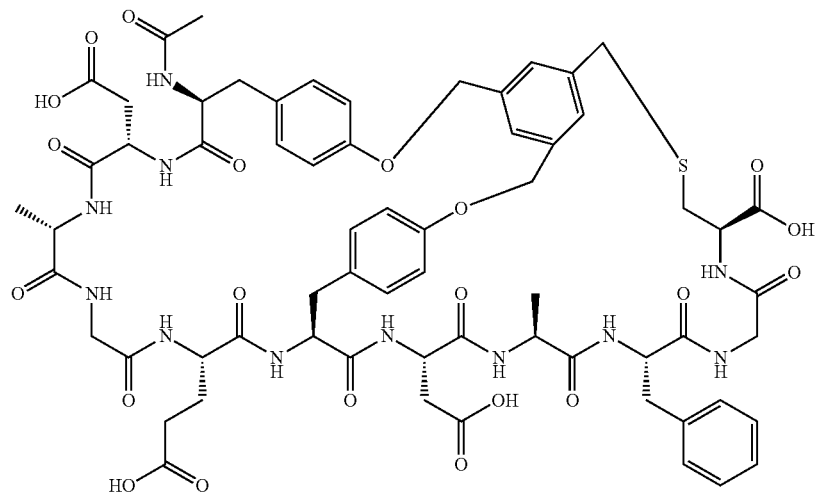
I-86
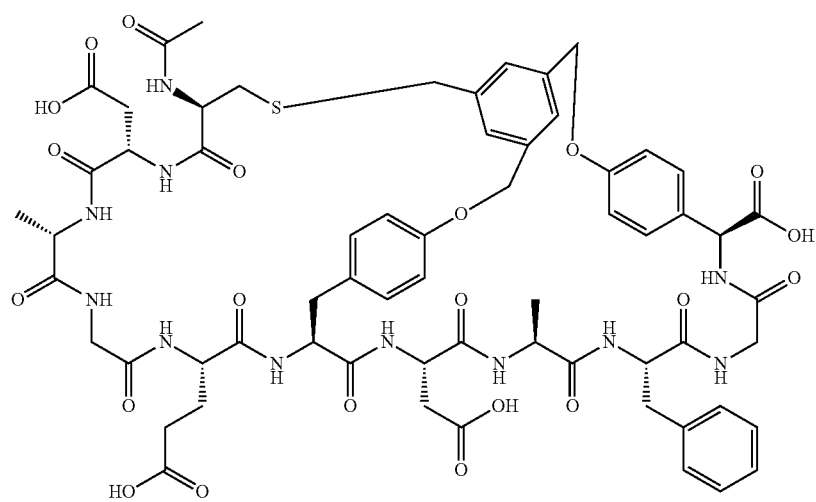
I-87
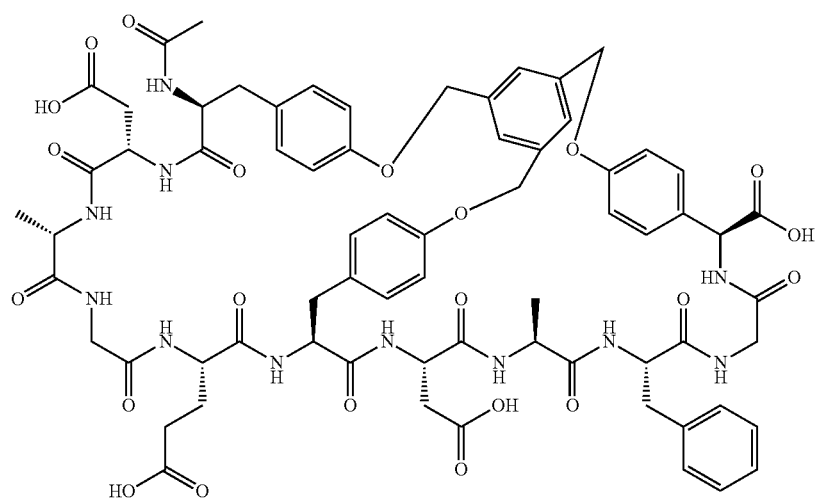

I-88
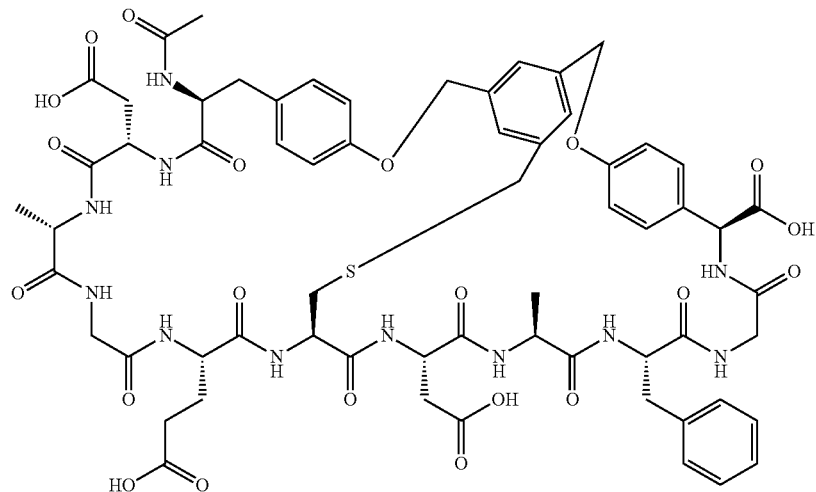
I-89
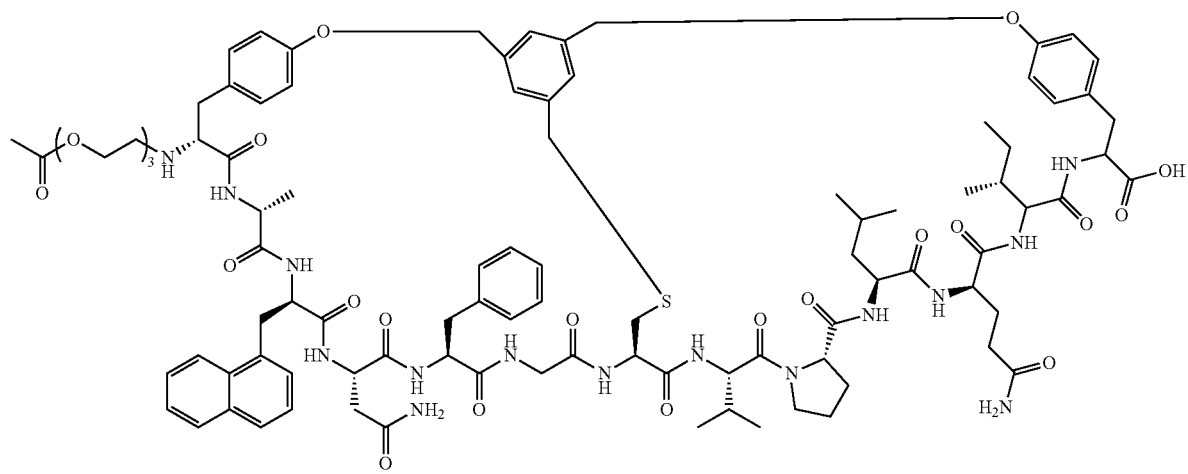
I-90
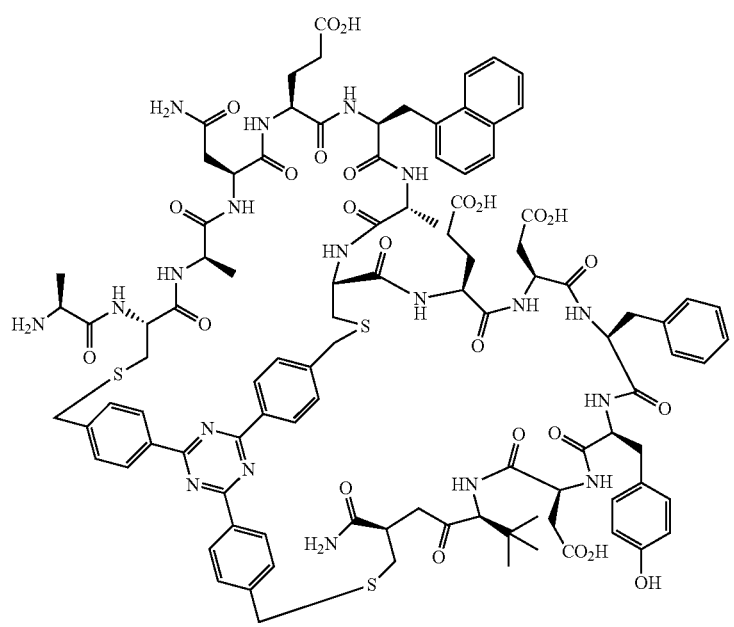

-continued
I-91
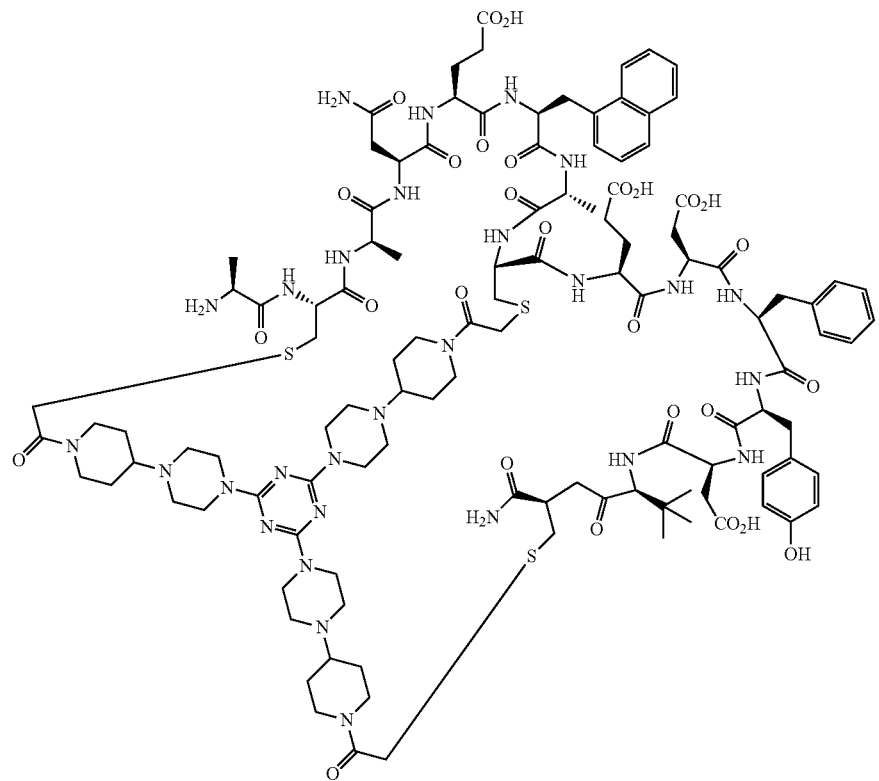
I-92
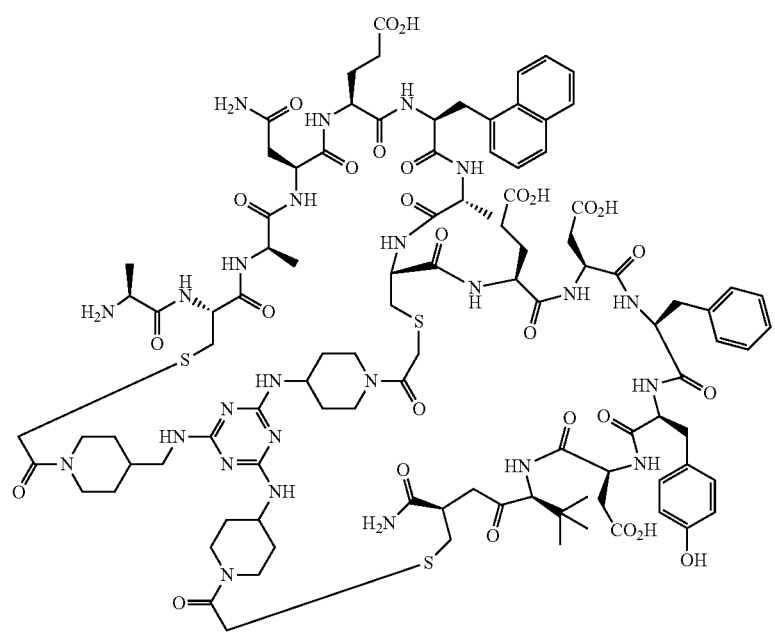

I-93
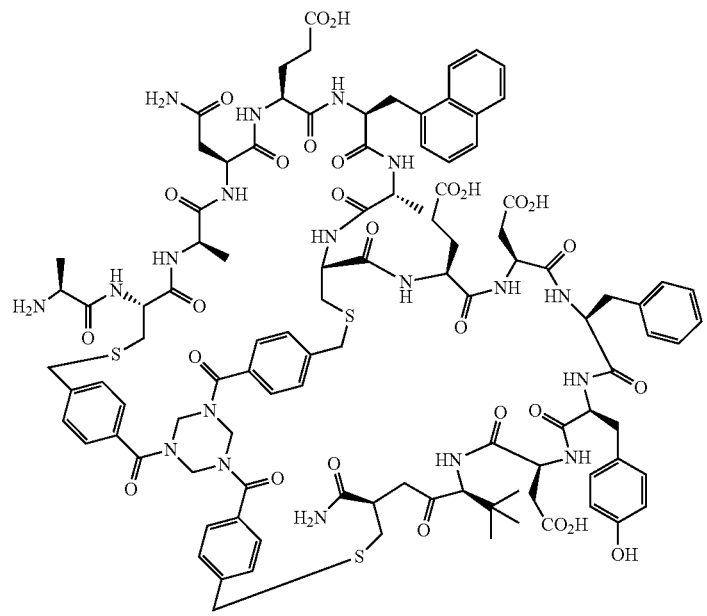
I-94
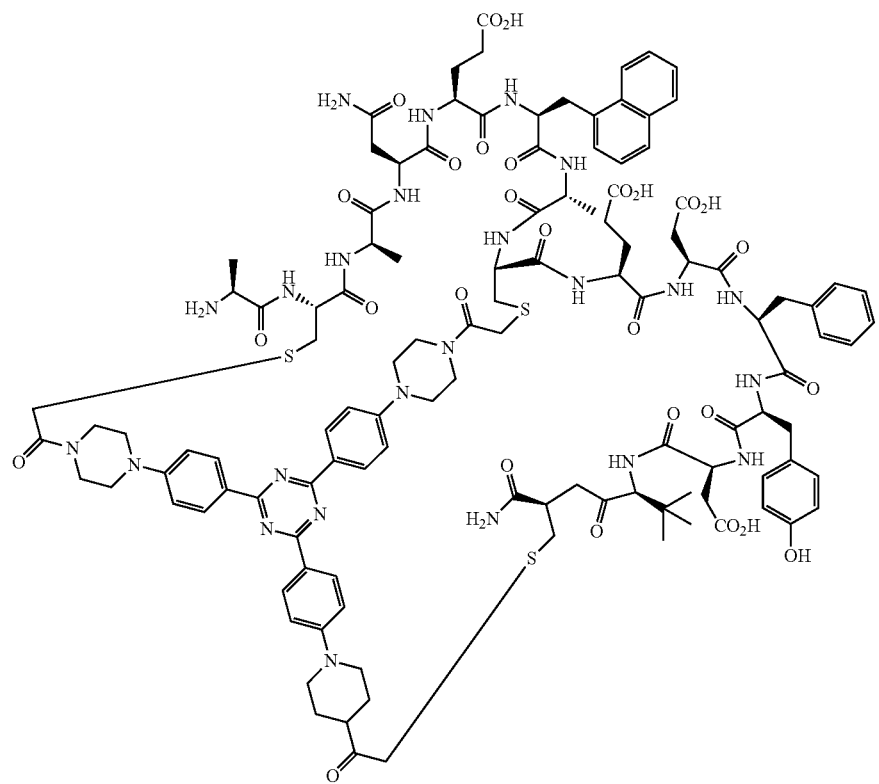

I-95
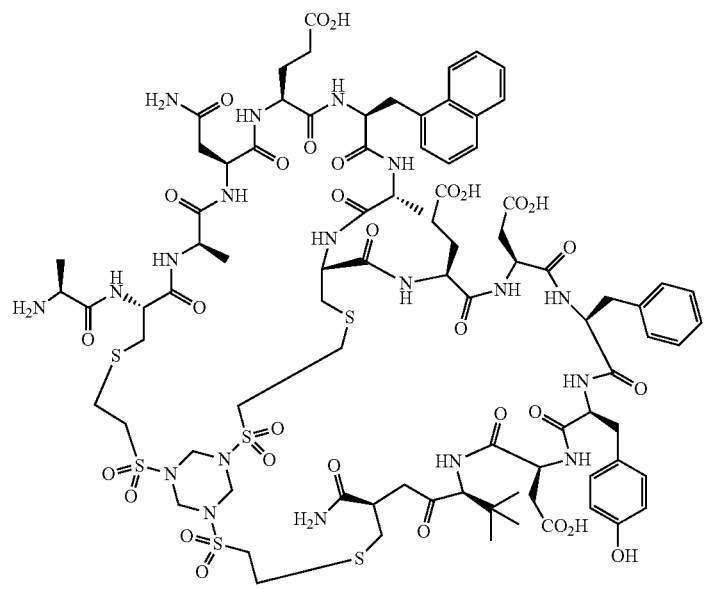
I-96
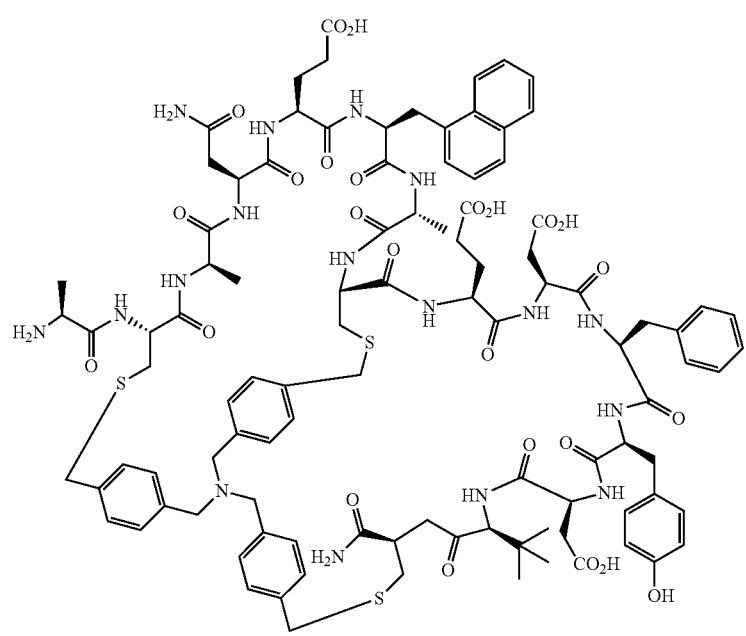

I-97
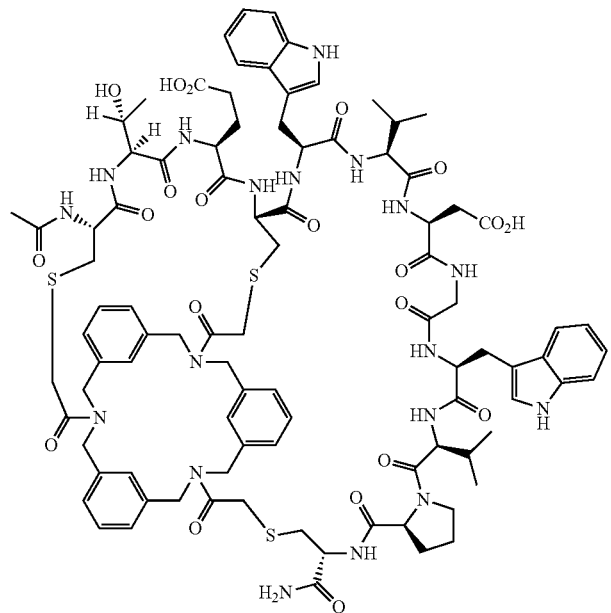
I-98
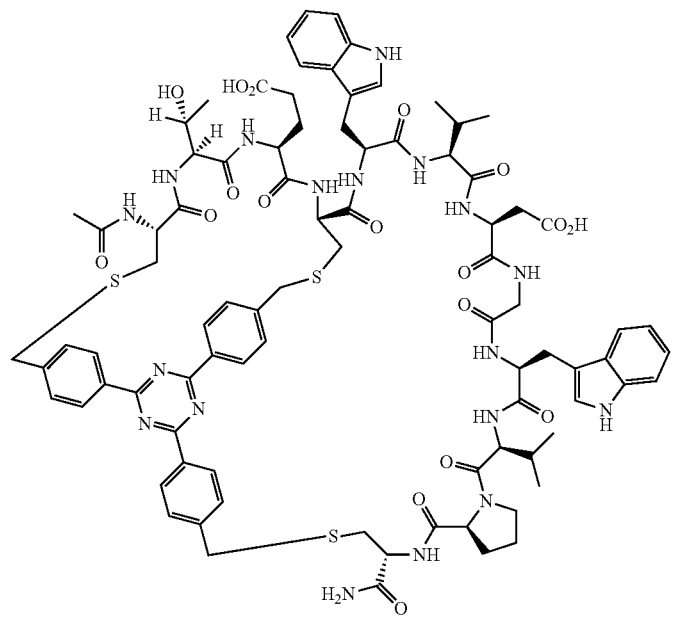

-continued
I-99
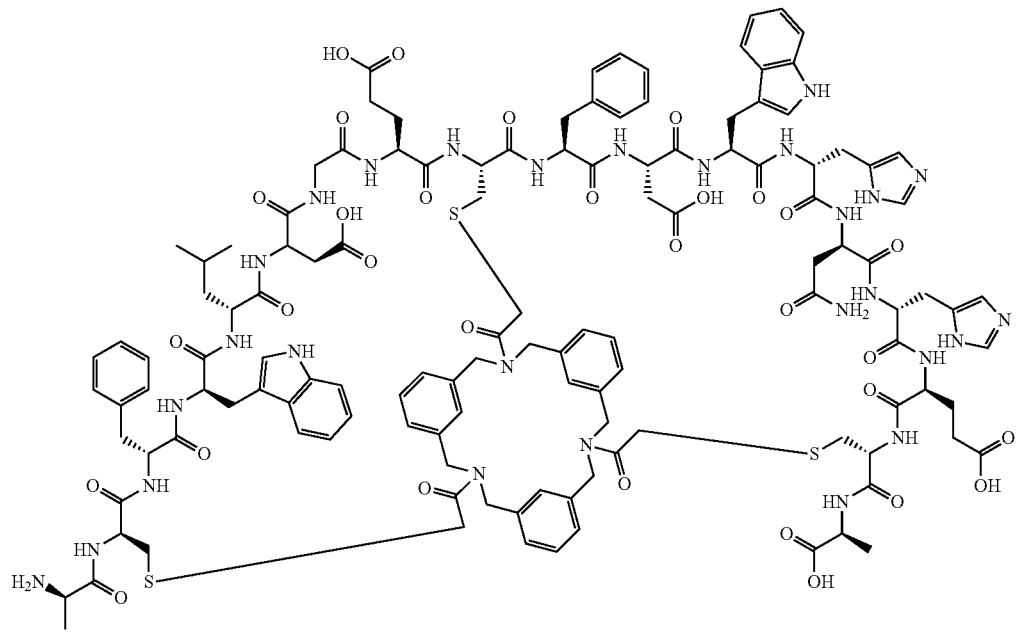
I-100
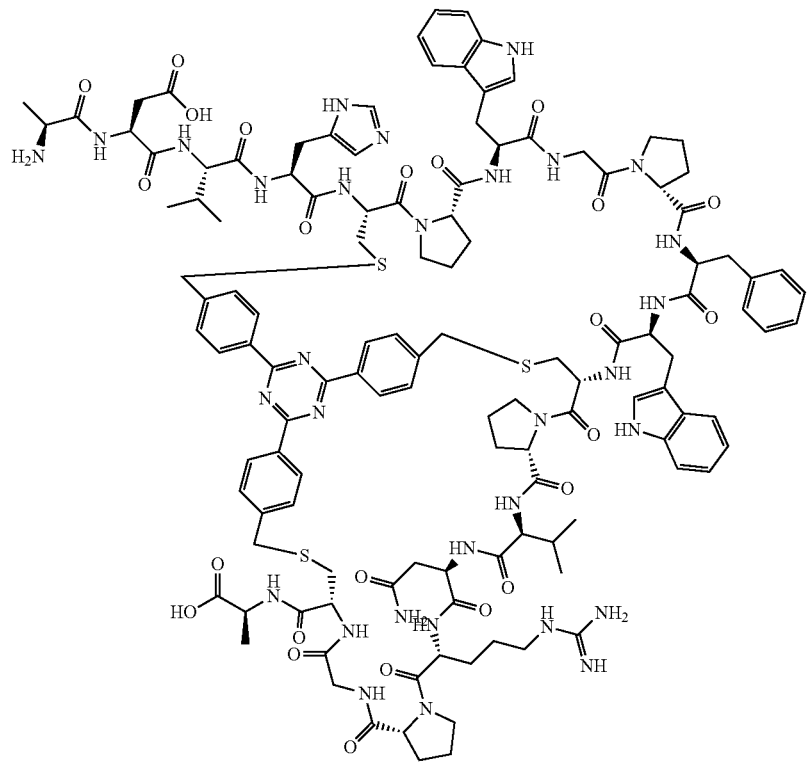

-continued
I-101
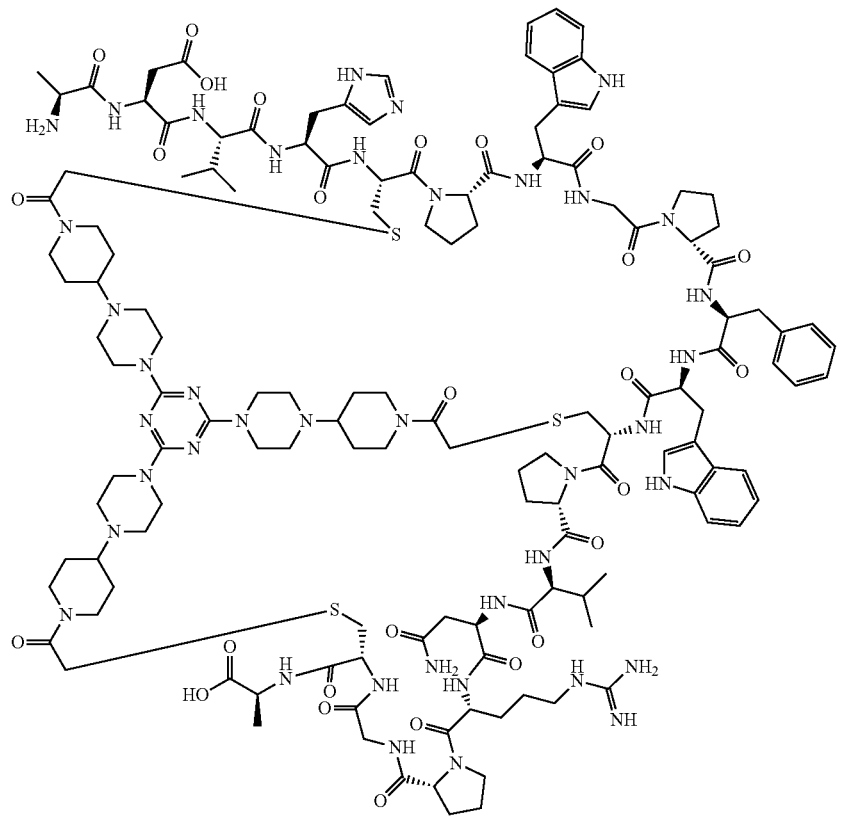
I-102
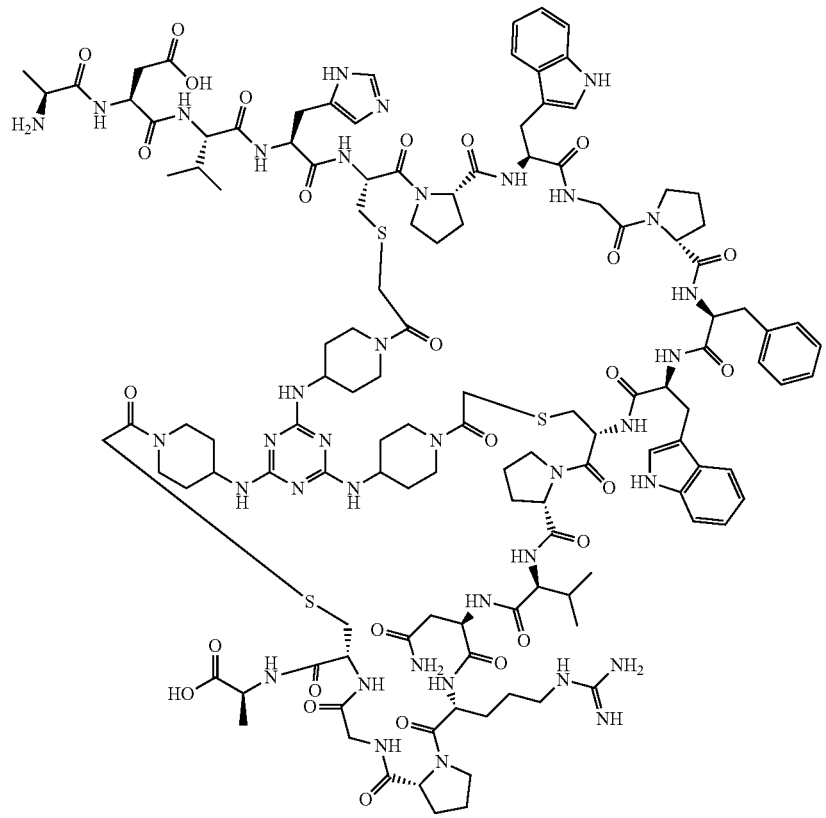

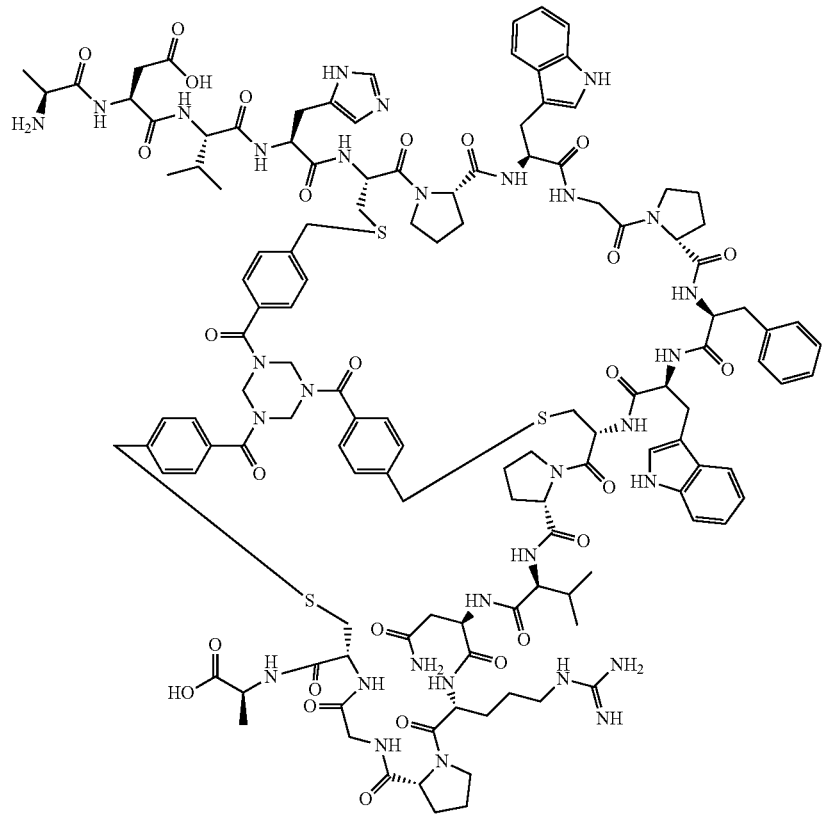
I-103
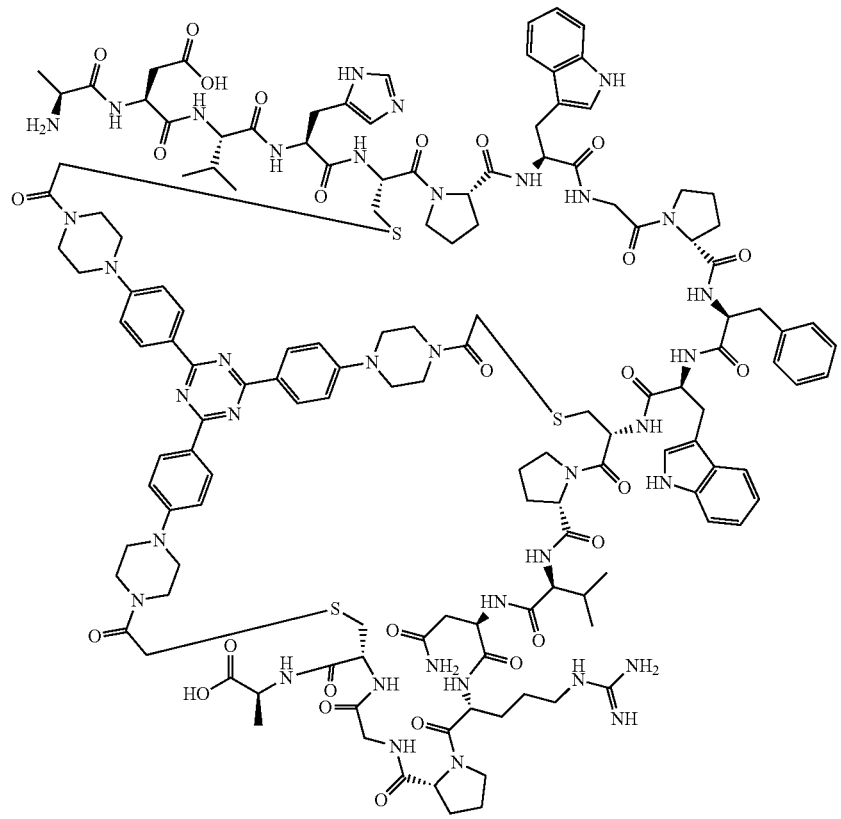
I-104

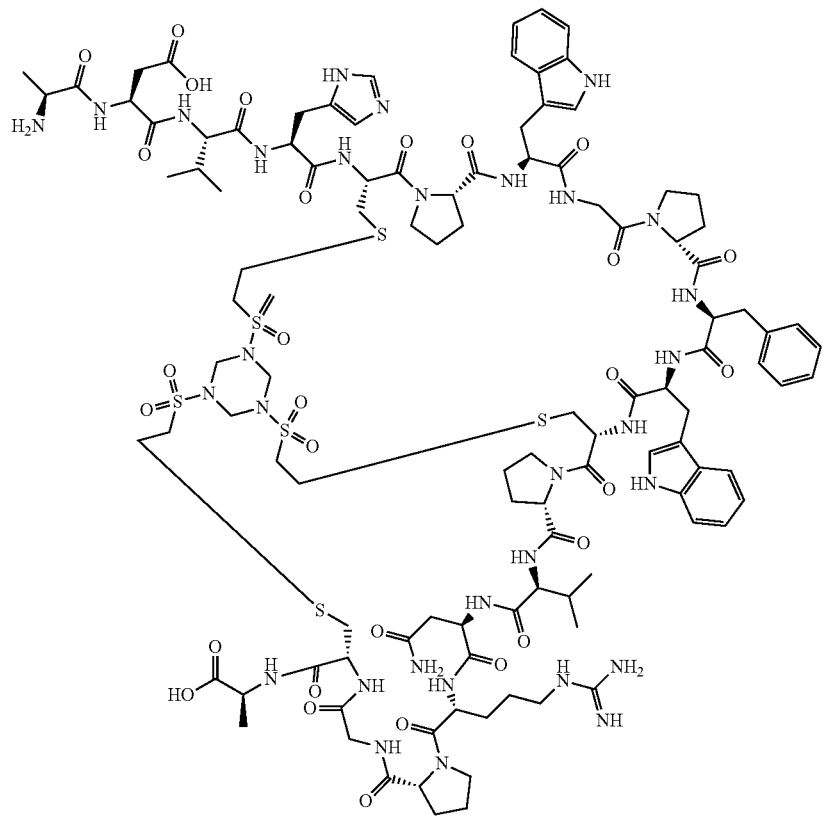
I-105
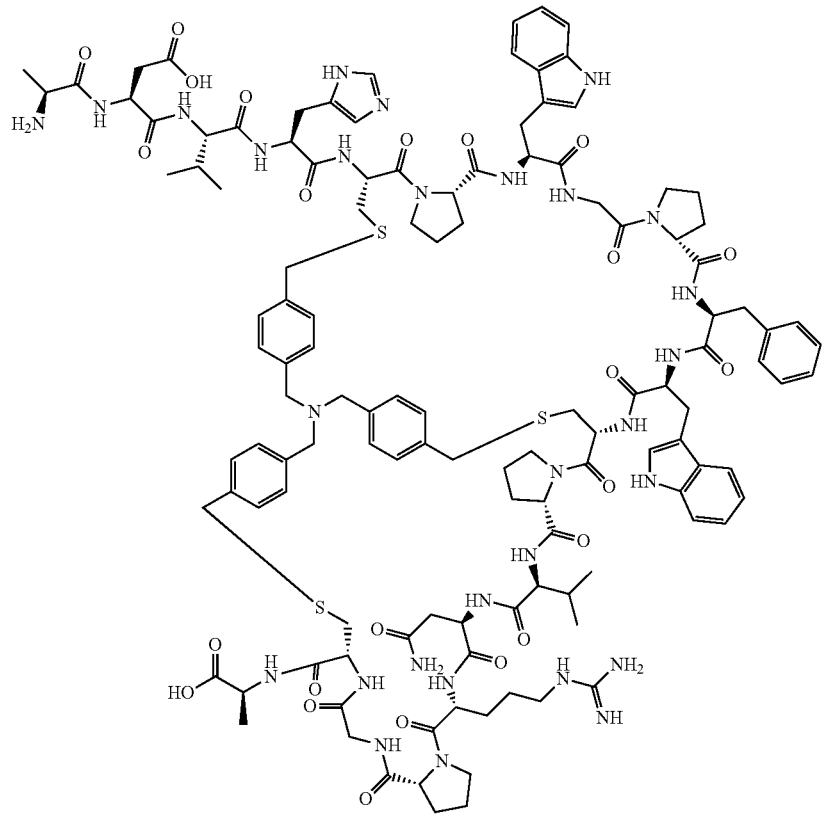
I-106

-continued
I-107
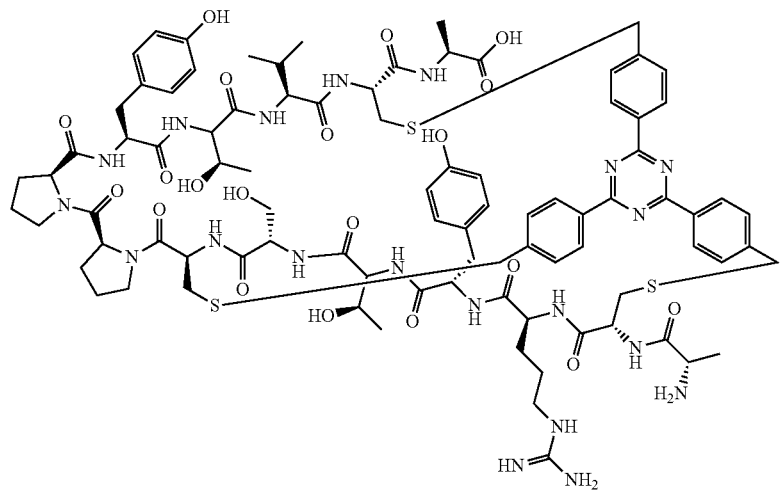
I-108
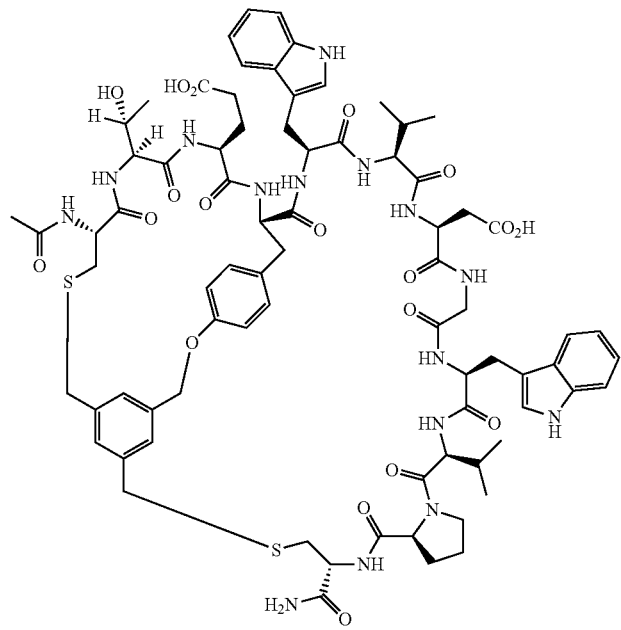

I-109

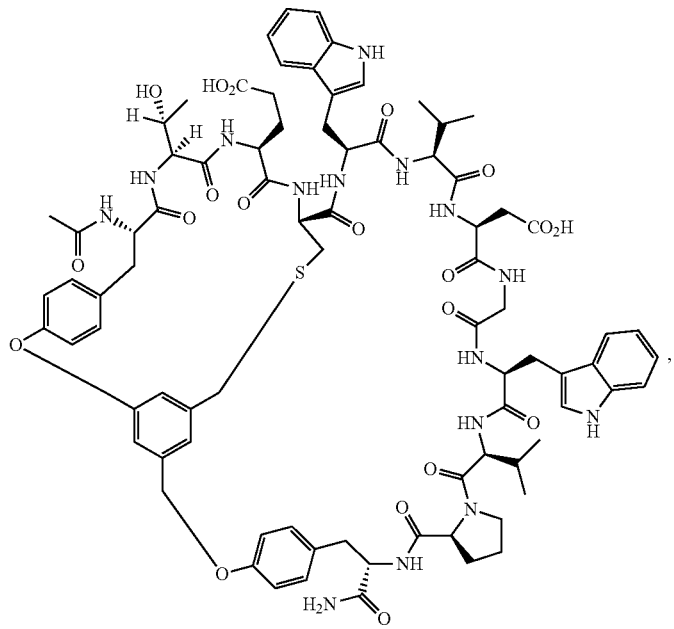

or a pharmaceutically acceptable salt thereof.

3. A compound of formula II:

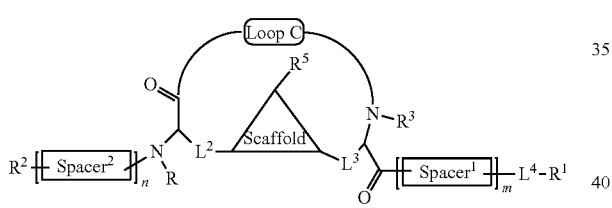

or a pharmaceutically acceptable salt thereof, wherein:

each of $L^2$ and $L^3$ is independently a covalent bond or a $C_{1-8}$ bivalent hydrocarbon chain wherein one, two or three methylene units of the chain are optionally and independently replaced by -$Cy^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,

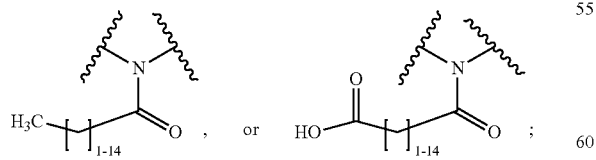

$L^4$ is a covalent bond, —O—, —N(R)—, or —N(R)CH$_2$CH$_2$N(R)—;

each R is independently hydrogen or $C_{1-4}$ aliphatic;

each -$Cy^1$- is independently an optionally substituted bivalent ring selected from phenylene, 3-7 membered saturated or partially unsaturated carbocyclylene, 4-7 membered saturated or partially unsaturated heterocyclylene having 1-2 heteroatoms independently selected from nitrogen, oxygen, or sulfur, 10-12 membered saturated or partially unsaturated bicyclic heterocyclylene having 1-4 heteroatoms independently selected from nitrogen, oxygen, or sulfur, 10-12 membered saturated or partially unsaturated tricyclic heterocyclylene having 1-4 heteroatoms independently selected from nitrogen, oxygen, or sulfur, 10-12 membered partially saturated bicyclic heteroarylene having 1-4 heteroatoms independently selected from nitrogen, oxygen, or sulfur, 10-12 membered partially saturated tricyclic heteroarylene having 1-4 heteroatoms independently selected from nitrogen, oxygen, or sulfur, 9-12 membered bicyclic heteroarylene having 1-4 heteroatoms independently selected from nitrogen, oxygen, or sulfur, 19-20 membered partially unsaturated tetracyclic heteroarylene having 1-4 heteroatoms independently selected from nitrogen, oxygen, or sulfur, or 5-6 membered heteroarylene having 1-4 heteroatoms independently selected from nitrogen, oxygen, or sulfur;

Scaffold is a trivalent group that connects and orients a cyclic peptide, wherein Scaffold and its $R^5$ substituent,

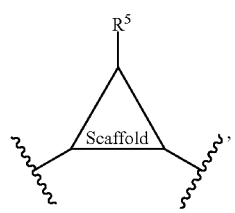

445 are selected from the group consisting of

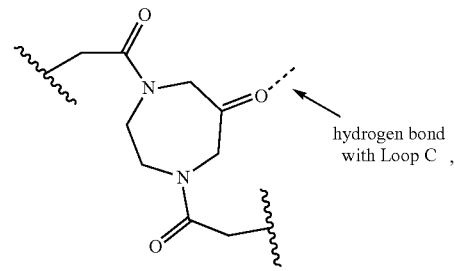
hydrogen bond with Loop C ,

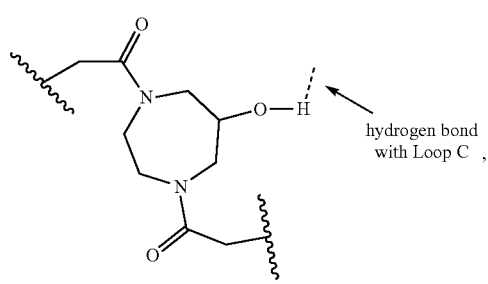
hydrogen bond with Loop C ,

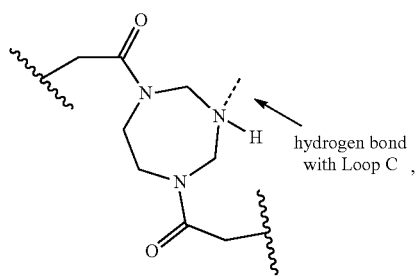
hydrogen bond with Loop C ,

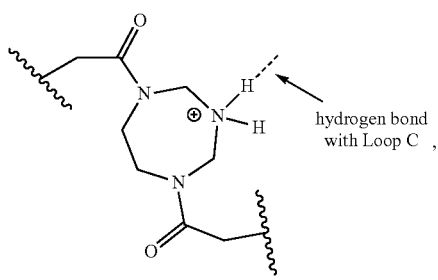
hydrogen bond with Loop C ,

446

-continued

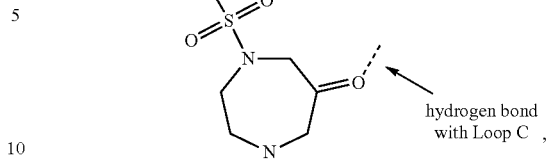
hydrogen bond with Loop C ,

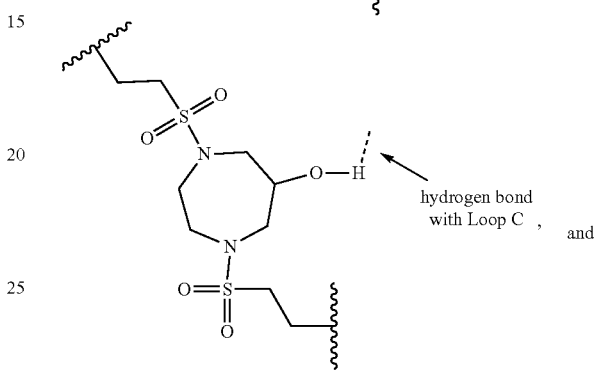
hydrogen bond with Loop C , and

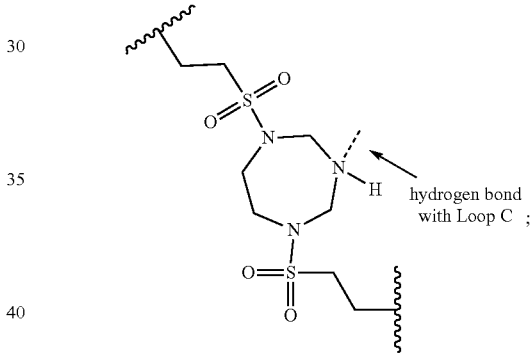
hydrogen bond with Loop C ;

Loop C is a bivalent natural or unnatural peptide attached to the amino acid residue linked to $L^2$ and the amino acid residue linked to $L^3$;

Spacer$^1$ is a covalent bond, a natural or unnatural amino acid wherein the amino group is connected to the C-terminus of the Bicycle via an amide bond, or a peptide wherein the N-terminal amino group of the peptide is connected to the C-terminus of the Bicycle via an amide bond;

Spacer$^2$ is a covalent bond, a natural or unnatural amino acid wherein the acid is connected to the N-terminus of the Bicycle via an amide bond, or a peptide wherein the C-terminal acid of the peptide is connected to the N-terminus of the Bicycle via an amide bond;

each of $R^1$ and $R^2$ is independently R,

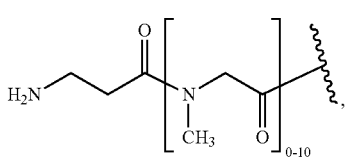

-continued
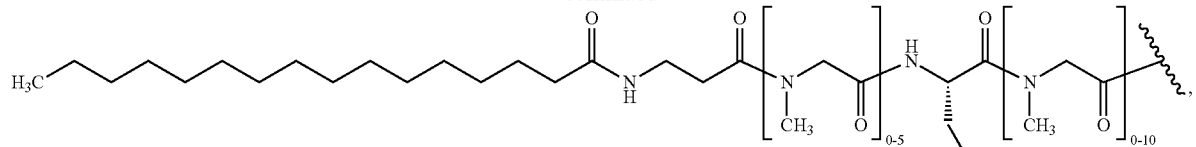
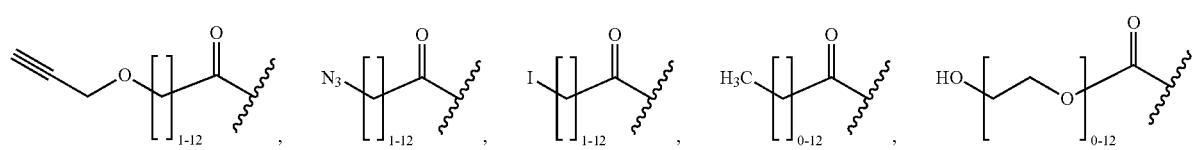
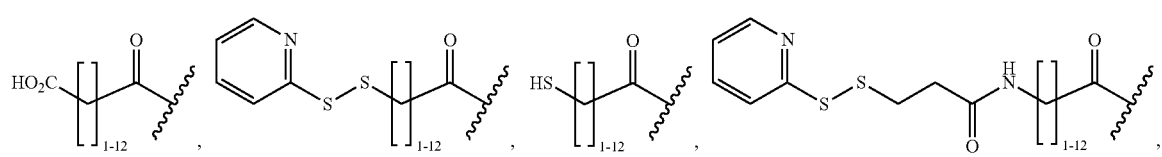
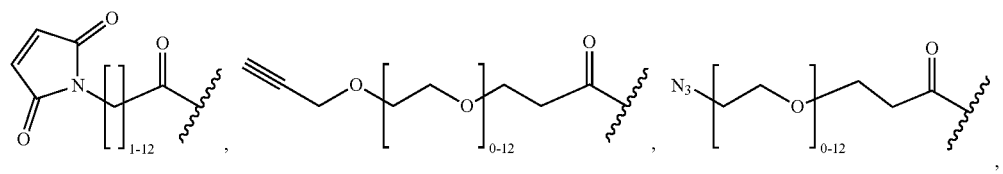
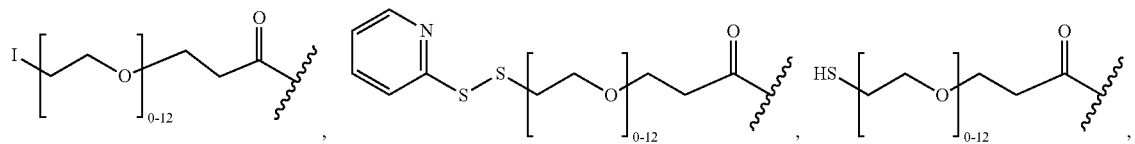
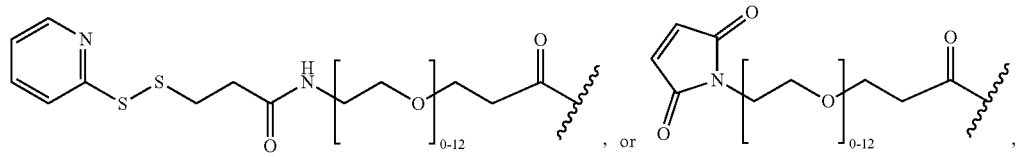
or -Linker-Conjugate;
each Linker is independently a covalent bond, or a $C_{1-8}$ bivalent hydrocarbon chain wherein one, two or three methylene units of the chain are optionally and independently replaced by -Cy$^1$-, —S—, —N(R)—, —O—, —C(O)—, —OC(O)—, —C(O)O—, —C(O)N(R)—, —N(R)C(O)—, —OC(O)N(R)—, —N(R)C(O)O—, —S(O)—, —S(O)$_2$—, —C(CH$_3$)=N—N(R)—, —N(R)N=C(CH$_3$)—, —N(R)CH$_2$C(O)—, —(CH$_2$CH$_2$O)$_{1-10}$—,
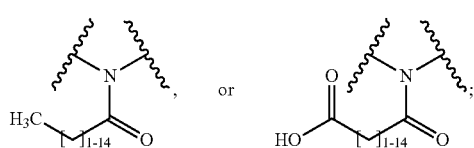

each Conjugate is independently a half life extension motif, a solubilizing group, a transporter recognition motif, a cell penetrant motif, a drug payload, or a detectable moiety;
each of $R^3$ is independently hydrogen or $C_{1-4}$ aliphatic;
m is 0 or 1; and
n is 0 or 1.
4. The compound of claim 3, wherein the compound is selected from
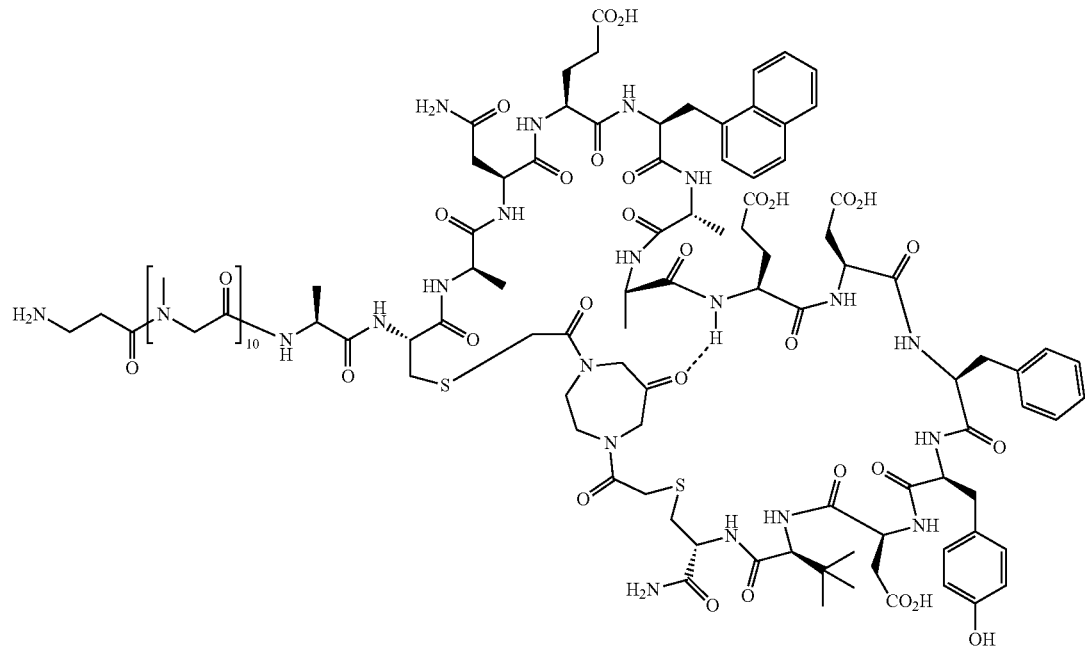
II-1
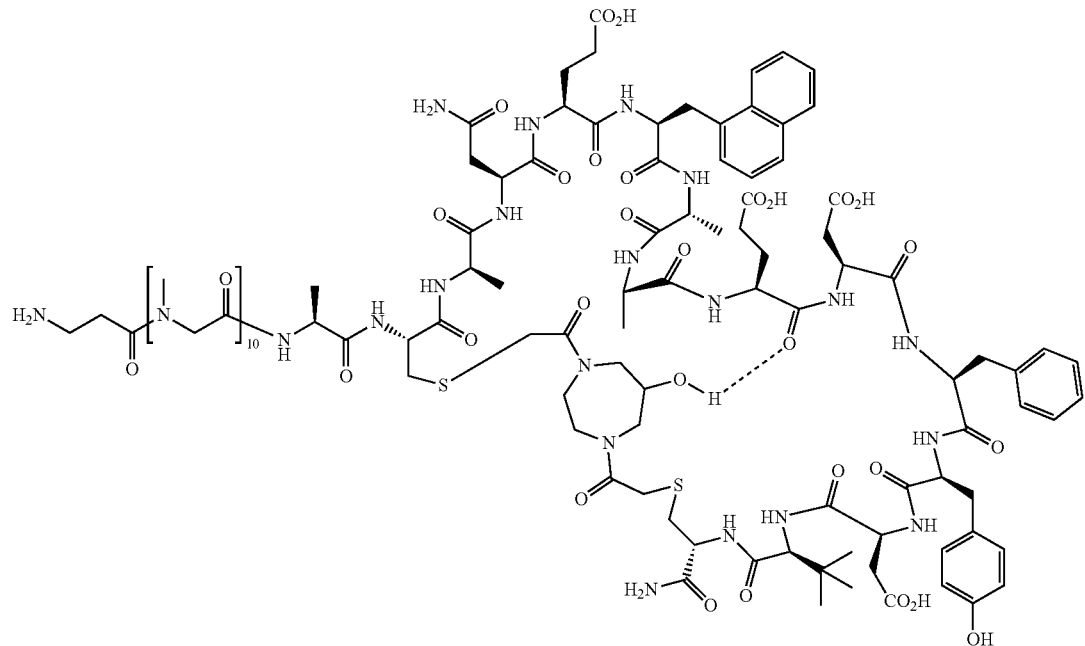
II-2

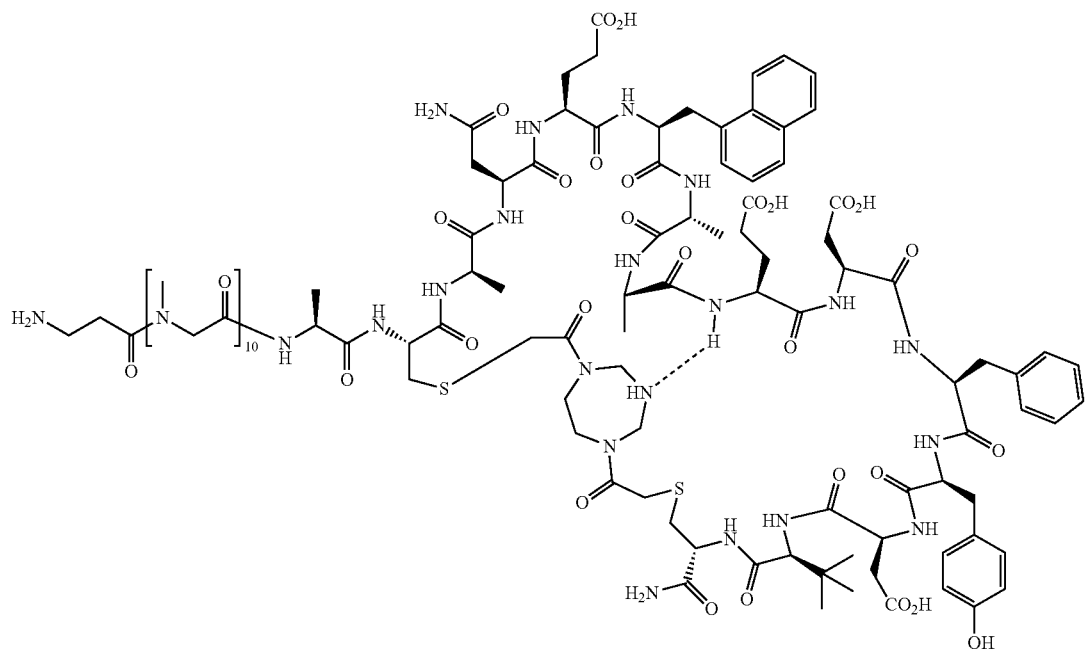
II-3
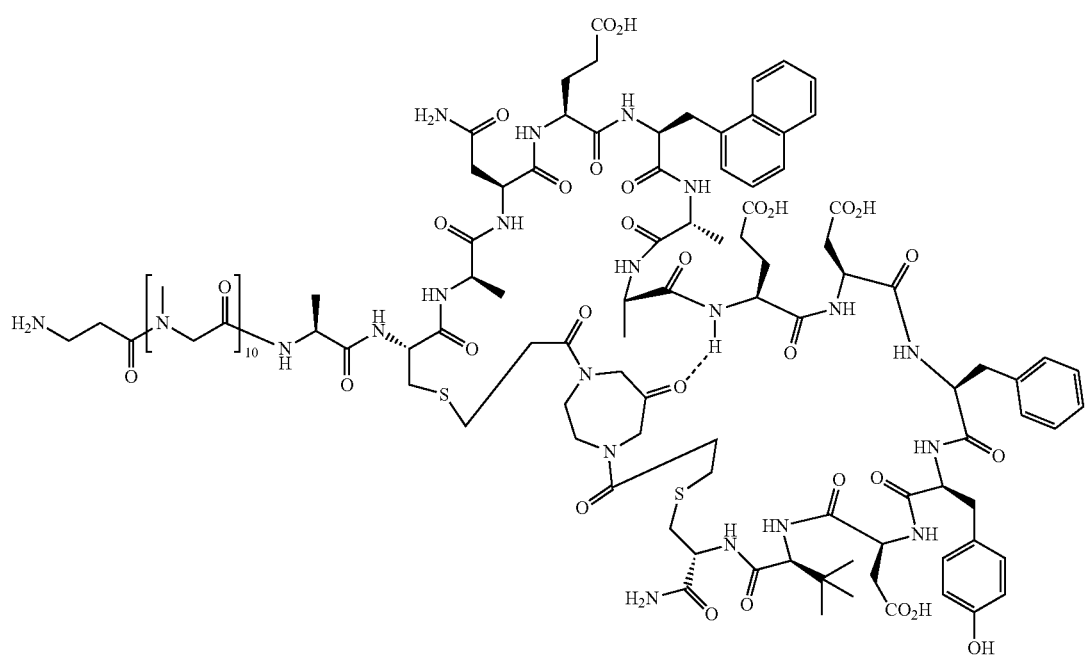
II-4

II-5
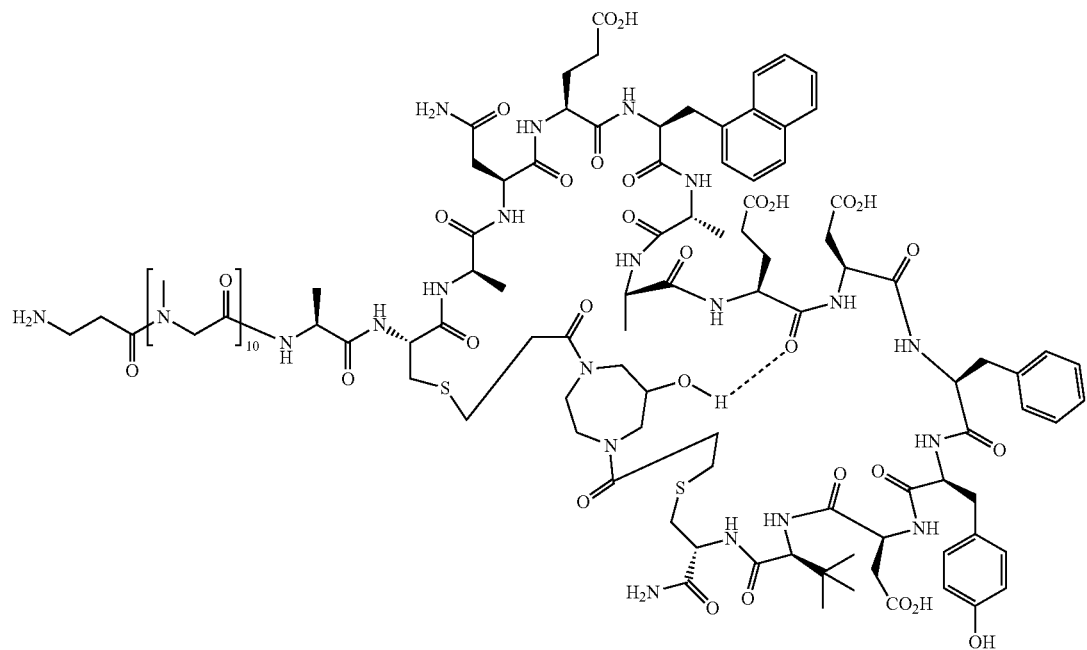
II-6
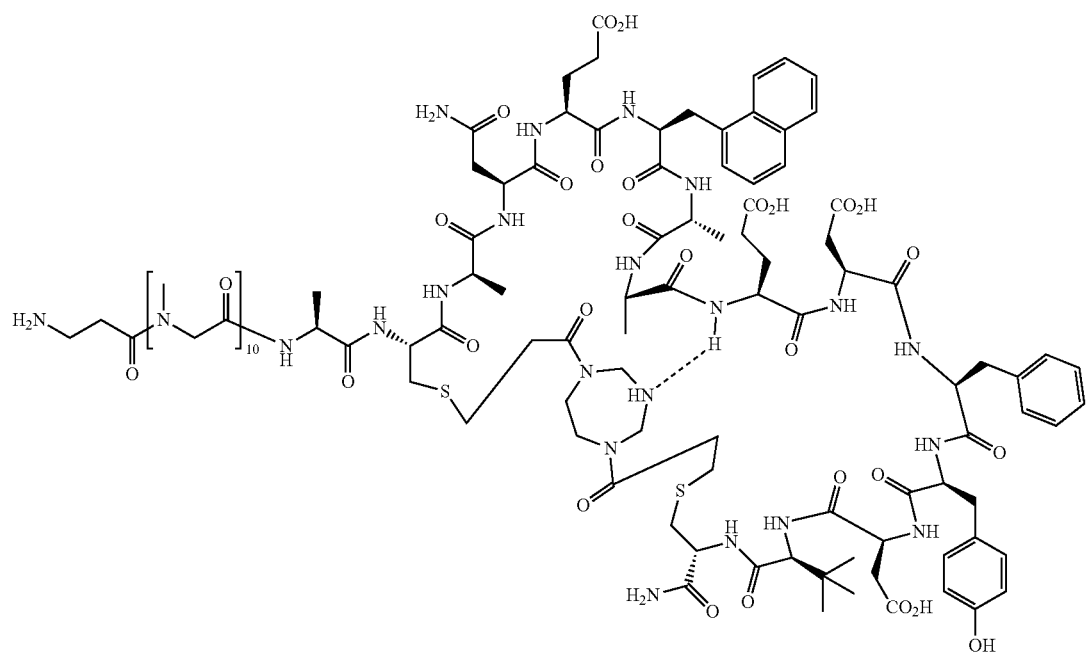

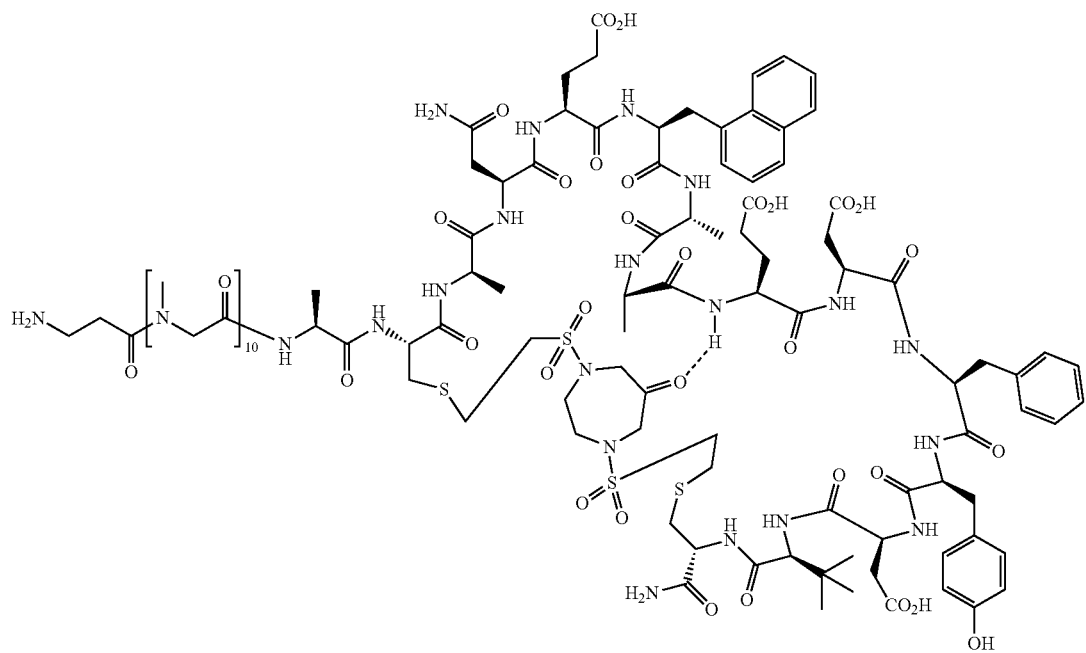
II-7
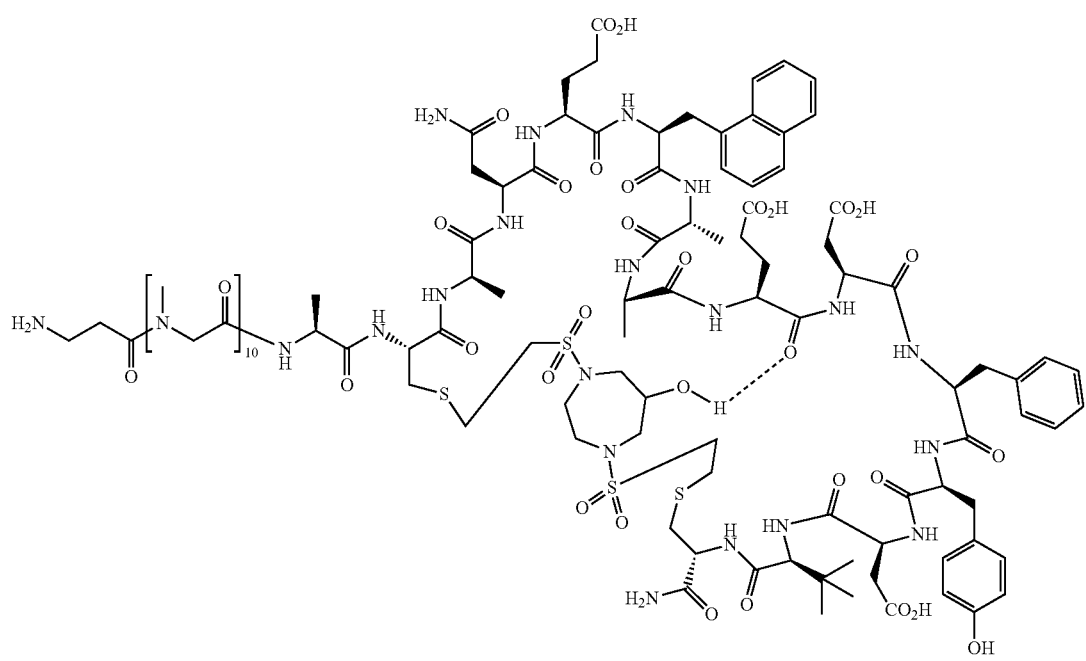
II-8

-continued
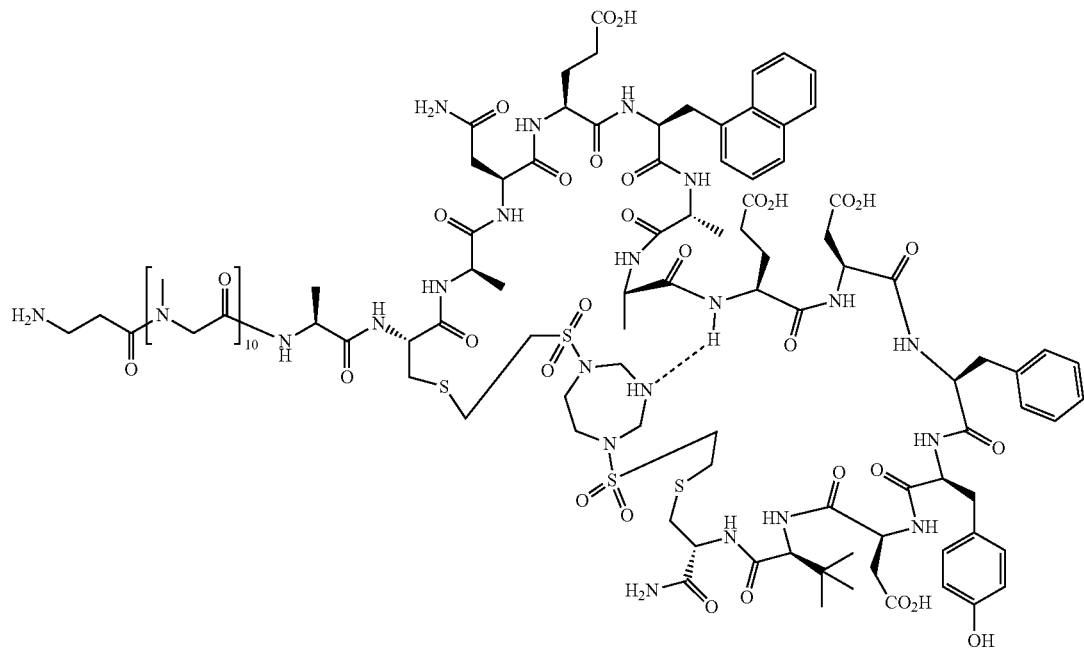
II-9
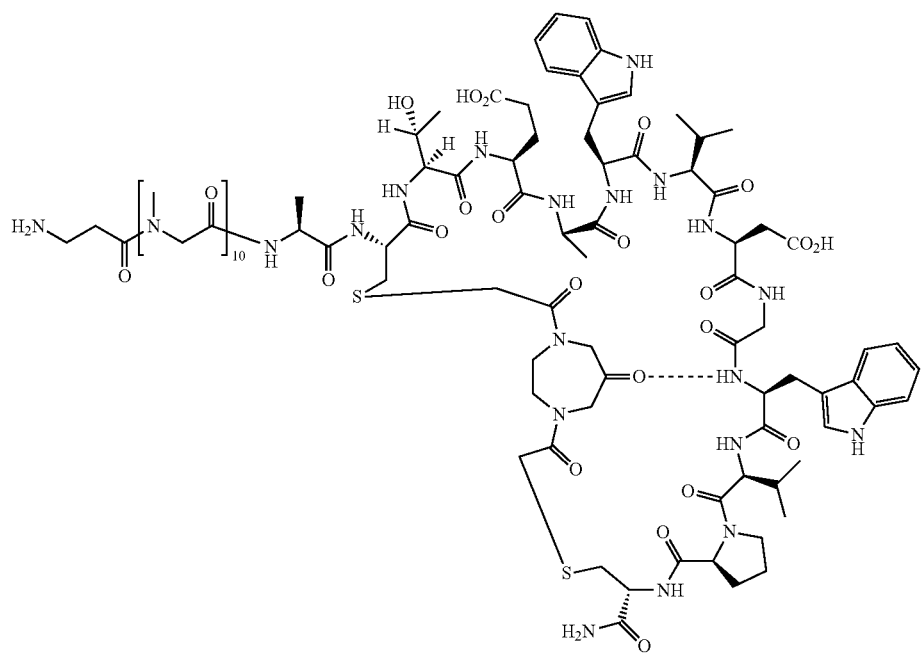
II-10

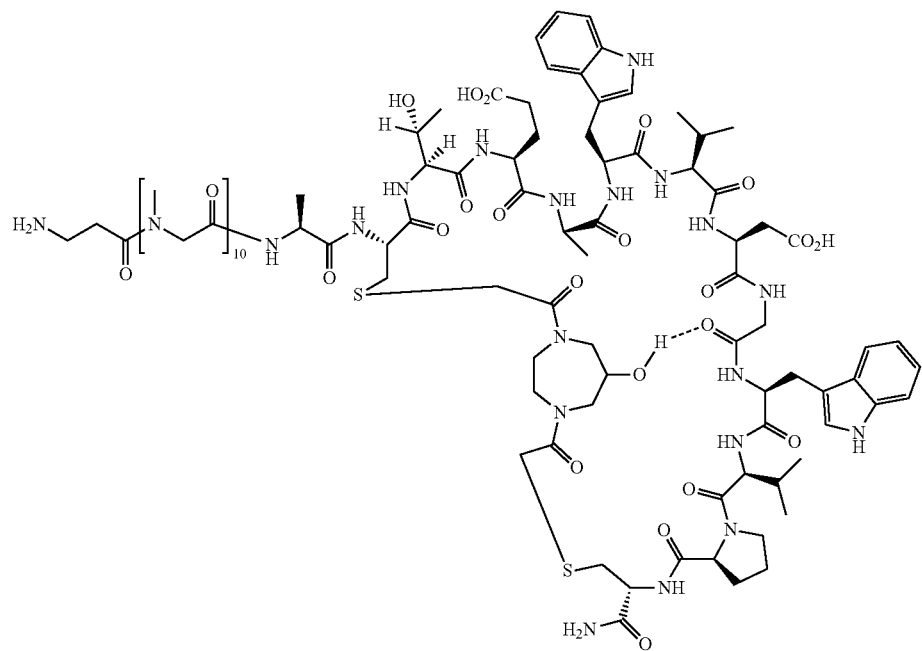
II-11
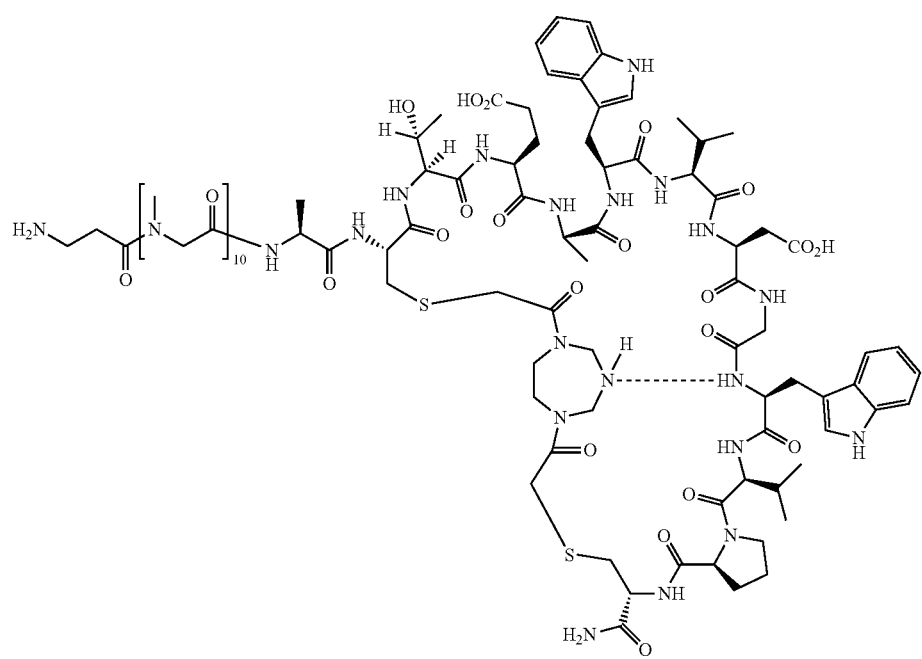
II-12

II-13
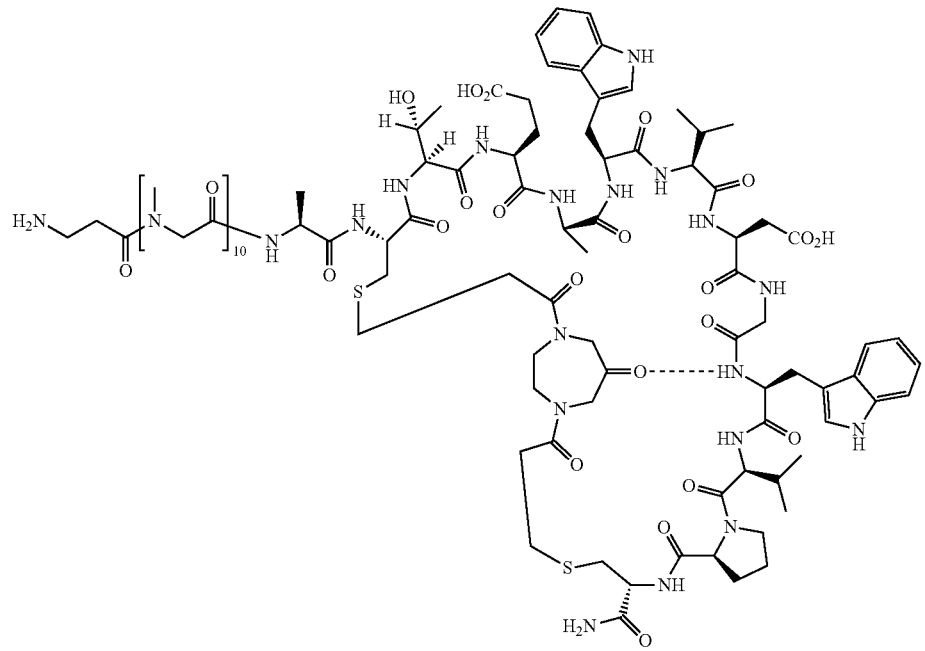
II-14
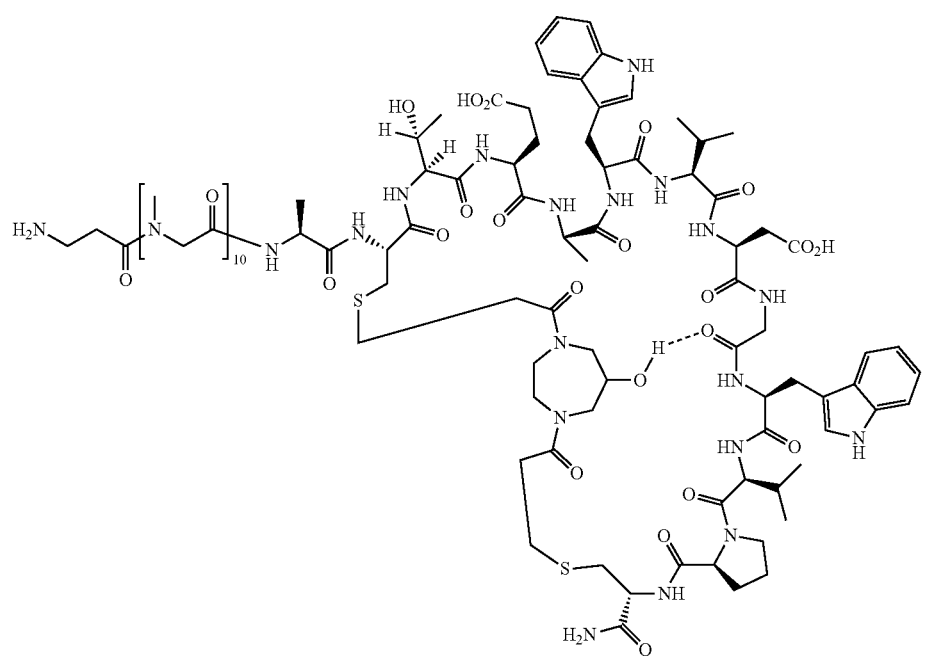

II-15
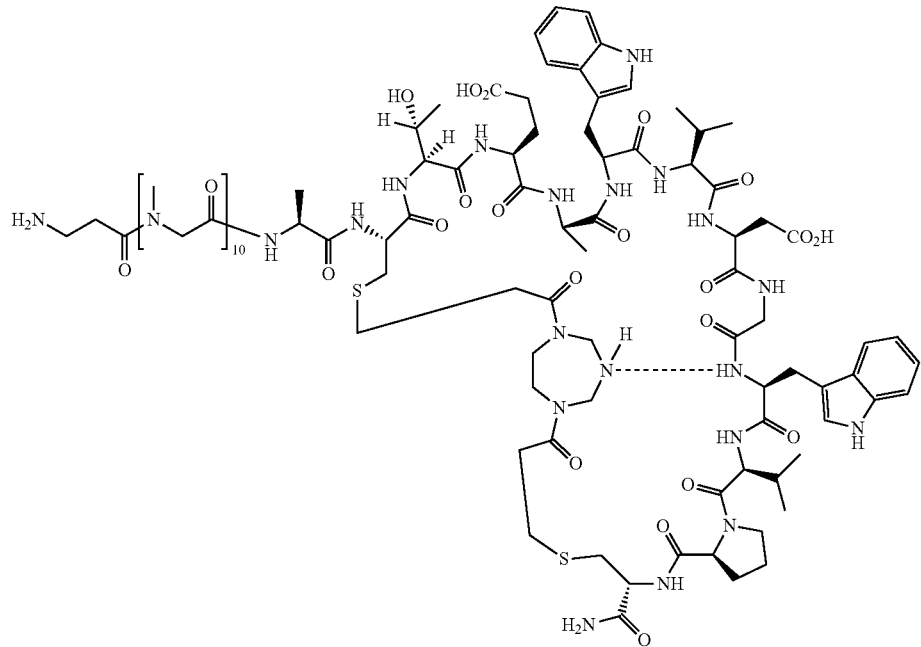
II-16
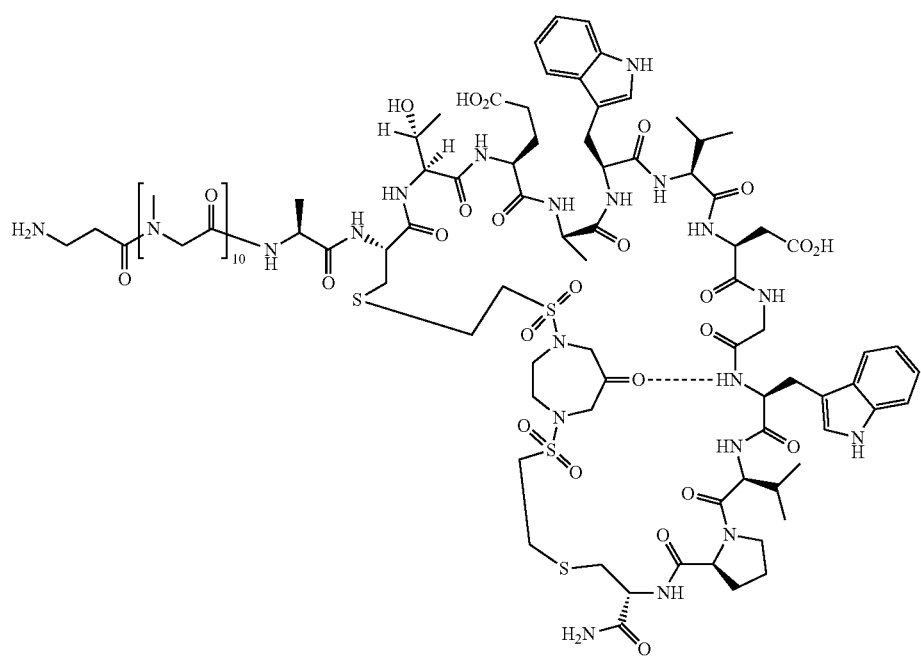

II-17
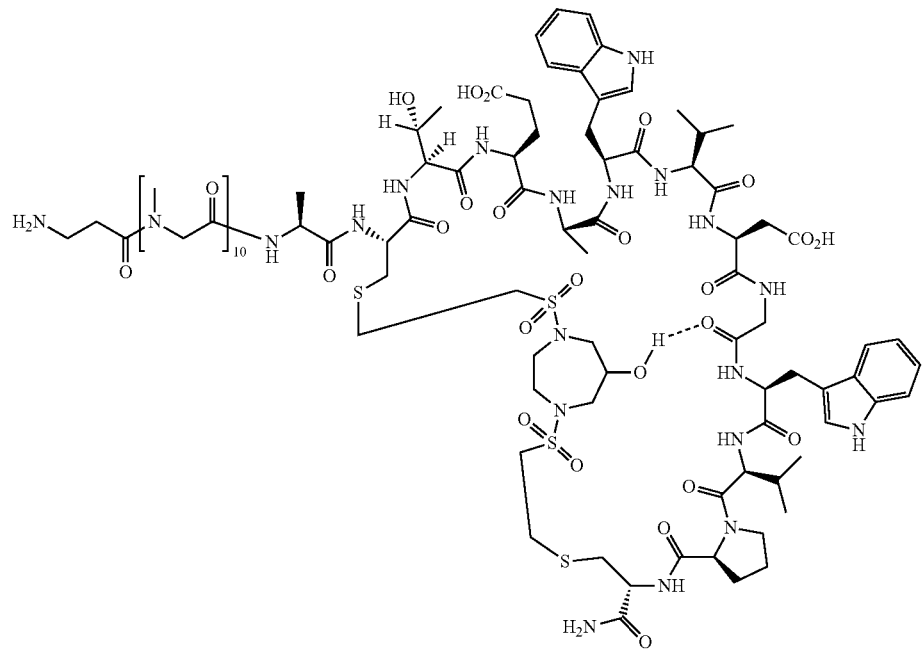
II-18
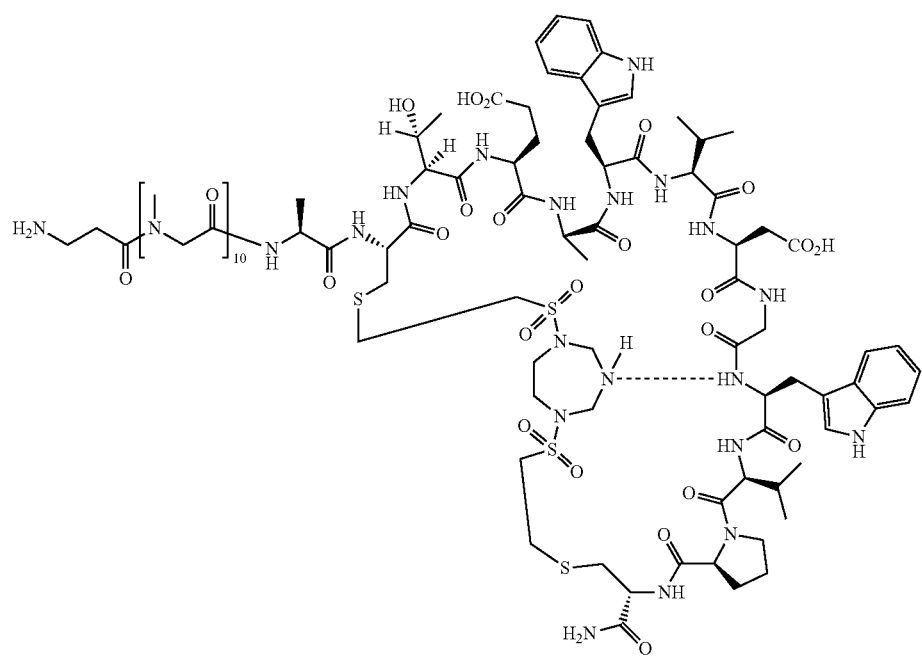

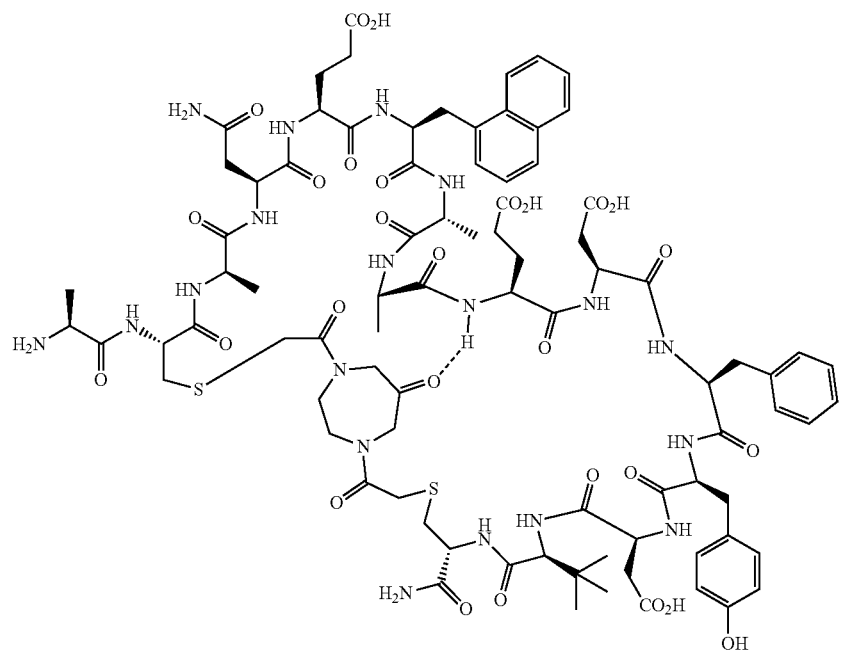
II-19
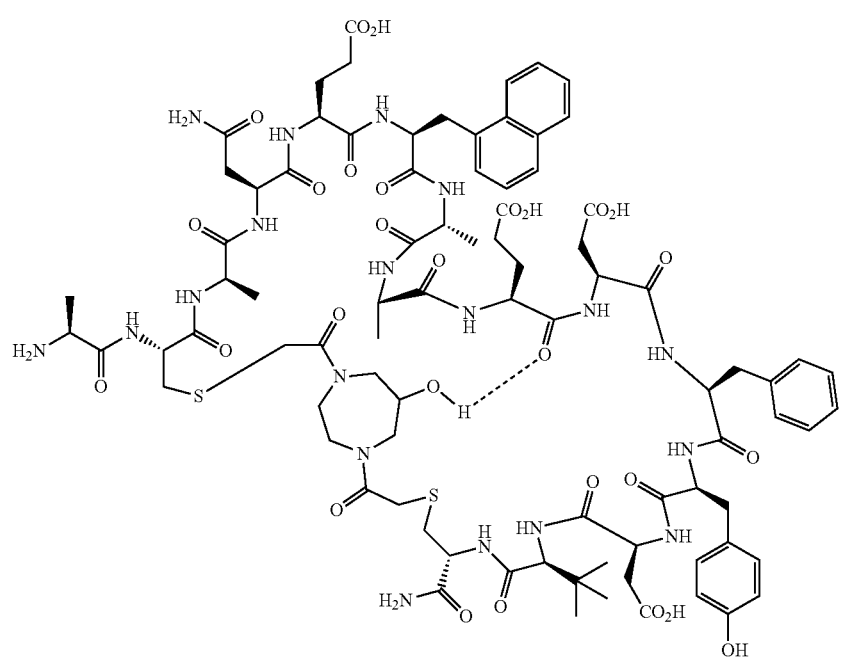
II-20

II-21
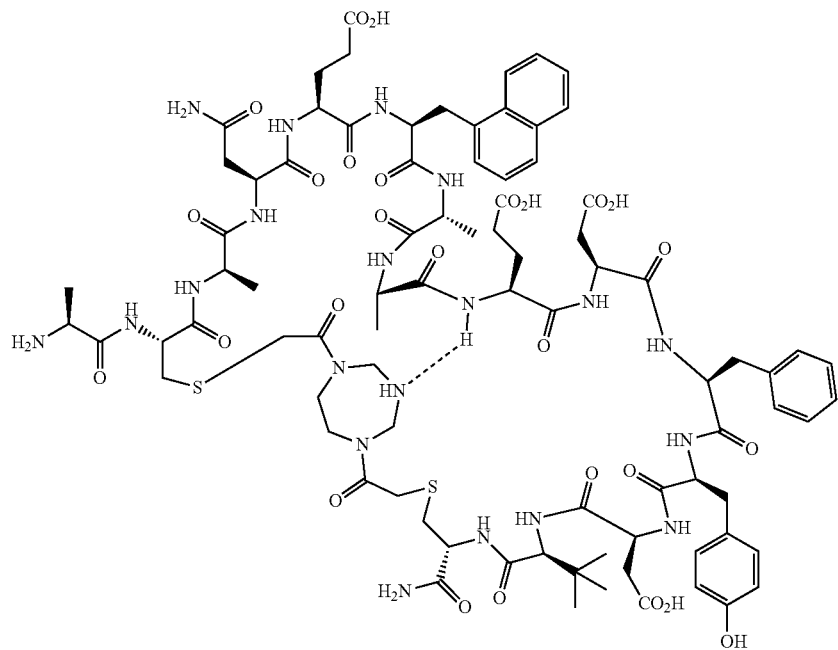
II-22
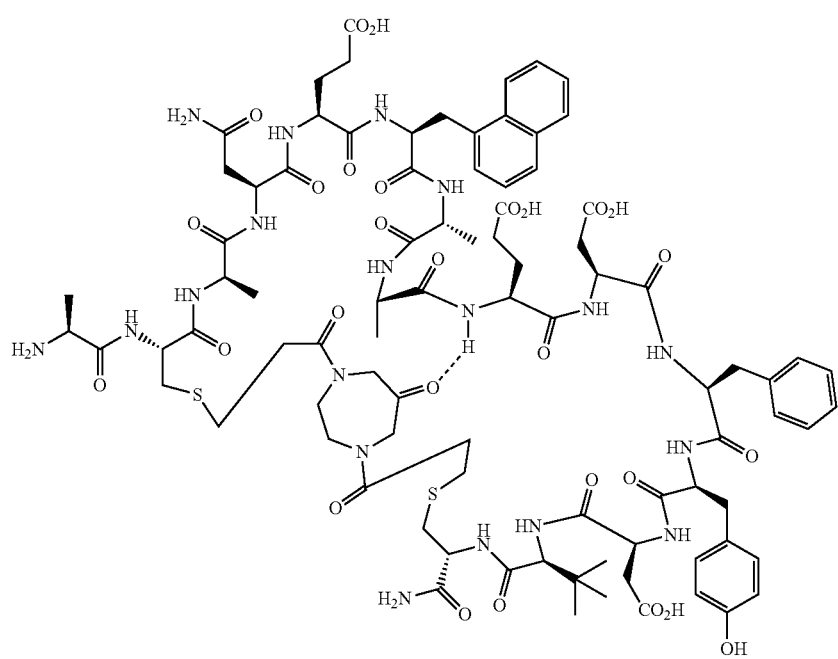

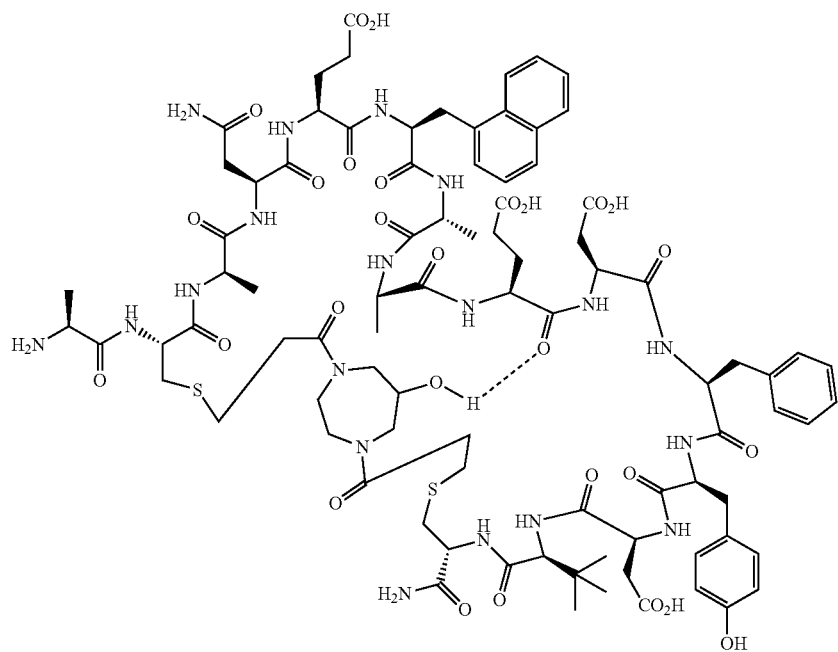
II-23
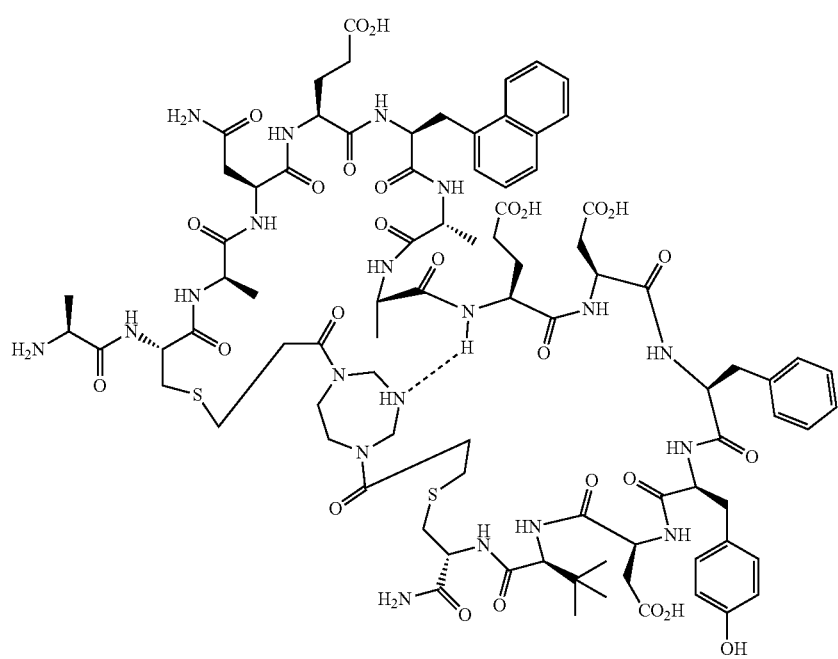
II-24

II-25
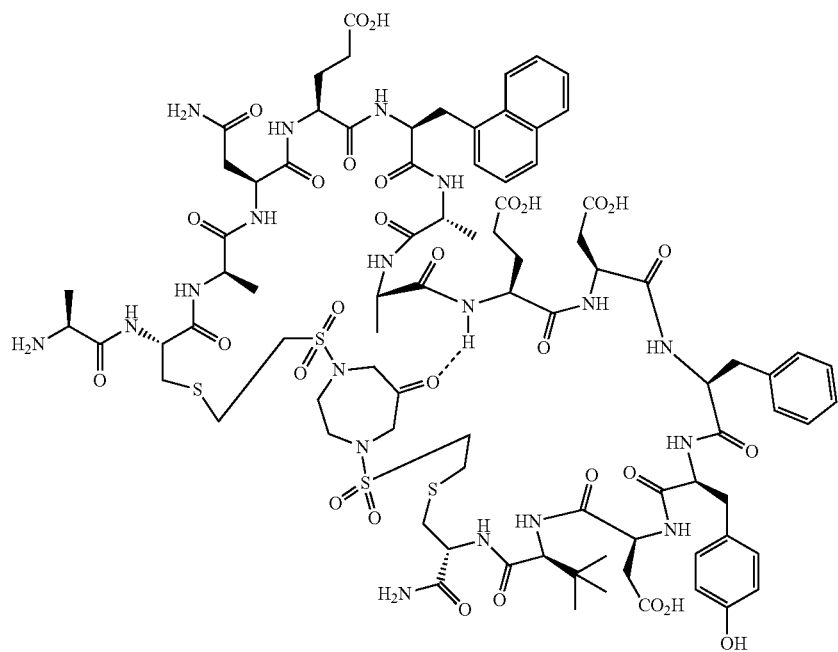
II-26
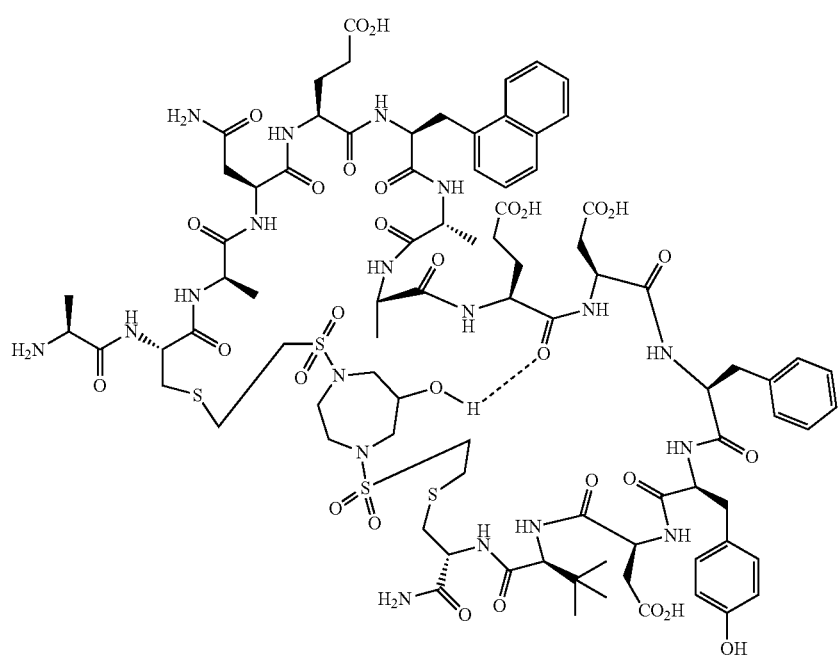

II-27
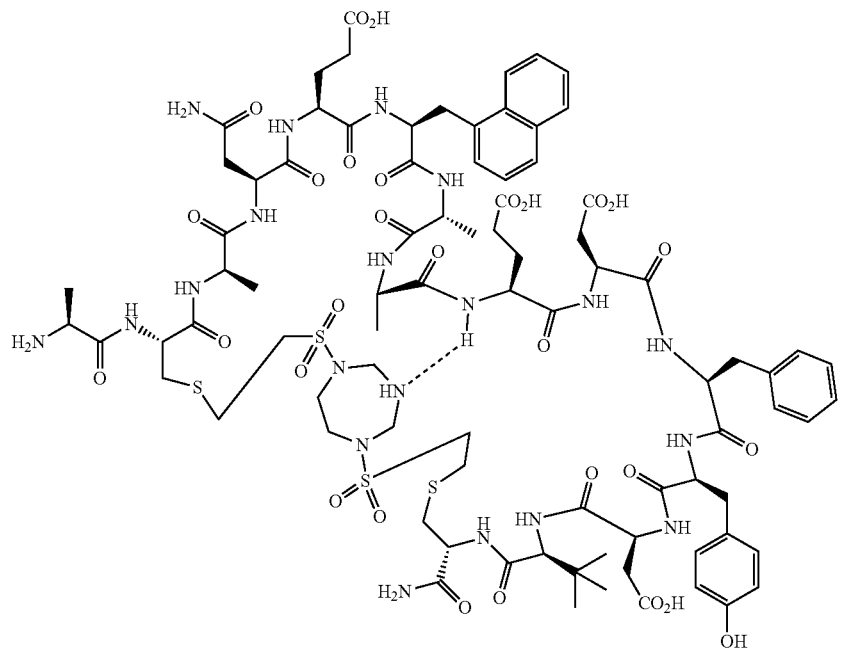
II-28
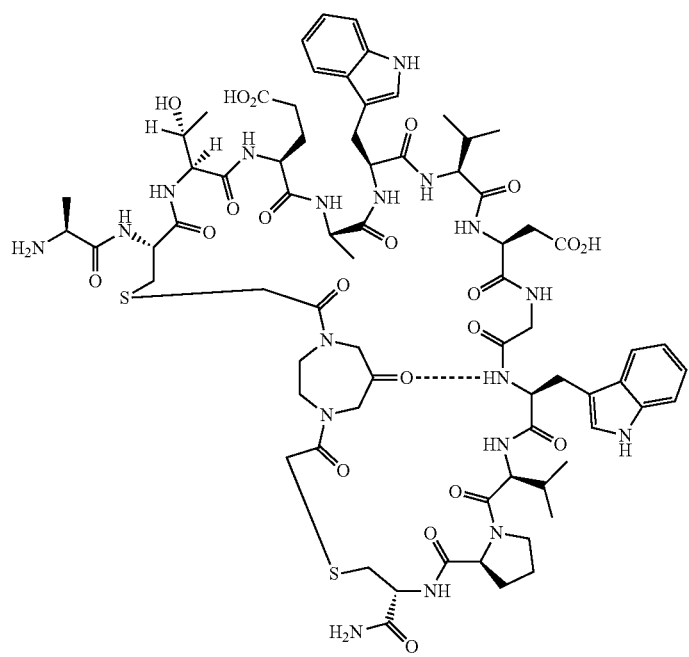

II-29
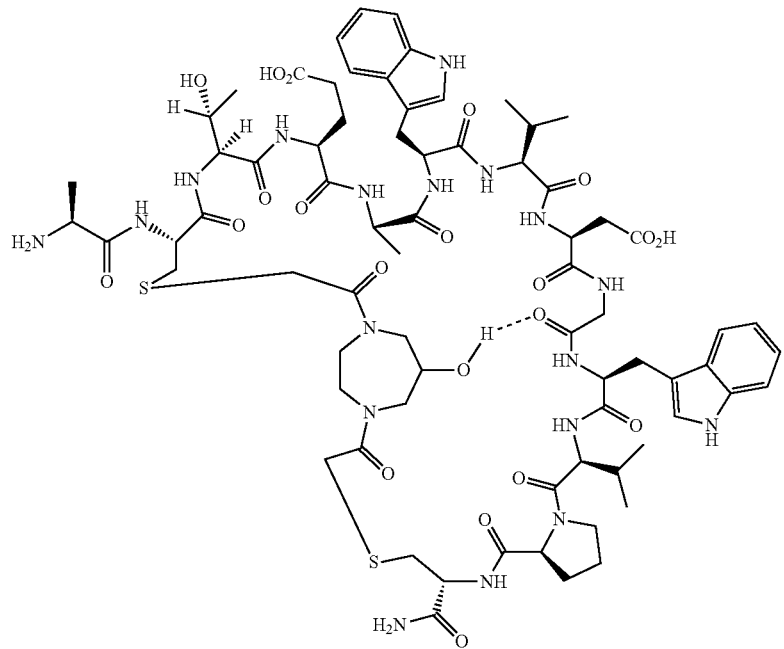
II-30
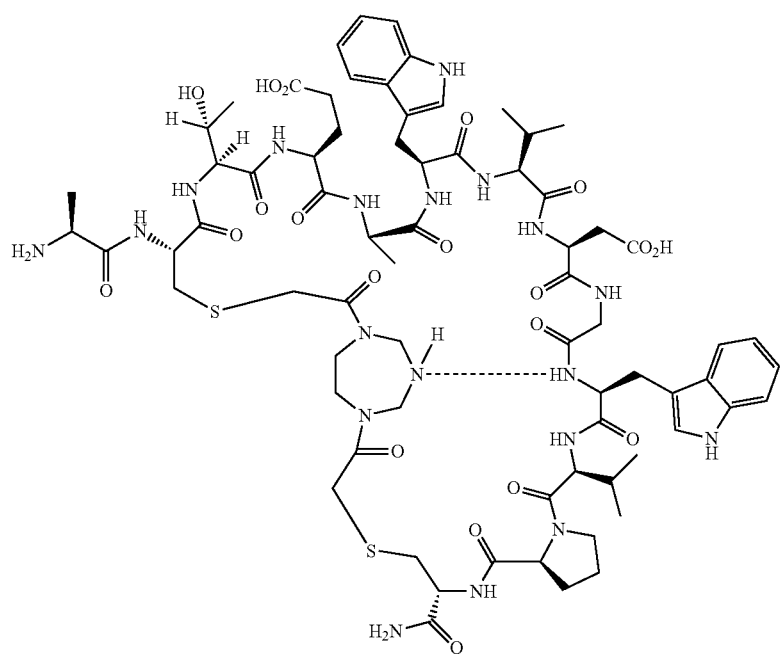

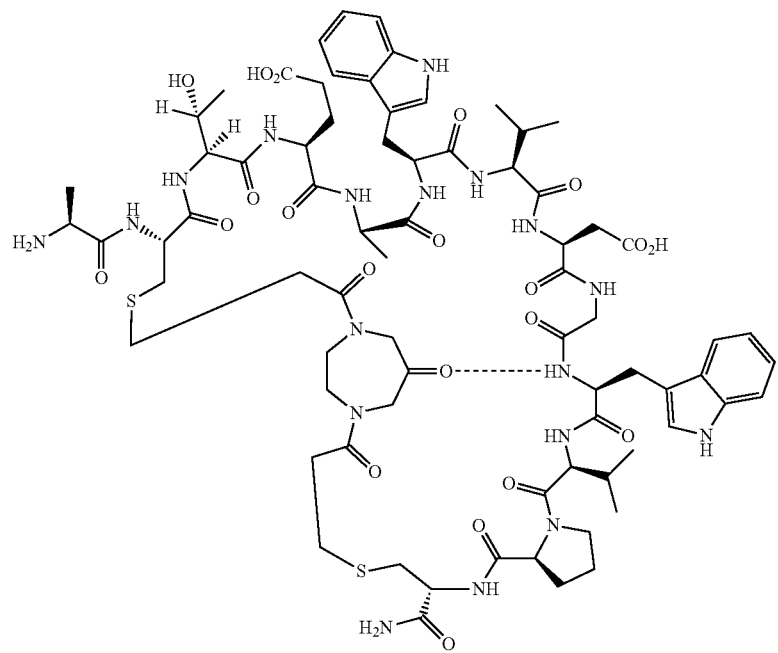
II-31
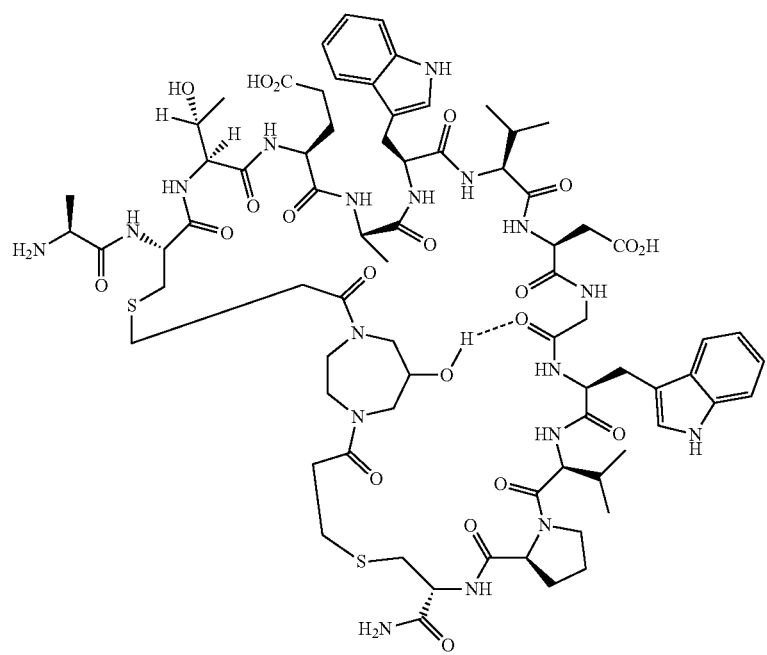
II-32

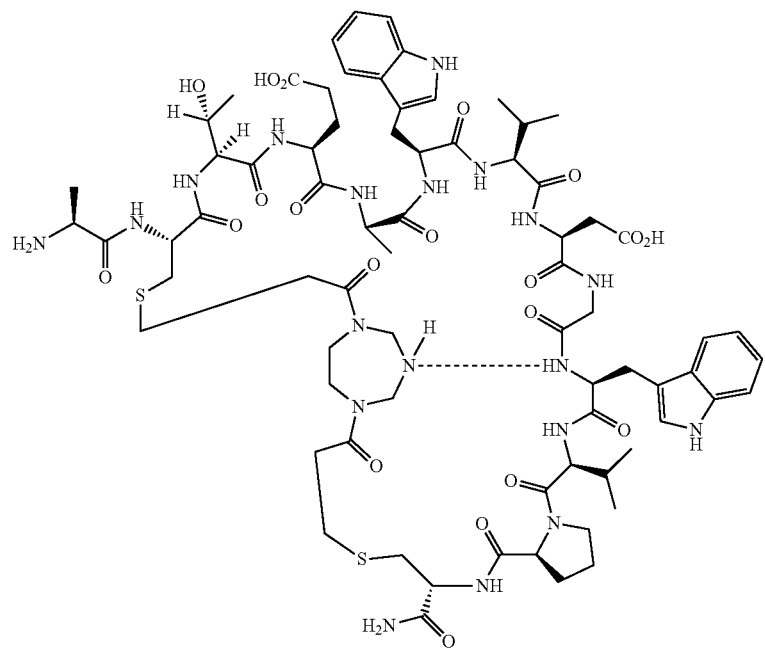
II-33
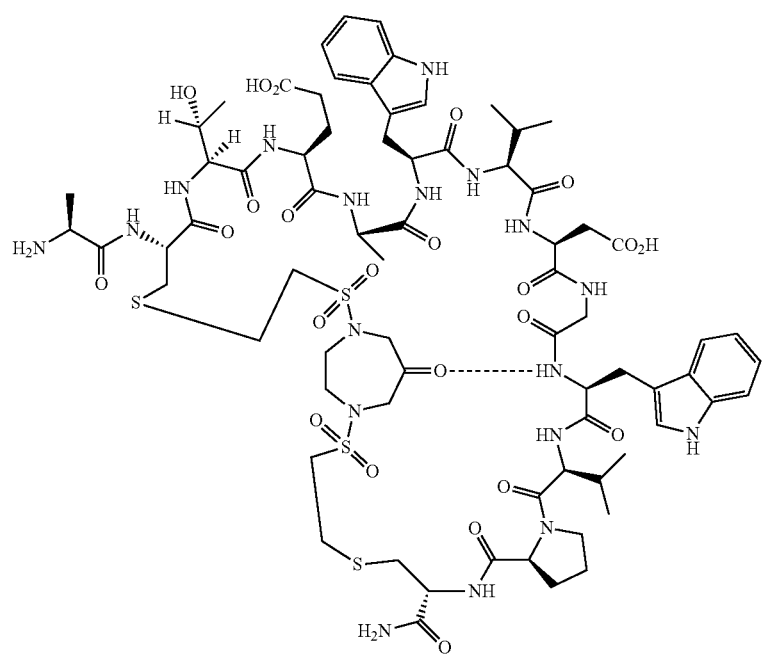
II-34

II-35

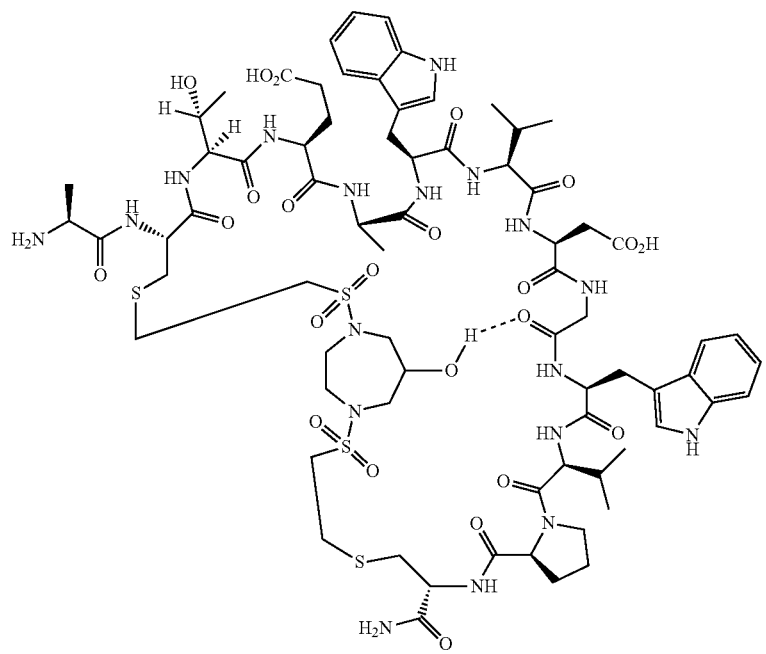

II-36

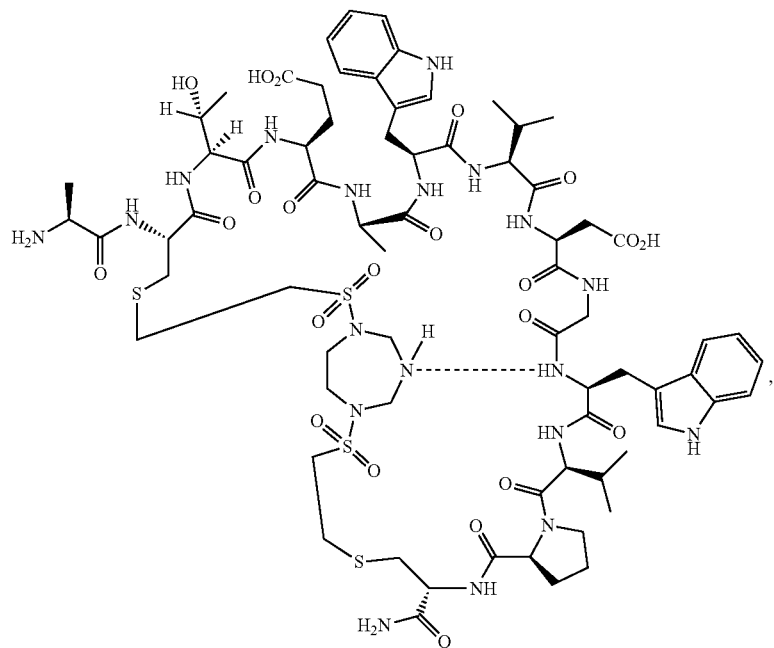

or a pharmaceutically acceptable salt thereof.

5. A pharmaceutical composition comprising a compound according to claim 1, or a pharmaceutically acceptable salt thereof, and a pharmaceutically acceptable carrier, adjuvant, or vehicle.

6. A method of inhibiting CAIX, MT1-MMP, CD38, EphA2, or PBP1A in a patient or biological sample comprising administering to said patient, or contacting said biological sample with a compound according to claim 1 or 3, or a pharmaceutically acceptable salt thereof.

7. A method of treating a CAIX-mediated, MT1-MMP-mediated, CD38-mediated, EphA2-mediated, or PBP1A-mediated disorder, disease, or condition in a patient comprising administering to said patient the pharmaceutical composition of claim 5.

8. A pharmaceutical composition comprising a compound according to claim 3, or a pharmaceutically acceptable salt thereof, and a pharmaceutically acceptable carrier, adjuvant, or vehicle.

9. A method of treating a CAIX-mediated, MT1-MMP-mediated, CD38-mediated, EphA2-mediated, or PBP1A-mediated disorder, disease, or condition in a patient comprising administering to said patient the pharmaceutical composition of claim 8.

10. The method of claim 7, wherein the CAIX-mediated or MT1-MMP-mediated disorder, disease or condition is selected from the group consisting of a cancer or a proliferative disorder.

11. The method of claim 10, wherein the cancer or proliferative disorder is selected from the group consisting of tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); hematological malignancies (i.e. leukemias, lymphomas) and pre-malignant hematological disorders and disorders of borderline malignancy including hematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukemias, natural killer [NK] cell lymphomas, Hodgkin's lymphomas, hairy cell leukemia, monoclonal gammopathy of uncertain significance, plasmacytoma, multiple myeloma, and post-transplant lymphoproliferative disorders), and hematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovia I sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and pediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

12. The method of claim 9, wherein the CAIX-mediated or MT1-MMP-mediated disorder, disease or condition is selected from the group consisting of a cancer or a proliferative disorder.

13. The method of claim 12, wherein the cancer or proliferative disorder is selected from the group consisting of tumors of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); hematological malignancies (i.e. leukemias, lymphomas) and pre-malignant hematological disorders and disorders of borderline malignancy including hematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukemias, natural killer [NK] cell lymphomas, Hodgkin's lymphomas, hairy cell leukemia, monoclonal gammopathy of uncertain significance, plasmacytoma, multiple myeloma, and post-transplant lymphoproliferative disorders), and hematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumors of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovia I sarcomas, epithelioid sarcomas, gastrointestinal stromal tumors, benign and malignant histiocytomas, and dermatofibrosarcomaprotuberans; tumors of the central or peripheral nervous system (for example astrocytomas, gliomas and glioblastomas, meningiomas, ependymomas, pineal tumors and schwannomas); endocrine tumors (for example pituitary tumors, adrenal tumors, islet cell tumors, parathyroid tumors, carcinoid tumors and medullary carcinoma of the thyroid); ocular and adnexal tumors (for example retinoblastoma); germ cell and trophoblastic tumors (for example teratomas, seminomas, dysgerminomas, hydatidiform moles and choriocarcinomas); and pediatric and embryonal tumors (for example medulloblastoma, neuroblastoma, Wilms tumor, and primitive neuroectodermal tumors); or syndromes, congenital or otherwise, which leave the patient susceptible to malignancy (for example Xeroderma Pigmentosum).

14. The compound of claim 1, wherein each of $L^1$, $L^2$, and $L^3$ is independently —CH$_2$S—, —CH$_2$O—, —CH₂CH₂O—, —CH₂NH—, —CH₂CH₂CH₂CH₂NH—, —CH₂N(CH₃)—, —CH₂CH₂CH₂CH₂N(CH₃)—, —CH₂SCH₂—, —CH₂OCH₂—, —CH₂CH₂OCH₂—, —CH₂NHCH₂—, —CH₂N(CH₃)CH₂—, —CH₂CH₂CH₂CH₂NHCH₂—, —CH₂CH₂CH₂CH₂N(CH₃)CH₂—, —CH₂SCH₂C(O)NH—, —CH₂OCH₂C(O)NH—, —CH₂CH₂OCH₂C(O)NH—, —CH₂NHCH₂C(O)NH—, —CH₂N(CH₃)CH₂C(O)NH—, —CH₂CH₂CH₂CH₂NHCH₂C(O)NH—, —CH₂CH₂CH₂CH₂N(CH₃)CH₂C(O)NH—, —CH₂SCH₂C(O)—, —CH₂OCH₂C(O)—, —CH₂CH₂OCH₂C(O)—, —CH₂NHCH₂C(O)—, —CH₂N(CH₃)CH₂C(O)—, —CH₂CH₂CH₂CH₂NHCH₂C(O)—, —CH₂CH₂CH₂CH₂N(CH₃)CH₂C(O)—, —CH₂SCH₂CH₂C(O)NH—, —CH₂OCH₂CH₂C(O)NH—, —CH₂CH₂OCH₂CH₂C(O)NH—, —CH₂NHCH₂CH₂C(O)NH—, —CH₂N(CH₃)CH₂CH₂C(O)NH—, —CH₂CH₂CH₂CH₂NHCH₂C(O)NH—, —CH₂CH₂CH₂CH₂N(CH₃)CH₂C(O)NH—, —CH₂SCH₂CH₂C(O)—, —CH₂OCH₂CH₂C(O)—, —CH₂CH₂OCH₂CH₂C(O)—, —CH₂NHCH₂CH₂C(O)—, —CH₂N(CH₃)CH₂CH₂C(O)—, —CH₂CH₂CH₂CH₂NHCH₂CH₂C(O)—, —CH₂CH₂CH₂CH₂N(CH₃)CH₂CH₂C(O)—, or

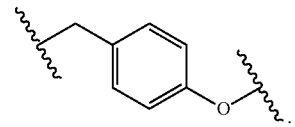 [SMILES: *Cc1ccc(O*)cc1]

15. The compound of claim 3, wherein each of $L^2$ and $L^3$ is independently —CH₂S—, —CH₂O—, —CH₂CH₂O—, —CH₂NH—, —CH₂CH₂CH₂CH₂NH—, —CH₂N(CH₃)—, —CH₂CH₂CH₂CH₂N(CH₃)—, —CH₂SCH₂—, —CH₂OCH₂—, —CH₂CH₂OCH₂—, —CH₂NHCH₂—, —CH₂N(CH₃)CH₂—, —CH₂CH₂CH₂CH₂NHCH₂—, —CH₂CH₂CH₂CH₂N(CH₃)CH₂—, —CH₂SCH₂C(O)NH—, —CH₂OCH₂C(O)NH—, —CH₂CH₂OCH₂C(O)NH—, —CH₂NHCH₂C(O)NH—, —CH₂N(CH₃)CH₂C(O)NH—, —CH₂CH₂CH₂CH₂NHCH₂C(O)NH—, —CH₂CH₂CH₂CH₂N(CH₃)CH₂C(O)NH—, —CH₂SCH₂C(O)—, —CH₂OCH₂C(O)—, —CH₂CH₂OCH₂C(O)—, —CH₂NHCH₂C(O)—, —CH₂N(CH₃)CH₂C(O)—, —CH₂CH₂CH₂CH₂NHCH₂C(O)—, —CH₂CH₂CH₂CH₂N(CH₃)CH₂C(O)—, —CH₂SCH₂CH₂C(O)NH—, —CH₂OCH₂CH₂C(O)NH—, —CH₂CH₂OCH₂CH₂C(O)NH—, —CH₂NHCH₂CH₂C(O)NH—, —CH₂N(CH₃)CH₂CH₂C(O)NH—, —CH₂CH₂CH₂CH₂NHCH₂C(O)NH—, —CH₂CH₂CH₂CH₂N(CH₃)CH₂C(O)NH—, —CH₂SCH₂CH₂C(O)—, —CH₂OCH₂CH₂C(O)—, —CH₂CH₂OCH₂CH₂C(O)—, —CH₂NHCH₂CH₂C(O)—, —CH₂N(CH₃)CH₂CH₂C(O)—, —CH₂CH₂CH₂CH₂NHCH₂CH₂C(O)—, —CH₂CH₂CH₂CH₂N(CH₃)CH₂CH₂C(O)—, or

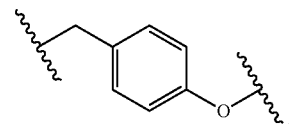

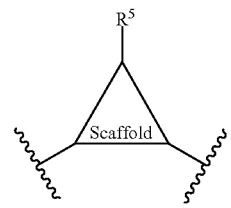

16. The compound of claim 3, wherein is

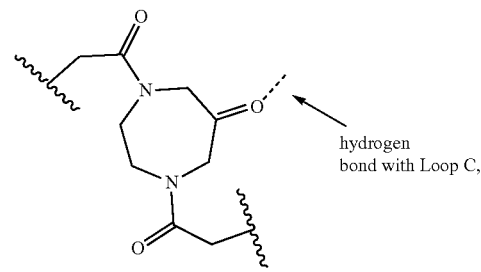

hydrogen bond with Loop C,

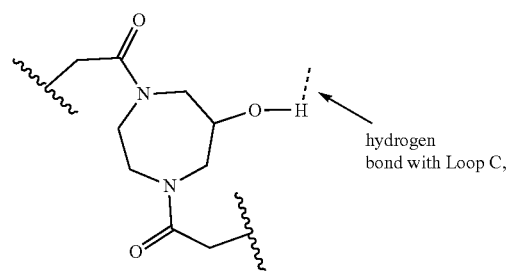

hydrogen bond with Loop C,

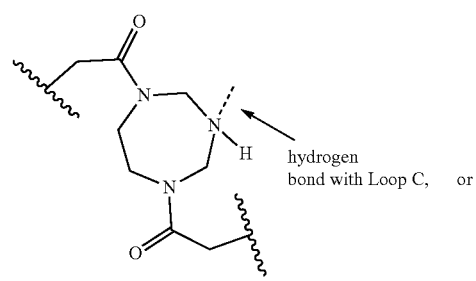

hydrogen bond with Loop C, or

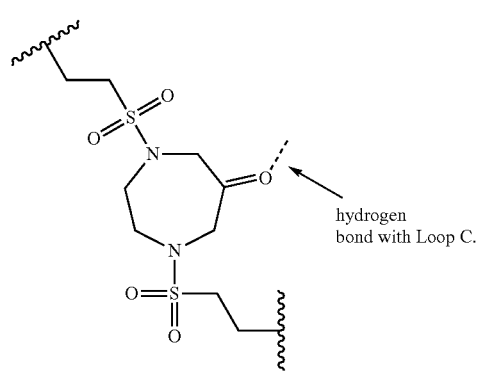

hydrogen bond with Loop C.

17. The compound of claim 1, wherein Loop A is selected from
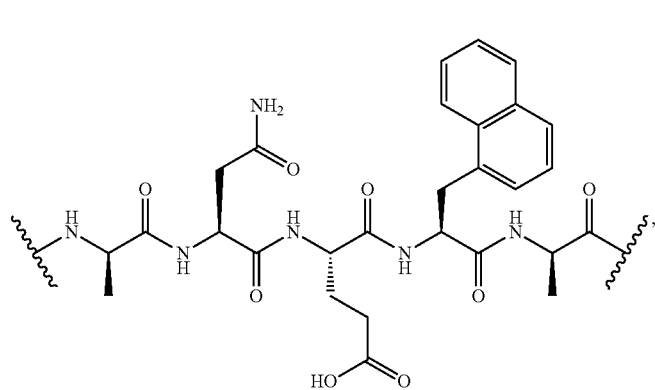
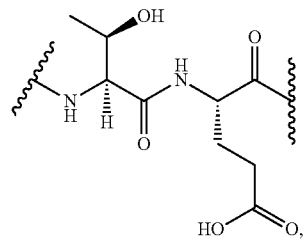
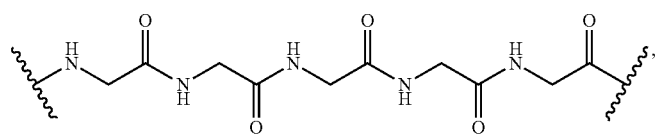
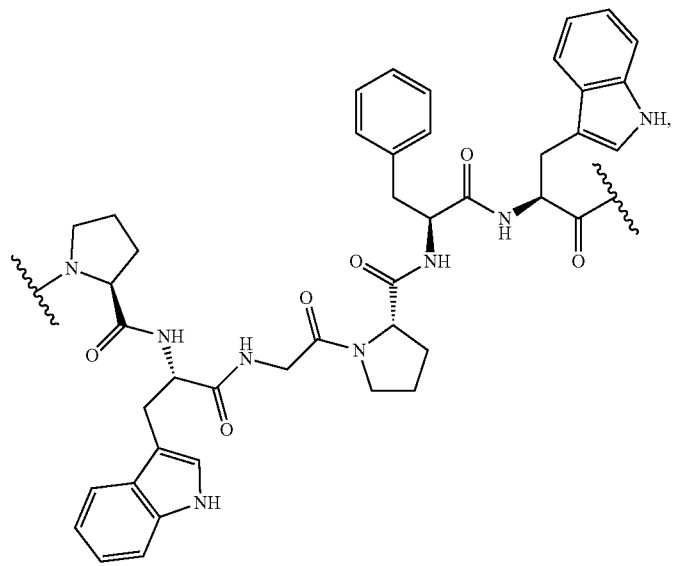
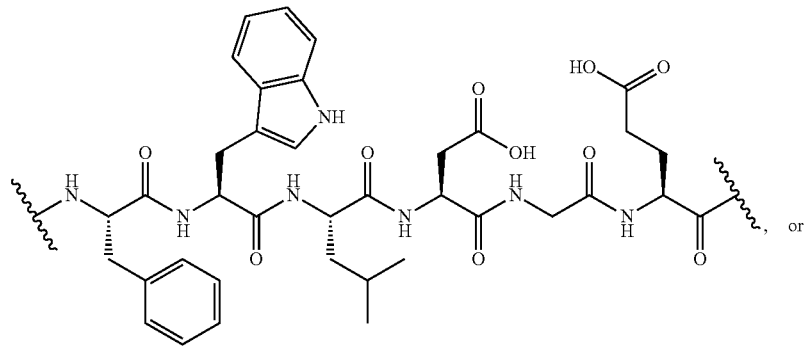

-continued
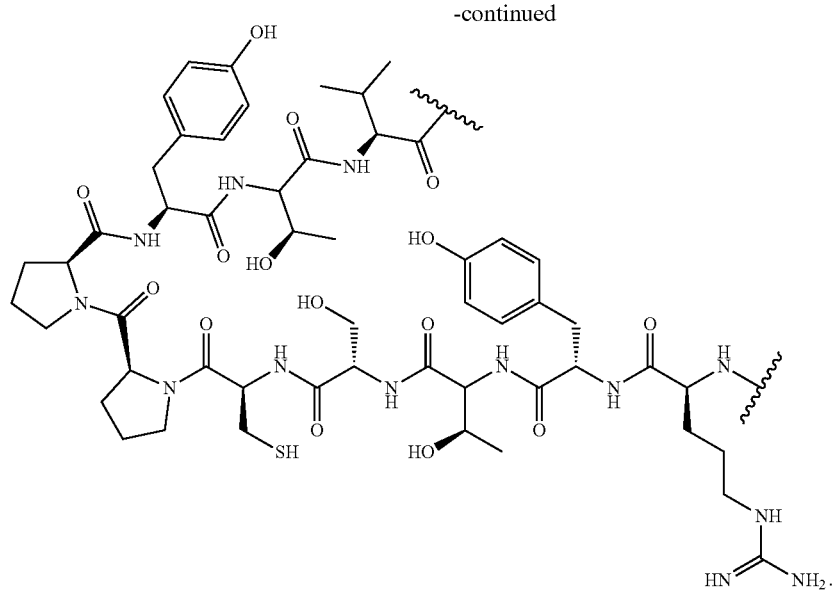
18. The compound of claim 1, wherein Loop B is selected from
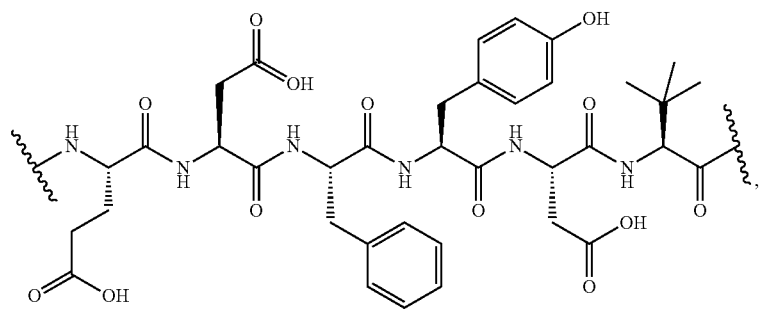
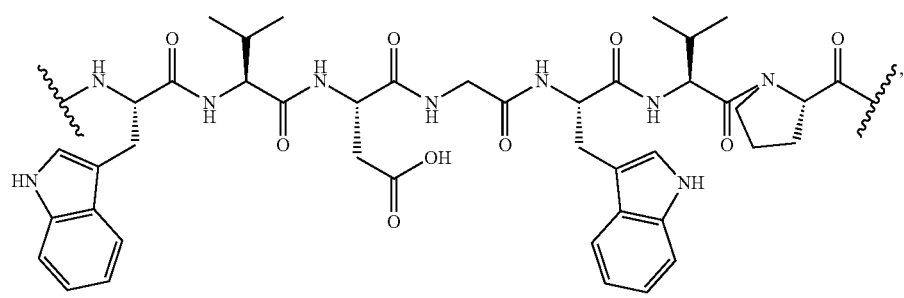
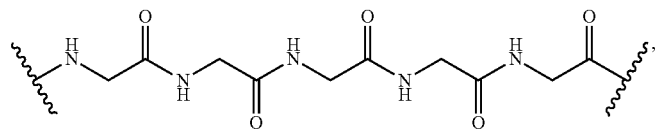

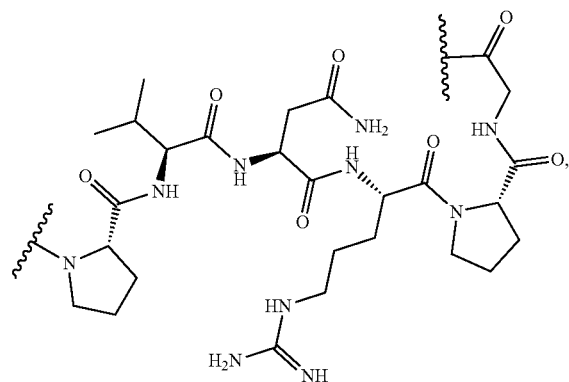
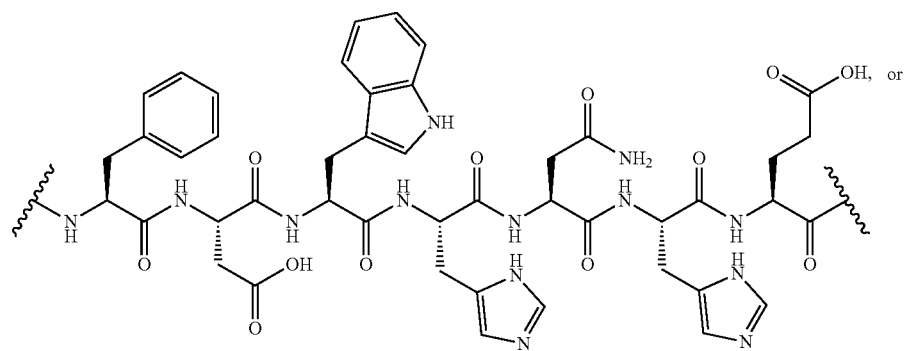
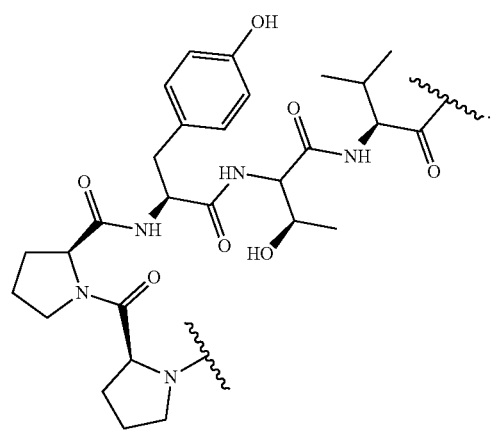 [SMILES: *C(=O)[C@@H](NC(=O)C(NC(=O)[C@H](Cc1ccc(O)cc1)NC(=O)[C@@H]1CCCN1C(=O)[C@@H]1CCCN1*)[C@@H](C)O)C(C)C]

19. The compound of claim 3, wherein Loop C is selected from
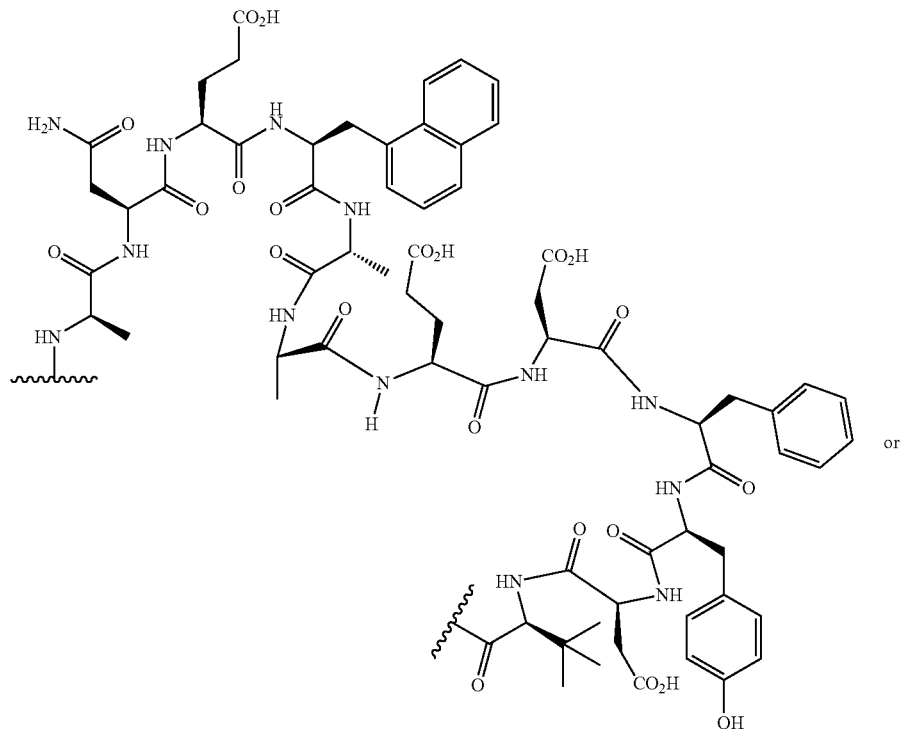
or
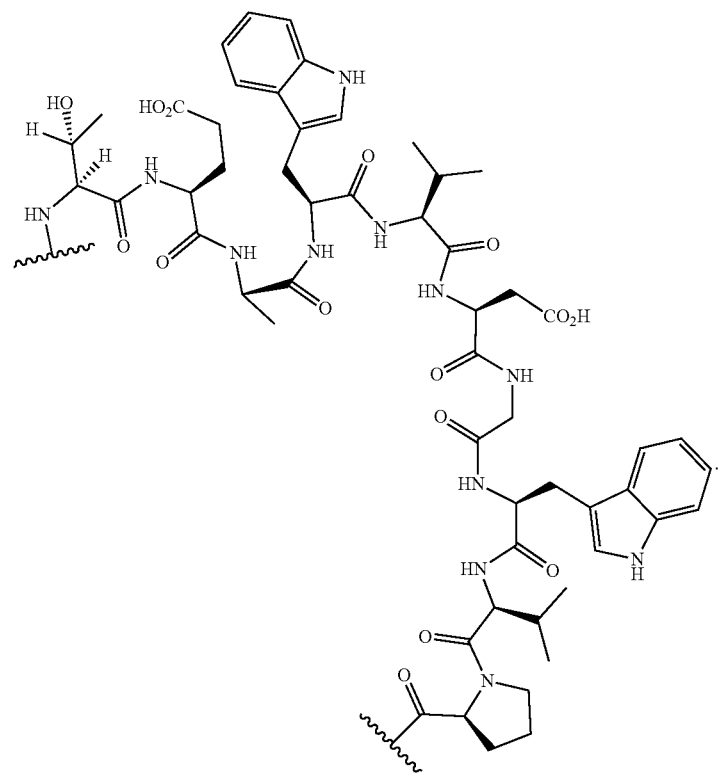

20. The compound of claim 1, wherein n is 1.
21. The compound of claim 20, wherein Spacer² is D-Alanine or
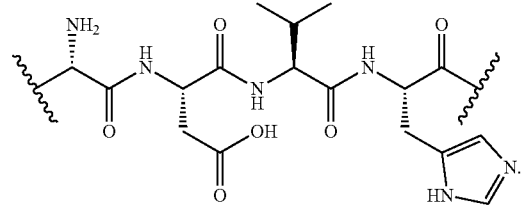 [SMILES: *C(=O)[C@H](Cc1cnc[nH]1)NC(=O)[C@@H](NC(=O)[C@H](CC(=O)O)NC(=O)[C@H](*)N)C(C)C]
22. The compound of claim 21, wherein R² is R,
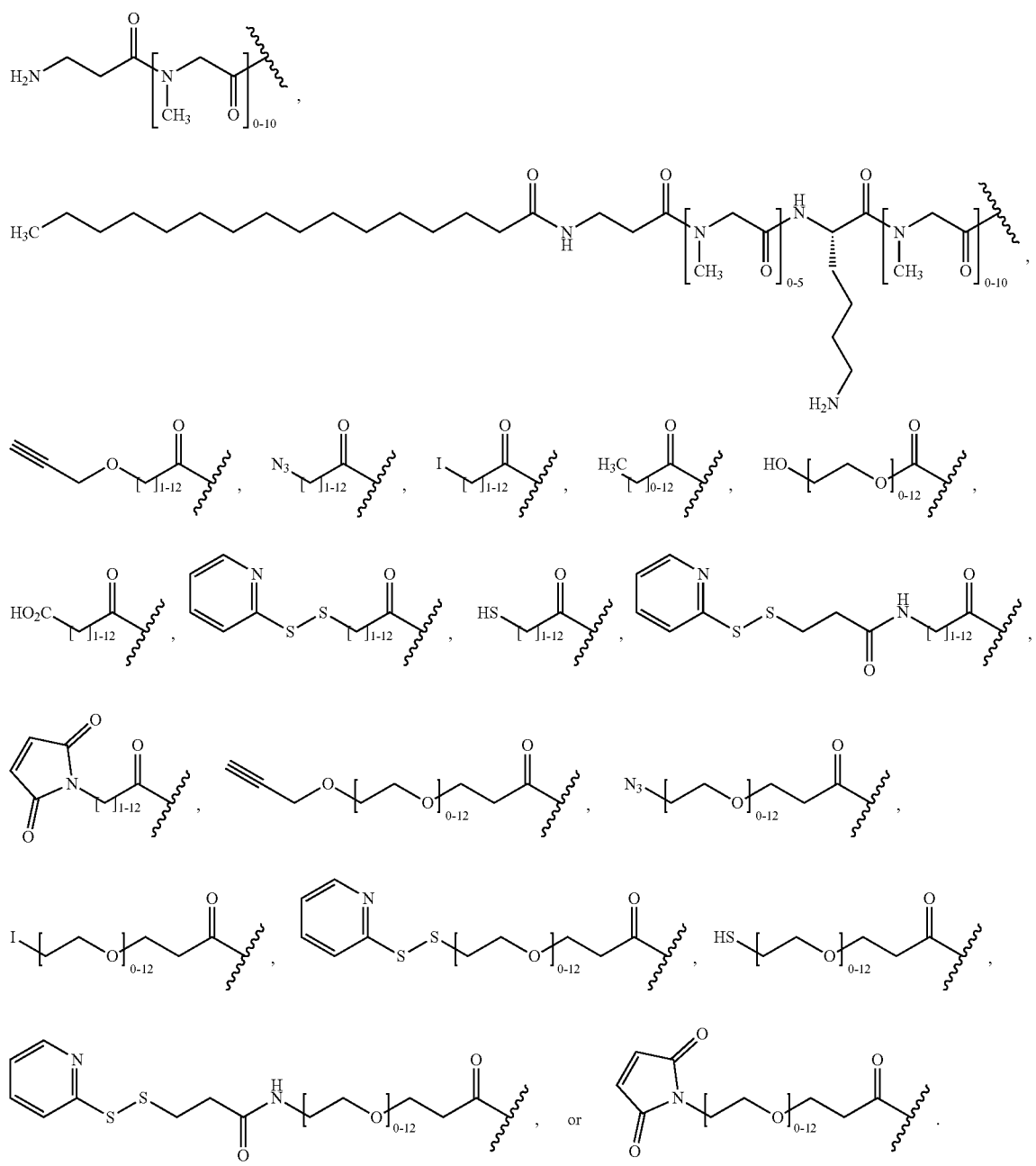

23. The compound of claim 1, wherein m is 0.
24. The compound of claim 23, wherein $L^4$ is a covalent bond, —O—, or —N(R)—.
25. The compound of claim 24, wherein, $R^1$ is R.

* * * * *

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Sar10
<220> FEATURE:
<221> NAME/KEY: MOD_RES
<222> LOCATION: (5)..(5)
<223> OTHER INFORMATION: D-Ala
<220> FEATURE:
<221> NAME/KEY: MOD_RES
<222> LOCATION: (8)..(8)
<223> OTHER INFORMATION: 1Nal
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (16)..(16)
<223> OTHER INFORMATION: tBu-Gly

<400> SEQUENCE: 1

Ala Xaa Ala Cys Ala Asn Glu Xaa Ala Cys Glu Asp Phe Tyr Asp Gly
1               5                   10                  15

Cys

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (2)..(2)
<223> OTHER INFORMATION: Sar10
```

<400> SEQUENCE: 2

Ala Xaa Ala Cys Thr Glu Cys Trp Val Asp Gly Trp Val Pro Cys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: 1Nal
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tBu-Gly

<400> SEQUENCE: 3

Ala Cys Ala Asn Glu Xaa Ala Cys Glu Asp Phe Tyr Asp Gly Cys
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Cys Thr Glu Cys Trp Val Asp Gly Trp Val Pro Cys
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Cys Phe Trp Leu Asp Gly Glu Cys Phe Asp Trp His Asn His Glu
1               5                   10                  15

Cys Ala

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Asp Val His Cys Pro Trp Gly Pro Phe Trp Cys Pro Val Asn Arg
1               5                   10                  15

Pro Gly Cys Ala
            20

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Cys Arg Tyr Thr Ser Cys Pro Pro Tyr Thr Val Cys Ala
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: 1Nal
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tBu-Gly

<400> SEQUENCE: 8

Ala Cys Ala Asn Glu Xaa Ala Ala Glu Asp Phe Tyr Asp Gly Cys
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Thr Glu Tyr Trp Val Asp Gly Trp Val Pro Cys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Thr Glu Cys Trp Val Asp Gly Trp Val Pro Tyr
1               5                   10

<210> SEQ ID NO 11
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Sar6
<220> FEATURE:
<221> NAME/KEY: MOD_RES
<222> LOCATION: (16)..(16)
<223> OTHER INFORMATION: Lys(F1)

<400> SEQUENCE: 11

Ala Cys Ala Glu Cys Trp Ile Asp Gly Trp Val Pro Cys Ala Xaa Lys
1               5                   10                  15

<210> SEQ ID NO 12
<211> LENGTH: 14
<212> TYPE: PRT
<213> ORGANISM: Human immunodeficiency virus

<400> SEQUENCE: 12

Gly Arg Lys Lys Arg Arg Gln Arg Arg Arg Pro Pro Gln Cys
1               5                   10
```